(12) United States Patent
Wilde et al.

(10) Patent No.: US 6,642,230 B2
(45) Date of Patent: Nov. 4, 2003

(54) IMIDAZOPYRIMIDINES AND IMIDAZOPYRIDINES FOR THE TREATMENT OF NEUROLOGICAL DISORDERS

(75) Inventors: Richard Gerald Wilde, Newark, DE (US); Rajagopal Bakthavatchalam, Wilmington, DE (US); James Peter Beck, Smyrna, DE (US); Argyrios Georgious Arvanitis, Kennett Square, PA (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 0 days.

(21) Appl. No.: 10/053,475

(22) Filed: Nov. 7, 2001

(65) Prior Publication Data

US 2003/0114468 A1 Jun. 19, 2003

Related U.S. Application Data

(62) Division of application No. 09/208,778, filed on Dec. 10, 1998, now Pat. No. 6,362,180, which is a continuation of application No. 09/109,877, filed on Jul. 2, 1998, now Pat. No. 6,143,743.
(60) Provisional application No. 60/080,665, filed on Apr. 3, 1998, and provisional application No. 60/051,628, filed on Jul. 3, 1997.

(51) Int. Cl.[7] .................. C07D 471/04; A61K 31/437
(52) U.S. Cl. .................. 514/234.2; 546/118; 514/303; 514/234.5; 514/255; 514/241; 514/269; 514/272; 514/274; 544/127; 544/362; 544/212; 544/322; 544/298; 544/333
(58) Field of Search .................. 546/118; 514/303, 514/234.2, 234.5, 255, 241, 269, 272, 274; 544/127, 362, 212, 322, 298, 333

(56) References Cited

U.S. PATENT DOCUMENTS

| | | | |
|---|---|---|---|
| 4,797,399 A | 1/1989 | Ueda et al. | 514/253 |
| 5,015,473 A | 5/1991 | Chen | 424/114 |
| 5,075,311 A | 12/1991 | Hubsch et al. | 514/258 |
| 5,102,880 A | 4/1992 | Chakravarty et al. | 514/212 |
| 5,128,327 A | 7/1992 | Chakravarty et al. | 514/81 |
| 5,145,959 A | 9/1992 | Hubsch et al. | 544/279 |
| 5,157,026 A | 10/1992 | Chakravarty et al. | 514/81 |
| 5,171,353 A | 12/1992 | Fischer et al. | 71/92 |
| 5,176,991 A | 1/1993 | Jones et al. | 430/569 |
| 5,178,997 A | 1/1993 | Maskasky | 430/569 |
| 5,187,159 A | 2/1993 | Greenlee et al. | 514/81 |
| 5,250,531 A | 10/1993 | Cooper | 514/256 |
| 5,260,322 A | 11/1993 | Nakasima et al. | 514/341 |
| 5,330,989 A | 7/1994 | Soll et al. | 514/258 |
| 5,332,814 A | 7/1994 | Moser | 544/229 |
| 5,332,820 A | 7/1994 | Duncia | 546/118 |
| 5,338,740 A | 8/1994 | Carpino et al. | 514/259 |
| 5,338,756 A | 8/1994 | Fortin et al. | 514/394 |
| 5,374,638 A | 12/1994 | Dhanoa et al. | 514/326 |
| 5,376,665 A | 12/1994 | Miyata et al. | 514/301 |
| 5,376,666 A | 12/1994 | Duncia | 514/303 |
| 5,385,925 A | 1/1995 | Narr et al. | 514/382 |
| 5,389,634 A | 2/1995 | Fortin et al. | 514/248 |
| 5,389,641 A | 2/1995 | Naka et al. | 514/303 |
| 5,395,840 A | 3/1995 | Muller et al. | 514/300 |
| 5,424,432 A * | 6/1995 | Fredenburgh et al. | 546/118 |
| 5,434,150 A | 7/1995 | Austel et al. | 514/228.5 |
| 5,444,068 A | 8/1995 | Heitsch et al. | 514/303 |
| 5,446,159 A | 8/1995 | Stucky et al. | 546/118 |
| 5,446,160 A | 8/1995 | Stucky et al. | 546/118 |
| 5,459,147 A | 10/1995 | Hauel et al. | 514/305 |
| 5,470,867 A | 11/1995 | Fortin et al. | 514/248 |
| 5,498,715 A | 3/1996 | Kuo et al. | 546/118 |
| 5,514,682 A | 5/1996 | Street | 514/266 |
| 5,541,324 A | 7/1996 | TenBrink et al. | 544/346 |
| 5,565,437 A | 10/1996 | Marquez et al. | 514/45 |
| 5,580,981 A | 12/1996 | Carpino | 544/262 |
| 5,587,393 A | 12/1996 | Narr et al. | 514/381 |
| 5,587,470 A | 12/1996 | Cook et al. | 536/23.1 |
| 5,597,826 A | 1/1997 | Howard et al. | 514/255 |
| 5,635,525 A | 6/1997 | Heitsch et al. | 514/394 |
| 5,684,029 A | 11/1997 | Narr et al. | 514/394 |

FOREIGN PATENT DOCUMENTS

| | | |
|---|---|---|
| AU | 96-72147 | 10/1997 |
| AU | 97-26365 | 10/1997 |

(List continued on next page.)

OTHER PUBLICATIONS

Mataka et al, Reduction of 4,7–Diphenyl–1, 2,5–thia (oxa) diazolo [3,4–c] pyridines Affording 2,5–Diphenyl–3,4–diaminopyridines and Ring Closure of the Diamines to Fluorescent Azaheterocycles, Jrnl of Heterocyclic Chem., 19/6, 1481–1488 (1982).

(List continued on next page.)

Primary Examiner—Mukund J. Shah
Assistant Examiner—Hong Liu
(74) Attorney, Agent, or Firm—Shah R. Makujina; Falim S. Fuzail; Woodcock Washburn LLP

(57) ABSTRACT

Corticotropin releasing factor (CRF) antagonists of formula (I):

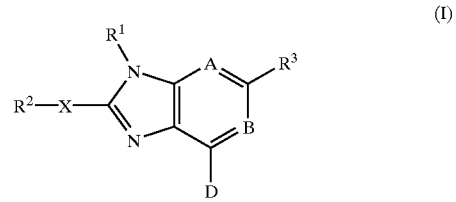

and their use in treating psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

5 Claims, No Drawings

FOREIGN PATENT DOCUMENTS

| | | | |
|---|---|---|---|
| CA | 2011222 | | 9/1990 |
| CA | 2024137 | | 3/1991 |
| CA | 2032831 | | 6/1991 |
| CA | 2062558 | | 9/1992 |
| CA | 2089698 | | 2/1993 |
| CA | 2099712 | | 6/1993 |
| CA | 2158996 | * | 10/1994 |
| CA | 2147798 | | 4/1995 |
| DE | 3921271 A | | 1/1991 |
| DE | 4208535 A | | 9/1992 |
| EP | 0345747 A2 | | 12/1989 |
| EP | 0399731 B1 | | 11/1990 |
| EP | 0400974 A2 | | 12/1990 |
| EP | 0416740 A2 | | 3/1991 |
| EP | 0434038 A1 | | 6/1991 |
| EP | 0445467 A1 | | 9/1991 |
| EP | 0466711 B1 | | 1/1992 |
| EP | 0480204 A1 | | 4/1992 |
| EP | 0520423 A2 | | 12/1992 |
| EP | 0353902 B1 | | 5/1993 |
| EP | 0542681 A1 | | 5/1993 |
| EP | 0574174 A2 | | 12/1993 |
| EP | 0577558 A2 | | 1/1994 |
| EP | 0706795 A2 | | 4/1996 |
| EP | 0773023 A1 | | 5/1997 |
| EP | 0812831 A1 | | 12/1997 |
| GB | 2263637 A | | 8/1993 |
| GB | 2272899 A | | 6/1994 |
| JP | 5-213754 | | 8/1993 |
| JP | 5-287209 | | 11/1993 |
| WO | WO88/03025 | | 5/1988 |
| WO | WO91/19715 | | 12/1991 |
| WO | WO93/03033 | | 2/1993 |
| WO | WO93/23396 | | 11/1993 |
| WO | WO94/10171 | | 5/1994 |
| WO | WO 9412461 | * | 6/1994 |
| WO | WO94/12461 | | 6/1994 |
| WO | WO94/18215 | | 8/1994 |
| WO | WO94/22859 | | 10/1994 |
| WO | WO95/10506 | | 4/1995 |
| WO | WO95/20597 | | 8/1995 |
| WO | WO95/21836 | | 8/1995 |
| WO | WO95/21838 | | 8/1995 |
| WO | WO95/33727 | | 12/1995 |
| WO | WO95/33750 | | 12/1995 |
| WO | WO95/34563 | | 12/1995 |
| WO | WO95/34564 | | 12/1995 |
| WO | WO96/01624 | | 1/1996 |
| WO | WO96/02535 A1 | | 2/1996 |
| WO | WO96/17076 | | 6/1996 |
| WO | WO96/17077 | | 6/1996 |
| WO | WO96/19478 | | 6/1996 |
| WO | WO96/24338 | | 8/1996 |
| WO | WO96/24375 | | 8/1996 |
| WO | WO97/08150 | | 3/1997 |
| WO | WO98/08847 | | 3/1998 |
| WO | WO98/35967 | | 8/1998 |

OTHER PUBLICATIONS

Kalme et al, Nucleophilic Substitution in . . . , Khim Geterotsikl Soedin, 12, 1646–1650, (1992).
Kiyama et al., Synthesis and Evaluation of Novel Nonpeptide Angiotensin II Receptor Antagonists . . . , Chem. Pharm Bull., 43/3, 450–460, (1995).
PCT International Search Report PCT/US/98/13913.
Schulz et al., 1996, Proc. Natl. Acad. Sci., 93, 10477–10482.
Chen et al., 1997, J. Med. Chem., 40, 1749–1754.
Wilde et al., Aug. 20, 2000, American Chemical Society National Mtg., Washington, DC, MEDI 123, Article.
Wilde et al., Mar. 29, 2000, Am Chemical Society National Mtg., San Francisco, MEDI 317, Article.

* cited by examiner

IMIDAZOPYRIMIDINES AND IMIDAZOPYRIDINES FOR THE TREATMENT OF NEUROLOGICAL DISORDERS

CROSS REFERENCE TO RELATED APPLICATIONS

This is a divisional of U.S. Ser. No. 09/208,778 filed Dec. 10, 1998, now U.S. Pat. No. 6,362,180 issued Mar. 26, 2002, which is a continuation of U.S. Ser. No. 09/109,877 filed Jul. 2, 1998, now U.S. Pat. No. 6,143,743 issued Nov. 7, 2000, which claims the benefit of U.S. Provisional Application No. 60/080,665 filed Apr. 3, 1998 and U.S. Provisional Application No. 60/051,628 filed Jul. 3, 1997.

FIELD OF THE INVENTION

The present invention relates to novel compounds, compositions, and methods for the treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. In particular, the present invention relates to novel imidazopyrimidines and imidazopyridines, pharmaceutical compositions containing such compounds and their use in treating psychiatric disorders, neurological diseases, immunological, cardiovascular or heart-related diseases and colonic hypersensitivity associated with psychopathological disturbance and stress.

BACKGROUND OF THE INVENTION

Corticotropin releasing factor (herein referred to as CRF), a 41 amino acid peptide, is the primary physiological regulator of proopiomelanocortin (POMC)—derived peptide secretion from the anterior pituitary gland [J. Rivier et al., *Proc. Nat. Acad. Sci.* (*USA*) 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provide evidence that CRF has a role in sychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats.

The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

It has been further postulated that CRF has a role in immunological, cardiovascular or heart-related diseases such as hypertension, tachycardia and congestive heart failure, stroke, osteoporosis, premature birth, psychosocial dwarfism, stress-induced fever, ulcer, diarrhea, post-operative ileus and colonic hypersensitivity associated with psychopathological disturbance and stress.

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical CRF9-41) in a variety of behavioral paradigms have demonstrated that the CRF antagonist produces "anxiolytic-like" effects qualitatively similar to the benzodiazepines (for review see G. F. Koob and K. T. Britton, In: *Corticotropin-Releasing Factor:*

*Basic and Clinical Studies of a Neuropeptide*, E. B. De Souza and C. B. Nemeroff eds., CRC Press p221 (1990)).

DuPont Merck PCT application US94/11050 describes corticotropin releasing factor antagonist compounds of the formula:

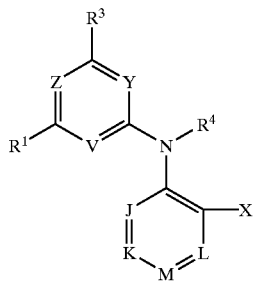

and their use to treat psychiatric disorders and neurological diseases. Included in the description are fused pyridines and pyrimidines of the formula:

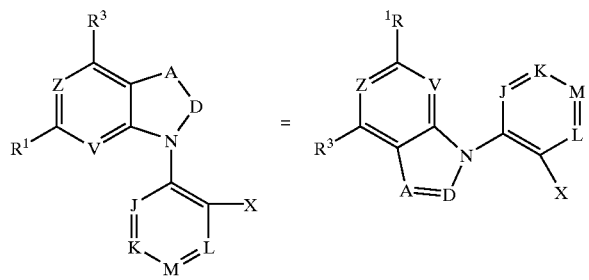

where: V is $CR^{1a}$ or N; Z is $CR^2$ or N; A is $CR^3O$ or N; and D is $CR^2$ or N.

Other compounds reported to have activity as corticotropin releasing factors are disclosed in WO 95/33750, WO 95/34563 and WO 95/33727.

SUMMARY OF THE INVENTION

In accordance with one aspect, the present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

According to another aspect, the present invention provides novel compounds of formula (I) (described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of formula (I), and methods of using such compounds for the suppression of CRF hypersecretion, and/or for the treatment of anxiogenic disorders.

According to yet another aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; in dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in mammals.

According to a still further aspect of the invention, the compounds provided by this invention (and especially labelled compounds of this invention) are also useful as standards and reagents in determining the ability of a potential pharmaceutical to bind to the CRF receptor.

DETAILED DESCRIPTION OF INVENTION

[1] Thus, in a first embodiment, the present invention provides a novel compound of formula I:

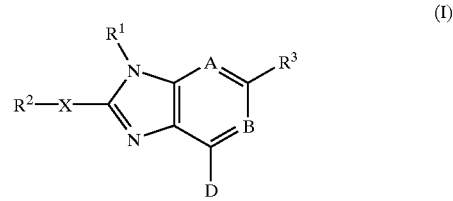

or a stereoisomer or pharmaceutically acceptable salt form thereof, wherein:

A is N or C—$R^7$;

B is N or C—$R^8$;

provided that at least one of the groups A and B is N;

D is an aryl or heteroaryl group attached through an unsaturated carbon atom;

X is selected from the group CH—$R^9$, N—$R^{10}$, O, S(O)$_n$ and a bond;

n is 0, 1 or 2;

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$—$C_{1-10}$ alkyl, —$SO_2$—$R^{1a}$, and —$SO_2$—$R^{1b}$;

$R^1$ is substituted with 0–1 substituents selected from the group —CN, —S(O)$_n R^{14b}$, —$COR^{13a}$, —$CO_2 R^{13a}$, —$NR^{15a}COR^{13a}$, —$N(COR^{13a})_2$, $NR^{15a}CONR^{13a}R^{16a}$, —$NR^{15a}CO_2 R^{14b}$, —$CONR^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —S(O)$_n$—, —$NR^{13a}$, —$NCO_2 R^{14b}$—, —$NCOR^{14b}$— and —$NSO_2 R^{14b}$—, and wherein $N_4$ in 1-piperazinyl is substituted with 0–1 substituents selected from the group $R^{13a}$, $CO_2 R^{14b}$, $COR^{14b}$ and $SO_2 R^{14b}$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —$OR^{13a}$, —$NR^{13a}R^{16a}$, $C_{1-4}$ alkoxy-$C_{1-4}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than:
(a) a cyclohexyl-$(CH_2)_2$— group;
(b) a 3-cyclopropyl-3-methoxypropyl group;
(c) an unsubstituted-(alkoxy)methyl group; and,
(d) a 1-hydroxyalkyl group;

also provided that when $R^1$ alkyl substituted with OH, then the carbon adjacent to the ring N is other than $CH_2$;

$R^{1a}$ is aryl and is selected from the group phenyl, naphthyl, indanyl and indenyl, each $R^{1a}$ being substituted with 0–1 —$OR^{17}$ and 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, SH, —S(O)$_n R^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2 R^{18}$, —$NR^{17a}R^{19a}$, and —$CONR^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —S(O)$_n R^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2 R^{18}$, —$NR^{17a}R^{19a}$, and —$CONR^{17a}R^{19a}$ and each heteroaryl being substituted on any nitrogen atom with 0–1 substituents selected from the group $R^{15a}$, $C_2 R^{14b}$, $COR^{14b}$ and $SO_2 R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —S(O)$_n R^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2 R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2 R^{14b}$, $COR^{14b}$ and $SO_2 R^{14b}$ and wherein any sulfur atom is optionally monooxidized or dioxidized;

provided that $R^1$ is other than a —$(CH_2)_{1-4}$-aryl, —$(CH_2)_{1-4}$-heteroaryl, or —$(CH_2)_{1-4}$-heterocycle, wherein the aryl, heteroaryl, or heterocycle group is substituted or unsubstituted;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^3$, $R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, ($C_{1-4}$ alkyl)$_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy<, $C_{1-4}$ alkylthio, $C_{1-4}$ alkyl sulfinyl, $C_{1-4}$ alkylsulfonyl, $C_{1-6}$ alkylamino and ($C_{1-4}$ alkyl)$_2$amino;

provided that when $R^1$ is unsubstituted $C_{1-10}$ alkyl, then $R^3$ is other than substituted or unsubstituted phenyl;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)— and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalky;

alternatively, In an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-norpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SC_2Me$ and acetyl;

heteroaryl is independently selected at each occurrence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$; and, provided that when D is imidazole or triazole, $R^1$ is other than unsubstituted $C_{1-6}$ linear or branched alkyl or $C_{3-6}$ cycloalkyl.

[2] In a preferred embodiment, the present invention provides a novel compound of formula Ia:

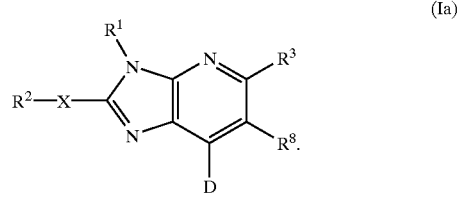

(Ia)

[2a] In a more preferred embodiment, the present invention provides a novel compound of formula Ia, wherein:

X is selected from the group O, $S(O)_n$ and a bond;

n is 0, 1 or 2;

$R^1$ is selected from the group $C_{1-6}$ alkyl, $C_{2-6}$ alkenyl, $C_{2-6}$ alkynyl, and $C_{3-8}$ cycloalkyl;

$R^1$ is substituted with 0–1 substituents selected from the group —CN, —$S(O)_nR^{14b}$, —$COR^{13a}$, —$CO_2R^{13a}$, and $C_{3-8}$ cycloalkyl, wherein 0–1 carbon atoms in the $C_{4-8}$ cycloalkyl is replaced by a group selected from the group —O—, —$S(O)_n$—, —$NR^{13a}$, —$NCO_2R^{14b}$, —$NCOR^{14b}$— and —$NSO_2R^{14b}$—;

$R^1$ is also substituted with 0–2 substituents independently selected at each occurrence from the group $R^{1a}$, $R^{1b}$, $C_{1-6}$ alkyl, $C_{2-6}$ alkenyl, $C_{2-8}$ alkynyl, Br, Cl, F, $CF_3$, $CF_2CF_3$, —$OR^{13a}$, —$NR^{13a}R^{16a}$, $C_{1-2}$ alkoxy-$C_{1-2}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is selected from the group phenyl and indanyl, each $R^{1a}$ being substituted with 0–1 —$OR^{17}$ and 0–5 substituents independently selected at each occurrence from the group $C_{1-4}$ alkyl, $C_{3-6}$ cycloalkyl, Br, Cl, F, $C_{1-4}$ haloalkyl, —CN, —$S(O)_nR^{18}$, —$COR^{17}$, —$NR^{17a}R^{19a}$, and —$CONR^{17a}R^{19a}$;

$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, $CF_3$, —CN, —$OR^{17}$, —$S(O)_nR^{18}$, —$COR^{17}$, —$NR^{17a}R^{19a}$, and —$CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

$R^3$ and $R^8$ are independently selected at each occurrence from the group H, Br, Cl, F, —CN, $C_{1-4}$ alkyl, $C_{3-6}$ cycloalkyl, $C_{1-4}$ alkoxy, $NH_2$, $C_{1-4}$ alkylamino, and $(C_{1-4}$ alkyl$)_2$-amino;

$R^9$ is independently selected at each occurrence from the group H, $C_{1-4}$ alkyl and $C_{3-8}$ cycloalkyl;

$R^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl $(C_{1-2}$ alkyl)—, and heteroaryl$(C_{1-2}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl $(C_{1-2}$ alkyl)—, and heteroaryl$(C_{1-2}$ alkyl)—;

$R^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

$R^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$, $R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, —$OR^{17}$, Br, Cl, F, $C_{1-4}$ haloalkyl, —CN, —$S(O)_nR^{18}$, —$COR^{17}$, —$CO_2R^{17}$, —$NR^{15}COR^{17}$, —$NR^{15}CO_2R^{18}$, —$NR^{17}R^{19}$, and —$CONR^{17}R^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —$OR^{17}$, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

[2b] In an even more preferred embodiment, the present invention provides a novel compound of formula Ia, wherein:

X is selected from the group O, S and a bond;

$R^1$ is substituted $C_{1-6}$ alkyl;

$R^1$ is substituted with 0–1 substituents selected from the group —CN, —$CO_2R^{13a}$, and $C_{3-8}$ cycloalkyl, wherein 0–1 carbon atoms in the $C_{4-8}$ cycloalkyl is replaced by a group selected from the group —O—, —$S(O)_n$—, and —$NR^{13a}$;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, —$OR^{13a}$, —$NR^{13a}R^{16a}$, $C_{1-2}$ alkoxy-$C_{1-2}$ alkyl, and $C_{3-6}$ cycloalkyl which is substituted with 0–1 $CH_3$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SQ_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2CH_3$, $CH(CH_3)_2$, and $CH_2CH_2CH_3$;

$R^3$ and $R^8$ are independently selected at each occurrence from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[2c] In a still more preferred embodiment, the present invention provides a novel compound of formula Ia, wherein:

$R^1$ is substituted $C_1$;

$R^1$ is substituted with 0–1 substituents selected from the group —CN, —$CO_2CH_3$, and —$CO_2CH_2CH_3$;

$R^1$ is also substituted with 0–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —$CH=CH_2$, —$CH=CH(CH_3)$, —$CH\equiv CH$, —$CH\equiv C(CH_3)$, —$CH_2CH_3$, —$CH_2CH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2CH_3$, and $CH(CH_3)_2$;

$R^3$ and $R^8$ are independently selected at each occurrence from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[2d] In a further preferred embodiment, the present invention provides a novel compound of formula Ia, wherein:

$R^1$ is substituted (cyclopropyl)—$C_1$ alkyl or (cyclobutyl)—$C_1$ alkyl;

$R^1$ is substituted with 0–1 —CN;

$R^1$ is also substituted with 0–1 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —$CH=CH_2$, —$CH=CH(CH_3)$, —$CH\equiv CH$, —$CH\equiv C(CH_3)$, —$CH_2OCH_3$, —$CH_2OH_2OCH_3$, F, $CF_3$, cyclopropyl, and $CH_3$-cyclopropyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$.

[2e] In another further preferred embodiment, the present invention provides a novel compound of formula Ia, wherein:

$R^1$ is (cyclopropyl)$C_1$ alkyl or (cyclobutyl)—$C_1$ alkyl substituted with 1 substituent independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —$CH=CH_2$, —$CH=CH(CH_3)$, —$CH\equiv CH$, —$CH\equiv C(CH_3)$, —$CH_2OCH_3$, —$CH_2CH_2OCH_3$, F, $CF_3$, cyclopropyl, and $CH_3$-cyclopropyl;

$R^{1a}$ is phenyl substituted with 0–2 substituents independently selected at each occurrence from the group $CH_3$, $CH_2CH_3$, Cl, F, and $CF_3$;

$R^{1b}$ is heteroaryl and is selected from the group furanyl, thienyl, and isoxazolyl, each heteroaryl being substituted on 0–2 carbon atoms with a substituent independently selected at each occurrence from the group $CH_3$, $OCH_3$, Cl, F, and $CF_3$.

[2f] In an even further preferred embodiment, the present invention provides a novel compound of formula Ia, wherein:

$R^1$ is selected from the group (cyclopropyl)CH—$CH_3$, (cyclopropyl)CH—$CH_2CH_3$, (cyclpropyl)CH—$CH_2OCH_3$, (cyclopropyl)CH—$CH_2CH_2CH_3$, (cycloppropyl)CH—$CH_2OCH_3$, (cyclopropyl)$_2$CH, phenyl(cyclopropyl)CH, furanyl(cyclopropyl)CH, thienyl(cyclopropyl)CH, isoxazolyl(cyclopropyl)CH, ($CH_3$-furanyl)(cyclopropyl)CH, (cyclobutyl)CH—$CH_3$, (cyclobutyl)CH—$CH_2CH_3$, (cyclobutyl)CH—$CH_2OCH_3$, (cyclobutyl)CH—$CH_2CH_2CH_3$, (cyclobutyl)CH—$CH_2CH_2OCH_3$, (cyclobutyl)$_2$CH, phenyl(cyclobutyl)CH, furanyl(cyclobutyl)CH, thienyl (cyclobutyl)CH, isoxazolyl(cyclobutyl)CH, and ($CH_3$-furanyl)(cyclobutyl)CH;

[2g] In another further preferred embodiment, the present invention provides a novel compound of formula Ia, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[2h] In another further preferred embodiment, the present invention provides a novel compound of formula Ia, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[2i] In another preferred embodiment, the present invention provides a novel compound of formula Ia, wherein the compound is selected from the group:

3-(1-cyclopropylpropyl)-7-(2,4-dichlorophenyl)-2-ethyl-3H-imidazo[4,5-b]pyridine;

3-(1-cyclopropylpropyl)-7-(2,4-dichlorophenyl)-2-methoxy-3H-imidazo[4,5-b]pyridine;

3-(1-cyclopropylpropyl)-7-(2,4-dichlorophenyl)-2-(methylsulfanyl)-3H-imidazo[4,5-b]pyridine;

7-[2-chloro-4-(trifluoromethyl)phenyl]-3-(1-cyclopropylpropyl)-2-ethyl-3H-imidazo[4,5-b]pyridine;

7-[2-chloro-4-(trifluoromethyl)phenyl]-3-(1-cyclopropylpropyl)-2-methoxy-3H-imidazo[4,5-b]pyridine;

7-[2-chloro-4-(trifluoromethyl)phenyl]-3-(1-cyclopropylpropyl)-2-(methylsulfanyl)-3H-imidazo[4,5-b]pyridine;

3-(1-cyclopropylpropyl)-2-ethyl-7-[2-methyl-4-(trifluoromethyl)phenyl]-3H-imidazo[4,5-b]pyridine;

7-(2-chloro-4-methoxyphenyl)-3-(1-cyclopropylpropyl)-2-ethyl-3H-imidazo[4,5-b]pyridine;

7-(2-chloro-4-methoxyphenyl)-3-(1-cyclopropylpropyl)-2-methoxy-3H-imidazo[4,5-b]pyridine;

3-(1-cyclopropylpropyl)-2-ethyl-7-(4-methoxy-2,5-dimethylphenyl)-3H-imidazo[4,5-b]pyridine;

3-(1-cyclopropylpropyl)-2-methoxy-7-(4-methoxy-2,5-dimethylphenyl)-3H-imidazo[4,5-b]pyridine;

7-(2-chloro-4-methoxyphenyl)-3-(1-cyclopropylpropyl)-2-ethyl-3H-imidazo[4,5-b]pyridine;

7-(2-chloro-4-methoxyphenyl)-3-(1-cyclopropylpropyl)-2-methoxy-3H-imidazo[4,5-b]pyridine;

7-(2-chloro-5-fluoro-4-methoxyphenyl)-3-(1-cyclopropylpropyl)-2-ethyl-3H-imidazo[4,5-b]pyridine;

7-(2-chloro-fluoro-4-methoxyphenyl)-3-(1-cyclopropylpropyl)-2-methoxy-3H-imidazo[4,5-b]pyridine;

7-(2-chloro-5-fluoro-4-methylphenyl)-3-(1-cyclopropylpropyl)-2-ethyl-3H-imidazo [4,5-b]pyridine;

7-(2-chloro-fluoro-4-methylphenyl)-3-(1-cyclopropylpropyl)-2-methoxy-3H-imidazo[4,5-b]pyridine;

3-(1-cyclopropylpropyl)-2-ethyl-7-(2,4,5-trimethylphenyl)-3H-imidazo[4,5-b]pyridine;

3-(1-cyclopropylpropyl)-2-methoxy-7-(2,4,5-trimethylphenyl)-3H-imidazo[4,5-b]pyridine;

3-(1-cyclopropylpropyl)-2-ethyl-7-(2,5,6-trimethyl-3-pyridinyl)-3H-imidazo[4,5-b]pyridine;

3-(1-cyclopropylpropyl)-2-methoxy-7-(2,5,6-trimethyl-3-pyridinyl)-3H-imidazo[4,5-b]pyridine;

3-(1-cyclopropylpropyl)-7-(2,6-dimethyl-3-pyridinyl)-2-ethyl-3H-imidazo[4,5-b]pyridine;

3-(1-cyclopropylpropyl)-7-(2,6-dimethyl-3-pyridinyl)-2-methoxy-3H-imidazo[4,5-b]pyridine;

3-(1-cyclopropylpropyl)-7-(2,6-dimethoxy-3-pyridinyl)-2-ethyl-3H-imidazo[4,5-b]pyridine;

7-(2,4-dichlorophenyl)-2-ethyl-3-(1-ethylpropyl)-3H-imidazo[4,5-b]pyridine;

7-(2,4-dichlorophenyl)-3-(1-ethylpropyl)-2-methoxy-3H-imidazo[4,5-b]pyridine;

7-[2-chloro-4-(trifluoromethyl)phenyl]-2-ethyl-3-(1-ethylpropyl)-3H-imidazo[4,5-b]pyridine;

7-[2-chloro-4-(trifluoromethyl)phenyl]-3-(1-ethylpropyl)-2-methoxy-3H-imidazo[4,5-b]pyridine;

7-[2-chloro-4-(methylsulfonyl)phenyl]-2-ethyl-3-(1-ethylpropyl)-3H-imidazo[4,5-b]pyridine;

7-[2-chloro-4-(methylsulfonyl)phenyl]-3-(1-ethylpropyl)-2-methoxy-3H-imidazo[4,5-b]pyridine;

2-ethyl-3-(1-ethylpropyl)-7-(4-methoxy-2,5-dimethylphenyl)-3H-imidazo[4,5-b]pyridine;

3-(1-ethylpropyl)-2-methoxy-7-(4-methoxy-2,5-dimethylphenyl)-3H-imidazo[4,5-b]pyridine;

7-(2-chloro-4-methoxyphenyl)-2-ethyl-3-(1-ethylpropyl)-3H-imidazo[4,5-b]pyridine;

7-(2-chloro-4-methoxyphenyl)-3-(1-ethylpropyl)-2-methoxy-3H-imidazo[4,5-b]pyridine;

2-ethyl-3-(1-ethylpropyl)-7-[4-methoxy-2-(trifluoromethyl)phenyl]-3H-imidazo[4,5-b]pyridine;

3-(1-ethylpropyl)-2-methoxy-7-[4-methoxy-2-(trifluoromethyl)phenyl]-3H-imidazo[4,5-b]pyridine;

7-(2,6-dimethoxy-3-pyridinyl)-2-ethyl-3-(1-ethylpropyl)-3H-imidazo[4,5-b]pyridine; 7-(2,6-dimethyl-3-pyridinyl)-2-ethyl-3-(1-ethylpropyl)-3H-imidazo[4,5-b]pyridine;

2-ethyl-3-(1-ethylpropyl)-7-(2,5,6-trimethyl-3-pyridinyl)-3H-imidazo[4,5-b]pyridine;

2-ethyl-3-(1-ethylpropyl)-7-(5-fluoro-4-methoxy-2-methylphenyl)-3H-imidazo[4,5-b]pyridine;

3-(1-ethylpropyl)-7-(5-fluoro-4-methoxy-2-methylphenyl)-2-methoxy-3H-imidazo[4,5-b]pyridine;

3-chloro-4-[2-ethyl-3-(1-ethylpropyl)-3H-imidazo[4,5-b]pyridin-7-yl]benzonitrile;

3-chloro-4-[3-(1-ethylpropyl)-2-methoxy-3H-imidazo[4,5-b]pyridin-7-yl]benzonitrile;

1-{3-chloro-4-[2-ethyl-3-(1-ethylpropyl)-3H-imidazo[4,5-b]pyridin-7-yl]phenyl}-1-ethanone;

1-{3-chloro-4-[3-(1-ethylpropyl)-2-methoxy-3H-imidazo[4,5-b]pyridin-7-yl]phenyl}-1-ethanone;

3-(dicyclopropylmethyl)-2-ethyl-7-(5-fluoro-4-methoxy-2-methylphenyl)-3H-imidazo[4,5-b]pyridine;

3-(dicyclopropylmethyl)-7-(5-fluoro-4-methoxy-2-methylphenyl)-2-methoxy-3H-imidazo[4,5-b]pyridine;

7-(2-chloro-4-methoxyphenyl)-3-(dicyclopropylmethyl)-2-ethyl-3H-imidazo[4,5-b]pyridine;

7-(2-chloro-4-methoxyphenyl)-3-(dicyclopropylmethyl)-2-methoxy-3H-imidazo[4,5-b]pyridine;

7-(2,4-dichlorophenyl)-3-(dicyclopropylmethyl)-2-ethyl-3H-imidazo[4,5-b]pyridine;

7-(2,4-dichlorophenyl)-3-(dicyclopropylmethyl)-2-methoxy-3H-imidazo[4,5-b]pyridine;

7-[2-chloro-4-(trifluoromethyl)phenyl]-3-(dicyclopropylmethyl)-2-ethyl-3H-imidazo[4,5-b]pyridine;

7-[2-chloro-4-(trifluoromethyl)phenyl]-3-(dicyclopropylmethyl)-2-methoxy-3H-imidazo[4,5-b]pyridine;

7-(2,4-dichlorophenyl)-2-ethyl-3-(1-ethyl-3-methoxypropyl)-3H-imidazo[4,5-b]pyridine;

7-(2,4-dichlorophenyl)-3-(1-ethyl-3-methoxypropyl)-2-methoxy-3H-imidazo[4,5-b]pyridine;

7-[2-chloro-4-(trifluoromethyl)phenyl]-2-ethyl-3-(1-ethyl-3-methoxypropyl)-3H-imidazo[4,5-b]pyridine;

7-[2-chloro-4-(trifluoromethyl)phenyl]-3-(1-ethyl-3-methoxypropyl)-2-methoxy-3H-imidazo[4,5-b]pyridine;

7-(2-chloro-4-methoxyphenyl)-2-ethyl-3-(1-ethyl-3-methoxypropyl)-3H-imidazo[4,5-b]pyridine;

7-(2-chloro-4-methoxyphenyl)-3-(1-ethyl-3-methoxypropyl)-2-methoxy-3H-imidazo[4,5-b]pyridine;

7-(2-chloro-5-fluoro-4-methoxyphenyl)-2-ethyl-3-(1-ethyl-3-methoxypropyl)-3H-imidazo[4,5-b]pyridine;

7-(2-chloro-5-fluoro-4-methoxyphenyl)-3-(1-ethyl-3-methoxypropyl)-2-methoxy-3H-imidazo[4,5-b]pyridine;

2-ethyl-3-(1-ethyl-3-methoxypropyl)-7-(4-methoxy-2,5-dimethylphenyl)-3H-imidazo[4,5-b]pyridine;

3-(1-ethyl-3-methoxypropyl)-2-methoxy-7-(4-methoxy-2,5-dimethylphenyl)-3H-imidazo[4,5-b]pyridine;

2-ethyl-3-(1-ethyl-3-methoxypropyl)-7-(5-fluoro-4-methoxy-2-methylphenyl)-3H-imidazo[4,5-b]pyridine;

3-(1-ethyl-3-methoxypropyl)-7-(5-fluoro-4-methoxy-2-methylphenyl)-2-methoxy-3H-imidazo[4,5-b]pyridine;

7-(2-chloro-5-fluoro-4-methylphenyl)-2-ethyl-3-(1-ethyl-3-methoxypropyl)-3H-imidazo[4,5-b]pyridine;

7-(2-chloro-5-fluoro-4-methylphenyl)-3-(1-ethyl-3-methoxypropyl)-2-methoxy-3H-imidazo[4,5-b]pyridine;

7-[2-chloro-4-(methylsulfonyl)phenyl]-2-ethyl-3-(1-ethyl-3-methoxypropyl)-3H-imidazo[4,5-b]pyridine;

7-[2-chloro-4-(methylsulfonyl)phenyl]-3-(1-ethyl-3-methoxypropyl)-2-methoxy-3H-imidazo[4,5-b]pyridine;

1-{3-chloro-4-[2-ethyl-3-(1-ethyl-3-methoxypropyl)-3H-imidazo[4,5-b]pyridin-7-yl]phenyl}-1-ethanone;

1-{3-chloro-4-[3-(1-ethyl-3-methoxypropyl)-2-methoxy-3H-imidazo[4,5-b]pyridin-7-yl]phenyl}-1-ethanone;

1-{5-[2-ethyl-3-(1-ethyl-3-methoxypropyl)-1H-imidazo[4,5-b]pyridin-7-yl]-6-methyl-2-pyridinyl}-1-ethanone;

1-{5-[3-(1-ethyl-3-methoxypropyl)-2-methoxy-3H-imidazo[4,5-b]pyridin-7-yl]-6-methyl-2-pyridinyl}-1-ethanone;

2-ethyl-3-(1-ethyl-3-methoxypropyl)-7-(6-methoxy-2-methyl-3-pyridinyl)-3H-imidazo[4,5-b]pyridine;

3-(1-ethyl-3-methoxypropyl)-2-methoxy-7-(6-methoxy-2-methyl-3-pyridinyl)-3H-imidazo[4,5-b]pyridine;

7-(2,6-dimethoxy-3-pyridinyl)-2-ethyl-3-(1-ethyl-3-methoxypropyl)-3H-imidazo[4,5-b]pyridine;

7-(2,6-dimethoxy-3-pyridinyl)-3-(1-ethyl-3-methoxypropyl)-2-methoxy-3H-imidazo[4,5-b]pyridine;

7-(2,6-dimethyl-3-pyridinyl)-2-ethyl-3-(1-ethyl-3-methoxypropyl)-3H-imidazo[4,5-b]pyridine;

7-(2,6-dimethyl-3-pyridinyl)-3-(1-ethyl-3-methoxypropyl)-2-methoxy-3H-imidazo[4,5-b]pyridine;

2-ethyl-3-(1-ethyl-3-methoxypropyl)-7-(2,5,6-trimethyl-3-pyridinyl)-3H-imidazo[4,5-b]pyridine;

3-(1-ethyl-3-methoxypropyl)-2-methoxy-7-(2,5,6-trimethyl-3-pyridinyl)-3H-imidazo[4,5-b]pyridine;

7-(2,4-dichlorophenyl)-2-ethyl-3-[1-(methoxymethyl)propyl]-3H-imidazo[4,5-b]pyridine;

7-(2,4-dichlorophenyl)-2-methoxy-3-[1-(methoxymethyl)propyl]-3H-imidazo[4,5-b]pyridine;

7-[2-chloro-4-(trifluoromethyl)phenyl]-2-ethyl-3-[1-(methoxymethyl)propyl]-3H-imidazo[4,5-b]pyridine;

7-[2-chloro-4-(trifluoromethyl)phenyl]-2-methoxy-3-[1-(methoxymethyl)propyl]-3H-imidazo[4,5-b]pyridine;

7-(2-chloro-5-fluoro-4-methylphenyl)-2-ethyl-3-[1-(methoxymethyl)propyl]-3H-imidazo[4,5-b]pyridine;

7-(2-chloro-5-fluoro-4-methylphenyl)-2-methoxy-3-[1-(methoxymethyl)propyl]-3H-imidazo[4,5-b]pyridine;

2-ethyl-7-(4-methoxy-2,5-dimethylphenyl)-3-[1-(methoxymethyl)propyl]-3H-imidazo[4,5-b]pyridine;

2-methoxy-7-(4-methoxy-2,5-dimethylphenyl)-3-[1-(methoxymethyl)propyl]-3H-imidazo[4,5-b]pyridine;

2-ethyl-7-(5-fluoro-4-methoxy-2-methylphenyl)-3-[1-(methoxymethyl)propyl]-3H-imidazo[4,5-b]pyridine;

7-(5-fluoro-4-methoxy-2-methylphenyl)-2-methoxy-3-[1-(methoxymethyl)propyl]-3H-imidazo[4,5-b]pyridine;

2-ethyl-3-[1-(methoxymethyl)propyl]-7-(6-methoxy-2-methyl-3-pyridinyl)-3H-imidazo[4,5-b]pyridine;

2-methoxy-3-[1-(methoxymethyl)propyl]-7-(6-methoxy-2-methyl-3-pyridinyl)-3H-imidazo[4,5-b]pyridine;

7-(2,6-dimethoxy-3-pyridinyl)-2-ethyl-3-[1-(methoxymethyl)propyl]-3H-imidazo[4,5-b]pyridine;

7-(2,6-dimethoxy-3-pyridinyl)-2-methoxy-3-[1-(methoxymethyl)propyl]-3H-imidazo[4,5-b]pyridine;

7-(2,6-dimethyl-3-pyridinyl)-2-ethyl-3-[1-(methoxymethyl)propyl]-3H-imidazo[4,5-b]pyridine;

7-(2,6-dimethyl-3-pyridinyl)-2-methoxy-3-[1-(methoxymethyl)propyl]-3H-imidazo[4,5-b]pyridine;

2-ethyl-3-[1-(methoxymethyl)propyl]-7-(2,5,6-trimethyl-3-pyridinyl)-3H-imidazo[4,5-b]pyridine;

2-methoxy-3-[1-(methoxymethyl)propyl]-7-(2,5,6-trimethyl-3-pyridinyl)-3H-imidazo[4,5-b]pyridine;

7-[2-chloro-4-(methylsulfonyl)phenyl]-2-ethyl-3-[1-(methoxymethyl)propyl]-3H-imidazo[4,5-b]pyridine; and 7-[2-chloro-4-(methylsulfonyl)phenyl]-2-methoxy-3-[1-(methoxymethyl)propyl]-3H-imidazo[4,5-b]pyridine;

or a pharmaceutically acceptable salt form thereof.

[2j] In another more preferred embodiment, the present invention provides a novel compound of formula Ia, wherein:

$R^1$ is $C_{3-8}$ cycloalkyl;

$R^1$ is substituted with 0–1 substituents selected from the group —CN, —S(O)$_n$R$^{14b}$, —COR$^{13a}$, —CO$_2$R$^{13a}$, —NR$^{15a}$COR$^{13a}$, —N(COR$^{13a}$)$_2$, —NR$^{15a}$CONR$^{13a}$R$^{16a}$, —NR$^{15a}$CO$_2$R$^{14b}$, —CONR$^{13a}$R$^{16a}$, 1-morpholinyl, 1-piperidinyl, 1-piperazinyl, and $C_{4-8}$ cycloalkyl, wherein 0–1 carbon atoms in the $C_{4-8}$ cycloalkyl is replaced by a group selected from the group —O—, —S(O)$_n$—, —NR$^{13a}$—, —NCO$_2$R$^{14b}$—, —NCOR$^{14b}$— and —NSO$_2$R$^{14b}$—, and wherein $N_4$ in 1-piperazinyl is substituted with 0–1 substituents selected from the group R$^{13a}$, CO$_2$R$^{14b}$, COR$^{14b}$ and SO$_2$R$^{14b}$; and, $R^1$ is also substituted with 0–3 substituents independently selected at each occurrence from the group R$^{1a}$, R$^{1b}$, R$^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, $C_{1-2}$ alkoxy-$C_{1-2}$ alkyl, and —NR$^{13a}$R$^{16a}$.

[2k] In another even more preferred embodiment, the present invention provides a novel compound of formula Ia, wherein:

X is selected from the group O, S(O)$_n$ and a bond;

n is 0, 1 or 2;

$R^1$ is selected from the group cyclopropyl, cyclobutyl, and cyclopentyl;

$R^1$ is substituted with 0–1 substituents selected from the group —CN, —S(O)$_n$R$^{14b}$, —COR$^{13a}$, —CO$_2$R$^{13a}$, and C$_{4-8}$ cycloalkyl, wherein one carbon atom in the C$_{4-8}$ cycloalkyl is replaced by a group selected from the group —O—, —S(O)$_n$—, —NR$^{13a}$—, —NCO$_2$R$^{14b}$—, —NOR$^{14b}$— and —NSO$_2$R$^{14b}$—;

$R^1$ is also substituted with 0–2 substituents independently selected at each occurrence from the group R$^{1a}$, R$^{1b}$, C$_{1-6}$ alkyl, C$_{2-8}$ alkenyl, C$_{2-8}$ alkynyl, Br, Cl, F, CF$_3$, CF$_2$CF$_3$, —OR$^{13a}$, C$_{1-2}$ alkoxy-C$_{1-2}$ alkyl, and —NR$^{13a}$R$^{16a}$;

$R^{1a}$ is aryl and is selected from the group phenyl and indanyl, each R$^{1a}$ being substituted with 0–1 —OR$^{17}$ and 0–5 substituents independently selected at each occurrence from the group C$_{1-4}$ alkyl, C$_{3-6}$ cycloalkyl, Br, Cl, F, C$_{1-4}$ haloalkyl, —CN, —S(O)$_n$R$^{18}$, —COR$^{17}$, —NR$^{17a}$R$^{19a}$, and —CONR$^{17a}$R$^{19a}$;

$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group C$_{1-4}$ alkyl, C$_{3-6}$ cycloalkyl, Br, Cl, F, CF$_3$, —CN, —OR$^{17}$, —S(O)$_m$R$^{18}$, —COR$^{17}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$;

$R^2$ is selected from the group C$_{1-4}$ alkyl, C$_{2-4}$ alkenyl, and C$_{2-4}$ alkynyl and is substituted with 0–1 substituents selected from the group —CN, OH, Cl, F, and C$_{1-4}$ alkoxy;

$R^9$ is independently selected at each occurrence from the group H, C$_{1-4}$ alkyl and C$_{3-8}$ cycloalkyl;

$R^3$ and $R^8$ are independently selected at each occurrence from the group H, Br, Cl, F, —CN, C$_{1-4}$ alkyl, C$_{3-6}$ cycloalkyl, C$_{1-4}$ alkoxy, NH$_2$, C$_{1-4}$ alkylamino, and (C$_{1-4}$ alkyl)$_2$-amino;

$R^{13}$ is selected from the group C$_{1-4}$ alkyl, C$_{1-2}$ haloalkyl, C$_{1-2}$ alkoxy-C$_{1-2}$ alkyl, C$_{3-6}$ cycloalkyl-C$_{1-2}$ alkyl, aryl (C$_{1-2}$ alkyl)—, and heteroaryl(C$_{1-2}$ alkyl)—;

$R^{13a}$ and $R^{16a}$ are independently selected at each occurrence from the group H, C$_{1-4}$ alkyl, C$_{1-4}$ haloalkyl, C$_{1-4}$ alkoxy-C$_{1-4}$ alkyl, C$_{3-6}$ cycloalkyl, and C$_{3-6}$ cycloalkyl-C$_{1-6}$ alkyl;

$R^{14}$ is selected from the group C$_{1-4}$ alkyl, C$_{1-2}$ haloalkyl, C$_{1-2}$ alkoxy-C$_{1-2}$ alkyl, C$_{3-6}$ cycloalkyl-C$_{1-2}$ alkyl, aryl (C$_{1-2}$ alkyl)—, and heteroaryl(C$_{1-2}$ alkyl)—;

$R^{14a}$ is selected from the group C$_{1-4}$ alkyl, C$_{1-2}$ haloalkyl, C$_{1-2}$ alkoxy-C$_{1-2}$ alkyl, and C$_{3-6}$ cycloalkyl-C$_{1-2}$ alkyl;

$R^{14b}$ is selected from the group C$_{1-4}$ alkyl, C$_{1-2}$ haloalkyl, C$_{1-2}$ alkoxy-C$_{1-2}$ alkyl, C$_{3-6}$ cycloalkyl, and C$_{3-6}$ cycloalkyl-C$_{1-2}$ alkyl;

$R^{15}$ is independently selected at each occurrence from the group H, C$_{1-4}$ alkyl, C$_{3-7}$ cycloalkyl, C$_{3-6}$ cycloalkyl-C$_{1-6}$ alkyl, phenyl and benzyl, each phenyl or benzyl being substituted on the aryl moiety with 0–3 groups chosen from the group C$_{1-4}$ alkyl, Br, Cl, F, C$_{1-4}$ haloalkyl, C$_{1-4}$ alkoxy, C$_{1-4}$ haloalkoxy, and dimethylamino;

$R^{15a}$ is independently selected at each occurrence from the group H, C$_{1-4}$ alkyl, C$_{3-7}$ cycloalkyl, and C$_{3-6}$ cycloalkyl-C$_{1-6}$ alkyl;

$R^{17}$, $R^{18}$ and $R^{19}$ are independently selected at each occurrence from the group H, C$_{1-6}$ alkyl, C$_{3-10}$ cycloalkyl, C$_{3-6}$ cycloalkyl-C$_{1-6}$ alkyl, C$_{1-2}$ alkoxy-C$_{1-2}$ alkyl, and C$_{1-4}$ haloalkyl;

alternatively, in an NR$^{17}$R$^{19}$ moiety, R$^{17}$ and R$^{19}$ taken together form 1-pyrrolidinyl, 1-morpholinyl, 1-piperidinyl or 1-piperazinyl, wherein N$_4$ in 1-piperazinyl is substituted with 0–1 substituents selected from the group R$^{13}$, CO$_2$R$^{14}$, COR$^{14}$ and SO$_2$R$^{14}$;

$R^{17a}$ and $R^{19a}$ are independently selected at each occurrence from the group H, C$_{1-6}$ alkyl, C$_{3-10}$ cycloalkyl, C$_{3-6}$ cycloalkyl-C$_{1-6}$ alkyl and C$_{1-4}$ haloalkyl;

aryl is phenyl substituted with 1–4 substituents independently selected at each occurrence from the group C$_{1-4}$ alkyl, C$_{3-6}$ cycloalkyl, —OR$^{17}$, Br, Cl, F, C$_{1-4}$ haloalkyl, —CN, —S(O)$_n$R$^{18}$, —COR$^{17}$, —CO$_2$R$^{17}$, —NR$^{15}$COR$^{17}$, —NR$^{15}$CO$_2$R$^{16}$, —NR$^{17}$R$^{19}$, and —CONR$^{17}$R$^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group C$_{1-6}$ alkyl, C$_{3-6}$ cycloalkyl, Br, Cl, F, C$_{1-4}$ haloalkyl, —CN, —OR$^{17}$, —S(O)$_m$R$^{18}$, —COR$^{17}$, —CO$_2$R$^{17}$, —OC(O)R$^{18}$, —NR$^{15}$COR$^{17}$, —N(COR$^{17}$)$_2$, —NR$^{15}$CO$_2$R$^{18}$, —NR$^{17}$R$^{19}$, and —CONR$^{17}$R$^{19}$ and each heteroaryl being substituted on any nitrogen atom with 0–1 substituents selected from the group R$^{15}$, CO$_2$R$^{14a}$, COR$^{14a}$ and SO$_2$R$^{14a}$.

[21] In another still more preferred embodiment, the present invention provides a novel compound of formula Ia, wherein:

X is selected from the group O, S and a bond;

$R^1$ is substituted with 0–1 substituents selected from the group —CN, —CO$_2$R$^{13a}$, and C$_{4-8}$ cycloalkyl, wherein 0–1 carbon atoms in the C$_{4-8}$ cycloalkyl is replaced by a group selected from the group —O—, —S(O)$_n$—, and —NR$^{13a}$—;

$R^1$ is also substituted with 0–2 substituents independently selected at each occurrence from the group R$^{1a}$, R$^{1b}$, C$_{1-6}$ alkyl, C$_{2-8}$ alkenyl, C$_{2-8}$ alkynyl, Br, Cl, F, CF$_3$, CF$_3$, —OR$^{13a}$, —OH, —OCH$_3$, —OCH$_2$CH$_3$, —CH$_2$OCH$_3$, CH$_2$CH$_2$OCH$_3$, and NR$^{13a}$R$^{16a}$;

$R^{1a}$ is aryl and is phenyl substituted with 0–1 substituents selected from OCH$_3$, OCH$_2$CH$_3$, OCH(CH$_3$)$_2$, OCH$_2$CH$_2$CH$_3$, and OCF$_3$, and 0–3 substituents independently selected at each occurrence from the group CH$_3$, CH$_2$CH$_3$, CH(CH$_3$)$_2$, CH$_2$CH$_2$CH$_3$, cyclopropyl, Br, Cl, F, CF$_3$, —CN, SCH$_3$, —NH$_2$, —NHCH$_3$, —N(CH$_3$)$_2$, —C(O)NH$_2$, —C(O)NHCH$_3$, and —C(O) N(CH$_3$)$_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group CH$_3$, CH$_2$CH$_3$, CH(CH$_3$)$_2$, CH$_2$CH$_2$CH$_3$, cyclopropyl, OCH$_3$, OCH$_2$CH$_3$, OCH (CH$_3$)$_2$, OCH$_2$CH$_2$CH$_3$, OCF$_3$, Br, Cl, F, CF$_3$, —CN, $SCH_3$, $-NH_2$, $-NHCH_3$, $-N(CH_3)_2$, $-C(O)NH_2$, $-C(O)NHCH_3$, and $-C(O)N(CH_3)_2$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, $CH(CH_3)_2$, and $CH_2CH_2CH_3$;

$R^3$ and $R^8$ are independently selected at each occurrence from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, $-CN$, $SCH_3$, $SO_2CH_3$, $-NH_2$, $-NHCH_3$, $-N(CH_3)_2$, $-C(O)NH_2$, $-C(O)NHCH_3$, and $-C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, $-CN$, $SCH_3$, $SO_2CH_3$, $-NH_2$, $-NHCH_3$, $-N(CH_3)_2$, $-C(O)NH_2$, $-C(O)NHCH_3$, and $-C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[2m] In another further preferred embodiment, the present invention provides a novel compound of formula Ia, wherein:

$R^1$ is substituted with 0–2 substituents independently selected at each occurrence from the group $R^{1a}$, $R^{1b}$, $CH_3$, $CH_2CH_3$, $CH(CH_3)_2$, $CH_2CH_2CH_3$, $-(CH_2)_3CH_3$, $-CH=CH_2$, $CH=CH(CH_3)$, $-CH\equiv CH$, $-CH\equiv-C(CH_3)$, $-CH_2OCH_3$, $-CH_2CH_2OCH_3$, F, and $CF_3$;

$R^{1a}$ is phenyl substituted with 0–1 substituents selected from $OCH_3$, $OCH_2CH_3$, $OCH(CH_3)_2$, $OCH_2CH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, $-CN$, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, $-CN$, and $SCH_3$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, and $CH(CH_3)_2$;

$R^3$ and $R^8$ are independently selected at each occurrence from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, $-CN$, $SCH_3$, $SO_2CH_3$, $-NH_2$, $-NHCH_3$, $-N(CH_3)_2$, $-C(O)NH_2$, $-C(O)NHCH_3$, and $-C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, $-CN$, $SCH_3$, $SO_2CH_3$, $-NH_2$, $-NHCH_3$, $-N(CH_3)_2$, $-C(O)NH_2$, $-C(O)NHCH_3$, and $-C(O)N(CH_3)_2$.

[2n] In another even further preferred embodiment, the present invention provides a novel compound of formula Ia, wherein:

$R^1$ is substituted with 0–2 substituents independently selected at each occurrence from the group $R^{1a}$, $CH_3$, $CH_2CH_3$, $CH(CH_3)_2$, $CH_2CH_2CH_3$, $-(CH_2)_3CH_3$, $-CH_2OCH_3$, $-CH_2CH_2OCH_3$, F, and $CF_3$; and, $R^{1a}$ is phenyl substituted with 0–2 substituents independently selected at each occurrence from the group $CH_3$, $CH_2CH_3$, $CH(CH_3)_2$, $CH_2CH_2CH_3$, Br, Cl, F, $CF_3$, $-CN$, and $SCH_3$.

[2o] In a still further preferred embodiment, the present invention provides a novel compound of formula Ia, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[2p] In another still further preferred embodiment, the present invention provides a novel compound of formula Ia, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[2q] In another more preferred embodiment, the present invention provides a novel compound of formula Ia, wherein:

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl and $C_{1-4}$ alkoxy-$C_{1-4}$ alkyl;

$R^1$ is substituted with a $C_{3-8}$ cycloalkyl group, wherein 0–1 carbon atoms in the $C_{4-8}$ cycloalkyl group is replaced by a group selected from the group $-O-$, $-S(O)_n-$, $-NR^{13a}-$, $-NCO_2R^{14b}-$, $-NCOR^{14b}-$ and $-NSO_2R^{14b}-$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, $-OR^{13a}$, $-NR^{13a}R^{16a}$, $C_{1-2}$ alkoxy-$C_{1-2}$ alkyl, and $C_{3-8}$ cycloalkyl which is substituted with 0–1 $R^9$ and in which 0–1 carbons of $C_{4-8}$ cycloalkyl is replaced by $-O-$;

provided that $R^1$ is other than a cyclohexyl-$(CH_2)_2-$ group;

$R^{1a}$ is aryl and is selected from the group phenyl, naphthyl, indanyl and indenyl, each $R^{1a}$ being substituted with 0–1 $-OR^{17}$ and 0–5 substituents independently selected at each occurrence from the group $C_{1-6}$ alkyl, $C_{3-6}$ cycloalkyl, Br, Cl, F, I, $C_{1-4}$ haloalkyl, $-CN$, nitro, SH, $-S(O)_nR^{18}$, $-COR^{17}$, $-OC(O)R^{18}$, $-NR^{15a}COR^{17}$, $-N(COR^{17})_2-$, —NR$^{15a}$CONR$^{17a}$R$^{19a}$, —NR$^{15a}$CO$_2$R$^{18}$, —NR$^{17a}$R$^{19a}$, and —CONR$^{17a}$R$^{19a}$;

R$^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group C$_{1-6}$ alkyl, C$_{3-6}$ cycloalkyl, Br, Cl, F, I, C$_{1-4}$ haloalkyl, —CN, nitro, —OR$^{17}$, SH, —S(O)$_m$R$^{18}$, —COR$^{17}$, —OC(O)R$^{18}$, —NR$^{15a}$COR$^{17}$, —N(COR$^{17}$)$_2$, —NR$^{15a}$CONR$^{17a}$R$^{19a}$, —NR$^{15a}$CO$_2$R$^{18}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$; and, R$^{1c}$ is heterocyclyl and is a saturated or partially saturated heteroaryl, each heterocyclyl being substituted on 0–4 carbon atoms with a substituent independently selected at each occurrence from the group C$_{1-6}$ alkyl, C$_{3-6}$ cycloalkyl, Br, Cl, F, I, C$_{1-4}$ haloalkyl, —CN, nitro, —OR$^{13a}$, SH, —S(O)$_n$R$^{14b}$, —COR$^{13a}$, —OC(O)R$^{14b}$, —NR$^{15a}$COR$^{13a}$, —N(COR$^{13a}$)$_2$, —NR$^{15a}$CONR$^{13a}$R$^{16a}$, —NR$^{15a}$CO$_2$R$^{14b}$, —NR$^{13a}$R$^{16a}$, and —CONR$^{13a}$R$^{16a}$ and each heterocyclyl being substituted on any nitrogen atom with 0–1 substituents selected from the group R$^{13a}$, CO$_2$R$^{14b}$, COR$^{14b}$ and SO$_2$R$^{14b}$ and wherein any sulfur atom is optionally monooxidized or dioxidized.

[2r] In another even more preferred embodiment, the present invention provides a novel compound of formula Ia, wherein:

X is selected from the group O, S(O)$_n$ and a bond;

n is 0, 1 or 2;

R$^1$ is selected from the group C$_{1-6}$ alkyl, C$_{2-6}$ alkenyl, C$_{2-6}$ alkynyl, and C$_{3-8}$ cycloalkyl;

R$^1$ is substituted with a C$_{3-6}$ cycloalkyl group, wherein 0–1 carbon atoms in the C$_{4-6}$ cycloalkyl group is replaced by a group selected from the group —O—, —S(O)$_n$—, and —NR$^{13a}$—;

R$^1$ is also substituted with 0–2 substituents independently selected at each occurrence from the group R$^{1a}$, R$^{1b}$, C$_{1-6}$ alkyl, C$_{2-8}$ alkenyl, C$_{2-8}$ alkynyl, Br, Cl, F, CF$_3$, CF$_2$CF$_3$, —OR$^{13a}$, —NR$^{13a}$R$^{16a}$, C$_{1-2}$ alkoxy-C$_{1-2}$ alkyl, and C$_{3-6}$ cycloalkyl which is substituted with 0–1 R$^9$ and in which 0–1 carbons of C$_{4-8}$ cycloalkyl is replaced by —O—;

R$^{1a}$ is aryl and is selected from the group phenyl and indanyl, each R$^{1a}$ being substituted with 0–1 —OR$^{17}$ and 0–5 substituents independently selected at each occurrence from the group C$_{1-4}$ alkyl, C$_{3-6}$ cycloalkyl, Br, Cl, F, C$_{1-4}$ haloalkyl, —CN, —S(O)$_n$R$^{18}$, —COR$^{17}$, —NR$^{17a}$R$^{19a}$, and —CONR$^{17a}$R$^{19a}$;

R$^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group C$_{1-4}$ alkyl, C$_{3-6}$ cycloalkyl, Br, Cl, F, CF$_3$, —CN, —OR$^{17}$, —S(O)$_m$R$^{18}$, —COR$^{17}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$;

R$^2$ is selected from the group C$_{1-4}$ alkyl, C$_{2-4}$ alkenyl, and C$_{2-4}$ alkynyl and is substituted with 0–1 substituents selected from the group —CN, OH, Cl, F, and C$_{1-4}$ alkoxy;

R$^9$ is independently selected at each occurrence from the group H, C$_{1-4}$ alkyl and C$_{3-8}$ cycloalkyl;

R$^3$ and R$^8$ are independently selected at each occurrence from the group H, Br, Cl, F, —CN, C$_{1-4}$ alkyl, C$_{3-6}$ cycloalkyl, C$_{1-4}$ alkoxy, NH$_2$, C$_{1-4}$ alkylamino, and (C$_{1-4}$ alkyl)$_2$-amino;

R$^{13}$ is selected from the group C$_{1-4}$ alkyl, C$_{1-2}$ haloalkyl, C$_{1-2}$ alkoxy-C$_{1-2}$ alkyl, C$_{3-6}$ cycloalkyl-C$_{1-2}$ alkyl, aryl (C$_{1-2}$ alkyl)—, and heteroaryl(C$_{1-2}$ alkyl)—;

R$^{13a}$ and R$^{16a}$ are independently selected at each occurrence from the group H, C$_{1-4}$ alkyl, C$_{1-4}$ haloalkyl, C$_{1-4}$ alkoxy-C$_{1-4}$ alkyl, C$_{3-6}$ cycloalkyl, and C$_{3-6}$ cycloalkyl-C$_{1-6}$ alkyl;

R$^{14}$ is selected from the group C$_{1-4}$ alkyl, C$_{1-2}$ haloalkyl, C$_{1-2}$ alkoxy-C$_{1-2}$ alkyl, C$_{3-6}$ cycloalkyl-C$_{1-2}$ alkyl, aryl (C$_{1-2}$ alkyl)—, and heteroaryl(C$_{1-2}$ alkyl)—;

R$^{14a}$ is selected from the group C$_{1-4}$ alkyl, C$_{1-2}$ haloalkyl, C$_{1-2}$ alkoxy-C$_{1-2}$ alkyl, and C$_{3-6}$ cycloalkyl-C$_{1-2}$ alkyl;

R$^{14b}$ is selected from the group C$_{1-4}$ alkyl, C$_{1-2}$ haloalkyl, C$_{1-2}$ alkoxy-C$_{1-2}$ alkyl, C$_{3-6}$ cycloalkyl, and C$_{3-6}$ cycloalkyl-C$_{1-2}$ alkyl;

R$^{15}$ is independently selected at each occurrence from the group H, C$_{1-4}$ alkyl, C$_{3-7}$ cycloalkyl, C$_{3-6}$ cycloalkyl-C$_{1-6}$ alkyl, phenyl and benzyl, each phenyl or benzyl being substituted on the aryl moiety with 0–3 groups chosen from the group C$_{1-4}$ alkyl, Br, Cl, F, C$_{1-4}$ haloalkyl, C$_{1-4}$ alkoxy, C$_{1-4}$ haloalkoxy, and dimethylamino;

R$^{15a}$ is independently selected at each occurrence from the group H, C$_{1-4}$ alkyl, C$_{3-7}$ cycloalkyl, and C$_{3-6}$ cycloalkyl-C$_{1-6}$ alkyl;

R$^{17}$, R$^{18}$ and R$^{19}$ are independently selected at each occurrence from the group H, C$_{1-6}$ alkyl, C$_{3-10}$ cycloalkyl, C$_{3-6}$ cycloalkyl-C$_{1-6}$ alkyl, C$_{1-2}$ alkoxy-C$_{1-2}$ alkyl, and C$_{1-4}$ haloalkyl;

alternatively, in an NR$^{17}$R$^{19}$ moiety, R$^{17}$ and R$^{19}$ taken together form 1-pyrrolidinyl, 1-morpholinyl, 1-piperidinyl or 1-piperazinyl, wherein N$_4$ in 1-piperazinyl is substituted with 0–1 substituents selected from the group R$^{13}$, CO$_2$R$^{14}$, COR$^{14}$ and SO$_2$R$^{14}$;

R$^{17a}$ and R$^{19a}$ are independently selected at each occurrence from the group H, C$_{1-6}$ alkyl, C$_{3-10}$ cycloalkyl, C$_{3-6}$ cycloalkyl-C$_{1-6}$ alkyl and C$_{1-4}$ haloalkyl;

aryl is phenyl substituted with 1–4 substituents independently selected at each occurrence from the group C$_{1-4}$ alkyl, C$_{3-6}$ cycloalkyl, —OR$^{17}$, Br, Cl, F, C$_{1-4}$ haloalkyl, —CN, —S(O)$_n$R$^{18}$, —COR$^{17}$, —CO$_2$R$^{17}$, —NR$^{15}$COR$^{17}$, —NR$^{15}$CO$_2$R$^{18}$, —NR$^{17}$R$^{19}$, and —CONR$^{17}$R$^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —$OR^{17}$, —$S(O)_m R^{18}$, —$COR^{17}$, —$CO_2 R^{17}$, —$OC(O)R^{18}$, —$NR^{15}COR^{17}$, —$N(COR^{17})_2$, —$NR^{15}CO_2 R^{18}$, —$NR^{17}R^{19}$, and —$CONR^{17}R^{19}$ and each heteroaryl being substituted on any nitrogen atom with 0–1 substituents selected from the group $R^{15}$, $CO_2 R^{14a}$, $COR^{14a}$ and $SO_2 R^{14a}$.

[2s] In another still more preferred embodiment, the present invention provides a novel compound of formula Ia, wherein:

X is selected from the group O, S and a bond;

$R^1$ is $C_{1-6}$ alkyl;

$R^1$ is substituted with a $C_{3-6}$ cycloalkyl, wherein 0–1 carbon atoms in the $C_{4-6}$ cycloalkyl is replaced by a group selected from the group —O—, —$S(O)_n$—, and —$NR^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, F, $CF_3$, —$OR^{13a}$, —$NR^{13a}R^{16a}$, —$CH_2OCH_3$, $CH_2CH_2OCH_3$ and $C_{3-6}$ cycloalkyl which is substituted with 0–1 $CH_3$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, $CH(CH_3)_2$, and $CH_2CH_2CH_3$;

$R^3$ and $R^8$ are independently selected at each occurrence from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCH_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[2t] In another further preferred embodiment, the present invention provides a novel compound of formula Ia, wherein:

$R^1$ is (cyclopropyl)$C_1$ alkyl or (cyclobutyl)$C_1$ alkyl;

$R^1$ is substituted with 1–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3$ $CH_3$, —CH=$CH_2$, —CH=$CH(CH_3)$, —CH≡CH, —CH≡$C(CH_3)$, —$CH_2OCH_3$, —$CH_2CH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, and $CH(CH_3)_2$;

$R^3$ and $R^8$ are independently selected at each occurrence from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[2u] In another even further preferred embodiment, the present invention provides a novel compound of formula Ia, wherein:

$R^1$ is (cyclopropyl)$C_1$ alkyl or (cyclobutyl)$C_1$ alkyl;

$R^1$ is substituted with 1–2 substituents independently selected at each occurrence from the group $R^{1a}$, $R^{1b}$, CH$_3$, CH$_2$CH$_3$, CH(CH$_3$)$_2$, CH$_2$CH$_2$CH$_3$, —(CH$_2$)$_3$CH$_3$, —CH═CH$_2$, —CH═CH(CH$_3$), —CH≡CH, —CH≡C(CH$_3$), —CH$_2$OCH$_3$, —CH$_2$CH$_2$OCH$_3$, F, CF$_3$, cyclopropyl, and CH$_3$-cyclopropyl;

R$^{1a}$ is phenyl substituted with 0–2 substituents independently selected at each occurrence from the group CH$_3$, CH$_2$CH$_3$, CH(CH$_3$)$_2$, CH$_2$CH$_2$CH$_3$, Br, Cl, F, CF$_3$, —CN, and SCH$_3$;

R$^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group CH$_3$, CH$_2$CH$_3$, CH(CH$_3$)$_2$, CH$_2$CH$_2$CH$_3$, OCH$_3$, OCH$_2$CH$_3$, OCF$_3$, Br, Cl, F, CF$_3$, —CN, and SCH$_3$.

[2v] In another further preferred embodiment, the present invention provides a novel compound of formula Ia, wherein:

D is phenyl substituted with 2–4 substituents independently selected at each occurrence from the group CH$_3$, CH$_2$CH$_3$, CH(CH$_3$)$_2$, CH$_2$CH$_2$CH$_3$, cyclopropyl, OCH$_3$, OCH$_2$CH$_3$, OCH(CH$_3$)$_2$, OCH$_2$CH$_2$CH$_3$, OCF$_3$, Br, Cl, F, and CF$_3$.

[2w] In another further preferred embodiment, the present invention provides a novel compound of formula Ia, wherein:

D is pyridyl substituted on 2–4 carbon atoms with a substituent independently selected at each occurrence from the group CH$_3$, CH$_2$CH$_3$, CH(CH$_3$)$_2$, CH$_2$CH$_2$CH$_3$, cyclopropyl, OCH$_3$, OCH$_2$CH$_3$, OCH(CH$_3$)$_2$, OCH$_2$CH$_2$CH$_3$, OCF$_3$, Br, Cl, F, and CF$_3$.

[3] In another preferred embodiment, the present invention provides a novel compound of formula Ib:

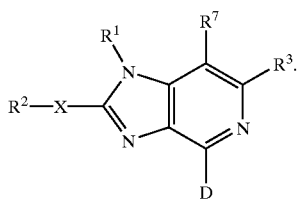

(Ib)

[3a] In another more preferred embodiment, the present invention provides a novel compound of formula Ib, wherein:

X is selected from the group O, S(O)$_n$ and a bond;
n is 0, 1 or 2;
R$^1$ is selected from the group C$_{1-6}$ alkyl, C$_{2-6}$ alkenyl, C$_{2-6}$ alkynyl, and C$_{3-8}$ cycloalkyl;
R$^1$ is substituted with 0–1 substituents selected from the group —CN, —S(O)$_n$R$^{14b}$, —COR$^{13a}$, —CO$_2$R$^{13a}$, and C$_{3-8}$ cycloalkyl, wherein 0–1 carbon atoms in the C$_{4-8}$ cycloalkyl is replaced by a group selected from the group —O—, —S(O)$_n$—, —NR$^{13a}$—, —NCO$_2$R$^{14b}$—, —NCOR$^{14b}$— and —NSO$_2$R$^{14b}$—;
R$^1$ is also substituted with 0–2 substituents independently selected at each occurrence from the group R$^{1a}$, R$^{1b}$, C$_{1-6}$ alkyl, C$_{2-8}$ alkenyl, C$_{2-8}$ alkynyl, Br, Cl, F, CF$_3$, CF$_2$CF$_3$, —OR$^{13a}$, —NR$^{13a}$R$^{16a}$, C$_{1-2}$ alkoxy-C$_{1-2}$ alkyl, and C$_{3-8}$ cycloalkyl which is substituted with 0–1 R$^9$ and in which 0–1 carbons of C$_{4-8}$ cycloalkyl is replaced by —O—;
provided that R$^1$ is other than a cyclohexyl-(CH$_2$)$_2$— group;

R$^{1a}$ is aryl and is selected from the group phenyl and indanyl, each R$^{1a}$ being substituted with 0–1 —OR$^{17}$ and 0–5 substituents independently selected at each occurrence from the group C$_{1-4}$ alkyl, C$_{3-6}$ cycloalkyl, Br, Cl, F, C$_{1-4}$ haloalkyl, —CN, —S(O)$_n$R$^{18}$, —COR$^{17}$, —NR$^{17a}$R$^{19a}$, and —CONR$^{17a}$R$^{19a}$;

R$^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group C$_{1-4}$ alkyl, C$_{3-6}$ cycloalkyl, Br, Cl, F, CF$_3$, —CN, —OR$^{17}$, —S(O)$_m$R$^{18}$, —COR$^{17}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$;

provided that R$^1$ is other than a —(CH$_2$)$_{1-4}$-aryl or —(CH$_2$)$_{1-4}$-heteroaryl wherein the aryl or heteroaryl group is substituted or unsubstituted;

R$^2$ is selected from the group C$_{1-4}$ alkyl, C$_{2-4}$ alkenyl, and C$_{2-4}$ alkynyl and is substituted with 0–1 substituents selected from the group —CN, OH, Cl, F, and C$_{1-4}$ alkoxy;

R$^3$ and R$^7$ are independently selected at each occurrence from the group H, Br, Cl, F, —CN, C$_{1-4}$ alkyl, C$_{3-6}$ cycloalkyl, C$_{1-4}$ alkoxy, NH$_2$, C$_{1-4}$ alkylamino, and (C$_{1-4}$ alkyl)$_2$-amino;

R$^9$ is independently selected at each occurrence from the group H, C$_{1-4}$ alkyl and C$_{3-8}$ cycloalkyl;

R$^{13}$ is selected from the group C$_{1-4}$ alkyl, C$_{1-2}$ haloalkyl, C$_{1-2}$ alkoxy-C$_{1-2}$ alkyl, C$_{3-6}$ cycloalkyl-C$_{1-2}$ alkyl, aryl (C$_{1-2}$ alkyl)—, and heteroaryl(C$_{1-2}$ alkyl)—;

R$^{13a}$ and R$^{16a}$ are independently selected at each occurrence from the group H, C$_{1-4}$ alkyl, C$_{1-4}$ haloalkyl, C$_{1-4}$ alkoxy-C$_{1-4}$ alkyl, C$_{3-6}$ cycloalkyl, and C$_{3-6}$ cycloalkyl-C$_{1-6}$ alkyl;

R$^{14}$ is selected from the group C$_{1-4}$ alkyl, C$_{1-2}$ haloalkyl, C$_{1-2}$ alkoxy-C$_{1-2}$ alkyl, C$_{3-6}$ cycloalkyl-C$_{1-2}$ alkyl, aryl (C$_{1-2}$ alkyl)—, and heteroaryl(C$_{1-2}$ alkyl)—;

R$^{14a}$ is selected from the group C$_{1-4}$ alkyl, C$_{1-2}$ haloalkyl, C$_{1-2}$ alkoxy-C$_{1-2}$ alkyl, and C$_{3-6}$ cycloalkyl-C$_{1-2}$ alkyl;

R$^{14b}$ is selected from the group C$_{1-4}$ alkyl, C$_{1-2}$ haloalkyl, C$_{1-2}$ alkoxy-C$_{1-2}$ alkyl, C$_{3-6}$ cycloalkyl, and C$_{3-6}$ cycloalkyl-C$_{1-2}$ alkyl;

R$^{15}$ is independently selected at each occurrence from the group H, C$_{1-4}$ alkyl, C$_{3-7}$ cycloalkyl, C$_{3-6}$ cycloalkyl-C$_{1-6}$ alkyl, phenyl and benzyl, each phenyl or benzyl being substituted on the aryl moiety with 0–3 groups chosen from the group C$_{1-4}$ alkyl, Br, Cl, F, C$_{1-4}$ haloalkyl, C$_{1-4}$ alkoxy, C$_{1-4}$ haloalkoxy, and dimethylamino;

R$^{15a}$ is independently selected at each occurrence from the group H, C$_{1-4}$ alkyl, C$_{3-7}$ cycloalkyl, and C$_{3-6}$ cycloalkyl-C$_{1-6}$ alkyl;

R$^{17}$, R$^{18}$ and R$^{19}$ are independently selected at each occurrence from the group H, C$_{1-6}$ alkyl, C$_{3-10}$ cycloalkyl, C$_{3-6}$ cycloalkyl-C$_{1-6}$ alkyl, C$_{1-2}$ alkoxy-C$_{1-2}$ alkyl, and C$_{1-4}$ haloalkyl;

alternatively, in an NR$^{17}$R$^{19}$ moiety, R$^{17}$ and R$^{19}$ taken together form 1-pyrrolidinyl, 1-morpholinyl, 1-piperidinyl or 1-piperazinyl, wherein N$_4$ in 1-piperazinyl is substituted with 0–1 substituents selected from the group R$^{13}$, CO$_2$R$^{14}$, COR$^{14}$ and SO$_2$R$^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, —$OR^{17}$, Br, Cl, F, $C_{1-4}$ haloalkyl, —CN, —$S(O)_nR^{18}$, —$COR^{17}$, —$CO_2R^{17}$, —$NR^{15}COR^{17}$, —$NR^{15}CO_2R^{18}$, —$NR^{17}R^{19}$, and —$CONR^{17}R^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —$OR^{17}$, —$S(O)_mR^{18}$, —$COR^{17}$, —$CO_2R^{17}$, —$OCO(O)R^{18}$, —$NR^{15}COR^{17}$, —$N(COR^{17})_2$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

[3b] In another even more preferred embodiment, the present invention provides a novel compound of formula Ib, wherein:

X is selected from the group O, S and a bond;

$R^1$ is substituted $C_{1-6}$ alkyl;

$R^1$ is substituted with 0–1 substituents selected from the group —CN, —$CO_2R^{13a}$, and $C_{3-8}$ cycloalkyl, wherein 0–1 carbon atoms in the $C_{4-8}$ cycloalkyl is replaced by a group selected from the group —O—, —$S(O)_n$—, and —$NR^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, —$OR^{13a}$, —$NR^{13a}R^{16a}$, $C_{1-2}$ alkoxy-$C_{1-2}$ alkyl, and $C_{3-6}$ cycloalkyl which is substituted with 0–1 $CH_3$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2CH_3$, $CH(CH_3)_2$, and $CH_2CH_2CH_3$;

$R^3$ and $R^7$ are independently selected at each occurrence from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[3c] In another still more preferred embodiment, the present invention provides a novel compound of formula Ib, wherein:

$R^1$ is substituted $C_1$;

$R^1$ is substituted with 0–1 substituents selected from the group —CN, —$CO_2CH_3$, and —$CO_2CH_2CH_3$;

$R^1$ is also substituted with 0–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH≡CH, —CH≡$C(CH_3)$, —$CH_2OCH_3$, —$CH_2CH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2CH_3$, and $CH(CH_3)_2$;

$R^3$ and $R^7$ are independently selected at each occurrence from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —C(O)$NH_2$, —C(O)$NHCH_3$, and —C(O)$N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $CO_2CH_3$, —$NH_2$, —$NHCH_3$, —$N(CH_3)_2$, —C(O)$NH_2$, —C(O)$NHCH_3$, and —C(O)$N(CH_3)_2$.

[3d] In another further preferred embodiment, the present invention provides a novel compound of formula Ib, wherein:

$R^1$ is substituted (cyclopropyl)—$C_1$ alkyl or (cyclobutyl)—$C_1$ alkyl;

$R^1$ is substituted with 0–1 —CN;

$R^1$ is also substituted with 0–1 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3$ $CH_3$, —CH=$CH_2$, —CH=CH($CH_3$), —CH≡CH, —CH≡C($CH_3$), Br, Cl, F, $CF_3$, cyclopropyl, and $CH_3$-cyclopropyl;

$R^1$ is also substituted with 0–1 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3$ $CH_3$, —CH=$CH_2$, —CH=CH($CH_3$), —CH≡CH, —CH≡C($CH_3$), —$CH_2CH_3$, —$CH_2CH_2OCH_3$, F, $CF_3$, cyclopropyl, and $CH_3$-cyclopropyl;

$R^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$.

[3e] In another further preferred embodiment, the present invention provides a novel compound of formula Ib, wherein:

$R^1$ is (cyclopropyl)$C_1$ alkyl or (cyclobutyl)—$C_1$ alkyl substituted with 1 substituent independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=CH($CH_3$), —CH≡CH, —CH≡C($CH_3$), —$CH_2OCH_3$, —$CH_2CH_2OCH_3$, F, $CF_3$, cyclopropyl, and $CH_3$-cyclopropyl;

$R^{1a}$ is phenyl substituted with 0–2 substituents independently selected at each occurrence from the group $CH_3$, $CH_2CH_3$, Cl, F, and $CF_3$;

$R^{1b}$ is heteroaryl and is selected from the group furanyl, thienyl, and isoxazolyl, each heteroaryl being substituted on 0–2 carbon atoms with a substituent independently selected at each occurrence from the group $CH_3$, $OCH_3$, Cl, F, and $CF_3$.

[3f] In an even further preferred embodiment, the present invention provides a novel compound of formula Ib, wherein:

$R^1$ is selected from the group (cyclopropyl)CH—$CH_3$, (cyclopropyl)CH—$CH_2CH_3$, (cyclopropyl)CH—$CH_2OCH_3$, (cyclopropyl)CH—$CH_2CH_2CH_3$, (cyclopropyl)CH—$CH_2CH_2OCH_3$, (cyclopropyl)$_2$CH, phenyl(cyclopropyl)CH, furanyl(cyclopropyl)CH, thienyl(cyclopropyl)CH, isoxazolyl(cyclopropyl)CH, ($CH_3$-furanyl)(cyclopropyl)CH, (cyclobutyl)CH—$CH_3$, (cyclobutyl)CH—$CH_2CH_3$, (cyclobutyl)CH—$CH_2OCH_3$, (cyclobutyl)CH—$CH_2CH_2CH_3$, (cyclobutyl)CH—$CH_2CH_2OCH_3$, (cyclobutyl)$_2$CH, phenyl(cyclobutyl)CH, furanyl(cyclobutyl)CH, thienyl (cyclobutyl)CH, isoxazolyl(cyclobutyl)CH, and ($CH_3$-furanyl)(cyclobutyl)CH.

[3g] In another further preferred embodiment, the present invention provides a novel compound of formula Ib, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[3h] In another further preferred embodiment, the present invention provides a novel compound of formula Ib, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[3i] In another preferred embodiment, the present invention provides a novel compound of formula Ib, wherein the compound is selected from the group:

1-(1-cyclopropylpropyl)-4-(2,4-dichlorophenyl)-2-ethyl-1H-imidazo[4,5-c]pyridine;

1-(1-cyclopropylpropyl)-4-(2,4-dichlorophenyl)-2-methoxy-1H-imidazo[4,5-c]pyridine;

1-(1-cyclopropylpropyl)-2-ethyl-4-[2-methyl-4-(trifluoromethyl)phenyl]-1H-imidazo[4,5-c]pyridine;

4-[2-chloro-4-(trifluoromethyl)phenyl]-1-(1-cyclopropylpropyl)-2-ethyl-1H-imidazo[4,5-c]pyridine;

4-[2-chloro-4-(trifluoromethyl)phenyl]-1-(1-cyclopropylpropyl)-2-methoxy-1H-imidazo[4,5-c]pyridine;

4-[2-chloro-4-(trifluoromethyl)phenyl]-1-(1-cyclopropylpropyl)-2-(methylsulfanyl)-1H-imidazo[4,5-c]pyridine;

4-(2-chloro-4-methoxyphenyl)-1-(1-cyclopropylpropyl)-2-ethyl-1H-imidazo[4,5-c]pyridine;

4-(2-chloro-4-methoxyphenyl)-1-(1-cyclopropylpropyl)-2-methoxy-1H-imidazo[4,5-c]pyridine;

1-(1-cyclopropylpropyl)-2-ethyl-4-(4-methoxy-2,5-dimethylphenyl)-1H-imidazo[4,5-c]pyridine;

1-(1-cyclopropylpropyl)-2-methoxy-4-(4-methoxy-2,5-dimethylphenyl)-1H-imidazo[4,5-c]pyridine;

4-(2-chloro-4-methoxyphenyl)-1-(1-cyclopropylpropyl)-2-ethyl-1H-imidazo[4,5-c]pyridine;

4-(2-chloro-4-methoxyphenyl)-1-(1-cyclopropylpropyl)-2-methoxy-1H-imidazo[4,5-c]pyridine;

4-(2-chloro-5-fluoro-4-methoxyphenyl)-1-(1-cyclopropylpropyl)-2-ethyl-1H-imidazo[4,5-c]pyridine;

4-(2-chloro-fluoro-4-methoxyphenyl)-1-(1-cyclopropylpropyl)-2-methoxy-1H-imidazo[4,5-c]pyridine;

4-(2-chloro-5-fluoro-4-methylphenyl)-1-(1-cyclopropylpropyl)-2-ethyl-1H-imidazo[4,5-c]pyridine;

2,4-(2-chloro-fluoro-4-methylphenyl)-1-(1-cyclopropylpropyl)-2-methoxy-1H-imidazo[4,5-c]pyridine;

1-(1-cyclopropylpropyl)-2-methoxy-4-(2,4,5-trimethylphenyl)-1H-imidazo[4,5-c]pyridine;

1-(1-cyclopropylpropyl)-2-ethyl-4-(2,4,5-trimethylphenyl)-1H-imidazo[4,5-c]pyridine;

1-(1-cyclopropylpropyl)-2-ethyl-4-(2,5,6-trimethyl-3-pyridinyl)-1H-imidazo[4,5-c]pyridine;

1-(1-cyclopropylpropyl)-2-methoxy-4-(2,5,6-trimethyl-3-pyridinyl)-1H-imidazo[4,5-c]pyridine;

1-(1-cyclopropylpropyl)-4-(2,6-dimethyl-3-pyridinyl)-2-ethyl-1H-imidazo[4,5-c]pyridine;

1-(1-cyclopropylpropyl)-4-(2,6-dimethyl-3-pyridinyl)-2-methoxy-1H-imidazo[4,5-c]pyridine;

1-(1-cyclopropylpropyl)-4-(2,6-dimethoxy-3-pyridinyl)-2-ethyl-1H-imidazo[4,5-c]pyridine;

4-(2,4-dichlorophenyl)-2-ethyl-1-(1-ethylpropyl)-1H-imidazo[4,5-c]pyridine;

4-(2,4-dichlorophenyl)-1-(1-ethylpropyl)-2-methoxy-1H-imidazo[4,5-c]pyridine;

4-[2-chloro-4-(trifluoromethyl)phenyl]-1-(1-ethylpropyl)-2-methoxy-1H-imidazo[4,5-c]pyridine;

4-[2-chloro-4-(trifluoromethyl)phenyl]-2-ethyl-1-(1-ethylpropyl)-1H-imidazo[4,5-c]pyridine;

4-[2-chloro-4-(methylsulfonyl)phenyl]-2-ethyl-1-(1-ethylpropyl)-1H-imidazo[4,5-c]pyridine;

4-[2-chloro-4-(methylsulfonyl)phenyl]-1-(1-ethylpropyl)-2-methoxy-1H-imidazo[4,5-c]pyridine;

2-ethyl-1-(1-ethylpropyl)-4-(4-methoxy-2,5-dimethylphenyl)-1H-imidazo[4,5-c]pyridine;

1-(1-ethylpropyl)-2-methoxy-4-(4-methoxy-2,5-dimethylphenyl)-1H-imidazo[4,5-c]pyridine;

4-(2-chloro-4-methoxyphenyl)-2-ethyl-1-(1-ethylpropyl)-1H-imidazo[4,5-c]pyridine;

4-(2-chloro-4-methoxyphenyl)-1-(1-ethylpropyl)-2-methoxy-1H-imidazo[4,5-c]pyridine;

2-ethyl-1-(1-ethylpropyl)-4-[4-methoxy-2-(trifluoromethyl)phenyl]-1H-imidazo[4,5-c]pyridine;

1-(1-ethylpropyl)-2-methoxy-4-[4-methoxy-2-(trifluoromethyl)phenyl]-1H-imidazo[4,5-c]pyridine;

1-(1-ethylpropyl)-4-(5-fluoro-4-methoxy-2-methylphenyl)-2-methoxy-1H-imidazo[4,5-c]pyridine;

2-ethyl-1-(1-ethylpropyl)-4-(5-fluoro-4-methoxy-2-methylphenyl)-1H-imidazo[4,5-c]pyridine;

3-chloro-4-[1-(1-ethylpropyl)-2-methoxy-1H-imidazo[4,5-c]pyridin-4-yl]benzonitrile;

3-chloro-4-[2-ethyl-1-(1-ethylpropyl)-1H-imidazo[4,5-c]pyridin-4-yl]benzonitrile;

1-{3-chloro-4-[2-ethyl-1-(1-ethylpropyl)-1H-imidazo[4,5-c]pyridin-4-yl]phenyl}-1-ethanone;.

1-{3-chloro-4-[1-(1-ethylpropyl)-2-methoxy-1H-imidazo[4,5-c]pyridin-4-yl]phenyl}-1-ethanone;

1-(dicyclopropylmethyl)-2-ethyl-4-(5-fluoro-4-methoxy-2-methylphenyl)-1H-imidazo[4,5-c]pyridine;

1-(dicyclopropylmethyl)-4-(5-fluoro-4-methoxy-2-methylphenyl)-2-methoxy-1H-imidazo[4,5-c]pyridine;

4-(2-chloro-4-methoxyphenyl)-1-(dicyclopropylmethyl)-2-ethyl-1H-imidazo[4,5-c]pyridine;

4-(2-chloro-4-methoxyphenyl)-1-(dicyclopropylmethyl)-2-methoxy-1H-imidazo[4,5-c]pyridine;

4-(2,4-dichlorophenyl)-1-(dicyclopropylmethyl)-2-ethyl-1H-imidazo[4,5-c]pyridine;

4-(2,4-dichlorophenyl)-1-(dicyclopropylmethyl)-2-methoxy-1H-imidazo[4,5-c]pyridine;

4-[2-chloro-4-(trifluoromethyl)phenyl]-1-(dicyclopropylmethyl)-2-ethyl-1H-imidazo[4,5-c]pyridine;

4-[2-chloro-4-(trifluoromethyl)phenyl]-1-(dicyclopropylmethyl)-2-methoxy-1H-imidazo[4,5-c]pyridine;

4-(2,4-dichlorophenyl)-1-(1-ethyl-3-methoxypropyl)-2-methoxy-1H-imidazo[4,5-c]pyridine;

4-(2,4-dichlorophenyl)-2-ethyl-1-(1-ethyl-3-methoxypropyl)-1H-imidazo[4,5-c]pyridine;

4-[2-chloro-4-(trifluoromethyl)phenyl]-1-(1-ethyl-3-methoxypropyl)-2-methoxy-1H-imidazo[4,5-c]pyridine;

4-[2-chloro-4-(trifluoromethyl)phenyl]-2-ethyl-1-(1-ethyl-3-methoxypropyl)-1H-imidazo[4,5-c]pyridine;

4-(2-chloro-4-methoxyphenyl)-1-(1-ethyl-3-methoxypropyl)-2-methoxy-1H-imidazo[4,5-c]pyridine;

4-(2-chloro-4-methoxyphenyl)-2-ethyl-1-(1-ethyl-3-methoxypropyl)-1H-imidazo[4,5-c]pyridine;

4-(2-chloro-5-fluoro-4-methoxyphenyl)-1-(1-ethyl-3-methoxypropyl)-2-methoxy-1H-imidazo[4,5-c]pyridine;

4-(2-chloro-5-fluoro-4-methoxyphenyl)-2-ethyl-1-(1-ethyl-3-methoxypropyl)-1H-imidazo[4,5-c]pyridine;

1-(1-ethyl-3-methoxypropyl)-2-methoxy-4-(4-methoxy-2,5-dimethylphenyl)-1H-imidazo[4,5-c]pyridine;

2-ethyl-1-(1-ethyl-3-methoxypropyl)-4-(4-methoxy-2,5-dimethylphenyl)-1H-imidazo[4,5-c]pyridine;

2-ethyl-1-(1-ethyl-3-methoxypropyl)-4-(5-fluoro-4-methoxy-2-methylphenyl)-1H-imidazo[4,5-c]pyridine;

1-(1-ethyl-3-methoxypropyl)-4-(5-fluoro-4-methoxy-2-methylphenyl)-2-methoxy-1H-imidazo[4,5-c]pyridine;

4-(2-chloro-5-fluoro-4-methylphenyl)-1-(1-ethyl-3-methoxypropyl)-2-methoxy-1H-imidazo[4,5-c]pyridine;

4-(2-chloro-5-fluoro-4-methylphenyl)-2-ethyl-1-(1-ethyl-3-methoxypropyl)-1H-imidazo[4,5-c]pyridine;

4-[2-chloro-4-(methylsulfonyl)phenyl]-1-(1-ethyl-3-methoxypropyl)-2-methoxy-1H-imidazo[4,5-c]pyridine;

4-[2-chloro-4-(methylsulfonyl)phenyl]-2-ethyl-1-(1-ethyl-3-methoxypropyl)-1H-imidazo[4,5-c]pyridine;

1-{3-chloro-4-[1-(1-ethyl-3-methoxypropyl)-2-methoxy-1H-imidazo[4,5-c]pyridin-4-yl]phenyl}-1-ethanone;

1-{3-chloro-4-[2-ethyl-1-(1-ethyl-3-methoxypropyl)-1H-imidazo[4,5-c]pyridin-4-yl]phenyl}-1-ethanone;

1-{5-[1-(1-ethyl-3-methoxypropyl)-2-methoxy-1H-imidazo[4,5-c]pyridin-4-yl]-6-methyl-2-pyridinyl}-1-ethanone;

1-{5-[2-ethyl-1-(1-ethyl-3-methoxypropyl)-1H-imidazo[4,5-c]pyridin-4-yl]-6-methyl-2-pyridinyl}-1-ethanone;

1-(1-ethyl-3-methoxypropyl)-2-methoxy-4-(6-methoxy-2-methyl-3-pyridinyl)-1H-imidazo[4,5-c]pyridine;

2-ethyl-1-(1-ethyl-3-methoxypropyl)-4-(6-methoxy-2-methyl-3-pyridinyl)-1H-imidazo[4,5-c]pyridine;

4-(2,6-dimethoxy-3-pyridinyl)-2-ethyl-1-(1-ethyl-3-methoxypropyl)-1H-imidazo[4,5-c]pyridine;

4-(2,6-dimethoxy-3-pyridinyl)-1-(1-ethyl-3-methoxypropyl)-2-methoxy-1H-imidazo[4,5-c]pyridine;

4-(2,6-dimethyl-3-pyridinyl)-1-(1-ethyl-3-methoxypropyl)-2-methoxy-1H-imidazo[4,5-c]pyridine;

4-(2,6-dimethyl-3-pyridinyl)-2-ethyl-1-(1-ethyl-3-methoxypropyl)-1H-imidazo[4,5-c]pyridine;

2-ethyl-1-(1-ethyl-3-methoxypropyl)-4-(2,5,6-trimethyl-3-pyridinyl)-1H-imidazo[4,5-c]pyridine;

1-(1-ethyl-3-methoxypropyl)-2-methoxy-4-(2,5,6-trimethyl-3-pyridinyl)-1H-imidazo[4,5-c]pyridine;

4-(2,4-dichlorophenyl)-2-ethyl-1-[1-(methoxymethyl)propyl]-1H-imidazo[4,5-c]pyridine;

4-(2,4-dichlorophenyl)-2-methoxy-1-[1-(methoxymethyl)propyl]-1H-imidazo[4,5-c]pyridine;

4-[2-chloro-4-(trifluoromethyl)phenyl]-2-ethyl-1-[1-(methoxymethyl)propyl]-1H-imidazo[4,5-c]pyridine;

4-[2-chloro-4-(trifluoromethyl)phenyl]-2-methoxy-1-[1-(methoxymethyl)propyl]-1H-imidazo[4,5-c]pyridine;

4-(2-chloro-5-fluoro-4-methylphenyl)-2-ethyl-1-[1-(methoxymethyl)propyl]-1H-imidazo[4,5-c]pyridine;

4-(2-chloro-5-fluoro-4-methylphenyl)-2-methoxy-1-[1-(methoxymethyl)propyl]-1H-imidazo[4,5-c]pyridine;

2-methoxy-4-(4-methoxy-2,5-dimethylphenyl)-1-[1-(methoxymethyl)propyl]-1H-imidazo[4,5-c]pyridine;

2-ethyl-4-(4-methoxy-2,5-dimethylphenyl)-1-[1-(methoxymethyl)propyl]-1H-imidazo[4,5-c]pyridine;

2-ethyl-4-(5-fluoro-4-methoxy-2-methylphenyl)-1-[1-(methoxymethyl)propyl]-1H-imidazo[4,5-c]pyridine;

4-(5-fluoro-4-methoxy-2-methylphenyl)-2-methoxy-1-[1-(methoxymethyl)propyl]-1H-imidazo[4,5-c]pyridine;

2-methoxy-1-[1-(methoxymethyl)propyl]-4-(6-methoxy-2-methyl-3-pyridinyl)-1H-imidazo[4,5-c]pyridine;

2-ethyl-1-[1-(methoxymethyl)propyl]-4-(6-methoxy-2-methyl-3-pyridinyl)-1H-imidazo[4,5-c]pyridine;

4-(2,6-dimethoxy-3-pyridinyl)-2-ethyl-1-[1-(methoxymethyl)propyl]-1H-imidazo[4,5-c]pyridine;

4-(2,6-dimethoxy-3-pyridinyl)-2-methoxy-1-[1-(methoxymethyl)propyl]-1H-imidazo[4,5-c]pyridine;

4-(2,6-dimethyl-3-pyridinyl)-2-ethyl-1-[1-(methoxymethyl)propyl]-1H-imidazo[4,5-c]pyridine;

4-(2,6-dimethyl-3-pyridinyl)-2-methoxy-1-[1-(methoxymethyl)propyl]-1H-imidazo[4,5-c]pyridine;

2-ethyl-1-[1-(methoxymethyl)propyl]-4-(2,5,6-trimethyl-3-pyridinyl)-1H-imidazo[4,5-c]pyridine;

2-methoxy-1-[1-(methoxymethyl)propyl]-4-(2,5,6-trimethyl-3-pyridinyl)-1H-imidazo[4,5-c]pyridine;

4-[2-chloro-4-(methylsulfonyl)phenyl]-2-ethyl-1-[1-(methoxymethyl)propyl]-1H-imidazo[4,5-c]pyridine; and 4-[2-chloro-4-(methylsulfonyl)phenyl]-2-methoxy-1-[1-(methoxymethyl)propyl]-1H-imidazo[4,5-c]pyridine;

or a pharmaceutically acceptable salt form thereof.

[3j] In another more preferred embodiment, the present invention provides a novel compound of formula Ib, wherein:

$R^1$ is $C_{3-8}$ cycloalkyl;

$R^1$ is substituted with 0–1 substituents selected from the group —CN, —S(O)$_n R^{14b}$, —COR$^{13a}$, —CO$_2 R^{13a}$, —NR$^{15a}$COR$^{13a}$, —N(COR$^{13a}$)$_2$, —NR$^{15a}$CONR$^{13a}R^{16a}$, —NR$^{15a}$CO$_2 R^{14b}$, —CONR$^{13a}R^{16a}$, 1-morpholinyl, 1-piperidinyl, 1-piperazinyl, and $C_{4-8}$ cycloalkyl, wherein 0–1 carbon atoms in the $C_{4-8}$ cycloalkyl is replaced by a group selected from the group —O—, —S(O)$_n$—, —NR$^{13a}$—, —NCO$_2 R^{14b}$—NCOR$^{14b}$— and —NSO$_2 R^{14b}$—, and wherein $N_4$ in 1-piperazinyl is substituted with 0–1 substituents selected from the group $R^{13a}$, CO$_2 R^{14b}$, COR$^{14b}$ and SO$_2 R^{14b}$; and, $R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, $C_{1-2}$ alkoxy-$C_{1-2}$ alkyl, and —NR$^{13a}R^{16a}$.

[3k] In another even more preferred embodiment, the present invention provides a novel compound of formula Ib, wherein:

X is selected from the group O, S(O)$_n$ and a bond;

n is 0, 1 or 2;

$R^1$ is selected from the group cyclopropyl, cyclobutyl, and cyclopentyl;

$R^1$ is substituted with 0–1 substituents selected from the group —CN, —S(O)$_n R^{14b}$, —COR$^{13a}$, —CO$_2 R^{13a}$, and $C_{4-8}$ cycloalkyl, wherein one carbon atom in the $C_{4-8}$ cycloalkyl is replaced by a group selected from the group —O—, —S(O)$_n$—, —NR$^{13a}$—, NCO$_2 R^{14b}$—, NCOR$^{14b}$— and —NSO$_2 R^{14b}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, CF$_3$, CF$_2$CF$_3$, —OR$^{13a}$, $C_{1-2}$ alkoxy-$C_{1-2}$ alkyl, and —NR$^{13a}R^{16a}$;

$R^{1a}$ is aryl and is selected from the group phenyl and indanyl, each $R^{1a}$ being substituted with 0–1 —OR$^{17}$ and 0–5 substituents independently selected at each occurrence from the group $C_{1-4}$ alkyl, $C_{3-6}$ cycloalkyl, Br, Cl, F, $C_{1-4}$ haloalkyl, —CN, —S(O)$_n R^{18}$, —COR$^{17}$, —NR$^{17a}R^{19a}$, and —CONR$^{17a}R^{19a}$;

$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, CF$_3$, —CN, —OR$^{17}$, —S(O)$_m R^{18}$, —COR$^{17}$, —NR$^{17a}R^{19a}$, and —CONR$^{17a}R^{19a}$ and each heteroaryl being substituted on any nitrogen atom with 0–1 substituents selected from the group $R^{15a}$, CO$_2 R^{14b}$, COR$^{14b}$ and SO$_2 R^{14b}$;

$R^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

$R^9$ is independently selected at each occurrence from the group H, $C_{1-4}$ alkyl and $C_{3-8}$ cycloalkyl;

$R^3$ and $R^7$ are independently selected at each occurrence from the group H, Br, Cl, F, —CN, $C_{1-4}$ alkyl, $C_{3-6}$ cycloalkyl, $C_{1-4}$ alkoxy, NH$_2$, $C_{1-4}$ alkylamino, and ($C_{1-4}$ alkyl)$_2$-amino;

$R^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)—, and heteroaryl($C_{1-2}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)—, and heteroaryl($C_{1-2}$ alkyl)—;

$R^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

$R^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$, $R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, —$OR^{17}$, Br, Cl, F, $C_{1-4}$ haloalkyl, —CN, —$S(O)_nR^{18}$, —$COR^{17}$, —$CO_2R^{17}$, —$NR^{15}COR^{17}$, —$NR^{15}CO_2R^{18}$, —$NR^{17}R^{19}$, and —$CONR^{17}R^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —$OR^{17}$, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

[3l] In another still more preferred embodiment, the present invention provides a novel compound of formula Ib, wherein:

X is selected from the group O, S and a bond;

$R^1$ is substituted with 0–1 substituents selected from the group —CN, —$CO_2R^{13a}$, and $C_{4-8}$ cycloalkyl, wherein 0–1 carbon atoms in the $C_{4-8}$ cycloalkyl is replaced by a group selected from the group —O—, —$S(O)_n$—, and —$NR^{13a}$—;

$R^1$ is also substituted with 0–2 substituents independently selected at each occurrence from the group $R^{1a}$, $R^{1b}$, $C_{16}$ alkyl, $C_{2-8}$ alkenyl, $C_{2-8}$ alkynyl, Br, Cl, F, $CF_3$, $CF_3$, —$OR^{13a}$, —OH, —$OCH_3$, —$OCH_2CH_3$, —$CH_2OCH_3$, —$CH_2CH_2OCH_3$, and —$NR^{13a}R^{16a}$;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, $CH(CH_3)_2$, and $CH_2CH_2CH_3$; $R^{15}$, $CO_2R^{14a}$, $COR^{14a}$ and $SO_2R^{14a}$.

$R^3$ and $R^7$ are independently selected at each occurrence from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[3m] In another further preferred embodiment, the present invention provides a novel compound of formula Ib, wherein:

$R^1$ is substituted with 0–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3$ $CH_3$, —CH=$CH_2$, —CH=$CH(CH_3)$, —CH≡CH, —CH≡$C(CH_3)$, —$CH_2OCH_3$, —$CH_2OH_2OCH_3$, F, and $CF_3$;

$R^{1a}$ is phenyl substituted with 0–1 substituents selected from $OCH_3$, $OCH_2CH_3$, $OCH(CH_3)_2$, $OCH_2CH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, and $CH(CH_3)_2$;

$R^3$ and $R^7$ are independently selected at each occurrence from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[3n] In another even further preferred embodiment, the present invention provides a novel compound of formula Ib, wherein:

$R^1$ is substituted with 0–2 substituents independently selected at each occurrence from the group $R^{1a}$, $CH_3$, $CH_2CH_3$, $CH(CH_3)_2$, $CH_2CH_2CH_3$, —$(CH_2)_3CH_3$, —$CH_2OCH_3$, —$CH_2CH_2OCH_3$, F, and $CF_3$; and, $R^{1a}$ is phenyl substituted with 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$.

[3o] In another still further preferred embodiment, the present invention provides a novel compound of formula Ib, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[3p] In another still further preferred embodiment, the present invention provides a novel compound of formula Ib, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[3q] In another more preferred embodiment, the present invention provides a novel compound of formula Ib, wherein:

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl and $C_{1-4}$ alkoxy-$C_{1-4}$ alkyl;

$R^1$ is substituted with a $C_{3-8}$ cycloalkyl group, wherein 0–1 carbon atoms in the $C_{4-8}$ cycloalkyl group is replaced by a group selected from the group —O—, —S(O)$_n$—, —NR$^{13a}$, —NCO$_2$R$^{14b}$, —NCOR$^{14b}$— and SO$_2$R$^{14b}$—.

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, —NR$^{13a}$R$^{16a}$, $C_{1-2}$ alkoxy$C_{1-2}$ alkyl, and $C_{3-8}$ cycloalkyl which is substituted with 0–1 R$^9$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is selected from the group phenyl, naphthyl, indanyl and indenyl, each $R^{1a}$ being substituted with 0–1 —OR$^{17}$ and 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, SH, —S(O)$_n$R$^{18}$, —COR$^{17}$, —OC(O)R$^{18}$, —NR$^{15a}$COR$^{17}$, —N(COR$^{17}$)$_2$, —NR$^{15a}$CONR$^{17a}$R$^{19a}$, —NR$^{15a}$CO$_2$R$^{18}$, —NR$^{17a}$R$^{19a}$, and —CONR$^{17a}$R$^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR$^{17}$, SH, —S(O)$_m$R$^{18}$, —COR$^{17}$, —OC(O)R$^{18}$, —NR$^{15a}$COR$^{17}$, —N(COR$^{17}$)$_2$, —NR$^{15a}$CONR$^{17a}$R$^{19a}$, —NR$^{15a}$CO$_2$R$^{18}$, —NR$^{17a}$R$^{19a}$, and —CONR$^{17a}$R$^{19a}$ and each heteroaryl being substituted on any nitrogen atom with 0–1 substituents selected from the group $R^{15a}$, CO$_2$R$^{14b}$, COR$^{14b}$ and SO$_2$R$^{14b}$; and, $R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR$^{13a}$, SH, —S(O)$_n$R$^{14b}$, —COR$^{13a}$, —OC(O)R$^{14b}$, —NR$^{15a}$COR$^{13a}$, —N(COR$^{13a}$)$_2$, —NR$^{15a}$CONR$^{13a}$R$^{16a}$, —NR$^{15a}$CO$_2$R$^{14b}$, —NR$^{13a}$R$^{16a}$, and CONR$^{13a}$R$^{16a}$ and each heterocyclyl being substituted on any nitrogen atom with 0–1 substituents selected from the group $R^{13a}$, CO$_2$R$^{14b}$, COR$^{14b}$ and SO$_2$R$^{14b}$ and wherein any sulfur atom is optionally monooxidized or dioxidized.

[3r] In another even more preferred embodiment, the present invention provides a novel compound of formula Ib, wherein:

X is selected from the group O, S(O)$_n$ and a bond;

n is 0, 1 or 2;

$R^1$ is selected from the group $C_{1-6}$ alkyl, $C_{2-6}$ alkenyl, $C_{2-6}$ alkynyl, $C_{3-8}$ cycloalkyl;

$R^1$ is substituted with a $C_{3-6}$ cycloalkyl group, wherein 0–1 carbon atoms in the $C_{4-6}$ cycloalkyl group is replaced by a group selected from the group —O—, —S(O)$_n$—, and —NR$^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, $CF_2CF_3$, $—OR^{13a}$, $—NR^{13a}R^{16a}$, $C_{1-2}$ alkoxy-$C_{1-2}$ alkyl, and $C_{3-6}$ cycloalkyl which is substituted with 0–1 $R^9$ and in which 0–1 carbons of $C_{4-8}$ cycloalkyl is replaced by —O—;

$R^{1a}$ is aryl and is selected from the group phenyl and indanyl, each $R^{1a}$ being substituted with 0–1 $—OR^{17}$ and 0–5 substituents independently selected at each occurrence from the group $C_{1-4}$ alkyl, $C_{3-6}$ cycloalkyl, Br, Cl, F, $C_{1-4}$ haloalkyl, $—CN$, $—S(O)_nR^{18}$, $—COR^{17}$, $—NR^{17a}R^{19a}$, and $R^{17a}R^{19a}$;

$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, $CF_3$, $—CN$, $—OR^{17}$, $—S(O)_mR^{18}$, $—COR^{17}$, $—NR^{17a}R^{19a}$, and $—CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

$R^2$ is selected from the group $C_{1-4}$ alkyl, $C_{2-4}$ alkenyl, and $C_{2-4}$ alkynyl and is substituted with 0–1 substituents selected from the group $—CN$, OH, Cl, F, and $C_{1-4}$ alkoxy;

$R^9$ is independently selected at each occurrence from the group H, $C_{1-4}$ alkyl and $C_{3-8}$ cycloalkyl;

$R^3$ and $R^7$ are independently selected at each occurrence from the group H, Br, Cl, F, $—CN$, $C_{1-4}$ alkyl, $C_{3-6}$ cycloalkyl, $C_{1-4}$ alkoxy, $NH_2$, $C_{1-4}$ alkylamino, and $(C_{1-4}$ alkyl$)_2$-amino;

$R^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl$(C_{1-2}$ alkyl)—, and heteroaryl$(C_{1-2}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl$(C_{1-2}$ alkyl)—, and heteroaryl$(C_{1-2}$ alkyl)—;

$R^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

$R^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$, $R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, $—OR^{17}$, Br, Cl, F, $C_{1-4}$ haloalkyl, $—CN$, $—S(O)_nR^{18}$, $—COR^{17}$, $—CO_2R^{17}$, $—NR^{15COR17}$, $—NR^{15}CO_2R^{18}$, $—NR^{17}R^{19}$, and $—CONR^{17}R^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, $—CN$, $—OR^{17}$, $—S(O)_mR^{18}$, $—COR^{17}$, $—CO_2R^{17}$, $—OC(O)R^{18}$, $—NR^{15}COR^{17}$, $—N(COR^{17})_2$, $—NR^{15}CO_2R^{18}$, $—NR^{17}R^{19}$, and $—CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$;

[3s] In another still more preferred embodiment, the present invention provides a novel compound of formula Ib, wherein:

X is selected from the group O, S and a bond;

$R^1$ is $C_{1-6}$ alkyl;

$R^1$ is substituted with a $C_{3-6}$ cycloalkyl, wherein 0–1 carbon atoms in the $C_{4-4}$ cycloalkyl is replaced by a group selected from the group —O—, $—S(O)_n—$, and $—NR^{13a}—$;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, F, $CF_3$, $—OR^{13a}$, $—NR^{13a}R^{16a}$, $—CH_2CH_3$, $—CH_2CH_2OCH_3$, and $C_{3-6}$ cycloalkyl which is substituted with 0–1 $CH_3$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, $—CN$, $SCH_3$, $—NH_2$, $—NHCH_3$, $—N(CH_3)_2$, $—C(O)NH_2$, $—C(O)NHCH_3$, and $—C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, $—CN$, $SCH_3$, $—NH_2$, $—NHCH_3$, $—N(CH_3)_2$, $—C(O)NH_2$, $—C(O)NHCH_3$, and $—C(O)N(CH_3)_2$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, $CH(CH_3)_2$, and $CH_2CH_2CH_3$;

$R^3$ and $R^7$ are independently selected at each occurrence from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2OH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[3t] In another further preferred embodiment, the present invention provides a novel compound of formula Ib, wherein:

$R^1$ is (cyclopropyl)$C_1$ alkyl or (cyclobutyl)$C_1$ alkyl;

$R^1$ is substituted with 1–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=CH($CH_3$), —CH≡CH, —CH≡C($CH_3$), —$CH_2OCH_3$, —$CH_2CH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, and $CH(CH_3)_2$;

$R^3$ and $R^7$ are independently selected at each occurrence from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[3u] In another even further preferred embodiment, the present invention provides a novel compound of formula Ib, wherein:

$R^1$ is (cyclopropyl)$C_1$ alkyl or (cyclobutyl)$C_1$ alkyl;

$R^1$ is substituted with 1–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=CH($CH_3$), —CH≡CH, —CH≡C($CH_3$), —$CH_2OCH_3$, —$CH_2CH_2OCH_3$, F, $CF_3$, cyclopropyl, and $CH_3$-cyclopropyl;

$R^{1a}$ is phenyl substituted with 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$.

[3v] In another further preferred embodiment, the present invention provides a novel compound of formula Ib, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[3w] In another further preferred embodiment, the present invention provides a novel compound of formula Ib, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[4] In another preferred embodiment, the present invention provides a novel compound of formula Ic:

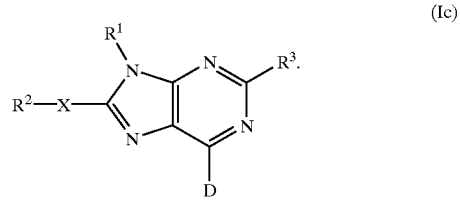

(Ic)

[4a] In another more preferred embodiment, the present invention provides a novel compound of formula Ic, wherein:

X is selected from the group O, S(O)$_n$ and a bond;

n is 0, 1 or 2;

$R^1$ is selected from the group $C_{1-6}$ alkyl, $C_{2-6}$ alkenyl, $C_{2-6}$ alkynyl, and $C_{3-8}$ cycloalkyl;

$R^1$ is substituted with 0–1 substituents selected from the group —CN, —S(O)$_n R^{14b}$, —$COR^{13a}$, —$CO_2R^{13a}$, and $C_{3-8}$ cycloalkyl, wherein 0–1 carbon atoms in the $C_{4-8}$ cycloalkyl is replaced by a group selected from the group —O—, —S(O)$_n$—, —NR$^{13a}$—, —NCO$_2$R$^{14b}$, —NCOR$^{14b}$— and —NSO$_2$R$^{14b}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, $CF_2CF_3$, —OR$^{13a}$, —NR$^{13a}$R$^{16a}$, $C_{1-2}$ alkoxy-$C_{1-2}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl-(CH$_2$)$_2$— group;

$R^{1a}$ is aryl and is selected from the group phenyl and indanyl, each $R^{1a}$ being substituted with 0–1 —OR$^{17}$ and 0–5 substituents independently selected at each occurrence from the group $C_{1-4}$ alkyl, $C_{3-6}$ cycloalkyl, Br, Cl, F, $C_{1-4}$ haloalkyl, —CN, —S(O)$_n$R$^{18}$, —COR$^{17}$, —NR$^{17a}$R$^{19a}$, and —CONR$^{17a}$R$^{19a}$;

$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, $CF_3$, —CN, —OR$^{17}$, —S(O)$_m$R$^{18}$, —COR$^{17}$, NR$^{17a}$R$^{19a}$, and —CONR$^{17a}$R$^{19}$a and each heteroaryl being substituted on any nitrogen atom with 0–1 substituents selected from the group $R^{15a}$, CO$_2$R$^{14b}$, COR$^{14b}$ and SO$_2$R$^{14b}$;

provided that $R^1$ is other than a —(CH$_2$)$_{1-4}$-aryl or —(CH$_2$)$_{1-4}$-heteroaryl wherein the aryl or heteroaryl group is substituted or unsubstituted;

$R^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

$R^3$ is selected from the group H, Br, Cl, F, —CN, $C_{1-4}$ alkyl, $C_{3-6}$ cycloalkyl, $C_{1-4}$ alkoxy, NH$_2$, $C_{1-4}$ alkylamino, and ($C_{1-4}$ alkyl)$_2$-amino;

$R^9$ is independently selected at each occurrence from the group H, $C_{1-4}$ alkyl and $C_{3-8}$ cycloalkyl;

$R^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)—, and heteroaryl($C_{1-2}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)—, and heteroaryl($C_{1-2}$ alkyl)—;

$R^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

$R^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$, $R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an NR$^{17}$R$^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, CO$_2$R$^{14}$, COR$^{14}$ and SO$_2$R$^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, —OR$^{17}$, Br, Cl, F, $C_{1-4}$ haloalkyl, —CN, —S(O)$_n$R$^{18}$, —COR$^{17}$, —CO$_2$R$^{17}$, —NR$^{15}$COR$^{17}$, —NR$^{15}$CO$_2$R$^{18}$, —NR$^{17}$R$^{19}$, and —CONR$^{17}$R$^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —OR$^{17}$, —S(O)$_n$R$^{18}$, —COR$^{17}$, —CO$_2$R$^{17}$, —OC(O)R$^{18}$, —NR$^{15}$COR$^{17}$, —N(COR$^{17}$)$_2$, —NR$^{15}$CO$_2$R$^{18}$, —NR$^{17}$R$^{19}$, and —CONR$^{17}$R$^{19}$ and each heteroaryl being substituted on any nitrogen atom with 0–1 substituents selected from the group $R^{15}$, CO$_2$R$^{14a}$, COR$^{14a}$ and SO$_2$R$^{14a}$.

[4b] In another even more preferred embodiment, the present invention provides a novel compound of formula Ic, wherein:

X is selected from the group O, S and a bond;

$R^1$ is substituted $C_{1-6}$ alkyl;

$R^1$ is substituted with 0–1 substituents selected from the group —CN, —CO$_2$R$^{13a}$, and $C_{3-8}$ cycloalkyl, wherein 0–1 carbon atoms in the $C_{4-8}$ cycloalkyl is replaced by a group selected from the group —O—, —S(O)$_n$—, and —NR$^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, OR$^{13a}$, —NR$^{13a}$R$^{16a}$, $C_{1-2}$ alkoxy-$C_2$ alkyl, and $C_{3-6}$ cycloalkyl which is substituted with 0–1 $CH_3$ and in which 0–1 carbons of $C_{4-8}$ cycloalkyl is replaced by —O—;

provided that $R^1$ is other than a cyclohexyl-(CH$_2$)$_2$— group;

$R^{1a}$ is aryl and is phenyl substituted with 0–1 substituents selected from OCH$_3$, OCH$_2$CH$_3$, OCH(CH$_3$)$_2$, OCH$_2$CH$_2$CH$_3$, and OCF$_3$, and 0–3 substituents independently selected at each occurrence from the group CH$_3$, CH$_2$CH$_3$, CH(CH$_3$)$_2$, CH$_2$CH$_2$CH$_3$, cyclopropyl, Br, Cl, F, $CF_3$, —CN, SCH$_3$, —NH$_2$, —NHCH$_3$, —N(CH$_3$)$_2$, —C(O)NH$_2$, —C(O)NHCH$_3$, and —C(O)N(CH$_3$)$_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2CH_3$, $CH(CH_3)_2$, and $CH_2CH_2CH_3$;

$R^3$ is selected from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[4c] In another still more preferred embodiment, the present invention provides a novel compound of formula Ic, wherein:

$R^1$ is substituted $C_1$;

$R^1$ is substituted with 0–1 substituents selected from the group —CN, —$CO_2CH_3$, and —$CO_2CH_2CH_3$;

$R^1$ is also substituted with 0–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH≡CH, —CH≡$C(CH_3)$, —$CH_2OCH_3$, —$CH_2OH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_{02}CH_3$, $COCH_3$ and $SO_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2CH_3$, and $CH(CH_3)_2$;

$R^3$ is selected from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[4d] In another further preferred embodiment, the present invention provides a novel compound of formula Ic, wherein:

$R^1$ is substituted (cyclopropyl)—$C_1$ alkyl or (cyclobutyl) $C_1$ alkyl;

$R^1$ is substituted with 0–1 —CN;

$R^1$ is also substituted with 0–1 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH≡CH, —CH≡$C(CH_3)$, —$CH_2OCH_3$, —$CH_2OH_2OCH_3$, F, $CF_3$, cyclopropyl, and $CH_3$-cyclopropyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$.

[4e] In another further preferred embodiment, the present invention provides a novel compound of formula Ic, wherein:

$R^1$ is (cyclopropyl)$C_1$ alkyl or (cyclobutyl)—$C_1$ alkyl substituted with 1 substituent independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH≡CH, —CH≡$C(CH_3)$, —$CH_2,CH_3$, —$CH_2CH_2OCH_3$, F, $CF_3$, cyclopropyl, and $CH_3$-cyclopropyl;

$R^{1a}$ is phenyl substituted with 0–2 substituents independently selected at each occurrence from the group $CH_3$, $CH_2CH_3$, Cl, F, and $CF_3$;

$R^{1b}$ is heteroaryl and is selected from the group furanyl, thienyl, and isoxazolyl, each heteroaryl being substituted on 0–2 carbon atoms with a substituent independently selected at each occurrence from the group $CH_3$, $OCH_3$, Cl, F, and $CF_3$.

[4f] In an even further preferred embodiment, the present invention provides a novel compound of formula Ic, wherein:

$R^1$ is selected from the group (cyclopropyl)CH—$CH_3$, (cyclopropyl)CH—$CH_2CH_3$, (cyclopropyl)CH—$CH_2OCH_3$, (cyclopropyl)CH—$CH_2CH_2CH_3$, (cyclopropyl)CH—$CH_2CH_2OCH_3$, (cyclopropyl)$_2$CH, phenyl(cyclopropyl)CH, furanyl(cyclopropyl)CH, thienyl(cyclopropyl)CH, isoxazolyl(cyclopropyl)CH, ($CH_3$-furanyl)(cyclopropyl)CH, (cyclobutyl)CH—$CH_3$, (cyclobutyl)CH—$CH_2CH_3$, (cyclobutyl)CH—$CH_2OCH_3$, (cyclobutyl)CH—$CH_2CH_2CH_3$, (cyclobutyl)CH—$OH_2C_2OCH_3$, (cyclobutyl)$_2$CH, phenyl(cyclobutyl)CH, furanyl(cyclobutyl)CH, thienyl(cyclobutyl)CH, isoxazolyl(cyclobutyl)CH, and ($CH_3$-furanyl)(cyclobutyl)CH.

[4g] In another further preferred embodiment, the present invention provides a novel compound of formula Ic, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[4h] In another further preferred embodiment, the present invention provides a novel compound of formula Ic, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[4i] In another preferred embodiment, the present invention provides a novel compound of formula Ic, wherein the compound is selected from the group:

6-(2,4-bis(trifluoromethyl)phenyl-9-(dicyclopropylmethyl)-8-ethyl-9H-purine;

6-(2-chloro-4-cyanophenyl)-9-(dicyclopropylmethyl)-8-ethyl-9H-purine;

6-(2-chloro-4-methoxy-5-chlorophenyl)-9-(dicyclopropylmethyl)-8-ethyl-9H-purine;

6-(2-chloro-4-methoxy-5-methylphenyl)-9-(dicyclopropylmethyl)-8-ethyl-9H-purine;

6-(2-chloro-4-methoxyphenyl)-8-ethyl-9-(2-hexyl)-9H-purine;

6-(2-chloro-4-methoxyphenyl)-8-ethyl-9-(2-pentyl)-9H-purine;

6-(2-chloro-4-methoxyphenyl)-8-ethyl-9-(3-heptyl)-9H-purine;

6-(2-chloro-4-methoxyphenyl)-8-ethyl-9-(3-hexyl)-9H-purine;

6-(2-chloro-4-methoxyphenyl)-8-ethyl-9-(4-heptyl)-9H-purine;

6-(2-chloro-4-methoxyphenyl)-9-(1-cyclopropylbutyl)-8-ethyl-9H-purine;

6-(2-chloro-4-methoxyphenyl)-9-(1-cyclopropylpropyl)-8-ethyl-9H-purine;

6-(2-chloro-4-methoxyphenyl)-9-(dicyclopropylmethyl)-8-ethyl-9H-purine;

6-(2-chloro-4-methoxyphenyl)-9-(dicyclopropylmethyl)-8-methoxy-9H-purine;

6-(2-chloro-4-methyl-5-fluorophenyl)-9-(dicyclopropylmethyl)-8-ethyl-9H-purine;

6-(2-chloro-4-methylphenyl)-8-ethyl-9-(2-pentyl)-9H-purine;

6-(2-chloro-4-methylphenyl)-8-ethyl-9-(4-heptyl)-9H-purine;

6-(2-chloro-4-methylphenyl)-9-(1-cyclopropylbutyl)-8-ethyl-9H-purine;

6-(2-chloro-4-methylphenyl)-9-(dicyclopropylmethyl)-8-ethyl-9H-purine;

6-(2-chloro-4-trifluoromethoxyphenyl)-8-ethyl-9-(2-pentyl)-9H-purine;

6-(2-chloro-4-trifluoromethoxyphenyl)-8-ethyl-9-(3-hexyl)-9H-purine;

6-(2-chloro-4-trifluoromethoxyphenyl)-9-(1-cyclopropylbutyl)-8-ethyl-9H-purine;

6-(2-chloro-4-trifluoromethoxyphenyl)-9-(1-cyclopropylpropyl)-8-ethyl-9H-purine;

6-(2-chloro-4-trifluoromethoxyphenyl)-9-(dicyclopropylmethyl)-8-ethyl-9H-purine;

6-(2-chloro-4-trifluoromethylphenyl)-8-ethyl-9-(1-hexyn-3-yl)-9H-purine;

6-(2-chloro-4-trifluoromethylphenyl)-8-ethyl-9-(1-pentyn-3-yl)-9H-purine;

6-(2-chloro-4-trifluoromethylphenyl)-8-ethyl-9-(1-pentyn-4-yl)-9H-purine;

6-(2-chloro-4-trifluoromethylphenyl)-8-ethyl-9-(1-phenyl-2-butynyl)-9H-purine;

6-(2-chloro-4-trifluoromethylphenyl)-8-ethyl-9-(2-heptyn-4-yl)-9H-purine;

6-(2-chloro-4-trifluoromethylphenyl)-8-ethyl-9-(2-hexyn-4-yl)-9H-purine;

6-(2-chloro-4-trifluoromethylphenyl)-8-ethyl-9-(2-pentyl)-9H-purine;

6-(2-chloro-4-trifluoromethylphenyl)-8-ethyl-9-(4-heptyl)-9H-purine;

6-(2-chloro-4-trifluoromethylphenyl)-8-ethyl-9-[(2-furanyl)-cyclopropylmethyl]-9H-purine;

6-(2-chloro-4-trifluoromethylphenyl)-8-ethyl-9-[1-(2-furanyl)propyl]-9H-purine;

6-(2-chloro-4-trifluoromethylphenyl)-9-(1-cyclobutylethyl)-8-ethyl-9H-purine;

6-(2-chloro-4-trifluoromethylphenyl)-9-(1-cyclopropyl-2-butynyl)-8-ethyl-9H-purine;

6-(2-chloro-4-trifluoromethylphenyl)-9-(1-cyclopropyl-2-propenyl)-8-ethyl-9H-purine;

6-(2-chloro-4-trifluoromethylphenyl)-9-(1-cyclopropylbutyl)-8-ethyl-9H-purine;

6-(2-chloro-4-trifluoromethylphenyl)-9-(1-cyclopropylpropyl)-8-ethyl-9H-purine;

6-(2-chloro-4-trifluoromethylphenyl)-9-(dicyclopropylmethyl)-8-ethyl-9H-purine;

6-(2-chloro-4-trifluoromethylphenyl)-9-(dicyclopropylmethyl)-8-methoxy-9H-purine;

6-(2-chloro-4-trifluoromethylphenyl)-9-[1-cyclopropyl-1-(2-thienyl)methyl]-8-ethyl-9H-purine;

9-(1-cyclobutylethyl)-6-(2,4-dichlorophenyl)-8-ethyl-9H-purine;

9-[1-cyclopropyl-(3-methylisoxazol-5-yl)methyl]-6-(2,4-dichlorophenyl)-8-ethyl-9H-purine;

9-(1-cyclopropyl-2-butynyl)-6-(2,4-dichlorophenyl)-8-ethyl-9H-purine;

9-(1-cyclopropyl-2-butynyl)-6-(2,4-dichlorophenyl)-8-ethyl-9H-purine;

9-(1-cyclopropyl-2-propenyl)-6-(2,4-dichloro-6-methylphenyl)-8-ethyl-9H-purine;

9-(1-cyclopropyl-2-propenyl)-6-(2,4-dichlorophenyl)-8-ethyl-9H-purine;

9-(1-cyclopropyl-2-propynyl)-8-ethyl-6-(2-trifluoromethyl-4-methoxyphenyl)-9H-purine;

9-(1-cyclopropyl-4'-fluorobenzyl)-6-(2,4-dichlorophenyl)-8-ethyl-9H-purine;

9-(1-cyclopropylbenzyl)-6-(2,4-dichlorophenyl)-8-ethyl-9H-purine;

9-(1-cyclopropylbenzyl)-8-ethyl-6-(2-trifluoromethyl-4-methoxyphenyl)-9H-purine;

9-(1-cyclopropylbutyl)-6-(2,4-dichlorophenyl)-8-ethyl-9H-purine;

9-(1-cyclopropylbutyl)-8-ethyl-6-(2,4,6-trimethylphenyl)-9H-purine;

9-(1-cyclopropylbutyl)-8-ethyl-6-(2-methyl-4,5-dimethoxyphenyl)-9H-purine;

9-(1-cyclopropylbutyl)-8-ethyl-6-(2-methyl-4-chlorophenyl)-9H-purine;

9-(1-cyclopropylbutyl)-8-ethyl-6-(2-methyl-4-methoxyphenyl)-9H-purine;

9-(1-cyclopropylbutyl)-8-ethyl-6-(2-trifluoromethyl-4-chlorophenyl)-9H-purine;

9-(1-cyclopropylbutyl)-8-ethyl-6-(2-trifluoromethyl-4-methoxyphenyl)-9H-purine;

9-(1-cyclopropylethyl)-6-(2,4-dichlorophenyl)-8-ethyl-9H-purine;

9-(1-cyclopropylethyl)-8-ethyl-6-(2-trifluoromethyl-4-chlorophenyl)-9H-purine;

9-(1-cyclopropylpentyl)-8-ethyl-6-(2-methyl-4-methoxyphenyl)-9H-purine;

9-(1-cyclopropylpropyl)-6-(2,4-dichloro-6-methylphenyl)-8-ethyl-9H-purine;

9-(1-cyclopropylpropyl)-6-(2,4-dichlorophenyl)-8-ethyl-9H-purine;

9-(1-cyclopropylpropyl)-8-ethyl-6-(2,4,6-trimethylphenyl)-9H-purine;

9-(1-cyclopropylpropyl)-8-ethyl-6-(2-trifluoromethyl-4-chlorophenyl)-9H-purine;

6-(2,4-dichloro-5-fluorophenyl)-9-(dicyclopropylmethyl)-8-ethyl-9H-purine;

6-(2,4-dichloro-6-methylphenyl)-8-ethyl-9-(2-penten-3-yl)-9H-purine;

6-(2,4-dichloro-6-methylphenyl)-9-(dicyclopropylmethyl)-8-ethyl-9H-purine;

6-(2,4-dichlorophenyl)-8-ethyl-9-(1-hexyn-3-yl)-9H-purine;

6-(2,4-dichlorophenyl)-8-ethyl-9-(1-methoxycarbonylpropyl)-9H-purine;

6-(2,4-dichlorophenyl)-8-ethyl-9-(1-phenyl-2-butynyl)-9H-purine;

6-(2,4-dichlorophenyl)-8-ethyl-9-(2-heptyn-4-yl)-9H-purine;

6-(2,4-dichlorophenyl)-8-ethyl-9-(2-hexyl)-9H-purine;

6-(2,4-dichlorophenyl)-8-ethyl-9-(2-hexyn-4-yl)-9H-purine;

6-(2,4-dichlorophenyl)-8-ethyl-9-(2-penten-3-yl)-9H-purine;

6-(2,4-dichlorophenyl)-8-ethyl-9-(2-pentyl)-9H-purine;

6-(2,4-dichlorophenyl)-8-ethyl-9-(3-heptyl)-9H-purine;

6-(2,4-.dichlorophenyl)-8-ethyl-9-(3-hexyl)-9H-purine;

6-(2,4-dichlorophenyl)-8-ethyl-9-(3-pentyl)-9H-purine;

6-(2,4-dichlorophenyl)-8-ethyl-9-(4-heptyl)-9H-purine;

6-(2,4-dichlorophenyl)-8-ethyl-9-[1-(2-methylcyclopropyl)ethyl]-9H-purine;

6-(2,4-dichlorophenyl)-9-(dicyclopropylmethyl)-8-ethyl-9H-purine;

6-(2,4-dichlorophenyl)-9-(dicyclopropylmethyl)-8-ethyl-9H-purine;

6-(2,4-dichlorophenyl)-9-(dicyclopropylmethyl)-8-methoxy-9H-purine;

6-(2,4-dichlorophenyl)-9-(diphenylmethyl)-8-ethyl-9H-purine;

9-(dicyclopropylmethyl)-6-(2,4-dimethylphenyl)-8-ethyl-9H-purine;

9-(dicyclopropylmethyl)-6-(2,4-dimethylphenyl)-8-ethyl-9H-purine;

9-(dicyclopropylmethyl)-6-(2,6-dimethoxypyridin-3-yl)-8-methoxy-9H-purine;

9-(dicyclopropylmethyl)-8-ethyl-6-(2,4,5-trichlorophenyl)-9H-purine;

9-(dicyclopropylmethyl)-8-ethyl-6-(2-methoxy-4-trifluoromethylphenyl)-9H-purine;

9-(dicyclopropylmethyl)-8-ethyl-6-(2-methyl-4,5-dimethoxyphenyl)-9H-purine;

9-(dicyclopropylmethyl)-8-ethyl-6-(2-methyl-4-chlorophenyl)-9H-purine;

9-(dicyclopropylmethyl)-8-ethyl-6-(2-methyl-4-dimethylaminophenyl)-9H-purine;

9-(dicyclopropylmethyl)-8-ethyl-6-(2-methyl-4-methoxy-5-chlorophenyl)-9H-purine;

9-(dicyclopropylmethyl)-8-ethyl-6-(2-methyl-4-methoxy-5-fluorophenyl)-9H-purine;

9-(dicyclopropylmethyl)-8-ethyl-6-(2-chloro-4-methoxy-5-fluorophenyl)-9H-purine;

9-(dicyclopropylmethyl)-8-ethyl-6-(2-methyl-4-methoxyphenyl)-9H-purine;

9-(dicyclopropylmethyl)-8-ethyl-6-(2-trifluoromethyl-4-chlorophenyl)-9H-purine;

9-(dicyclopropylmethyl)-8-ethyl-6-(2-trifluoromethyl-4-methoxyphenyl)-9H-purine;

9-(dicyclopropylmethyl)-8-ethyl-6-(2-trifluoromethyl-4-propyloxyphenyl)-9H-purine;

6-(2,6-dimethoxypyridin-3-yl)-8-ethyl-9-(2-pentyl)-9H-purine;

6-(2,4-dimethylphenyl)-8-ethyl-9-(2-pentyl)-9H-purine;

8-ethyl-6-(2-methyl-4,5-dimethoxyphenyl)-9-(2-pentyl)-9H-purine;

8-ethyl-6-(2-methyl-4,5-dimethoxyphenyl)-9-(3-pentyl)-9H-purine;

8-ethyl-9-(1-hexen-3-yl)-6-(2-methyl-4,5-dimethoxyphenyl)-9H-purine;

8-ethyl-9-(1-hexen-3-yl)-6-(2-trifluoromethyl-4-methoxyphenyl)-9H-purine;

8-ethyl-9-(2-hexyl)-6-(2-trifluoromethyl-4-methoxyphenyl)-9H-purine;

8-ethyl-9-(2-pentyl)-6-(2-trifluoromethyl-4-methoxyphenyl)-9H-purine;

8-ethyl-9-(3-hexyl)-6-(2-methyl-4-methoxyphenyl)-9H-purine;

8-ethyl-9-(3-hexyl)-6-(2-trifluoromethyl-4-methoxyphenyl)-9H-purine;

8-ethyl-9-(3-pentyl)-6-(2-trifluoromethyl-4-chlorophenyl)-9H-purine;

8-ethyl-9-(4-heptyl)-6-(2-methyl-4-chlorophenyl)-9H-purine;

8-ethyl-9-(4-heptyl)-6-(2-methyl-4-methoxyphenyl)-9H-purine;

8-ethyl-9-(4-heptyl)-6-(2-trifluoromethyl-4-chlorophenyl)-9H-purine;

8-ethyl-9-(4-b eptyl)-6-(2-trifluoromethyl-4-methoxyphenyl)-9H-purine; and 9-(dicyclopropylmethyl)-8-ethyl-6-(2-methyl-6-methoxy-3-pyridyl)-9H-purine;

or a pharmaceutically acceptable salt form thereof.

[4j] In another more preferred embodiment, the present invention provides a novel compound of formula Ic, wherein:

$R^1$ is $C_{3-8}$ cycloalkyl;

$R^1$ is substituted with 0–1 substituents selected from the group —CN, —S(O)$_n$R$^{14b}$, —COR$^{13a}$, —CO$_2$R$^{13a}$, —NR$^{15a}$COR$^{13a}$, —N(COR$^{13a}$)$_2$, NR$^{15a}$CONR$^{13a}$R$^{16a}$, —NR$^{15a}$CO$_2$R$^{14b}$, —CONR$^{13a}$R$^{16a}$, 1-morpholinyl, 1-piperidinyl, 1-piperazinyl, and $C_{4-8}$ cycloalkyl, wherein 0–1 carbon atoms in the $C_{4-8}$ cycloalkyl is replaced by a group selected from the group —O—, —S(O)$_n$—, —NR$^{13a}$—, —NCO$_2$R$^{14b}$—, —NCOR$^{14b}$— and —NSO$_2$R$^{14b}$—, and wherein N$_4$ in 1-piperazinyl is substituted with 0–1 substituents selected from the group R$^{13a}$, CO$_2$R$^{14b}$, COR$^{14b}$ and SO$_2$R$^{14b}$; and, $R^1$ is also substituted with 0–3 substituents independently selected at each occurrence from the group R$^{1a}$, R$^{1b}$, R$^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, $C_{1-2}$ alkoxy-$C_{1-2}$ alkyl, and —NR$^{13a}$R$^{16a}$.

[4k] In another even more preferred embodiment, the present invention provides a novel compound of formula Ic, wherein:

X is selected from the group O, S(O)$_n$ and a bond;

n is 0, 1 or 2;

$R^1$ is selected from the group cyclopropyl, cyclobutyl, and cyclopentyl;

$R^1$ is substituted with 0–1 substituents selected from the group —CN, —S(O)$_n$R$^{14b}$, —COR$^{13a}$, —CO$_2$R$^{13a}$, and $C_{4-8}$ cycloalkyl, wherein one carbon atom in the $C_{4-8}$ cycloalkyl is replaced by a group selected from the group —O—, —S(O)$_n$—, —NR$^{13a}$—, —NCO$_2$R$^{14b}$—, —NCOR$^{14b}$— and —NSO$_2$R$^{14b}$—;

$R^1$ is also substituted with 0–2 substituents independently selected at each occurrence from the group R$^{1a}$, R$^{1b}$, $C_{1-6}$ alkyl, $C_{2-8}$ alkenyl, $C_{2-8}$ alkynyl, Br, Cl, F, CF$_3$, CF$_2$CF$_3$, —OR$^{13a}$, $C_{1-2}$ alkoxy-$C_{1-2}$ alkyl, and —NR$^{13a}$R$^{16a}$;

$R^{1a}$ is aryl and is selected from the group phenyl and indanyl, each R$^{1a}$ being substituted with 0–1 —OR$^{17}$ and 0–5 substituents independently selected at each occurrence from the group $C_{1-4}$ alkyl, $C_{3-6}$ cycloalkyl, Br, Cl, F, $C_{1-4}$ haloalkyl, —CN, —S(O)$_n$R$^{18}$, —COR$^{17}$, —NR$^{17a}$R$^{19a}$, and —CONR$^{17a}$R$^{19a}$;

$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, CF$_3$, —CN, —OR$^{17}$, —S(O)$_m$R$^{18}$, —COR$^{17}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$;

$R^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

$R^9$ is independently selected at each occurrence from the group H, $C_{1-4}$ alkyl and $C_{3-8}$ cycloalkyl;

$R^3$ is selected from the group H, Br, Cl, F, —CN, $C_{1-4}$ alkyl, $C_{3-6}$ cycloalkyl, $C_{1-4}$ alkoxy, NH$_2$, $C_{1-4}$ alkylamino, and ($C_{1-4}$ alkyl)$_2$-amino;

$R^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)—, and heteroaryl($C_{1-2}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)—, and heteroaryl($C_{1-2}$ alkyl)—;

$R^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

$R^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$, $R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an NR$^{17}$R$^{19}$ moiety, R$^{17}$ and R$^{19}$ taken together form 1-pyrrolidinyl, 1-morpholinyl, 1-piperidinyl or 1-piperazinyl, wherein N$_4$ in 1-piperazinyl is substituted with 0–1 substituents selected from the group R$^{13}$, CO$_2$R$^{14}$, COR$^{14}$ and SO$_2$R$^{14}$, $R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, —OR$^{17}$, Br, Cl, F, $C_{1-4}$ haloalkyl, —CN, —S(O)$_n$R$^{18}$, —COR$^{17}$, —CO$_2$R$^{17}$, —NR$^{15}$COR$^{17}$, —NR$^{15}$CO$_2$R$^{18}$, —NR$^{17}$R$^{19}$, and —CONR$^{17}$R$^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —$OR^{17}$, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

[4l] In another still more preferred embodiment, the present invention provides a novel compound of formula Ic, wherein:

X is selected from the group C, S and a bond;

$R^1$ is substituted with 0–1 substituents selected from the group —CN, $OC_2R^{13a}$, and $C_{4-8}$ cycloalkyl, wherein 0–1 carbon atoms in the $C_{4-8}$ cycloalkyl is replaced by a group selected from the group —O—, —$S(O)_n$—, and —$NR^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, $CF_3$, —$OR^{13a}$, —OH, —$OCH_3$, —$OCH_2CH_3$, —$OH_2OCH_3$, —$CH_2CH_2CH_3$, and $NR^{13a}R^{16a}$;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, $CH(CH_3)_2$, and $CH_2CH_2CH_3$;

$R^3$ is selected from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(Q)N(CH_3)_2$ and each heteroaryl being substituted on any nitrogen atom with 0–1 substituents selected from the group $CH_3$, $CO_2CH_3$, $COCH_3$ and $SO_2CH_3$.

[4m] In another further preferred embodiment, the present invention provides a novel compound of formula Ic, wherein:

$R^1$ is substituted with 0–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH≡CH, —CH≡$C(CH_3)$, —$CH_2OCH_3$, —$CH_2CH_2OCH_3$, F, and $CF_3$;

$R^{1a}$ is phenyl substituted with 0–1 substituents selected from $OCH_3$, $OCH_2CH_3$, $OCH(CH_3)_2$, $OCH_2CH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, and $CH(CH_3)_2$;

$R^3$ is selected from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $_{OCH2}CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[4n] In another even further preferred embodiment, the present invention provides a novel compound of formula Ic, wherein:

$R^1$ is substituted with 0–2 substituents independently selected at each occurrence from the group $R^{1a}$, $CH_3$, $CH_2CH_3$, $CH(CH_3)_2$, $CH_2CH_2CH_3$, —$(CH_2)_3CH_3$, —$CH_2OCH_3$, —$CH_2CH_2OCH_3$, F, and $CF_3$; and, $R^{1a}$ is phenyl substituted with 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$.

[4o] In another still further preferred embodiment, the present invention provides a novel compound of formula Ic, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[4p] In another still further preferred embodiment, the present invention provides a novel compound of formula Ic, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[4q] In another more preferred embodiment, the present invention provides a novel compound of formula Ic, wherein:

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl and $C_{1-4}$ alkoxy-$C_{1-4}$ alkyl;

$R^1$ is substituted with a $C_{3-8}$ cycloalkyl group, wherein 0–1 carbon atoms in the $C_{4-8}$ cycloalkyl group is replaced by a group selected from the group —O—, —S(O)$_n$—, —NR$^{13a}$, —NCO$_2$R$^{14b}$—, —NCOR$^{14b}$— and —NSO$_2$R$^{14b}$—;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, —NR$^{13a}$R$^{16a}$, $C_{1-2}$ alkoxy-$C_{1-2}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is selected from the group phenyl, naphthyl, indanyl and indenyl, each $R^{1a}$ being substituted with 0–1 —OR$^{17}$ and 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, SH, —S(O)$_n$R$^{18}$, —COR$^{17}$, —OC(O)R$^{18}$, —NR$^{15a}$COR$^{17}$, —N(COR$^{17}$)$_2$, —NR$^{15a}$CONR$^{17a}$R$^{19a}$, —NR$^{15a}$CO$_2$R$^{18}$, —NR$^{17a}$R$^{19a}$, and —CONR$^{17a}$R$^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR$^{17}$, SH, —S(O)$_m$R$^{18}$, —COR$^{17}$, —OC(O)R$^{18}$, —NR$^{15a}$COR$^{17}$, —N(COR$^{17}$)$_2$, —NR$^{15a}$CONR$^{17a}$R$^{19a}$, —NR$^{15a}$CO$_2$R, —NR$^{17a}$R$^{19a}$ and —CONR$^{17a}$R$^{19a}$ and each heteroaryl being substituted on any nitrogen atom with 0–1 substituents selected from the group $R^{15a}$, $CO_2R^{14b}$, $COR^{14b}$ and $SO_2R^{14b}$; and, $R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR$^{13a}$, SH, —S(O)$_n$R$^{14b}$, —COR$^{13a}$, —OC(O)R$^{14b}$, —NR$^{15a}$COR$^{13a}$, —N(COR$^{13a}$)$_2$, —NR$^{15a}$CONR$^{13a}$R$^{16a}$, —NR$^{15a}$CO$_2$R$^{14b}$, —NR$^{13a}$R$^{16a}$, and —CONR$^{13a}$R$^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized.

[4r] In another even more preferred embodiment, the present invention provides a novel compound of formula Ic, wherein:

X is selected from the group O, $S(O)_n$ and a bond;

n is 0, 1 or 2;

$R^1$ is selected from the group $C_{1-6}$ alkyl, $C_{2-6}$ alkenyl, $C_{2-6}$ alkynyl, and $C_{3-8}$ cycloalkyl;

$R^1$ is substituted with a $C_{3-6}$ cycloalkyl group, wherein 0–1 carbon atoms in the $C_{4-6}$ cycloalkyl group is replaced by a group selected from the group —O—, —S(O)$_n$—, and —NR$^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, $CF_2CF_3$, —OR$^{13a}$, —NR$^{13a}$R$^{16a}$, $C_{1-2}$ alkoxy-$C_{1-2}$ alkyl, and $C_{3-6}$ cycloalkyl which is substituted with 0–1 $R^9$ and in which 0–1 carbons of $C_{4-8}$ cycloalkyl is replaced by —O—;

$R^{1a}$ is aryl and is selected from the group phenyl and indanyl, each $R^{1a}$ being substituted with 0–1 —OR$^{17}$ and 0–5 substituents independently selected at each occurrence from the group $C_{1-4}$ alkyl, $C_{3-6}$ cycloalkyl, Br, Cl, F, $C_{1-4}$ haloalkyl, —CN, —S(O)$_n$R$^{18}$, —COR$^{17}$, —NR$^{17a}$R$^{19a}$, and CONR$^{17a}$R$^{19a}$;

$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, $CF_3$, —CN, —OR$^{17}$, —S(O)$_m$R$^{18}$, —COR$^{17}$, —NR$^{17a}$R$^{19a}$, and —CONR$^{17a}$R$^{19}$a and each heteroaryl being substituted on any nitrogen atom with 0–1 substituents selected from the group $R^{15a}$, $CO_2R^{14b}$, $COR^{14b}$ and $SO_2R^{14b}$;

$R^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

$R^9$ is independently selected at each occurrence from the group H, $C_{1-4}$ alkyl and $C_{3-8}$ cycloalkyl;

$R^3$ is selected from the group H, Br, Cl, F, —CN, $C_{1-4}$ alkyl, $C_{3-6}$ cycloalkyl, $C_{1-4}$ alkoxy, $NH_2$, $C_{1-4}$ alkylamino, and $(C_{1-4}$ alkyl$)_2$-amino;

$R^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl $(C_{1-2}$ alkyl)—, and heteroaryl$(C_{1-2}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl $(C_{1-2}$ alkyl)—, and heteroaryl$(C_{1-2}$ alkyl)—;

$R^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

$R^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$, $R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, —$OR^{17}$, Br, Cl, F, $C_{1-4}$ haloalkyl, —CN, —$S(O)_nR^{18}$, —$COR^{17}$, —$CO_2R^{17}$, —$NR^{15}COR^{17}$, —$NR^{15}CO_2R^{18}$, —$NR^{17}R^{19}$, and —$CONR^{17}R^{19}$; and, heteroaryl is independently selected at each occurrence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —$OR^{17}$, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$;

[4s] In another still more preferred embodiment, the present invention provides a novel compound of formula Ic, wherein:

X is selected from the group O, S and a bond;

$R^1$ is $C_{1-6}$ alkyl;

$R^1$ is substituted with a $C_{3-6}$ cycloalkyl, wherein 0–1 carbon atoms in the $C_{4-4}$ cycloalkyl is replaced by a group selected from the group —O—, —$S(O)_n$—, and —$NR^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, F, $CF_3$, —$OR^{13a}$, —$NR^{13a}R^{16a}$, —$CH_2OCH_3$, —$CH_2CH_2OCH_3$, and $C_{3-6}$ cycloalkyl which is substituted with 0–1 $CH_3$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, $CH(CH_3)_2$, and $CH_2CH_2CH_3$;

$R^3$ is selected from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurrence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(C)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[4t] In another further preferred embodiment, the present invention provides a novel compound of formula Ic, wherein:

$R^1$ is (cyclopropyl)$C_1$ alkyl or (cyclobutyl)$C_1$ alkyl;

$R^1$ is substituted with 1–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3$$CH_3$, —CH=$CH_2$, —CH=$CH(CH_3)$, —CH=CH, —CH≡$C(CH_3)$, —$CH_2OCH_3$, —$CH_2CH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, and $CH(CH_3)_2$;

$R^3$ is selected from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[4u] In another even further preferred embodiment, the present invention provides a novel compound of formula Ic, wherein:

$R^1$ is (cyclopropyl)$C_1$ alkyl or (cyclobutyl)$C_1$ alkyl;

$R^1$ is substituted with 1–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH≡CH, —CH≡$C(CH_3)$, —$CH_2OCH_3$, —$CH_2CH_2OCH_3$, F, $CF_3$, cyclopropyl, and $CH_3$-cyclopropyl;

$R^{1a}$ is-phenyl substituted with 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$.

[4v] In another further preferred embodiment, the present invention provides a novel compound of formula Ic, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[4w] In another further preferred embodiment, the present invention provides a novel compound of formula Ic, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[51] In a third embodiment, the present invention provides a novel pharmaceutical composition, comprising: a pharmaceutically acceptable carrier arid a therapeutically effective amount of a compound of formula (I):

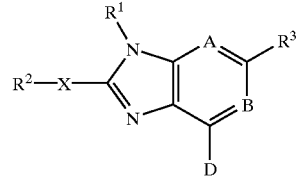

(I)

or a stereoisomer or pharmaceutically acceptable salt form thereof, wherein:

A is N or C—$R^7$;

B is N or C—$R^8$;

provided that at least one of the groups A and B is N;

D is an aryl or heteroaryl group attached through an unsaturated carbon atom;

X is selected from the group CH—$R^9$, N—$R^{10}$, O, $S(O)_n$ and a bond;

n is 0, 1 or 2;

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$—$C_{1-10}$ alkyl, —$SO_2$—$R^{1a}$, and —$SO_2$—$R^{1b}$;

$R^1$ is substituted with 0–1 substituents selected from the group —CN, —$S(O)_nR^{14b}$, —$COR^{13a}$, —$CO_2R^{13a}$, —$NR^{15a}COR^{13a}$, —$N(COR^{13a})_2$, —$NR^{15a}CONR^{13a}R^{16a}$, —$NR^{15a}CO_2R^{14b}$, —$CONR^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —$S(O)_n$—, —$NR^{13a}$—, —$NCO_2R^{14b}$—, —$NCOR^{14b}$— and —$NSO_2R^{14b}$— and wherein $N_4$ in 1-piperazinyl is substituted with 0–1 substituents selected from the group $R^{13a}$, $CO_2R^{14b}$, $COR^{14b}$ and $SO_2R^{14b}$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —$OR^{13a}$, —$NR^{13a}R^{16a}$, and $C_{3-8}$ cycloalkyl which is substituted with 0–1 $R^9$ and in which 0–1 carbons of $C_{4-8}$ cycloalkyl is replaced by —O—;

provided that $R^1$ is other than:
(a) a 3-cyclopropyl-3-methoxypropyl group;
(b) an unsubstituted-(alkoxy)methyl group; and,
(c) a 1-hydroxyalkyl group;

also provided that when $R^1$ alkyl substituted with OH, then the carbon adjacent to the ring N is other than $CH_2$;

$R^{1a}$ is aryl and is selected from the group phenyl, naphthyl, indanyl and indenyl, each $R^{1a}$ being substituted with 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_nR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_nR^{18}$, —$COR^{17}$, —$OC(O)R^{18}$, —$NR^{15a}COR^{17}$, —$N(COR^{17})_2$, $NR^{15a}CONR^{17a}R^{19a}$, —$NR^{15a}CO_2R^{18}$, —$NR^{17a}R^{19a}$, and —$CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_nR^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^3$, $R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $(C_{1-4}$ alkyl$)_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and $(C_{1-4}$ alkyl$)_2$amino;

provided that when $R^1$ is unsubstituted $C_{1-1}$ o alkyl, then $R^3$ is other than substituted or unsubstituted phenyl;

$R^9$ and $R^{10}$ are independently selected at each occurrence from the group H, $C_{1-4}$ alkyl, $C_{3-8}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)— and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl; and, heteroaryl is independently selected at each occurrence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR$^{17}$, SH, —S(O)$_m$R$^{18}$, —COR$^{17}$, —CO$_2$R$^{17}$, —OC(O)R$^{18}$, —NR$^{15}$COR$^{17}$, —N(COR$^{17}$)$_2$, —NR$^{15}$CONR$^{17}$R$^{19}$, —NR$^{15}$CO$_2$R$^{18}$, —NR$^{17}$R$^{19}$, and —CONR$^{17}$R$^{19}$ and each heteroaryl being substituted on any nitrogen atom with 0–1 substituents selected from the group R$^{15}$, CO$_2$R$^{14a}$, COR$^{14a}$ and SO$_2$R$^{14a}$.

[6] In a second embodiment, the present invention provides a novel method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals, comprising: administering to the mammal a therapeutically effective amount of a compound of formula (I):

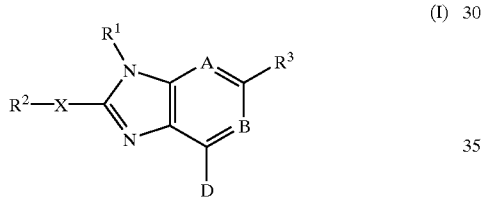

or a stereoisomer or pharmaceutically acceptable salt form thereof, wherein:

A is N or C—R$^7$;

B is N or C—R$^8$;

provided that at least one of the groups A and B is N;

D is an aryl or heteroaryl group attached through an unsaturated carbon atom;

X is selected from the group CH—R$^9$, N—R$^{10}$, O, S(O)$_n$ and a bond;

n is 0, 1 or 2;

R$^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —SO$_2$—$C_{1-10}$ alkyl, —SO$_2$—R$^{1a}$, and —SO$_2$—R$^{1b}$;

R$^1$ is substituted with 0–1 substituents selected from the group —CN, —S(O)$_n$R$^{14b}$, —COR$^{13a}$, —CO$_2$R$^{13a}$, —NR$^{15a}$COR$^{13a}$, —N(COR$^{13a}$)$_2$, —NR$^{15a}$CONR$^{13a}$R$^{16a}$, —NR$^{15a}$CO$_2$R$^{14b}$, —CONR$^{13a}$R$^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —S(O)$_n$—, —NR$^{13a}$, —NCO$_2$R$^{14b}$—, —NCOR$^{14}$— and —NSO$_2$R$^{14b}$—, and wherein N$_4$ in 1-piperazinyl is substituted with 0–1 substituents selected from the group R$^{13a}$, CO$_2$R$^{14b}$, COR$^{14b}$ and SO$_2$R$^{14b}$;

R$^1$ is also substituted with 0–3 substituents independently selected at each occurrence from the group R$^{1a}$, R$^{1b}$, R$^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, —NR$^{13a}$R$^{16a}$, and $C_{3-8}$ cycloalkyl which is substituted with 0–1 R$^9$ and in which 0–1 carbons of $C_{4-8}$ cycloalkyl is replaced by —O—;

provided that R$^1$ is other than:
(a) a 3-cyclopropyl-3-methoxypropyl group;
(b) an unsubstituted-(alkoxy)methyl group; and,
(c) a 1-hydroxyalkyl group;

also provided that when R$^1$ alkyl substituted with OH, then the carbon adjacent to the ring N is other than CH$_2$;

R$^{1a}$ is aryl and is selected from the group phenyl, naphthyl, indanyl and indenyl, each R$^{1a}$ being substituted with 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, —OR$^{17}$, SH, —S(O)$_n$R$^{18}$, —COR$^{17}$, —OC(O)R$^{18}$, —NR$^{15a}$COR$^{17}$, —N(COR$^{17}$)$_2$, —NR$^{15a}$CONR$^{17a}$R$^{19a}$, —NR$^{15a}$CO$_2$R$^8$, —NR$^{17a}$R$^{19a}$, and —CONR$^{17a}$R$^{19a}$;

R$^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{16}$ alkyl, $C_{3-6}$ cycloalkyl, Br, Cl, F, I, $C_{1-4}$ haloalkyl, —CN, nitro, —OR$^{17}$, SH, —S(O)$_m$R$^{18}$, —COR$^{17}$, —OC(O)R$^{18}$, —NR$^{15a}$COR$^{17}$, —N(COR$^{17}$)$_2$, —NR$^{15a}$CONR$^{17a}$R$^{19a}$, —NR$^{15a}$CO$_2$R$^{18}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$;

R$^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR$^{13a}$, SH, —S(O)$_n$R$^{14b}$, —COR$^{13a}$, —OC(O)R$^{14b}$, —NR$^{15a}$COR$^{13a}$, —N(COR$^{13a}$)$_2$, —NR$^{15a}$CONR$^{13a}$R$^{16a}$, —NR$^{15a}$CO$_2$R$^{14b}$, —NR$^{13a}$R$^{16a}$, and —CONR$^{13a}$R$^{16a}$ and each heterocyclyl being substituted on any nitrogen atom with 0–1 substituents selected from the group R$^{13a}$, CO$_2$R$^{14b}$, COR$^{14b}$ and SO$_2$R$^{14b}$ and wherein any sulfur atom is optionally monooxidized or dioxidized;

R$^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively R$^2$, in the case where X is a bond, is selected from the group —CN, CF$_3$ and C$_2$F$_5$;

R$^3$, R$^7$ and R$^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, (C$_{1-4}$ alkyl)$_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and $(C_{1-4}$ alkyl$)_2$amino;

provided that when $R^1$ is unsubstituted $C_{1-10}$ alkyl, then $R^3$ is other than substituted or unsubstituted phenyl;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)— and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence form the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein, $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein, $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl $R^{13}$, $CO_2R^{14}$, $COR^{14}$ and $SO_2R^{14}$; being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_n$ $R^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl; and, heteroaryl is independently selected at each occurrence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

In another preferred embodiment, $R^1$ is other than a cyclohexyl-$(CH_2)_{1, 2, 3, 4, 5, 6, 7, 8, 9, \text{ or } 10}$— group.

In another preferred embodiment, $R^1$ is other than an aryl-$(CH_2)_{1, 2, 3, 4, 5, 6, 7, 8, 9, \text{ or } 10}$— group, wherein the aryl group is substituted or unsubstituted.

In another preferred embodiment, $R^1$ is other than a heteroaryl-$(CH_2)_{1, 2, 3, 4, 5, 6, 7, 8, 9, \text{ or } 10}$— group, wherein the heteroaryl group is substituted or unsubstituted.

In another preferred embodiment, $R^1$ is other than a heterocyclyl-$(CH_2)_{1, 2, 3, 4, 5, 6, 7, 8, 9, \text{ or } 10}$— group, wherein the heterocyclyl group is substituted or unsubstituted.

In another preferred embodiment, when D is imidazole or triazole, $R^1$ is other than unsubstituted $C_{1, 2, 3, 4, 5, 6, 7, 8, 9,}$ or 10 linear or branched alkyl or $C_{3, 4, 5, 6, 7,}$ or 8 cycloalkyl.

In another preferred embodiment, $R^{1a}$ is not substituted with $OR^{17}$.

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. The term "alkyl" includes both branched and straight-chain alkyl having the specified number of carbon atoms. "Alkenyl" includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-,bi- or polycyclic ring systems, such as cyclopropyl, cyclobutyl, cyclopentyl, cyclohexyl, and so forth. "Halo" or "halogen, includes fluoro, chloro, bromo, and iodo.

The term 'substituted", as used herein, means that one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "pharmaceutically acceptable salts" includes acid or base salts of the compounds of formulas (I) and (II). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Reminaton's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) or (II) in vivo when such prodrug is administered to a mammalian subject. Prodrugs of the compounds of formula (I) and (II) are prepared by modifying functional groups present in the compounds in such a way that the modifications are cleaved, either in routine manipulation or in vivo, to the parent compounds. Prodrugs include compounds wherein hydroxy, amine, or sulfhydryl groups are abonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and (II); and the like.

The term "therapeutically effective amount" of a compound of this invention means an amount effective to antagonize abnormal level of CRF or treat the symptoms of affective disorder, anxiety, depression, immunological, cardiovascular or heart-related diseases and colonic hypersensitivity associated with psychopathological disturbance and stress in a host.

Synthesis

Compounds of formula (I) can be prepared by the following synthetic routes and schemes. Where a detailed description is not provided, it is assumed that those skilled in the art of organic synthesis will readily understand the meaning.

Synthesis of compounds of formula (I) may be prepared by the reaction shown in Scheme 1.

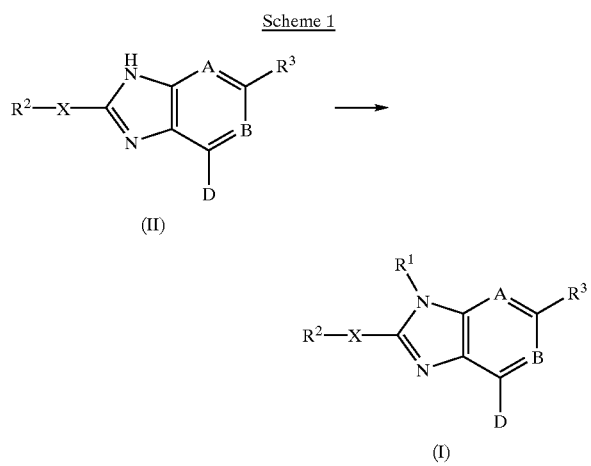

A compound of formula (II) can be alkylated on the imidazole nitrogen atom with an appropriate reagent. Typical conditions for this transformation include treatment of compound (II) with a base, such as sodium hydride, potassium tert-butoxide, sodium hexamethyldisilazide, etc., followed by a reagent J—R$^1$, where J represents a halide (chloride, bromide or iodide) or psuedohalide (tosylate, mesylate, triflate, etc.), at an appropriate temperature (0° C. or room temperature, with warming if necessary) in a solvent such as tetrahydrofuran, dimethylformamide or dimethylsulfoxide. Alternatively, this reaction may be performed using the Mitsunobu conditions (Mitsunobu, *Synthesis* 1981, pp. 1–28).The compound (II) is treated with an alcohol compound R$^1$OH, along with a phosphine (triphenyl, tributyl, etc.) and a phosphine-activating reagent such as diethyl azodicarboxylate.

Compounds of Formula (II) may be prepared according to the route shown in Scheme 2.

Scheme 2

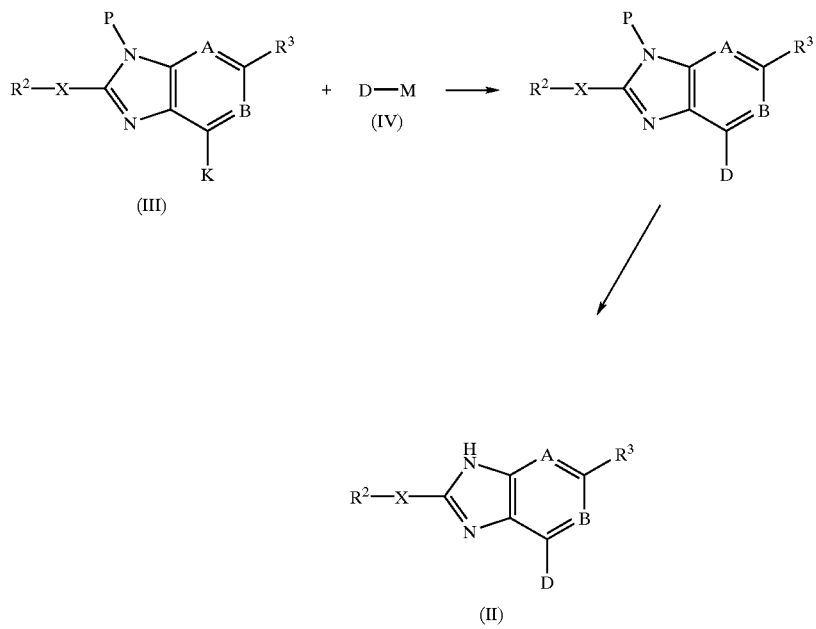

A compound of Formula (III) may be coupled to an aromatic compound of Formula (IV), with elimination of the elements of M—K. For compound (III), K represents a halide, psuedohalide (such as mesylate, tosylate or triflate), or thiomethyl, and P represents a protecting group (if the conditions of the reaction warrant protection of the imidazole N—H; otherwise, P can be H). Suitable P groups may include benzyl, 4-methoxybenzyl, methoxymethyl, trimethylsilylethoxymethyl, tert-butoxycarbonyl or benzyloxycarbonyl. For compound (IV), M represents groups such as lithium, bromomagnesium, chlorozinc, (dihydroxy) boron, (dialkoxy)boron, trialkylstannyl and the like. The coupling reaction may be performed in the presence of an appropriate catalyst, such as tetrakis(triphenylphosphine) palladium, bis(triphenylphosphine)palladium dichloride, [1,3-bis(diphenylphosphino)propane]nickel dichloride, etc. Two particularly useful methods involve the coupling of chloroheterocycles with in-situ-prepared arylzinc reagents according to the method of Negishi et al. (*J. Org. Chem.* 1977, 42, 1821), and the coupling with arylboronic esters according to the method of Suzuki et al. (*Chem. Letters* 1989, 1405). Appropriate solvents for reactions of this type usually include tetrahydrofuran, diethyl ether, dimethylformamide, or dimethylsulfoxide. Typical temperatures range from ambient up to the boiling point of the solvent. Once coupled, the P group may be removed to afford compound (II). Conditions for the removal of the protecting groups are well known to those familiar to the art of organic synthesis; e.g. hydrogenation to remove benzyl or benzyloxycarbonyl, a fluoride source (such as tetrabutylammonium fluoride) to remove silylethoxymethyl, an acid source (such as trifluoroacetic acid) to remove tert-butoxycarbonyl or 4-methoxybenzyl, etc.

Compounds of formula (III) can be prepared according to the plan shown in Scheme 3.

Scheme 3

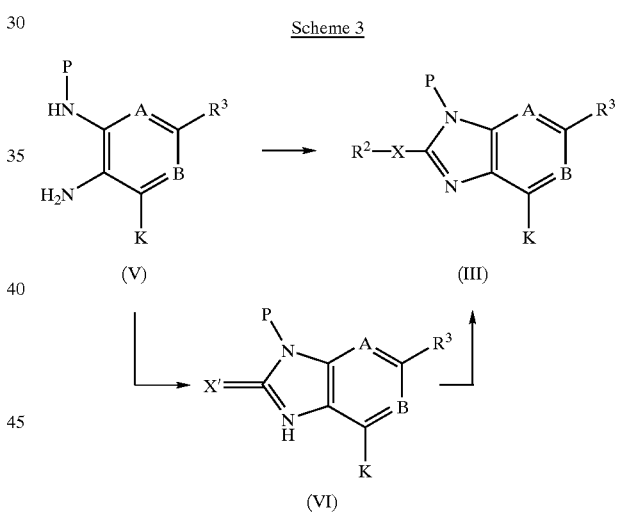

A diamine compound of formula (V) (in this case, P is a group such as benzyl, which can be introduced already attached to the nitrogen atom; otherwise, P could represent H initially, and another protecting group being introduced in a later step) is used in a cyclocondensation reaction to make the imidazole ring. The conditions used will, of course, depend on the X group chosen, and may include the intermediacy of the compound (VI). A review of imidazole-forming reactions may be found in *Comprehensive Heterocyclic Chemistry* (Pergamon Press, 1984) vol. 5, pp. 457–498.

Preparation of compounds of formula (V) wherein both A and B are nitrogen atoms may proceed according to the route of Scheme 4.

Scheme 4

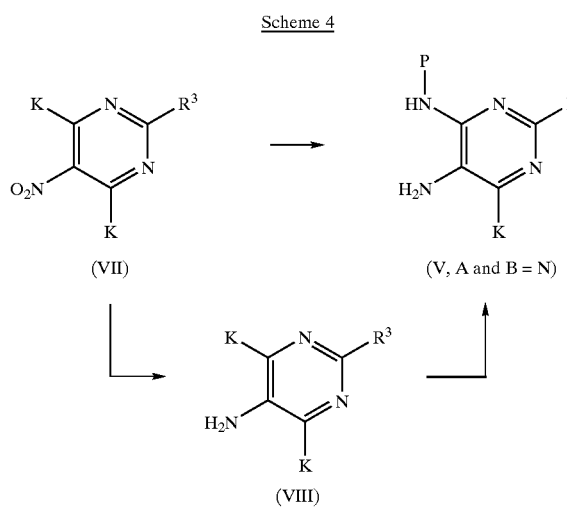

A compound of formula (VII) may be available from commercial sources, particularly for K=chloride. Compounds bearing psuedohalide K groups may be available from the corresponding dihydroxy compounds by treatment with an appropriate activating reagent, such as an organosulfonic anhydride or sulfonyl chloride. Compound (VII) may be converted to (V) by either (i) monoalkylation with a compound P—$NH_2$, followed by reduction of the nitro group; (ii) reduction of the nitro group, to give an amine compound of formula (VIII), followed by monoalkylation with a compound P—$NH_2$; or (iii) use of a source of ammonia (ammonia gas, ammonium hydroxide, etc.) in either route, followed by protection of the amine group with the group P. Pyrimidine chemistry of this type is well represented in the literature, and is reviewed in *Comprehensive Heterocyclic Chemistry*, vol. 6. Alkylation of chloropyrimidines with amine compounds can be accomplished under either acidic (e.g. HCl or acetic) or basic (trialkylamines, potassium tert-butoxide, etc.) conditions. Nitro groups in compounds of this type can be reduced to amino groups using one of any number of conditions, including catalytic hydrogenation, tin dichloride, sodium dithionite, zinc metal, iron powder, etc.

Preparation of compounds of formula (V) wherein either A or B represent nitrogen atoms is shown in Scheme 5.

Scheme 5

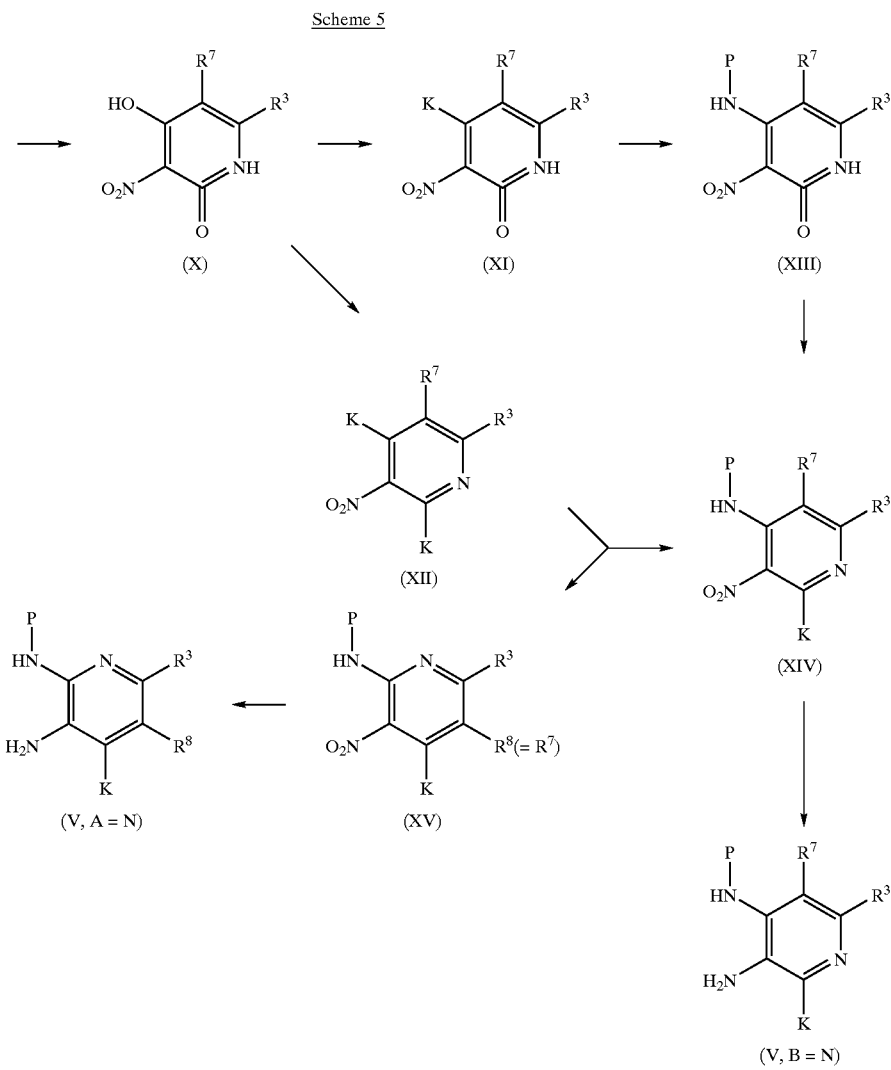

An hydroxypyridone compound of formula (IX) can be nitrated to give compound (X) employing conditions such as concentrated or fuming nitric acid, optionally in the presence of concentrated sulfuric or acetic acid. The hydroxypyridone can be selectively monoactivated with a K group to give a compound of formula (XI); one method to do this involves treatment of the dicyclohexylamine salt of compound (X) with phosphorus oxychloride to give (XI) wherein K=Cl. Alternatively, both the hydroxy and pyridone groups in compound (X) can be activated at the same time, using stronger conditions such as phosphorus oxychloride and heat, or excess toluenesulfonic anhydride, to give compound (XII). Compound (XI) may be converted to the protected amine compound (XIII) using the same general route discussed above for the pyrimidines. Selective monoalkylation using compound (XII) is also possible, but will probably give mixtures of regioisomeric products (XIV) and (XV). The nitro groups in these compounds can then be reduced as discussed above, to give compounds for formula (V) wherein either A or B is nitrogen.

An alternative approach to the method involving introduction of the $R^1$ group at the initial step is shown in Scheme 6.

(=NH)D, where D represents a group like $OCH_3$, $SCH_3$ or $SO_2CH_3$. For X=O, the ring is formed using a reagent of the structure $(R^2O)_4C$ (with acetic acid catalysis), provided one has access to the reagent with the $R^2$ group of choice (see Brown and Lynn, *J. Chem. Soc. Perkin Trans. I* 1974, 349). Alternatively, the diamine (XIX) is treated with phosgene, followed by O-alkylation to introduce the $R^2$ group (such as a reagent like $R^2$—I or $R^2$—Br). A similar route can be used for X=S, which would use thiophosgene or some similar reagent, followed by S-alkylation with the $R^2$ group. The sulfur atom in this compound (and sulfide groups throughout the molecule in general) can be oxidized to either the sulfoxide or sulfone if desired by treatment with an appropriate oxidizing agent such as potassium permanganate, potassium peroxomonosulfate or m-chloroperbenzoic acid. Finally, compound (XX) can be used in an aryl coupling reaction as described above to replace the K group with the desired aryl group in compound (I).

Methods of synthesis of compounds $R^1$—OH, $R^1$—J and $R^1$—$NH_2$ are related, in that the alcohol can be used in the synthesis of the other two compounds, as is shown in Scheme 7.

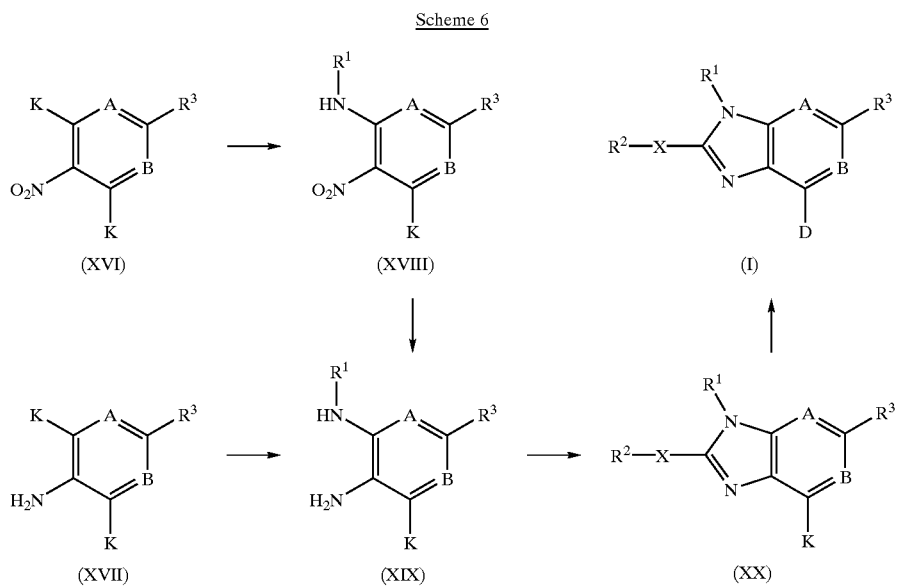

This is particularly useful in the cases where $R^1$ represents a group where alkylation of compound (II) is impractical (e.g. a very bulky $R^1$ group), but can also be used in a general manner. Here, compounds of formula (XVI) or (XVII) (either amino- or nitro-pyridines or pyrimidines) are alkylated with an amine reagent $R^1$—$NH_2$, under either acidic or basic conditions as described above. Nitro compound (XVIII) can be converted to amine compound (XIX) by nitro reduction reactions described earlier. Compound (XIX) can be cyclized to imidazole compound (XX). As above, this reaction will depend upon the choice of X group. For example, for X=$CHR^9$, one can use an orthoester reagent such as $R^2CH(R^9)C(OR)_3$, with heating in neat solution or high-boiling solvents, and the optional presence of an acid catalyst (such as hydrochloric or sulfuric acid) (see Montgomery and Temple, *J. Org. Chem.* 1960, 25, 395). For X=$NR^{10}$, the cyclization is performed using reagents such as an guanidine reagent of the structure $R^2R^{10}N$—C(=NH)$NH_2$ or a urea-derived reagent of the structure $R^2R^{10}N$—C

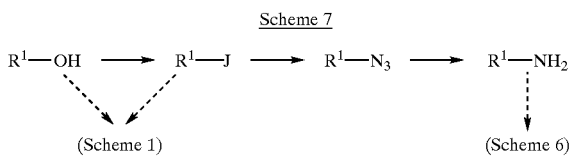

For example, the hydroxy group may be converted to the following J groups, using the indicated reagents (this route is not limited to these J groups): methanesulfonate, using methanesulfonyl chloride or anhydride and an appropriate base; toluenesulfonate, using toluenesulfonyl chloride or anhydride and an appropriate base; iodide; using iodine/ triphenylphosphine; bromide, using phosphorus tribromide or carbon tetrabromide/triphenylphosphine; or trifluoromethanesulfonate, using trifluoromethane-sulfonic anhydride and an appropriate base. Both compounds $R^1$—OH and $R^1$—J are used in the methods portrayed in Scheme 1. Conversion of $R^1$—J to $R^1$—$N_3$ requires the use of an azide source, such as sodium azide, and a solvent such as dimethylsulfoxide or dimethylformamide, or water and a phase-transfer catalyst (such as tetrabutylammonium hydrogen sulfate). Reduction of the azide compound $R^1$—$N_3$ to $R^1$—$NH_2$ may be accomplished using reagents such as sodium borohydride or triphenylphosphine, or hydrogen gas and a catalyst (such as palladium on carbon). The amine $R^1$—$NH_2$ may then be employed in the methods portrayed in Scheme 6.

In the cases where the compound $R^1$—OH could be represented by a structure of formula (XXI) (Scheme 8), wherein $R^{1a}$ and $R^{1b}$ represents substructures which, taken together with the carbinol methine group, comprise the entire group $R^1$, this compound may be prepared by addition to a carbonyl compound.

Scheme 8

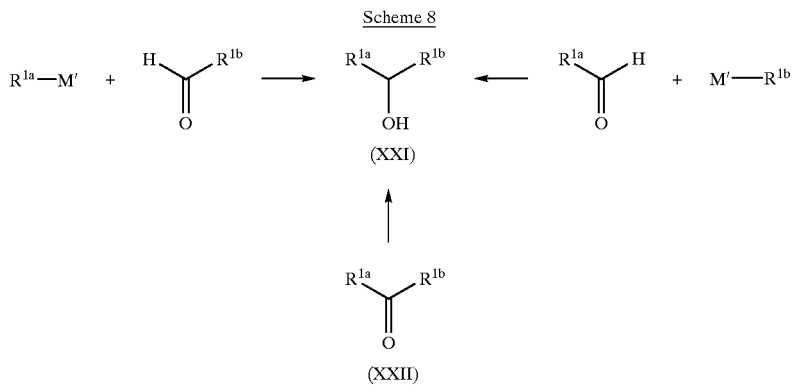

This route is particularly useful in the case where $R^{1a}$ or $R^{1b}$ represents a cycloalkyl group, such as cyclopropyl. An organometallic reagent (where M' represents a metallic group, such as Li, CuCN, CuI, MgCl, MgBr, MgI, ZnCl, CrCl, etc.) can be allowed to react with an aldehyde reagent to prepare the alcohol compound of formula (XXI). Alternatively, a ketone of formula (XXII) may be treated with a reducing agent, such as sodium borohydride, lithium aluminum hydride, etc., which will also generate the alcohol of formula (XXI). Standard methods of ketone synthesis may be used where appropriate in the preparation of compounds for formula (XXII), which will be familiar to those skilled in the art of organic synthesis.

An homologous approach may also be employed in the synthesis of alcohols $R^1$—OH, involving the ring-opening reaction of cyclic ether compounds with organometallic reagents (Scheme 9).

Scheme 9

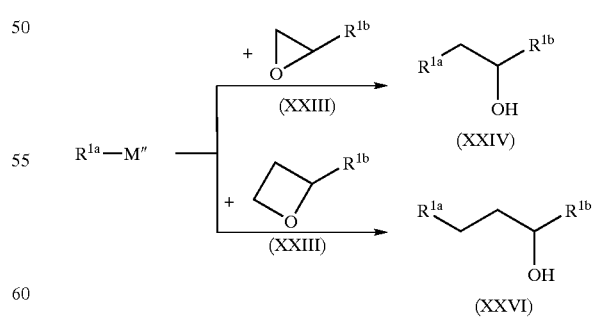

Here, an organometallic reagent R$^{1a}$M' is used, where M" represents metals such as Mg, Zn or Cu. Especially useful is the method described in Huynh, et al., Tetrahedron Letters 1979, (17), pp. 1503–1506, where organomagnesium reagents are allowed to react with cyclic ethers with catalysis provided by copper(I) iodide. Use of an epoxide compound of formula (XXIII) in this manner would result in synthesis of an alcohol compound of formula (XXIV), and use of an oxetane compound of formula (XXV) would generate an alcohol of formula (XXVI). Both compounds (XXIV) and (XXVI) are variants of R$^1$—OH.

Synthesis of compound R$^1$—NH$_2$ with formula (XXVII) is portrayed in Scheme 10.

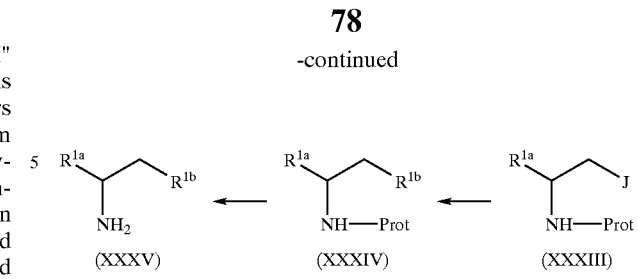

Scheme 10

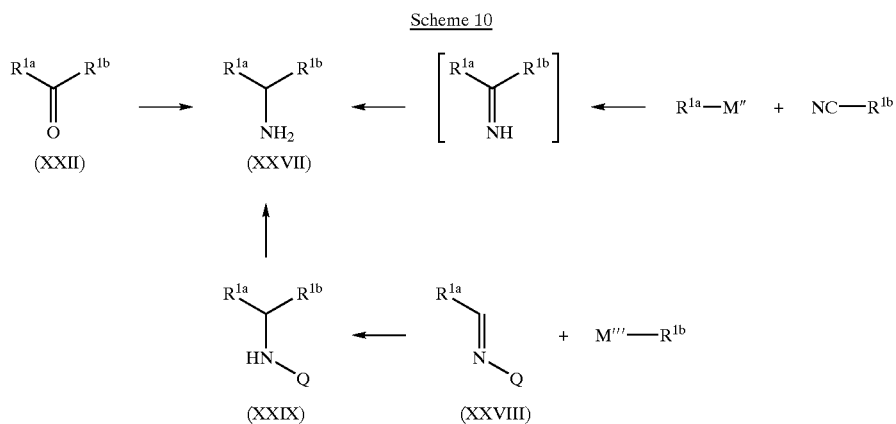

A simple reductive amination of ketone (XXII) will produce amine (XXVII). This reaction may be performed using anhydrous ammonia in the presence of hydrogen and a catalyst. Alternatively, addition of an organometallic reagent to a nitrile compound gives and imine, which may be treated in situ with a reducing agent (such as sodium cyanoborohydride) to give amine (XXVII). Finally, a compound of formula (XXVIII), wherein Q is an optionally-substituted oxygen atom (i.e. an oxime) or nitrogen atom (i.e. a hydrazone), may be allowed to react with an organometallic reagent R$^{1b}$—M'". Here, metallic groups M'" such as MgBr, CuCl or CeCl$_2$ have been used in additions to oximes or hydrazones. The intermediate addition products of formula (XXIX) may be subjected to reductive cleavage (using conditions such as sodium/liquid ammonia or catalytic hydrogenation), which will afford amines (XXVII).

Amino acids, either naturally-occurring or synthetic, are potential sources of useful starting materials for the synthesis of the compounds of this invention. Scheme 11 shows some possible applications of this approach.

Scheme 11

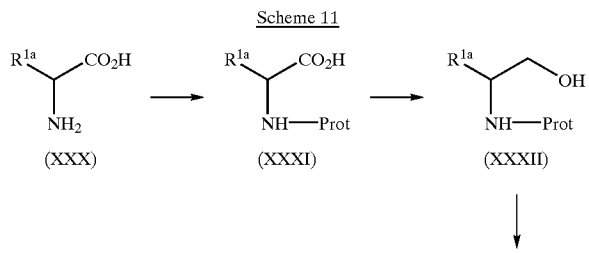

Protected amino acids of formula (XXXI) are prepared from the parent compounds of formula (XXX); useful protecting groups ("Prot") include tert-butoxycarbonyl, benzyloxycarbonyl and triphenylmethyl. Standard texts in peptide chemistry describe this protection. The carboxylic acid group may be reduced using reagents such as lithium borohydride, which gives alcohol (XXXII). The hydroxy group may be converted to a leaving group "J" as described before. The compound of formula (XXXIII) may be treated with appropriate reagents to produce a wide variety of functional groups included in the scope of this invention (compound (XXXIV)); displacement of J with cyanide (sodium cyanide in warm dimethylformamide may be used here) gives a nitrile, displacement of J with a mercaptan (in the presence of a base, such as potassium carbonate) gives a disulfide, displacement of J with a secondary amine gives a tertiary amine, etc.

The compounds of Formula (I) with unsaturated R$^1$ groups can be a further source of compounds covered under this invention. Unsaturated (double and triple) bonds can take part in cycloaddition chemistry with appropriate reagents (Scheme 12). Cycloaddition of an alkyne compound of Formula XXXVI with 1,3-dienes to give six-membered ring compounds like that of Formula XXXVII (commonly known as the Diels-Alder reaction), and cycloaddition with 3-atom dipolar reagents to give heterocyclic compounds of Formula XXXVIII, are familiar to those skilled in the art of organic synthesis. One specific example of this approach is the synthesis of an isoxazole compounds of Formula XXXIX from the alkyne XXXVI and a nitrile oxide reagent.

Scheme 12
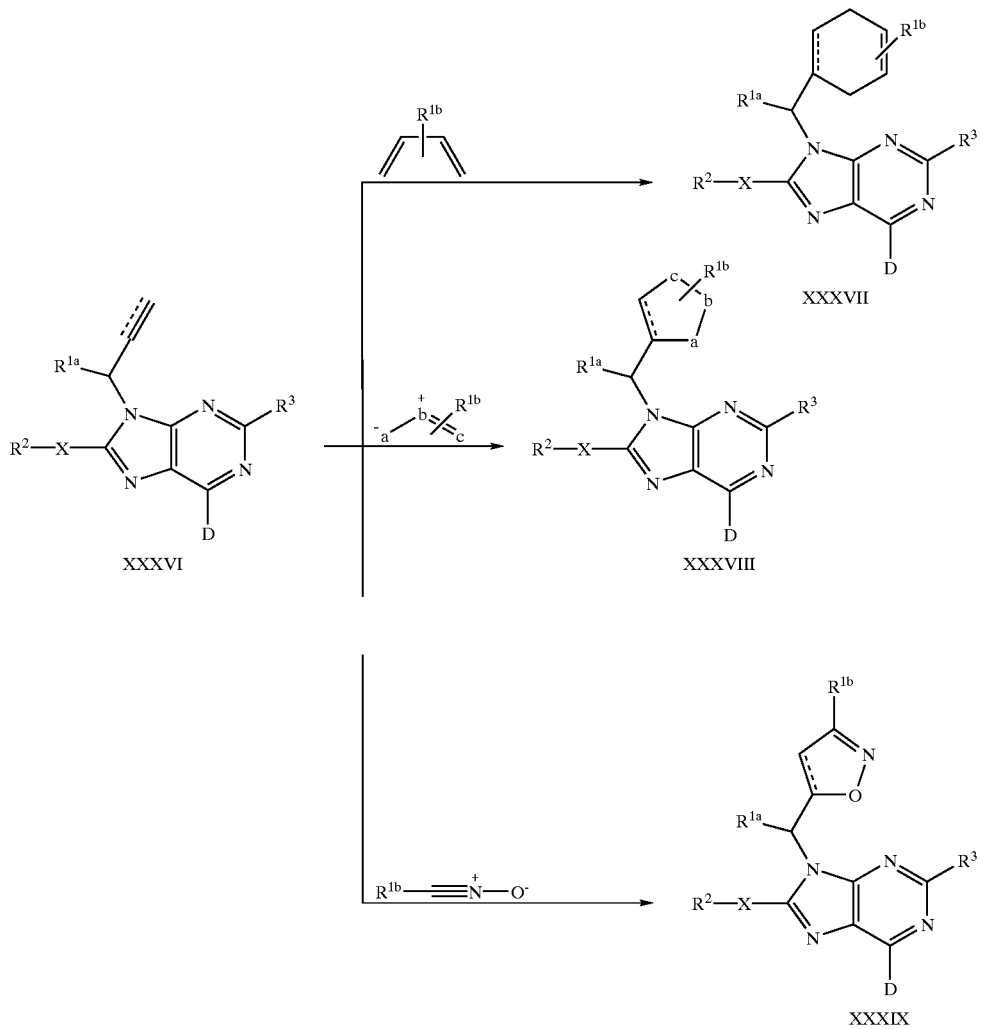
The synthetic procedure in Scheme 13 shown below may be used to prepare 4,5-c imidazopyridines.
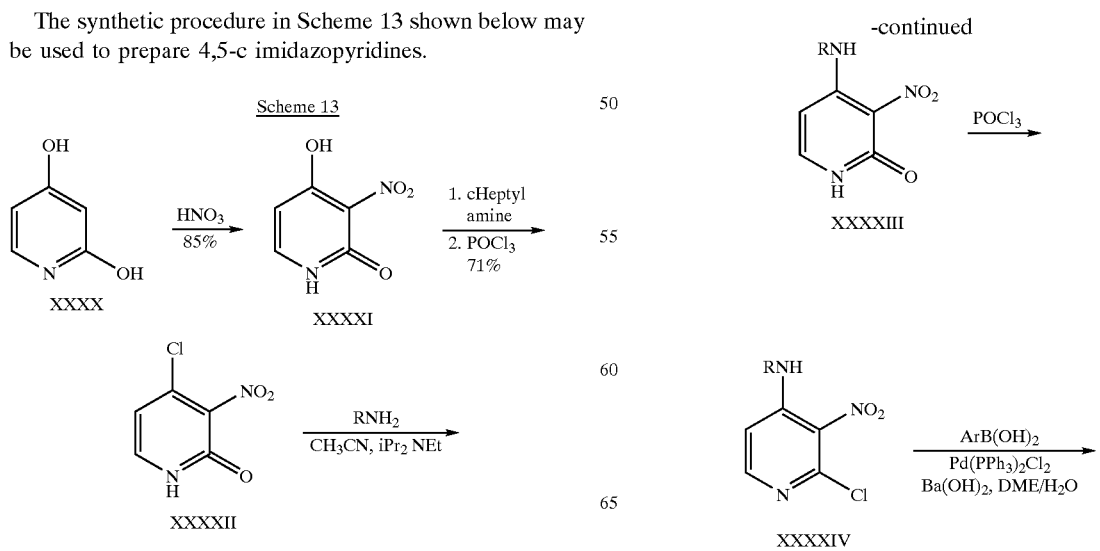

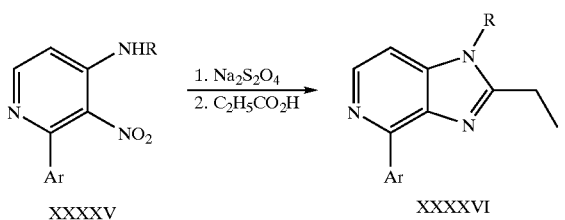

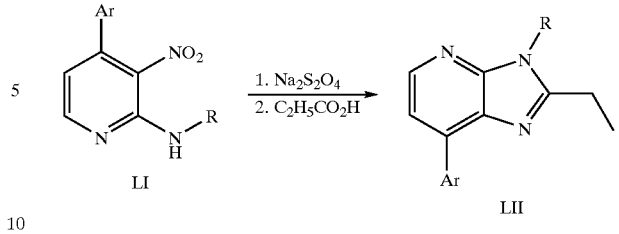

Nitration of 2,4-dihydroxypyridine (XXXX) with HNO$_3$ as described earlier (Koagel et al. Recl. Trav. Chim. Pays-Bas. 29, 38, 67, 1948) gave the corresponding 3-nitropyridone (XXXXI) which was treated with an organic amine base, such as cycloheptyl amine to give selectively the corresponding 4-chloropyridone (XXXXIII). This in turn was reacted with a primary amine RNH$_2$, where R is a group described earlier in an aprotic or protic solvent, such as CH$_3$CN, DMSO, DMF, or an alkyl alcohol in the presence of an organic or inorganic base, such as a trialkylamine, K$_2$CO$_3$, Na$_2$CO$_3$ etc, and in temperature range of 20–200° C. to give the 4-amino adduct (XXXXIII). Pyridone (XXXXIII) was converted to the 2-chloropyridine (XXXXIV) by treatment with POCl$_3$, and (XXXXIV) was coupled with an arylboronic acid ArB(OH)$_2$ under palladium catalysis to give (XXXXV). Nitropyridine (XXXXV) was reduced to the corresponding aminopyridine by use of Na$_2$S$_2$O$_4$ or a Fe, Sn or SnCl$_2$ and converted to the imidazo[4,5-c]pyridine in refluxing propionic acid. The same transformation can be affected by the use of a nitrile, an imidate, thioimidate or trialkylorthopropionate.

The synthetic procedure in Scheme 14 shown below may be used to prepare 4,5-b imidazopyridines.

Scheme 14

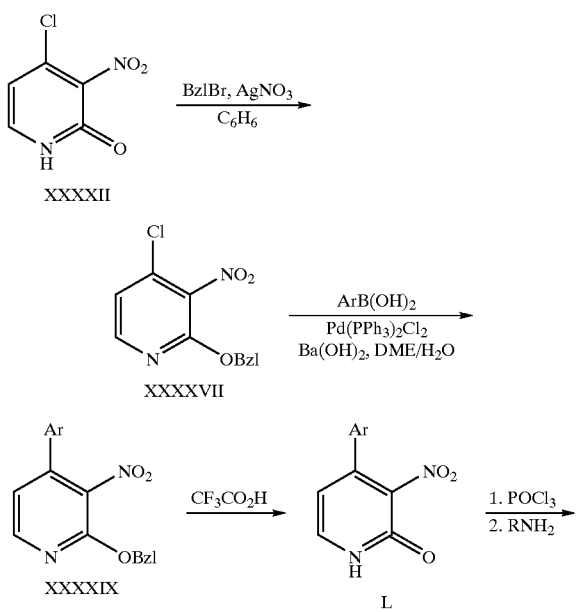

Reaction of 4-chloropyridone (XXXXII) with an aryl halide, such as benzyl bromide in benzene and in the presence of Ag$_2$CO$_3$ as described in Scheme 13 (Smith A. M.; et al. J. Med. Chem. 36, 8, 1993) and at temperature ranges of 30–80° C. afforded the corresponding 2-benzyloxypyridine (XXXXVII). This was coupled with an arylboronic acid, ArB(OH)$_2$ under palladium-catalyzed conditions to give (XXXXIX). The benzyloxy group can be removed by treatment with a strong acid, such as trifluoroacetic, triflic, sulfuric, HCl, etc. to give pyridone (L). This was converted to the 2-halopyridine with the action of POX$_3$, PX$_5$ or the corresponding triflate, tosylate or mesylate, which was displaced with a primary amine RNH$_2$ to give (LI). The nitro group was reduced under conditions described in scheme 13 and the aminopyridine was cyclized to the imidazolo[4,5-b]pyridine (LII) under conditions described in scheme 13.

The following examples are provided to describe the invention in further detail. These examples, which set forth the best mode presently contemplated for carrying out the invention, are intended to illustrate and not to limit the invention.

The methods discussed below in the preparation of 8-ethyl-9-(1-ethylpentyl)-6-(2,4,6-trimethylphenyl)purine (Table 1, Example 2, Structure A) and 9-butyl-8-ethyl-6-(2,4,6-trimethylphenyl)purine (Table 1, Example 27, Structure A) may be used to prepare all of the examples of Structure A contained in Table 1, Table 1A and Table 1B, with minor procedural modifications where necessary and use of reagents of the appropriate structure.

The methods discussed below in the preparation of 3-(1-cyclopropylpropyl)-7-(2,4-dichlorophenyl)-2-ethyl-3H-imidazo[4,5-b]pyridine (Table 1, Example 38, Structure B) and 1-(1-cyclopropylpropyl)-4-(2,4-dichlorophenyl)-2-ethyl-1H-imidazo[4,5-c]pyridine (Table 1, Example 38, Structure C) may be used to prepare many of the examples of Structures B and C contained in Table 1, Table 1A, Table 1B and Table 1C, with minor procedural modifications where necessary and use of reagents of the appropriate structure.

EXAMPLE 2

Preparation of 8-Ethyl-9-(1-ethylpentyl)-6-(2,4,6-trimethylphenyl)purine

Part A. A solution of 5-amino-4,6-dichloropyrimidine (10.0 g, 61.0 mmol) and triethylamine (12.8 mL, 91.5 mmol) in ethanol (100 mL) was treated with benzylamine (7.30 mL, 67.1 mmol), and heated to 50° C. overnight. The resulting mixture was cooled, and the resulting crystalline solid was collected by filtration. The solid was triturated with hexane, refiltered and dried under vacuum. A second crop was collected from the mother liquor and purified like the first crop to afford in total 12.67 g (48.8 mmol, 80%) of 5-amino-6-benzylamino-4-chloropyrimidine. TLC R$_F$ 0.10 (30:70 ethyl acetate-hexane). $^1$H NMR (300 MHz, CDCl$_3$): d 7.62

(1H, s), 7.13–6.97 (5H, m), 6.61 (1H, br t, J=5 Hz), 4.43 (2H, d, J=5.5 Hz), 4.24 (2H, br s). MS (NH$_3$—CI): m/e 238 (4), 237 (33), 236 (15), 235 (100).

Part B. A solution of the diamine from Part A (10.45 g, 44.5 mmol) and 3 drops concentrated hydrochloric acid in triethyl orthopropionate (70 mL) was heated to 100° C. for 1 hour, then cooled, poured into water (200 mL) and extracted with ethyl acetate (2×200 mL). The extracts were washed in sequence with brine (100 mL), then combined, dried over anhydrous sodium sulfate, filtered and evaporated. The residue was separated by column chromatography (silica gel, 20:80 ethyl acetate-hexane) to afford the product, N-(6-benzylamino-4-chloropyrimidin-5-yl)-O-ethyl-propionimidate (12.82 g, 40.2 mmol, 90%) as a crystalline solid, m.p. 85–86° C. TLC R$_F$ 0.25 (20:80 ethyl acetate-hexane). $^1$H NMR (300 MHz, CDCl$_3$): d 8.19 (1H, s), 7.35–7.29 (5H, m), 5.21 (1H, br t, J=5 Hz), 4.70 (2H, d, J=5.9 Hz), 4.29 (2H, br), 2.15 (2H, br q, J=7.3 Hz), 1.35 (3H, t, J=7.0 Hz), 1.06 (3H, t, J=7.3 Hz). MS (NH$_3$—CI): m/e 322 (6), 321 (34), 320 (20), 319 (100).

Part C. A solution of the imidate compound prepared in Part B above (10.66 g, 33.4 mmol) and p-toluenesulfonic acid monohydrate (100 mg) in diphenyl ether (10 mL) was heated to 170° C. for 2 hours. The resulting mixture was cooled and poured into 50 mL water. This was extracted with ethyl acetate (2×50 mL), and the extracts were washed in sequence with brine (50 mL), combined, dried over anhydrous sodium sulfate, filtered and evaporated. The residual material was separated by column chromatography (silica gel, hexane to remove diphenyl ether, then 30:70 ethyl acetate-hexane) to afford the product, 9-benzyl-6-chloro-8-ethylpurine, as an oil (8.16 g, 29.9 mmol, 89%). TLC R$_F$ 0.20 (30:70 ethyl acetate-hexane). $^1$H NMR (300 MHz, CDCl$_3$): d 8.72 (1H, s), 7.37–7.29 (3H, m), 7.19–7.14 (2H, m), 5.46 (2H, s), 2.89 (2H, q, J=7.7 Hz), 1.38 (3H, t, J=7.7 Hz). MS (NH$_3$—CI): m/e 276 (6), 275 (36), 274 (20), 273 (100).

Part D. A solution of zinc chloride (5.32 g, 39.1 mmol) in anhydrous, freshly-distilled tetrahydrofuran (50 mL) was treated at ambient temperature with a solution of mesitylmagnesium bromide (39.1 mL, 1.0 M, 39.1 mmol) in diethyl ether. After 45 minutes, a separate flask containing a solution of bis(triphenylphosphine)-palladium dichloride (0.92 g, 1.3 mmol) in tetrahydrofuran (30 mL) was treated with a solution of diisobutylaluminum hydride (2.6 mL, 1.0 M, 2.6 mmol) in hexane. This mixture was allowed to stir for 15 minutes, then treated with the mesitylzinc chloride solution dropwise by cannula. Then, the chloropurine compound in 10 mL tetrahydrofuran solution was added by syringe, and the mixture was allowed to stir for 12 hours at ambient temperature. It was poured into water (150 mL), and acidified with dropwise addition of 1 N aqueous hydrochloric acid until the mixture is homogeneous. This is extracted with ethyl acetate (2×150 mL), and the extracts were washed in sequence with saturated brine solution (100 mL), combined, dried over anhydrous sodium sulfate, filtered and evaporated. The residue was separated by column chromatography (silica gel, 30:70 ethyl acetate-hexane) to afford the product, 9-benzyl-8-ethyl-6-(2,4,6-trimethylphenyl)purine (6.68 g, 18.7 mmol, 72%), as an off-white waxy solid, m.p. 121–122° C. $^1$H NMR (300 MHz, CDCl$_3$): d 9.00 (1H, s), 7.38–7.31 (3H, m), 7.23–7.21 (2H, m), 6.96 (2H, s), 5.50 (2H, s), 2.84 (2H, q, J=7.6 Hz), 2.33 (3H, s), 2.06 (6H, s), 1.26 (3H, t, J=7.5 Hz). MS (NH$_3$—CI): m/e 359 (3), 358 (26), 357 (100).

Part E. A solution of the benzyl compound from Part D above (5.33 g, 14.95 mmol) in trifluoroacetic acid (320 mL) partitioned into four Parr bottles, and each was treated with 0.8 g 20% palladium hydroxide on carbon. The bottles were each subjected to hydrogenation (50 psi) in shaker apparati for 18 hours. The atmospheres were purged with nitrogen, and the solutions were combined, filtered through celite and evaporated. The residual material was separated by column chromatography (silica gel, 50:50 ethyl acetate-hexane) to afford the product, 8-ethyl-6-(2,4,6-trimethylphenyl)purine (3.75 g, 14.1 mmol, 94%), as a white crystalline solid, m.p. 215–217° C. TLC R$_F$ 0.17 (50:50 ethyl acetate-hexane). $^1$H NMR (300 MHz, CDCl$_3$): d 12.35 (1H, br s), 9.03 (1H, s), 6.96 (2H, s), 3.05 (2H, q, J=7.7 Hz), 2.32 (3H, s), 2.05 (6H, s), 1.50 (3H, t, J=7.7 Hz). MS (NH$_3$—CI): m/e 269 (2), 268 (19), 267 (100).

Part F. A solution of the purine compound from Part E above (200 mg, 0.75 mmol), 3-heptanol (0.13 mL, 0.90 mmol) and triphenylphosphine (0.24 g, 0.90 mmol) in freshly-distilled tetrahydrofuran (5 mL) was cooled to 0° C., and treated with diethyl azodicarboxylate (0.14 mL, 0.90 mmol) dropwise by syringe. The mixture was allowed to stir for 12 hours, then evaporated. The residual material was separated by column chromatography (silica gel, 15:85 ethyl acetate-hexane) to, afford the title product as a white solid (0.152 g, 0.42 mmol, 56%), m.p. 99–100° C. TLC R$_F$ 0.17 (10:90 ethyl acetate-hexane). $^1$H NMR (300 MHz, CDCl$_3$): d 8.91 (1H, s), 6.95 (2H, s), 4.22 (1H, br), 2.92 (2H, q, J=7.7 Hz), 2.41 (2H, br), 2.32 (3H, s), 2.10–1.98 (2H, m), 2.05 (3H, s), 2.04 (3H, s), 1.37 (3H, t, J=7.5 Hz), 1.34–1.23 (4H, m), 0.84 (3H, t, J=7.1 Hz), 0.81 (3H, t, J=7.5 Hz). MS (NH$_3$—CI): m/e 367 (3), 366 (27), 365 (100).

EXAMPLE 27

Preparation of 9-Butyl-8-ethyl-6-(2,4,6-trimethylphenyl)purine

A solution of 8-ethyl-6-(2,4,6-trimethylphenyl)purine (200 mg, 0.75 mmol) in anhydrous dimethylformamide (5 mL) was cooled to 0° C., and treated with sodium hydride dispersion in mineral oil (72 mg 50% w/w, 1.50 mmol). After 1 hour, bromobutane (0.10 mL, 0.90 mmol) was added by syringe, and the mixture was allowed to stir for 12 hours. It was poured into ethyl acetate (120 mL), and was washed with water (3×120 mL) and brine (100 mL). The aqueous layers were back-extracted in sequence with ethyl acetate (120 mL), and the extracts were combined, dried over anhydrous sodium sulfate, filtered and evaporated. The residue was separated by column chromatography (silica gel, 20:80 ethyl acetate-hexane) to afford the title product as a viscous oil (64.2 mg, 0.20 mmol, 27%). TLC R$_F$ 0.20 (30:70 ethyl acetate-hexane). $^1$H NMR (300 MHz, CDCl$_3$): d 8.96 (1H, s), 6.95 (2H, s), 4.25 (2H, t, J=7.5 Hz), 2.93 (2H, q, J=7.7 Hz), 2.32 (3H, s), 2.04 (6H, s), 1.91–1.86 (2H, m), 1.50–1.38 (2H, m), 1.39 (3H, t, J=7.7 Hz), 1.01 (3H, t, J=7.5 Hz). MS (NH$_3$—CI): m/e 325 (3), 324 (23), 323 (100).

EXAMPLE 35

Preparation of 6-(2,4-Dichlorophenyl)-8-ethyl-9-(1-ethylpentyl)purine

A solution of 2,4-dichlorobenzeneboronic acid (572 mg, 3.00 mmol) and ethylene glycol (205 mg, 3.30 mmol) in benzene (20 mL) was heated to reflux with azeotropic removal of water for a period of 8 h. The resulting solution was cooled, and treated with 6-chloro-8-ethyl-9-(1-ethylpentyl)purine (see Example 2, Part C above; 562 mg, 2.00 mmol), thallium carbonate (1.03 g, 2.20 mmol) and tetrakis(triphenylphosphine)palladium (116 mg, 0.10 mmol). The resulting mixture was heated to reflux with stirring for 12 h, then cooled, filtered through celite and evaporated. The resulting residue was separated by column chromatography (silica gel, 10:90 ethyl acetate-hexane) to afford the title compound as a viscous oil (530 mg, 1.35 mmol, 68%). TLC $R_F$ 0.31 (20:80 ethyl acetate-hexane). $^1$H NMR (300 MHz, CDCl$_3$): d 8.94 (1H, s), 7.71 (1H, d, J=8.4 Hz), 7.58 (1H, d, J=1.8 Hz), 7.41 (1H, dd, J=8.4, 1.8 Hz), 4.27 (1H, br), 2.95 (2H, q, J=7.3 Hz), 2.41 (2H, br), 2.11–1.98 (2H, br), 1.42 (3H, t, J=7.3 Hz), 1.37–1.20 (3H, m), 1.09–0.99 (1H, m), 0.84 (3H, t, J=7.7 Hz), 0.82 (3H, t, J=7.7 Hz). MS (NH$_3$—CI): m/e calc'd for C$_{20}$H$_{25}$NCl$_2$: 391.1456, found 391.1458; 395 (11), 394 (14), 393 (71), 392 (29), 391 (100).

EXAMPLE 38

Preparation of 3-(1-Cyclopropylpropyl)-7-(2,4-dichlorophenyl)-2-ethyl-3H-imidazo[4,5-b]pyridine Part A. 2,4-Dihydroxypyridine (15.0 g, 135 mmol) was heated in HNO$_3$ (85 mL) at 80° C. for 15–20 min at which time it went into solution. The temperature was maintained for 5 min and after cooling it was poured into ice/water (~200 mL). The precipitated solid was collected and dried (19.0 g, 90% yield). $^1$H NMR (300 MHz, dmso d6): 12.3–12.5 (1H, brs), 11.75–11.95 (1H, brs), 7.41 (1H, d J=7.3 Hz), 5.99 (1H, d J=7.3 Hz).

Part B. 4-Hydroxy-3-nitropyridone (8.0 g, 51.25 mmol) and cycloheptyl amine (6.8 mL, 53.4 mmol) were heated at reflux in methanol (100 mL) for 15 min. The solvent was stripped off and the residual solid was washed with 1:1 EWtOAc/hexanes and dried under vacuum. The cycloheptyl amine salt was stirred in POCl$_3$ (60 mL) for 40 h and poured into ice/water (600 mL). The precipitated produced was collected and dried under vacuum (7.0 g, 78% yield). $^1$H NMR (300 MHz, dmso d6): 12.8–13.05 (1H, brs), 7.73 (1h, d J=7.0 Hz), 6.50 (1H, d J=7.0 Hz).

Part C. 4-Chloro-3-nitro-pyridone (0.5 g, 2.86 mmol) Ag$_2$CO$_3$ (0.83 g, 3 mmol) and benzyl bromide (0.36 mL, 3 mmol) were stirred in dry benzene (20 mL) at 60° C. for 5 h. The reaction mixture was filtered and stripped in vacuo. The residue was chromatographed on silica gel (10% EtOAc/hexanes eluent) to give the product (0.6 g, 79%). $^1$H NMR (300 MHz, CDCl$_3$): 8.15 (1H, d J=4.0 Hz), 7.30–7.42 (5 H, m), 7.04 (1H, d J=4.0 Hz), 5.50 (2H, s).

Part D. 2-Benzyloxy-4-chloro-3-nitropyridine (0.5 g, 1.9 mmol), 2,4-dichlorophenylboronic acid (0.363 g, 1.9 mmol) Pd(PPh$_3$)$_2$Cl$_2$ (76 mg, 0.11 mmol) and Ba(OH)$_2$.8H$_2$O (0.6 g, 1.9 mmol) were heated at reflux in 1,2-dimethoxyethane (6 mL), and water (6 mL) for 5 h. The mixture was partitioned between EtOAc (100 mL) and water (30 mL) and the EtOAc was washed with water, brine, dried and stripped in vacuo. The residue was chromatographed on silica gel (10% EtOAc/hexanes eluent) to give the product (370 mg, 52% yield). $^1$H NMR (300 MHz, CDCl$_3$): 8.31 (1H, d J=5.1 Hz), 7.51 (1H, d J=2.2 Hz), 7.30–7.43 (6H, m), 7.20 (1H, d J 8.0 Hz), 6.91 (1H, d J=5.1 Hz), 5.56 (2h, s).

Part E. 2-Benzyloxy-4-(2,4-dichlorophenyl)-3-nitropyridine (1.65 g, 4.39 mmol) was stirred in CF$_3$CO$_2$H(5 mL) at 25° C. for 4 h. The CF$_3$CO$_2$H was stripped in vacuo and the residue was washed with 20% EtOAc/hexanes and used in the next reaction. $^1$H NMR (300 MHz, CDCl$_3$): 7.62 (1H, d J=7.0 Hz), 7.53 (1H, d J=2.2 Hz), 7.34 (1H, dd J=7.0, 2.2 Hz), 7.22 (1H, d J=8.1 Hz), 6.33 (1H, d J=7.0 Hz).

Part F. 4-(2,4-dichlorophenyl)-3-nitropyridone (4.39 mmol) was heated at reflux in POCl$_3$ (5 mL) for 5 h. After cooling it was poured into ice/water (~60 mL) and extracted with EtOAc (2×100 mL). The EtOAc was washed with sat NaHCO$_3$, brine, dried and stripped in vacuo. Used in the next reaction without further purification. $^1$H NMR (300 MHz, CDCl$_3$): 8.60 (1H, d J=5.2 Hz), 7.54 (1H, d, J=2.2 Hz), 7.36 (1H, dd J=8.1, 2.2 Hz), 7.20 (1H, d J=8.1 Hz).

Part C. 2-Chloro-4-(2,4-dichlorophenyl)-3-nitropyridine (0.5 g, 1.65 mmol) 1-cyclopropylpropylamine hydrochloride (461 mg, 3.4 mmol) and diisopropyl ethylamine (1.26 mL, 0.72 mmol) were heated at reflux in CH$_3$CN (10 mL) for 64 h. The mixture was partitioned between EtOAc (70 mL) and water (40 mL). The aqueous layer was extracted with EtOAc (50 mL) and the combined EtOAc exctracts washed with brine, dried and stripped in vacuo. The residue was chromatographed on silica gel (10% EtOAc/hexanes eluent) to give the product (310 mg, 51% yield). $^1$H NMR (300 MHz, CDCl$_3$): 8.29 (1H, d J=4.7 Hz), 7.76 (1H, brd J=8.0 Hz), 7.46 (1H, d J=2.2 Hz), 7.32 (1H, dd J=8.5, 2.2 Hz), 7.15 (1H, d J=8.5 Hz), 3.72–3.85 (1H, m)), 1.70–1.80 (2H, m), 0.90–1.08 (4H, m), 0.30–0.66 (4H, m).

Part H. 2-(1-cyclopropyl)propylamino-4-(2,4-dichlorophenyl)-3-nitropyridine (310 mg, 0.85 mmol) was dissolved in dioxane (8 mL) and water (8 mL) containing conc NH$_4$OH (0.3 mL) was added, followed by Na$_2$S$_2$O$_4$ (1.1 g, 6.86 mmol). The reaction was stirred at 25° C. for 4 h and extracted with EtOAc (100 mL) The EtOAc was washed with brine, dried and stripped in vacuo. The residue was chromatographed on silica gel (25% EtOAc/hexanes and 1% conc NH$_4$OH eluent) to give the product (150 mg, 53% yield). $^1$H NMR (300 MHz, CDCl$_3$): 7.73 (1H, d J=5.5 Hz), 7.53 (1H, d J=1.8 Hz), 7.35 (1H, dd J=8.1, 1.8 Hz), 7.24 (1H, d J=8.1 Hz), 6.35 (1H, d J=5.5 Hz), 4.3 (1H, brs), 3.5 (1H, brs), 3.42–3.55 (1H, m), 3.04 (2H, brs), 1.70–1.81 (2H, m), 0.88–1.08 (4H, m), 0.3–0.6 (4H, m).

Part I. 3-amino-2-(1-cyclopropyl)propylamino-4-(2,4-dichlorophenyl)-pyridine (140 mg, 0.42 mmol) was heated at reflux in propionic acid (5 mL) for 23 h. Then the mixture was diluted with water (50 mL), neutralized with solid NaHCO$_3$ and basified with 50%NaOH. Then it was extracted with EtOAc (80 mL) and the EtOAc was dried and stripped in vacuo. The residue was chromatographed on silica gel (10% and 20%EtOAc/hexanes eluant) to give the product, which was crystallized from hexanes (70 mg, 45% yield) mp 118–119° C. $^1$H NMR (300 MHz, CDCl$_3$): 8.31 (1H, d J=4.7 Hz), 7.62 (1H, d J=7.2 Hz), 7.55 (1H, d J=1.8 Hz), 7.37 (1H, dd J=7.2, 1.8 Hz), 7.23 (1H, d J=4.7 Hz), 3.50–3.70 (1H, brs), 2.87–2.96 (2H, q), 2.36–2.56(1H, m), 2.18–2.35 (1H, m), 1.90–2.05 (1H, m), 1.38 (3H, t), 0.86 (3H, t), 0.75–0.84 (1H, m), 0.40–0.54 (1H, m), 0.15–0.25 (1H, m).

EXAMPLE 38A

Preparation of 1-(1-Cyclopropylpropyl)-4-(2,4-dichlorophenyl)-2-ethyl-1H-imidazo[4,5-c]pyridine Part A. A mixture of 4-chloro-3-nitro-2-pyridone (2.0 g, 11.4 mmol), 1-cyclopropylpropyl amine hydrochloride (1.5 g, 11.4 mmol) and N,N-diisopropylethylamine (4.8 ml, 27.4 mmol) in CH$_3$CN (50 ml) were stirred at 25° C. for 16 h and at reflux for 4 h. After cooling it was stripped in vacuo, and the residue was partitioned between EtOAc (100 mL) and H$_2$O (50 mL). The insolubles were separated, washed with H$_2$O and EtOAc and vacuum dried 1.51 g. The filtrate layers were separated and the aqueous layer was extracted with EtOAc (2×50 mL). The Combined extracts were washed with brine, dried over MgSO$_4$, filtered and concd. in vacuo.

The residue was washed with EtOAc (2×) and vacuum dried, to give 0.69 g; yellow solid. Combined wt. of 4-(1-cyclopropylpropyl)amino-3-nitro-2-pyridone 2.20 g, 81% yield. $^1$H NMR (300 MHz, dmso d6): 11.19 (1H, br), 8.94 (1H, d J=8.8 Hz), 7.33 (1H, t J=6.9 Hz), 6.03 (1H, d J=7.7 Hz), 3.18–3.24 (1H, m)r, 1.60–1.74 (2H, m), 1.03–1.11(1H, m), 0.91 (3H, t), 0.40–0.60 (1H, m), 0.20–0.39 (1H, m).

Part B. 4-(1-Cyclopropyl)propylamino-3-nitro-2-pyridone (2.20 g, 9.27 mmol) was stirring in POCl$_3$ (15 mL) at 25° C. for 16 h. Then it was poured into ice/water (220 mL) and stirred until all the POCl$_3$ had reacted. The mixture was neutralized with solid NaHCO$_3$, filtered and extracted with EtOAc (3×60 mL). The combined organic extracts were washed with brine, dried over MgSO$_4$, filtered and stripped in vacuo. The crude oil was chromatographed on silica gel (100 g.) and eluted with a gradient from 10–20% EtOAc/hexane to afford 1.91 g 2-chloro-4-(1-cyclopropylpropyl)amino-3-nitropyridine, 81% yield. $^1$H NMR (300 MHz, CDCl$_3$): 7.96 (1H, d J=6.3 Hz), 6.58 (1H, d J=6.3 Hz), 6.52 (1H, brd J=5.5 Hz), 2.90–3.00 (1H, m), 1.61–1.82 (2H, m), 1.01 (3H, t J=7.7 Hz), 0.90–1.02 (1H, m), 0.51–0.70 (2H, m), 0.21–0.34 (2H, m).

Part C. In a dried flask, under N$_2$, a mixture of 2-chloro-4-(1-cyclopropyl)propylamino-3-nitropyridine (730 mg, 2.85 mmol), 2,4-dichlorophenylboronic acid (544 mg, 2.85 mmol), dichlorobis(triphenylphosphine)palladium(III) (114 mg, 0.17 mmol) and barium hydroxide octahydrate (899 mg, 2.85 mmol) was heated at reflux in dimethoxyethane (8.6 mL) and H$_2$O (8.6 mL for 1.5 h. After cooling it was partitioned between EtOAc (100 mL) and water (20 mL) and filtered through celite. The aqueous layer was extracted with EtOAc (2×50 mL). The combined organics were washed with brine, dried over MgSO$_4$, filtered and stripped in vacuo. The residue was chromatographed on silica gel (40 gm), and eluted with 30% EtOAc/hexane to afford a yellow oil, 1.00 g, 90% yield. $^1$H NMR (300 MHz, CDCl$_3$): 8.24 (1H, d J=6.2 Hz), 7.87 (1H, brd J=7.3 Hz), 7.43 (1H, s), 7.34 (2H, s), 6.71 (1H, d J=6.2 Hz), 3.00–3.10 (1H, m), 1.70–1.85 (2H, m), 0.95–1.15 (4H, m), 0.50–0.71 (2H, m), 0.25–0.40 (2H, m).

Part D. The product from Part C (0.94 g, 2.57 mmol), by dissolving in dioxane (26 ml), H$_2$O (26 ml) and conc. NH$_4$OH (1.0 ml) while adding Na$_2$S$_2$O$_4$ and stirring at room temperature for 2 hrs. Added CH$_2$Cl$_2$ and extracted. Extracted the aqueous layer with CH$_2$Cl$_2$ (2×). Combined the organics and washed with brine, dried over MgSO$_4$, filtered and concd. in vacuo to give a yellow solid, 1.01 g. It was carried over to the next reaction without purification.

Part E. The amine from Part D (1.01 g, 3.00 mmol) was cyclized by refluxing with propionic acid (27 ml, 365.45 mmol) for 8 hrs. Allowed to cool to RT. then basified with 1M NaOH and 50% NaOH. Extracted with EtOAc (2×60 mL) and CH$_2$Cl$_2$(60 mL). Combined the organics and washed with H$_2$O, brine, dried over MgSO$_4$, filtered and concd. in vacuo. The crude oil was chromatographed on silica gel (40 g.) and eluted with 30% EtOAc/hexane to obtain a pale yellow solid (triturated from hexane), 520 mg, 46% yield. H NMR (300 MHz, CDCl$_3$): 8.43 (1H, d J=5.8 Hz), 7.63 (1H, d J=8.1 Hz), 7.55 (1H, d J=1.8 Hz), 7.46 (1H, d J=5.8 Hz), 7.36 (1H, dd J=8.1 , 1.8 Hz), 3.40–3.50 (1H, m), 2.80–2.90 (2H, q J=7.7 Hz), 2.10–2.30 (2H, m), 1.50–1.64 (1H, m), 1.37 (3H, t J=7.3 Hz), 0.87 (3H, t J=7.3 Hz), 0.81–0.91 (1H, m), 0.48–0.58 (2H, m), 0.18–0.26 (1H, m). Elemental analysis calcd for C$_{20}$H$_{21}$N$_3$Cl$_2$: C, 64.18; H, 5.665; N, 11.23; found: C, 64.37; H, 5.66; N, 11.15.

EXAMPLE 831

Preparation of 6-(2-Chloro-4-methoxyphenyl)-9-dicyclopropylmethyl-8-ethylpurine

Part A. A solution of dicyclopropyl ketone (50 g) in absolute methanol (150 mL) in an autoclave vessel was charged with W4 Raney nickel (12 g, washed free of water and in methanol slurry) and then anhydrous ammonia (17 g). The mixture was subjected to 120 atm of hydrogen at 150–160° C. for 5 hours, then cooled and excess gasses purged. The resulting slurry was filtered through celite, and the filtrate was distilled to about one-third the original volume (atmospheric pressure, Vigreaux column). The pot solution was cooled to 0° C., diluted with 3 volumes diethyl ether, and treated with 4 N hydrochloric acid solution in anhydrous dioxane until precipitate formation ceased. The solid product (dicyclopropylmethylamine hydrochloride) was collected by filtration, washed with excess diethyl ether, and dried under vacuum (45.22 g, 306 mmol, 67%). $^1$H NMR (300 MHz, methanol-d$_4$): d 1.94 (1H, t, J=9.3 Hz), 1.11–0.99 (2H, m), 0.75–0.59 (4H, m), 0.48–0.37 (4H, m). MS (NH$_3$-DCI): m/e 114 (5), 113 (100).

Part B. A solution of 5-amino-4,6-dichloropyrimidine (5.00 g, 30.5 mmol) and diisopropylethylamine (12.0 mL, 68.9 mmol) in ethanol (100 mL) was treated with the amine from Part A (3.81 g, 25.8 mmol), and heated to reflux for 72 h. The resulting mixture was cooled and poured into water (300 mL), which was extracted with ethyl acetate (2×300 mL). The extracts were washed with brine, combined, dried over sodium sulfate, filtered and evaporated. The residual oil was separated by column chromatography (30:70 ethyl acetate-hexane), and the desired product, 5-amino-4-chloro-6-dicyclopropylmethylaminopyrimidine, was triturated with warm ether-hexane, collected by filtration, and dried under vacuum (3.15 g, 13.2 mmol, 43%). m.p. 137–138° C. TLC R$_F$ 0.17 (30:70 ethyl acetate-hexane). $^1$H NMR (300 MHz, CDCl$_3$): d 8.01 (1H, s), 4.95 (1H, br d, J=7.3 Hz), 3.45 (1H, q, J=7.0 Hz), 3.37 (2H, br s), 1.06–0.94 (2H, m), 0.59–0.32 (8H, m). MS (NH$_3$—CI): m/e 243 (1), 242 (5), 241 (36), 240 (16), 239 (100).

Part C. A solution of the diamine from Part B (1.80 g, 7.54 mmol) and 1 drop concentrated hydrochloric acid in triethyl orthopropionate (12 mL) was heated to 100° C. for 6 hours. The excess orthoester was removed by distillation (partial vacuum, short-path), and the pot residue solidified to give the product, N-(4-chloro-6-dicyclopropylmethylaminopyrimidin-5-yl)-O-ethyl-propionimidate. $^1$H NMR (300 MHz, CDCl$_3$): d 8.08 (1H, s), 4.84 (1H, br d, J=8.0 Hz), 4.35 (2H, br), 3.45 (1H, q, J=7.7 Hz), 2.14 (2H, q, J=7.3 Hz), 1.41 (3H, t, J=7.1 Hz), 1.08 (3H, t, J=7.7 Hz), 1.03–0.93 (2H, m), 0.58–0.27 (8H, m). MS (NH$_3$—CI): m/e 327 (1), 326 (7); 325 (36), 324 (21), 323 (100).

Part D. A solution of the imidate compound prepared in Part C above and p-toluenesulfonic acid monohydrate (50 mg) in diphenyl ether (10 mL) was heated to 170° C. for 2 hours. The resulting mixture was cooled and separated by column chromatography (silica gel, hexane to remove diphenyl ether, then 30:70 ethyl acetate-hexane) to afford the product, 6-chloro-9-dicyclopropylmethyl-8-ethylpurine, as an solid (1.42 g, 5.13 mmol, 68% for both steps C and D). m.p. 99–100° C. TLC $R_F$ 0.26 (30:70 ethyl acetate-hexane). $^1$H NMR (300 MHz, CDCl$_3$): d 8.63 (1H, s), 2.99 (2H, br), 1.92 (1H, br), 1.50 (3H, t, J=7.3 Hz), 0.87–0.78 (2H, m), 0.50–0.39 (4H, m), 0.20–0.10 (4H, m). MS (NH$_3$—Cl): m/e 280 (6), 279 (36), 278 (19), 277 (100).

Part E. A solution of 4-amino-3-chlorophenol hydrochloride (18.6 g, 103 mmol) and sodium acetate (18.6 g, 227 mmol) in glacial acetic acid (200 mL) was heated to gentle reflux for 12 hours, then cooled and poured into 4 volumes water. This was neutralized with portion wise addition of sodium bicarbonate, and the resulting mixture was extracted with ethyl acetate (2×500 mL). The extracts were washed with brine, combined, dried over magnesium sulfate, filtered and evaporated. The resulting solid was triturated with warm ether; filtration and vacuum drying gave 4-acetamido-3-chlorophenol (16.1 g, 86.7 mmol, 84%). m.p. 128–129° C. TLC $R_F$ 0.14 (50:50 ethyl acetate-hexane). $^1$H NMR (300 MHz, 4:1 CDCl$_3$.CD$_3$OD): d 7.66 (1H, d, J=8.8 Hz), 6.88 (1H, d, J=1.7 Hz), 6.74 (1H, dd, J=8.8, 1.7 Hz), 2.19 (3H, s). MS (H$_2$O-GC/MS): m/e 186 (100).

Part F. A solution of the phenol of Part E (14.6 g, 78.8 mmol), methyl iodide (10.0 mL, 160 mmol), and sodium carbonate (10.0 g, 94.3 mmol) in acetonitrile (200 mL) was heated to reflux for 48 hours, the cooled and poured into water (800 mL). This was extracted with ethyl acetate (2×800 mL), and the extracts were washed with brine, combined, dried over magnesium sulfate, filtered and evaporated. The resulting solid was recrystallized from ether-ethyl acetate to afford pure product, 2-chloro-4-methoxyacetanilide (13.2 g, 66.3 mmol, 84%), m.p. 118–119° C. (ether-ethyl acetate). TLC $R_F$ 0.30 (50:50 ethyl acetate-hexane). $^1$H NMR (300 MHz, CDCl$_3$): d 8.15 (1H, d, J=9.2 Hz), 7.39 (1H, br s), 6.92 (1H, d, J 3.0 Hz), 6.82 (1H, dd, J=9.2, 3.0 Hz), 3.78 (3H, s), 2.22 (3H, s). MS (NH$_3$—Cl): m/e 219 (19), 217 (60), 202 (40), 201 (14), 200 (100).

Part G. A solution of the amide from Part F (10.1 g, 50.7 mmol) and sodium hydroxide (10 mL, 5 N, 50 mmol) in 95% ethanol (200 mL) was heated to 50° C. for 24 hours. Then, an additional 5 mL sodium hydroxide solution was added, and the mixture was heated to full reflux for an additional 48 hours. The solution was cooled and evaporated, and the residual material was partitioned between ether and water. The aqueous phase was extracted a second time with ether, and the-extracts were washed with brine, combined, dried over sodium sulfate, filtered and evaporated. The resulting product, 2-chloro-4-methoxyaniline, was purified by elution through a short column of silica gel with 30:70 ethyl acetate-hexane, and the eluant was evaporated (7.98 g, 100%).

Part H. A solution of the aniline from Part G (7.98 g, 50 mmol) in conc. HCl (25 mL) was cooled to −5° C., and treated dropwise with a concentrated aqueous solution of sodium nitrite (3.80 g, 55.1 mmol). After 30 minutes, the mixture was charged with 15 mL cyclohexane and 15 mL dichloromethane, then treated dropwise with a concentrated aqueous solution of potassium iodide (16.6 g, 100 mmol). This mixture was allowed to stir for 4 hours, then was extracted with dichloromethane (2×100 mL). The extracts were washed in sequence with 1 N aqueous sodium bisulfite (100 mL) and brine (60 mL), then combined, dried over magnesium sulfate, filtered and evaporated to afford suffi ciently pure product, 3-chloro-4-iodoanisole (7.00 g, 26.1 mmol, 52%). TLC $R_F$ 0.39 (5:95 ethyl acetate-hexane). $^1$H NMR (300 MHz, CDCl$_3$): d 7.69 (1H, d, J=8.8 Hz), 7.03 (1H, d, J=3.0 Hz), 6.57 (1H, dd, J=8.8, 3.0 Hz), 3.78 (3H, s). MS (H$_2$O-GC/MS): m/e 269 (100).

Part I. A solution of the iodide compound from Part H(7.00 g, 26.1 mmol) in anhydrous tetrahydrofuran (50 mL) was cooled to −90° C., and treated with a hexane solution of n-butyllithium (16.5 mL, 1.6 M, 26.4 mmol). After 15 minutes, the solution was treated with triisopropylborate (6.10 mL, 26.4 mmol) and was allowed to warm to ambient temperature over 6 hours. The resulting mixture was treated with 6 N aqueous HCl (5 mL) and water (5 mL), which was stirred for 1 hour, then poured into water (100 mL) and extracted with ethyl acetate (2×100 mL). The extracts were washed in sequence with 1 N aqueous sodium bisulfite and brine (80 mL each), combined, dried over sodium sulfate, filtered and evaporated. The residual solid was triturated with 1:1 ether-hexane, collected by filtration and dried under vacuum to afford pure product, 2-chloro-4-methoxybenzeneboronic acid (3.05 g, 16.4 mmol, 63%). m.p. 191–195° C.

Part J. A solution of the chloride from Part D (770 mg, 2.78 mmol), the boronic acid from Part I (770 mg, 4.13 mmol), 2 N aqueous sodium carbonate solution (4 mL, 8 mmol) and triphenylphosphine (164 mg, 0.625 mmol) in DME (20 mL) was degassed by repeated cycles of brief vacuum pumping followed by nitrogen purging. To this was added palladium(II) acetate (35 mg, 0.156 mmol), and the mixture was degassed again and then heated to reflux for 14 hours. It was cooled, and poured into water (100 mL). This mixture was extracted with ethyl acetate (2×100 mL), and the extracts were washed in sequence with brine (60 mL), combined, dried over sodium sulfate, filtered and evaporated. The residual material was separated by column chromatography (silica gel, 15:85 ethyl acetate-hexane) to afford the title product as a solid. This was recrystallized to purity from hexane (791 mg, 2.07 mmol, 74%). m.p. 139–140° C. (hexane). TLC $R_F$ 0.18 (30:70 ethyl acetate-hexane). $^1$H NMR (300 MHz, CDCl$_3$): d 8.93 (1H, s), 7.74 (1H, d, J=8.4, Hz), 7.10 (1H, d, J=2.6 Hz), 6.96 (1H, dd, J=8.4, 2.6 Hz), 4.20 (1H, v br), 3.87 (3H, s), 2.97 (2H, v br), 2.00 (2H, v br), 1.44 (3H, br t, J=7 Hz), 0.89–0.79 (2H, m), 0.62–0.52 (2H, m), 0.51–0.40 (2H, m), 0.26–0.16 (2H, m). MS (NH$_3$—Cl): m/e 387 (1), 386 (9), 385 (41), 384 (30), 383 (100). Analysis calc'd for $C_{21}H_{23}ClN_4O$: C, 65.87; H, 6.05; N, 14.63; found: C, 65.77; H, 6.03; N, 14.57.

In Table 1, Table 1A and Table 1B, melting point data correspond to compounds of Structure A unless otherwise indicated.

TABLE 1

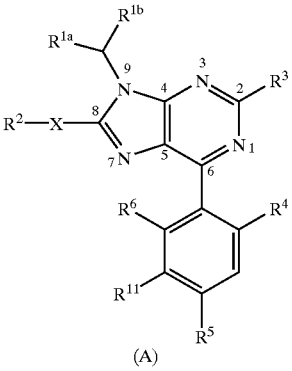

(A) (B) (C)

| Ex. No. | $R^2$ | X | $R^3$ | $R^4$ | $R^5$ | $R^{11}$ | $R^6$ | $R^{1a}$ | $R^{1b}$ | mp. °C.[a] |
|---|---|---|---|---|---|---|---|---|---|---|
| 1 | $CH_3$ | $CH_2$ | H | $CH_3$ | $CH_3$ | H | $CH_3$ | $C_2H_5$ | $C_2H_5$ | 128–129 |
| 2 | $CH_3$ | $CH_2$ | H | $CH_3$ | $CH_3$ | H | $CH_3$ | $C_2H_5$ | $C_4H_9$ | 99–100 |
| 3 | $CH_3$ | $CH_2$ | H | $CH_3$ | $CH_3$ | H | $CH_3$ | $C_2H_5$ | $CH_2OCH_3$ | oil |
| 4 | $CH_3$ | $CH_2$ | H | $CH_3$ | $CH_3$ | H | $CH_3$ | $C_2H_5$ | $C_6H_5$ | — |
| 5 | $CH_3$ | $CH_2$ | H | $CH_3$ | $CH_3$ | H | $CH_3$ | $C_2H_5$ | $c\text{-}C_3H_5$ | 143–145 |
| 6 | $CH_3$ | $CH_2$ | H | $CH_3$ | $CH_3$ | H | $CH_3$ | $C_2H_5$ | $C_6H_{13}$ | — |
| 7 | $CH_3$ | $CH_2$ | H | $CH_3$ | $CH_3$ | H | $CH_3$ | $C_2H_5$ | $C_3H_7$ | 68–71 |
| 8 | $CH_3$ | $CH_2$ | H | $CH_3$ | $CH_3$ | H | $CH_3$ | $C_2H_5$ | $(CH_2)_2OCH_3$ | oil |
| 9 | $CH_3$ | $CH_2$ | H | $CH_3$ | $CH_3$ | H | $CH_3$ | $C_2H_5$ | $(CH_2)_2OH$ | 196–197 |
| 10 | $CH_3$ | $CH_2$ | H | $CH_3$ | $CH_3$ | H | $CH_3$ | $C_2H_5$ | $(CH_2)_2\text{—}(Q1)^b$ | oil |
| 11 | $CH_3$ | $CH_2$ | H | $CH_3$ | $CH_3$ | H | $CH_3$ | $C_2H_5$ | $(CH_2)_2\text{—}(Q2)^b$ | oil |
| 12 | $CH_3$ | $CH_2$ | H | $CH_3$ | $CH_3$ | H | $CH_3$ | $C_2H_5$ | $CH_2N(CH_3)_2$ | — |
| 13 | $CH_3$ | $CH_2$ | H | $CH_3$ | $CH_3$ | H | $CH_3$ | $c\text{-}C_3H_5$ | $C_4H_9$ | 120–121 |
| 14 | $CH_3$ | $CH_2$ | H | $CH_3$ | $CH_3$ | H | $CH_3$ | $c\text{-}C_3H_5$ | $(CH_2)_2OH$ | 209–210 |
| 15 | $CH_3$ | $CH_2$ | H | $CH_3$ | $CH_3$ | H | $CH_3$ | $c\text{-}C_3H_5$ | H | 140–150 |
| 16 | $CH_3$ | $CH_2$ | H | $CH_3$ | $CH_3$ | H | $CH_3$ | $c\text{-}C_3H_5$ | $c\text{-}C_3H_5$ | 186–187 |
| 17 | $CH_3$ | $CH_2$ | H | $CH_3$ | $CH_3$ | H | $CH_3$ | H | $C_6H_5$ | 121–122 |
| 18 | $CH_3$ | $CH_2$ | H | $CH_3$ | $CH_3$ | H | $CH_3$ | H | $3\text{-}(CH_3O)\text{—}C_6H_4$ | oil |
| 19 | $CH_3$ | $CH_2$ | H | $CH_3$ | $CH_3$ | H | $CH_3$ | H | $2\text{-Br—}C_6H_4$ | 84–85 |
| 20 | $CH_3$ | $CH_2$ | H | $CH_3$ | $CH_3$ | H | $CH_3$ | H | $4\text{-}CH_3\text{—}C_6H_4$ | 48–50 |
| 21 | $CH_3$ | $CH_2$ | H | $CH_3$ | $CH_3$ | H | $CH_3$ | H | $4\text{-}C_6H_5\text{—}C_6H_4$ | — |
| 22 | $CH_3$ | $CH_2$ | H | $CH_3$ | $CH_3$ | H | $CH_3$ | H | $2\text{-}(C_4H_9)\text{—}C_4H_9$ | — |
| 23 | $CH_3$ | $CH_2$ | H | $CH_3$ | $CH_3$ | H | $CH_3$ | H | $3\text{-}(C_4H_9)\text{—}C_5H_{10}$ | — |
| 24 | $CH_3$ | $CH_2$ | H | $CH_3$ | $CH_3$ | H | $CH_3$ | H | $(CH_2)_2OCH_3$ | — |
| 25 | $CH_3$ | $CH_2$ | H | $CH_3$ | $CH_3$ | H | $CH_3$ | H | $CH_2OCH_3$ | — |
| 26 | $CH_3$ | $CH_2$ | H | $CH_3$ | $CH_3$ | H | $CH_3$ | H | $C_2H_5$ | 120–123 |
| 27 | $CH_3$ | $CH_2$ | H | $CH_3$ | $CH_3$ | H | $CH_3$ | H | $C_3H_7$ | oil |
| 28 | $CH_3$ | $CH_2$ | H | $CH_3$ | $CH_3$ | H | $CH_3$ | H | $C_4H_9$ | oil |
| 29 | $CH_3$ | $CH_2$ | H | $CH_3$ | $CH_3$ | H | $CH_3$ | $CH_2OCH_3$ | $CH_2OCH_3$ | — |
| 30 | $CH_3$ | $CH_2$ | H | $CH_3$ | $CH_3$ | H | $CH_3$ | $C_2H_5$ | $OC_2H_5$ | 91–93 |
| 31 | $CH_3$ | $CH_2$ | H | $CH_3$ | $CH_3$ | H | $CH_3$ | H | $(CH_3)_2CH$ | 120–121 |
| 32 | $CH_3$ | $CH_2$ | H | $CH_3$ | CH | H | $CH_3$ | H | $O(CH_2)_2\text{—}CCH_3$ | — |
| 33 | $CH_3$ | $CH_2$ | H | $CH_3$ | $CH_3$ | H | $CH_3$ | $CH_2OCH_3$ | $C_6H_5$ | — |
| 34 | $CH_3$ | $CH_2$ | H | Cl | Cl | H | H | $C_2H_5$ | $C_2H_5$ | oil |
| 35 | $CH_3$ | $CH_2$ | H | Cl | Cl | H | H | $C_2H_5$ | $C_4H_9$ | oil |
| 36 | $CH_3$ | $CH_2$ | H | Cl | Cl | H | H | $C_2H_5$ | $CH_2OCH_3$ | — |
| 37 | $CH_3$ | $CH_2$ | H | Cl | Cl | H | H | $C_2H_5$ | $C_6H_5$ | — |
| 38 | $CH_3$ | $CH_2$ | H | Cl | Cl | H | H | $C_2H_5$ | $c\text{-}C_3H_5$ | oil (A) 118–119 (B) 125–126 (C) |
| 39 | $CH_3$ | $CH_2$ | H | Cl | Cl | H | H | $C_2H_5$ | $C_6H_{13}$ | — |
| 40 | $CH_3$ | $CH_2$ | H | Cl | Cl | H | H | $C_2H_5$ | $C_3H_7$ | oil |
| 41 | $CH_3$ | $CH_2$ | H | Cl | Cl | H | H | $C_2H_5$ | $(CH_2)_2OCH_3$ | — |
| 42 | $CH_3$ | $CH_2$ | H | Cl | Cl | H | H | $C_2H_5$ | $CH_2CN$ | — |
| 43 | $CH_3$ | $CH_2$ | H | Cl | Cl | H | H | $C_2H_5$ | $(CH_2)_2\text{—}(Q1)^b$ | — |
| 44 | $CH_3$ | $CH_2$ | H | Cl | Cl | H | H | $C_2H_5$ | $(CH_2)_2\text{—}(Q2)^c$ | — |
| 45 | $CH_3$ | $CH_2$ | H | Cl | Cl | H | H | $C_2H_5$ | $CH_2N(CH_3)_2$ | — |
| 46 | $CH_3$ | $CH_2$ | H | Cl | Cl | H | H | $c\text{-}C_3H_5$ | $C_4H_9$ | — |
| 47 | $CH_3$ | $CH_2$ | H | Cl | Cl | H | H | $c\text{-}C_3H_5$ | $CH_2OCH_3$ | — |
| 48 | $CH_3$ | $CH_2$ | H | Cl | Cl | H | H | $c\text{-}C_3H_5$ | $C_6H_5$ | oil |
| 49 | $CH_3$ | $CH_2$ | H | Cl | Cl | H | H | $c\text{-}C_3H_5$ | $c\text{-}C_3H_5$ | 156–157 |
| 50 | $CH_3$ | $CH_2$ | H | Cl | Cl | H | H | H | $C_6H_5$ | oil |
| 51 | $CH_3$ | $CH_2$ | H | Cl | Cl | H | H | H | $3\text{-}(CH_3O)\text{—}C_6H_4$ | oil |
| 52 | $CH_3$ | $CH_2$ | H | Cl | Cl | H | H | H | $2\text{-Br—}C_6H_4$ | — |

TABLE 1-continued

| | | | | | | | | | |
|---|---|---|---|---|---|---|---|---|---|
| 53 | CH₃ | CH₂ | H | Cl | Cl | H | H | H | 4-CH₃—C₆H₄ | 114–115 |
| 54 | CH₃ | CH₂ | H | Cl | Cl | H | H | H | 4-C₆H₅—C₆H₄ | oil |
| 55 | CH₃ | CH₂ | H | Cl | Cl | H | H | H | 2-(C₄H₉)-C₄H₉ | — |
| 56 | CH₃ | CH₂ | H | Cl | Cl | H | H | H | 3-(C₄H₉)-C₅H₁₀ | — |
| 57 | CH₃ | CH₂ | H | Cl | Cl | H | H | H | (CH₂)₂OCH₃ | — |
| 58 | CH₃ | CH₂ | H | Cl | Cl | H | H | H | CH₂OCH₃ | — |
| 59 | CH₃ | CH₂ | H | Cl | Cl | H | H | H | C₂H₅ | — |
| 60 | CH₃ | CH₂ | H | Cl | Cl | H | H | H | C₃H₇ | — |
| 61 | CH₃ | CH₂ | H | Cl | Cl | H | H | H | C₄H₉ | — |
| 62 | CH₃ | CH₂ | H | Cl | Cl | H | H | CH₂OCH₃ | CH₂OCH₃ | — |
| 63 | CH₃ | CH₂ | H | Cl | Cl | H | H | C₂H₅ | OC₂H₅ | — |
| 64 | CH₃ | CH₂ | H | Cl | Cl | H | H | H | OC₂H₅ | — |
| 65 | CH₃ | CH₂ | H | Cl | Cl | H | H | H | O(CH₂)₂—OCH₃ | — |
| 66 | CH₃ | CH₂ | H | Cl | Cl | H | H | CH₂OCH₃ | C₆H₅ | — |
| 67 | CH₃ | CH₂ | H | CH₃ | OCH₃ | H | CH₃ | C₂H₅ | C₂H₅ | — |
| 68 | CH₃ | CH₂ | H | CH₃ | OCH₃ | H | CH₃ | C₂H₅ | C₄H₉ | oil |
| 69 | CH₃ | CH₂ | H | CH₃ | OCH₃ | H | CH₃ | C₂H₅ | CH₂OCH₃ | — |
| 70 | CH₃ | CH₂ | H | CH₃ | OCH₃ | H | CH₃ | C₂H₅ | C₆H₅ | — |
| 71 | CH₃ | CH₂ | H | CH₃ | OCH₃ | H | CH₃ | C₂H₅ | c-C₃H₅ | — |
| 72 | CH₃ | CH₂ | H | CH₃ | OCH₃ | H | CH₃ | C₂H₅ | C₆H₁₃ | — |
| 73 | CH₃ | CH₂ | H | CH₃ | OCH₃ | H | CH₃ | C₂H₅ | C₃H₇ | — |
| 74 | CH₃ | CH₂ | H | CH₃ | OCH₃ | H | CH₃ | C₂H₅ | (CH₂)₂OCH₃ | — |
| 75 | CH₃ | CH₂ | H | CH₃ | OCH₃ | H | CH₃ | C₂H₅ | CH₂CN | — |
| 76 | CH₃ | CH₂ | H | CH₃ | OCH₃ | H | CH₃ | C₂H₅ | (CH₂)₂—(Q1)[b] | — |
| 77 | CH₃ | CH₂ | H | CH₃ | OCH₃ | H | CH₃ | C₂H₅ | (CH₂)₂—(Q2)[c] | — |
| 78 | CH₃ | CH₂ | H | CH₃ | OCH₃ | H | CH₃ | C₂H₅ | CH₂N(CH₃)₂ | — |
| 79 | CH₃ | CH₂ | H | CH₃ | OCH₃ | H | CH₃ | c-C₃H₅ | C₄H₉ | — |
| 80 | CH₃ | CH₂ | H | CH₃ | OCH₃ | H | CH₃ | c-C₃H₅ | CH₂OCH₃ | — |
| 81 | CH₃ | CH₂ | H | CH₃ | OCH₃ | H | CH₃ | c-C₃H₅ | C₆H₅ | — |
| 82 | CH₃ | CH₂ | H | CH₃ | OCH₃ | H | CH₃ | c-C₃H₅ | c-C₃H₅ | 167–169 |
| 83 | CH₃ | CH₂ | H | CH₃ | OCH₃ | H | CH₃ | H | C₆H₅ | 134–135 |
| 84 | CH₃ | CH₂ | H | CH₃ | OCH₃ | H | CH₃ | H | 3-(CH₃O)—C₆H₄ | — |
| 85 | CH₃ | CH₂ | H | CH₃ | OCH₃ | H | CH₃ | H | 2-Br—C₆H₄ | — |
| 86 | CH₃ | CH₂ | H | CH₃ | OCH₃ | H | CH₃ | H | 4-CH₃—C₆H₄ | — |
| 87 | CH₃ | CH₂ | H | CH₃ | OCH₃ | H | CH₃ | H | 4-C₆H₅—C₆H₄ | — |
| 88 | CH₃ | CH₂ | H | CH₃ | OCH₃ | H | CH₃ | H | 2-(C₄H₉)—C₄H₉ | — |
| 89 | CH₃ | CH₂ | H | CH₃ | OCH₃ | H | CH₃ | H | 3-(C₄H₉)—C₅H₁₀ | — |
| 90 | CH₃ | CH₂ | H | CH₃ | OCH₃ | H | CH₃ | H | (CH₃)₂OCH₃ | — |
| 91 | CH₃ | CH₂ | H | CH₃ | OCH₃ | H | CH₃ | H | CH₂OCH₃ | — |
| 92 | CH₃ | CH₂ | H | CH₃ | OCH₃ | H | CH₃ | H | C₂H₅ | — |
| 93 | CH₃ | CH₂ | H | CH₃ | OCH₃ | H | CH₃ | H | C₃H₇ | — |
| 94 | CH₃ | CH₂ | H | CH₃ | OCH₃ | H | CH₃ | H | C₄H₉ | — |
| 95 | CH₃ | CH₂ | H | CH₃ | OCH₃ | H | CH₃ | CH₂OCH₃ | CH₂OCH₃ | — |
| 96 | CH₃ | CH₂ | H | CH₃ | OCH₃ | H | CH₃ | C₂H₅ | OC₂H₅ | — |
| 97 | CH₃ | CH₂ | H | CH₃ | OCH₃ | H | CH₃ | H | OC₂H₅ | — |
| 98 | CH₃ | CH₂ | H | CH₃ | OCH₃ | H | CH₃ | H | O(CH₂)₂—OCH₃ | — |
| 99 | CH₃ | CH₂ | H | CH₃ | OCH₃ | H | CH₃ | CH₂OCH₃ | C₆H₅ | — |
| 100 | CH₃ | CH₂ | H | CH₃ | CH₃ | H | CH₃ | H | CH₃ | 138–140 |
| 101 | H | CH₂ | H | CH₃ | CH₃ | H | CH₃ | C₂H₅ | C₂H₅ | 198–199 |
| 102 | H | CH₂ | H | CH₃ | CH₃ | H | CH₃ | C₂H₅ | C₄H₉ | 147–148 |
| 103 | H | CH₂ | H | CH₃ | CH₃ | H | CH₃ | C₂H₅ | CH₂OCH₃ | 140–142 |
| 104 | H | CH₂ | H | CH₃ | CH₃ | H | CH₃ | C₂H₅ | C₆H₅ | — |
| 105 | H | CH₂ | H | CH₃ | CH₃ | H | CH₃ | C₂H₅ | c-C₃H₅ | — |
| 106 | H | CH₂ | H | CH₃ | CH₃ | H | CH₃ | C₂H₅ | C₆H₁₃ | — |
| 107 | H | CH₂ | H | CH₃ | CH₃ | H | CH₃ | C₂H₅ | C₃H₇ | — |
| 108 | H | CH₂ | H | CH₃ | CH₃ | H | CH₃ | C₂H₅ | (CH₂)₂OCH₃ | — |
| 109 | H | CH₂ | H | CH₃ | CH₃ | H | CH₃ | C₂H₅ | CH₂CN | — |
| 110 | H | CH₂ | H | CH₃ | CH₃ | H | CH₃ | C₂H₅ | (CH₂)₂—(Q1)[b] | — |
| 111 | H | CH₂ | H | CH₃ | CH₃ | H | CH₃ | C₂H₅ | (CH₂)₂—(Q2)[c] | — |
| 112 | H | CH₂ | H | CH₃ | CH₃ | H | CH₃ | C₂H₅ | CH₂N(CH₃)₂ | — |
| 113 | H | CH₂ | H | CH₃ | CH₃ | H | CH₃ | c-C₃H₅ | C₄H₉ | — |
| 114 | H | CH₂ | H | CH₃ | CH₃ | H | CH₃ | c-C₃H₅ | CH₂OCH₃ | — |
| 115 | H | CH₂ | H | CH₃ | CH₃ | H | CH₃ | c-C₃H₅ | C₆H₅ | — |
| 116 | H | CH₂ | H | CH₃ | CH₃ | H | CH₃ | c-C₃H₅ | c-C₃H₅ | — |
| 117 | H | CH₂ | H | CH₃ | CH₃ | H | CH₃ | H | C₆H₅ | — |
| 118 | H | CH₂ | H | CH₃ | CH₃ | H | CH₃ | H | 3-(CH₃O)—C₆H₄ | — |
| 119 | H | CH₂ | H | CH₃ | CH₃ | H | CH₃ | H | 2-Br—C₆H₄ | — |
| 120 | H | CH₂ | H | CH₃ | CH₃ | H | CH₃ | H | 4-CH₃—C₆H₄ | — |
| 121 | H | CH₂ | H | CH₃ | CH₃ | H | CH₃ | H | 4-C₆H₅—C₆H₄ | — |
| 122 | H | CH₂ | H | CH₃ | CH₃ | H | CH₃ | H | 3-C₇H₁₅ | oil |
| 123 | H | CH₂ | H | CH₃ | CH₃ | H | CH₃ | H | 2-(C₂H₅)—C₆H₁₂ | oil |
| 124 | H | CH₂ | H | CH₃ | CH₃ | H | CH₃ | H | (CH₂)₂OCH₃ | — |
| 125 | H | CH₂ | H | CH₃ | CH₃ | H | CH₃ | H | CH₂OCH₃ | — |
| 126 | H | CH₂ | H | CH₃ | CH₃ | H | CH₃ | H | C₂H₅ | — |
| 127 | H | CH₂ | Y | CH₃ | CH₃ | H | CH₃ | H | C₃H₇ | — |
| 128 | H | CH₂ | H | CH₃ | CH₃ | H | CH₃ | H | C₄H₉ | — |
| 129 | H | CH₂ | H | CH₃ | CH₃ | H | CH₃ | CH₂OCH₃ | CH₂OCH₃ | — |
| 130 | H | CH₂ | H | CH₃ | CH₃ | H | CH₃ | C₂H₅ | OC₂H₅ | — |
| 131 | H | CH₂ | H | CH₃ | CH₃ | H | CH₃ | H | OC₂H₅ | — |

TABLE 1-continued

| | | | | | | | | | |
|---|---|---|---|---|---|---|---|---|---|
| 132 | H | CH$_2$ | H | CH$_3$ | CH$_3$ | H | CH$_3$ | H | O(CH$_2$)$_2$—OCH$_3$ | — |
| 133 | H | CH$_2$ | H | CH$_3$ | CH$_3$ | H | CH$_3$ | CH$_2$OCH$_3$ | C$_6$H$_5$ | — |
| 134 | H | CH$_2$ | H | Cl | Cl | H | H | C$_2$H$_5$ | C$_2$H$_5$ | — |
| 135 | H | CH$_2$ | H | Cl | Cl | H | H | C$_2$H$_5$ | C$_4$H$_9$ | — |
| 136 | H | CH$_2$ | H | Cl | Cl | H | H | C$_2$H$_5$ | CH$_2$OCH$_3$ | — |
| 137 | H | CH$_2$ | H | Cl | Cl | H | H | C$_2$H$_5$ | C$_6$H$_5$ | — |
| 138 | H | CH$_2$ | H | Cl | Cl | H | H | C$_2$H$_5$ | c-C$_3$H$_5$ | — |
| 139 | H | CH$_2$ | H | Cl | Cl | H | H | C$_2$H$_5$ | C$_6$H$_{13}$ | — |
| 140 | H | CH$_2$ | H | Cl | Cl | H | H | C$_2$H$_5$ | C$_3$H$_7$ | — |
| 141 | H | CH$_2$ | H | Cl | Cl | H | H | C$_2$H$_5$ | (CH$_2$)$_2$OCH$_3$ | — |
| 142 | H | CH$_2$ | H | Cl | Cl | H | H | C$_2$H$_5$ | CH$_2$CN | — |
| 143 | H | CH$_2$ | H | Cl | Cl | H | H | C$_2$H$_5$ | (CH$_2$)$_2$—(Q1)$^b$ | — |
| 144 | H | CH$_2$ | H | Cl | Cl | H | H | C$_2$H$_5$ | (CH$_2$)$_2$—(Q2)$^c$ | — |
| 145 | H | CH$_2$ | H | Cl | Cl | H | H | C$_2$H$_5$ | CH$_2$N(CH$_3$)$_2$ | — |
| 146 | H | CH$_2$ | H | Cl | Cl | H | H | c-C$_3$H$_5$ | C$_4$H$_9$ | — |
| 147 | H | CH$_2$ | H | Cl | Cl | H | H | c-C$_3$H$_5$ | CH$_2$OCH$_3$ | — |
| 148 | H | CH$_2$ | H | Cl | Cl | H | H | c-C$_3$H$_5$ | C$_6$H$_5$ | — |
| 149 | H | CH$_2$ | H | Cl | Cl | H | H | c-C$_3$H$_5$ | c-C$_3$H$_5$ | — |
| 150 | H | CH$_2$ | H | Cl | Cl | H | H | H | C$_6$H$_5$ | — |
| 151 | H | CH$_2$ | H | Cl | Cl | H | H | H | 3-(CH$_3$O)—C$_6$H$_4$ | — |
| 152 | H | CH$_2$ | H | Cl | Cl | H | H | H | 2-Br—C$_6$H$_4$ | — |
| 153 | H | CH$_2$ | H | Cl | Cl | H | H | H | 4-CH$_3$—C$_6$H$_4$ | — |
| 154 | H | CH$_2$ | H | Cl | Cl | H | H | H | 4-C$_6$H$_5$—C$_4$H$_4$ | — |
| 155 | H | CH$_2$ | H | Cl | Cl | H | H | H | 2-(C$_4$H$_9$)—C$_4$H$_9$ | — |
| 156 | H | CH$_2$ | H | Cl | Cl | H | H | H | 3-(C$_4$H$_9$)—C$_5$H$_{10}$ | — |
| 157 | H | CH$_2$ | H | Cl | Cl | H | H | H | (CH$_2$)$_2$OCH$_3$ | — |
| 158 | H | CH$_2$ | H | Cl | Cl | H | H | H | CH$_2$OCH$_3$ | — |
| 159 | H | CH$_2$ | H | Cl | Cl | H | H | H | C$_2$H$_5$ | — |
| 160 | H | CH$_2$ | H | Cl | Cl | H | H | H | C$_3$H$_7$ | — |
| 161 | H | CH$_2$ | H | Cl | Cl | H | H | H | C$_4$H$_9$ | — |
| 162 | H | CH$_2$ | H | Cl | Cl | H | H | CH$_2$OCH$_3$ | CH$_2$OCH$_3$ | — |
| 163 | H | CH$_2$ | H | Cl | Cl | H | H | C$_2$H$_5$ | OC$_2$H$_5$ | — |
| 164 | H | CH$_2$ | H | Cl | Cl | H | H | H | OC$_2$H$_5$ | — |
| 165 | H | CH$_2$ | H | Cl | Cl | H | H | H | O(CH$_2$)$_2$—OCH$_3$ | — |
| 166 | H | CH$_2$ | H | Cl | Cl | H | H | CH$_2$OCH$_3$ | C$_6$H$_5$ | — |
| 167 | H | CH$_2$ | H | CH$_3$ | OCH$_3$ | H | CH$_3$ | C$_2$H$_5$ | C$_2$H$_5$ | — |
| 168 | H | CH$_2$ | H | CH$_3$ | OCH$_3$ | H | CH$_3$ | C$_2$H$_5$ | C$_4$H$_9$ | — |
| 169 | H | CH$_2$ | H | CH$_3$ | OCH$_3$ | H | CH$_3$ | C$_2$H$_5$ | CH$_2$OCH$_3$ | — |
| 170 | H | CH$_2$ | H | CH$_3$ | OCH$_2$ | H | CH$_3$ | C$_2$H$_5$ | C$_6$H$_5$ | — |
| 171 | H | CH$_2$ | H | CH$_3$ | OCH$_3$ | H | CH$_3$ | C$_2$H$_5$ | c-C$_3$H$_5$ | — |
| 172 | H | CH$_2$ | H | CH$_3$ | OCH$_3$ | H | CH$_3$ | C$_2$H$_5$ | C$_6$H$_{13}$ | — |
| 173 | H | CH$_2$ | H | CH$_3$ | OCH$_3$ | H | CH$_3$ | C$_2$H$_5$ | C$_3$H$_7$ | — |
| 174 | H | CH$_2$ | H | CH$_3$ | OCH$_3$ | H | CH$_3$ | C$_2$H$_5$ | (CH$_2$)$_2$OCH$_3$ | — |
| 175 | H | CH$_2$ | H | CH$_3$ | OCH$_3$ | H | CH$_3$ | C$_2$H$_5$ | CH$_2$CN | — |
| 176 | H | CH$_2$ | H | CH$_3$ | OCH$_3$ | H | CH$_3$ | C$_2$H$_5$ | (CH$_2$)$_2$—(Q1)$^b$ | — |
| 177 | H | CH$_2$ | H | CH$_3$ | OCH$_3$ | H | CH$_3$ | C$_2$H$_5$ | (CH$_2$)$_2$—(Q2)$^c$ | — |
| 178 | H | CH$_2$ | H | CH$_3$ | OCH$_3$ | H | CH$_3$ | C$_2$H$_5$ | CH$_2$N(CH$_3$)$_2$ | — |
| 179 | H | CH$_2$ | H | CH$_3$ | OCH$_3$ | H | CH$_3$ | c-C$_3$H$_5$ | C$_4$H$_9$ | — |
| 180 | H | CH$_2$ | H | CH$_3$ | OCH$_3$ | H | CH$_3$ | c-C$_3$H$_5$ | CH$_2$OCH$_3$ | — |
| 181 | H | CH$_2$ | H | CH$_3$ | OCH$_3$ | H | CH$_3$ | c-C$_3$H$_5$ | C$_6$H$_5$ | — |
| 182 | H | CH$_2$ | H | CH$_3$ | OCH$_3$ | H | CH$_3$ | c-C$_3$H$_5$ | c-C$_3$H$_5$ | — |
| 183 | H | CH$_2$ | H | CH$_3$ | OCH$_3$ | H | CH$_3$ | H | C$_6$H$_5$ | — |
| 184 | H | CH$_2$ | H | CH$_3$ | OCH$_3$ | H | CH$_3$ | H | 3-(CH$_3$O)—C$_6$H$_4$ | — |
| 185 | H | CH$_2$ | H | CH$_3$ | OCH$_3$ | H | CH$_3$ | H | 2-Br—C$_6$H$_4$ | — |
| 186 | H | CH$_2$ | H | CH$_3$ | OCH$_3$ | H | CH$_3$ | H | 4-CH$_3$—C$_6$H$_4$ | — |
| 187 | H | CH$_2$ | H | CH$_3$ | OCH$_3$ | H | CH$_3$ | H | 4-C$_6$H$_5$—C$_6$H$_4$ | — |
| 188 | H | CH$_2$ | H | CH$_3$ | OCH$_3$ | H | CH$_3$ | H | 2-(C$_4$H$_9$)—C$_4$H$_9$ | — |
| 189 | H | CH$_2$ | H | CH$_3$ | OCH$_3$ | H | CH$_3$ | H | 3-(C$_4$H$_9$)—C$_5$H$_{10}$ | — |
| 190 | H | CH$_2$ | H | CH$_3$ | OCH$_3$ | H | CH$_3$ | H | (CH$_2$)$_2$OCH$_3$ | — |
| 191 | H | CH$_2$ | H | CH$_3$ | OCH$_3$ | H | CH$_3$ | H | CH$_2$OCH$_3$ | — |
| 192 | H | CH$_2$ | H | CH$_3$ | OCH$_3$ | H | CH$_3$ | H | C$_2$H$_5$ | — |
| 193 | H | CH$_2$ | H | CH$_3$ | OCH$_3$ | H | CH$_3$ | H | C$_3$H$_7$ | — |
| 194 | H | CH$_2$ | H | CH$_3$ | OCH$_3$ | H | CH$_3$ | H | C$_4$H$_9$ | — |
| 195 | H | CH$_2$ | H | CH$_3$ | OCH$_3$ | H | CH$_3$ | CH$_2$OCH$_3$ | CH$_2$OCH$_3$ | — |
| 196 | H | CH$_2$ | H | CH$_3$ | OCH$_3$ | H | CH$_3$ | C$_2$H$_5$ | OC$_2$H$_5$ | — |
| 197 | H | CH$_2$ | H | CH$_3$ | OCH$_3$ | H | CH$_3$ | H | OC$_2$H$_5$ | — |
| 198 | H | CH$_2$ | H | CH$_3$ | OCH$_3$ | H | CH$_3$ | H | O(CH$_2$)$_2$—OCH$_3$ | — |
| 199 | H | CH$_2$ | H | CH$_3$ | OCH$_3$ | H | CH$_3$ | CH$_2$OCH$_3$ | C$_6$H$_5$ | — |
| 200 | CH$_3$ | CH$_2$ | H | CH$_3$ | CH$_3$ | H | CH$_3$ | CH$_3$ | C$_2$H$_5$ | 98–100 |
| 201 | CH$_3$ | O | H | CH$_3$ | CH$_3$ | H | CH$_3$ | C$_2$H$_5$ | C$_2$H$_5$ | — |
| 202 | CH$_3$ | O | H | CH$_3$ | CH$_3$ | H | CH$_3$ | C$_2$H$_5$ | C$_4$H$_9$ | oil |
| 203 | CH$_3$ | O | H | CH$_3$ | CH$_3$ | H | CH$_3$ | C$_2$H$_5$ | CH$_2$OCH$_3$ | — |
| 204 | CH$_3$ | O | H | CH$_3$ | CH$_3$ | H | CH$_3$ | C$_2$H$_5$ | C$_6$H$_5$ | — |
| 205 | CH$_3$ | O | H | CH$_3$ | CH$_3$ | H | CH$_3$ | C$_2$H$_5$ | c-C$_3$H$_5$ | — |
| 206 | CH$_3$ | O | H | CH$_3$ | CH$_3$ | H | CH$_3$ | C$_2$H$_5$ | C$_6$H$_{13}$ | — |
| 207 | CH$_3$ | O | H | CH$_3$ | CH$_3$ | H | CH$_3$ | C$_2$H$_5$ | C$_3$H$_7$ | — |
| 208 | CH$_3$ | O | H | CH$_3$ | CH$_3$ | H | CH$_3$ | C$_2$H$_5$ | (CH$_2$)$_2$OCH$_3$ | — |
| 209 | CH$_3$ | O | H | CH$_3$ | CH$_3$ | H | CH$_3$ | C$_2$H$_5$ | CH$_2$CN | — |
| 210 | CH$_3$ | O | H | CH$_3$ | CH$_3$ | H | CH$_3$ | C$_2$H$_5$ | (CH$_2$)$_2$—(Q1)$^b$ | — |

TABLE 1-continued

| | | | | | | | | | |
|---|---|---|---|---|---|---|---|---|---|
| 211 | CH$_3$ | O | H | CH$_3$ | CH$_3$ | H | CH$_3$ | C$_2$H$_5$ | (CH$_2$)$_2$—(Q2)$^c$ | — |
| 212 | CH$_3$ | O | H | CH$_3$ | CH$_3$ | H | CH$_3$ | C$_2$H$_5$ | CH$_2$N(CH$_3$)$_2$ | — |
| 213 | CH$_3$ | O | H | CH$_3$ | CH$_3$ | H | CH$_3$ | c-C$_3$H$_5$ | C$_4$H$_9$ | — |
| 214 | CH$_3$ | O | H | CH$_3$ | CH$_3$ | H | CH$_3$ | c-C$_3$H$_5$ | CH$_2$OCH$_3$ | — |
| 215 | CH$_3$ | O | H | CH$_3$ | CH$_3$ | H | CH$_3$ | c-C$_3$H$_5$ | C$_6$H$_5$ | — |
| 216 | CH$_3$ | O | H | CH$_3$ | CH$_3$ | H | CH$_3$ | c-C$_3$H$_5$ | c-C$_3$H$_5$ | — |
| 217 | CH$_3$ | O | H | CH$_3$ | CH$_3$ | H | CH$_3$ | H | C$_6$H$_5$ | — |
| 218 | CH$_3$ | O | H | CH$_3$ | CH$_3$ | H | CH$_3$ | H | 3-(CH$_3$O)—C$_6$H$_4$ | — |
| 219 | CH$_3$ | O | H | CH$_3$ | CH$_3$ | H | CH$_3$ | H | 2-Br—C$_6$H$_4$ | — |
| 220 | CH$_3$ | O | H | CH$_3$ | CH$_3$ | H | CH$_3$ | H | 4-CH$_3$—C$_6$H$_4$ | — |
| 221 | CH$_3$ | O | H | CH$_3$ | CH$_3$ | H | CH$_3$ | H | 4-C$_6$H$_5$—C$_6$H$_4$ | — |
| 222 | CH$_3$ | O | H | CH$_3$ | CH$_3$ | H | CH$_3$ | H | 2-(C$_4$H$_9$)—C$_4$H$_8$ | — |
| 223 | CH$_3$ | O | H | CH$_3$ | CH$_3$ | H | CH$_3$ | H | 3-(C$_4$H$_9$)—C$_5$H$_{10}$ | — |
| 224 | CH$_3$ | O | H | CH$_3$ | CH$_3$ | H | CH$_3$ | H | (CH$_2$)$_2$OCH$_3$ | — |
| 225 | CH$_3$ | O | H | CH$_3$ | CH$_3$ | H | CH$_3$ | H | CH$_2$OCH$_3$ | — |
| 226 | CH$_3$ | O | H | CH$_3$ | CH$_3$ | H | CH$_3$ | H | C$_2$H$_5$ | — |
| 227 | CH$_3$ | O | H | CH$_3$ | CH$_3$ | H | CH$_3$ | H | C$_3$H$_7$ | — |
| 228 | CH$_3$ | O | H | CH$_3$ | CH$_3$ | H | CH$_3$ | H | C$_4$H$_9$ | — |
| 229 | CH$_3$ | O | H | CH$_3$ | CH$_3$ | H | CH$_3$ | CH$_2$OCH$_3$ | CH$_2$OCH$_3$ | — |
| 230 | CH$_3$ | O | H | CH$_3$ | CH$_3$ | H | CH$_3$ | C$_2$H$_5$ | OC$_2$H$_5$ | — |
| 231 | CH$_3$ | O | H | CH$_3$ | CH$_3$ | H | CH$_3$ | C$_3$H$_7$ | OC$_2$H$_5$ | — |
| 232 | CH$_3$ | O | H | CH$_3$ | CH$_3$ | H | CH$_3$ | H | O(CH$_2$)$_2$—OCH$_3$ | — |
| 233 | CH$_3$ | O | H | CH$_3$ | CH$_3$ | H | CH$_3$ | CH$_2$OCH$_3$ | C$_6$H$_5$ | — |
| 234 | CH$_3$ | O | H | Cl | Cl | H | H | C$_2$H$_5$ | C$_2$H$_5$ | — |
| 235 | CH$_3$ | O | H | Cl | Cl | H | H | C$_2$H$_5$ | C$_4$H$_9$ | — |
| 236 | CH$_3$ | O | H | Cl | Cl | H | H | C$_2$H$_5$ | CH$_2$OCH$_3$ | — |
| 237 | CH$_3$ | O | H | Cl | Cl | H | H | C$_2$H$_5$ | C$_6$H$_5$ | — |
| 238 | CH$_3$ | O | H | Cl | Cl | H | H | C$_2$H$_5$ | c-C$_3$H$_5$ | — |
| 239 | CH$_3$ | O | H | Cl | Cl | H | H | C$_2$H$_5$ | C$_6$H$_{13}$ | — |
| 240 | CH$_3$ | O | H | Cl | Cl | H | H | C$_2$H$_5$ | C$_3$H$_7$ | — |
| 241 | CH$_3$ | O | H | Cl | Cl | H | H | C$_2$H$_5$ | (CH$_2$)$_2$OCH$_3$ | — |
| 242 | CH$_3$ | O | H | Cl | Cl | H | H | C$_2$H$_5$ | CH$_2$CN | — |
| 243 | CH$_3$ | O | H | Cl | Cl | H | H | C$_2$H$_5$ | (CH$_2$)$_2$—(Q1)$^b$ | — |
| 244 | CH$_3$ | O | H | Cl | Cl | H | H | C$_2$H$_5$ | (CH$_2$)$_2$—(Q2)$^c$ | — |
| 245 | CH$_3$ | O | H | Cl | Cl | H | H | C$_2$H$_5$ | CH$_2$H(CH$_3$)$_2$ | — |
| 246 | CH$_3$ | O | H | Cl | Cl | H | H | c-C$_3$H$_5$ | C$_4$H$_9$ | — |
| 247 | CH$_3$ | O | H | Cl | Cl | H | H | c-C$_3$H$_5$ | CH$_2$OCH$_3$ | — |
| 248 | CH$_3$ | O | H | Cl | Cl | H | H | c-C$_3$H$_5$ | C$_6$H$_5$ | — |
| 249 | CH$_3$ | O | H | Cl | Cl | H | H | c-C$_3$H$_5$ | c-C$_3$H$_5$ | 132–134 |
| 250 | CH$_3$ | O | H | Cl | Cl | H | H | H | C$_6$H$_5$ | — |
| 251 | CH$_3$ | O | H | Cl | Cl | H | H | H | 3-(CH$_3$O)—C$_6$H$_4$ | — |
| 252 | CH$_3$ | O | H | Cl | Cl | H | H | H | 2-Br—C$_6$H$_4$ | — |
| 253 | CH$_3$ | O | H | Cl | Cl | H | H | H | 4-CH$_3$—C$_6$H$_4$ | — |
| 254 | CH$_3$ | O | H | Cl | Cl | H | H | H | 4-C$_6$H$_5$—C$_6$H$_4$ | — |
| 255 | CH$_3$ | O | H | Cl | Cl | H | H | H | 2-(C$_4$H$_9$)—C$_4$H$_9$ | — |
| 256 | CH$_3$ | O | H | Cl | Cl | H | H | H | 3-(C$_4$H$_9$)—C$_5$H$_{10}$ | — |
| 257 | CH$_3$ | O | H | Cl | Cl | H | H | H | (CH$_2$)$_2$OCH$_3$ | — |
| 258 | CH$_3$ | O | H | Cl | Cl | H | H | H | CH$_2$OCH$_3$ | — |
| 259 | CH$_3$ | O | H | Cl | Cl | H | H | H | C$_2$H$_5$ | — |
| 260 | CH$_3$ | O | H | Cl | Cl | H | H | H | C$_3$H$_7$ | — |
| 261 | CH$_3$ | O | H | Cl | Cl | H | H | H | C$_4$H$_9$ | — |
| 262 | CH$_3$ | O | H | Cl | Cl | H | H | CH$_2$OCH$_3$ | CH$_2$OCH$_3$ | — |
| 263 | CH$_3$ | O | H | Cl | Cl | H | H | C$_2$H$_5$ | OC$_2$H$_5$ | — |
| 264 | CH$_3$ | O | H | Cl | Cl | H | H | H | OC$_2$H$_5$ | — |
| 265 | CH$_3$ | O | H | Cl | Cl | H | H | H | O(CH$_2$)$_2$—OCH$_3$ | — |
| 266 | CH$_3$ | O | H | Cl | Cl | H | H | CH$_2$OCH$_3$ | C$_6$H$_5$ | — |
| 267 | CH$_3$ | O | H | CH$_3$ | OCH$_3$ | H | CH$_3$ | C$_2$H$_5$ | C$_2$H$_5$ | — |
| 268 | CH$_3$ | O | H | CH$_3$ | OCH$_3$ | H | CH$_3$ | C$_2$H$_5$ | C$_4$H$_9$ | — |
| 269 | CH$_3$ | O | H | CH$_3$ | OCH$_3$ | H | CH$_3$ | C$_2$H$_5$ | CH$_2$OCH$_3$ | — |
| 270 | CH$_3$ | O | H | CH$_3$ | OCH$_3$ | H | CH$_3$ | C$_2$H$_5$ | C$_6$H$_5$ | — |
| 271 | CH$_3$ | O | H | CH$_3$ | OCH$_3$ | H | CH$_3$ | C$_2$H$_5$ | c-C$_3$H$_5$ | — |
| 272 | CH$_3$ | O | H | CH$_3$ | OCH$_3$ | H | CH$_3$ | C$_2$H$_5$ | C$_6$H$_{13}$ | — |
| 273 | CH$_3$ | O | H | CH$_3$ | OCH$_3$ | H | CH$_3$ | C$_2$H$_5$ | C$_3$H$_7$ | — |
| 274 | CH$_3$ | O | H | CH$_3$ | OCH$_3$ | H | CH$_3$ | C$_2$H$_5$ | (CH$_2$)$_2$OCH$_3$ | — |
| 275 | CH$_3$ | O | H | CH$_3$ | OCH$_3$ | H | CH$_3$ | C$_2$H$_5$ | CH$_2$CN | — |
| 276 | CH$_3$ | O | H | CH$_3$ | OCH$_3$ | H | CH$_3$ | C$_2$H$_5$ | (CH$_2$)$_2$—(Q1)$^b$ | — |
| 277 | CH$_3$ | O | H | CH$_3$ | OCH$_3$ | H | CH$_3$ | C$_2$H$_5$ | (CH$_2$)$_2$—(Q2)$^c$ | — |
| 278 | CH$_3$ | O | H | CH$_3$ | OCH$_3$ | H | CH$_3$ | C$_2$H$_5$ | CH$_2$N(CH$_3$)$_2$ | — |
| 279 | CH$_3$ | O | H | CH$_3$ | OCH$_3$ | H | CH$_3$ | c-C$_3$H$_5$ | C$_4$H$_9$ | — |
| 280 | CH$_3$ | O | H | CH$_3$ | OCH$_3$ | H | CH$_3$ | c-C$_3$H$_5$ | CH$_2$OCH$_3$ | — |
| 281 | CH$_3$ | O | H | CH$_3$ | OCH$_3$ | H | CH$_3$ | c-C$_3$H$_5$ | C$_6$H$_5$ | — |
| 282 | CH$_3$ | O | H | CH$_3$ | OCH$_3$ | H | CH$_3$ | c-C$_3$H$_5$ | c-C$_3$H$_5$ | — |
| 283 | CH$_3$ | O | H | CH$_3$ | OCH$_3$ | H | CH$_3$ | H | C$_6$H$_5$ | — |
| 284 | CH$_3$ | O | H | CH$_3$ | OCH$_3$ | H | CH$_3$ | H | 3-(CH$_3$O)—C$_6$H$_4$ | — |
| 285 | CH$_3$ | O | H | CH$_3$ | OCH$_3$ | H | CH$_3$ | H | 2-Br—C$_6$H$_4$ | — |
| 286 | CH$_3$ | O | H | CH$_3$ | OCH$_3$ | H | CH$_3$ | H | 4-CH$_3$—C$_6$H$_4$ | — |
| 287 | CH$_3$ | O | H | CH$_3$ | OCH$_3$ | H | CH$_3$ | H | 4-C$_6$H$_5$—C$_6$H$_4$ | — |
| 288 | CH$_3$ | O | H | CH$_3$ | OCH$_3$ | H | CH$_3$ | H | 2-(C$_4$H$_9$)—C$_4$H$_9$ | — |
| 289 | CH$_3$ | O | H | CH$_3$ | OCH$_3$ | H | CH$_3$ | H | 3-(C$_4$H$_9$)—C$_5$H$_{10}$ | — |

TABLE 1-continued

| | | | | | | | | | | |
|---|---|---|---|---|---|---|---|---|---|---|
| 290 | CH$_3$ | O | H | CH$_3$ | OCH$_3$ | H | CH$_3$ | H | (CH$_2$)$_2$OCH$_3$ | — |
| 291 | CH$_3$ | O | H | CH$_3$ | OCH$_3$ | H | CH$_3$ | H | CH$_2$OCH$_3$ | — |
| 292 | CH$_3$ | O | H | CH$_3$ | OCH$_3$ | H | CH$_3$ | H | C$_2$H$_5$ | — |
| 293 | CH$_3$ | O | H | CH$_3$ | OCH$_3$ | H | CH$_3$ | H | C$_3$H$_7$ | — |
| 294 | CH$_3$ | O | H | CH$_3$ | OCH$_3$ | H | CH$_3$ | H | C$_4$H$_9$ | — |
| 295 | CH$_3$ | O | H | CH$_3$ | OCH$_3$ | H | CH$_3$ | CH$_2$OCH$_3$ | CH$_2$OCH$_3$ | — |
| 296 | CH$_3$ | O | H | CH$_3$ | OCH$_3$ | H | CH$_3$ | C$_2$H$_5$ | OC$_2$H$_5$ | — |
| 297 | CH$_3$ | O | H | CH$_3$ | OCH$_3$ | H | CH$_3$ | H | OC$_2$H$_5$ | — |
| 298 | CH$_3$ | O | H | CH$_3$ | OCH$_3$ | H | CH$_3$ | H | O(CH$_2$)$_2$—OCH$_3$ | — |
| 299 | CH$_3$ | O | H | CH$_3$ | OCH$_3$ | H | CH$_3$ | CH$_2$OCH$_3$ | C$_6$H$_5$ | — |
| 300 | CH$_3$ | CH$_2$ | CH$_3$ | H | Cl | H | H | c-C$_3$H$_5$ | c-C$_3$H$_5$ | 106–109 |
| 301 | CH$_3$ | S | H | CH$_3$ | CH$_3$ | H | CH$_3$ | C$_2$H$_5$ | C$_2$H$_5$ | — |
| 302 | CH$_3$ | S | H | CH$_3$ | CH$_3$ | H | CH$_3$ | C$_2$H$_5$ | C$_4$H$_9$ | — |
| 303 | CH$_3$ | S | H | CH$_3$ | CH$_3$ | H | CH$_3$ | C$_2$H$_5$ | CH$_2$OCH$_3$ | — |
| 304 | CH$_3$ | S | H | CH$_3$ | CH$_3$ | H | CH$_3$ | C$_2$H$_5$ | C$_6$H$_5$ | — |
| 305 | CH$_3$ | S | H | CH$_3$ | CH$_3$ | H | CH$_3$ | C$_2$H$_5$ | c-C$_3$H$_5$ | — |
| 306 | CH$_3$ | S | H | CH$_3$ | CH$_3$ | H | CH$_3$ | C$_2$H$_5$ | C$_6$H$_{13}$ | — |
| 307 | CH$_3$ | S | H | CH$_3$ | CH$_3$ | H | CH$_3$ | C$_2$H$_5$ | C$_3$H$_7$ | — |
| 308 | CH$_3$ | S | H | CH$_3$ | CH$_3$ | H | CH$_3$ | C$_2$H$_5$ | (CH$_2$)$_2$OCH$_3$ | — |
| 309 | CH$_3$ | S | H | CH$_3$ | CH$_3$ | H | CH$_3$ | C$_2$H$_5$ | CH$_2$CN | — |
| 310 | CH$_3$ | S | H | CH$_3$ | CH$_3$ | H | CH$_3$ | C$_2$H$_5$ | (CH$_2$)$_2$—(Q1)[b] | — |
| 311 | CH$_3$ | S | H | CH$_3$ | CH$_3$ | H | CH$_3$ | C$_2$H$_5$ | (CH$_2$)$_2$—(Q1)[c] | — |
| 312 | CH$_3$ | S | H | CH$_3$ | CH$_3$ | H | CH$_3$ | C$_2$H$_5$ | CH$_2$N(CH$_3$)$_2$ | — |
| 313 | CH$_3$ | S | H | CH$_3$ | CH$_3$ | H | CH$_3$ | c-C$_3$H$_5$ | C$_4$H$_9$ | — |
| 314 | CH$_3$ | S | H | CH$_3$ | CH$_3$ | H | CH$_3$ | c-C$_3$H$_5$ | CH$_2$OCH$_3$ | — |
| 315 | CH$_3$ | S | H | CH$_3$ | CH$_3$ | H | CH$_3$ | c-C$_3$H$_5$ | C$_6$H$_5$ | — |
| 316 | CH$_3$ | S | H | CH$_3$ | CH$_3$ | H | CH | c-C$_3$H$_5$ | c-C$_3$H$_5$ | — |
| 317 | CH$_3$ | S | H | CH$_3$ | CH$_3$ | H | CH$_3$ | H | C$_6$H$_5$ | — |
| 318 | CH$_3$ | S | H | CH$_3$ | CH$_3$ | H | CH$_3$ | H | 3-(CH$_3$O)—C$_6$H$_4$ | — |
| 319 | CH$_3$ | S | H | CH$_3$ | CH$_3$ | H | CH$_3$ | H | 2-Br—C$_6$H$_4$ | — |
| 320 | CH$_3$ | S | H | CH$_3$ | CH$_3$ | H | CH$_3$ | H | 4-CH$_3$—C$_6$H$_4$ | — |
| 321 | CH$_3$ | S | H | CH$_3$ | CH$_3$ | H | CH$_3$ | H | 4-C$_6$H$_5$—C$_6$H$_4$ | — |
| 322 | CH$_3$ | S | H | CH$_3$ | CH$_3$ | H | CH$_3$ | H | 2-(C$_4$H$_9$)—C$_4$H$_9$ | — |
| 323 | CH$_3$ | S | H | CH$_3$ | CH$_3$ | H | CH$_3$ | H | 3-(C$_4$H$_9$)—C$_5$H$_{10}$ | — |
| 324 | CH$_3$ | S | H | CH$_3$ | CH$_3$ | H | CH$_3$ | H | (CH$_2$)$_2$OCH$_3$ | — |
| 325 | CH$_3$ | S | H | CH$_3$ | CH$_3$ | H | CH$_3$ | H | CH$_2$OCH$_3$ | — |
| 326 | CH$_3$ | S | H | CH$_3$ | CH$_3$ | H | CH$_3$ | H | C$_2$H$_5$ | — |
| 327 | CH$_3$ | S | H | CH$_3$ | CH$_3$ | H | CH$_3$ | H | C$_3$H$_7$ | — |
| 328 | CH$_3$ | S | H | CH$_3$ | CH$_3$ | H | CH$_3$ | H | C$_4$H$_9$ | — |
| 329 | CH$_3$ | S | H | CH$_3$ | CH$_3$ | H | CH$_3$ | CH$_2$OCH$_3$ | CH$_2$OCH$_3$ | — |
| 330 | CH$_3$ | S | H | CH$_3$ | CH$_3$ | H | CH$_3$ | C$_2$H$_5$ | OC$_2$H$_5$ | — |
| 331 | CH$_3$ | S | H | CH$_3$ | CH$_3$ | H | CH$_3$ | H | OC$_2$H$_5$ | — |
| 332 | CH$_3$ | S | H | CH$_3$ | CH$_3$ | H | CH$_3$ | H | O(CH$_2$)$_2$—OCH$_3$ | — |
| 333 | CH$_3$ | S | H | CH$_3$ | CH$_3$ | H | CH$_3$ | CH$_2$OCH$_3$ | C$_6$H$_5$ | — |
| 334 | CH$_3$ | S | H | Cl | Cl | H | H | C$_2$H$_5$ | C$_2$H$_5$ | — |
| 335 | CH$_3$ | S | H | Cl | Cl | H | H | C$_2$H$_5$ | C$_4$H$_9$ | — |
| 336 | CH$_3$ | S | H | Cl | Cl | H | H | C$_2$H$_5$ | CH$_2$OCH$_3$ | — |
| 337 | CH$_3$ | S | H | Cl | Cl | H | H | C$_2$H$_5$ | C$_6$H$_5$ | — |
| 338 | CH$_3$ | S | H | Cl | Cl | H | H | C$_2$H$_5$ | c-C$_3$H$_5$ | — |
| 339 | CH$_3$ | S | H | Cl | Cl | H | H | C$_2$H$_5$ | C$_6$H$_{13}$ | — |
| 340 | CH$_3$ | S | H | Cl | Cl | H | H | C$_2$H$_5$ | C$_3$H$_7$ | — |
| 341 | CH$_3$ | S | H | Cl | Cl | H | H | C$_2$H$_5$ | (CH$_2$)$_2$OCH$_3$ | — |
| 342 | CH$_3$ | S | H | Cl | Cl | H | H | C$_2$H$_5$ | CH$_2$CN | — |
| 343 | CH$_3$ | S | H | Cl | Cl | H | H | C$_2$H$_6$ | (CH$_2$)$_2$—(Q1)[b] | — |
| 344 | CH$_3$ | S | H | Cl | Cl | H | H | C$_2$H$_5$ | (CH$_2$)$_2$—(Q2)[c] | — |
| 345 | CH$_3$ | S | H | Cl | Cl | H | H | C$_2$H$_5$ | CH$_2$N(CH$_3$)$_2$ | — |
| 346 | CH$_3$ | S | H | Cl | Cl | H | H | c-C$_3$H$_5$ | C$_4$H$_9$ | — |
| 347 | CH$_3$ | S | H | Cl | Cl | H | H | c-C$_3$H$_5$ | CH$_2$OCH$_3$ | — |
| 348 | CH$_3$ | S | H | Cl | Cl | H | H | c-C$_3$H$_5$ | C$_6$H$_5$ | — |
| 349 | CH$_3$ | S | H | Cl | Cl | H | H | c-C$_3$H$_5$ | c-C$_3$H$_5$ | — |
| 350 | CH$_3$ | S | H | Cl | Cl | H | H | H | C$_6$H$_5$ | — |
| 351 | CH$_3$ | S | H | Cl | Cl | H | H | H | 3-(CH$_3$O)—C$_6$H$_4$ | — |
| 352 | CH$_3$ | S | H | Cl | Cl | H | H | H | 2-Br—C$_6$H$_4$ | — |
| 353 | CH$_3$ | S | H | Cl | Cl | H | H | H | 4-CH$_3$—C$_6$H$_4$ | — |
| 354 | CH$_3$ | S | H | Cl | Cl | H | H | H | 4-C$_6$H$_5$—C$_6$H$_4$ | — |
| 355 | CH$_3$ | S | H | Cl | Cl | H | H | H | 2-(C$_4$H$_9$)—C$_4$H$_8$ | — |
| 356 | CH$_3$ | S | H | Cl | Cl | H | H | H | 3-(C$_4$H$_9$)—C$_5$H$_{10}$ | — |
| 357 | CH$_3$ | S | H | Cl | Cl | H | H | H | (CH$_2$)$_2$OCH$_3$ | — |
| 358 | CH$_3$ | S | H | Cl | Cl | H | H | H | CH$_2$OCH$_3$ | — |
| 359 | CH$_3$ | S | H | Cl | Cl | H | H | H | C$_2$H$_5$ | — |
| 360 | CH$_3$ | S | H | Cl | Cl | H | H | H | C$_3$H$_7$ | — |
| 361 | CH$_3$ | S | H | Cl | Cl | H | H | H | C$_4$H$_9$ | — |
| 362 | CH$_3$ | S | H | Cl | Cl | H | H | CH$_2$OCH$_3$ | CH$_2$OCH$_3$ | — |
| 363 | CH$_3$ | S | H | Cl | Cl | H | H | C$_2$H$_5$ | OC$_2$H$_5$ | — |
| 364 | CH$_3$ | S | H | Cl | Cl | H | H | H | OC$_2$H$_5$ | — |
| 365 | CH$_3$ | S | H | Cl | Cl | H | H | H | O(CH$_2$)$_2$—OCH$_3$ | — |
| 366 | CH$_3$ | S | H | Cl | Cl | H | H | CH$_2$OCH$_3$ | C$_6$H$_5$ | — |
| 367 | CH$_3$ | S | H | CH$_3$ | OCH$_3$ | H | CH$_3$ | C$_2$H$_5$ | C$_2$H$_5$ | — |
| 368 | CH$_3$ | S | H | CH$_3$ | OCH$_3$ | H | CH$_3$ | C$_2$H$_5$ | C$_4$H$_9$ | — |

TABLE 1-continued

| | | | | | | | | | |
|---|---|---|---|---|---|---|---|---|---|
| 369 | $CH_3$ | S | H | $CH_3$ | $OCH_3$ | H | $CH_3$ | $C_2H_5$ | $CH_2OCH_3$ | — |
| 370 | $CH_3$ | S | H | $CH_3$ | $OCH_3$ | H | $CH_3$ | $C_2H_5$ | $C_6H_5$ | — |
| 371 | $CH_3$ | S | H | $CH_3$ | $OCH_3$ | H | $CH_3$ | $C_2H_5$ | $c\text{-}C_3H_5$ | — |
| 372 | $CH_3$ | S | H | $CH_3$ | $OCH_3$ | H | $CH_3$ | $C_2H_5$ | $C_6H_{13}$ | — |
| 373 | $CH_3$ | S | H | $CH_3$ | $OCH_3$ | H | $CH_3$ | $C_2H_5$ | $C_3H_7$ | — |
| 374 | $CH_3$ | S | H | $CH_3$ | $OCH_3$ | H | $CH_3$ | $C_2H_5$ | $(CH_2)_2OCH_3$ | — |
| 375 | $CH_3$ | S | H | $CH_3$ | $OCH_3$ | H | $CH_3$ | $C_2H_5$ | $CH_2CN$ | — |
| 376 | $CH_3$ | S | H | $CH_3$ | $OCH_3$ | H | $CH_3$ | $C_2H_5$ | $(CH_2)_2\text{—}(Q1)^b$ | — |
| 377 | $CH_3$ | S | H | $CH_3$ | $OCH_3$ | H | $CH_3$ | $C_2H_5$ | $(CH_2)_2\text{—}(Q2)^c$ | — |
| 378 | $CH_3$ | S | H | $CH_3$ | $OCH_3$ | H | $CH_3$ | $C_2H_5$ | $CH_2N(CH_3)_2$ | — |
| 379 | $CH_3$ | S | H | $CH_3$ | $OCH_3$ | H | $CH_3$ | $c\text{-}C_3H_5$ | $C_4H_9$ | — |
| 380 | $CH_3$ | S | H | $CH_3$ | $OCH_3$ | H | $CH_3$ | $c\text{-}C_3H_5$ | $CH_2OCH_3$ | — |
| 381 | $CH_3$ | S | H | $CH_3$ | $OCH_3$ | H | $CH_3$ | $c\text{-}C_3H_5$ | $C_6H_5$ | — |
| 382 | $CH_3$ | S | H | $CH_3$ | $OCH_3$ | H | $CH_3$ | $c\text{-}C_3H_5$ | $c\text{-}C_3H_5$ | — |
| 383 | $CH_3$ | S | H | $CH_3$ | $OCH_3$ | H | $CH_3$ | H | $C_6H_5$ | — |
| 384 | $CH_3$ | S | H | $CH_3$ | $OCH_3$ | H | $CH_3$ | H | $3\text{-}(CH_3O)\text{—}C_6H_4$ | — |
| 385 | $CH_3$ | S | H | $CH_3$ | $OCH_3$ | H | $CH_3$ | H | $2\text{-}Br\text{—}C_6H_4$ | — |
| 386 | $CH_3$ | S | H | $CH_3$ | $OCH_3$ | H | $CH_3$ | H | $4\text{-}CH_3\text{—}C_6H_4$ | — |
| 387 | $CH_3$ | S | H | $CH_3$ | $OCH_3$ | H | $CH_3$ | H | $4\text{-}C_6H_5\text{—}C_6H_4$ | — |
| 388 | $CH_3$ | S | H | $CH_3$ | $OCH_3$ | H | $CH_3$ | H | $2\text{-}(C_4H_9)\text{—}C_4H_9$ | — |
| 389 | $CH_3$ | S | H | $CH_3$ | $OCH_3$ | H | $CH_3$ | H | $3\text{-}(C_4H_9)\text{—}C_5H_{10}$ | — |
| 390 | $CH_3$ | S | H | $CH_3$ | $OCH_3$ | H | $CH_3$ | H | $(CH_2)_2OCH_3$ | — |
| 391 | $CH_3$ | S | H | $CH_3$ | $OCH_3$ | H | $CH_3$ | H | $CH_2OCH_3$ | — |
| 392 | $CH_3$ | S | H | $CH_3$ | $OCH_3$ | H | $CH_3$ | H | $C_2H_5$ | — |
| 393 | $CH_3$ | S | H | $CH_3$ | $OCH_3$ | H | $CH_3$ | H | $C_3H_7$ | — |
| 394 | $CH_3$ | S | H | $CH_3$ | $OCH_3$ | H | $CH_3$ | H | $C_4H_9$ | — |
| 395 | $CH_3$ | S | H | $CH_3$ | $OCH_3$ | H | $CH_3$ | $CH_2OCH_3$ | $CH_2OCH_3$ | — |
| 396 | $CH_3$ | S | H | $CH_3$ | $OCH_3$ | H | $CH_3$ | $C_2H_5$ | $OC_2H_5$ | — |
| 397 | $CH_3$ | S | H | $CH_3$ | $OCH_3$ | H | $CH_3$ | H | $OC_2H_5$ | — |
| 398 | $CH_3$ | S | H | $CH_3$ | $OCH_3$ | H | $CH_3$ | H | $O(CH_2)_2\text{—}OCH_3$ | — |
| 399 | $CH_3$ | S | H | $CH_3$ | $OCH_3$ | H | $CH_3$ | $CH_2OCH_3$ | $C_6H_5$ | — |
| 400 | $CH_3$ | $CH_2$ | H | $CH_3$ | Cl | H | $CH_3$ | $C_3H_7$ | $c\text{-}C_3H_5$ | 153–156 |
| 401 | $CH_3$ | $CH_2$ | $CH_3$ | $CH_3$ | $CH_3$ | H | $CH_3$ | $C_2H_5$ | $C_2H_5$ | — |
| 402 | $CH_3$ | $CH_2$ | $CH_3$ | $CH_3$ | $CH_3$ | H | $CH_3$ | $c\text{-}C_3H_5$ | $C_4H_9$ | 107–108 |
| 403 | $CH_3$ | $CH_2$ | $CH_3$ | $CH_3$ | $CH_3$ | H | $CH_3$ | $c\text{-}C_3H_5$ | $c\text{-}C_3H_5$ | 187–188 |
| 404 | $CH_3$ | $CH_2$ | $CH_3$ | $CH_3$ | $CH_3$ | H | $CH_3$ | H | $C_4H_9$ | oil |
| 405 | $CH_3$ | $CH_2$ | $CH_3$ | $CH_3$ | $CH_3$ | H | $CH_3$ | $C_2H_5$ | $C_4H_9$ | 98–99 |
| 406 | $CH_3$ | $CH_2$ | $CH_3$ | $CH_3$ | $CH_3$ | H | $CH_3$ | H | $C_6H_5$ | 149–150 |
| 407 | $CH_3$ | $CH_2$ | $CH_3$ | $CH_3$ | $CH_3$ | H | $CH_3$ | $C_2H_5$ | $(CH_2)_2OCH_3$ | — |
| 408 | $CH_3$ | $CH_2$ | $CH_3$ | $CH_3$ | $CH_3$ | H | $CH_3$ | H | $(CH_2)_2OCH_3$ | — |
| 409 | $CH_3$ | $CH_2$ | $CH_3$ | $CH_3$ | $CH_3$ | H | $CH_3$ | $CH_2OCH_3$ | $CH_2OCH_3$ | — |
| 410 | $CH_3$ | $CH_2$ | $CH_3$ | $CH_3$ | $CH_3$ | H | $CH_3$ | $C_2H_5$ | $CH_2OCH_3$ | — |
| 411 | $CH_3$ | $CH_2$ | H | $CH_3$ | Cl | H | H | $C_2H_5$ | $C_2H_5$ | — |
| 412 | $CH_3$ | $CH_2$ | H | $CH_3$ | Cl | H | H | $c\text{-}C_3H_5$ | $C_4H_9$ | — |
| 413 | $CH_3$ | $CH_2$ | H | $CH_3$ | Cl | H | H | $c\text{-}C_3H_5$ | $c\text{-}C_3H_5$ | 139–140 |
| 414 | $CH_3$ | $CH_2$ | H | $CH_3$ | Cl | H | H | $CH_3$ | $C_3H_7$ | oil (A, C) |
| 415 | $CH_3$ | $CH_2$ | H | $CH_3$ | Cl | H | H | $C_2H_5$ | $C_4H_9$ | oil |
| 416 | $CH_3$ | $CH_2$ | H | $CH_2$ | Cl | H | H | H | $C_6H_5$ | — |
| 417 | $CH_3$ | $CH_2$ | H | $CH_3$ | Cl | H | H | $C_2H_5$ | $(CH_2)_2OCH_3$ | — |
| 418 | $CH_3$ | $CH_2$ | H | $CH_3$ | Cl | H | H | H | $(CH_2)_2OCH_3$ | — |
| 419 | $CH_3$ | $CH_2$ | H | $CH_3$ | Cl | H | H | $CH_2OCH_3$ | $CH_2OCH_3$ | — |
| 420 | $CH_3$ | $CH_2$ | H | $CH_3$ | Cl | H | H | $C_2H_5$ | $CH_2OCH_3$ | — |
| 421 | $CH_3$ | $CH_2$ | H | Cl | $CH_3$ | H | H | $C_2H_5$ | $C_2H_5$ | — |
| 422 | $CH_3$ | $CH_2$ | H | Cl | $CH_3$ | H | H | $c\text{-}C_3H_5$ | $C_4H_9$ | — |
| 423 | $CH_3$ | $CH_2$ | H | Cl | $CH_3$ | H | H | $c\text{-}C_3H_5$ | $c\text{-}C_3H_5$ | 177–178 |
| 424 | $CH_3$ | $CH_2$ | H | Cl | $CH_3$ | H | H | $CH_3$ | $C_3H_7$ | oil |
| 425 | $CH_3$ | $CH_2$ | H | Cl | $CH_3$ | H | H | $C_2H_5$ | $C_4H_9$ | — |
| 426 | $CH_3$ | $CH_2$ | H | Cl | $CH_3$ | H | H | H | $C_6H_5$ | — |
| 427 | $CH_3$ | $CH_2$ | H | Cl | $CH_3$ | H | H | $C_2H_5$ | $(CH_2)_2OCH_3$ | — |
| 428 | $CH_3$ | $CH_2$ | H | Cl | $CH_3$ | H | H | H | $(CH_2)_2OCH_3$ | — |
| 429 | $CH_3$ | $CH_2$ | H | Cl | $CH_3$ | H | H | $CH_2OCH_3$ | $CH_2OCH_3$ | — |
| 430 | $CH_3$ | $CH_2$ | H | Cl | $CH_3$ | H | H | $C_2H_5$ | $CH_2OCH_3$ | — |
| 431 | $CH_3$ | $CH_2$ | H | Cl | Cl | H | $OCH_3$ | $C_3H_7$ | $c\text{-}C_3H_5$ | 141–144 |
| 432 | $CH_3$ | $CH_2$ | H | $CH_3$ | $CH_3$ | H | $OCH_3$ | $C_2H_5$ | $C_3H_7$ | 108–110 |
| 433 | $CH_3$ | $CH_2$ | H | Cl | Cl | H | $CH_3$ | $c\text{-}C_3H_5$ | $c\text{-}C_3H_5$ | 194–195 |
| 434 | $CH_3$ | $CH_2$ | H | $CH_3$ | $CH_3$ | H | $CH_3$ | $C_2H_5$ | $c\text{-}C_3H_5CH_2$ | oil |
| 435 | $CH_3$ | $CH_2$ | H | $CH_3$ | $CH_3$ | H | $CH_3$ | $C_2H_5$ | $CH_2OH$ | 155–157 |
| 436 | $CH_3$ | $CH_2$ | H | $CH_3$ | $OCH_3$ | H | H | $C_2H_5$ | $c\text{-}C_3H_5CH_2$ | oil |
| 437 | $CH_3$ | $CH_2$ | H | $CH_3$ | $OCH_3$ | H | H | $CH_3$ | $C_3H_7$ | oil |
| 438 | $CH_3$ | $CH_2$ | H | $CH_3$ | $OCH_3$ | H | H | H | $4\text{-}(CH_3O)\text{—}C_6H_4$ | oil |
| 439 | $CH_3$ | $CH_2$ | H | $CH_3$ | $OCH_3$ | H | H | $C_2H_5$ | $c\text{-}C_3H_5$ | oil |
| 440 | $CH_3$ | $CH_2$ | H | $CH_3$ | $OCH_3$ | H | H | $CH_3$ | $C_5H_{11}$ | oil |
| 441 | $CH_3$ | $CH_2$ | H | Cl | $NMe_2$ | H | H | $C_2H_5$ | $C_2H_5$ | — |
| 442 | $CH_3$ | $CH_2$ | H | Cl | $NMe_2$ | H | H | $c\text{-}C_3H_5$ | $C_4H_9$ | — |
| 443 | $CH_3$ | $CH_2$ | H | Cl | $NMe_2$ | H | H | $c\text{-}C_3H_5$ | $c\text{-}C_3H_5$ | — |
| 444 | $CH_3$ | $CH_2$ | H | Cl | $NMe_2$ | H | H | H | $C_3H_7$ | — |
| 445 | $CH_3$ | $CH_2$ | H | Cl | $NMe_2$ | H | H | $C_2H_5$ | $C_4H_9$ | — |
| 446 | $CH_3$ | $CH_2$ | H | Cl | $NMe_2$ | H | H | H | $C_6H_5$ | — |

TABLE 1-continued

| | | | | | | | | | |
|---|---|---|---|---|---|---|---|---|---|
| 447 | CH$_3$ | CH$_2$ | H | Cl | NMe$_2$ | H | H | C$_2$H$_5$ | (CH$_2$)$_2$OCH$_3$ | — |
| 448 | CH$_3$ | CH$_2$ | H | Cl | NMe$_2$ | H | H | H | (CH$_2$)$_2$OCH$_3$ | — |
| 449 | CH$_3$ | CH$_2$ | H | Cl | NMe$_2$ | H | H | CH$_2$OCH$_3$ | CH$_2$OCH$_3$ | — |
| 450 | CH$_3$ | CH$_2$ | H | Cl | NMe$_2$ | H | H | C$_2$H$_5$ | CH$_2$OCH$_3$ | — |
| 451 | CH$_3$ | CH$_2$ | H | CH$_3$ | NMe$_2$ | H | H | C$_2$H$_5$ | C$_2$H$_5$ | — |
| 452 | CH$_3$ | CH$_2$ | H | CH$_3$ | NMe$_2$ | H | H | c-C$_3$H$_5$ | C$_4$H$_9$ | — |
| 453 | CH$_3$ | CH$_2$ | H | CH$_3$ | NMe$_2$ | H | H | c-C$_3$H$_5$ | c-C$_3$H$_5$ | — |
| 454 | CH$_3$ | CH$_2$ | H | CH$_3$ | NMe$_2$ | H | H | H | C$_3$H$_7$ | — |
| 455 | CH$_3$ | CH$_2$ | H | CH$_3$ | NMe$_2$ | H | H | C$_2$H$_5$ | C$_4$H$_9$ | — |
| 456 | CH$_3$ | CH$_2$ | H | CH$_3$ | NMe$_2$ | H | H | H | C$_6$H$_5$ | — |
| 457 | CH$_3$ | CH$_2$ | H | CH$_3$ | NMe$_2$ | H | H | C$_2$H$_5$ | (CH$_2$)$_2$OCH$_3$ | — |
| 458 | CH$_3$ | CH$_2$ | H | CH$_3$ | NMe$_2$ | H | H | H | (CH$_2$)$_2$OCH$_3$ | — |
| 459 | CH$_3$ | CH$_2$ | H | CH$_3$ | NMe$_2$ | H | H | CH$_2$OCH$_3$ | CH$_2$OCH$_3$ | — |
| 460 | CH$_3$ | CH$_2$ | H | CH$_3$ | NMe$_2$ | H | H | C$_2$H$_5$ | CH$_2$OCH$_3$ | — |
| 461 | CH$_3$ | CH$_2$ | NMe$_2$ | CH$_3$ | CH$_3$ | H | CH$_3$ | C$_2$H$_5$ | C$_2$H$_5$ | — |
| 462 | CH$_3$ | CH$_2$ | NMe$_2$ | CH$_3$ | CH$_3$ | H | CH$_3$ | c-C$_3$H$_5$ | C$_4$H$_9$ | — |
| 463 | CH$_3$ | CH$_2$ | NMe$_2$ | CH$_3$ | CH$_3$ | H | CH$_3$ | c-C$_3$H$_5$ | c-C$_3$H$_5$ | — |
| 464 | CH$_3$ | CH$_2$ | NMe$_2$ | CH$_3$ | CH$_3$ | H | CH$_3$ | H | C$_3$H$_7$ | — |
| 465 | CH$_3$ | CH$_2$ | NMe$_2$ | CH$_3$ | CH$_3$ | H | CH$_3$ | C$_2$H$_5$ | C$_4$H$_9$ | — |
| 466 | CH$_3$ | CH$_2$ | NMe$_2$ | CH$_3$ | CH$_3$ | H | CH$_3$ | H | C$_6$H$_5$ | — |
| 467 | CH$_3$ | CH$_2$ | NMe$_2$ | CH$_3$ | CH$_3$ | H | CH$_3$ | C$_2$H$_5$ | (CH$_2$)$_2$OCH$_3$ | — |
| 468 | CH$_3$ | CH$_2$ | NMe$_2$ | CH$_3$ | CH$_3$ | H | CH$_3$ | H | (CH$_2$)$_2$OCH$_3$ | — |
| 469 | CH$_3$ | CH$_2$ | NMe$_2$ | CH$_3$ | CH$_3$ | H | CH$_3$ | CH$_2$OCH$_3$ | CH$_2$OCH$_3$ | — |
| 470 | CH$_3$ | CH$_2$ | NMe$_2$ | CH$_3$ | CH$_3$ | H | CH$_3$ | C$_2$H$_5$ | CH$_2$OCH$_3$ | — |
| 471 | C$_2$H$_5$ | CH$_2$ | H | CH$_3$ | CH$_3$ | H | CH$_3$ | C$_2$H$_5$ | C$_2$H$_5$ | — |
| 472 | C$_2$H$_5$ | CH$_2$ | H | CH$_3$ | CH$_3$ | H | CH$_3$ | c-C$_3$H$_5$ | C$_4$H$_9$ | — |
| 473 | C$_2$H$_5$ | CH$_2$ | H | CH$_3$ | CH$_3$ | H | CH$_3$ | c-C$_3$H$_5$ | c-C$_3$H$_5$ | — |
| 474 | C$_2$H$_5$ | CH$_2$ | H | CH$_3$ | CH$_3$ | H | CH$_3$ | H | C$_3$H$_7$ | — |
| 475 | C$_2$H$_5$ | CH$_2$ | H | CH$_3$ | CH$_3$ | H | CH$_3$ | C$_2$H$_5$ | C$_4$H$_9$ | 92–95 |
| 476 | C$_2$H$_5$ | CH$_2$ | H | CH$_3$ | CH$_3$ | H | CH$_3$ | H | C$_6$H$_5$ | — |
| 477 | C$_2$H$_5$ | CH$_2$ | H | CH$_3$ | CH$_3$ | H | CH$_3$ | C$_2$H$_5$ | (CH$_2$)$_2$OCH$_3$ | — |
| 478 | C$_2$H$_5$ | CH$_2$ | H | CH$_3$ | CH$_3$ | H | CH$_3$ | H | (CH$_2$)$_2$OCH$_3$ | — |
| 479 | C$_2$H$_5$ | CH$_2$ | H | CH$_3$ | CH$_3$ | H | CH$_3$ | CH$_2$OCH$_3$ | CH$_2$OCH$_3$ | — |
| 480 | C$_2$H$_5$ | CH$_2$ | H | CH$_3$ | CH$_3$ | H | CH$_3$ | C$_2$H$_5$ | CH$_2$OCH$_3$ | — |
| 481 | CH$_3$ | CHCH$_3$ | H | CH$_3$ | CH$_3$ | H | CH$_3$ | C$_2$H$_5$ | C$_2$H$_5$ | — |
| 482 | CH$_3$ | CHCH$_3$ | H | CH$_3$ | CH$_3$ | H | CH$_3$ | c-C$_3$H$_5$ | C$_4$H$_9$ | — |
| 483 | CH$_3$ | CHCH$_3$ | H | CH$_3$ | CH$_3$ | H | CH$_3$ | c-C$_3$H$_5$ | c-C$_3$H$_5$ | — |
| 484 | CH$_3$ | CHCH$_3$ | H | CH$_3$ | CH$_3$ | H | CH$_3$ | H | C$_3$H$_7$ | — |
| 485 | CH$_3$ | CHCH$_3$ | H | CH$_3$ | CH$_3$ | H | CH$_3$ | C$_2$H$_5$ | C$_4$H$_9$ | — |
| 486 | CH$_3$ | CHCH$_3$ | H | CH$_3$ | CH$_3$ | H | CH$_3$ | H | C$_6$H$_5$ | — |
| 487 | CH$_3$ | CHCH$_3$ | H | CH$_3$ | CH$_3$ | H | CH$_3$ | C$_2$H$_5$ | (CH$_2$)$_2$OCH$_3$ | — |
| 488 | CH$_3$ | CHCH$_3$ | H | CH$_3$ | CH$_3$ | H | CH$_3$ | H | (CH$_2$)$_2$OCH$_3$ | — |
| 489 | CH$_3$ | CHCH$_3$ | H | CH$_3$ | CH$_3$ | H | CH$_3$ | CH$_2$OCH$_3$ | CH$_2$OCH$_3$ | — |
| 490 | CH$_3$ | CHCH$_3$ | H | CH$_3$ | CH$_3$ | H | CH$_3$ | C$_2$H$_5$ | CH$_2$OCH$_3$ | — |
| 491 | CH$_3$ | CH$_2$ | H | CH$_3$ | CH$_3$ | H | H | C$_2$H$_5$ | C$_2$H$_5$ | 96–97 |
| 492 | CH$_3$ | CH$_2$ | H | CH$_3$ | CH$_3$ | H | H | c-C$_3$H$_5$ | C$_4$H$_9$ | — |
| 493 | CH$_3$ | CH$_2$ | H | CH$_3$ | CH$_3$ | H | H | c-C$_3$H$_5$ | c-C$_3$H$_5$ | 149–150 |
| 494 | CH$_3$ | CH$_2$ | H | CH$_3$ | CH$_3$ | H | H | H | C$_3$H$_7$ | 99–100 |
| 495 | CH$_3$ | CH$_2$ | H | CH$_3$ | CH$_3$ | H | H | C$_2$H$_5$ | C$_4$H$_9$ | — |
| 496 | CH$_3$ | CH$_2$ | H | CH$_3$ | CH$_3$ | H | H | H | C$_6$H$_5$ | — |
| 497 | CH$_3$ | CH$_2$ | H | CH$_3$ | CH$_3$ | H | H | C$_2$H$_5$ | (CH$_2$)$_2$OCH$_3$ | — |
| 498 | CH$_3$ | CH$_2$ | H | CH$_3$ | CH$_3$ | H | H | H | (CH$_2$)$_2$OCH$_3$ | — |
| 499 | CH$_3$ | CH$_2$ | H | CH$_3$ | CH$_3$ | H | H | CH$_2$OCH$_3$ | CH$_2$OCH$_3$ | — |
| 500 | CH$_3$ | CH$_2$ | H | CH$_3$ | CH$_3$ | H | H | C$_2$H$_5$ | CH$_2$OCH$_3$ | — |
| 501 | CH$_3$ | CH$_2$ | H | CH$_3$ | CH$_3$ | H | CH$_3$ | CH$_3$ | C$_3$H$_7$ | — |
| 502 | CH$_3$ | CH$_2$ | H | CH$_3$ | CH$_3$ | H | CH$_3$ | CH$_3$ | C$_4$H$_9$ | oil |
| 503 | CH$_3$ | CH$_2$ | H | CH$_3$ | CH$_3$ | H | CH$_3$ | CH$_3$ | C$_5$H$_{11}$ | oil |
| 504 | CH$_3$ | CH$_2$ | H | CH$_3$ | CH$_3$ | H | CH$_3$ | C$_2$H$_5$ | 2-C$_4$H$_9$ | 109–110 |
| 505 | CH$_3$ | CH$_2$ | H | CH$_3$ | CH$_3$ | H | CH$_3$ | C$_2$H$_5$ | CH$_2$OC$_2$H$_5$ | — |
| 506 | CH$_3$ | CH$_2$ | H | Cl | Cl | H | H | CH$_3$ | C$_3$H$_7$ | oil (A, B, C) |
| 507 | CH$_3$ | CH$_2$ | H | Cl | Cl | H | H | CH$_3$ | C$_4$H$_9$ | oil |
| 508 | CH$_3$ | CH$_2$ | H | Cl | Cl | H | H | CH$_3$ | C$_5$H$_{11}$ | — |
| 509 | CH$_3$ | CH$_2$ | H | Cl | Cl | H | H | C$_2$H$_5$ | 2-C$_4$H$_9$ | — |
| 510 | CH$_3$ | CH$_2$ | H | Cl | Cl | H | H | C$_2$H$_5$ | CH$_2$OC$_2$H$_5$ | — |
| 511 | CH$_3$ | CH$_2$ | H | Cl | CF$_3$ | H | H | C$_2$H$_5$ | c-C$_3$H$_5$ | oil (A) 78–80 (B) 116–117 (C) |
| 512 | CH$_3$ | CH$_2$ | H | Cl | CF$_3$ | H | H | c-C$_3$H$_5$ | c-C$_3$H$_5$ | 145–146 |
| 513 | CH$_3$ | CH$_2$ | H | Cl | CF$_3$ | H | H | C$_2$H$_5$ | C$_4$H$_9$ | oil |
| 514 | CH$_3$ | CH$_2$ | H | Cl | CF$_3$ | H | H | C$_2$H$_5$ | C$_2$H$_5$ | oil |
| 515 | CH$_3$ | CH$_2$ | H | Cl | CF$_3$ | H | H | C$_2$H$_5$ | CH$_2$OC$_2$H$_5$ | — |
| 516 | CH$_3$ | CH$_2$ | H | OCH$_3$ | Cl | H | Cl | C$_2$H$_5$ | c-C$_3$H$_5$ | — |
| 517 | CH$_3$ | CH$_2$ | H | OCH$_3$ | Cl | H | Cl | c-C$_3$H$_5$ | c-C$_3$H$_5$ | 183–184 |
| 518 | CH$_3$ | CH$_2$ | H | OCH$_3$ | Cl | H | Cl | C$_2$H$_5$ | C$_4$H$_9$ | 109–110 |
| 519 | CH$_3$ | CH$_2$ | H | OCH$_3$ | Cl | H | Cl | C$_2$H$_5$ | (CH$_2$)$_2$OCH$_3$ | — |

TABLE 1-continued

| | | | | | | | | | | |
|---|---|---|---|---|---|---|---|---|---|---|
| 520 | CH₃ | CH₂ | H | OCH₃ | Cl | H | Cl | C₂H₅ | CH₂OC₂H₅ | — |
| 521 | CH₃ | CH₂ | H | CH₃ | CH₃ | H | CH₃ | C₃H₇ | C₃H₇ | 115–120 |
| 522 | CH₃ | O | H | CH₃ | CH₃ | H | CH₃ | C₃H₇ | C₃H₇ | — |
| 523 | CH₃ | CH₂ | H | Cl | Cl | H | H | C₃H₇ | C₃H₇ | 99–101 |
| 524 | CH₃ | CH₂ | H | CH₃ | OCH₃ | H | H | C₃H₇ | C₃H₇ | oil |
| 525 | CH₃ | CH₂ | H | OCH₃ | CH₃ | H | CH₃ | C₃H₇ | C₃H₇ | 109–111 |
| 526 | CH₃ | CH₂ | H | CH₃ | Cl | H | H | C₃H₇ | C₃H₇ | oil |
| 527 | CH₃ | CH₂ | H | CH₃ | CH₃ | CH₃ | H | C₃H₇ | C₃H₇ | — |
| 528 | CH₃ | CH₂ | H | Cl | CF₃ | H | H | C₃H₇ | C₃H₇ | oil |
| 529 | CH₃ | CH₂ | H | Cl | CF₃ | H | Cl | C₃H₇ | C₃H₇ | — |
| 530 | CH₃ | CH₂ | H | OCH₃ | Cl | H | Cl | C₃H₇ | C₃H₇ | 129–131 |
| 531 | CH₃ | CH₂ | H | CH₃ | CH₃ | H | CH₃ | CH₃ | (CH₃)₂CHCH₂ | 77–85 |
| 532 | CH₃ | O | H | CH₃ | CH₃ | H | CH₃ | CH₃ | (CH₃)₂CHCH₂ | — |
| 533 | CH₃ | CH₂ | H | Cl | Cl | H | H | CH₃ | (CH₃)₂CHCH₂ | — |
| 534 | CH₃ | CH₂ | H | CH₃ | OCH₃ | H | H | CH₃ | (CH₃)₂CHCH₂ | — |
| 535 | CH₃ | CH₂ | H | OCH₃ | CH₃ | H | CH₃ | CH₃ | (CH₃)₂CHCH₂ | — |
| 536 | CH₃ | CH₂ | H | CH₃ | Cl | H | H | CH₃ | (CH₃)₂CHCH₂ | — |
| 537 | CH₃ | CH₂ | H | CH₃ | CH₃ | CH₃ | H | CH₃ | (CH₃)₂CHCH₂ | — |
| 538 | CH₃ | CH₂ | H | Cl | CF₃ | H | H | C₂H₅ | (CH₃)₂CH | oil |
| 539 | CH₃ | CH₂ | H | Cl | CF₃ | H | Cl | CH₃ | (CH₃)₂CHCH₂ | — |
| 540 | CH₃ | CH₂ | H | OCH₃ | Cl | H | Cl | CH₃ | (CH₃)₂CHCH₂ | — |
| 541 | CH₃ | CH₂ | H | CH₃ | CH₃ | H | CH₃ | CH₃ | c-C₃H₅ | 118–127 |
| 542 | CH₃ | O | H | CH₃ | CH₃ | H | CH₃ | CH₃ | c-C₃H₅ | — |
| 543 | CH₃ | CH₂ | H | Cl | Cl | H | H | CH₃ | c-C₃H₅ | oil |
| 544 | CH₃ | CH₂ | H | CH₃ | OCH₃ | H | H | CH₃ | c-C₃H₅ | oil |
| 545 | CH₃ | CH₂ | H | OCH₃ | CH₃ | H | CH₃ | CH₃ | c-C₃H₅ | — |
| 546 | CH₃ | CH₂ | H | CH₃ | Cl | H | H | CH₃ | c-C₃H₅ | — |
| 547 | CH₃ | CH₂ | H | CH₃ | CH₃ | CH₃ | H | CH₃ | c-C₃H₅ | — |
| 548 | CH₃ | CH₂ | H | Cl | CF₃ | H | H | CH₃ | c-C₃H₅ | oil |
| 549 | CH₃ | CH₂ | H | Cl | CF₃ | H | Cl | CH₃ | c-C₃H₅ | — |
| 550 | CH₃ | CH₂ | H | OCH₃ | Cl | H | Cl | CH₃ | c-C₃H₅ | — |
| 551 | CH₃ | CH₂ | H | CH₃ | CH₃ | H | CH₃ | CH₃ | CH₃ | oil |
| 552 | CH₃ | O | H | CH₃ | CH₃ | H | CH₃ | CH₃ | CH₃ | — |
| 553 | CH₃ | CH₂ | H | Cl | Cl | H | H | CH₃ | CH₃ | — |
| 554 | CH₃ | CH₂ | H | CH₃ | OCH₃ | H | H | CH₃ | CH₃ | — |
| 555 | CH₃ | CH₂ | H | OCH₃ | CH₃ | H | CH₃ | CH₃ | CH₃ | — |
| 556 | CH₃ | CH₂ | H | CH₃ | Cl | H | H | CH₃ | CH₃ | — |
| 557 | CH₃ | CH₂ | H | CH₃ | CH₃ | CH₃ | H | CH₃ | CH₃ | — |
| 558 | CH₃ | CH₂ | H | Cl | CF₃ | H | H | CH₃ | C₄H₉ | oil |
| 559 | CH₃ | CH₂ | H | Cl | CF₃ | H | Cl | CH₃ | CH₃ | — |
| 560 | CH₃ | CH₂ | H | OCH₃ | Cl | H | Cl | CH₃ | CH₃ | — |
| 561 | CH₃ | CH₂ | H | CH₃ | CH₃ | H | CH₃ | C₂H₅ | C₅H₁₁ | 102–103 |
| 562 | CH₃ | O | H | CH₃ | CH₃ | H | CH₃ | C₂H₅ | C₅H₁₁ | — |
| 563 | CH₃ | CH₂ | H | Cl | Cl | H | H | C₂H₅ | C₅H₁₁ | — |
| 564 | CH₃ | CH₂ | H | CH₃ | OCH₃ | H | H | C₂H₅ | C₄H₉ | oil |
| 565 | CH₃ | CH₂ | H | OCH₃ | CH₃ | H | CH₃ | C₂H₅ | C₅H₁₁ | — |
| 566 | CH₃ | CH₂ | H | CH₃ | Cl | H | H | C₂H₅ | C₅H₁₁ | — |
| 567 | CH₃ | CH₂ | H | CH₃ | CH₃ | CH₃ | H | C₂H₅ | C₅H₁₁ | — |
| 568 | CH₃ | CH₂ | H | Cl | CF₃ | H | H | C₂H₅ | C₅H₁₁ | — |
| 569 | CH₃ | CH₂ | H | Cl | CF₃ | H | Cl | C₂H₅ | C₅H₁₁ | — |
| 570 | CH₃ | CH₂ | H | OCH₃ | Cl | H | Cl | C₂H₅ | C₅H₁₁ | — |
| 571 | CH₃ | CH₂ | H | CH₃ | CH₃ | H | CH₃ | C₂H₅ | C₂H₅(CH₂)₂ | oil |
| 572 | CH₃ | O | H | CH₃ | CH₃ | H | CH₃ | C₂H₅ | C₂H₅(CH₂)₂ | — |
| 573 | CH₃ | CH₂ | H | Cl | Cl | H | H | C₂H₅ | C₂H₅(CH₂)₂ | — |
| 574 | CH₃ | CH₂ | H | CH₃ | OCH₃ | H | H | C₂H₅ | C₂H₅(CH₂)₂ | — |
| 575 | CH₃ | CH₂ | H | OCH₃ | CH₃ | H | CH₃ | C₂H₅ | C₂H₅(CH₂)₂ | — |
| 576 | CH₃ | CH₂ | H | CH₃ | Cl | H | H | C₂H₅ | C₂H₅(CH₂)₂ | — |
| 577 | CH₃ | CH₂ | H | CH₃ | CH₃ | CH₃ | H | C₂H₅ | C₂H₅(CH₂)₂ | — |
| 578 | CH₃ | CH₂ | H | Cl | CF₃ | H | H | C₂H₅ | C₂H₅(CH₂)₂ | — |
| 579 | CH₃ | CH₂ | H | Cl | CF₃ | H | Cl | C₂H₅ | C₂H₅(CH₂)₂ | — |
| 580 | CH₃ | CH₂ | H | OCH₃ | Cl | H | Cl | C₂H₅ | C₂H₅(CH₂)₂ | — |
| 581 | CH₃ | CH₂ | H | CH₃ | CH₃ | H | CH₃ | C₂H₅ | C₂H₅OCH₂ | oil |
| 582 | CH₃ | O | H | CH₃ | CH₃ | H | CH₃ | C₂H₅ | C₂H₅OCH₂ | — |
| 583 | CH₃ | CH₂ | H | Cl | Cl | H | H | C₂H₅ | C₂H₅OCH₂ | — |
| 584 | CH₃ | CH₂ | H | CH₃ | OCH₃ | H | H | C₂H₅ | C₂H₅OCH₂ | — |
| 585 | CH₃ | CH₂ | H | OCH₃ | CH₃ | H | CH₃ | C₂H₅ | C₂H₅OCH₂ | — |
| 586 | CH₃ | CH₂ | H | CH₃ | Cl | H | H | C₂H₅ | C₂H₅OCH₂ | — |
| 587 | CH₃ | CH₂ | H | CH₃ | CH₃ | CH₃ | H | C₂H₅ | C₂H₅OCH₂ | — |
| 588 | CH₃ | CH₂ | H | Cl | CF₃ | H | H | C₂H₅ | C₂H₅OCH₂ | — |
| 589 | CH₃ | CH₂ | H | Cl | CF₃ | H | Cl | C₂H₅ | C₂H₅OCH₂ | — |
| 590 | CH₃ | CH₂ | H | OCH₃ | Cl | H | Cl | C₂H₅ | C₂H₅OCH₂ | — |
| 591 | CH₃ | CH₂ | H | CH₃ | CH₃ | H | CH₃ | H | c-C₃H₅CH(OMe)(CH₂)₂ | oil |
| 592 | CH₃ | O | H | CH₃ | CH₃ | H | CH₃ | H | c-C₃H₅CH(OMe)(CH₂)₂ | — |
| 593 | CH₃ | CH₂ | H | Cl | Cl | H | H | H | c-C₃H₅CH(OMe)(CH₂)₂ | — |
| 594 | CH₃ | CH₂ | H | CH₃ | OCH₃ | H | H | H | c-C₃H₅CH(OMe)(CH₂)₂ | — |

TABLE 1-continued

| | | | | | | | | | | |
|---|---|---|---|---|---|---|---|---|---|---|
| 595 | CH$_3$ | CH$_2$ | H | OCH$_3$ | CH$_3$ | H | CH$_3$ | H | c-C$_3$H$_5$CH(OMe)(CH$_2$)$_2$ | — |
| 596 | CH$_3$ | CH$_2$ | H | CH$_3$ | Cl | H | H | H | c-C$_3$H$_5$CH(OMe)(CH$_2$)$_2$ | — |
| 597 | CH$_3$ | CH$_2$ | H | CH$_3$ | CH$_3$ | CH$_3$ | H | H | c-C$_3$H$_5$CH(OMe)(CH$_2$)$_2$ | — |
| 598 | CH$_3$ | CH$_2$ | H | Cl | CF$_3$ | H | H | H | c-C$_3$H$_5$CH(OMe)(CH$_2$)$_2$ | — |
| 599 | CH$_3$ | CH$_2$ | H | Cl | CF$_3$ | H | Cl | H | c-C$_3$H$_5$CH(OMe)(CH$_2$)$_2$ | — |
| 600 | CH$_3$ | CH$_2$ | H | OCH$_3$ | Cl | H | Cl | H | c-C$_3$H$_5$CH(OMe)(CH$_2$)$_2$ | — |
| 601 | CH$_3$ | CH$_2$ | CH$_3$ | Cl | Cl | H | H | C$_2$H$_5$ | C$_2$H$_5$ | — |
| 602 | CH$_3$ | CH$_2$ | CH$_3$ | Cl | Cl | H | H | c-C$_3$H$_5$ | C$_4$H$_9$ | — |
| 603 | CH$_3$ | CH$_2$ | CH$_3$ | Cl | Cl | H | H | c-C$_3$H$_5$ | c-C$_3$H$_5$ | 155–156 |
| 604 | CH$_3$ | CH$_2$ | CH$_3$ | Cl | Cl | H | H | H | C$_4$H$_9$ | — |
| 605 | CH$_3$ | CH$_2$ | CH$_3$ | Cl | Cl | H | H | C$_2$H$_5$ | C$_4$H$_9$ | — |
| 606 | CH$_3$ | CH$_2$ | CH$_3$ | Cl | Cl | H | H | H | C$_6$H$_5$ | — |
| 607 | CH$_3$ | CH$_2$ | CH$_3$ | Cl | Cl | H | H | C$_2$H$_5$ | (CH$_2$)$_2$OCH$_3$ | — |
| 608 | CH$_3$ | CH$_2$ | CH$_3$ | Cl | Cl | H | H | CH$_3$ | C$_4$H$_9$ | — |
| 609 | CH$_3$ | CH$_2$ | CH$_3$ | Cl | Cl | H | H | C$_3$H$_7$ | C$_3$H$_7$ | — |
| 610 | CH$_3$ | CH$_2$ | CH$_3$ | Cl | Cl | H | H | C$_2$H$_5$ | C$_3$H$_7$ | — |
| 611 | CH$_3$ | CH$_2$ | CH$_3$ | OCH$_3$ | CH$_3$ | H | CH$_3$ | C$_2$H$_5$ | C$_2$H$_5$ | — |
| 612 | CH$_3$ | CH$_2$ | CH$_3$ | OCH$_3$ | CH$_3$ | H | CH$_3$ | c-C$_3$H$_5$ | C$_4$H$_9$ | — |
| 613 | CH$_3$ | CH$_2$ | CH$_3$ | OCH$_3$ | CH$_3$ | H | CH$_3$ | c-C$_3$H$_5$ | c-C$_3$H$_5$ | — |
| 614 | CH$_3$ | CH$_2$ | CH$_3$ | OCH$_3$ | CH$_3$ | H | CH$_3$ | H | C$_4$H$_9$ | — |
| 615 | CH$_3$ | CH$_2$ | CH$_3$ | OCH$_3$ | CH$_3$ | H | CH$_3$ | C$_2$H$_5$ | C$_4$H$_9$ | — |
| 616 | CH$_3$ | CH$_2$ | CH$_3$ | OCH$_3$ | CH$_3$ | H | CH$_3$ | H | C$_6$H$_5$ | — |
| 617 | CH$_3$ | CH$_2$ | CH$_3$ | OCH$_3$ | CH$_3$ | H | CH$_3$ | C$_2$H$_5$ | (CH$_2$)$_2$OCH$_3$ | — |
| 618 | CH$_3$ | CH$_2$ | CH$_3$ | OCH$_3$ | CH$_3$ | H | CH$_3$ | CH$_3$ | C$_4$H$_9$ | — |
| 619 | CH$_3$ | CH$_2$ | CH$_3$ | OCH$_3$ | CH$_3$ | H | CH$_3$ | C$_3$H$_7$ | C$_3$H$_7$ | — |
| 620 | CH$_3$ | CH$_2$ | CH$_3$ | OCH$_3$ | CH$_3$ | H | CH$_3$ | C$_2$H$_5$ | C$_3$H$_7$ | — |
| 621 | CH$_3$ | CH$_2$ | CH$_3$ | CH$_3$ | OCH$_3$ | H | H | C$_2$H$_5$ | C$_2$H$_5$ | — |
| 622 | CH$_3$ | CH$_2$ | CH$_3$ | CH$_3$ | OCH$_3$ | H | H | c-C$_3$H$_5$ | C$_4$H$_9$ | — |
| 623 | CH$_3$ | CH$_2$ | CH$_3$ | CH$_3$ | OCH$_3$ | H | H | c-C$_3$H$_5$ | c-C$_3$H$_5$ | — |
| 624 | CH$_3$ | CH$_2$ | CH$_3$ | CH$_3$ | OCH$_3$ | H | H | H | C$_4$H$_9$ | — |
| 625 | CH$_3$ | CH$_2$ | CH$_3$ | CH$_3$ | OCH$_3$ | H | H | C$_2$H$_5$ | C$_4$H$_9$ | — |
| 626 | CH$_3$ | CH$_2$ | CH$_3$ | CH$_3$ | OCH$_3$ | H | H | H | C$_6$H$_5$ | — |
| 627 | CH$_3$ | CH$_2$ | CH$_3$ | CH$_3$ | OCH$_3$ | H | H | C$_2$H$_5$ | (CH$_2$)$_2$OCH$_3$ | — |
| 628 | CH$_3$ | CH$_2$ | CH$_3$ | CH$_3$ | OCH$_3$ | H | H | CH$_3$ | C$_4$H$_9$ | — |
| 629 | CH$_3$ | CH$_2$ | CH$_3$ | CH$_3$ | OCH$_3$ | H | H | C$_3$H$_7$ | C$_3$H$_7$ | — |
| 630 | CH$_3$ | CH$_2$ | CH$_3$ | CH$_3$ | OCH$_3$ | H | H | C$_2$H$_5$ | C$_3$H$_7$ | — |
| 631 | CH$_3$ | CH$_2$ | CH$_3$ | CH$_3$ | Cl | H | H | C$_2$H$_5$ | C$_2$H$_5$ | — |
| 632 | CH$_3$ | CH$_2$ | CH$_3$ | CH$_3$ | Cl | H | H | c-C$_3$H$_5$ | C$_4$H$_9$ | — |
| 633 | CH$_3$ | CH$_2$ | CH$_3$ | CH$_3$ | Cl | H | H | c-C$_3$H$_5$ | c-C$_3$H$_5$ | — |
| 634 | CH$_3$ | CH$_2$ | CH$_3$ | CH$_3$ | Cl | H | H | H | C$_4$H$_9$ | — |
| 635 | CH$_3$ | CH$_2$ | CH$_3$ | CH$_3$ | Cl | H | H | C$_2$H$_5$ | C$_4$H$_9$ | — |
| 636 | CH$_3$ | CH$_2$ | CH$_3$ | CH$_3$ | Cl | H | H | H | C$_6$H$_5$ | — |
| 637 | CH$_3$ | CH$_2$ | CH$_3$ | CH$_3$ | Cl | H | H | C$_2$H$_5$ | (CH$_2$)$_2$OCH$_3$ | — |
| 638 | CH$_3$ | CH$_2$ | CH$_3$ | CH$_3$ | Cl | H | H | CH$_3$ | C$_4$H$_9$ | — |
| 639 | CH$_3$ | CH$_2$ | CH$_3$ | CH$_3$ | Cl | H | H | C$_3$H$_7$ | C$_3$H$_7$ | — |
| 640 | CH$_3$ | CH$_2$ | CH$_3$ | CH$_3$ | Cl | H | H | C$_2$H$_5$ | C$_3$H$_7$ | — |
| 641 | CH$_3$ | CH$_2$ | CH$_3$ | Cl | CF$_3$ | H | H | C$_2$H$_5$ | C$_2$H$_5$ | — |
| 642 | CH$_3$ | CH$_2$ | CH$_3$ | Cl | CF$_3$ | H | H | c-C$_3$H$_5$ | C$_4$H$_9$ | — |
| 643 | CH$_3$ | CH$_2$ | CH$_3$ | Cl | CF$_3$ | H | H | c-C$_3$H$_5$ | c-C$_3$H$_5$ | — |
| 644 | CH$_3$ | CH$_2$ | CH$_3$ | Cl | CF$_3$ | H | H | H | C$_4$H$_9$ | — |
| 645 | CH$_3$ | CH$_2$ | CH$_3$ | Cl | CF$_3$ | H | H | C$_2$H$_5$ | C$_4$H$_9$ | — |
| 646 | CH$_3$ | CH$_2$ | CH$_3$ | Cl | CF$_3$ | H | H | H | C$_6$H$_5$ | — |
| 647 | CH$_3$ | CH$_2$ | CH$_3$ | Cl | CF$_3$ | H | H | C$_2$H$_5$ | (CH$_2$)$_2$OCH$_3$ | — |
| 648 | CH$_3$ | CH$_2$ | CH$_3$ | Cl | CF$_3$ | H | H | CH$_3$ | C$_4$H$_9$ | — |
| 649 | CH$_3$ | CH$_2$ | CH$_3$ | Cl | CF$_3$ | H | H | C$_3$H$_7$ | C$_3$H$_7$ | — |
| 650 | CH$_3$ | CH$_2$ | CH$_3$ | Cl | CF$_3$ | H | H | C$_2$H$_5$ | C$_3$H$_7$ | — |
| 651 | CH$_3$ | CH$_2$ | CH$_3$ | Cl | CF$_3$ | H | Cl | C$_2$H$_5$ | C$_2$H$_5$ | — |
| 652 | CH$_3$ | CH$_2$ | CH$_3$ | Cl | CF$_3$ | H | Cl | c-C$_3$H$_5$ | C$_4$H$_9$ | — |
| 653 | CH$_3$ | CH$_2$ | CH$_3$ | Cl | CF$_3$ | H | Cl | c-C$_3$H$_5$ | c-C$_3$H$_5$ | — |
| 654 | CH$_3$ | CH$_2$ | CH$_3$ | Cl | CF$_3$ | H | Cl | H | C$_4$H$_9$ | — |
| 655 | CH$_3$ | CH$_2$ | CH$_3$ | Cl | CF$_3$ | H | Cl | C$_2$H$_5$ | C$_4$H$_9$ | — |
| 656 | CH$_3$ | CH$_2$ | CH$_3$ | Cl | CF$_3$ | H | Cl | H | C$_6$H$_5$ | — |
| 657 | CH$_3$ | CH$_2$ | CH$_3$ | Cl | CF$_3$ | H | Cl | C$_2$H$_5$ | (CH$_2$)$_2$OCH$_3$ | — |
| 658 | CH$_3$ | CH$_2$ | CH$_3$ | Cl | CF$_3$ | H | Cl | CH$_3$ | C$_4$H$_9$ | — |
| 659 | CH$_3$ | CH$_2$ | CH$_3$ | Cl | CF$_3$ | H | Cl | C$_3$H$_7$ | C$_3$H$_7$ | — |
| 660 | CH$_3$ | CH$_2$ | CH$_3$ | Cl | CF$_3$ | H | Cl | C$_2$H$_5$ | C$_3$H$_7$ | — |
| 661 | CH$_3$ | CH$_2$ | CH$_3$ | OCH$_3$ | Cl | H | Cl | C$_2$H$_5$ | C$_2$H$_5$ | — |
| 662 | CH$_3$ | CH$_2$ | CH$_3$ | OCH$_3$ | Cl | H | Cl | c-C$_3$H$_5$ | C$_4$H$_9$ | — |
| 663 | CH$_3$ | CH$_2$ | CH$_3$ | OCH$_3$ | Cl | H | Cl | c-C$_3$H$_5$ | c-C$_3$H$_5$ | — |
| 664 | CH$_3$ | CH$_2$ | CH$_3$ | OCH$_3$ | Cl | H | Cl | H | C$_4$H$_9$ | — |
| 665 | CH$_3$ | CH$_2$ | CH$_3$ | OCH$_3$ | Cl | H | Cl | C$_2$H$_5$ | C$_4$H$_9$ | — |
| 666 | CH$_3$ | CH$_2$ | CH$_3$ | OCH$_3$ | Cl | H | Cl | H | C$_6$H$_5$ | — |
| 667 | CH$_3$ | CH$_2$ | CH$_3$ | OCH$_3$ | Cl | H | Cl | C$_2$H$_5$ | (CH$_2$)$_2$OCH$_3$ | — |

TABLE 1-continued

| | | | | | | | | | | |
|---|---|---|---|---|---|---|---|---|---|---|
| 668 | CH$_3$ | CH$_2$ | CH$_3$ | OCH$_3$ | Cl | H | Cl | CH$_3$ | C$_4$H$_9$ | — |
| 669 | CH$_3$ | CH$_2$ | CH$_3$ | OCH$_3$ | Cl | H | Cl | C$_3$H$_7$ | C$_3$H$_7$ | — |
| 670 | CH$_3$ | CH$_2$ | CH$_3$ | OCH$_3$ | Cl | H | Cl | C$_3$H$_5$ | C$_3$H$_7$ | — |
| 671 | CH$_3$ | CH$_2$ | CH$_3$ | CH$_3$ | CH$_3$ | H | H | C$_2$H$_5$ | C$_2$H$_5$ | — |
| 672 | CH$_3$ | CH$_2$ | CH$_3$ | CH$_3$ | CH$_3$ | H | H | c-C$_3$H$_5$ | C$_4$H$_9$ | — |
| 673 | CH$_3$ | CH$_2$ | CH$_3$ | CH$_3$ | CH$_3$ | H | H | c-C$_3$H$_5$ | c-C$_3$H$_5$ | — |
| 674 | CH$_3$ | CH$_2$ | CH$_3$ | CH$_3$ | CH$_3$ | H | H | H | C$_4$H$_9$ | — |
| 675 | CH$_3$ | CH$_2$ | CH$_3$ | CH$_3$ | CH$_3$ | H | H | C$_2$H$_5$ | C$_4$H$_9$ | — |
| 676 | CH$_3$ | CH$_2$ | CH$_3$ | CH$_3$ | CH$_3$ | H | H | H | C$_6$H$_5$ | — |
| 677 | CH$_3$ | CH$_2$ | CH$_3$ | CH$_3$ | CH$_3$ | H | H | C$_2$H$_5$ | (CH$_2$)$_2$OCH$_3$ | — |
| 678 | CH$_3$ | CH$_2$ | CH$_3$ | CH$_3$ | CH$_3$ | H | H | CH$_3$ | C$_4$H$_9$ | — |
| 679 | CH$_3$ | CH$_2$ | CH$_3$ | CH$_3$ | CH$_3$ | H | H | C$_3$H$_7$ | C$_3$H$_7$ | — |
| 680 | CH$_3$ | CH$_2$ | CH$_3$ | CH$_3$ | CH$_3$ | H | H | C$_2$H$_5$ | C$_3$H$_7$ | — |
| 681 | CH$_3$ | CH$_2$ | H | CH$_3$ | OCH$_3$ | H | H | C$_2$H$_5$ | C$_4$H$_9$ | — |
| 682 | CH$_3$ | CH$_2$ | H | OCH$_3$ | CH$_3$ | H | CH$_3$ | C$_2$H$_5$ | C$_4$H$_9$ | 107–109 |
| 683 | CH$_3$ | CH$_2$ | H | Cl | CF$_3$ | H | Cl | C$_2$H$_5$ | C$_4$H$_9$ | — |
| 684 | CH$_3$ | CH$_2$ | H | CH$_3$ | CH$_3$ | CH$_3$ | H | C$_2$H$_5$ | C$_4$H$_9$ | — |
| 685 | CH$_3$ | CH$_2$ | H | CH$_3$ | OCH$_3$ | H | H | c-C$_3$H$_5$ | c-C$_3$H$_5$ | 101–103 |
| 686 | CH$_3$ | CH$_2$ | H | OCH$_3$ | CH$_3$ | H | CH$_3$ | c-C$_3$H$_5$ | c-C$_3$H$_5$ | 187–188 |
| 687 | CH$_3$ | CH$_2$ | H | Cl | CF$_3$ | H | Cl | c-C$_3$H$_5$ | c-C$_3$H$_5$ | — |
| 688 | CH$_3$ | CH$_2$ | H | CH$_3$ | CH$_3$ | CH$_3$ | H | c-C$_3$H$_5$ | c-C$_3$H$_5$ | 119–121 |
| 689 | CH$_3$ | CH$_2$ | H | CH$_3$ | OCH$_3$ | H | H | H | C$_6$H$_5$ | 108–109 |
| 690 | CH$_3$ | CH$_2$ | H | OCH$_3$ | CH$_3$ | H | CH$_3$ | H | C$_6$H$_5$ | oil |
| 691 | CH$_3$ | CH$_2$ | H | Cl | CF$_3$ | H | Cl | H | C$_6$H$_5$ | — |
| 692 | CH$_3$ | CH$_2$ | H | CH$_3$ | CH$_3$ | CH$_3$ | H | H | C$_6$H$_5$ | oil |
| 693 | CH$_3$ | CH$_2$ | H | CH$_3$ | OCH$_3$ | H | H | c-C$_3$H$_5$ | C$_4$H$_9$ | oil |
| 694 | CH$_3$ | CH$_2$ | H | OCH$_3$ | CH$_3$ | H | CH$_3$ | c-C$_3$H$_5$ | C$_4$H$_9$ | — |
| 695 | CH$_3$ | CH$_2$ | H | Cl | CF$_3$ | H | Cl | c-C$_3$H$_5$ | C$_4$H$_9$ | — |
| 696 | CH$_3$ | CH$_2$ | H | CH$_3$ | CH$_3$ | CH$_3$ | H | c-C$_3$H$_5$ | C$_4$H$_9$ | — |
| 697 | CH$_3$ | CH$_2$ | H | CH$_3$ | OCH$_3$ | H | H | CH$_3$ | C$_4$H$_9$ | oil |
| 698 | CH$_3$ | CH$_2$ | H | OCH$_3$ | CH$_3$ | H | CH$_3$ | CH$_3$ | C$_4$H$_9$ | — |
| 699 | CH$_3$ | CH$_2$ | H | Cl | CF$_3$ | H | Cl | CH$_3$ | C$_4$H$_9$ | — |
| 700 | CH$_3$ | CH$_2$ | H | CH$_3$ | CH$_3$ | CH$_3$ | H | CH$_3$ | C$_4$H$_9$ | — |
| 701 | CH$_3$ | O | H | CH$_3$ | OCH$_3$ | H | H | C$_2$H$_5$ | C$_4$H$_9$ | — |
| 702 | CH$_3$ | O | H | OCH$_3$ | CH$_3$ | H | CH$_3$ | C$_2$H$_5$ | C$_4$H$_9$ | — |
| 703 | CH$_3$ | O | H | Cl | CF$_3$ | H | Cl | C$_2$H$_5$ | C$_4$H$_9$ | — |
| 704 | CH$_3$ | O | H | CH$_3$ | CH$_3$ | CH$_3$ | H | C$_2$H$_5$ | C$_4$H$_9$ | — |
| 705 | CH$_3$ | O | H | CH$_3$ | OCH$_3$ | H | H | c-C$_3$H$_5$ | c-C$_3$H$_5$ | — |
| 706 | CH$_3$ | O | H | OCH$_3$ | CH$_3$ | H | CH$_3$ | c-C$_3$H$_5$ | c-C$_3$H$_5$ | — |
| 707 | CH$_3$ | O | H | Cl | CF$_3$ | H | Cl | c-C$_3$H$_5$ | c-C$_3$H$_5$ | — |
| 708 | CH$_3$ | O | H | CH$_3$ | CH$_3$ | CH$_3$ | H | c-C$_3$H$_5$ | c-C$_3$H$_5$ | — |
| 709 | CH$_3$ | O | H | CH$_3$ | OCH$_3$ | H | H | H | C$_6$H$_5$ | — |
| 710 | CH$_3$ | O | H | OCH$_3$ | CH$_3$ | H | CH$_3$ | H | C$_6$H$_5$ | — |
| 711 | CH$_3$ | O | H | Cl | CF$_3$ | H | Cl | H | C$_6$H$_5$ | — |
| 712 | CH$_3$ | O | H | CH$_3$ | CH$_3$ | CH$_3$ | H | H | C$_6$H$_5$ | — |
| 713 | CH$_3$ | O | H | CH$_3$ | OCH$_3$ | H | H | c-C$_3$H$_5$ | C$_4$H$_9$ | — |
| 714 | CH$_3$ | O | H | OCH$_3$ | CH$_3$ | H | CH$_3$ | c-C$_3$H$_5$ | C$_4$H$_9$ | — |
| 715 | CH$_3$ | O | H | Cl | CF$_3$ | H | Cl | c-C$_3$H$_5$ | C$_4$H$_9$ | — |
| 716 | CH$_3$ | O | H | CH$_3$ | CH$_3$ | CH$_3$ | H | c-C$_3$H$_5$ | C$_4$H$_9$ | — |
| 717 | CH$_3$ | O | H | CH$_3$ | OCH$_3$ | H | H | CH$_3$ | C$_4$H$_9$ | — |
| 718 | CH$_3$ | O | H | OCH$_3$ | CH$_3$ | H | CH$_3$ | CH$_3$ | C$_4$H$_9$ | — |
| 719 | CH$_3$ | O | H | Cl | CF$_3$ | H | Cl | CH$_3$ | C$_4$H$_9$ | — |
| 720 | CH$_3$ | O | H | CH$_3$ | CH$_3$ | CH$_3$ | H | CH$_3$ | C$_4$H$_9$ | — |
| 721 | CH$_3$ | CH$_2$ | H | CH$_3$ | CH$_3$ | H | CH$_3$ | C$_2$H$_5$ | CH(CH$_3$)$_2$ | 146–147 |
| 722 | CH$_3$ | CH$_2$ | H | Cl | Cl | H | H | C$_2$H$_5$ | CH(CH$_3$)$_2$ | — |
| 723 | CH$_3$ | CH$_2$ | H | Cl | CH$_3$ | H | H | C$_2$H$_5$ | CH(CH$_3$)$_2$ | — |
| 724 | CH$_3$ | CH$_2$ | H | Cl | OCH$_3$ | H | H | C$_2$H$_5$ | CH(CH$_3$)$_2$ | oil |
| 725 | CH$_3$ | CH$_2$ | H | CH$_3$ | OCH$_3$ | H | H | C$_2$H$_5$ | CH(CH$_3$)$_2$ | oil |
| 726 | CH$_3$ | CH$_2$ | H | Cl | CF$_3$ | H | H | C$_2$H$_5$ | CH(CH$_3$)$_2$ | — |
| 727 | CH$_3$ | CH$_2$ | H | CF$_3$ | Cl | H | H | C$_2$H$_5$ | CH(CH$_3$)$_2$ | oil |
| 728 | CH$_3$ | CH$_2$ | H | CH$_3$ | Cl | H | H | C$_2$H$_5$ | CH(CH$_3$)$_2$ | — |
| 729 | CH$_3$ | CH$_2$ | H | CF$_3$ | CF$_3$ | H | H | C$_2$H$_5$ | CH(CH$_3$)$_2$ | — |
| 730 | CH$_3$ | CH$_2$ | H | Cl | CN | H | H | C$_2$H$_5$ | CH(CH$_3$)$_2$ | — |
| 731 | CH$_3$ | CH$_2$ | H | Cl | Cl | F | H | C$_2$H$_5$ | CH(CH$_3$)$_2$ | — |
| 732 | CH$_3$ | CH$_2$ | H | Cl | Cl | Cl | H | C$_2$H$_5$ | CH(CH$_3$)$_2$ | — |
| 733 | CH$_3$ | CH$_2$ | H | CH$_3$ | OCH$_3$ | F | H | C$_2$H$_5$ | CH(CH$_3$)$_2$ | — |
| 734 | CH$_3$ | CH$_2$ | H | CH$_3$ | OCH$_3$ | Cl | H | C$_2$H$_5$ | CH(CH$_3$)$_2$ | — |
| 735 | CH$_3$ | CH$_2$ | H | Cl | CH$_3$ | F | H | C$_2$H$_5$ | CH(CH$_3$)$_2$ | — |
| 736 | CH$_3$ | CH$_2$ | H | Cl | CF$_3$ | Cl | H | C$_2$H$_5$ | CH(CH$_3$)$_2$ | — |
| 737 | CH$_3$ | CH$_2$ | H | Cl | CF$_3$ | F | H | C$_2$H$_5$ | CH(CH$_3$)$_2$ | — |
| 738 | CH$_3$ | CH$_2$ | H | Cl | OCH$_3$ | Cl | H | C$_2$H$_5$ | CH(CH$_3$)$_2$ | — |
| 739 | CH$_3$ | CH$_2$ | H | Cl | OCH$_3$ | F | H | C$_2$H$_5$ | CH(CH$_3$)$_2$ | — |
| 740 | CH$_3$ | CH$_2$ | H | Cl | OCH$_3$ | CH$_3$ | H | C$_2$H$_5$ | CH(CH$_3$)$_2$ | — |
| 741 | CH$_3$ | CH$_2$ | H | CH$_3$ | OCH$_3$ | CH$_3$ | H | C$_2$H$_5$ | CH(CH$_3$)$_2$ | — |
| 742 | CH$_3$ | CH$_2$ | H | Cl | H | Cl | H | C$_2$H$_5$ | CH(CH$_3$)$_2$ | — |
| 743 | CH$_3$ | CH$_2$ | H | Cl | Cl | OCH$_3$ | H | C$_2$H$_5$ | CH(CH$_3$)$_2$ | — |
| 744 | CH$_3$ | CH$_2$ | H | Cl | CH$_3$ | OCH$_3$ | H | C$_2$H$_5$ | CH(CH$_3$)$_2$ | — |
| 745 | CH$_3$ | CH$_2$ | H | CH$_3$ | Cl | OCH$_3$ | H | C$_2$H$_5$ | CH(CH$_3$)$_2$ | — |
| 746 | CH$_3$ | CH$_2$ | H | CH$_3$ | CH$_3$ | OCH$_3$ | H | C$_2$H$_5$ | CH(CH$_3$)$_2$ | — |

TABLE 1-continued

| | | | | | | | | | | |
|---|---|---|---|---|---|---|---|---|---|---|
| 747 | CH$_3$ | CH$_2$ | H | CH$_3$ | CH$_3$ | H | CH$_3$ | C$_3$H$_7$ | c-C$_3$H$_5$ | 140–143 |
| 748 | CH$_3$ | CH$_2$ | H | Cl | Cl | H | H | C$_3$H$_7$ | c-C$_3$H$_5$ | 107–108 (A) 79–82 (C) |
| 749 | CH$_3$ | CH$_2$ | H | Cl | CH$_3$ | H | H | C$_3$H$_7$ | c-C$_3$H$_5$ | 106–108 |
| 750 | CH$_3$ | CH$_2$ | H | Cl | OCH$_3$ | H | H | C$_3$H$_7$ | c-C$_3$H$_5$ | oil |
| 751 | CH$_3$ | CH$_2$ | H | CH$_3$ | OCH$_3$ | H | H | C$_3$H$_7$ | c-C$_3$H$_5$ | oil |
| 752 | CH$_3$ | CH$_2$ | H | Cl | CF$_3$ | H | H | C$_3$H$_7$ | c-C$_3$H$_5$ | 108–109 |
| 753 | CH$_3$ | CH$_2$ | H | CF$_3$ | Cl | H | H | C$_3$H$_7$ | c-C$_3$H$_5$ | oil (A) 95–97 (C) |
| 754 | CH$_3$ | CH$_2$ | H | CH$_3$ | Cl | H | H | C$_3$H$_7$ | c-C$_3$H$_5$ | 87–88 |
| 755 | CH$_3$ | CF$_3$ | H | CF$_3$ | CF$_3$ | H | H | C$_3$H$_7$ | c-C$_3$H$_5$ | — |
| 756 | CH$_3$ | CH$_2$ | H | Cl | CN | H | H | C$_3$H$_7$ | c-C$_3$H$_5$ | — |
| 757 | CH$_3$ | CH$_2$ | H | Cl | Cl | F | H | C$_3$H$_7$ | c-C$_3$H$_5$ | — |
| 758 | CH$_3$ | CH$_2$ | H | Cl | Cl | Cl | H | C$_3$H$_7$ | c-C$_3$H$_5$ | — |
| 759 | CH$_3$ | CH$_2$ | H | CH$_3$ | OCH$_3$ | F | H | C$_3$H$_7$ | c-C$_3$H$_5$ | — |
| 760 | CH$_3$ | CH$_2$ | H | CH$_3$ | OCH$_3$ | Cl | H | C$_3$H$_7$ | c-C$_3$H$_5$ | — |
| 761 | CH$_3$ | CH$_2$ | H | Cl | CH$_3$ | F | H | C$_3$H$_7$ | c-C$_3$H$_5$ | — |
| 762 | CH$_3$ | CH$_2$ | H | Cl | CF$_3$ | Cl | H | C$_3$H$_7$ | c-C$_3$H$_5$ | — |
| 763 | CH$_3$ | CH$_2$ | H | Cl | CF$_3$ | F | H | C$_3$H$_7$ | c-C$_3$H$_5$ | — |
| 764 | CH$_3$ | CH$_2$ | H | Cl | OCH$_3$ | Cl | H | C$_3$H$_7$ | c-C$_3$H$_5$ | — |
| 765 | CH$_3$ | CH$_2$ | H | Cl | OCH$_3$ | F | H | C$_3$H$_7$ | c-C$_3$H$_5$ | — |
| 766 | CH$_3$ | CH$_2$ | H | Cl | OCH$_3$ | CH$_3$ | H | C$_3$H$_7$ | c-C$_3$H$_5$ | — |
| 767 | CH$_3$ | CH$_2$ | H | CH$_3$ | OCH$_3$ | CH$_3$ | H | C$_3$H$_7$ | c-C$_3$H$_5$ | oil |
| 768 | CH$_3$ | CH$_2$ | H | Cl | H | Cl | H | C$_3$H$_7$ | c-C$_3$H$_5$ | — |
| 769 | CH$_3$ | CH$_2$ | H | Cl | Cl | OCH$_3$ | H | C$_3$H$_7$ | c-C$_3$H$_5$ | — |
| 770 | CH$_3$ | CH$_2$ | H | Cl | CH$_3$ | OCH$_3$ | H | C$_3$H$_7$ | c-C$_3$H$_5$ | — |
| 771 | CH$_3$ | CH$_2$ | H | CH$_3$ | Cl | OCH$_3$ | H | C$_3$H$_7$ | c-C$_3$H$_5$ | — |
| 772 | CH$_3$ | CH$_2$ | H | CH$_3$ | CH$_3$ | OCH$_3$ | H | C$_3$H$_7$ | c-C$_3$H$_5$ | — |
| 773 | CH$_3$ | CH$_2$ | H | CH$_3$ | CH$_3$ | H | CH$_3$ | CH$_3$ | CH$_2$Cl | 109–110 |
| 774 | CH$_3$ | CH$_2$ | H | Cl | Cl | H | H | C$_2$H$_5$ | C$_3$H$_7$ | — |
| 775 | CH$_3$ | CH$_2$ | H | Cl | CH$_3$ | H | H | C$_2$H$_5$ | C$_3$H$_7$ | — |
| 776 | CH$_3$ | CH$_2$ | H | CH$_3$ | OCH$_3$ | H | H | C$_2$H$_5$ | C$_3$H$_7$ | oil |
| 777 | CH$_3$ | CH$_2$ | H | CH$_3$ | OCH$_3$ | H | H | C$_2$H$_5$ | C$_3$H$_7$ | oil |
| 778 | CH$_3$ | CH$_2$ | H | Cl | CF$_3$ | H | H | C$_2$H$_5$ | C$_3$H$_7$ | oil |
| 779 | CH$_3$ | CH$_2$ | H | CF$_3$ | Cl | H | H | C$_2$H$_5$ | C$_3$H$_7$ | oil |
| 780 | CH$_3$ | CH$_2$ | H | CH$_3$ | Cl | H | H | C$_2$H$_5$ | C$_3$H$_7$ | — |
| 781 | CH$_3$ | CH$_2$ | H | CF$_3$ | CF$_3$ | H | H | C$_2$H$_5$ | C$_3$H$_7$ | — |
| 782 | CH$_3$ | CH$_2$ | H | Cl | CN | H | H | C$_2$H$_5$ | C$_3$H$_7$ | — |
| 783 | CH$_3$ | CH$_2$ | H | Cl | Cl | F | H | C$_2$H$_5$ | C$_3$H$_7$ | — |
| 784 | CH$_3$ | CH$_2$ | H | Cl | Cl | Cl | H | C$_2$H$_5$ | C$_3$H$_7$ | — |
| 785 | CH$_3$ | CH$_2$ | H | CH$_3$ | OCH$_3$ | F | H | C$_2$H$_5$ | C$_3$H$_7$ | — |
| 786 | CH$_3$ | CH$_2$ | H | CH$_3$ | OCH$_3$ | Cl | H | C$_2$H$_5$ | C$_3$H$_7$ | — |
| 787 | CH$_3$ | CH$_2$ | H | Cl | CH$_3$ | F | H | C$_2$H$_5$ | C$_3$H$_7$ | — |
| 788 | CH$_3$ | CH$_2$ | H | Cl | CF$_3$ | Cl | H | C$_2$H$_5$ | C$_3$H$_7$ | — |
| 789 | CH$_3$ | CH$_2$ | H | Cl | CF$_3$ | F | H | C$_2$H$_5$ | C$_3$H$_7$ | — |
| 790 | CH$_3$ | CH$_2$ | H | Cl | OCH$_3$ | Cl | H | C$_2$H$_5$ | C$_3$H$_7$ | — |
| 791 | CH$_3$ | CH$_2$ | H | Cl | OCH$_3$ | F | H | C$_2$H$_5$ | C$_3$H$_7$ | — |
| 792 | CH$_2$ | CH$_3$ | H | Cl | OCH$_3$ | CH$_3$ | H | C$_2$H$_5$ | C$_3$H$_7$ | — |
| 793 | CH$_3$ | CH$_2$ | H | CH$_3$ | OCH$_3$ | CH$_3$ | H | C$_2$H$_5$ | C$_3$H$_7$ | oil |
| 794 | CH$_3$ | CH$_2$ | H | Cl | H | Cl | H | C$_2$H$_5$ | C$_3$H$_7$ | — |
| 795 | CH$_3$ | CH$_2$ | H | Cl | Cl | OCH$_3$ | H | C$_2$H$_5$ | C$_3$H$_7$ | — |
| 796 | CH$_3$ | CH$_2$ | H | Cl | CH$_3$ | OCH$_3$ | H | C$_2$H$_5$ | C$_3$H$_7$ | — |
| 797 | CH$_3$ | CH$_2$ | H | CH$_3$ | Cl | OCH$_3$ | H | C$_2$H$_5$ | C$_3$H$_7$ | — |
| 798 | CH$_3$ | CH$_2$ | H | CH$_3$ | CH$_3$ | OCH$_3$ | H | C$_2$H$_5$ | C$_3$H$_7$ | — |
| 799 | CH$_3$ | CH$_2$ | H | CH$_3$ | CH$_3$ | H | C$_2$H$_5$ | C$_3$H$_7$ | oil |
| 800 | CH$_3$ | CH$_2$ | H | CF$_3$ | Cl | H | H | H | 4-CH$_3$O—C$_6$H$_4$ | 138–139 |
| 801 | CH$_3$ | CH$_2$ | H | CF$_3$ | Cl | H | H | c-C$_3$H$_5$ | c-C$_3$H$_5$ | 138–139 |
| 802 | CH$_3$ | CH$_2$ | H | CF$_3$ | Cl | H | H | C$_2$H$_5$ | c-C$_3$H$_5$ | oil (A) 122–125 (C) |
| 803 | CH$_3$ | CH$_2$ | H | CF$_3$ | Cl | H | H | CH$_3$ | c-C$_3$H$_5$ | oil |
| 804 | CH$_3$ | CH$_2$ | H | CF$_3$ | Cl | H | H | CH$_3$ | C$_3$H$_7$ | oil |
| 805 | CH$_3$ | CH$_2$ | H | CF$_3$ | Cl | H | H | CH$_3$ | C$_4$H$_9$ | oil |
| 806 | CH$_3$ | CH$_2$ | H | CF$_3$ | Cl | H | H | CH$_3$ | C$_5$H$_{11}$ | — |
| 807 | CH$_3$ | CH$_2$ | H | CF$_3$ | Cl | H | H | C$_2$H$_5$ | C$_4$H$_9$ | oil |
| 808 | CH$_3$ | CH$_2$ | H | CF$_3$ | Cl | H | H | C$_3$H$_7$ | C$_3$H$_7$ | oil |
| 809 | CH$_3$ | CH$_2$ | H | CF$_3$ | Cl | H | H | C$_2$H$_5$ | C$_2$H$_5$ | oil |
| 810 | CH$_3$ | CH$_2$ | H | Cl | CN | H | H | H | 4-CH$_3$O—C$_6$H$_4$ | — |
| 811 | CH$_3$ | CH$_2$ | H | Cl | CN | H | H | c-C$_3$H$_5$ | c-C$_3$H$_5$ | 180–182 |
| 812 | CH$_3$ | CH$_2$ | H | Cl | CN | H | H | C$_2$H$_5$ | c-C$_3$H$_5$ | — |
| 813 | CH$_3$ | CH$_2$ | H | Cl | CN | H | H | CH$_3$ | c-C$_3$H$_5$ | — |
| 814 | CH$_3$ | CH$_2$ | H | Cl | CN | H | H | CH$_3$ | C$_3$H$_7$ | — |
| 815 | CH$_3$ | CH$_2$ | H | Cl | CN | H | H | CH$_3$ | C$_4$H$_9$ | — |
| 816 | CH$_3$ | CH$_2$ | H | Cl | CN | H | H | CH$_3$ | C$_5$H$_{11}$ | — |

TABLE 1-continued

| | | | | | | | | | | |
|---|---|---|---|---|---|---|---|---|---|---|
| 817 | CH₃ | CH₂ | H | Cl | CN | H | H | C₂H₅ | C₄H₉ | — |
| 818 | CH₃ | CH₂ | H | Cl | CN | H | H | C₃H₇ | C₃H₇ | — |
| 819 | CH₃ | CH₂ | H | Cl | CN | H | H | C₂H₅ | C₂H₅ | — |
| 820 | CH₃ | CH₂ | H | CF₃ | CF₃ | H | H | H | 4-CH₃O—C₆H₄ | — |
| 821 | CH₃ | CH₂ | H | CF₃ | CF₃ | H | H | c-C₃H₅ | c-C₃H₅ | 149–150 |
| 822 | CH₃ | CH₂ | H | CF₃ | CF₃ | H | H | C₂H₅ | c-C₃H₅ | — |
| 823 | CH₃ | CH₂ | H | CF₃ | CF₃ | H | H | CH₃ | c-C₃H₅ | — |
| 824 | CH₃ | CH₂ | H | CF₃ | CF₃ | H | H | CH₃ | C₃H₇ | oil |
| 825 | CH₃ | CH₂ | H | CF₃ | CF₃ | H | H | CH₃ | C₄H₉ | — |
| 826 | CH₃ | CH₂ | H | CF₃ | CF₃ | H | H | CH₃ | C₅H₁₁ | — |
| 827 | CH₃ | CH₂ | H | CF₃ | CF₃ | H | H | C₂H₅ | C₄H₉ | — |
| 828 | CH₃ | CH₂ | H | CF₃ | CF₃ | H | H | C₃H₇ | C₃H₇ | — |
| 829 | CH₃ | CH₂ | H | CF₃ | CF₃ | H | H | C₂H₅ | C₂H₅ | — |
| 830 | CH₃ | CH₂ | H | Cl | OCH₃ | H | H | H | 4-CH₃O—C₆H₄ | 58–60 |
| 831 | CH₃ | CH₂ | H | Cl | OCH₃ | H | H | c-C₃H₅ | c-C₃H₅ | 139–140 |
| 832 | CH₃ | CH₂ | H | Cl | OCH₃ | H | H | C₂H₅ | c-C₃H₅ | oil |
| 833 | CH₃ | CH₂ | H | Cl | OCH₃ | H | H | H | c-C₃H₅ | oil |
| 834 | CH₃ | CH₂ | H | Cl | OCH₃ | H | H | CH₃ | C₃H₇ | oil |
| 835 | CH₃ | CH₂ | H | Cl | OCH₃ | H | H | CH₃ | C₄H₉ | oil |
| 836 | CH₃ | CH₂ | H | Cl | OCH₃ | H | H | CH₃ | C₅H₁₁ | oil |
| 837 | CH₃ | CH₂ | H | Cl | OCH₃ | H | H | C₂H₅ | C₄H₉ | oil |
| 838 | CH₃ | CH₂ | H | Cl | OCH₃ | H | H | C₃H₇ | C₃H₇ | oil |
| 839 | CH₃ | CH₂ | H | Cl | OCH₃ | H | H | C₂H₅ | C₂H₅ | oil |
| 840 | CH₃ | CH₂ | H | Cl | Cl | H | H | H | 4-CH₃O—C₆H₄ | — |
| 841 | CH₃ | CH₂ | H | Cl | Cl | F | H | c-C₃H₅ | c-C₃H₅ | 148–149 |
| 842 | CH₃ | CH₂ | H | Cl | Cl | F | H | C₂H₅ | c-C₃H₅ | — |
| 843 | CH₃ | CH₂ | H | Cl | Cl | F | H | CH₃ | c-C₃H₅ | — |
| 844 | CH₃ | CH₂ | H | Cl | Cl | F | H | CH₃ | C₃H₇ | — |
| 845 | CH₃ | CH₂ | H | Cl | Cl | F | H | CH₃ | C₄H₉ | — |
| 846 | CH₃ | CH₂ | H | Cl | Cl | F | H | CH₃ | C₅H₁₁ | — |
| 847 | CH₃ | CH₂ | H | Cl | Cl | F | H | C₂H₅ | C₄H₉ | — |
| 848 | CH₃ | CH₂ | H | Cl | Cl | F | H | C₃H₇ | C₃H₇ | — |
| 849 | CH₃ | CH₂ | H | Cl | Cl | F | H | C₂H₅ | C₂H₅ | — |
| 850 | CH₃ | CH₂ | H | Cl | Cl | Cl | H | H | 4-CH₃O—C₆H₅ | — |
| 851 | CH₃ | CH₂ | H | Cl | Cl | Cl | H | c-C₃H₅ | c-C₃H₅ | — |
| 852 | CH₃ | CH₂ | H | Cl | Cl | Cl | H | C₂H₅ | c-C₃H₅ | — |
| 853 | CH₃ | CH₂ | H | Cl | Cl | Cl | H | CH₃ | c-C₃H₅ | — |
| 854 | CH₃ | CH₂ | H | Cl | Cl | Cl | H | CH₃ | C₃H₇ | — |
| 855 | CH₃ | CH₂ | H | Cl | Cl | Cl | H | CH₃ | C₄H₉ | — |
| 856 | CH₃ | CH₂ | H | Cl | Cl | Cl | H | CH₃ | C₅H₁₁ | — |
| 857 | CH₃ | CH₂ | H | Cl | Cl | Cl | H | C₂H₅ | C₄H₉ | — |
| 858 | CH₃ | CH₂ | H | Cl | Cl | Cl | H | C₃H₇ | C₃H₇ | — |
| 859 | CH₃ | CH₂ | H | Cl | Cl | Cl | H | C₂H₅ | C₂H₅ | — |
| 860 | CH₃ | CH₂ | H | CH₃ | OCH₃ | F | H | H | 4-CH₃O—C₆H₄ | — |
| 861 | CH₃ | CH₂ | H | CH₃ | OCH₃ | F | H | c-C₃H₅ | c-C₃H₅ | 128–129 |
| 862 | CH₃ | CH₂ | H | CH₃ | OCH₃ | F | H | C₂H₅ | c-C₃H₅ | — |
| 863 | CH₃ | CH₂ | H | CH₃ | OCH₃ | F | H | CH₃ | c-C₃H₅ | — |
| 864 | CH₃ | CH₂ | H | CH₃ | OCH₃ | F | H | CH₃ | C₃H₇ | — |
| 865 | CH₃ | CH₂ | H | CH₃ | OCH₃ | F | H | CH₃ | C₄H₉ | — |
| 866 | CH₃ | CH₂ | H | CH₃ | OCH₃ | F | H | CH₃ | C₅H₁₁ | — |
| 867 | CH₃ | CH₂ | H | CH₃ | OCH₃ | F | H | C₂H₅ | C₄H₉ | — |
| 868 | CH₃ | CH₂ | H | CH₃ | OCH₃ | F | H | C₃H₇ | C₃H₇ | — |
| 869 | CH₃ | CH₂ | H | CH₃ | OCH₃ | F | H | C₂H₅ | C₂H₅ | — |
| 870 | CH₃ | CH₂ | H | CH₃ | OCH₃ | Cl | H | H | 4-CH₃O—C₆H₄ | oil |
| 871 | CH₃ | CH₂ | H | CH₃ | OCH₃ | Cl | H | c-C₃H₅ | c-C₃H₅ | 179–181 |
| 872 | CH₃ | CH₂ | H | CH₃ | OCH₃ | Cl | H | C₂H₅ | c-C₃H₅ | — |
| 873 | CH₃ | CH₂ | H | CH₃ | OCH₃ | Cl | H | CH₃ | c-C₃H₅ | — |
| 874 | CH₃ | CH₂ | H | CH₃ | OCH₃ | Cl | H | CH₃ | C₃H₇ | — |
| 875 | CH₃ | CH₂ | H | CH₃ | OCH₃ | Cl | H | CH₃ | C₄H₉ | — |
| 876 | CH₃ | CH₂ | H | CH₃ | OCH₃ | Cl | H | CH₃ | C₅H₁₁ | — |
| 877 | CH₃ | CH₂ | H | CH₃ | OCH₃ | Cl | H | C₂H₅ | C₄H₉ | — |
| 878 | CH₃ | CH₂ | H | CH₃ | OCH₃ | Cl | H | C₃H₇ | C₃H₇ | — |
| 879 | CH₃ | CH₂ | H | CH₃ | OCH₃ | Cl | H | C₂H₅ | C₂H₅ | — |
| 880 | CH₃ | CH₂ | H | Cl | CH₃ | F | H | H | 4-CH₃O—C₆H₄ | — |
| 881 | CH₃ | CH₂ | H | Cl | CH₃ | F | H | c-C₃H₅ | c-C₃H₅ | 130–131 |
| 882 | CH₃ | CH₂ | H | Cl | CH₃ | F | H | C₂H₅ | c-C₃H₅ | — |
| 883 | CH₃ | CH₂ | H | Cl | CH₃ | F | H | CH₃ | c-C₃H₅ | — |
| 884 | CH₃ | CH₂ | H | Cl | CH₃ | F | H | CH₃ | C₃H₇ | — |
| 885 | CH₃ | CH₂ | H | Cl | CH₃ | F | H | CH₃ | C₄H₉ | — |
| 886 | CH₃ | CH₂ | H | Cl | CH₃ | F | H | CH₃ | C₅H₁₁ | — |
| 887 | CH₃ | CH₂ | H | Cl | CH₃ | F | H | C₂H₅ | C₄H₉ | — |
| 888 | CH₃ | CH₂ | H | Cl | CH₃ | F | H | C₃H₇ | C₃H₇ | — |
| 889 | CH₃ | CH₂ | H | Cl | CH₃ | F | H | C₂H₅ | C₂H₅ | — |
| 890 | CH₃ | CH₂ | H | Cl | CF₃ | Cl | H | H | 4-CH₃O—C₆H₄ | — |
| 891 | CH₃ | CH₂ | H | Cl | CF₃ | Cl | H | c-C₃H₅ | c-C₃H₅ | — |
| 892 | CH₃ | CH₂ | H | Cl | CF₃ | Cl | H | C₂H₅ | c-C₃H₅ | — |
| 893 | CH₃ | CH₂ | H | Cl | CF₃ | Cl | H | CH₃ | c-C₃H₅ | — |
| 894 | CH₂ | CH₂ | H | Cl | CF₃ | Cl | H | CH₃ | C₃H₇ | — |
| 895 | CH₃ | CH₂ | H | Cl | CF₃ | Cl | H | CH₃ | C₄H₉ | — |

TABLE 1-continued

| | | | | | | | | | | |
|---|---|---|---|---|---|---|---|---|---|---|
| 896 | $CH_3$ | $CH_2$ | H | Cl | $CF_3$ | Cl | H | $CH_3$ | $C_5H_{11}$ | — |
| 897 | $CH_3$ | $CH_2$ | H | Cl | $CF_3$ | Cl | H | $C_2H_5$ | $C_4H_9$ | — |
| 898 | $CH_3$ | $CH_2$ | H | Cl | $CF_3$ | Cl | H | $C_3H_7$ | $C_3H_7$ | — |
| 899 | $CH_3$ | $CH_2$ | H | Cl | $CF_3$ | Cl | H | $C_2H_5$ | $C_2H_5$ | — |
| 900 | $CH_3$ | $CH_2$ | H | $CH_3$ | $OCH_3$ | H | H | H | $C_4H_9$ | oil |
| 901 | $CH_3$ | $CH_2$ | H | $CH_3$ | $OCH_3$ | H | H | $C_2H_5$ | $C_2H_5$ | 69–73 |
| 902 | $CH_3$ | $CH_2$ | H | Cl | $CH_3$ | H | H | $C_3H_7$ | $C_3H_7$ | oil |
| 903 | $CH_3$ | $CH_2$ | H | Cl | $CF_3$ | F | H | H | 4-$CH_3O$—$C_6H_4$ | — |
| 904 | $CH_3$ | $CH_2$ | H | Cl | $CF_3$ | F | H | c-$C_3H_5$ | c-$C_3H_5$ | — |
| 905 | $CH_3$ | $CH_2$ | H | Cl | $CF_3$ | F | H | $C_2H_5$ | c-$C_3H_5$ | — |
| 906 | $CH_3$ | $CH_2$ | H | Cl | $CF_3$ | F | H | $CH_3$ | c-$C_3H_5$ | — |
| 907 | $CH_3$ | $CH_2$ | H | Cl | $CF_3$ | F | H | $CH_3$ | $C_3H_7$ | — |
| 908 | $CH_3$ | $CH_2$ | H | Cl | $CF_3$ | F | H | $CH_3$ | $C_4H_9$ | — |
| 909 | $CH_3$ | $CH_2$ | H | Cl | $CF_3$ | F | H | $CH_3$ | $C_5H_{11}$ | — |
| 910 | $CH_3$ | $CH_2$ | H | Cl | $CF_3$ | F | H | $C_2H_5$ | $C_4H_9$ | — |
| 911 | $CH_3$ | $CH_2$ | H | Cl | $CF_3$ | F | H | $C_3H_7$ | $C_3H_7$ | — |
| 912 | $CH_3$ | $CH_2$ | H | Cl | $CF_3$ | F | H | $C_2H_5$ | $C_2H_5$ | — |
| 913 | $CH_3$ | $CH_2$ | H | Cl | $OCH_3$ | Cl | H | H | 4-$CH_3O$—$C_6H_4$ | — |
| 914 | $CH_3$ | $CH_2$ | H | Cl | $OCH_3$ | Cl | H | c-$C_3H_5$ | c-$C_3H_5$ | oil |
| 915 | $CH_3$ | $CH_2$ | H | Cl | $OCH_3$ | Cl | H | $C_2H_5$ | c-$C_3H_5$ | — |
| 916 | $CH_3$ | $CH_2$ | H | Cl | $OCH_3$ | Cl | H | $CH_3$ | c-$C_3H_5$ | — |
| 917 | $CH_3$ | $CH_2$ | H | Cl | $OCH_3$ | Cl | H | $CH_3$ | $C_3H_7$ | — |
| 918 | $CH_3$ | $CH_2$ | H | Cl | $OCH_3$ | Cl | H | $CH_3$ | $C_4H_9$ | — |
| 919 | $CH_3$ | $CH_2$ | H | Cl | $OCH_3$ | Cl | H | $CH_3$ | $C_5H_{11}$ | — |
| 920 | $CH_3$ | $CH_2$ | H | Cl | $OCH_3$ | Cl | H | $C_2H_5$ | $C_4H_9$ | — |
| 921 | $CH_3$ | $CH_2$ | H | Cl | $OCH_3$ | Cl | H | $C_3H_7$ | $C_3H_7$ | — |
| 922 | $CH_3$ | $CH_2$ | H | Cl | $OCH_3$ | Cl | H | $C_2H_5$ | $C_2H_5$ | — |
| 923 | $CH_3$ | $CH_2$ | H | Cl | $OCH_3$ | F | H | H | 4-$CH_3O$—$C_6H_4$ | — |
| 924 | $CH_3$ | $CH_2$ | H | Cl | $OCH_3$ | F | H | c-$C_3H_5$ | c-$C_3H_5$ | — |
| 925 | $CH_3$ | $CH_2$ | H | Cl | $OCH_3$ | F | H | $C_2H_5$ | c-$C_3H_5$ | — |
| 926 | $CH_3$ | $CH_2$ | H | Cl | $OCH_3$ | F | H | $CH_3$ | c-$C_3H_5$ | — |
| 927 | $CH_3$ | $CH_2$ | H | Cl | $OCH_3$ | F | H | $CH_3$ | $C_3H_7$ | — |
| 928 | $CH_3$ | $CH_2$ | H | Cl | $OCH_3$ | F | H | $CH_3$ | $C_4H_9$ | — |
| 929 | $CH_3$ | $CH_2$ | H | Cl | $OCH_3$ | F | H | $CH_3$ | $C_5H_{11}$ | — |
| 930 | $CH_3$ | $CH_2$ | H | Cl | $OCH_3$ | F | H | $C_2H_5$ | $C_4H_9$ | — |
| 931 | $CH_3$ | $CH_2$ | H | Cl | $OCH_3$ | F | H | $C_3H_7$ | $C_3H_7$ | — |
| 932 | $CH_3$ | $CH_2$ | H | Cl | $OCH_3$ | F | H | $C_2H_5$ | $C_2H_5$ | — |
| 933 | $CH_3$ | $CH_2$ | H | Cl | $OCH_3$ | $CH_3$ | H | H | 4-$CH_3O$—$C_6H_4$ | — |
| 934 | $CH_3$ | $CH_2$ | H | Cl | $OCH_3$ | $CH_3$ | H | c-$C_3H_5$ | c-$C_3H_5$ | 150–151 |
| 935 | $CH_3$ | $CH_2$ | H | Cl | $OCH_3$ | $CH_3$ | H | $C_2H_5$ | c-$C_3H_5$ | — |
| 936 | $CH_3$ | $CH_2$ | H | Cl | $OCH_3$ | $CH_3$ | H | $CH_3$ | c-$C_3H_5$ | — |
| 937 | $CH_3$ | $CH_2$ | H | Cl | $OCH_3$ | $CH_3$ | H | $CH_3$ | $C_3H_7$ | — |
| 938 | $CH_3$ | $CH_2$ | H | Cl | $OCH_3$ | $CH_3$ | H | $CH_3$ | $C_4H_9$ | — |
| 939 | $CH_3$ | $CH_2$ | H | Cl | $OCH_3$ | $CH_3$ | H | $CH_3$ | $C_5H_{11}$ | — |
| 940 | $CH_3$ | $CH_2$ | H | Cl | $OCH_3$ | $CH_3$ | H | $C_2H_5$ | $C_4H_9$ | — |
| 941 | $CH_3$ | $CH_2$ | H | Cl | $OCH_3$ | $CH_3$ | H | $C_3H_7$ | $C_3H_7$ | — |
| 942 | $CH_3$ | $CH_2$ | H | Cl | $OCH_3$ | $CH_3$ | H | $C_2H_5$ | $C_2H_5$ | — |
| 943 | $CH_3$ | $CH_2$ | H | $CH_3$ | $OCH_3$ | $CH_3$ | H | H | 4-$CH_3O$—$C_6H_4$ | — |
| 944 | $CH_3$ | $CH_2$ | H | $CH_3$ | $OCH_3$ | $CH_3$ | H | c-$C_3H_5$ | c-$C_3H_5$ | 148–151 |
| 945 | $CH_3$ | $CH_2$ | H | $CH_3$ | $OCH_3$ | $CH_3$ | H | $C_2H_5$ | c-$C_3H_5$ | oil |
| 946 | $CH_3$ | $CH_2$ | H | $CH_3$ | $OCH_3$ | $CH_3$ | H | $CH_3$ | c-$C_3H_5$ | — |
| 947 | $CH_3$ | $CH_2$ | H | $CH_3$ | $OCH_3$ | $CH_3$ | H | $CH_3$ | $C_3H_7$ | oil |
| 948 | $CH_3$ | $CH_2$ | H | $CH_3$ | $OCH_3$ | $CH_3$ | H | $CH_3$ | $C_4H_9$ | — |
| 949 | $CH_3$ | $CH_2$ | H | $CH_3$ | $OCH_3$ | $CH_3$ | H | $CH_3$ | $C_5H_{11}$ | — |
| 950 | $CH_3$ | $CH_2$ | H | $CH_3$ | $OCH_3$ | $CH_3$ | H | $C_2H_5$ | $C_4H_9$ | — |
| 951 | $CH_3$ | $CH_2$ | H | $CH_3$ | $OCH_3$ | $CH_3$ | H | $C_3H_7$ | $C_3H_7$ | oil |
| 952 | $CH_3$ | $CH_2$ | H | $CH_3$ | $OCH_3$ | $CH_3$ | H | $C_2H_5$ | $C_2H_5$ | oil |
| 953 | $CH_3$ | $CH_2$ | H | Cl | H | Cl | H | H | 4-$CH_3O$—$C_6H_4$ | — |
| 954 | $CH_3$ | $CH_2$ | H | Cl | H | Cl | H | c-$C_3H_5$ | c-$C_3H_5$ | 151–153 |
| 955 | $CH_3$ | $CH_2$ | H | Cl | H | Cl | H | $C_2H_5$ | c-$C_3H_5$ | — |
| 956 | $CH_3$ | $CH_2$ | H | Cl | H | Cl | H | $CH_3$ | c-$C_3H_5$ | — |
| 957 | $CH_3$ | $CH_2$ | H | Cl | H | Cl | H | $CH_3$ | $C_3H_7$ | — |
| 958 | $CH_3$ | $CH_2$ | H | Cl | H | Cl | H | $CH_3$ | $C_4H_9$ | — |
| 959 | $CH_3$ | $CH_2$ | H | Cl | H | Cl | H | $CH_3$ | $C_5H_{11}$ | — |
| 960 | $CH_3$ | $CH_2$ | H | Cl | H | Cl | H | $C_2H_5$ | $C_4H_9$ | — |
| 961 | $CH_3$ | $CH_2$ | H | Cl | H | Cl | H | $C_3H_7$ | $C_3H_7$ | — |
| 962 | $CH_3$ | $CH_2$ | H | Cl | H | Cl | H | $C_2H_5$ | $C_2H_5$ | — |
| 963 | $CH_3$ | $CH_2$ | H | Cl | Cl | $OCH_3$ | H | H | 4-$CH_3O$—$C_6H_4$ | — |
| 964 | $CH_3$ | $CH_2$ | H | Cl | Cl | $OCH_3$ | H | c-$C_3H_5$ | c-$C_3H_5$ | — |
| 965 | $CH_3$ | $CH_2$ | H | Cl | Cl | $OCH_3$ | H | $C_2H_5$ | c-$C_3H_5$ | — |
| 966 | $CH_3$ | $CH_2$ | H | Cl | Cl | $OCH_3$ | H | $CH_3$ | c-$C_3H_5$ | — |
| 967 | $CH_3$ | $CH_2$ | H | Cl | Cl | $OCH_3$ | H | $CH_3$ | $C_3H_7$ | — |
| 968 | $CH_3$ | $CH_2$ | H | Cl | Cl | $OCH_3$ | H | $CH_3$ | $C_4H_9$ | — |
| 969 | $CH_3$ | $CH_2$ | H | Cl | Cl | $OCH_3$ | H | $CH_3$ | $C_4H_{11}$ | — |
| 970 | $CH_3$ | $CH_2$ | H | Cl | Cl | $OCH_3$ | H | $C_2H_5$ | $C_4H_9$ | — |
| 971 | $CH_3$ | $CH_2$ | H | Cl | Cl | $OCH_3$ | H | $C_3H_7$ | $C_3H_7$ | — |
| 972 | $CH_3$ | $CH_2$ | H | Cl | Cl | $OCH_3$ | H | $C_2H_5$ | $C_2H_5$ | — |
| 973 | $CH_3$ | $CH_2$ | H | Cl | $CH_3$ | $OCH_3$ | H | H | 4-$CH_3O$—$C_6H_4$ | — |
| 974 | $CH_3$ | $CH_2$ | H | Cl | $CH_3$ | $OCH_3$ | H | c-$C_3H_5$ | c-$C_3H_5$ | — |

TABLE 1-continued

| | | | | | | | | | | |
|---|---|---|---|---|---|---|---|---|---|---|
| 975 | $CH_3$ | $CH_2$ | H | Cl | $CH_3$ | $OCH_3$ | H | $C_2H_5$ | c-$C_3H_5$ | — |
| 976 | $CH_3$ | $CH_2$ | H | Cl | $CH_3$ | $OCH_3$ | H | $CH_3$ | c-$C_3H_5$ | — |
| 977 | $CH_3$ | $CH_2$ | H | Cl | $CH_3$ | $OCH_3$ | H | $CH_3$ | $C_3H_7$ | — |
| 978 | $CH_3$ | $CH_2$ | H | Cl | $CH_3$ | $OCH_3$ | H | $CH_3$ | $C_4H_9$ | — |
| 979 | $CH_3$ | $CH_2$ | H | Cl | $CH_3$ | $OCH_3$ | H | $CH_3$ | $C_5H_{11}$ | — |
| 980 | $CH_3$ | $CH_2$ | H | Cl | $CH_3$ | $OCH_3$ | H | $C_2H_5$ | $C_4H_9$ | — |
| 981 | $CH_3$ | $CH_2$ | H | Cl | $CH_3$ | $OCH_3$ | H | $C_3H_7$ | $C_3H_7$ | — |
| 982 | $CH_3$ | $CH_2$ | H | Cl | $CH_3$ | $OCH_3$ | H | $C_2H_5$ | $C_2H_5$ | — |
| 983 | $CH_3$ | $CH_2$ | H | $CH_3$ | Cl | $OCH_3$ | H | H | 4-$CH_3O$—$C_6H_4$ | — |
| 984 | $CH_3$ | $CH_2$ | H | $CH_3$ | Cl | $OCH_3$ | H | c-$C_3H_5$ | c-$C_3H_5$ | — |
| 985 | $CH_3$ | $CH_2$ | H | $CH_3$ | Cl | $OCH_3$ | H | $C_2H_5$ | c-$C_3H_5$ | — |
| 986 | $CH_3$ | $CH_2$ | H | $CH_3$ | Cl | $OCH_3$ | H | $CH_3$ | c-$C_3H_5$ | — |
| 987 | $CH_3$ | $CH_2$ | H | $CH_3$ | Cl | $OCH_3$ | H | $CH_3$ | $C_3H_7$ | — |
| 988 | $CH_3$ | $CH_2$ | H | $CH_3$ | Cl | $OCH_3$ | H | $CH_2$ | $C_4H_9$ | — |
| 989 | $CH_3$ | $CH_2$ | H | $CH_3$ | Cl | $OCH_3$ | H | $CH_3$ | $C_5H_{11}$ | — |
| 990 | $CH_3$ | $CH_2$ | H | $CH_3$ | Cl | $OCH_3$ | H | $C_2H_5$ | $C_4H_9$ | — |
| 991 | $CH_3$ | $CH_2$ | H | $CH_3$ | Cl | $OCH_3$ | H | $C_3H_7$ | $C_3H_7$ | — |
| 992 | $CH_3$ | $CH_2$ | H | $CH_3$ | Cl | $OCH_3$ | H | $C_2H_5$ | $C_2H_5$ | — |
| 993 | $CH_3$ | $CH_2$ | H | $CH_3$ | $CH_3$ | $OCH_3$ | H | H | 4-$CH_3O$—$C_6H_4$ | — |
| 994 | $CH_3$ | $CH_2$ | H | $CH_3$ | $CH_3$ | $OCH_3$ | H | c-$C_3H_5$ | c-$C_3H_5$ | — |
| 995 | $CH_3$ | $CH_2$ | H | $CH_3$ | $CH_3$ | $OCH_3$ | H | $C_2H_5$ | c-$C_3H_5$ | — |
| 996 | $CH_3$ | $CH_2$ | H | $CH_3$ | $CH_3$ | $OCH_3$ | H | $CH_3$ | c-$C_3H_5$ | — |
| 997 | $CH_3$ | $CH_2$ | H | $CH_3$ | $CH_3$ | $OCH_3$ | H | $CH_3$ | $C_3H_7$ | — |
| 998 | $CH_3$ | $CH_2$ | H | $CH_3$ | $CH_3$ | $OCH_3$ | H | $CH_3$ | $C_4H_9$ | — |
| 999 | $CH_3$ | $CH_2$ | H | $CH_3$ | $CH_3$ | $OCH_3$ | H | $CH_3$ | $C_5H_{11}$ | — |
| 1000 | $CH_3$ | $CH_2$ | H | $CH_3$ | $CH_3$ | $OCH_3$ | H | $C_2H_5$ | $C_4H_9$ | — |
| 1001 | $CH_3$ | $CH_2$ | H | $CH_3$ | $CH_3$ | $OCH_3$ | H | $C_3H_7$ | $C_3H_7$ | — |
| 1002 | $CH_3$ | $CH_2$ | H | $CH_3$ | $CH_3$ | $OCH_3$ | H | $C_2H_5$ | $C_2H_5$ | — |
| 1003 | $CH_3$ | $CH_2$ | H | $CH_3$ | $OCH_3$ | $OCH_3$ | H | H | 4-$CH_3O$—$C_6H_4$ | oil |
| 1004 | $CH_3$ | $CH_2$ | H | $CH_3$ | $OCH_3$ | $OCH_3$ | H | c-$C_3H_5$ | c-$C_3H_5$ | 138–140 |
| 1005 | $CH_3$ | $CH_2$ | H | $CH_3$ | $OCH_3$ | $OCH_3$ | H | $C_2H_5$ | c-$C_3H_5$ | — |
| 1006 | $CH_3$ | $CH_2$ | H | $CH_3$ | $OCH_3$ | $OCH_3$ | H | $CH_3$ | c-$C_3H_5$ | — |
| 1007 | $CH_3$ | $CH_2$ | H | $CH_3$ | $OCH_3$ | $OCH_3$ | H | $CH_3$ | $C_3H_7$ | — |
| 1008 | $CH_3$ | $CH_2$ | H | $CH_3$ | $OCH_3$ | $OCH_3$ | H | $CH_3$ | $C_4H_9$ | — |
| 1009 | $CH_3$ | $CH_2$ | H | $CH_3$ | $OCH_3$ | $OCH_3$ | H | $CH_3$ | $C_5H_{11}$ | — |
| 1010 | $CH_3$ | $CH_2$ | H | $CH_3$ | $OCH_3$ | $OCH_3$ | H | $C_2H_5$ | $C_4H_9$ | — |
| 1011 | $CH_3$ | $CH_2$ | H | $CH_3$ | $OCH_3$ | $OCH_3$ | H | $C_3H_7$ | $C_3H_7$ | — |
| 1012 | $CH_3$ | $CH_2$ | H | $CH_3$ | $OCH_3$ | $OCH_3$ | H | $C_2H_5$ | $C_2H_5$ | oil |
| 1013 | $CH_3$ | $CH_2$ | H | Cl | $OCH_3$ | $OCH_3$ | H | H | 4-$CH_3O$—$C_6H_4$ | — |
| 1014 | $CH_3$ | $CH_2$ | H | Cl | $OCH_3$ | $OCH_3$ | H | c-$C_3H_5$ | c-$C_3H_5$ | — |
| 1015 | $CH_3$ | $CH_2$ | H | Cl | $OCH_3$ | $OCH_3$ | H | $C_2H_5$ | c-$C_3H_5$ | — |
| 1016 | $CH_3$ | $CH_2$ | H | Cl | $OCH_3$ | $OCH_3$ | H | $CH_3$ | c-$C_3H_5$ | — |
| 1017 | $CH_3$ | $CH_2$ | H | Cl | $OCH_3$ | $OCH_3$ | H | $CH_3$ | $C_3H_7$ | — |
| 1018 | $CH_3$ | $CH_2$ | H | Cl | $OCH_3$ | $OCH_3$ | H | $CH_3$ | $C_4H_9$ | — |
| 1019 | $CH_3$ | $CH_2$ | H | Cl | $OCH_3$ | $OCH_3$ | H | $CH_3$ | $C_5H_{11}$ | — |
| 1020 | $CH_3$ | $CH_2$ | H | Cl | $OCH_3$ | $OCH_3$ | H | $C_2H_5$ | $C_4H_9$ | — |
| 1021 | $CH_3$ | $CH_2$ | H | Cl | $OCH_3$ | $OCH_3$ | H | $C_3H_7$ | $C_3H_7$ | — |
| 1022 | $CH_3$ | $CH_2$ | H | Cl | $OCH_3$ | $OCH_3$ | H | $C_2H_5$ | $C_2H_5$ | — |
| 1023 | $CH_3$ | $CH_2$ | H | Cl | $OCF_3$ | H | H | H | 4-$CH_3O$—$C_6H_4$ | oil |
| 1024 | $CH_3$ | $CH_2$ | H | Cl | $OCF_3$ | H | H | c-$C_3H_5$ | c-$C_3H_5$ | 119–120 |
| 1025 | $CH_3$ | $CH_2$ | H | Cl | $OCF_3$ | H | H | $C_2H_5$ | c-$C_3H_5$ | 103–104 |
| 1026 | $CH_3$ | $CH_2$ | H | Cl | $OCF_3$ | H | H | $CH_3$ | c-$C_3H_5$ | — |
| 1027 | $CH_3$ | $CH_2$ | H | Cl | $OCF_3$ | H | H | $CH_3$ | $C_3H_7$ | oil |
| 1028 | $CH_3$ | $CH_2$ | H | Cl | $OCF_3$ | H | H | $CH_3$ | $C_4H_9$ | oil |
| 1029 | $CH_3$ | $CH_2$ | H | Cl | $OCF_3$ | H | H | $CH_3$ | $C_5H_{11}$ | — |
| 1030 | $CH_3$ | $CH_2$ | H | Cl | $OCF_3$ | H | H | $C_2H_5$ | $C_4H_9$ | — |
| 1031 | $CH_3$ | $CH_2$ | H | Cl | $OCF_3$ | H | H | $C_3H_7$ | $C_3H_7$ | — |
| 1032 | $CH_3$ | $CH_2$ | H | Cl | $OCF_3$ | H | H | $C_2H_5$ | $C_2H_5$ | oil |
| 1033 | $CH_3$ | $CH_2$ | H | Cl | $SCF_3$ | H | H | H | 4-$CH_3O$—$C_6H_4$ | — |
| 1034 | $CH_3$ | $CH_2$ | H | Cl | $SCF_3$ | H | H | c-$C_3H_5$ | c-$C_3H_5$ | — |
| 1035 | $CH_3$ | $CH_2$ | H | Cl | $SCF_3$ | H | H | $C_2H_5$ | c-$C_3H_5$ | — |
| 1036 | $CH_3$ | $CH_2$ | H | Cl | $SCF_3$ | H | H | $CH_3$ | c-$C_3H_5$ | — |
| 1037 | $CH_3$ | $CH_2$ | H | Cl | $SCF_3$ | H | H | $CH_3$ | $C_3H_7$ | — |
| 1038 | $CH_3$ | $CH_2$ | H | Cl | $SCF_3$ | H | H | $CH_3$ | $C_4H_9$ | — |
| 1039 | $CH_3$ | $CH_2$ | H | Cl | $SCF_3$ | H | H | $CH_3$ | $C_5H_{11}$ | — |
| 1040 | $CH_3$ | $CH_2$ | H | Cl | $SCF_3$ | H | H | $C_2H_5$ | $C_4H_9$ | — |
| 1041 | $CH_3$ | $CH_2$ | H | Cl | $SCF_3$ | H | H | $C_3H_7$ | $C_3H_7$ | — |
| 1042 | $CH_3$ | $CH_2$ | H | Cl | $SCF_3$ | H | H | $C_2H_5$ | $C_2H_5$ | — |
| 1044 | $CH_3$ | $CH_2$ | H | Cl | $CF_3$ | H | H | H | 4-$CH_3O$—$C_6H_4$ | 105–107 |
| 1045 | $CH_3$ | $CH_2$ | H | $CF_3$ | Q3 | H | H | c-$C_3H_5$ | c-$C_3H_5$ | 168–169 |
| 1046 | $CH_3$ | $CH_2$ | H | Cl | Q3 | H | H | c-$C_3H_5$ | c-$C_3H_5$ | 130–132 |
| 1047 | $CH_3$ | $CH_2$ | H | $CF_3$ | $SCH_3$ | H | H | c-$C_3H_5$ | c-$C_3H_5$ | — |
| 1048 | $CH_3$ | $CH_2$ | H | Cl | $SCH_3$ | H | H | c-$C_3H_5$ | c-$C_3H_5$ | — |
| 1049 | $CH_3$ | $CH_2$ | H | $CF_3$ | $COCH_3$ | H | H | c-$C_3H_5$ | c-$C_3H_5$ | — |
| 1050 | $CH_3$ | $CH_2$ | H | Cl | $COCH_3$ | H | H | c-$C_3H_5$ | c-$C_3H_5$ | — |
| 1051 | $CH_3$ | $CH_2$ | H | $CF_3$ | $CHCH_2$ | H | H | c-$C_3H_5$ | c-$C_3H_5$ | — |
| 1052 | $CH_3$ | $CH_2$ | H | Cl | $CHCH_2$ | H | H | c-$C_3H_5$ | c-$C_3H_5$ | — |
| 1053 | $CH_3$ | $CH_2$ | H | Cl | $CH_3$ | H | H | H | 4-$CH_3O$—$C_6H_4$ | 113–115 |
| 1054 | $CH_3$ | $CH_2$ | H | $OCH_3$ | $OCH_3$ | H | H | H | 4-$CH_3O$—$C_6H_4$ | — |

TABLE 1-continued

| | | | | | | | | | | |
|---|---|---|---|---|---|---|---|---|---|---|
| 1055 | CH$_3$ | CH$_2$ | H | OCH$_3$ | OCH$_3$ | H | H | c-C$_3$H$_5$ | c-C$_3$H$_5$ | 128–130 |
| 1056 | CH$_3$ | CH$_2$ | H | OCH$_3$ | OCH$_3$ | H | H | C$_2$H$_5$ | c-C$_3$H$_5$ | — |
| 1057 | CH$_3$ | CH$_2$ | H | OCH$_3$ | OCH$_3$ | H | H | CH$_3$ | c-C$_3$H$_5$ | — |
| 1058 | CH$_3$ | CH$_2$ | H | OCH$_3$ | OCH$_3$ | H | H | CH$_3$ | C$_3$H$_7$ | — |
| 1059 | CH$_3$ | CH$_2$ | H | OCH$_3$ | OCH$_3$ | H | H | CH$_3$ | C$_4$H$_9$ | — |
| 1060 | CH$_3$ | CH$_2$ | H | OCH$_3$ | OCH$_3$ | H | H | CH$_3$ | C$_5$H$_{11}$ | — |
| 1061 | CH$_3$ | CH$_2$ | H | OCH$_3$ | OCH$_3$ | H | H | C$_2$H$_5$ | C$_4$H$_9$ | — |
| 1062 | CH$_3$ | CH$_2$ | H | OCH$_3$ | OCH$_3$ | H | H | C$_3$H$_7$ | C$_3$H$_7$ | — |
| 1063 | CH$_3$ | CH$_2$ | H | OCH$_3$ | OCH$_3$ | H | H | C$_2$H$_5$ | C$_2$H$_5$ | — |
| 1064 | CH$_3$ | CH$_2$ | H | OCH$_3$ | CF$_3$ | H | H | H | 4-CH$_3$O—C$_6$H$_4$ | — |
| 1065 | CH$_3$ | CH$_2$ | H | OCH$_3$ | CF$_3$ | H | H | c-C$_3$H$_5$ | c-C$_3$H$_5$ | 158–159 |
| 1066 | CH$_3$ | CH$_2$ | H | OCH$_3$ | CF$_3$ | H | H | C$_2$H$_5$ | c-C$_3$H$_5$ | — |
| 1067 | CH$_3$ | CH$_2$ | H | OCH$_3$ | CF$_3$ | H | H | CH$_3$ | c-C$_3$H$_5$ | — |
| 1068 | CH$_3$ | CH$_2$ | H | OCH$_3$ | CF$_3$ | H | H | CH$_3$ | C$_3$H$_7$ | — |
| 1069 | CH$_3$ | CH$_2$ | H | OCH$_3$ | CF$_3$ | H | H | CH$_3$ | C$_4$H$_9$ | — |
| 1070 | CH$_3$ | CH$_2$ | H | OCH$_3$ | CF$_3$ | H | H | CH$_3$ | C$_5$H$_{11}$ | — |
| 1071 | CH$_3$ | CH$_2$ | H | OCH$_3$ | CF$_3$ | H | H | C$_2$H$_5$ | C$_4$H$_9$ | — |
| 1072 | CH$_3$ | CH$_2$ | H | OCH$_3$ | CF$_3$ | H | H | C$_3$H$_7$ | C$_3$H$_7$ | — |
| 1073 | CH$_3$ | CH$_2$ | H | OCH$_3$ | CF$_3$ | H | H | C$_2$H$_5$ | C$_2$H$_5$ | — |
| 1074 | CH$_3$ | CH$_2$ | H | CF$_3$ | OCH$_3$ | H | H | H | 4-CH$_3$O—C$_6$H$_4$ | oil |
| 1075 | CH$_3$ | CH$_2$ | H | CF$_3$ | OCH$_3$ | H | H | c-C$_3$H$_5$ | c-C$_3$H$_5$ | 129–130 |
| 1076 | CH$_3$ | CH$_2$ | H | CF$_3$ | OCH$_3$ | H | H | C$_2$H$_5$ | c-C$_3$H$_5$ | 119–122 |
| 1077 | CH$_3$ | CH$_2$ | H | CF$_3$ | OCH$_3$ | H | H | CH$_3$ | c-C$_3$H$_5$ | — |
| 1078 | CH$_3$ | CH$_2$ | H | CF$_3$ | OCH$_3$ | H | H | CH$_3$ | C$_3$H$_7$ | oil |
| 1079 | CH$_3$ | CH$_2$ | H | CF$_3$ | OCH$_3$ | H | H | CH$_3$ | C$_4$H$_9$ | oil |
| 1080 | CH$_3$ | CH$_2$ | H | CF$_3$ | OCH$_3$ | H | H | CH$_3$ | C$_5$H$_{11}$ | — |
| 1081 | CH$_3$ | CH$_2$ | H | CF$_3$ | OCH$_3$ | H | H | C$_2$H$_5$ | C$_4$H$_9$ | — |
| 1082 | CH$_3$ | CH$_2$ | H | CF$_3$ | OCH$_3$ | H | H | C$_3$H$_7$ | C$_3$H$_7$ | oil |
| 1083 | CH$_3$ | CH$_2$ | H | CF$_3$ | OCH$_3$ | H | H | C$_2$H$_5$ | C$_2$H$_5$ | 77–78 |
| 1084 | CH$_3$ | CH$_2$ | H | OCH$_3$ | Cl | OCH$_3$ | H | H | 4-CH$_3$O—C$_6$H$_4$ | — |
| 1085 | CH$_3$ | CH$_2$ | H | OCH$_3$ | Cl | OCH$_3$ | H | c-C$_3$H$_5$ | c-C$_3$H$_5$ | — |
| 1086 | CH$_3$ | CH$_2$ | H | OCH$_3$ | Cl | OCH$_3$ | H | C$_2$H$_5$ | c-C$_3$H$_5$ | — |
| 1087 | CH$_3$ | CH$_2$ | H | OCH$_3$ | Cl | OCH$_3$ | H | CH$_3$ | c-C$_3$H$_5$ | — |
| 1088 | CH$_3$ | CH$_2$ | H | OCH$_3$ | Cl | OCH$_3$ | H | CH$_3$ | C$_3$H$_7$ | — |
| 1089 | CH$_3$ | CH$_2$ | H | OCH$_3$ | Cl | OCH$_3$ | H | CH$_3$ | C$_4$H$_9$ | — |
| 1090 | CH$_3$ | CH$_2$ | H | OCH$_3$ | Cl | OCH$_3$ | H | CH$_3$ | C$_5$H$_{11}$ | — |
| 1091 | CH$_3$ | CH$_2$ | H | OCH$_3$ | Cl | OCH$_3$ | H | C$_2$H$_5$ | C$_4$H$_9$ | — |
| 1092 | CH$_3$ | CH$_2$ | H | OCH$_3$ | Cl | OCH$_3$ | H | C$_3$H$_7$ | C$_3$H$_7$ | — |
| 1093 | CH$_3$ | CH$_2$ | H | OCH$_3$ | Cl | OCH$_3$ | H | C$_2$H$_5$ | C$_2$H$_5$ | — |
| 1094 | CH$_3$ | CH$_2$ | H | OCH$_3$ | CH$_3$ | OCH$_3$ | H | H | 4-CH$_3$O—C$_6$H$_4$ | — |
| 1095 | CH$_3$ | CH$_2$ | H | OCH$_3$ | CH$_3$ | OCH$_3$ | H | c-C$_3$H$_5$ | c-C$_3$H$_5$ | — |
| 1096 | CH$_3$ | CH$_2$ | H | OCH$_3$ | CH$_3$ | OCH$_3$ | H | C$_2$H$_5$ | c-C$_3$H$_5$ | — |
| 1097 | CH$_3$ | CH$_2$ | H | OCH$_3$ | CH$_3$ | OCH$_3$ | H | CH$_3$ | c-C$_3$H$_5$ | — |
| 1098 | CH$_3$ | CH$_2$ | H | OCH$_3$ | CH$_3$ | OCH$_3$ | H | CH$_3$ | C$_3$H$_7$ | — |
| 1099 | CH$_3$ | CH$_2$ | H | OCH$_3$ | CH$_3$ | OCH$_3$ | H | CH$_3$ | C$_4$H$_9$ | — |
| 1100 | CH$_3$ | CH$_2$ | H | OCH$_3$ | CH$_3$ | OCH$_3$ | H | CH$_3$ | C$_5$H$_{11}$ | — |
| 1101 | CH$_3$ | CH$_2$ | H | OCH$_3$ | CH$_3$ | OCH$_3$ | H | C$_2$H$_5$ | C$_4$H$_9$ | — |
| 1102 | CH$_3$ | CH$_2$ | H | OCH$_3$ | CH$_3$ | OCH$_3$ | H | C$_3$H$_7$ | C$_3$H$_7$ | — |
| 1103 | CH$_3$ | CH$_2$ | H | OCH$_3$ | CH$_3$ | OCH$_3$ | H | C$_2$H$_5$ | C$_2$H$_5$ | — |
| 1104 | CH$_3$ | CH$_2$ | H | OCH$_3$ | CH$_3$ | OCH$_3$ | H | H | 4-CH$_3$O—C$_6$H$_4$ | — |
| 1105 | CH$_3$ | CH$_2$ | H | OCH$_3$ | CH$_3$ | OCH$_3$ | H | c-C$_3$H$_5$ | c-C$_3$H$_5$ | — |
| 1106 | CH$_3$ | CH$_2$ | H | OCH$_3$ | CH$_3$ | OCH$_3$ | H | C$_2$H$_5$ | c-C$_3$H$_5$ | — |
| 1107 | CH$_3$ | CH$_2$ | H | OCH$_3$ | CH$_3$ | OCH$_3$ | H | CH$_3$ | c-C$_3$H$_5$ | — |
| 1108 | CH$_3$ | CH$_2$ | H | OCH$_3$ | CF$_3$ | OCH$_3$ | H | CH$_3$ | C$_3$H$_7$ | — |
| 1109 | CH$_3$ | CH$_2$ | H | OCH$_3$ | CF$_3$ | OCH$_3$ | H | CH$_3$ | C$_4$H$_9$ | — |
| 1110 | CH$_3$ | CH$_2$ | H | OCH$_3$ | CF$_3$ | OCH$_3$ | H | CH$_3$ | C$_5$H$_{11}$ | — |
| 1111 | CH$_3$ | CH$_2$ | H | OCH$_3$ | CF$_3$ | OCH$_3$ | H | C$_2$H$_5$ | C$_4$H$_9$ | — |
| 1112 | CH$_3$ | CH$_2$ | H | OCH$_3$ | CF$_3$ | OCH$_3$ | H | C$_3$H$_7$ | C$_3$H$_7$ | — |
| 1113 | CH$_3$ | CH$_2$ | H | OCH$_3$ | CF$_3$ | OCH$_3$ | H | C$_2$H$_5$ | C$_2$H$_5$ | — |
| 1114 | CH$_3$ | CH$_2$ | H | OCH$_3$ | CN | OCH$_3$ | H | H | 4-CH$_3$O—C$_6$H$_4$ | — |
| 1115 | CH$_3$ | CH$_2$ | H | OCH$_3$ | CN | OCH$_3$ | H | c-C$_3$H$_5$ | c-C$_3$H$_5$ | — |
| 1116 | CH$_3$ | CH$_2$ | H | OCH$_3$ | CN | OCH$_3$ | H | C$_2$H$_5$ | c-C$_3$H$_5$ | — |
| 1117 | CH$_3$ | CH$_2$ | H | OCH$_3$ | CN | OCH$_3$ | H | CH$_3$ | c-C$_3$H$_5$ | — |
| 1118 | CH$_3$ | CH$_2$ | H | OCH$_3$ | CN | OCH$_3$ | H | CH$_3$ | C$_3$H$_7$ | — |
| 1119 | CH$_3$ | CH$_2$ | H | OCH$_3$ | CN | OCH$_3$ | H | CH$_3$ | C$_4$H$_9$ | — |
| 1120 | CH$_3$ | CH$_2$ | H | OCH$_3$ | CN | OCH$_3$ | H | CH$_3$ | C$_5$H$_{11}$ | — |
| 1121 | CH$_3$ | CH$_2$ | H | OCH$_3$ | CN | OCH$_3$ | H | C$_2$H$_5$ | C$_4$H$_9$ | — |
| 1122 | CH$_3$ | CH$_2$ | H | OCH$_3$ | CN | OCH$_3$ | H | C$_3$H$_7$ | C$_3$H$_7$ | — |
| 1123 | CH$_3$ | CH$_2$ | H | OCH$_3$ | CN | OCH$_3$ | H | C$_2$H$_5$ | C$_2$H$_5$ | — |
| 1124 | CH$_3$ | CH$_2$ | H | OCH$_3$ | OCH$_3$ | OCH$_3$ | H | H | 4-CH$_3$O—C$_6$H$_4$ | — |
| 1125 | CH$_3$ | CH$_2$ | H | OCH$_3$ | OCH$_3$ | OCH$_3$ | H | c-C$_3$H$_5$ | c-C$_3$H$_5$ | — |
| 1126 | CH$_3$ | CH$_2$ | H | OCH$_3$ | OCH$_3$ | OCH$_3$ | H | C$_2$H$_5$ | c-C$_3$H$_5$ | — |
| 1127 | CH$_3$ | CH$_2$ | H | OCH$_3$ | OCH$_3$ | OCH$_3$ | H | CH$_3$ | c-C$_3$H$_5$ | — |
| 1128 | CH$_3$ | CH$_2$ | H | OCH$_3$ | OCH$_3$ | OCH$_3$ | H | CH$_3$ | C$_3$H$_7$ | — |
| 1129 | CH$_3$ | CH$_2$ | H | OCH$_3$ | OCH$_3$ | OCH$_3$ | H | CH$_3$ | C$_4$H$_9$ | — |
| 1130 | CH$_3$ | CH$_2$ | H | OCH$_3$ | OCH$_3$ | OCH$_3$ | H | CH$_3$ | C$_5$H$_{11}$ | — |
| 1131 | CH$_3$ | CH$_2$ | H | OCH$_3$ | OCH$_3$ | OCH$_3$ | H | C$_2$H$_5$ | C$_4$H$_9$ | — |
| 1132 | CH$_3$ | CH$_2$ | H | OCH$_3$ | OCH$_3$ | OCH$_3$ | H | C$_3$H$_7$ | C$_3$H$_7$ | — |
| 1133 | CH$_3$ | CH$_2$ | H | OCH$_3$ | OCH$_3$ | OCH$_3$ | H | C$_2$H$_5$ | C$_2$H$_5$ | — |

TABLE 1-continued

| | | | | | | | | | | |
|---|---|---|---|---|---|---|---|---|---|---|
| 1134 | CH₃ | CH₂ | H | CH₃ | CH₃ | H | CH₃ | C₂H₅ | CH₂OSO₂CH₃ | 110–111 |
| 1135 | CH₃ | CH₂ | H | CH₃ | CH₃ | H | CH₃ | C₂H₅ | CH₂SCH₃ | 134–135 |
| 1136 | CH₃ | CH₂ | H | CH₃ | CH₃ | H | CH₃ | C₂H₅ | CH₂Cl | 140–141 |
| 1137 | CH₃ | CH₂ | H | CH₃ | CH₃ | H | CH₃ | C₂H₅ | CH₂CN | 142–147 |
| 1138 | CH₃ | CH₂ | H | Cl | Cl | H | H | C₂H₅ | CH₂OSO₂CH₃ | — |
| 1139 | CH₃ | CH₂ | H | Cl | Cl | H | H | C₂H₅ | CH₂SCH₃ | — |
| 1140 | CH₃ | CH₂ | H | Cl | Cl | H | H | C₂H₅ | CH₂Cl | — |
| 1141 | CH₃ | CH₂ | H | Cl | Cl | H | H | C₂H₅ | CH₂CN | — |
| 1142 | CH₃ | CH₂ | H | Cl | CF₃ | H | H | C₂H₅ | CH₂OSO₂CH₃ | — |
| 1143 | CH₃ | CH₂ | H | Cl | CF₃ | H | H | C₂H₅ | CH₂SCH₃ | — |
| 1144 | CH₃ | CH₂ | H | Cl | CF₃ | H | H | C₂H₅ | CH₂Cl | — |
| 1145 | CH₃ | CH₂ | H | Cl | CF₃ | H | H | C₂H₅ | CH₂CN | — |
| 1146 | CH₃ | CH₂ | H | Cl | OCH₃ | H | H | C₂H₅ | CH₂OSO₂CH₃ | — |
| 1147 | CH₃ | CH₂ | H | Cl | OCH₃ | H | H | C₂H₅ | CH₂SCH₃ | — |
| 1148 | CH₃ | CH₂ | H | Cl | OCH₃ | H | H | C₂H₅ | CH₂Cl | — |
| 1149 | CH₃ | CH₂ | H | Cl | OCH₃ | H | H | C₂H₅ | CH₂CN | — |
| 1150 | CH₃ | CH₂ | H | CF₃ | OCH₃ | H | H | C₃H₇ | c-C₃H₅ | oil |
| 1151 | CH₃ | CH₂ | H | Cl | CF₃ | H | H | CH₃ | C₃H₇ | 97–98 |
| 1152 | CH₃ | CH₂ | H | CH₃ | OCH₃ | CH₃ | H | C₆H₅ | c-C₃H₅ | — |
| 1153 | CH₃ | CH₂ | H | Cl | CF₃ | H | H | C₆H₅ | c-C₃H₅ | oil |
| 1154 | CH₃ | CH₂ | H | Cl | OCH₃ | H | H | C₆H₅ | c-C₃H₅ | — |
| 1155 | CH₃ | CH₂ | H | Cl | OCF₃ | H | H | C₆H₅ | c-C₃H₅ | oil |
| 1156 | CH₃ | CH₂ | H | Cl | CH₃ | H | H | C₆H₅ | c-C₃H₅ | 119–120 |
| 1157 | CH₃ | CH₂ | H | CF₃ | OCH₃ | H | H | C₆H₅ | c-C₃H₅ | oil |
| 1158 | CH₃ | CH₂ | H | Cl | Cl | H | CH₃ | C₆H₅ | c-C₃H₅ | oil |
| 1159 | CH₃ | CH₂ | H | CH₃ | OCH₃ | Cl | H | C₆H₅ | c-C₃H₅ | — |
| 1160 | CH₃ | CH₂ | H | CH₃ | OCH₃ | F | H | C₆H₅ | c-C₃H₅ | — |
| 1161 | CH₃ | CH₂ | H | Cl | Cl | H | H | 4-F—C₆H₄ | c-C₃H₅ | oil |
| 1162 | CH₃ | CH₂ | H | CH₃ | OCH₃ | CH₃ | H | 4-F—C₆H₄ | c-C₃H₅ | — |
| 1163 | CH₃ | CH₂ | H | Cl | CF₃ | H | H | 4-F—C₆H₄ | c-C₃H₅ | oil |
| 1164 | CH₃ | CH₂ | H | Cl | OCH₃ | H | H | 4-F—C₆H₄ | c-C₃H₅ | — |
| 1165 | CH₃ | CH₂ | H | Cl | OCF₃ | H | H | 4-F—C₆H₄ | c-C₃H₅ | — |
| 1166 | CH₃ | CH₂ | H | Cl | CH₃ | H | H | 4-F—C₆H₄ | c-C₃H₅ | — |
| 1167 | CH₃ | CH₂ | H | CF₃ | OCH₃ | H | H | 4-F—C₆H₄ | c-C₃H₅ | — |
| 1168 | CH₃ | CH₂ | H | Cl | Cl | H | CH₃ | 4-F—C₆H₄ | c-C₃H₅ | — |
| 1169 | CH₃ | CH₂ | H | CH₃ | OCH₃ | Cl | H | 4-F—C₆H₄ | c-C₃H₅ | — |
| 1170 | CH₃ | CH₂ | H | CH₃ | OCH₃ | F | H | 4-F—C₆H₄ | c-C₃H₅ | — |
| 1171 | CH₃ | CH₂ | H | Cl | Cl | H | H | CH₃ | c-C₄H₇ | 109–110 |
| 1172 | CH₃ | CH₂ | H | CH₃ | OCH₃ | CH₃ | H | CH₃ | c-C₄H₇ | — |
| 1173 | CH₃ | CH₂ | H | Cl | CF₃ | H | H | CH₃ | c-C₄H₇ | 136–137 |
| 1174 | CH₃ | CH₂ | H | Cl | OCH₃ | H | H | CH₃ | c-C₄H₇ | — |
| 1175 | CH₃ | CH₂ | H | Cl | OCF₃ | H | H | CH₃ | c-C₄H₇ | — |
| 1176 | CH₃ | CH₂ | H | Cl | CH₃ | H | H | CH₃ | c-C₄H₇ | — |
| 1177 | CH₃ | CH₂ | H | CF₃ | OCH₃ | H | H | CH₃ | c-C₄H₇ | — |
| 1178 | CH₃ | CH₂ | H | Cl | Cl | H | CH₃ | CH₃ | c-C₄H₇ | — |
| 1179 | CH₃ | CH₂ | H | CH₃ | OCH₃ | Cl | H | CH₃ | c-C₄H₇ | — |
| 1180 | CH₃ | CH₂ | H | CH₃ | OCH₃ | F | H | CH₃ | c-C₄H₇ | — |
| 1181 | CH₃ | CH₂ | H | Cl | Cl | H | H | C₂H₅ | c-C₄H₇ | — |
| 1182 | CH₃ | CH₂ | H | CH₃ | OCH₃ | CH₃ | H | C₂H₅ | c-C₄H₇ | — |
| 1183 | CH₃ | CH₂ | H | Cl | CF₃ | H | H | C₂H₅ | c-C₄H₇ | — |
| 1184 | CH₃ | CH₂ | H | Cl | OCH₃ | H | H | C₂H₅ | c-C₄H₇ | — |
| 1185 | CH₃ | CH₂ | H | Cl | OCF₃ | H | H | C₂H₅ | c-C₄H₇ | — |
| 1186 | CH₃ | CH₂ | H | Cl | CH₃ | H | H | C₂H₅ | c-C₄H₇ | — |
| 1187 | CH₃ | CH₂ | H | CF₃ | OCH₃ | H | H | C₂H₅ | c-C₄H₇ | — |
| 1188 | CH₃ | CH₂ | H | Cl | Cl | H | CH₃ | C₂H₅ | c-C₄H₇ | — |
| 1189 | CH₃ | CH₂ | H | CH₃ | OCH₃ | Cl | H | C₂H₅ | c-C₄H₇ | — |
| 1190 | CH₃ | CH₂ | H | CH₃ | OCH₃ | F | H | C₂H₅ | c-C₄H₇ | — |
| 1191 | CH₃ | CH₂ | H | Cl | Cl | H | H | C₃H₇ | c-C₄H₇ | — |
| 1192 | CH₃ | CH₂ | H | CH₃ | OCH₃ | CH₃ | H | C₃H₇ | c-C₄H₇ | — |
| 1193 | CH₃ | CH₂ | H | Cl | CF₃ | H | H | C₃H₇ | c-C₄H₇ | — |
| 1194 | CH₃ | CH₂ | H | Cl | OCH₃ | H | H | C₃H₇ | c-C₄H₇ | — |
| 1195 | CH₃ | CH₂ | H | Cl | OCF₃ | H | H | C₃H₇ | c-C₄H₇ | — |
| 1196 | CH₃ | CH₂ | H | Cl | CH₃ | H | H | C₃H₇ | c-C₄H₇ | — |
| 1197 | CH₃ | CH₂ | H | CF₃ | OCH₃ | H | H | C₃H₇ | c-C₄H₇ | — |
| 1198 | CH₃ | CH₂ | H | Cl | Cl | H | CH₃ | C₃H₇ | c-C₄H₇ | — |
| 1199 | CH₃ | CH₂ | H | CH₃ | OCH₃ | Cl | H | C₃H₇ | c-C₄H₇ | — |
| 1200 | CH₃ | CH₂ | H | CH₃ | OCH₃ | F | H | C₃H₇ | c-C₄H₇ | — |
| 1201 | CH₃ | CH₂ | H | Cl | Cl | H | H | c-C₄H₇ | c-C₄H₇ | — |
| 1202 | CH₃ | CH₂ | H | CH₃ | OCH₃ | CH₃ | H | c-C₄H₇ | c-C₄H₇ | — |
| 1203 | CH₃ | CH₂ | H | Cl | CF₃ | H | H | c-C₄H₇ | c-C₄H₇ | — |
| 1204 | CH₃ | CH₂ | H | Cl | OCH₃ | H | H | c-C₄H₇ | c-C₄H₇ | — |
| 1205 | CH₃ | CH₂ | H | Cl | OCF₃ | H | H | c-C₄H₇ | c-C₄H₇ | — |
| 1206 | CH₃ | CH₂ | H | Cl | CH₃ | H | H | c-C₄H₇ | c-C₄H₇ | — |
| 1207 | CH₃ | CH₂ | H | CF₃ | OCH₃ | H | H | c-C₄H₇ | c-C₄H₇ | — |
| 1208 | CH₃ | CH₂ | H | Cl | Cl | H | CH₃ | c-C₄H₇ | c-C₄H₇ | — |
| 1209 | CH₃ | CH₂ | H | CH₃ | OCH₃ | Cl | H | c-C₄H₇ | c-C₄H₇ | — |
| 1210 | CH₃ | CH₂ | H | CH₃ | OCH₃ | F | H | c-C₄H₇ | c-C₄H₇ | — |
| 1211 | CH₃ | S | H | SCH₃ | Cl | H | Cl | C₂H₅ | C₃H₇ | 63–65 |
| 1212 | CH₃ | CH₂ | H | OCH₃ | Cl | H | H | c-C₃H₅ | c-C₃H₅ | 152–154 |

TABLE 1-continued

| | | | | | | | | | | |
|---|---|---|---|---|---|---|---|---|---|---|
| 1213 | $CH_3$ | $CH_2$ | H | $OCH_3$ | Cl | H | H | $C_2H_5$ | c-$C_3H_5$ | — |
| 1214 | $CH_3$ | $CH_2$ | H | $OCH_3$ | Cl | H | H | $C_3H_7$ | c-$C_3H_5$ | — |
| 1215 | $CH_3$ | $CH_2$ | H | $OCH_3$ | Cl | H | H | $CH_3$ | c-$C_3H_7$ | — |
| 1216 | $CH_3$ | $CH_2$ | H | $OCH_3$ | Cl | H | H | $CH_3$ | $C_3H_7$ | — |
| 1217 | $CH_3$ | $CH_2$ | H | $OCH_3$ | Cl | H | H | $C_2H_5$ | $C_3H_7$ | — |
| 1218 | $CH_3$ | $CH_2$ | H | $OCH_3$ | Cl | H | H | $C_2H_5$ | $C_2H_5$ | — |
| 1219 | $CH_3$ | $CH_2$ | H | $OCH_3$ | Cl | H | H | $C_3H_7$ | $C_3H_7$ | — |
| 1220 | $CH_3$ | $CH_2$ | H | $OCH_3$ | Cl | H | H | $CH_3$ | $C_4H_9$ | — |
| 1221 | $CH_3$ | $CH_2$ | H | $OCH_3$ | Cl | H | H | H | 4-$CH_3O$—$C_6H_4$ | — |
| 1222 | $CH_3$ | $CH_2$ | H | $OCH_3$ | $CH_3$ | H | H | c-$C_3H_5$ | c-$C_3H_5$ | oil |
| 1223 | $CH_3$ | $CH_2$ | H | $OCH_3$ | $CH_3$ | H | H | $C_2H_5$ | c-$C_3H_5$ | — |
| 1224 | $CH_3$ | $CH_2$ | H | $OCH_3$ | $CH_3$ | H | H | $C_3H_7$ | c-$C_3H_5$ | — |
| 1225 | $CH_3$ | $CH_2$ | H | $OCH_3$ | $CH_3$ | H | H | $CH_3$ | c-$C_4H_7$ | — |
| 1226 | $CH_3$ | $CH_2$ | H | $OCH_3$ | $CH_3$ | H | H | $CH_3$ | $C_3H_7$ | — |
| 1227 | $CH_3$ | $CH_2$ | H | $OCH_3$ | $CH_3$ | H | H | $C_2H_5$ | $C_3H_7$ | — |
| 1228 | $CH_3$ | $CH_2$ | H | $OCH_3$ | $CH_3$ | H | H | $C_2H_5$ | $C_2H_5$ | — |
| 1229 | $CH_3$ | $CH_2$ | H | $OCH_3$ | $CH_3$ | H | H | $C_3H_7$ | $C_3H_7$ | — |
| 1230 | $CH_3$ | $CH_2$ | H | $OCH_3$ | $CH_3$ | H | H | $CH_3$ | $C_4H_9$ | — |
| 1231 | $CH_3$ | $CH_2$ | H | $OCH_3$ | $OCH_3$ | H | H | H | 4-$CH_3O$—$C_6H_4$ | — |
| 1232 | $CH_3$ | $CH_2$ | H | $OCH_3$ | $OCH_3$ | H | F | c-$C_3H_5$ | c-$C_3H_5$ | 176–178 |
| 1233 | $CH_3$ | $CH_2$ | H | $OCH_3$ | $OCH_3$ | H | F | $C_2H_5$ | c-$C_3H_5$ | — |
| 1234 | $CH_3$ | $CH_2$ | H | $OCH_3$ | $OCH_3$ | H | F | $C_3H_7$ | c-$C_3H_5$ | — |
| 1235 | $CH_3$ | $CH_2$ | H | $OCH_3$ | $OCH_3$ | H | F | $CH_3$ | c-$C_4H_7$ | — |
| 1236 | $CH_3$ | $CH_2$ | H | $OCH_3$ | $OCH_3$ | H | F | $CH_3$ | $C_3H_7$ | — |
| 1237 | $CH_3$ | $CH_2$ | H | $OCH_3$ | $OCH_3$ | H | F | $C_2H_5$ | $C_3H_7$ | — |
| 1238 | $CH_3$ | $CH_2$ | H | $OCH_3$ | $OCH_3$ | H | F | $C_2H_5$ | $C_2H_5$ | — |
| 1239 | $CH_3$ | $CH_2$ | H | $OCH_3$ | $OCH_3$ | H | F | $C_3H_7$ | $C_3H_7$ | — |
| 1240 | $CH_3$ | $CH_2$ | H | $OCH_3$ | $OCH_3$ | H | F | $CH_3$ | $C_4H_9$ | — |
| 1241 | $CH_3$ | $CH_2$ | H | $OCH_3$ | $OCH_3$ | H | F | H | 4-$CH_3O$—$C_6H_4$ | — |
| 1242 | $CH_3$ | $CH_2$ | H | $CF_3$ | F | H | H | c-$C_3H_5$ | c-$C_3H_5$ | — |
| 1243 | $CH_3$ | $CH_2$ | H | $CF_3$ | F | H | H | $C_2H_5$ | c-$C_3H_5$ | — |
| 1244 | $CH_3$ | $CH_2$ | H | $CF_3$ | F | H | H | $C_3H_7$ | c-$C_3H_5$ | 115–118 |
| 1245 | $CH_3$ | $CH_2$ | H | $CF_3$ | F | H | H | $CH_3$ | c-$C_4H_7$ | — |
| 1246 | $CH_3$ | $CH_2$ | H | $CF_3$ | F | H | H | $CH_3$ | $C_3H_7$ | — |
| 1247 | $CH_3$ | $CH_2$ | H | $CF_3$ | F | H | H | $C_2H_5$ | $C_3H_7$ | — |
| 1248 | $CH_3$ | $CH_2$ | H | $CF_3$ | F | H | H | $C_2H_5$ | $C_2H_5$ | — |
| 1249 | $CH_3$ | $CH_2$ | H | $CF_3$ | F | H | H | $C_3H_7$ | $C_3H_9$ | — |
| 1250 | $CH_3$ | $CH_2$ | H | $CF_3$ | F | H | H | $CH_3$ | $C_4H_9$ | — |
| 1251 | $CH_3$ | $CH_2$ | H | $CF_3$ | F | H | H | H | 4-$CH_3O$—$C_6H_4$ | 57–70 |
| 1252 | $CH_3$ | $CH_2$ | H | $CF_3$ | F | H | H | $BnOCH_2$ | $BnOCH_2$ | oil |
| 1253 | $CH_3$ | $CH_2$ | H | $CF_3$ | F | H | H | $CH_3$ | $C_6H_5$ | 119–120 |
| 1254 | $CH_3$ | $CH_2$ | H | $CF_3$ | F | H | H | $C_6H_5$ | $C_6H_5$ | 135–139 |
| 1255 | $CH_3$ | $CH_2$ | H | Cl | $OCF_3$ | H | H | $C_3H_7$ | c-$C_3H_5$ | oil |
| 1256 | $CH_3$ | $CH_2$ | H | Cl | $OCF_3$ | H | H | $C_2H_5$ | $C_3H_7$ | oil |
| 1257 | $CH_3$ | $CH_2$ | H | Cl | $CF_3$ | H | H | H | $CH_2$=CH—CH=CH | 83–85 |
| 1258 | $CH_3$ | $CH_2$ | H | $CF_3$ | OBn | H | H | c-$C_3H_5$ | c-$C_3H_5$ | 163–165 |
| 1259 | $CH_3$ | $CH_2$ | H | $CF_3$ | OH | H | H | c-$C_3H_5$ | c-$C_3H_5$ | 245–246 |
| 1260 | $CH_3$ | $CH_2$ | H | $CF_3$ | $OC_3H_7$ | H | H | c-$C_3H_5$ | c-$C_3H_5$ | 127–128 |
| 1261 | $CH_3$ | $CH_2$ | H | $CF_3$ | $OC_3H_7$ | H | H | $C_2H_5$ | c-$C_3H_5$ | — |
| 1262 | $CH_3$ | $CH_2$ | H | $CF_3$ | $OC_3H_7$ | H | H | $C_3H_7$ | c-$C_3H_5$ | — |
| 1263 | $CH_3$ | $CH_2$ | H | $CF_3$ | $OC_3H_7$ | H | H | $CH_3$ | c-$C_4H_7$ | — |
| 1264 | $CH_3$ | $CH_2$ | H | $CF_3$ | $OC_3H_7$ | H | H | $CH_3$ | $C_3H_7$ | — |
| 1265 | $CH_3$ | $CH_2$ | H | $CF_3$ | $OC_3H_7$ | H | H | $C_2H_5$ | $C_3H_7$ | — |
| 1266 | $CH_3$ | $CH_2$ | H | $CF_3$ | $OC_3H_7$ | H | H | $C_2H_5$ | $C_2H_5$ | — |
| 1267 | $CH_3$ | $CH_2$ | H | $CF_3$ | $OC_3H_7$ | H | H | $C_3H_7$ | $C_3H_7$ | — |
| 1268 | $CH_3$ | $CH_2$ | H | $CF_3$ | $OC_3H_7$ | H | H | $CH_3$ | $C_4H_9$ | — |
| 1269 | $CH_3$ | $CH_2$ | H | $CF_3$ | $OC_3H_7$ | H | H | H | 4-$CH_3O$—$C_6H_4$ | — |
| 1284 | $CH_3$ | $CH_2$ | H | $CH_3$ | OH | F | H | c-$C_3H_5$ | c-$C_3H_5$ | — |
| 1285 | $CH_3$ | $CH_2$ | H | $CH_3$ | OH | F | H | $C_2H_5$ | c-$C_3H_5$ | — |
| 1286 | $CH_3$ | $CH_2$ | H | $CH_3$ | OH | F | H | $C_3H_7$ | c-$C_3H_5$ | — |
| 1287 | $CH_3$ | $CH_2$ | H | $CH_3$ | OH | F | H | $CH_3$ | c-$C_4H_7$ | — |
| 1288 | $CH_3$ | $CH_2$ | H | $CH_3$ | OH | F | H | $CH_3$ | $C_3H_7$ | — |
| 1289 | $CH_3$ | $CH_2$ | H | $CH_3$ | OH | F | H | $C_2H_5$ | $C_3H_7$ | — |
| 1290 | $CH_3$ | $CH_2$ | H | $CH_3$ | OH | F | H | $C_2H_5$ | $C_2H_5$ | — |
| 1291 | $CH_3$ | $CH_2$ | H | $CH_3$ | OH | F | H | $C_3H_7$ | $C_3H_7$ | — |
| 1292 | $CH_3$ | $CH_2$ | H | $CH_3$ | OH | F | H | $CH_3$ | $C_4H_9$ | — |
| 1293 | $CH_3$ | $CH_2$ | H | $CH_3$ | OH | F | H | H | 4-$CH_3O$—$C_6H_4$ | — |
| 1294 | $CH_3$ | $CH_2$ | H | $CH_3$ | $OCH_3$ | $OCH_3$ | H | $CH_3$ | $CH_3$ | 101–102 |
| 1295 | $CH_3$ | $CH_2$ | H | $CH_3$ | $OCH_3$ | $OCH_3$ | H | $CH_3$ | $C_3H_5$ | oil |
| 1296 | $CH_3$ | $CH_2$ | H | Cl | Cl | H | H | $C_2H_5$ | 4-$CH_3O$—$C_6H_4$ | oil |
| 1297 | $CH_3$ | $CH_2$ | H | Cl | Cl | H | $CH_3$ | $C_2H_5$ | $C_2H_5$ | 133–135 |
| 1298 | $CH_3$ | $CH_2$ | H | Cl | Cl | H | $CH_3$ | $C_2H_5$ | $C_3H_7$ | 123–125 |
| 1299 | $CH_3$ | $CH_2$ | H | Cl | Cl | H | $CH_3$ | $C_3H_7$ | $C_3H_7$ | 125–127 |
| 1300 | $CH_3$ | $CH_2$ | H | Cl | Cl | H | $CH_3$ | $C_2H_5$ | c-$C_3H_5$ | 157–159 |
| 1301 | $CH_3$ | O | H | $CH_3$ | $OCH_3$ | $CH_3$ | H | c-$C_3H_5$ | c-$C_3H_5$ | — |
| 1302 | $CH_3$ | O | H | Cl | $CF_3$ | H | H | c-$C_3H_5$ | c-$C_3H_5$ | 149–150 |
| 1303 | $CH_3$ | O | H | Cl | $OCH_3$ | H | H | c-$C_3H_5$ | c-$C_3H_5$ | 124–125 |
| 1304 | $CH_3$ | O | H | Cl | $COF_3$ | H | H | c-$C_3H_5$ | c-$C_3H_5$ | — |
| 1305 | $CH_3$ | O | H | Cl | $CH_3$ | H | H | c-$C_3H_5$ | c-$C_3H_5$ | — |

TABLE 1-continued

| 1306 | CH$_3$ | O | H | CF$_3$ | OCH$_3$ | H | H | c-C$_3$H$_5$ | c-C$_3$H$_5$ | — |
|---|---|---|---|---|---|---|---|---|---|---|
| 1307 | CH$_3$ | O | H | Cl | Cl | H | CH$_3$ | c-C$_3$H$_5$ | c-C$_3$H$_5$ | — |
| 1308 | CH$_3$ | O | H | CH$_3$ | OCH$_3$ | Cl | H | c-C$_3$H$_5$ | c-C$_3$H$_5$ | — |
| 1309 | CH$_3$ | O | H | CH$_3$ | OCH$_3$ | F | H | c-C$_3$H$_5$ | c-C$_3$H$_5$ | — |
| 1310 | CH$_3$ | O | H | CH$_3$ | OCH$_3$ | CH$_3$ | H | CH$_3$ | C$_3$H$_7$ | — |
| 1311 | CH$_3$ | O | H | Cl | CF$_3$ | H | H | CH$_3$ | C$_3$H$_7$ | — |
| 1312 | CH$_3$ | O | H | Cl | OCH$_3$ | H | H | CH$_3$ | C$_3$H$_7$ | — |
| 1313 | CH$_3$ | O | H | Cl | OCF$_3$ | H | H | CH$_3$ | C$_3$H$_7$ | — |
| 1314 | CH$_3$ | O | H | Cl | CH$_3$ | H | H | CH$_3$ | C$_3$H$_7$ | — |
| 1315 | CH$_3$ | O | H | CF$_3$ | OCH$_3$ | H | H | CH$_3$ | C$_3$H$_7$ | — |
| 1316 | CH$_3$ | O | H | Cl | Cl | H | CH$_3$ | CH$_3$ | C$_3$H$_7$ | — |
| 1317 | CH$_3$ | O | H | CH$_3$ | OCH$_3$ | Cl | H | CH$_3$ | C$_3$H$_7$ | — |
| 1318 | CH$_3$ | O | H | CH$_3$ | OCH$_3$ | F | H | CH$_3$ | C$_3$H$_7$ | — |
| 1319 | CH$_3$ | CH$_2$ | H | Cl | Cl | H | H | C$_6$H$_5$ | C$_6$H$_5$ | oil |
| 1320 | CH$_3$ | CH$_2$ | H | Cl | Cl | H | H | C$_6$H$_5$ | CH$_3$ | oil |
| 1321 | CH$_3$ | CH$_2$ | H | Cl | Cl | H | H | c-C$_3$H$_5$ | 2-CH$_3$—C$_6$H$_4$ | oil |
| 1322 | CH$_3$ | CH$_2$ | H | Cl | Cl | H | H | C$_4$H$_9$ | CH(CH$_2$OH)$_2$ | oil |
| 1323 | CH$_3$ | CH$_2$ | H | Cl | Cl | H | H | C$_6$H$_5$ | CO$_2$C$_2$H$_5$ | oil |
| 1324 | CH$_3$ | CH$_2$ | H | Cl | Cl | H | H | C$_6$H$_5$ | CO$_2$H | oil |
| 1325 | CH$_3$ | CH$_2$ | H | Cl | Cl | H | H | C$_6$H$_5$ | CH$_2$OH | oil |
| 1326 | CH$_3$ | CH$_2$ | H | CH$_3$ | OCH$_3$ | Cl | H | H | 2-Cl—C$_6$H$_4$ | oil |
| 1327 | CH$_3$ | CH$_2$ | H | CH$_3$ | OCH$_3$ | Cl | H | H | 3-Cl—C$_6$H$_4$ | oil |
| 1328 | CH$_3$ | CH$_2$ | H | CH$_3$ | OCH$_3$ | Cl | H | H | 4-Cl—C$_6$H$_4$ | oil |
| 1329 | CH$_3$ | CH$_2$ | H | CH$_3$ | OCH$_3$ | Cl | H | H | 3-CH$_3$O—C$_6$H$_4$ | oil |
| 1330 | CH$_3$ | CH$_2$ | H | CH$_3$ | OCH$_3$ | Cl | H | H | 3-CN—C$_6$H$_4$ | oil |
| 1331 | CH$_3$ | CH$_2$ | H | CH$_3$ | OCH$_3$ | Cl | H | H | 4-CN—C$_6$H$_4$ | oil |
| 1332 | CH$_3$ | CH$_2$ | H | CH$_3$ | OCH$_3$ | Cl | H | H | 4-BnO—C$_6$H$_4$ | oil |
| 1333 | CH$_3$ | CH$_2$ | H | CH$_3$ | OCH$_3$ | Cl | H | H | 2,5-(CH$_3$O)—C$_6$H$_3$ | oil |
| 1334 | CH$_3$ | CH$_2$ | H | CH$_3$ | OCH$_3$ | Cl | H | H | 2-CH$_3$O—C$_6$H$_4$ | oil |
| 1335 | CH$_3$ | CH$_2$ | H | Cl | Cl | H | H | CN | c-C$_3$H$_5$ | oil |
| 1336 | CH$_3$ | CH$_2$ | H | Cl | Cl | H | H | CH$_3$ | CH$_2$OC$_2$H$_5$ | 96–97 |
| 1337 | CH$_3$ | CH$_2$ | H | Cl | Cl | H | H | H | CH(OH)CH$_2$OC$_6$H$_5$ | oil |
| 1338 | CH$_3$ | CH$_2$ | H | Cl | Cl | H | H | H | CH(OH)CH$_2$C$_6$H$_5$ | oil |
| 1339 | CH$_3$ | CH$_2$ | H | Cl | Cl | H | H | H | CH(OH)C$_3$H$_7$ | oil |
| 1340 | CH$_3$ | CH$_2$ | H | Cl | Cl | H | H | CH(CH$_3$)$_2$ | C(O)-1-morpholinyl | 154–155 |
| 1341 | CH$_3$ | CH$_2$ | H | Cl | Cl | H | H | C$_2$H$_5$ | CO$_2$CH$_3$ | oil |
| 1342 | CH$_3$ | CH$_2$ | H | Cl | Cl | H | H | CH$_3$ | CO$_2$CH$_3$ | oil |
| 1343 | CH$_3$ | CH$_2$ | H | Cl | Cl | H | H | CH$_3$ | CH | oil |
| 1344 | CH$_3$ | CH$_2$ | H | Cl | Cl | H | H | CH$_3$ | COCH$_3$ | oil |
| 1345 | CH$_3$ | CH$_2$ | H | Cl | Cl | H | H | H | 2-Cl—C$_6$H$_4$ | 149–152 |
| 1346 | CH$_3$ | CH$_2$ | H | Cl | Cl | H | H | H | 3-Cl—C$_6$H$_4$ | oil |
| 1347 | CH$_3$ | CH$_2$ | H | Cl | Cl | H | H | H | 4-F—C$_6$H$_4$ | 148–149 |
| 1348 | CH$_3$ | CH$_2$ | H | Cl | Cl | H | H | H | 4-CN—C$_6$H$_4$ | 199–200 |
| 1349 | CH$_3$ | CH$_2$ | H | Cl | Cl | H | H | H | 4-Cl—C$_6$H$_4$ | 183–184 |
| 1350 | CH$_3$ | CH$_2$ | H | Cl | Cl | H | H | c-C$_3$H$_5$ | c-C$_4$H$_7$ | — |
| 1351 | CH$_3$ | CH$_2$ | H | CH$_3$ | OCH$_3$ | CH$_3$ | H | c-C$_3$H$_5$ | c-C$_4$H$_7$ | — |
| 1352 | CH$_3$ | CH$_2$ | H | Cl | CF$_3$ | H | H | c-C$_3$H$_5$ | c-C$_4$H$_7$ | — |
| 1353 | CH$_3$ | CH$_2$ | H | Cl | OCH$_3$ | H | H | c-C$_3$H$_5$ | c-C$_4$H$_7$ | — |
| 1354 | CH$_3$ | CH$_2$ | H | Cl | OCF$_3$ | H | H | c-C$_3$H$_5$ | c-C$_4$H$_7$ | — |
| 1355 | CH$_3$ | CH$_2$ | H | Cl | CH$_3$ | H | H | c-C$_3$H$_5$ | c-C$_4$H$_7$ | — |
| 1356 | CH$_3$ | CH$_2$ | H | CF$_3$ | OCH$_3$ | H | H | c-C$_3$H$_5$ | c-C$_4$H$_7$ | — |
| 1357 | CH$_3$ | CH$_2$ | H | Cl | Cl | H | CH$_3$ | c-C$_3$H$_5$ | c-C$_4$H$_7$ | — |
| 1358 | CH$_3$ | CH$_2$ | H | CH$_3$ | OCH$_3$ | Cl | H | c-C$_3$H$_5$ | c-C$_4$H$_7$ | — |
| 1359 | CH$_3$ | CH$_2$ | H | CH$_3$ | OCH$_3$ | F | H | c-C$_3$H$_5$ | c-C$_4$H$_7$ | — |
| 1360 | CH$_3$ | CH$_2$ | H | Cl | OCH$_3$ | F | H | c-C$_3$H$_5$ | c-C$_3$H$_5$ | — |
| 1361 | CH$_3$ | CH$_2$ | H | Cl | OCH$_3$ | F | H | C$_2$H$_5$ | c-C$_3$H$_5$ | — |
| 1362 | CH$_3$ | CH$_2$ | H | Cl | OCH$_3$ | F | H | C$_3$H$_7$ | c-C$_3$H$_5$ | — |
| 1363 | CH$_3$ | CH$_2$ | H | Cl | OCH$_3$ | F | H | CH$_3$ | c-C$_4$H$_7$ | — |
| 1364 | CH$_3$ | CH$_2$ | H | Cl | OCH$_3$ | F | H | CH$_3$ | C$_3$H$_7$ | — |
| 1365 | CH$_3$ | CH$_2$ | H | Cl | OCH$_3$ | F | H | C$_2$H$_5$ | C$_3$H$_7$ | — |
| 1366 | CH$_3$ | CH$_2$ | H | Cl | OCH$_3$ | F | H | C$_2$H$_5$ | C$_2$H$_5$ | — |
| 1367 | CH$_3$ | CH$_2$ | H | Cl | OCH$_3$ | F | H | C$_3$H$_7$ | C$_3$H$_7$ | — |
| 1368 | CH$_3$ | CH$_2$ | H | Cl | OCH$_3$ | F | H | CH$_3$ | C$_4$H$_9$ | — |
| 1369 | CH$_3$ | CH$_2$ | H | Cl | OCH$_3$ | F | H | H | 4-CH$_3$O—C$_6$H$_4$ | — |
| 1370 | CH$_3$ | CH$_2$ | H | CF$_3$ | OCH$_3$ | H | H | C$_2$H$_5$ | C$_3$H$_7$ | oil |
| 1371 | CH$_3$ | CH$_2$ | H | Cl | Cl | H | H | CH$_3$ | 2-CH$_3$-c-C$_3$H$_4$ | oil |
| 1372 | CH$_3$ | CH$_2$ | H | CH$_3$ | OCH$_3$ | CH$_3$ | H | CH$_3$ | 2-CH$_3$-c-C$_3$H$_4$ | — |
| 1373 | CH$_3$ | CH$_2$ | H | Cl | CF$_3$ | H | H | CH$_3$ | 2-CH$_3$-c-C$_3$H$_4$ | — |
| 1374 | CH$_3$ | CH$_2$ | H | Cl | OCH$_3$ | H | H | CH$_3$ | 2-CH$_3$-c-C$_3$H$_4$ | — |
| 1375 | CH$_3$ | CH$_2$ | H | Cl | OCF$_3$ | H | H | CH$_3$ | 2-CH$_3$-c-C$_3$H$_4$ | — |
| 1376 | CH$_3$ | CH$_2$ | H | Cl | CH | H | H | CH$_3$ | 2-CH$_3$-c-C$_3$H$_4$ | — |
| 1377 | CH$_3$ | CH$_2$ | H | CF$_3$ | OCH$_3$ | H | H | CH$_3$ | 2-CH$_3$-c-C$_3$H$_4$ | — |
| 1378 | CH$_3$ | CH$_2$ | H | Cl | Cl | H | CH$_3$ | CH$_3$ | 2-CH$_3$-c-C$_3$H$_4$ | — |
| 1379 | CH$_3$ | CH$_2$ | H | CH$_3$ | OCH$_3$ | Cl | H | CH$_3$ | 2-CH$_3$-c-C$_3$H$_4$ | — |
| 1380 | CH$_3$ | O | H | Cl | Cl | H | H | CH$_3$ | 2-CH$_3$-c-C$_3$H$_4$ | — |
| 1381 | CH$_3$ | CH$_2$ | H | Cl | Cl | H | H | CH$_3$ | 2-C$_6$H$_5$-c-C$_3$H$_4$ | — |
| 1382 | CH$_3$ | CH$_2$ | H | CH$_3$ | OCH$_3$ | CH$_3$ | H | CH$_3$ | 2-C$_6$H$_5$-c-C$_3$H$_4$ | — |

TABLE 1-continued

| | | | | | | | | | | |
|---|---|---|---|---|---|---|---|---|---|---|
| 1383 | CH₃ | CH₂ | H | Cl | CF₃ | H | H | CH₃ | 2-C₆H₅-c-C₃H₄ | — |
| 1384 | CH₃ | CH₂ | H | Cl | OCH₃ | H | H | CH₃ | 2-C₆H₅-c-C₃H₄ | — |
| 1385 | CH₃ | CH₂ | H | Cl | OCF₃ | H | H | CH₃ | 2-C₆H₅-c-C₃H₄ | — |
| 1386 | CH₃ | CH₂ | H | Cl | CH₃ | H | H | CH₃ | 2-C₆H₅-c-C₃H₄ | — |
| 1387 | CH₃ | CH₂ | H | CF₃ | OCH₃ | H | H | CH₃ | 2-C₆H₅-c-C₃H₄ | — |
| 1388 | CH₃ | CH₂ | H | Cl | Cl | H | CH₃ | CH₃ | 2-C₆H₅-c-C₃H₄ | — |
| 1389 | CH₃ | CH₂ | H | CH₃ | OCH₃ | Cl | H | CH₃ | 2-C₆H₅-c-C₃H₄ | — |
| 1390 | CH₃ | O | H | Cl | Cl | H | H | CH₃ | 2-C₆H₅-c-C₃H₄ | — |
| 1391 | CH₃ | CH₂ | H | Cl | Cl | H | H | CH₃ | 2-(2-pyridyl)-c-C₃H₄ | — |
| 1392 | CH₃ | CH₂ | H | CH₃ | OCH₃ | CH₃ | H | CH₃ | 2-(2-pyridyl)-c-C₃H₄ | — |
| 1393 | CH₃ | CH₂ | H | Cl | CF₃ | H | H | CH₃ | 2-(2-pyridyl)-c-C₃H₄ | — |
| 1394 | CH₃ | CH₂ | H | Cl | OCH₃ | H | H | CH₃ | 2-(2-pyridyl)-c-C₃H₄ | — |
| 1395 | CH₃ | CH₂ | H | Cl | OCF₃ | H | H | CH₃ | 2-(2-pyridyl)-c-C₃H₄ | — |
| 1396 | CH₃ | CH₂ | H | Cl | CH₃ | H | H | CH₃ | 2-(2-pyridyl)-c-C₃H₄ | — |
| 1397 | CH₃ | CH₂ | H | CF₃ | OCH₃ | H | H | CH₃ | 2-(2-pyridyl)-c-C₃H₄ | — |
| 1398 | CH₃ | CH₂ | H | Cl | Cl | H | CH₃ | CH₃ | 2-(2-pyridyl)-c-C₃H₄ | — |
| 1399 | CH₃ | CH₂ | H | CH₃ | OCH₃ | Cl | H | CH₃ | 2-(2-pyridyl)-c-C₃H₄ | — |
| 1400 | CH₃ | O | H | Cl | Cl | H | H | CH₃ | 2-(2-pyridyl)-c-C₃H₄ | — |

Key:
[a]Where the compound is indicated as an "oil", data is provided below:

Example 3 spectral data: TLC $R_f$ 0.27(30:70 ethyl acetate-hexane). $^1$H NMR(300MHz, CDCl₃): δ8.90(1H, s), 6.95 (2H, s), 4.45(1H, br), 4.27–4.17(2H, m), 3.85(1H, dd, J=9.5, 4.8Hz), 3.27(3H, s), 2.94(2H, q, J=7.5Hz), 2.56–2.46 (1H, m), 2.32(3H, s), 2.06(3H, s), 2.03(3H, s), 1.37(3H, t, J=7.5Hz), 0.85(3H, t, J=7.5Hz). MS(NH₃—Cl): m/e 355 (3), 354(25), 353(100). Analysis calc'd for C₂₁H₂₈N₄O.1.5H₂O: C, 66.46; H, 8.23; N, 14.76; found: C, 67.00; H, 8.10; N, 14.38.

Example 8 spectral data: TLC $R_f$ 0.34(50:50 ethyl acetate-hexane). $^1$H NMR(300MHz, CDCl₃): δ8.89(1H, s), 6.95 (2H, s), 4.46(1H, br), 3.41–3.33(1H, m), 3.22(3H, s), 2.94(2H, q, J=7.3Hz), 2.93–2.85(1H, m), 2.84–2.69(2H, m), 2.51(1H, br), 2.32(3H, s), 2.30–2.20(1H, m), 2.04(6H, s), 1.37(3H, t, J=7.7Hz), 0.84(3H, t, J=7.3Hz). MS(NH₃—Cl): m/e calc'd for C₂₂H₃₀N₄O: 366.2420, found 366.2400; 369(3), 368(27), 367(100).

Example 10 spectral data: TLC $R_F$ 0.13(ethyl acetate). $^1$H NMR(300MHz, CDCl₃): δ8.93(1H, s), 8.10(3H, s), 7.96 (1H, s), 6.96(2H, s), 4.39(1H, br), 4.24–4.14(1H, m), 4.12–4.00(1H, m), 3.20(1H, br), 2.80(2H, q, J=7.0Hz), 2.78–2.68(1H, m), 2.42(1H, br), 2.33(3H, s), 2.13–2.04(1H, m), 2.06(3H, s), 2.03(3H, s), 1.33(3H, t, J=7.5Hz), 0.80 (3H, t, J=7.3Hz). MS(NH₃—Cl): m/e calc'd for C₂₃H₃₀N₇: 404.2563, found 404.2556; 406(4), 405(28), 404(100).

Example 11 spectral data: TLC $R_F$ 0.60(ethyl acetate). $^1$H NMR(300MHz, CDCl₃): δ8.92(1H, s), 8.51(1H, s), 6.96 (2H, s), 4.78–4.68(1H, m), 4.57–4.47(1H, m), 4.32–4.22(1H, m), 3.43(1H, br), 2.81(2H, q, J=6.9Hz), 2.78(1H, br), 2.43(1H, br), 2.33(3H, s), 2.10–2.00(1H, m), 2.07(3H, s), 2.03(3H, s), 1.32(3H, t, J=7.0Hz), 0.78(3H, t, J=7.5Hz). MS(NH₃—Cl): m/e calc'd for C₂₂H₂₉N₉: 405.2515, found 405.2509; 407(4), 406(27), 405(100).

Example 18 spectral data: TLC $R_F$ 0.20(30:70 ethyl acetate-hexane). $^1$H NMR(300MHz, CDCl₃): δ9.00(1H, s), 7.26 (1H, obscured), 6.96(2H, s), 6.86–6.76(3H, m), 5.46(2H, s), 3.76(3H, s), 2.85(2H, q, J=7.7Hz), 2.33(3H, s), 2.06 (6H, s), 1.28(3H, t, J=7.7Hz). MS(NH₃—Cl): m/e 389(4), 388(28), 387(100). Analysis calc'd for C₂₄H₂₆N₄O: C, 74.58; H, 6.78; N, 14.50; found: C, 74.36; H, 6.73; N, 13.83.

Example 27 spectral data: TLC $R_F$ 0.20(30:70 ethyl acetate-hexane). $^1$H NMR(300MHz, CDCl₃): δ8.96(1H, s), 6.95 (2H, s), 4.25(2H, t, J=7.5Hz), 2.93(2H, q, J=7.7Hz), 2.32(3H, s), 2.04(6H, s), 1.91–1.86(2H, m), 1.50–1.38(2H, m), 1.39(3H, t, J=7.7Hz), 1.01(3H, t, J=7.5Hz). MS(NH₃—Cl): m/e 325(3), 324(23), 323(100).

Example 28 spectral data: TLC $R_F$ 0.28(30:70 ethyl acetate-hexane). $^1$H NMR(300MHz, CDCl₃): δ8.96(1H, s), 6.95 (2H, s), 4.24(2H, t, J=7.9Hz), 2.93(2H, q, J=7.6Hz), 2.32(3H, s), 2.04(6H, s), 1.90(2H, m), 1.44–1.36(7H, m), 0.93 (3H, t, J=7.1Hz). MS(NH₃—Cl): m/e 339(3), 338(25), 337(100). Analysis calc'd for C₂₁H₂₈N₄: C, 74.96; H, 8.40; N, 16.65; found: C, 74.24; H, 8.22; N, 16.25.

Example 34 spectral data: MS(ESI): m/e 365(M+2), 363(M+H⁻, 100%).

Example 35 spectral data: TLC $R_F$ 0.31(20:80 ethyl acetate-hexane). $^1$H NMR(300MHz, CDCl₃): δ8.94(1H, s), 7.71 (1H, d, J=8.4Hz), 7.58(1H, d, J=1.8Hz), 7.41(1H, dd, J=8.4, 1.8Hz), 4.27(1H, br), 2.95(2H, q, J=7.3Hz), 2.41(2H, br), 2.11–1.98(2H, br), 1.42(3H, t, J=7.3Hz), 1.37–1.20(3H, m), 1.09–0.99(1H, m), 0.84(3H, t, J=7.7Hz), 0.82(3H, t, J=7.7Hz). MS(NH₃—Cl): m/e calc'd for C₂₀H₂₅N₄Cl₂: 391.1456, found 391.1458; 395(11), 394(14), 393(71), 392 (29), 391(100).

Example 38 spectral data: MS(NH₃—Cl): m/e 375(M+H⁺, 100%).

Example 40 spectral data: MS(NH₃—Cl): m/e 377(M+H⁺, 100%).

Example 48 spectral data: MS(NH₃—Cl): m/e 423(M+H⁺, 100%).

Example 50 spectral data: TLC $R_F$ 0.27(30:70 ethyl acetate-hexane). $^1$H NMR(300MHz, CDCl₃): δ9.03(1H, s), 7.70 (1H, d, J=8.0Hz), 7.59(1H, d, J=1.8Hz), 7.41(1H, dd, J=8.0, 1.8Hz), 7.36–7.30(2H, m), 7.24–7.19(3H, m), 5.50(2H, s), 2.87(2H, q, J=7.5Hz), 1.31(3H, t, J=7.5Hz). MS(NH₃—Cl): m/e calc'd for C₂₀H₁₆N₄Cl₂: 382.0752, found 382.0746; 388(3), 387(12), 386(16), 385(66), 384(26), 383(100).

Example 51 spectral data: MS(NH₃—Cl): m/e 413(M+H⁺, 100%).

Example 54 spectral data: MS(NH₃—Cl): m/e 459(M+H⁺, 100%).

Example 68 spectral data: TLC $R_F$ 0.28(30:70 ethyl acetate-hexane). $^1$H NMR(300MHz, CDCl₃): δ8.91(1H, s), 6.69 (2H, s), 4.30–4.19(1H, m), 3.82(3H, s), 2.92(2H, q, J=7.6Hz), 2.41(1H, br), 2.08(3H, s), 2.07(3H, s), 2.06(1H, br), 1.38(3H, t, J=7.6Hz), 1.36–1.22(4H, m), 1.10–0.98(1H, m), 0.96–0.87(1H, m), 0.84(3H, t, J=7.0Hz), 0.81(3H, t, J=6.7Hz). MS(NH₃—Cl): m/e 383(4), 382(27), 381(100).

TABLE 1-continued

Example 122 spectral data: TLC $R_F$ 0.10(20:80 ethyl acetate-hexane). $^1$H NMR(300MHz, CDCl$_3$): δ8.97(1H, s), 6.94(2H, s), 4.14(2H, d, J=7.7Hz), 3.48(1H, q, J=7.0Hz), 2.63(3H, s), 2.31(3H, s), 2.01(6H, s), 1.43–1.19(8H, m), 0.94(3H, t, J=7.3Hz), 0.84(3H, t, J=7.0Hz). MS(NH$_3$—CI): m/e 367(3), 366(25), 365(100).
Example 123 spectral data: TLC $R_F$ 0.24(30:70 ethyl acetate-hexane). $^1$H NMR(300MHz, CDCl$_3$): δ8.97(1H, s), 6.94(2H, s), 4.25(2H, t, J=8.1Hz), 3.48(1H, q, J=7.1Hz), 2.63(3H, s), 2.31(3H, s), 2.01(6H, s), 1.81(2H, m), 1.47–1.19(8H, m), 0.91(6H, m). MS(NH$_3$—CI): m/e 381(4), 380(27), 379(100). Analysis calc'd for C$_{24}$H$_{14}$N$_4$: C, 76.15; H, 9.05; N, 14.80; found: C, 76.29; H, 9.09; N, 14.75.
Example 202 spectral data: TLC RF 0.20(10:90 ethyl acetate-hexane). 1H NMR(300MHz, CDCl$_3$): d8.82(1H, s), 6.96(2H, s), 4.46–4.38(1H, m), 4.13(3H, s), 2.34(3H, s), 2.28–2.11(2H, m), 2.07(6H, s), 1.95–1.81(2H, m), 1.38–1.17(3H, m), 1.14–0.99(1H, m), 0.83(3H, t, J=7.7Hz), 0.80(3H, t, J=7.7Hz). MS(NH3—CI): m/e calc'd for C$_{22}$H$_{30}$N$_4$O: 366.2420, found 366.2408; 369(4), 368(26), 367(100).
Example 404 spectral data: TLC $R_F$ 0.20(20:80 ethyl acetate-hexane). $^1$H NMR(300MHz, CDCl$_3$): δ6.93(2H, s), 4.20(2H, t, J=7.7Hz), 2.90(2H, q, J=7.6Hz), 2.83(3H, s), 2.30(3H, s), 2.03(6H, s), 1.88(2H, m), 1.42–1.34(7H, m), 0.93(3H, t, J=6Hz). MS(NH$_3$—CI): m/e 353(3), 352(27), 351(100).
Example 414 spectral data: TLC $R_F$ 0.36(20:80 ethyl acetate-hexane). $^1$H NMR(300MHz, CDCl$_3$): δ8.92(1H, s), 7.66(1H, d, J=8.1Hz), 7.32–7.26(2H, m), 4.54(1H, m), 2.95(2H, q, J=7.4Hz), 2.43(3H, s), 2.39(1H, m), 2.03(1H, m), 1.74(3H, d, J=7.0Hz), 1.41(3H, t, J=7.5Hz), 1.31(1H, m), 1.16(1H, m), 0.92(3H, t, J=7.3Hz). MS(NH$_3$—CI): m/e calc'd for C$_{19}$H$_{24}$N$_4$Cl: 343.1690, found 343.1704; 346(7), 345(34), 344(23), 343(100).
Example 415 spectral data: TLC $R_F$ 0.25(10:90 ethyl acetate-hexane). $^1$H NMR(300MHz, CDCl$_3$): δ8.91(1H, s), 7.71(1H, d, J=8.1Hz), 7.34–7.30(2H, m), 4.30–4.20(1H, m), 2.94(2H, q, J=7.5Hz), 2.50–2.35(2H, m), 2.44(3H, s), 2.08–1.95(2H, m), 1.43(3H, t, J=7.5Hz), 1.29(3H, m), 1.08–0.98(1H, m), 0.84(3H, t, J=7.0Hz), 0.81(3H, t, J=7.3Hz). MS(NH$_3$—CI): m/e 374(7), 373(33), 372(25), 371(100). Analysis calc'd for C$_{21}$H$_{27}$ClN$_4$: C, 68.00; H, 7.35; N, 15.10; found: C, 68.25; H, 7.30; N, 14.85.
Example 424 spectral data: TLC $R_F$ 0.28(5:95 ethyl acetate-dichloromethane). $^1$H NMR(300MHz, CDCl$_3$): δ8.95 (1H, s), 7.60(1H, d, J=7.7Hz), 7.37(1H, d, J=0.8Hz), 7.21(1H, dd, J=7.7, 0.8Hz), 4.58–4.50(1H, m), 2.96(2H, dq, J=7.5, 2.0Hz), 2.46–2.33(1H, m), 2.40(3H, s) 2.08–1.96(1H, m), 1.74(3H, d, J=6.6Hz), 1.40(3H, t, J=7.5Hz), 1.39–1.22(1H, m), 1.20–1.08(1H, m), 0.92(3H, t, J=7.3Hz). MS(NH$_3$—CI): m/e calc'd for C$_{19}$H$_{24}$ClN$_4$: 343.1690, found 343.1697; 346(8), 345(38), 344(25), 343(100).
Example 434 spectral data: TLC $R_F$ 0.78(50:50 ethyl acetate-hexane). $^1$H NMR(300MHz, CDCl$_3$): δ8.90(1H, s), 6.95(2H, s), 2.97(2H, J=7.3Hz), 2.60–2.50(1H, m), 2.41–2.33(1H, m), 2.32(3H, s), 2.20–2.10(1H, m), 2.05(3H, s), 2.02(3H, s), 1.85–1.80(1H, m), 1.39(3H, t, J=7.5Hz), 0.85(3H, t, J=7.5Hz), 0.50–0.35(2H, m), 0.25–0.15(1H, m), 0.10–0.00(1H, m). MS(NH$_3$—CI): m/e calc'd for C$_{23}$H$_{30}$N$_4$: 362.2470, found 362.2458; 365(4), 364(27), 363(100).
Example 436 spectral data: TLC $R_F$ 0.31(30:70 ethyl acetate-hexane). $^1$H NMR(300MHz, CDCl$_3$): δ8.88(1H, s), 7.77(1H, d, J=9.2Hz), 6.87(2H, m), 4.40–4.25(1H, m), 3.86(3H, s), 2.99(2H, q, J=7.5Hz), 2.60–2.35(2H, m), 2.47 (3H, s), 2.15–2.00(1H, m), 1.80–1.70(1H, m), 1.45(3H, t, J=7.5Hz), 0.84(3H, t, J=7.5Hz), 0.50–0.35(2H, m), 0.30–0.20(1H, m), 0.10–0.00(1H, m), −0.85—0.95(1H, m).
Example 437 spectral data: TLC $R_F$ 0.25(30:70 ethyl acetate-hexane). $^1$H NMR(300MHz, CDCl$_3$): δ8.90(1H, s), 7.73(1H, d, J=9.2Hz), 6.89–6.86(2H, m), 4.58–4.51(1H, m), 3.86(3H, s), 2.95(2H, dq, J=7.6, 1.8Hz), 2.47(3H, s), 2.45–2.34(1H, m), 2.07–1.97(1H, m), 1.73(3H, d, J=7.0Hz), 1.42(3H, t, J=7.6Hz), 1.40–1.27(1H, m), 1.20–1.07(1H, m), 0.92(3H, t, J=7.4Hz). MS(NH$_3$—CI): m/e calc'd for C$_{20}$H$_{27}$N$_4$O: 339.2185, found 339.2187; 341(3), 340(22), 339(100). Analysis calc'd for C$_{20}$H$_{26}$N$_4$O: C, 70.98; H, 7.74; N, 16.55; found: C, 69.97; H, 7.48; N, 15.84.
Example 438 spectral data: TLC $R_F$ 0.42(40:60 ethyl acetate-hexane). $^1$H NMR(300MHz, CDCl$_3$): δ8.98(1H, s), 7.77(1H, d, J=9.1Hz), 7.17(2H, d, J=8.8Hz), 6.90–6.83(4H, m), 5.42(2H, s), 3.86(3H, s), 3.78(3H, s), 2.86(2H, q, J=7.5Hz), 2.49(3H, s), 1.33(3H, t, J=7.5Hz). MS(NH$_3$—CI): m/e 391(4), 390(26), 389(100). Analysis calc'd for C$_{23}$H$_{24}$N$_4$O$_2$: C, 71.11; H, 6.24; N, 14.42; found: C, 71.14; H, 5.97; H, 14.03.
Example 439 spectral data: TLC $R_F$ 0.41(30:70 ethyl acetate-hexane). $^1$H NMR(300MHz, CDCl$_3$): δ8.89(1H, s), 7.77(1H, d, J=3.1Hz), 6.89(2H, m), 3.86(3H, s), 3.53(1H, m), 2.91(2H, q, J=7.5Hz), 2.49(3H, s), 2.28(1H, m), 2.21 (1H, m), 1.43(3H, t, J=7.3Hz), 0.86(3H, t, J=7.3Hz), 0.78(2H, m), 0.46(2H, m), 0.20(1H, m).
Example 440 spectral data: TLC $R_F$ 0.28(30:70 ethyl acetate-hexane). $^1$H NMR(300MHz, CDCl$_3$): δ8.89(1H, s), 7.73(1H, d, J=9.1Hz), 6.90–6.86(2H, m), 4.60–4.40(1H, m), 3.86(3H, s), 2.95(2H, dq, J=7.7, 2.2Hz), 2.47(3H, s), 2.44–2.36(1H, m), 2.05–1.98(1H, m), 1.74(3H, d, J=7.0Hz), 1.42(3H, t, J=7.5Hz), 1.40–1.20(5H, m), 1.13–1.05(1H, m), 0.830(3H, t, J=6.6Hz).
Example 502 spectral data: TLC $R_F$ 0.63(50:50 ethyl acetate-hexane). $^1$H NMR(300MHz, CDCl$_3$): δ8.92(1H, s), 6.95(2H, s), 4.60–4.47(1H, m), 2.93(2H, q, J=7.7Hz), 2.43–2.33(1H, m), 2.32(3H, s), 2.16–2.06(1H, m), 2.05(3H, s), 2.03(3H, s), 1.76(3H, d, J=7.0Hz), 1.36(3H, t, J=7.7Hz), 1.36–1.20(4H, m), 0.86(3H, t, J=7.2Hz). MS(NH$_3$—CI): m/e calc'd for C$_{22}$H$_{30}$N$_4$: 350.2470, found 350.2480; 353(3), 352(28), 351(100).
Example 503 spectral data: $^1$H NMR(300MHz, CDCl$_3$): δ8.92(1H, s), 6.94(2H, s), 4.58–4.48(1H, m), 2.93(2H, q, J=7.3Hz), 2.32(3H, s), 2.05(3H, s), 2.02(3H, s), 1.76(3H, d, J=6.6Hz), 1.36(3H, t, J=7.3Hz), 1.34–1.05(8H, m), 0.88 (3H, t, J=7Hz). MS(NH$_3$—CI): m/e calc'd for C$_{23}$H$_{32}$N$_4$: 365.2705, found 365.2685; 367(3), 366(27), 365(100).
Example 506 spectral data: TLC $R_F$ 0.28(20:80 ethyl acetate-hexane). $^1$H NMR(300MHz, CDCl$_3$): δ8.95(1H, s), 7.67(1H, d, J=8.4Hz), 7.57(1H, d, =1.8Hz), 7.42–7.37(1H, m), 4.56(1H, hextet, J=7.1Hz), 2.99(2H, q, J=7.5Hz), 2.43–2.33(1H, m), 2.09–1.97(1H, m), 1.74(3H, d, J=7.0Hz), 1.41(3H, t, J=7.5Hz), 1.35–1.07(2H, m), 0.92(3H, t, J=7.3Hz), 367(12), 366(14), 365(67), 364(24), 363(100).
Example 507 spectral data: MS(NH$_3$—CI): m/e 377(M+H$^+$, 100%).
Example 511 spectral data: TLC $R_F$ 0.51(30:70 ethyl acetate-hexane). $^1$H NMR(300MHz, CDCl$_3$): δ8.97(1H, s), 7.87(1H, d, J=8.1Hz), 7.83(1H, d, =1.1Hz), 7.68(1H, dd, J=8.1, 1.1Hz), 3.60–3.51(1H, m), 2.94(2H, q, J=7.5Hz), 2.53–2.39(1H, m), 2.36–2.20(1H, m), 1.96(1H, br), 1.42(3H, t, J=7.5Hz), 0.88(3H, t, J=7.3Hz), 0.88–0.78(1H, m), 0.52–0.44(2H, m), 0.24–0.16(1H, m), MS(NH$_3$—CI): m/e 412(7), 411(33), 410(23), 409(100).
Example 513 spectral data: TLC $R_F$ 0.62(30:70 ethyl acetate-hexane). $^1$H NMR(300MHz, CDCl$_3$): δ8.97(1H, s), 7.87(1H, d, J=8.0Hz), 7.83(1H, d, J=0.7Hz), 7.68(1H, dd, J=8.0, 0.7Hz), 4.21(1H, br), 2.96(2H, q, J=7.5Hz), 2.42 (2H, br), 2.12–1.97(2H, m), 1.43(3H, t, J=7.5Hz), 1.40–1.20(4H, m), 0.85(3H, t, J=7.3Hz), 0.83(3H, t, J=7.6Hz). MS(NH$_3$—CI): m/e 428(8), 427(38), 426(29), 425(100).
Example 514 spectral data: TLC $R_F$ 0.50(30:70 ethyl acetate-hexane). $^1$H NMR(300MHz, CDCl$_3$): δ8.96(1H, s), 7.86(1H, d, J=8.1Hz), 7.83(1H, d, J=0.8Hz), 7.68(1H, dd, J=8.1, 0.8Hz), 4.20(1H, br), 2.97(2H, q, J=7.7Hz), 2.54–2.39(2H, m), 2.15–2.01(2H, m), 1.43(3H, t, J=7.7Hz), 0.84(6H, t, J=7.5Hz). MS(NH$_3$—CI): m/e 400(7), 399 (37), 398(26), 397(100).
Example 524 spectral data: TLC $R_F$ 0.50(30:70 ethyl acetate-hexane). $^1$H NMR(300MHz, CDCl$_3$: δ8.89(1H, s), 7.76 (1H, d, J=9.1Hz), 6.90–6.87(2H, m), 4.35(1H, v br), 3.86(3H, s), 2.93(2H, q, J=7.6Hz), 2.48(3H, s), 2.39(2H, br), 2.00–1.90(2H, m), 1.43(3H, t, J=7.6Hz), 1.38–1.22(2H, m), 1.18–1.02(2H, m), 0.90(6H, t, J=7.3Hz). MS(NH$_3$—CI): m/e calc'd for C$_{22}$H$_{31}$N$_4$O: 367.2498, found 367.2506; 369(3), 368(25), 367(100).

TABLE 1-continued

Example 526 spectral data: TLC $R_F$ 0.28(10:90 ethyl acetate-hexane). $^1$H HMR(300MHz, CDCl$_3$): δ8.91(1H, s), 7.69(1H, d, J=8.1Hz), 7.34–7.30(2H, m), 4.40–4.35(1H, m), 2.93(2H, q, J=7.4Hz), 2.44(3H, s), 2.38(2H, m), 1.96 (2H, m), 1.43(3H, t, J=7.5Hz), 1.35–1.22(2H, m), 1.15–1.05(2H, m), 0.90(6H, t, J=7.1Hz). MS(NH$_3$—CI): m/e 374 (8), 373(35), 372(25), 371(100). Analysis calc'd for C$_{21}$H$_{27}$N$_4$Cl: C, 68.00; H, 7.35; N, 15.10; found: C, 67.89; H, 7.38; N, 14.94.
Example 528 spectral data: TLC $R_F$ 0.65(30:70 ethyl acetate-hexane). $^1$H NMR(300MHz, CDCl$_3$): δ8.97(1H, s), 7.86(1H, d, J=8.0Hz), 7.82(1H, d, J=1.1Hz), 7.67(1H, dd, J=8.0, 1.1Hz), 4.38(1H, br), 2.95(2H, g, J=7.5Hz), 2.39 (2H, br), 2.04–1.92(2H, br), 1.42(3H, t, J=7.5Hz), 1.40–1.21(3H, m), 1.19–1.03(1H, m), 0.91(6H, t, J=7.3Hz). MS(NH$_3$—CI): m/e 428(8), 427(37), 426(27), 425(100).
Example 538 spectral data: TLC $R_F$ 0.56(30:70 ethyl acetate-hexane). $^1$H NMR(300MHz, CDCl$_3$): δ8.96(1H, s), 7.88(1H, d, J=8.0Hz), 7.83(1H, d, J=0.8Hz), 7.68(1H, dd, J=8.0, 0.8Hz), 3.77(1H, br), 2.95(2H, q, J=7.5Hz), 2.61 (1H, br), 2.08(1H, br), 1.45(3H, t, J=7.5Hz), 1.36–1.25(1H, m), 1.17(3H, d, J=6.6Hz), 0.71(3H, t, J=7.3Hz), 0.69 (3H, d, J=7.0Hz). MS(NH$_3$—CI): m/e 414(7), 413(33), 412(24), 411(100).
Example 534 spectral data: MS(ESI): m/e 363(M+2), 361(M$^+$, 100%).
Example 544 spectral data: TLC $R_F$ 0.63(50:50 ethyl acetate-hexane). $^1$H NMR(300MHz, CDCl$_3$): δ8.90(1H, s), 7.74(1H, d, J=9.1Hz), 6.89–6.86(2H, m), 3.86(3H, s), 3.79–3.73(1H, m), 2.93(3H, dq, J=7.7, 2.6Hz), 2.49(3H, s), 2.03–1.99(1H, m), 1.81(3H, d, J=6.9Hz), 1.41(3H, t, J=7.3Hz), 0.84–0.74(2H, m), 0.53–0.41(2H, m), 0.28–0.21(1H, m).
Example 548 spectral data: TLC $R_F$ 0.42(30:70 ethyl acetate-hexane). $^1$H NMR(300MHz, CDCl$_3$): δ8.99(1H, s), 7.84(1H, d, J=7.7Hz), 7.82(1H, d, J=0.9Hz), 7.68(1H, dd, J=7.7, 0.9Hz), 3.83–3.70(1H, m), 3.00–2.90(2H, m), 2.09–1.98(1H, m), 1.83(3H, d, J=7.0Hz), 1.40(3H, t, J=7.5Hz), 0.88–0.78(1H, m), 0.57–0.41(2H, m), 0.30–0.20(1H, m), MS(NH$_3$—CI): m/e 398(6), 397(31), 396(22), 395(100).
Example 551 spectral data: TLC $R_F$ 0.56(50:50 ethyl acetate-hexane). $^1$H NMR(300MHz, CCDl$_3$): δ8.93(1H, s), 6.94(2H, s), 4.75(1H, heptet, J=7.0Hz), 2.95(2H, q, J=7.7Hz), 2.32(3H, s), 2.04(6H, s), 1.80(6H, d, J=7.0Hz), 1.36 (3H, t, J=7.7Hz). MS(NH$_3$—CI): m/e 311(4), 310(34), 309(100); Analysis calc'd for C$_{19}$H$_{24}$N$_4$·0.5H$_2$O: C, 71.89; H, 7.94; N, 17.65; found: C, 71.59; H, 7.83; N, 17.41.
Example 558 spectral data: TLC $R_F$ 0.53(30:70 ethyl acetate-hexane). $^1$H NMR(300MHz, CCDl$_3$): δ8.98(1H, s), 7.86–7.81(2H, m), 7.67(1H, dd, J=8.4, 1.1Hz), 4.60–4.48(1H, m), 3.01–2.93(2H, m), 2.49–2.35(1H, m), 2.13–2.00 (1H, m), 1.76(3H, d, J=7.0Hz), 1.41(3H, t, J=7.5Hz), 1.40–1.20(4H, m), 0.87(3H, t, J=7.3Hz). MS(NH$_3$—CI): m/e 414(8), 413(38), 412(27), 411(100).
Example 564 spectral data: TLC $R_F$ 0.34(30:70 ethyl acetate-hexane). $^1$H NMR(300MHz, CCDl$_3$): δ8.89(1H, s), 7.77(1H, d, J=9.2Hz), 6.89(2H, m), 4.30–4.20(1H, m), 3.86(3H, s), 2.93(2H, q, J=7.5Hz), 2.48(3H, s), 2.45–2.35 (2H, m), 2.10–1.95(2H, m), 1.44(3H, t, J=7.5Hz), 1.40–1.20(3H, m), 1.10–0.95(1H, m), 0.84(3H, t, J=7.3Hz), 0.81 (3H, t, J =7.3Hz).
Example 571 spectral data: TLC $R_F$ 0.40(50:50 ethyl acetate-hexane). $^1$H NMR(300MHz, CDCl$_3$): δ8.89(1H, s), 6.95(2H, s), 4.51(1H, br), 3.44–3.24(4H, m), 2.96(2H, q, J=7.3Hz), 2.95–2.87(1H, m), 2.85–2.75(1H, m), 2.59–2.49 (1H, m), 2.32(3H, s), 2.27–2.18(1H, m), 2.04(3H, s), 2.04(3H, s), 1.38(3H, t, J=7.7Hz), 1.12(3H, t, J=7.0Hz), 0.84 (3H, t, J=7.3Hz), MS(NH$_3$—CI): m/e calc'd for C$_{23}$H$_{32}$N$_4$O: 380.2576, found 380.2554; 383(4), 362(26), 381(100).
Example 581 spectral data: TLC $R_F$ 0.33(30:70 ethyl acetate-hexane). $^1$H NMR(300MHz, CDCl$_3$): δ8.89(1H, s), 6.95(2H, m), 4.49–4.39(1H, m), 4.23–4.13(1H, m), 3.91(1H, dd, J=9.9, 4.8Hz), 3.48(1H, dq, J=9.1, 7.0Hz), 3.30(1H, dq, J=9.1, 7.0Hz), 2.95(2H, q, J=7.7Hz), 2.60–2.47(1H, m), 2.32(3H, s), 2.15–2.01(1H, m), 2.04(3H, s), 2.03(3H, s), 1.37(3H, t, J=7.5Hz), 1.00(3H, t, J=7.0Hz), 0.86(3H, t, J=7.3Hz). MS(NH$_3$—CI): m/e calc'd for C$_{22}$H$_{31}$N$_4$O: 367.2498, found 367.2497; 369(4), 368(27), 367(100).
Example 591 spectral data: TLC $R_F$ 0.42(50:50 ethyl acetate-hexane). $^1$H NMR(300MHz, CDCl$_3$): δ8.91(1H, s), 6.95(2H, s), 3.76(1H, br), 3.47–3.40(1H, m), 3.21(3H, s), 2.99–2.90(1H, m), 2.88(2H, q, J=7.3Hz), 2.76(1H, br), 2.51–2.41(1H, m), 2.32(3H, s), 2.09(1H, br), 2.08(3H, s), 2.04(3H, s), 1.35(3H, t, J=7.3Hz), 0.84–0.76(1H, m), 0.56–0.44(2H, m), 0.30–0.21(1H, m). MS(NH$_3$—CI): m/e calc'd for C$_{23}$H$_{31}$N$_4$O: 379.2498, found 379.2514; 381 (4), 380(27), 379(100).
Example 690 spectral data: TLC $R_F$ 0.12(30:70 ethyl acetate-hexane). $^1$H NMR(300MHz, CDCl$_3$): δ9.01(1H, s), 7.38–7.22(5H, m), 6.75(1H, s), 6.69(1H, s), 5.48(2H, s), 3.70(3H, s), 2.84(2H, q, J=7.7Hz), 2.37(3H, s), 2.05(3H, s), 1.26(3H, t, J=7.7Hz). MS(NH$_3$—CI): m/e 375(4), 374(28), 373(100).
Example 692 spectral data: TLC $R_F$ 0.32(30:70 ethyl acetate-hexane). $^1$H NMR(300MHz, CDCl$_3$): δ8.98(1H, s), 7.48(1H, s), 7.37–7.18(5H, m), 7.11(1H, s), 5.49(2H, s), 2.84(2H, q, J=7.3Hz), 2.38(3H, s), 2.29(6H, s), 1.31(3H, t, J=7.3Hz). MS(NH$_3$—CI): m/e calc'd for C$_{23}$H$_{24}$N$_4$: 356.2001, found 356.1978; 359(4), 358(28), 357(100).
Example 693 spectral data: TLC $R_F$ 0.22(20:80 ethyl acetate-hexane). $^1$H NMR(300MHz, CDCl$_3$): δ8.90(1H, s), 7.78(1H, d, J=9.5Hz), 6.90–6.87(2H, m), 3.86(3H, s), 3.62(1H, br), 2.91(2H, q, J=7.5Hz), 2.50(3H, s), 2.40(1H, br), 2.26–2.13(1H, m), 1.92(1H, br), 1.58(1H, br), 1.43(3H, t, J=7.5Hz), 1.35–1.25(1H, m), 1.13–1.03(1H, m), 0.95–0.75 (2H, m), 0.85(3H, t, J=7.1Hz), 0.54–0.42(2H, m), 0.22–0.17(1H, m). MS(NH$_3$—CI): m/e 381(4), 380(25), 379(100).
Example 697 spectral data: TLC $R_F$ 0.28(30:70 ethyl acetate-hexane). $^1$H NNR(300MHz, CDCl$_3$): δ8.89(1H, s), 7.74(1H, d, J=9.5Hz), 6.90–6.86(2H, m), 4.58–4.45(1H, m), 2.95(2H, dq, J=7.7, 2.2Hz), 2.48(3H, s), 2.45–2.35(1H, m), 2.09–1.99(1H, m), 1.74(3H, d, J=7.0Hz), 1.42(3H, t, J=7.5Hz), 1.37–1.23(3H, m), 1.11–1.03(1H, m), 0.86(3H, t, J=7.0Hz).
Example 724 spectral data: TLC $R_F$ 0.45(30:70 ethyl acetate-hexane). $^1$H NMR(300MHz, CDCl$_3$): δ8.92(1H, s), 7.75(1H, d, J=8.4Hz), 7.09(1H, d, J=2.6Hz), 6.96(1H, dd, J=8.4, 2.6Hz), 3.87(3H, s), 3.76(1H, br), 2.94(2H, q, J=7.3Hz), 2.61(1H, br), 2.09(1H, br), 1.45(3H, t, J=7.3Hz), 1.36–1.26(1H, m), 1.15(3H, d, J=6.6Hz), 0.71(3H, t, J=7.3Hz), 0.68(3H, d, J=6.6Hz). MS(NH$_3$—CI): m/e 377(1), 376(8), 375(38), 374(25), 373(100).
Example 725 spectral data: TLC $R_F$ 0.31(30:70 ethyl acetate-hexane). $^1$H NMR(300MHz, CDCl$_3$): δ8.88(1H, s), 7.80(1H, d, J=9.2Hz), 6.89(2H, m), 3.86(3H, s), 3.75(1H, m), 2.92(2H, q, J=7.4Hz), 2.60(1H, m), 2.48(3H, s), 2.05 (1H, m), 1.46(3H, t, J=7.4Hz), 1.16(3H, d, =7.0Hz), 0.70(3H, t, J=7.3Hz), 0.67(3H, d, J=6.6Hz).
Example 727 spectral data: TLC $R_F$ 0.44(30:70 ethyl acetate-hexane). $^1$H NMR(300MHz, CDCl$_3$): δ8.90(1H, s), 7.84(1H, d, =2.2Hz), 7.74(1H, d, J=8.4Hz), 7.65(1H, dd, J=8.4, 2.2Hz), 3.76(1H, br), 2.93(1H, q, J=7.3Hz), 2.60 (1H, br), 2.08(1H, br), 1.42(3H, t, J=7.3Hz), 1.37–1.27(1H, m), 1.16(3H, d, J=7.0Hz), 0.69(3H, t, J=7.3Hz), 0.67 (3H, d, J=7.0Hz). MS(NH$_3$—CI): m/e 414(7), 413(33), 412(27), 411(100).
Example 750 spectral data: TLC $R_F$ 0.42(30:70 ethyl acetate-hexane). $^1$H NMR(300MHz, CDCl$_3$): δ8.94(1H, s), 7.73(1H, d, J=8.4Hz), 7.10(1H, d, J=2.6Hz), 6.96(1H, dd, J=8.4, 2.6Hz), 3.87(3H, s), 3.63(1H, v br), 2.92(2H, q, J=7.3Hz), 2.38(1H, br), 2.22–2.10(1H, m), 1.94(1H, br), 1.42(3H, t, J=7.3Hz), 1.41–1.29(1H, m), 1.23–1.08(1H, m), 0.91(3H, t, J=7.3Hz), 0.89–0.79(1H, m), 0.51–0.41(2H, m), 0.25–0.15(1H, m). MS(NH$_3$—CI): m/e 388(8), 387(34), 386(25), 385(100).
Example 751 spectral data: TLC $R_F$ 0.36(40:60 ethyl acetate-hexane). $^1$H NMR(300MHz, CDCl$_3$): δ8.89(1H, s), 7.77(1H, d, J=9.1Hz), 6.90(2H, m), 3.86(3H, s), 3.62(1H, m), 2.84(2H, q, J=7.5Hz), 2.49(3H, s), 2.40(1H, m), 2.19 (1H, m), 1.90(1H, m), 1.43(3H, t, J=7.5Hz), 1.38(1H, m), 1.19(1H, m), 0.91(3H, t, J=7.3Hz), 0.80(1H, m), 0.49(2H, m), 0.21(1H, m).

TABLE 1-continued

Example 753 spectral data: TLC $R_F$ 0.44(30:70 ethyl acetate-hexane). $^1$H NMR(300MHz, CDCl$_3$): δ8.92(1H, s), 7.84(1H, d, J=1.8Hz), 7.73(1H, d, J=8.5Hz), 7.65(1H, dd, J=8.5, 1.8Hz), 3.65(1H, br), 2.92(1H, q, J=7.5Hz), 2.38 (1H, br), 2.25–2.14(1H, m), 1.94(1H, br), 1.43–1.26(1H, m), 1.40(3H, t, J=7.5Hz), 1.21–1.06(1H, m), 0.92(3H, t, J=7.3Hz), 0.91–0.79(1H, m), 0.52–0.44(2H, m), 0.22–0.16(1H, m). MS(NH$_3$—CI): m/e 426(9), 425(42), 424(31), 423(100).

Example 767 spectral data: MS(NH$_3$—CI): m/e 379(M+H$^+$, 100%).

Example 776 spectral data: TLC $R_F$ 0.41(30:70 ethyl acetate-hexane). $^1$H NMR(300MHz, CDCl$_3$): δ8.93(1H, s), 7.73(1H, d, J=8.4Hz) 7.09(1H, d, J=2.6Hz), 6.96(1H, dd, J=8.4, 2.6Hz), 4.28(1H, br), 3.87(3H, s), 2.95(2H, q, J=7.3Hz), 2.41(2H, br), 2.10–1.93(2H, m), 1.43(3H, t, J=7.3Hz), 1.40–1.23(1H, m), 1.18–1.03(1H, m), 0.91(3H, t, J=7.3Hz), 0.82(3H, t, J=7.5Hz). MS(NH$_3$—CI): m/e calc'd for C$_{20}$H$_{28}$ClN$_4$O: 373.1795, found 373.1815; 376(8), 375(35), 374(24), 373(100).

Example 777 spectral data: TLC $R_F$ 0.46(30:70 ethyl acetate-hexane). $^1$H NMR(300MHz, CDCl$_3$): δ8.89(1H, s), 7.76(1H, d, J=9.0Hz), 6.90–6.87(2H, m), 4.29(1H, br), 3.86(3H, s), 2.94(2H, q, J=7.4Hz), 2.48(3H, s), 2.40(2H, br), 2.10–1.92(2H, m), 1.44(3H, t, J=7.4Hz), 1.37–1.22(1H, m), 1.18–1.02(1H, m), 0.90(3H, t, J=7.3Hz), 0.81(3H, t, J=7.3Hz). MS(NH$_3$—CI): m/e calc'd for C$_{21}$H$_{29}$N$_4$O: 353.2341, found 353.2328; 355(3), 354(23), 353(100).

Example 778 spectral data: TLC $R_F$ 0.58(30:70 ethyl acetate-hexane). $^1$H NMR(300MHz, CDCl$_3$): δ8.97(1H, s), 7.86(1H, d, J=8.0Hz), 7.83(1H, d, J=0.8Hz), 7.68(1H, dd, J=8.0, 0.8Hz), 4.30(1H, br), 2.96(2H, q, J=7.5Hz), 2.41 (2H, br), 2.11–1.95(2H, m), 1.43(3H, t, J=7.5Hz), 1.42–1.22(2H, m), 0.92(3H, t, J=7.3Hz), 0.83(3H, t, J=7.3Hz). MS(NH$_3$—CI): m/e 414(8), 413(39), 412(28), 411(100).

Example 779 spectral data: TLC $R_F$ 0.44(30:70 ethyl acetate-hexane). $^1$H NMR(300MHz, CDCl$_3$): δ8.91(1H, s), 7.84(1H, d, J=1.8Hz), 7.72(1H, d, J=8.0Hz), 7.65(1H, dd, J=8.0, 1.8Hz), 4.31(1H, br), 2.94(1H, q, J=7.5Hz), 2.40 (2H, br), 2.10–1.93(2H, m), 1.40(3H, t, J=7.5Hz), 1.37–1.21(1H, m), 1.19–1.02(1H, m), 0.91(3H, t, J=7.3Hz), 0.81 (3H, t, J=7.3Hz). MS(NH$_3$—CI): m/e 414(9), 413(43), 412(31), 411(100).

Example 793 spectral data: MS(NH$_3$—CI): m/e 367(M+H$^+$, 100%).

Example 799 spectral data: TLC $R_F$ 0.61(30:70 ethyl acetate-hexane). $^1$H NMR(300MHz, CDCl$_3$): δ8.90(1H, s), 7.47(1H, s), 7.10(1H, s), 4.28(1H, br), 2.93(2H, q, J=7.3Hz), 2.41(1H, br), 2.36(3H, s), 2.28(6H, s), 2.07–1.91(3H, m), 1.42(3H, t, J=7.3Hz), 1.35–1.21(1H, m), 1.19–1.03(1H, m), 0.90(3H, t, J=7.2Hz), 0.81(3H, t, J=7.3Hz). MS(NH$_3$—CI): m/e calc'd for C$_{22}$H$_{30}$N$_4$: 350.2470, found 350.2476; 353(3), 352(24), 351(100).

Example 802 spectral data: TLC $R_F$ 0.38(30:70 ethyl acetate-hexane). $^1$H NMR(300MHz, CDCl$_3$): δ8.92(1H, s), 7.84(1H, d, J=1.8Hz), 7.73(1H, d, J=8.4Hz), 7.65(1H, dd, J=8.4, 1.8Hz), 3.53(1H, br), 2.91(1H, q, J=7.4Hz), 2.52–2.35(1H, m), 2.34–2.20(1H, m), 1.95(1H, br), 1.40(3H, t, J=7.4Hz), 0.89–0.79(1H, m), 0.87(3H, t, J=7.3Hz), 0.55–0.42(2H, m), 0.25–0.15(1H, m). MS(NH$_3$—CI): m/e 412(8), 411(41), 410(29), 409(100).

Example 803 spectral data: TLC $R_F$ 0.33(30:70 ethyl acetate-hexane). $^1$H NMR(300MHz, CDCl$_3$): δ8.93(1H, s), 7.85(1H, d, J=2.2Hz), 7.71(1H, d, J=8.4Hz), 7.64(1H, dd, J=6.4, 2.2Hz), 3.77(1H, dq, J=9.9, 7.0Hz), 2.93(1H, dq, J=7.5, 2.0Hz), 2.09–1.98(1H, m), 1.82(3H, d, J=7.0Hz), 1.39(3H, t, J=7.5Hz), 0.86–0.78(1H, m), 0.59–0.50(1H, m), 0.49–0.40(1H, m), 0.29–0.20(1H, m). MS(NH$_3$—CI): m/e 399(2), 398(8), 397(39), 396(24), 395(100).

Example 804 spectral data: TLC $R_F$ 0.31(20:80 ethyl acetate-hexane). $^1$H NMR(300MHz, CDCl$_3$): δ8.92(1H, s), 7.84(1H, d, J=1.8Hz), 7.71–7.62(2H, m), 4.55(1H, m), 2.95(2H, q, J=7.5Hz), 2.43–2.32(1H, m), 2.10–1.98(1H, m), 1.75(3H, d, J=7.0Hz), 1.39(3H, t, J=7.5Hz), 1.38–1.27(1H, m), 1.19–1.09(1H, m), 0.93(3H, t, J=7.1Hz). MS(NH$_3$—CI): m/e 400(7), 399(32), 398(22), 397(100). Analysis calc'd for C$_{19}$H$_{20}$ClF$_3$N$_4$: C, 57.51; H, 5.08; N, 14.12; found: C, 57.55; H, 5.06; N, 13.95.

Example 805 spectral data: TLC $R_F$ 0.41(30:70 ethyl acetate-hexane). $^1$H NMR(300MHz, CDCl$_3$): δ8.92(1H, s), 7.84(1H, d, J=1.8Hz), 7.70(1H, d, J=8.0Hz), 7.64(1H, dd, J=8.0, 1.8Hz), 4.58–4.49(1H, m), 2.95(1H, q, J=7.5Hz), 2.45–2.33(1H, m), 2.11–2.00(1H, m), 1.75(3H, d, J=6.6Hz), 1.39(3H, t, J=7.5Hz), 1.38–1.21(4H, n), 0.86(3H, t, J=7.0Hz). MS(NH$_3$—CI): m/e 414(8), 413(40), 412(29), 411(100).

Example 807 spectral data: TLC $R_F$ 0.49(30:70 ethyl acetate-hexane). $^1$H NMR(300MHz, CDCl$_3$): δ8.91(1H, s), 7.84(1H, d, J=1.8Hz), 7.73(1H, d, J=8.4Hz), 7.65(1H, dd, J=8.4, 1.8Hz), 4.38–4.19(1H, m), 2.94(1H, q, J=7.5Hz), 2.40(2H, br), 2.10–1.98(2H, m), 1.41(3H, t, J=7.5Hz), 1.38–1.20(3H, m), 1.09–0.99(1H, m), 0.84(3H, t, J=7.0Hz), 0.81(3H, t, J=7.5Hz). MS(NH$_3$—CI): m/e 428(7), 427(32), 426(25), 425(100).

Example 808 spectral data: TLC $R_F$ 0.51(30:70 ethyl acetate-hexane). $^1$H NMR(300MHz, CDCl$_3$): δ8.91(1H, s), 7.84(1H, d, J=1.8Hz), 7.72(1H, d, J=8.4Hz), 7.64(1H, dd, J=8.4, 1.8Hz), 4.37(1H, br), 2.93(1H, q, J=7.5Hz), 2.38 (2H, br), 2.02–1.90(2H, m), 1.40(3H, t, J=7.5Hz), 1.38–1.20(2H, m), 1.18–1.01(2H, m), 0.90(6H, t, J=7.3Hz). MS(NH$_3$—CI): m/e 428(8), 427(39), 426(30), 425(100).

Example 809 spectral data: TLC $R_F$ 0.40(30:70 ethyl acetate-hexane). $^1$H NMR(300MHz, CDCl$_3$): δ8.90(1H, s), 7.84(1H, d, J=2.2Hz), 7.72(1H, d, J=8.1Hz), 7.65(1H, dd, J=8.1, 2.2Hz), 4.20(1H, br), 2.94(1H, q, J=7.5Hz), 2.51–2.38(2H, m), 2.13–2.00(2H, m), 1.41(3H, t, J=7.5Hz), 0.82(6H, t, J=7.5Hz). MS(NH$_3$—CI): m/e 400(7), 399 (36), 398(25), 397(100).

Example 824 spectral data: TLC $R_F$ 0.27(20:80 ethyl acetate-hexane). $^1$H NMR(300MHz, CDCl$_3$): δ8.94(1H, s), 8.10(1H, s), 7.94(1H, d, J=8.8Hz), 7.87(1H, d, J=8.1Hz), 4.56(1H, m), 2.96(2H, q, J=7.5Hz), 2.40(1H, m), 2.10–2.00(1H, m), 1.76(3H, d, J=7.0Hz), 1.39(3H, t, J=7.5Hz), 1.33–1.10(2H, m), 0.93(3H, t, J=7.1Hz). $^{19}$F NMR (300MHz, CDCl$_3$): δ-58.2, -63.4. MS(NH$_3$—CI): m/e 433(3), 432(24), 431(100).

Example 832 spectral data: TLC $R_F$ 0.34(30:70 ethyl acetate-hexane). $^1$H NMR(300MHz, CDCl$_3$): δ8.94(1H, s), 7.73(1H, d, J=8.5Hz), 7.10(1H, d, J=2.6Hz), 6.96(1H, dd, J=8.5, 2.6Hz), 3.87(3H, s), 3.55(1H, br), 2.92(2H, q, J=7.3Hz), 2.53–2.35(1H, m), 2.31–2.18(1H, m), 1.96(1H, br), 1.42(3H, t, J=7.3Hz), 0.87(3H, t, J=7.5Hz), 0.87–0.79 (1H, m), 0.53–0.43(2H, m), 0.25–0.15(1H, m). MS(NH$_3$—CI): m/e 374(8), 373(34), 372(24), 371(100).

Example 833 spectral data: TLC $R_F$ 0.20(30:70 ethyl acetate-hexane). $^1$H NMR(300MHz, CDCl$_3$): δ8.96(1H, s), 7.70(1H, d, J=8.4Hz), 7.10(1H, d, J=2.5Hz), 6.96(1H, dd, J=8.4, 2.5Hz), 4.16(2H, d, J=7.0Hz), 3.87(3H, s), 3.01 (2H, q, J=7.3Hz), 1.46(3H, t, J=7.3Hz), 1.37–1.27(1H, m), 0.66–0.52(4H, m). MS(NH$_3$—CI): m/e 346(6), 345(32), 344(23), 343(100).

Example 834 spectral data: TLC $R_F$ 0.18(30:70 ethyl acetate-hexane). $^1$H NMR(300MHz, CDCl$_3$): δ8.94(1H, s), 7.69(1H, d, J=8.4Hz), 7.09(1H, d, J=1Hz), 6.96(1H, dd, J=8.4, 1Hz), 4.60–4.50(1H, m), 3.87(3H, s), 2.97(2H, q, J=7.3Hz), 2.49–2.33(1H, m), 2.09–1.97(1H, m), 1.74(3H, d, J=7.0Hz), 1.41(3H, t, J=7.5Hz), 1.40–1.22(1H, m), 1.21–1.09(1H, m), 0.92(3H, t, J=7.1Hz). MS(NH$_3$—CI): m/e calc'd for C$_{19}$H$_{24}$ClN$_4$O: 359.1639, found 359.1623; 362(7), 361(33), 360(23), 359(100). Analysis calc'd for C$_{19}$H$_{23}$ClN$_4$O.0.5H$_2$O: C, 62.20; H, 6.32; N, 15.27; found: C, 62.33; H, 6.36; N, 14.86.

Example 835 spectral data: TLC $R_F$ 0.39(30:70 ethyl acetate-hexane). $^1$H NMR(300MHz, CDCl$_3$): δ8.94(1H, s), 7.69(1H, d, J=8.4Hz), 7.09(1H, d, J=2.5Hz), 6.95(1H, dd, J=8.4, 2.5Hz), 4.53–4.47(1H, m), 3.87(3H, s), 3.01–2.92 (2H, m), 2.48–2.35(1H, m), 2.11–1.99(1H, m), 1.74(3H, d, J=6.9Hz), 1.41(3H, t, J=7.5Hz), 1.38–1.22(3H, m), 1.14–1.00(1H, m), 0.86(3H, t, J=7.1Hz). MS(NH$_3$—CI): m/e 376(7), 375(33), 374(23), 373(100).

TABLE 1-continued

Example 836 spectral data: TLC $R_F$ 0.42(30:70 ethyl acetate-hexane). $^1$H NMR(300MHz, CDCl$_3$): δ8.94(1H, s), 7.79(1H, d, J=8.8Hz), 7.09(1H, d, J=2.5Hz), 6.95(1H, dd, J=8.8, 2.5Hz), 4.55–4.47(1H, m), 3.87(3H, s), 3.01–2.92 (2H, m), 2.48–2.35(1H, m), 2.10–1.97(1H, m), 1.74(3H, d, J=7.0Hz), 1.41(3H, t, J=7.5Hz), 1.35–1.20(5H, m), 1.18–1.02(1H, m), 0.84(3H, t, J=7.0Hz). MS(NH$_3$—CI): m/e calc'd for C$_{21}$H$_{28}$ClN$_4$O: 387.1952, found 387.1944; 391(1), 390(8), 389(35), 388(25), 387(100).

Example 837 spectral data: TLC $R_F$ 0.45(30:70 ethyl acetate-hexane). $^1$H NMR(300MHz, CDCl$_3$): δ8.93(1H, s), 7.73(1H, d, J=8.8Hz), 7.09(1H, d, J=2.6Hz), 6.96(1H, dd, J=8.8, 2.6Hz), 4.25(1H, br), 3.87(3H, s), 2.95(2H, q, J=7.3Hz), 2.41(2H, br), 2.10–2.00(2H, m), 1.43(3H, t, J=7.3Hz), 1.37–1.20(3H, m), 1.12–0.98(1H, m), 0.84(3H, t, J=7.3Hz), 0.82(3H, t, J=7.4Hz). MS(NH$_3$—CI): m/e 390(8), 389(34), 388(25), 387(100).

Example 838 spectral data: TLC $R_F$ 0.48(30:70 ethyl acetate-hexane). $^1$H NMR(300MHz, CDCl$_3$): δ8.94(1H, s), 7.72(1H, d, J=8.5Hz), 7.09(1H, d, J=2.2Hz), 6.96(1H, dd, J=8.5, 2.2Hz), 4.36(1H, v br), 3.87(3H, s), 2.94(2H, q, J=7.3Hz), 2.39(2H, br), 2.02–1.90(2H, m), 1.42(3H, t, J=7.3Hz), 1.39–1.21(2H, m), 1.18–1.03(2H, m), 0.90(6H, t, J=7.3Hz). MS(NH$_3$—CI): m/e calc'd for C$_{21}$H$_{28}$ClN$_4$O: 387.1952, found 387.1958; 391(1), 390(8), 389(34), 388 (26), 387(100).

Example 839 spectral data: TLR $R_F$ 0.36(30:70 ethyl acetate-hexane). $^1$H NMR(300MHz, CDCl$_3$): δ8.93(1H, s), 7.73(1H, d, J=8.5Hz), 7.09(1H, d, J=2.6Hz), 6.96(1H, dd, J=8.5, 2.6Hz), 4.19(1H, br s), 3.87(3H, s), 2.96(2H, q, J=7.5Hz), 2.52–2.38(2H, m), 2.03–1.99(2H, m), 1.43(3H, t, J=7.5Hz), 0.83(6H, t, J=7.3Hz). MS(NH$_3$—CI): m/e calc'd for C$_{19}$H$_{24}$ClN$_4$O: 359.1639, found 359.1632; 362(7), 361(34), 360(23), 359(100).

Example 870 spectral data: MS(NH$_3$—CI): m/e 423(M+H$^+$, 100%).

Example 900 spectral data: TLC $R_F$ 0.38(50:50 ethyl acetate-hexane). $^1$H NMR(300MHz, CDCl$_3$): δ8.93(1H, s), 7.75(1H, d, J=9.2Hz), 6.90–6.86(2H, m), 4.23(2H, t, J=7.7Hz), 3.86(3H, s), 2.95(2H, q, J=7.7Hz), 2.48(3H, s), 1.93–1.83(2H, m), 1.45(3H, t, J=7.6Hz), 1.43–1.36(4H, m), 0.92(3H, t, J=7.0Hz).

Example 902 spectral data: TLC $R_F$ 0.28(5:95 ethyl acetate-dichloromethane). $^1$H NMR(300MHz, CDCl$_3$): δ8.94 (1H, s), 7.63(1H, d, J=8.1Hz), 7.37(1H, d, J=1.0Hz), 7.21(1H, dd, J=8.1, 1.0Hz), 4.38(1H, br), 2.94(2H, q, J=7.5Hz), 2.41(3H, s), 2.40(2H, br), 2.00–1.90(2H, m), 1.42(3H, t, J=7.5Hz), 1.35–1.22(2H, m), 1.17–1.03(2H, m), 0.90(6H, t, J=7.3Hz). MS(NH$_3$—CI): m/e calc'd for C$_{21}$H$_{28}$ClN$_4$: 371.2002, found 371.1993; 374(8), 373(34), 372 (25), 371(100).

Example 944 spectral data: MS(NH$_3$—CI): m/e 377(M+H$^+$, 100%).
Example 945 spectral data: MS(NH$_3$—CI): m/e 365(M+H$^+$, 100%).
Example 947 spectral data: MS(NH$_3$—CI): m/e 353(M+H$^+$, 100%).
Example 951 spectral data: MS(NH$_3$—CI): m/e 381(M+H$^+$, 100%).
Example 952 spectral data: MS(NH$_3$—CI): m/e 353(M+H$^+$, 100%).

Example 1003 spectral data: TLC $R_F$ 0.10(30:70 ethyl acetate-hexane). $^1$H NMR(300MHz, CDCl$_3$): δ8.99(1H, s), 7.43(1H, s), 7.19(2H, d, J=8.8Hz), 6.86(2H, d, J=8.8Hz), 6.84(1H, s), 5.42(2H, s), 3.94(3H, s), 3.91(3H, s), 3.78(3H, s), 2.86(2H, q, J=7.7Hz), 2.45(3H, s), 1.35(3H, t, J=7.7Hz). MS(NH$_3$—CI): m/e 421(4), 420(27), 419(100). Analysis calculated for C$_{24}$H$_{26}$N$_4$O$_3$: C, 68.88; H, 6.26; N, 13.39; found: C, 68.53; H, 6.30; N, 12.96.

Example 1012 spectral data: m.p. 147–148° C. TLC $R_F$ 0.18(30:70 ethyl acetate-hexane). $^1$H NMR(300MHz, CDCl$_3$): δ8.88(1H, s), 7.60(1H, s), 6.77(1H, s), 4.61(2H, t, J=8.6Hz), 3.44(1H, v br), 3.24(2H, t, J=8.6Hz), 2.94(2H, br), 2.44(3H, s), 2.03(2H, v br), 1.45(3H, br t, J=6Hz), 0.89–0.79(2H, m), 0.58(2H, br), 0.50–0.40(2H, m), 0.27–0.17(2H, m). MS(NH$_3$—CI): m/e 377(4), 376(27), 375(100). Analysis calc'd for C$_{23}$H$_{26}$N$_4$O: C, 73.77; H, 7.01; N, 14.96; found: C, 73.69; H, 7.08; N, 14.40.

Example 1023 spectral data: TLC $R_F$ 0.22(30:70 ethyl acetate-hexane). $^1$H NMR(300MHz, CDCl$_3$): δ9.04(1H, s), 7.78(1H, d, =8.4Hz), 7.44(1H, d, J=1.1Hz), 7.30(1H, d, J=8.4, 1.1Hz), 7.20(2H, d, J=8.5Hz), 6.87(2H, d, =8.5Hz), 5.44 (2H, s), 3.79(3H, s), 2.90(2H, q, J=7.5Hz), 1.32(3H, t, J=7.5Hz). MS(NH$_3$—CI): m/e 467(1), 466(8), 465(35), 464 (27), 463(100).

Example 1027 spectral data: TLC $R_F$ 0.41(25:75 ethyl acetate-hexane). $^1$H NMR(300MHz, CDCl$_3$): δ8.96(1H, s), 7.76(1H, d, J=8.4Hz), 7.45–7.44(1H, m), 7.27(1H, dm, J=8Hz), 4.61–4.51(1H, m), 2.98(2H, dq, J=7.5, 1.6Hz), 2.48–2.35(1H, m), 2.10–1.98(1H, m), 1.75(3H, d, J=7.0Hz), 1.41(3H, t, J=7.5Hz), 1.35–1.22(2H, m), 0.93(3H, t, J=7.2Hz). MS(NH$_3$—CI): m/e calculated for C$_{19}$H$_{21}$ClF$_3$N$_4$O: 413.1349, found 413.1344; 416(8), 415(35), 414(24), 413(100).

Example 1028 spectral data: TLC $R_F$ 0.45(25:75 ethyl acetate-hexane). $^1$H NMR(300MHz, CDCl$_3$): δ8.96(1H, s), 7.77(1H, d, J=8.4Hz), 7.44(1H, m), 7.27(1H, dm, J=8Hz), 4.57–4.49(1H, m), 2.97(2H, dq, J=7.7, 1.7Hz), 2.47–2.36 (1H, m), 2.12–2.02(1H, m), 1.75(3H, d, J=7.0Hz), 1.41(3H, t, J=7.7Hz), 1.33–1.21(4H, m), 0.86(3H, t, J=7.3Hz). MS(NH$_3$—CI): m/e calculated for C$_{20}$H$_{23}$ClF$_3$N$_4$O: 427.1509, found 427.1507; 430(8), 429(35), 428(25), 427(100).

Example 1032 spectral data: TLC $R_F$ 0.44(25:75 ethyl acetate-hexane). $^1$H NMR(300MHz, CDCl$_3$): δ8.95(1H, s), 7.80(1H, d, J=8.4Hz), 7.45–7.44(1H, m), 7.30(1H, dm, J=8Hz), 4.23–4.17(1H, m), 2.97(2H, q, J=7.6Hz), 2.54–2.39 (2H, m), 2.14–2.00(2H, m), 1.43(3H, t, J=7.6Hz), 0.84(6H, t, J=7.3Hz). MS(NH$_3$—CI): m/e calculated for C$_{19}$H$_{21}$ClF$_3$N$_4$O: 413.1368, found 413.1373; 416(8), 415(34), 414(24), 413(100).

Example 1150 spectral data: TLC $R_F$ 0.23(30:70 ethyl acetate-hexane). $^1$H NMR(300MHz, CDCl$_3$): δ8.90(1H, s), 7.73(1H, d, J=8.8Hz), 7.36(1H, d, J=2.6Hz), 7.17(1H, dd, J=8.8, 2.6Hz), 3.92(3H, s), 3.70–3.55(1H, m), 2.91(2H, q, J=7.4Hz), 2.45–2.35(1H, m), 2.25–2.15(1H, m), 2.00–1.90(1H, m), 1.40(3H, t, J=7.4Hz), 1.40–1.30(1H, m), 1.20–1.10(1H, m), 0.91(3H, t, J=7.2Hz), 0.87–0.77(1H, m), 0.54–0.44(2H, m), 0.25–0.15(1H, m). MS(NH$_3$—CI): m/e calc'd for C$_{22}$H$_{26}$F$_3$N$_4$O: 419.2057; found 419.2058; 421(3), 420(26), 419(100).

Example 1153 spectral data: TLC $R_F$ 0.48(30:70 ethyl acetate-hexane). $^1$H NMR(300MHz, CDCl$_3$): δ9.00(1H, s), 7.89(1H, d, J=8.0Hz), 7.84(1H, s), 7.69(1H, d, J=8.0Hz), 7.40–7.30(5H, m), 5.14(1H, d, J=10.2Hz), 2.82(1H, dq, J=15.5, 7.7Hz), 2.68(1H, dq, J=15.5, 7.7Hz), 2.15(1H, br), 1.23(3H, t, J=7.7Hz), 1.13–1.03(1H, m), 0.78–0.62(2H, m), 0.53–0.43(1H, m). MS(NH$_3$—CI): m/e calculated for C$_{24}$H$_{21}$ClF$_3$N$_4$: 457.1407, found 457.1389; 460(9), 459 (35), 458(29), 457(100).

Example 1155 spectral data: TLC $R_F$ 0.46(25:75 ethyl acetate-hexane). $^1$H NMR(300MHz, CDCl$_3$): δ8.98(1H, s), 7.83(1H, d, J=8.4Hz), 7.46–7.27(7H, m), 5.13(1H, d, J=10.7Hz), 2.88–2.62(2H, m), 2.15(1H, br), 1.26(3H, t, J=7.5Hz), 1.12–1.02(1H, m), 0.78–0.62(2H, m), 0.54–0.44(1H, m). MS(NH$_3$—CI): m/e calculated for C$_{24}$H$_{21}$ClF$_3$N$_4$O: 473.1361, found 473.1365; 476(9), 475(36), 474(29), 473(100).

Example 1157 spectral data: TLC $R_F$ 0.19(30:70 ethyl acetate-hexane). $^1$H NMR(300MHz, CDCl$_3$): δ8.93(1H, s), 7.77(1H, d, J=8.8Hz), 7.40–7.30(6H, m), 7.19(1H, dd, J=8.8, 2.2Hz), 5.13(1H, d, J=10.6Hz), 3.92(3H, s), 2.79(1H, dq, J=15, 7.7Hz), 2.64(1H, dq, J=15, 7.7Hz), 2.12(1H, br), 1.21(3H, t, J=7.7Hz), 1.10–1.00(1H, m), 0.77–0.62(2H, m), 0.55–0.45(1H, m). MS(NH$_3$—CI): m/e calc'd for C$_{25}$H$_{24}$F$_3$N$_4$O: 453.1902, found 453.1903; 455(4), 454(28), 453(100).

Example 1158 spectral data: TLC $R_F$ 0.16(20:80 ethyl acetate-hexane). $^1$H NMR(300MHz, CDCl$_3$): δ8.98(1H, s), 7.46–7.25(7H, m), 5.12(1H, br d, J=9Hz), 2.85–2.62(2H, m), 2.14(1H, br), 2.13(3H, d, J=0.7Hz), 1.18(3H, dq, J=7.7, 4.1Hz), 0.75–0.35(4H, m). MS(NH$_3$—CI): m/e calc'd for C$_{24}$H$_{23}$Cl$_2$N$_4$: 437.1300, found 437.1294; 440(19), 439(67), 438(32), 437(100).

TABLE 1-continued

Example 1161 spectral data: MS(NH$_3$—CI): m/e 441(M+H$^+$, 100%).
Example 1163 spectral data: TLC R$_F$ 0.44(30:70 ethyl acetate-hexane). $^1$H NMR(300MHz, CDCl$_3$): δ9.00(1H, s), 7.89(1H, d, 8.4Hz), 7.84(1H, s), 7.69(1H, d, J=8.4Hz), 7.38(2H, d, J=9Hz), 7.05(2H, d, J=9Hz), 5.08(1H, d, J=10.2Hz), 2.82(1H, dq, J=15.5, 7.7Hz), 2.68(1H, dq, J=15.5, 7.7Hz), 2.14(1H, m), 1.25(3H, t, J=7.7Hz), 1.10–1.01 (H, m), 0.74–0.62(2H, m), 0.51–0.41(1H, m). MS(NH$_3$—CI): m/e calculated for C$_{24}$H$_{20}$ClF$_4$N$_4$: 475.1313, found (30), 475(100).
Example 1222 spectral data: MS(NH$_3$—CI): m/e 363(M+H$^+$, 100%).
Example 1252 spectral data: TLC R$_F$ 0.24(20:80 ethyl acetate-hexane). $^1$H NMR(300MHz, CDCl$_3$): δ8.72(1H, s), 7.87(1H, dd, J=8.8, 5.5Hz), 7.46(1H, dd, J=8.8, 2.5Hz), 7.35–7.26(1H, m), 7.24–7.18(6H, m), 7.08–7.01(4H, m), 4.89–4.79(1H, m), 4.49(2H, d, J=12.1Hz), 4.37(2H, d, J=12.1Hz), 4.27(2H, t, J=9.3Hz), 4.01(2H, dd, J=9.9, 5.2Hz), 2.98(2H, q, J=7.7Hz), 1.39(3H, t, J=7.7Hz). MS(NH$_3$—CI): m/e calc'd for C$_{31}$H$_{29}$F$_6$N$_4$O$_2$: 565.2227, found 565.2226; 567(7), 566(36), 565(100).
Example 1255 spectral data: TLC R$_F$ 0.50(25:75 ethyl acetate-hexane). $^1$H NMR(300MHz, CDCl$_3$): δ8.96(1H, s), 7.80(1H, d, J=8.4Hz), 7.45–7.43(1H, m), 7.31–7.27(1H, dm, J=8Hz), 3.80–3.73(1H, m), 2.93(2H, q, J=7.3Hz), 2.40 (1H, br), 2.25–2.14(1H, m), 1.95(1H, br), 1.42(3H, t, J=7.5Hz), 1.35–1.10(2H, m), 0.92(3H, t, J=7.3Hz), 0.91–0.80 (1H, m), 0.53–0.44(2H, m), 0.24–0.14(1H, m). MS(NH$_3$—CI): m/e calculated for C$_{21}$H$_{23}$ClF$_3$N$_4$O: 439.1519, found 439.1524; 442(8), 441(34), 440(26), 439(100).
Example 1256 spectral data: TLC R$_F$ 0.48(25:75 ethyl acetate-hexane). $^1$H NMR(300MHz, CDCl$_3$): δ8.95(1H, s), 7.79(1H, d, J=8.4Hz), 7.45–7.43(1H, m), 7.27(1H, dm, J=8Hz), 4.35–4.25(1H, m), 2.96(2H, q, J=7.4Hz), 2.42(2H, br), 2.12–1.93(2H, m), 1.43(3H, t, J=7.4Hz), 1.37–1.22(2H, m), 0.91(3H, t, J=7.2Hz), 0.83(3H, t, J=7.5Hz). MS(NH$_3$—CI): m/e calculated for C$_{20}$H$_{23}$ClF$_3$N$_4$O: 427.1514, found 427.1515; 430(8), 429(34), 428(25), 427(100).
Example 1295 spectral data: TLC R$_F$ 0.37(50:50 ethyl acetate-hexane). $^1$H NMR(300MHz, CDCl$_3$): δ8.91(1H, s), 7.38(1H, s), 6.83(1H, s), 4.46(1H, m, J=7.3Hz), 3.94(3H, s), 3.91(3H, s), 2.96(2H, q, J=7.6Hz), 2.49–2.39(1H, m), 2.43(3H, s), 2.12–2.02(1H, m), 1.75(3H, d, J=6.5Hz), 1.44(3H, t, J=7.5Hz), 0.86(3H, t, J=7.5Hz). MS(NH$_3$—CI): m/e calc'd for C$_{20}$H$_{27}$N$_4$O$_2$: 355.2134, found 355.2139; 357(3), 356(23), 355(100).
Example 1296 spectral data: TLC R$_F$ 0.37(30:70 ethyl acetate-hexane). $^1$H NMR(300MHz, CDCl$_3$): δ9.00(1H, s), 7.68(1H, d, J=8.4Hz), 7.57(1H, d, J=2.2Hz), 7.39(1H, dd, J=8.4, 2.2Hz), 7.27(2H, d, J=8.4Hz), 6.89(2H, d, J=8.4Hz), 5.56(1H, dd, J=9.7, 7.4Hz), 3.79(3H, s), 2.92–2.75(3H, m), 2.65–2.55(1H, m), 1.31(3H, t, J=7.5Hz), 0.92 (3H, t, J=6.6Hz). MS(NH$_3$—CI): m/e calc'd for C$_{23}$H$_{23}$Cl$_2$N$_4$O: 441.1249, found 441.1247; 445(12), 444(18), 443 (67), 442(30), 441(100).
Example 1319 spectral data: MS(NH$_3$—CI): m/e 459(M+H$^+$, 100%).
Example 1320 spectral data: $^1$H NMR(300MHz, CDCl$_3$): δ8.99(s, 1H), 7.68(d, 1H, J=8.4Hz), 7.58(d, 1H, J=1.9Hz), 7.42–7.3(m, 6H), 6.04(q, 1H), 2.82,(m, 2H), 2.16(d, 3H, J=7.4Hz), 1.27(t, 3H, J=7.3, 7.7Hz).
Example 1321 7906-5 spectral data: $^1$H NMR(300MHz, CDCl$_3$): δ9.02(s, 1H), 7.98(d, 1H), 7.71(d, 1H), 7.57(d, 1H), 7.42–7.26(m, 3H), 7.15(m, 1H), 5.38(d, 1H), 2.65(m, 1H), 2.4(m, 1H), 1.85(m, 1H) 1.82(s, 3H), 0.97(t, 3H), 0.8(m, 2H), 0.6(m, 2H).
Example 1322 spectral data: MS(NH$_3$—CI): m/e 437(M+H$^+$, 100%).
Example 1323 spectral data: MS(NH$_3$—CI): m/e 455(M+H$^+$, 100%).
Example 1324 spectral data: MS(ESI): m/e 425(M+H$^+$), 381(M+H$^+$ —CO$_2$, 100%).
Example 1325 spectral data: MS(NH$_3$—CI): m/e 413(M+H$^+$, 100%).
Example 1326 spectral data: MS(NH$_3$—CI): m/e 427(M+H$^+$, 100%).
Example 1327 spectral data: MS(NH$_3$—CI): m/e 427(M+H$^+$, 100%).
Example 1328 spectral data: MS(NH$_3$—CI): m/e 427(M+H$^+$, 100%).
Example 1329 spectral data: MS(NH$_3$—CI): m/e 423(M+H$^+$, 100%).
Example 1330 spectral data: MS(NH$_3$—CI): m/e 418(M+H$^+$, 100%).
Example 1331 spectral data: MS(NH$_3$—CI): m/e 418(M+H$^+$, 100%).
Example 1332 spectral data: MS(NH$_3$—CI): m/e 499(M+H$^+$, 100%).
Example 1333 spectral data: MS(NH$_3$—CI): m/e 453(M+H$^+$, 100%).
Example 1334 spectral data: MS(NH$_3$—CI): m/e 423(M+H$^+$, 100%).
Example 1335 spectral data: MS(NH$_3$—CI): m/e 372(M+H$^+$, 100%).
Example 1337 spectral data: MS(NH$_3$—CI): m/e 443(M+H$^+$, 100%).
Example 1338 spectral data: MS(NH$_3$—CI): m/e 427(M+H$^+$, 100%).
Example 1339 spectral data: MS(NH$_3$—CI): m/e 379(M+H$^+$, 100%).
Example 1341 spectral data: MS(NH$_3$—CI): m/e 393(M+H$^+$, 100%).
Example 1342 spectral data: MS(NH$_3$—CI): m/e 378(M+H$^+$, 100%).
Example 1343 spectral data: MS(NH$_3$—CI): m/e 346(M+H$^+$, 100%).
Example 1344 spectral data: MS(NH$_3$—CI): m/e 363(M+H$^+$, 100%).
Example 1346 spectral data: MS(NH$_3$—CI): m/e 416(M+H$^+$, 100%).
Example 1370 spectral data: TLC R$_F$ 0.23(30:70 ethyl acetate-hexane). $^1$H NMR(300MHz, CDCl$_3$): δ8.89(1H, s), 7.72(1H, d, J=8.4Hz), 7.35(1H, d, J=2.5Hz), 7.17(1H, dd, J=8.4, 2.5Hz), 4.27(1H, br), 3.91(3H, s), 2.93(2H, q, J=7.7Hz), 2.40(2H, br), 2.10–1.95(2H, m), 1.41(3H, t, J=7.7Hz), 1.39–1.27(1H, m), 1.20–1.07(1H, m), 0.91(3H, t, J=7.3Hz), 0.81(3H, t, J=7.5Hz). MS(NH$_3$—CI): m/e calc'd for C$_{22}$H$_{26}$F$_3$N$_4$O: 407.2058, found 407.2052; 409(3), 408(24), 407(100).
Example 1371 spectral data: MS(ESI): m/e 377(M+2), 375(M$^+$, 100%).
$^b$Q1 = 2-tetrazolyl
$^c$Q2 = 1,2,4-triazol-2-yl

TABLE 1A

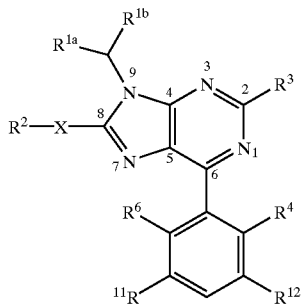
(A)

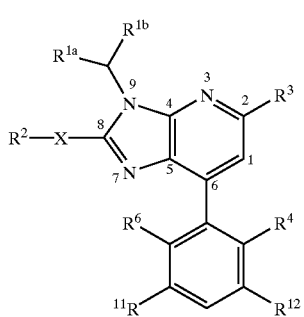
(B)

TABLE 1A-continued

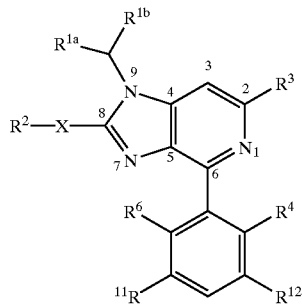
(C)

| Ex. No. | R² | X | R³ | R⁴ | R¹² | R¹¹ | R⁶ | R¹ᵃ | R¹ᵇ | mp, °C.ᵃ |
|---|---|---|---|---|---|---|---|---|---|---|
| 1043 | CH₃ | CH₂ | H | CH₃ | CH₃ | CH₃ | H | CH₃ | C₃H₇ | oil |

Key:
ᵃWhere the compound is indicated as an "oil", data is provided below:

Example 1043 spectral data: TLC $R_F$ 0.40 (30:70 ethyl acetate-hexane). ¹H NMR (300 MHz, CDCl₃): δ 8.91(1H, s), 7.43(1H, s), 7.10(1H, s), 4.60–4.50(1H, m), 2.94(2H, dq, J=7.5, 2.0Hz), 2.45–2.35(1H, m), 2.35(3H, s), 2.28(6H, s), 2.07–1.97(1H, m), 1.73(3H, d, J=6.9Hz), 1.41(3H, t, J=7.5Hz), 1.40–1.27(1H, m), 1.20–1.07(1H, m), 0.92(3H, t, J=7.3Hz). MS(NH₃—CI): m/e calc'd for C₂₃H₂₉N₄: 337.2392, found 337.2396; 339 (3), 338(23), 337(100). Analysis calc'd for C₂₁H₂₈N₄: C, 74.96; H, 8.40; N, 16.65; found: C, 74.28; H, 8.02; N, 16.37.

TABLE 1B

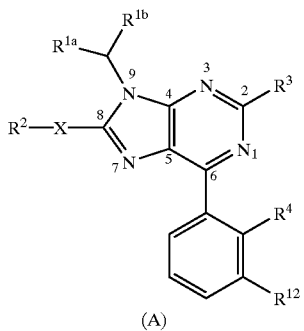
(A)

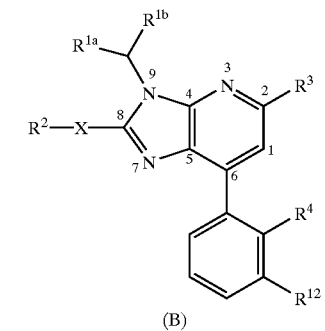
(B)

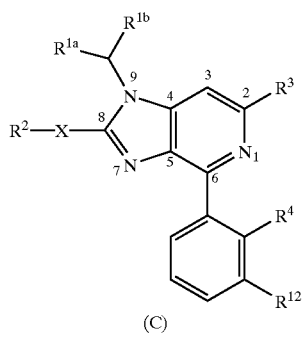
(C)

| Ex. No. | R² | X | R⁴ | R⁵ | R¹ᵃ | R¹ᵇ | mp, °C.ᵃ |
|---|---|---|---|---|---|---|---|
| 1270 | CH₃ | CH₂ | CF₃ | O(CH₂)₂—OH | c-C₃H₅ | c-C₃H₅ | — |
| 1271 | CH₃ | CH₂ | CF₃ | OCH₂CO₂— | c-C₃H₅ | c-C₃H₅ | — |

TABLE 1B-continued

| Ex. No. | | | | | | | mp, °C. |
|---|---|---|---|---|---|---|---|
| 1272 | CH₃ | CH₂ | CF₃ | OCH₂CO—N(CH₃)₂ | c-C₃H₅ | c-C₃H₅ | — |
| 1273 | CH₃ | CH₂ | CF₃ | O(CH₂)₂—NMe₃⁺Cl⁻ | c-C₃H₅ | c-C₃H₅ | — |
| 1274 | CH₃ | CH₂ | CF₃ | OCH₂CH—(OH)C₂H₅ | c-C₃H₅ | c-C₃H₅ | — |
| 1275 | CH₃ | CH₂ | OCH₂OCH₃ | CH₃ | CH₃ | C₃H₇ | 77–79 |
| 1276 | CH₃ | CH₂ | OH | CH₃ | CH₃ | C₃H₇ | — |
| 1277 | CH₃ | CH₂ | OC₂H₅ | CH₃ | CH₃ | C₃H₇ | — |
| 1278 | CH₃ | CH₂ | OC₃H₇ | CH₃ | CH₃ | C₃H₇ | — |
| 1279 | CH₃ | CH₂ | O(CH₂)₂—OH | CH₃ | CH₃ | C₃H₇ | — |
| 1280 | CH₃ | CH₂ | OCH₂CO₂—C₂H₅ | CH₃ | CH₃ | C₃H₇ | — |
| 1281 | CH₃ | CH₂ | OCH₂CO—N(CH₃)₂ | CH₃ | CH₃ | C₃H₇ | — |
| 1282 | CH₃ | CH₂ | O(CH₂)₂—NMe₃⁺Cl⁻ | CH₃ | CH₃ | C₃H₇ | — |
| 1283 | CH₃ | CH₂ | OCH₂CH—(OH)C₂H₅ | CH₃ | CH₃ | C₃H₇ | — |

TABLE 1C

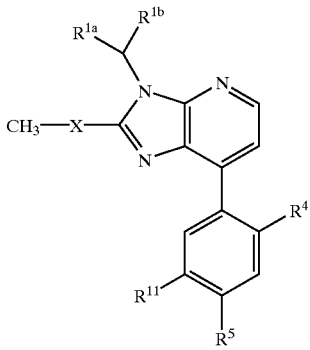
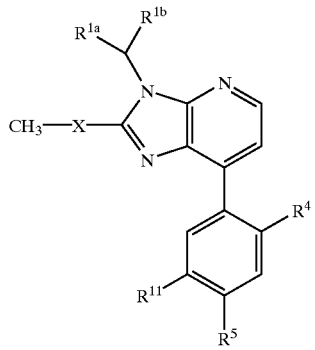

| Ex. No. | X | R⁴ | R⁵ | R¹¹ | R¹ᵃ | R¹ᵇ | mp, °C. |
|---|---|---|---|---|---|---|---|
| 1501 | CH₂ | Cl | CF₃ | H | C₃H₇ | OCH₃ | 76–78 |
| 1502 | CH₂ | Cl | CF₃ | H | C₂H₅ | C₂H₄OCH₃ | oil |
| 1503 | CH₂ | Cl | Cl | H | C₂H₅ | C₂H₄OCH₃ | — |
| 1504 | CH₂ | Cl | OCH₃ | H | C₂H₅ | C₂H₄OCH₃ | — |
| 1505 | CH₂ | CF₃ | OCH₃ | H | C₂H₅ | C₂H₄OCH₃ | — |
| 1506 | CH₂ | Cl | SO₂CH₃ | H | C₂H₅ | C₂H₄OCH₃ | — |
| 1507 | CH₂ | Cl | COCH₃ | H | C₂H₅ | C₂H₄OCH₃ | — |
| 1508 | CH₂ | CH₃ | OCH₃ | CH₃ | C₂H₅ | C₂H₄OCH₃ | — |
| 1509 | CH₂ | Cl | CH₃ | F | C₂H₅ | C₂H₄OCH₃ | — |
| 1510 | CH₂ | CH₃ | OCH₃ | F | C₂H₅ | C₂H₄OCH₃ | — |
| 1511 | CH₂ | CH₃ | CH₃ | CH₃ | C₂H₅ | C₂H₄OCH₃ | — |
| 1512 | CH₂ | Cl | CF₃ | H | c-C₃H₅ | C₂H₄OCH₃ | — |
| 1513 | CH₂ | Cl | Cl | H | c-C₃H₅ | C₂H₄OCH₃ | — |
| 1514 | CH₂ | Cl | OCH₃ | H | c-C₃H₅ | C₂H₄OCH₃ | — |
| 1515 | CH₂ | CF₃ | OCH₃ | H | c-C₃H₅ | C₂H₄OCH₃ | — |
| 1516 | CH₂ | Cl | SO₂CH₃ | H | c-C₃H₅ | C₂H₄OCH₃ | — |
| 1517 | CH₂ | Cl | COCH₃ | H | c-C₃H₅ | C₂H₄OCH₃ | — |
| 1518 | CH₂ | CH₃ | OCH₃ | CH₃ | c-C₃H₅ | C₂H₄OCH₃ | — |
| 1519 | CH₂ | Cl | CH₃ | F | c-C₃H₅ | C₂H₄OCH₃ | — |
| 1520 | CH₂ | CH₃ | OCH₃ | F | c-C₃H₅ | C₂H₄OCH₃ | — |
| 1521 | CH₂ | CH₃ | CH₃ | CH₃ | c-C₃H₅ | C₂H₄OCH₃ | — |
| 1522 | CH₂ | Cl | CF₃ | H | C₂H₅ | CH₂OCH₃ | oil |
| 1523 | CH₂ | Cl | Cl | H | C₂H₅ | CH₂OCH₃ | — |
| 1524 | CH₂ | Cl | OCH₃ | H | C₂H₅ | CH₂OCH₃ | — |
| 1525 | CH₂ | CF₃ | OCH₃ | H | C₂H₅ | CH₂OCH₃ | — |
| 1526 | CH₂ | Cl | SO₂CH₃ | H | C₂H₅ | CH₂OCH₃ | — |
| 1527 | CH₂ | Cl | COCH₃ | H | C₂H₅ | CH₂OCH₃ | — |
| 1528 | CH₂ | CH₃ | OCH₃ | CH₃ | C₂H₅ | CH₂OCH₃ | — |
| 1529 | CH₂ | Cl | CH₃ | F | C₂H₅ | CH₂OCH₃ | — |
| 1530 | CH₂ | CH₃ | OCH₃ | F | C₂H₅ | CH₂OCH₃ | — |
| 1531 | CH₂ | CH₃ | CH₃ | CH₃ | C₂H₅ | CH₂OCH₃ | — |
| 1532 | CH₂ | Cl | CF₃ | H | c-C₃H₅ | CH₂OCH₃ | — |
| 1533 | CH₂ | Cl | Cl | H | c-C₃H₅ | CH₂OCH₃ | — |
| 1534 | CH₂ | Cl | OCH₃ | H | c-C₃H₅ | CH₂OCH₃ | — |
| 1535 | CH₂ | CF₃ | OCH₃ | H | c-C₃H₅ | CH₂OCH₃ | — |
| 1536 | CH₂ | Cl | SO₂CH₃ | H | c-C₃H₅ | CH₂OCH₃ | — |
| 1537 | CH₂ | Cl | COCH₃ | H | c-C₃H₅ | CH₂OCH₃ | — |
| 1538 | CH₂ | CH₃ | OCH₃ | CH₃ | c-C₃H₅ | CH₂OCH₃ | — |
| 1539 | CH₂ | Cl | CH₃ | F | c-C₃H₅ | CH₂OCH₃ | — |
| 1540 | CH₂ | CH₃ | OCH₃ | F | c-C₃H₅ | CH₂OCH₃ | — |
| 1541 | CH₂ | CH₃ | CH₃ | CH₃ | c-C₃H₅ | CH₂OCH₃ | — |
| 1542 | O | Cl | CF₃ | H | C₂H₅ | C₂H₄OCH₃ | oil |
| 1543 | O | Cl | Cl | H | C₂H₅ | C₂H₄OCH₃ | — |
| 1544 | O | Cl | OCH₃ | H | C₂H₅ | C₂H₄OCH₃ | — |
| 1545 | O | CF₃ | OCH₃ | H | C₂H₅ | C₂H₄OCH₃ | — |
| 1546 | O | Cl | SO₂CH₃ | H | C₂H₅ | C₂H₄OCH₃ | — |
| 1547 | O | Cl | COCH₃ | H | C₂H₅ | C₂H₄OCH₃ | — |
| 1548 | O | CH₃ | OCH₃ | CH₃ | C₂H₅ | C₂H₄OCH₃ | — |
| 1549 | O | Cl | CH₃ | F | C₂H₅ | C₂H₄OCH₃ | — |
| 1550 | O | CH₃ | OCH₃ | F | C₂H₅ | C₂H₄OCH₃ | — |
| 1551 | O | CH₃ | CH₃ | CH₃ | C₂H₅ | C₂H₄OCH₃ | — |
| 1552 | O | Cl | CF₃ | H | c-C₃H₅ | C₂H₄OCH₃ | — |
| 1553 | O | Cl | Cl | H | c-C₃H₅ | C₂H₄OCH₃ | — |
| 1554 | O | Cl | OCH₃ | H | c-C₃H₅ | C₂H₄OCH₃ | — |
| 1555 | O | CF₃ | OCH₃ | H | c-C₃H₅ | C₂H₄OCH₃ | — |
| 1556 | O | Cl | SO₂CH₃ | H | c-C₃H₅ | C₂H₄OCH₃ | — |
| 1557 | O | Cl | COCH₃ | H | c-C₃H₅ | C₂H₄OCH₃ | — |
| 1558 | O | CH₃ | OCH₃ | CH₃ | c-C₃H₅ | C₂H₄OCH₃ | — |
| 1559 | O | Cl | CH₃ | F | c-C₃H₅ | C₂H₄OCH₃ | — |
| 1560 | O | CH₃ | OCH₃ | F | c-C₃H₅ | C₂H₄OCH₃ | — |
| 1561 | O | CH₃ | CH₃ | CH₃ | c-C₃H₅ | C₂H₄OCH₃ | — |
| 1562 | O | Cl | CF₃ | H | C₂H₅ | CH₂OCH₃ | oil |
| 1563 | O | Cl | OCH₃ | H | C₂H₅ | CH₂OCH₃ | — |
| 1564 | O | CF₃ | OCH₃ | H | C₂H₅ | CH₂OCH₃ | — |

TABLE 1C-continued

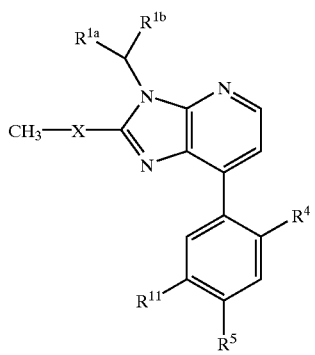

| Ex. No. | X | R$^4$ | R$^5$ | R$^{11}$ | R$^{1a}$ | R$^{1b}$ | mp, °C. |
|---|---|---|---|---|---|---|---|
| 1565 | O | Cl | SO$_2$CH$_3$ | H | C$_2$H$_5$ | CH$_2$OCH$_3$ | — |
| 1566 | O | Cl | COCH$_3$ | H | C$_2$H$_5$ | CH$_2$OCH$_3$ | — |
| 1567 | O | CH$_3$ | OCH$_3$ | CH$_3$ | C$_2$H$_5$ | CH$_2$OCH$_3$ | — |
| 1568 | O | Cl | CH$_3$ | F | C$_2$H$_5$ | CH$_2$OCH$_3$ | — |
| 1569 | O | CH$_3$ | OCH$_3$ | F | C$_2$H$_5$ | CH$_2$OCH$_3$ | — |
| 1570 | O | CH$_3$ | CH$_3$ | CH$_3$ | C$_2$H$_5$ | CH$_2$OCH$_3$ | — |
| 1571 | O | Cl | CF$_3$ | H | c-C$_3$H$_5$ | CH$_2$OCH$_3$ | — |
| 1572 | O | Cl | Cl | H | c-C$_3$H$_5$ | CH$_2$OCH$_3$ | — |
| 1573 | O | Cl | OCH$_3$ | H | c-C$_3$H$_5$ | CH$_2$OCH$_3$ | — |
| 1574 | O | CF$_3$ | OCH$_3$ | H | c-C$_3$H$_5$ | CH$_2$OCH$_3$ | — |
| 1575 | O | Cl | SO$_2$CH$_3$ | H | c-C$_3$H$_5$ | CH$_2$OCH$_3$ | — |
| 1576 | O | Cl | COCH$_3$ | H | c-C$_3$H$_5$ | CH$_2$OCH$_3$ | — |
| 1577 | O | CH$_3$ | OCH$_3$ | CH$_3$ | c-C$_3$H$_5$ | CH$_2$OCH$_3$ | — |
| 1578 | O | Cl | CH$_3$ | F | c-C$_3$H$_5$ | CH$_2$OCH$_3$ | — |
| 1579 | O | CH$_3$ | OCH$_3$ | F | c-C$_3$H$_5$ | CH$_2$OCH$_3$ | — |
| 1580 | O | CH$_3$ | CH$_3$ | CH$_3$ | c-C$_3$H$_5$ | CH$_2$OCH$_3$ | — |

TABLE 1D

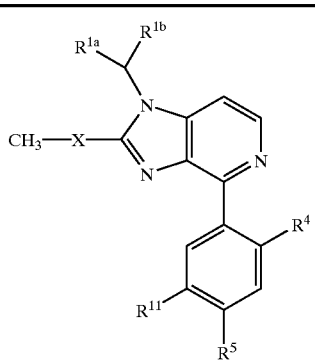

| Ex. No. | X | R$^4$ | R$^5$ | R$^{11}$ | R$^{1a}$ | R$^{1b}$ | mp, °C. |
|---|---|---|---|---|---|---|---|
| 1601 | CH$_2$ | CH$_3$ | Cl | H | C$_2$H$_5$ | c-C$_3$H$_5$ | 109–111 |
| 1602 | CH$_2$ | Cl | Cl | H | C$_2$H$_5$ | C$_2$H$_4$OCH$_3$ | — |
| 1603 | CH$_2$ | Cl | OCH$_3$ | H | C$_2$H$_5$ | C$_2$H$_4$OCH$_3$ | — |
| 1604 | CH$_2$ | CF$_3$ | OCH$_3$ | H | C$_2$H$_5$ | C$_2$H$_4$OCH$_3$ | — |
| 1605 | CH$_2$ | Cl | SO$_2$CH$_3$ | H | C$_2$H$_5$ | C$_2$H$_4$OCH$_3$ | — |
| 1606 | CH$_2$ | Cl | COCH$_3$ | H | C$_2$H$_5$ | C$_2$H$_4$OCH$_3$ | — |
| 1607 | CH$_2$ | CH$_3$ | OCH$_3$ | CH$_3$ | C$_2$H$_5$ | C$_2$H$_4$OCH$_3$ | — |
| 1608 | CH$_2$ | Cl | CH$_3$ | F | C$_2$H$_5$ | C$_2$H$_4$OCH$_3$ | — |
| 1609 | CH$_2$ | CH$_3$ | OCH$_3$ | F | C$_2$H$_5$ | C$_2$H$_4$OCH$_3$ | — |
| 1610 | CH$_2$ | CH$_3$ | CH$_3$ | CH$_3$ | C$_2$H$_5$ | C$_2$H$_4$OCH$_3$ | — |
| 1611 | CH$_2$ | Cl | CF$_3$ | H | c-C$_3$H$_5$ | C$_2$H$_4$OCH$_3$ | — |
| 1612 | CH$_2$ | Cl | Cl | H | c-C$_3$H$_5$ | C$_2$H$_4$OCH$_3$ | — |
| 1613 | CH$_2$ | Cl | OCH$_3$ | H | c-C$_3$H$_5$ | C$_2$H$_4$OCH$_3$ | — |
| 1614 | CH$_2$ | CF$_3$ | OCH$_3$ | H | c-C$_3$H$_5$ | C$_2$H$_4$OCH$_3$ | — |
| 1615 | CH$_2$ | Cl | SO$_2$CH$_3$ | H | c-C$_3$H$_5$ | C$_2$H$_4$OCH$_3$ | — |
| 1616 | CH$_2$ | Cl | COCH$_3$ | H | c-C$_3$H$_5$ | C$_2$H$_4$OCH$_3$ | — |

TABLE 1D-continued

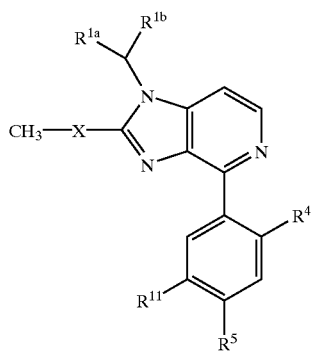

| Ex. No. | X | R$^4$ | R$^5$ | R$^{11}$ | R$^{1a}$ | R$^{1b}$ | mp, °C. |
|---|---|---|---|---|---|---|---|
| 1617 | CH$_2$ | CH$_3$ | OCH$_3$ | CH$_3$ | c-C$_3$H$_5$ | C$_2$H$_4$OCH$_3$ | — |
| 1618 | CH$_2$ | Cl | CH$_3$ | F | c-C$_3$H$_5$ | C$_2$H$_4$OCH$_3$ | — |
| 1619 | CH$_2$ | CH$_3$ | OCH$_3$ | F | c-C$_3$H$_5$ | C$_2$H$_4$OCH$_3$ | — |
| 1620 | CH$_2$ | CH$_3$ | CH$_3$ | CH$_3$ | c-C$_3$H$_5$ | C$_2$H$_4$OCH$_3$ | — |
| 1621 | CH$_2$ | Cl | CF$_3$ | H | C$_2$H$_5$ | CH$_2$OCH$_3$ | oil |
| 1622 | CH$_2$ | Cl | Cl | H | C$_2$H$_5$ | CH$_2$OCH$_3$ | — |
| 1623 | CH$_2$ | Cl | OCH$_3$ | H | C$_2$H$_5$ | CH$_2$OCH$_3$ | — |
| 1624 | CH$_2$ | CF$_3$ | OCH$_3$ | H | C$_2$H$_5$ | CH$_2$OCH$_3$ | — |
| 1625 | CH$_2$ | Cl | SO$_2$CH$_3$ | H | C$_2$H$_5$ | CH$_2$OCH$_3$ | — |
| 1626 | CH$_2$ | Cl | COCH$_3$ | H | C$_2$H$_5$ | CH$_2$OCH$_3$ | — |
| 1627 | CH$_2$ | CH$_3$ | OCH$_3$ | CH$_3$ | C$_2$H$_5$ | CH$_2$OCH$_3$ | — |
| 1628 | CH$_2$ | Cl | CH$_3$ | F | C$_2$H$_5$ | CH$_2$OCH$_3$ | — |
| 1629 | CH$_2$ | CH$_3$ | OCH$_3$ | F | C$_2$H$_5$ | CH$_2$OCH$_3$ | — |
| 1630 | CH$_2$ | CH$_3$ | CH$_3$ | CH$_3$ | C$_2$H$_5$ | CH$_2$OCH$_3$ | — |
| 1631 | CH$_2$ | Cl | CF$_3$ | H | c-C$_3$H$_5$ | CH$_2$OCH$_3$ | — |
| 1632 | CH$_2$ | Cl | Cl | H | c-C$_3$H$_5$ | CH$_2$OCH$_3$ | — |
| 1633 | CH$_2$ | Cl | OCH$_3$ | H | c-C$_3$H$_5$ | CH$_2$OCH$_3$ | — |
| 1634 | CH$_2$ | CF$_3$ | OCH$_3$ | H | c-C$_3$H$_5$ | CH$_2$OCH$_3$ | — |
| 1635 | CH$_2$ | Cl | SO$_2$CH$_3$ | H | c-C$_3$H$_5$ | CH$_2$OCH$_3$ | — |
| 1636 | CH$_2$ | Cl | COCH$_3$ | H | c-C$_3$H$_5$ | CH$_2$OCH$_3$ | — |
| 1637 | CH$_2$ | CH$_3$ | OCH$_3$ | CH$_3$ | c-C$_3$H$_5$ | CH$_2$OCH$_3$ | — |
| 1638 | CH$_2$ | Cl | CH$_3$ | F | c-C$_3$H$_5$ | CH$_2$OCH$_3$ | — |
| 1639 | CH$_2$ | CH$_3$ | OCH$_3$ | F | c-C$_3$H$_5$ | CH$_2$OCH$_3$ | — |
| 1640 | CH$_2$ | CH$_3$ | CH$_3$ | CH$_3$ | c-C$_3$H$_5$ | CH$_2$OCH$_3$ | — |
| 1641 | O | Cl | CF$_3$ | H | C$_2$H$_5$ | C$_2$H$_4$OCH$_3$ | oil |
| 1642 | O | Cl | Cl | H | C$_2$H$_5$ | C$_2$H$_4$OCH$_3$ | — |
| 1643 | O | Cl | OCH$_3$ | H | C$_2$H$_5$ | C$_2$H$_4$OCH$_3$ | — |
| 1644 | O | CF$_3$ | OCH$_3$ | H | C$_2$H$_5$ | C$_2$H$_4$OCH$_3$ | — |
| 1645 | O | Cl | SO$_2$CH$_3$ | H | C$_2$H$_5$ | C$_2$H$_4$OCH$_3$ | — |
| 1646 | O | Cl | COCH$_3$ | H | C$_2$H$_5$ | C$_2$H$_4$OCH$_3$ | — |
| 1647 | O | CH$_3$ | OCH$_3$ | CH$_3$ | C$_2$H$_5$ | C$_2$H$_4$OCH$_3$ | — |
| 1648 | O | Cl | CH$_3$ | F | C$_2$H$_5$ | C$_2$H$_4$OCH$_3$ | — |
| 1649 | O | CH$_3$ | OCH$_3$ | F | C$_2$H$_5$ | C$_2$H$_4$OCH$_3$ | — |
| 1650 | O | CH$_3$ | CH$_3$ | CH$_3$ | C$_2$H$_5$ | C$_2$H$_4$OCH$_3$ | — |
| 1651 | O | Cl | CF$_3$ | H | c-C$_3$H$_5$ | C$_2$H$_4$OCH$_3$ | — |
| 1652 | O | Cl | Cl | H | c-C$_3$H$_5$ | C$_2$H$_4$OCH$_3$ | — |
| 1653 | O | Cl | OCH$_3$ | H | c-C$_3$H$_5$ | C$_2$H$_4$OCH$_3$ | — |
| 1654 | O | CF$_3$ | OCH$_3$ | H | c-C$_3$H$_5$ | C$_2$H$_4$OCH$_3$ | — |
| 1655 | O | Cl | SO$_2$CH$_3$ | H | c-C$_3$H$_5$ | C$_2$H$_4$OCH$_3$ | — |
| 1656 | O | Cl | COCH$_3$ | H | c-C$_3$H$_5$ | C$_2$H$_4$OCH$_3$ | — |
| 1657 | O | CH$_3$ | OCH$_3$ | CH$_3$ | c-C$_3$H$_5$ | C$_2$H$_4$OCH$_3$ | — |
| 1658 | O | Cl | CH$_3$ | F | c-C$_3$H$_5$ | C$_2$H$_4$OCH$_3$ | — |
| 1659 | O | CH$_3$ | OCH$_3$ | F | c-C$_3$H$_5$ | C$_2$H$_4$OCH$_3$ | — |
| 1660 | O | CH$_3$ | CH$_3$ | CH$_3$ | c-C$_3$H$_5$ | C$_2$H$_4$OCH$_3$ | — |
| 1661 | O | Cl | CF$_3$ | H | C$_2$H$_5$ | CH$_2$OCH$_3$ | oil |
| 1662 | O | Cl | OCH$_3$ | H | C$_2$H$_5$ | CH$_2$OCH$_3$ | — |
| 1663 | O | CF$_3$ | OCH$_3$ | H | C$_2$H$_5$ | CH$_2$OCH$_3$ | — |
| 1664 | O | Cl | SO$_2$CH$_3$ | H | C$_2$H$_5$ | CH$_2$OCH$_3$ | — |
| 1665 | O | Cl | COCH$_3$ | H | C$_2$H$_5$ | CH$_2$OCH$_3$ | — |
| 1666 | O | CH$_3$ | OCH$_3$ | CH$_3$ | C$_2$H$_5$ | CH$_2$OCH$_3$ | — |
| 1667 | O | Cl | CH$_3$ | F | C$_2$H$_5$ | CH$_2$OCH$_3$ | — |
| 1668 | O | CH$_3$ | OCH$_3$ | F | C$_2$H$_5$ | CH$_2$OCH$_3$ | — |
| 1669 | O | CH$_3$ | CH$_3$ | CH$_3$ | C$_2$H$_5$ | CH$_2$OCH$_3$ | — |
| 1670 | O | Cl | CF$_3$ | H | c-C$_3$H$_5$ | CH$_2$OCH$_3$ | — |
| 1671 | O | Cl | Cl | H | c-C$_3$H$_5$ | CH$_2$OCH$_3$ | — |
| 1672 | O | Cl | OCH$_3$ | H | c-C$_3$H$_5$ | CH$_2$OCH$_3$ | — |
| 1673 | O | CF$_3$ | OCH$_3$ | H | c-C$_3$H$_5$ | CH$_2$OCH$_3$ | — |
| 1674 | O | Cl | SO$_2$CH$_3$ | H | c-C$_3$H$_5$ | CH$_2$OCH$_3$ | — |

TABLE 1D-continued

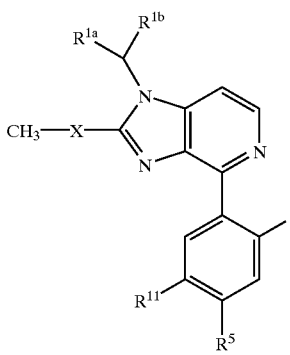

| Ex. No. | X | R⁴ | R⁵ | R¹¹ | R¹ᵃ | R¹ᵇ | mp, ° C. |
|---|---|---|---|---|---|---|---|
| 1675 | O | Cl | COCH$_3$ | H | c-C$_3$H$_5$ | CH$_2$OCH$_3$ | — |
| 1676 | O | CH$_3$ | OCH$_3$ | CH$_3$ | c-C$_3$H$_5$ | CH$_2$OCH$_3$ | — |
| 1677 | O | Cl | CH$_3$ | F | c-C$_3$H$_5$ | CH$_2$OCH$_3$ | — |
| 1678 | O | CH$_3$ | OCH$_3$ | F | c-C$_3$H$_5$ | CH$_2$OCH$_3$ | — |
| 1679 | O | CH$_3$ | CH$_3$ | CH$_3$ | c-C$_3$H$_5$ | CH$_2$OCH$_3$ | — |

The methods discussed below in the preparation of 1-benzyl-6-methyl-4-(2,4,6-trimethylphenyl)imidazo[4,5-c]pyridine (Example 2001, Table 2, Structure A) may be used to prepare all of the examples of Structure A contained in Table 2, with minor procedural modifications where necessary and use of reagents of the appropriate structure.

The methods of Schemes 13 and 14 may be used to prepare many of the examples of Structure B and Structure C contained in Table 2, with minor procedural modifications where necessary and use of reagents of the appropriate structure.

EXAMPLE 2001

Preparation of 1-Benzyl-6-methyl-4-(2,4,6-trimethylphenyl)imidazo[4,5-c]pyridine Part A. A solution of 4-chloro-6-methyl-3-nitropyridone (5.0 g, 26.5 mmol) in acetonitrile (93 mL) was treated with benzylamine (2.89 mL, 26.5 mmol) and diisopropylethylamine (5.54 mL, 31.8 mmol). The mixture was heated to reflux for 4 hrs., then cooled to ambient temperature and allowed to stir for 12 hrs. The mixture was partitioned between dichloromethane and water (200 mL each), and the aqueous layer was extracted with dichloromethane (200 mL). The extracts were washed in sequence with water (200 mL) and combined, and the resulting precipitate was collected by filtration. The filtrate was dried over sodium sulfate, refiltered and evaporated to afford a second crop of crystalline product, 4-benzylamino-6-methyl-3-nitropyridone (6.74 g total, 26.0 mmol, 98%). m.p. 246–247° C. TLC R$_F$ 0.35 (10:90 isopropanol-ethyl acetate). $^1$H NMR (300 MHz, CDCl$_3$): d 10.48 (1H, br s), 9.69 (1H, br s), 7.41–7.26 (5H, m), 5.66 (1H, s), 4.57 (2H, d, J=5.5 Hz), 2.26 (3H, s). MS (NH$_3$—CI): m/e 261 (10), 260 (70), 226 (100).

Part B. A solution of the pyridone from Part A (6.72 g, 25.9 mmol) in phosphorus oxychloride (52 mL, 25.5 mmol) was stirred at ambient temperature for 3 d. The reaction mixture was poured into a mixture of ice (150 g) and dichloromethane (200 mL). After the ice had melted, 100 mL more dichloromethane was added, and the pH of the mixture was adjusted to 7 with solid NaHCO$_3$. The mixture was separated, and the aqueous phase was extracted with dichloromethane. The extracts were combined, dried over sodium sulfate, filtered and evaporated to afford the product (4-benzylamino-2-chloro-6-methyl-3-nitropyridine) as a bright yellow crystalline solid (6.45 g, 23.2 mmol, 90%). TLC R$_F$ 0.76 (ethyl acetate). $^1$H NMR (300 MHz, CDCl$_3$): d 7.43–7.26 (5H, m), 7.04 (1H, br), 6.47 (1H, s), 4.48 (2H, d, J=5.5 Hz), 2.40 (3H, s). MS (NH$_3$—CI): m/e 281 (5), 280 (35), 279 (17), 278 (100).

Part C. A solution of the nitro compound from Part B above (6.42 g, 23.1 mmol) in methanol (162 mL) was treated with iron powder (13.61 g) and glacial acetic acid (13.6 mL). The resulting mixture was heated to reflux for 2 h, then cooled, filtered through celite (with methanol washing) and evaporated. The residual material was taken up in dichloromethane (231 mL) and 1 N aq. HCl (162 mL), and adjusted to neutral pH by addition of solid NaHCO$_3$. This mixture was filtered through celite and separated, and the aqueous phase was extracted with dichloromethane. The extracts were combined, dried over Na$_2$SO$_4$, filtered and evaporated to afford the product, 3-amino-4-benzylamino-2-chloro-6-methylpyridine, as a solid (5.59 g, 22.6 mmol, 98%). m.p. 177–178° C. TLC R$_F$ 0.60 (ethyl acetate). $^1$H NMR (300 MHz, CDCl$_3$): d 7.41–7.32 (5H, m), 6.33 (1H, s), 4.54 (1H, br), 4.36 (2H, d, J=5.1 Hz), 3.30 (2H, br s), 2.35 (3H, s). MS (NH$_3$—CI): m/e 251 (6), 250 (37), 249 (19), 248 (100).

Part D. A suspension of the diamine from Part C above (2.15 g, 8.68 mmol) in triethyl orthopropionate (5 mL) was treated with conc. HCl (3 drops), and heated to reflux for 1 h, then cooled and the excess orthoester removed by vacuum distillation. The pot residue was taken up in ethyl acetate (120 mL), which was washed with water and brine (100 mL each). The aqueous phases were back-extracted in sequence with ethyl acetate, and the extracts were combined, dried over Na$_2$SO$_4$, filtered and evaporated to afford N-(4-benzylamino-2-chloro-6-methylpyridin-3-yl)propionamide O-ethyl imidate (2.62 g, 91%). TLC R$_F$ 0.40 (30:70 ethyl acetate-hexane). $^1$H NMR (300 MHz, CDCl$_3$): d 7.39–7.29 (5H, m), 6.29 (1H, s), 4.64 (1H, br t, J=5.8 Hz), 4.37 (2H, d, J=5.8 Hz), 4.25 (2H, br), 2.35 (3H, s), 2.18–2.11 (2H, m), 1.36 (3H, t, J=7.0 Hz), 1.06 (3H, t, J=7.7 Hz). MS (NH$_3$—CI): m/e 335 (7), 334 (34), 333 (22), 332 (100).

Part E. A solution of the compound from Part D (2.62 g, 7.90 mmol) in phenyl ether (10 mL) was heated to 170° C. for 6 h, then cooled and poured into ethyl acetate (150 mL). This was washed with water and brine (100 mL each), then dried over Na$_2$SO$_4$, filtered and evaporated. The residual liquid was separated by column chromatography (hexane, then ethyl acetate) to afford the product, 1-benzyl-4-chloro-2-ethyl-6-methylimidazo[4,5-c]pyridine, as an oil (2.16 g, 96 %). m.p. 140–141° C. TLC R$_F$ 0.06 (30:70 ethyl acetate-hexane). $^1$H NMR (300 MHz, CDCl$_3$): d 7.36–7.32 (3H, m), 7.02–6.98 (2H, m), 6.93 (1H, s), 5.31 (2H, s), 2.89 (2H, q, J=7.3 Hz), 2.58 (3H, s), 1.39 (3H, t, J=7.3 Hz). MS (NH$_3$—CI): m/e 289 (6), 288 (35), 287 (20), 286 (100).

Part F. A solution of zinc chloride (538 mg) in tetrahydrofuran (7 mL) was treated with a tetrahydrofuran solution of 2-mesitylmagnesium bromide (3.95 mL, 1.0 M), and stirred for 1 h. In another flask, a solution of bis(triphenylphosphine)palladium chloride (93 mg, 0.132 mmol) in tetrahydrofuran (5 mL) was treated with a hexane solution of diisobutylaluminum hydride (0.263 mL, 1.0 M), and this solution was stirred for 20 min. The arylzinc solution was then delivered by cannula to the flask containing the palladium catalyst, which was followed by the chloride prepared in Part E. The mixture was heated to reflux for 12 h, then cooled, and poured into water (100 mL). This was extracted with ethyl acetate (2×150 mL), and the extracts were washed with brine, combined, dried over Na$_2$SO$_4$, filtered and evaporated. The residual material was separated by column chromatography (1:1 ethyl acetate-hexane) to afford the title product as a solid, recrystallized to purity from ether (187 mg, 29%). m.p. 177–180° C.

(ether). TLC R$_F$ 0.27 (50:50 ethyl acetate-hexane). $^1$H NMR (300 MHz, CDCl$_3$): d 7.38–7.32 (3H, m), 7.10–7.05 (2H, m), 6.96 (1H, s), 6.93 (2H, s), 5.32 (2H, s), 2.84 (2H, q, J=7.3 Hz), 2.64 (3H, s), 2.30 (3H, s), 2.02 (6H, s), 1.26 (3H, t, J=7.3 Hz). MS (NH$_3$CI): m/e 372 (4), 371 (29), 370 (100). Analysis calc'd for C$_{25}$H$_{27}$N$_3$: C, 81.26; H, 7.38; N, 11.37; found: C, 80.70; H, 7.26; N, 11.20.

TABLE 2

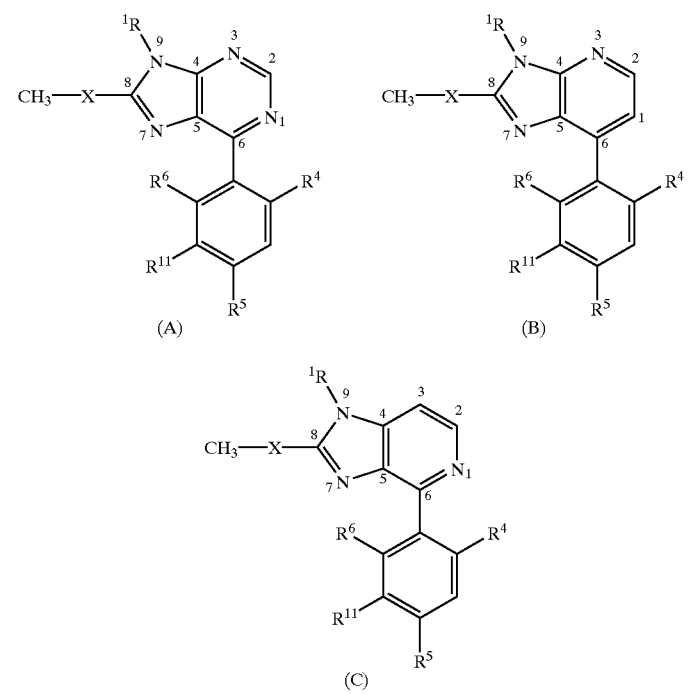

| Ex. No. | X | R$^4$ | R$^5$ | R$^{11}$ | R$^6$ | R$^1$ | mp, ° C.$^a$ |
|---|---|---|---|---|---|---|---|
| 2001 | CH$_2$ | Cl | Cl | H | H | c-C$_4$H$_7$ | — |
| 2002 | CH$_2$ | Cl | Cl | H | H | c-C$_5$H$_9$ | 111–112 |
| 2003 | CH$_2$ | Cl | Cl | H | H | c-C$_6$H$_{11}$ | oil |
| 2004 | CH$_2$ | Cl | Cl | H | H | c-C$_7$H$_{13}$ | 128–130 |
| 2005 | CH$_2$ | Cl | Cl | H | H | c-C$_8$H$_{15}$ | — |
| 2006 | CH$_2$ | Cl | Cl | H | H | 2-CH$_3$-c-C$_5$H$_8$ | oil |
| 2007 | CH$_2$ | Cl | Cl | H | H | 3-CH$_3$-c-C$_5$H$_8$ | — |
| 2008 | CH$_2$ | Cl | Cl | H | H | 2-OCH$_3$-c-C$_5$H$_8$ | — |
| 2009 | CH$_2$ | Cl | Cl | H | H | 2,5-(CH$_3$)$_2$-c-C$_5$H$_7$ | — |
| 2010 | CH$_2$ | Cl | Cl | H | H | 2-(CH$_3$)$_2$CH-5-CH$_3$-c-C$_6$H$_9$ | — |
| 2011 | CH$_2$ | Cl | Cl | H | H | 9-fluorenyl | oil |
| 2012 | CH$_2$ | Cl | Cl | H | H | 1-tetrahydronaphthyl | oil |
| 2013 | CH$_2$ | Cl | Cl | H | H | 1-indanyl | oil |
| 2014 | CH$_2$ | Cl | Cl | H | H | 4-chromanyl | oil |
| 2015 | CH$_2$ | Cl | Cl | H | H | 2-oxo-c-C$_5$H$_7$ | 166–168 |
| 2016 | CH$_2$ | Cl | Cl | H | H | 5-dibenzosuberyl | — |
| 2017 | CH$_2$ | Cl | Cl | H | H | 5-dibenzosuberenyl | — |
| 2018 | CH$_2$ | Cl | CF$_3$ | H | H | c-C$_4$H$_7$ | — |
| 2019 | CH$_2$ | Cl | CF$_3$ | H | H | c-C$_5$H$_9$ | 146–147 |
| 2020 | CH$_2$ | Cl | CF$_3$ | H | H | c-C$_6$H$_{11}$ | oil |
| 2021 | CH$_2$ | Cl | CF$_3$ | H | H | c-C$_7$H$_{13}$ | 129–130 |
| 2022 | CH$_2$ | Cl | CF$_3$ | H | H | c-C$_8$H$_{15}$ | — |
| 2023 | CH$_2$ | Cl | CF$_3$ | H | H | 2-CH$_3$-c-C$_5$H$_8$ | 98–99 |
| 2024 | CH$_2$ | Cl | CF$_3$ | H | H | 3-CH$_3$-c-C$_5$H$_8$ | — |
| 2025 | CH$_2$ | Cl | CF$_3$ | H | H | 2-OCH$_3$-c-C$_5$H$_8$ | — |
| 2026 | CH$_2$ | Cl | CF$_3$ | H | H | 2,5-(CH$_3$)$_2$-c-C$_5$H$_7$ | — |
| 2027 | CH$_2$ | Cl | CF$_3$ | H | H | 2-(CH$_3$)$_2$CH-5-CH$_3$-c-C$_6$H$_9$ | — |
| 2028 | CH$_2$ | Cl | CF$_3$ | H | H | 9-fluorenyl | — |
| 2029 | CH$_2$ | Cl | CF$_3$ | H | H | 1-tetrahydronaphthyl | — |
| 2030 | CH$_2$ | Cl | CF$_3$ | H | H | 1-indanyl | — |
| 2031 | CH$_2$ | Cl | CF$_3$ | H | H | 4-chromanyl | — |
| 2032 | CH$_2$ | Cl | CF$_3$ | H | H | 2-oxo-c-C$_5$H$_7$ | — |
| 2033 | CH$_2$ | Cl | CF$_3$ | H | H | 5-dibenzosuberyl | — |

TABLE 2-continued

| | | | | | | |
|---|---|---|---|---|---|---|
| 2034 | $CH_2$ | Cl | $CF_3$ | H | H | 5-dibenzosuberenyl | — |
| 2035 | $CH_2$ | Cl | $OCH_3$ | H | H | c-$C_4H_7$ | — |
| 2036 | $CH_2$ | Cl | $OCH_3$ | H | H | c-$C_5H_9$ | — |
| 2037 | $CH_2$ | Cl | $OCH_3$ | H | H | c-$C_6H_{11}$ | — |
| 2038 | $CH_2$ | Cl | $OCH_3$ | H | H | c-$C_7H_{13}$ | — |
| 2039 | $CH_2$ | Cl | $OCH_3$ | H | H | c-$C_8H_{15}$ | — |
| 2040 | $CH_2$ | Cl | $OCH_3$ | H | H | 2-$CH_3$-c-$C_5H_8$ | — |
| 2041 | $CH_2$ | Cl | $OCH_3$ | H | H | 3-$CH_3$-c-$C_5H_8$ | — |
| 2042 | $CH_2$ | Cl | $OCH_3$ | H | H | 2-$OCH_3$-c-$C_5H_8$ | — |
| 2043 | $CH_2$ | Cl | $OCH_3$ | H | H | 2,5-$(CH_3)_2$-c-$C_5H_7$ | — |
| 2044 | $CH_2$ | Cl | $OCH_3$ | H | H | 2-$(CH_3)_2CH$-5-$CH_3$-c-$C_6H_9$ | — |
| 2045 | $CH_2$ | Cl | $OCH_3$ | H | H | 9-fluorenyl | — |
| 2046 | $CH_2$ | Cl | $OCH_3$ | H | H | 1-tetrahydronaphthyl | — |
| 2047 | $CH_2$ | Cl | $OCH_3$ | H | H | 1-indanyl | — |
| 2048 | $CH_2$ | Cl | $OCH_3$ | H | H | 4-chromanyl | — |
| 2049 | $CH_2$ | Cl | $OCH_3$ | H | H | 2-oxo-c-$C_5H_7$ | — |
| 2050 | $CH_2$ | Cl | $OCH_3$ | H | H | 5-dibenzosuberyl | — |
| 2051 | $CH_2$ | Cl | $OCH_3$ | H | H | 5-dibenzosuberenyl | — |
| 2052 | $CH_2$ | Cl | $OCF_3$ | H | H | c-$C_4H_7$ | — |
| 2053 | $CH_2$ | Cl | $OCF_3$ | H | H | c-$C_5H_9$ | oil |
| 2054 | $CH_2$ | Cl | $OCF_3$ | H | H | c-$C_6H_{11}$ | — |
| 2055 | $CH_2$ | Cl | $OCF_3$ | H | H | c-$C_7H_{13}$ | — |
| 2056 | $CH_2$ | Cl | $OCF_3$ | H | H | c-$C_8H_{15}$ | — |
| 2057 | $CH_2$ | Cl | $OCF_3$ | H | H | 2-$CH_3$-c-$C_5H_8$ | — |
| 2058 | $CH_2$ | Cl | $OCF_3$ | H | H | 3-$CH_3$-c-$C_5H_8$ | — |
| 2059 | $CH_2$ | Cl | $OCF_3$ | H | H | 2-$OCH_3$-c-$C_5H_8$ | — |
| 2060 | $CH_2$ | Cl | $OCF_3$ | H | H | 2,5-$(CH_3)_2$-c-$C_5H_7$ | — |
| 2061 | $CH_2$ | Cl | $OCF_3$ | H | H | 2-$(CH_3)_2CH$-5-$CH_3$-c-$C_6H_9$ | — |
| 2062 | $CH_2$ | Cl | $OCF_3$ | H | H | 9-fluorenyl | — |
| 2063 | $CH_2$ | Cl | $OCF_3$ | H | H | 1-tetrahydronaphthyl | — |
| 2064 | $CH_2$ | Cl | $OCF_3$ | H | H | 1-indanyl | — |
| 2065 | $CH_2$ | Cl | $OCF_3$ | H | H | 4-chromanyl | — |
| 2066 | $CH_2$ | Cl | $OCF_3$ | H | H | 2-oxo-c-$C_5H_7$ | — |
| 2067 | $CH_2$ | Cl | $OCF_3$ | H | H | 5-dibenzosuberyl | — |
| 2068 | $CH_2$ | Cl | $OCF_3$ | H | H | 5-dibenzosuberenyl | — |
| 2069 | $CH_2$ | Cl | $CH_3$ | H | H | c-$C_4H_7$ | — |
| 2070 | $CH_2$ | Cl | $CH_3$ | H | H | c-$C_5H_9$ | — |
| 2071 | $CH_2$ | Cl | $CH_3$ | H | H | c-$C_6H_{11}$ | — |
| 2072 | $CH_2$ | Cl | $CH_3$ | H | H | c-$C_7H_{13}$ | — |
| 2073 | $CH_2$ | Cl | $CH_3$ | H | H | c-$C_8H_{15}$ | — |
| 2074 | $CH_2$ | Cl | $CH_3$ | H | H | 2-$CH_3$-c-$C_5H_8$ | — |
| 2075 | $CH_2$ | Cl | $CH_3$ | H | H | 3-$CH_3$-c-$C_5H_8$ | — |
| 2076 | $CH_2$ | Cl | $CH_3$ | H | H | 2-$OCH_3$-c-$C_5H_8$ | — |
| 2077 | $CH_2$ | Cl | $CH_3$ | H | H | 2,5-$(CH_3)_2$-c-$C_5H_7$ | — |
| 2078 | $CH_2$ | Cl | $CH_3$ | H | H | 2-$(CH_3)_2CH$-5-$CH_3$-c-$C_6H_9$ | — |
| 2079 | $CH_2$ | Cl | $CH_3$ | H | H | 9-fluorenyl | — |
| 2080 | $CH_2$ | Cl | $CH_3$ | H | H | 1-tetrahydronaphthyl | — |
| 2081 | $CH_2$ | Cl | $CH_3$ | H | H | 1-indanyl | — |
| 2082 | $CH_2$ | Cl | $CH_3$ | H | H | 4-chromanyl | — |
| 2083 | $CH_2$ | Cl | $CH_3$ | H | H | 2-oxo-c-$C_5H_7$ | — |
| 2084 | $CH_2$ | Cl | $CH_3$ | H | H | 5-dibenzosuberyl | — |
| 2085 | $CH_2$ | Cl | $CH_3$ | H | H | 5-dibenzosuberenyl | — |
| 2086 | $CH_2$ | $CF_3$ | Cl | H | H | c-$C_4H_7$ | — |
| 2087 | $CH_2$ | $CF_3$ | Cl | H | H | c-$C_5H_9$ | 143–145 |
| 2088 | $CH_2$ | $CF_3$ | Cl | H | H | c-$C_6H_{11}$ | — |
| 2089 | $CH_2$ | $CF_3$ | Cl | H | H | c-$C_7H_{13}$ | — |
| 2090 | $CH_2$ | $CF_3$ | Cl | H | H | c-$C_8H_{15}$ | — |
| 2091 | $CH_2$ | $CF_3$ | Cl | H | H | 2-$CH_3$-c-$C_5H_8$ | — |
| 2092 | $CH_2$ | $CF_3$ | Cl | H | H | 3-$CH_3$-c-$C_5H_8$ | — |
| 2093 | $CH_2$ | $CF_3$ | Cl | H | H | 2-$OCH_3$-c-$C_5H_8$ | — |
| 2094 | $CH_2$ | $CF_3$ | Cl | H | H | 2,5-$(CH_3)_2$-c-$C_5H_7$ | — |
| 2095 | $CH_2$ | $CF_3$ | Cl | H | H | 2-$(CH_3)_2CH$-5-$CH_3$-c-$C_6H_9$ | — |
| 2096 | $CH_2$ | $CF_3$ | Cl | H | H | 9-fluorenyl | — |
| 2097 | $CH_2$ | $CF_3$ | Cl | H | H | 1-tetrahydronaphthyl | — |
| 2098 | $CH_2$ | $CF_3$ | Cl | H | H | 1-indanyl | — |
| 2099 | $CH_2$ | $CF_3$ | Cl | H | H | 4-chromanyl | — |
| 2100 | $CH_2$ | $CF_3$ | Cl | H | H | 2-oxo-c-$C_5H_7$ | — |
| 2101 | $CH_2$ | $CF_3$ | Cl | H | H | 5-dibenzosuberyl | — |
| 2102 | $CH_2$ | $CF_3$ | Cl | H | H | 5-dibenzosuberenyl | — |
| 2103 | $CH_2$ | $CF_3$ | $OCH_3$ | H | H | c-$C_4H_7$ | — |
| 2104 | $CH_2$ | $CF_3$ | $OCH_3$ | H | H | c-$C_5H_9$ | 103–106 |
| 2105 | $CH_2$ | $CF_3$ | $OCH_3$ | H | H | c-$C_6H_{11}$ | — |
| 2106 | $CH_2$ | $CF_3$ | $OCH_3$ | H | H | c-$C_7H_{13}$ | — |
| 2107 | $CH_2$ | $CF_3$ | $OCH_3$ | H | H | c-$C_8H_{15}$ | — |
| 2108 | $CH_2$ | $CF_3$ | $OCH_3$ | H | H | 2-$CH_3$-c-$C_5H_8$ | — |
| 2109 | $CH_2$ | $CF_3$ | $OCH_3$ | H | H | 3-$CH_3$-c-$C_5H_8$ | — |
| 2110 | $CH_2$ | $CF_3$ | $OCH_3$ | H | H | 2-$OCH_3$-c-$C_5H_8$ | — |
| 2111 | $CH_2$ | $CF_3$ | $OCH_3$ | H | H | 2,5-$(CH_3)_2$-c-$C_5H_7$ | — |
| 2112 | $CH_2$ | $CF_3$ | $OCH_3$ | H | H | 2-$(CH_3)_2CH$-5-$CH_3$-c-$C_6H_9$ | — |

TABLE 2-continued

| | | | | | | |
|---|---|---|---|---|---|---|
| 2113 | $CH_2$ | $CF_3$ | $OCH_3$ | H | H | 9-fluorenyl | — |
| 2114 | $CH_2$ | $CF_3$ | $OCH_3$ | H | H | 1-tetrahydronaphthyl | — |
| 2115 | $CH_2$ | $CF_3$ | $OCH_3$ | H | H | 1-indanyl | — |
| 2116 | $CH_2$ | $CF_3$ | $OCH_3$ | H | H | 4-chromanyl | — |
| 2117 | $CH_2$ | $CF_3$ | $OCH_3$ | H | H | 2-oxo-c-$C_5H_7$ | — |
| 2118 | $CH_2$ | $CF_3$ | $OCH_3$ | H | H | 5-dibenzosuberyl | — |
| 2119 | $CH_2$ | $CF_3$ | $OCH_3$ | H | H | 5-dibenzosuberenyl | — |
| 2120 | $CH_2$ | $CF_3$ | F | H | H | c-$C_4H_7$ | — |
| 2121 | $CH_2$ | $CF_3$ | F | H | H | c-$C_5H_9$ | — |
| 2122 | $CH_2$ | $CF_3$ | F | H | H | c-$C_6H_{11}$ | — |
| 2123 | $CH_2$ | $CF_3$ | F | H | H | c-$C_7H_{13}$ | 119–122 |
| 2124 | $CH_2$ | $CF_3$ | F | H | H | c-$C_8H_{15}$ | — |
| 2125 | $CH_2$ | $CF_3$ | F | H | H | 2-$CH_3$-c-$C_5H_8$ | — |
| 2126 | $CH_2$ | $CF_3$ | F | H | H | 3-$CH_3$-c-$C_5H_8$ | — |
| 2127 | $CH_2$ | $CF_3$ | F | H | H | 2-$OCH_3$-c-$C_5H_8$ | — |
| 2128 | $CH_2$ | $CF_3$ | F | H | H | 2,5-$(CH_3)_2$-c-$C_5H_7$ | — |
| 2129 | $CH_2$ | $CF_3$ | F | H | H | 2-$(CH_3)_2CH$-5-$CH_3$-c-$C_6H_9$ | 155–156 |
| 2130 | $CH_2$ | $CF_3$ | F | H | H | 9-fluorenyl | 184–185 |
| 2131 | $CH_2$ | $CF_3$ | F | H | H | 1-tetrahydronaphthyl | — |
| 2132 | $CH_2$ | $CF_3$ | F | H | H | 1-indanyl | — |
| 2133 | $CH_2$ | $CF_3$ | F | H | H | 4-chromanyl | — |
| 2134 | $CH_2$ | $CF_3$ | F | H | H | 2-oxo-c-$C_5H_7$ | — |
| 2135 | $CH_2$ | $CF_3$ | F | H | H | 5-dibenzosuberyl | — |
| 2136 | $CH_2$ | $CF_3$ | F | H | H | 5-dibenzosuberenyl | — |
| 2137 | $CH_2$ | $CH_3$ | $OCH_3$ | $CH_3$ | H | c-$C_4H_7$ | — |
| 2138 | $CH_2$ | $CH_3$ | $OCH_3$ | $CH_3$ | H | c-$C_5H_9$ | — |
| 2139 | $CH_2$ | $CH_3$ | $OCH_3$ | $CH_3$ | H | c-$C_6H_{11}$ | — |
| 2140 | $CH_2$ | $CH_3$ | $OCH_3$ | $CH_3$ | H | c-$C_7H_{13}$ | — |
| 2141 | $CH_2$ | $CH_3$ | $OCH_3$ | $CH_3$ | H | c-$C_8H_{15}$ | — |
| 2142 | $CH_2$ | $CH_3$ | $OCH_3$ | $CH_3$ | H | 2-$CH_3$-c-$C_5H_8$ | — |
| 2143 | $CH_2$ | $CH_3$ | $OCH_3$ | $CH_3$ | H | 3-$CH_3$-c-$C_5H_8$ | — |
| 2144 | $CH_2$ | $CH_3$ | $OCH_3$ | $CH_3$ | H | 2-$OCH_3$-c-$C_5H_8$ | — |
| 2145 | $CH_2$ | $CH_3$ | $OCH_3$ | $CH_3$ | H | 2,5-$(CH_3)_2$-c-$C_5H_7$ | — |
| 2146 | $CH_2$ | $CH_3$ | $OCH_3$ | $CH_3$ | H | 2-$(CH_3)_2CH$-5-$CH_3$-c-$C_6H_9$ | — |
| 2147 | $CH_2$ | $CH_3$ | $OCH_3$ | $CH_3$ | H | 9-fluorenyl | — |
| 2148 | $CH_2$ | $CH_3$ | $OCH_3$ | $CH_3$ | H | 1-tetrahydronaphthyl | — |
| 2149 | $CH_2$ | $CH_3$ | $OCH_3$ | $CH_3$ | H | 1-indanyl | — |
| 2150 | $CH_2$ | $CH_3$ | $OCH_3$ | $CH_3$ | H | 4-chromanyl | — |
| 2151 | $CH_2$ | $CH_3$ | $OCH_3$ | $CH_3$ | H | 2-oxo-c-$C_5H_7$ | — |
| 2152 | $CH_2$ | $CH_3$ | $OCH_3$ | $CH_3$ | H | 5-dibenzosuberyl | — |
| 2153 | $CH_2$ | $CH_3$ | $OCH_3$ | $CH_3$ | H | 5-dibenzosuberenyl | — |
| 2154 | $CH_2$ | $CH_3$ | $OCH_3$ | Cl | H | c-$C_4H_7$ | — |
| 2155 | $CH_2$ | $CH_3$ | $OCH_3$ | Cl | H | c-$C_5H_9$ | 115–116 |
| 2156 | $CH_2$ | $CH_3$ | $OCH_3$ | Cl | H | c-$C_6H_{11}$ | — |
| 2157 | $CH_2$ | $CH_3$ | $OCH_3$ | Cl | H | c-$C_7H_{13}$ | — |
| 2158 | $CH_2$ | $CH_3$ | $OCH_3$ | Cl | H | c-$C_8H_{15}$ | — |
| 2159 | $CH_2$ | $CH_3$ | $OCH_3$ | Cl | H | 2-$CH_3$-c-$C_5H_8$ | — |
| 2160 | $CH_2$ | $CH_3$ | $OCH_3$ | Cl | H | 3-$CH_3$-c-$C_5H_8$ | — |
| 2161 | $CH_2$ | $CH_3$ | $OCH_3$ | Cl | H | 2-$OCH_3$-c-$C_5H_8$ | — |
| 2162 | $CH_2$ | $CH_3$ | $OCH_3$ | Cl | H | 2,5-$(CH_3)_2$-c-$C_5H_7$ | — |
| 2163 | $CH_2$ | $CH_3$ | $OCH_3$ | Cl | H | 2-$(CH_3)_2CH$-5-$CH_3$-c-$C_6H_9$ | — |
| 2164 | $CH_2$ | $CH_3$ | $OCH_3$ | Cl | H | 9-fluorenyl | — |
| 2165 | $CH_2$ | $CH_3$ | $OCH_3$ | Cl | H | 1-tetrahydronaphthyl | — |
| 2166 | $CH_2$ | $CH_3$ | $OCH_3$ | Cl | H | 1-indanyl | — |
| 2167 | $CH_2$ | $CH_3$ | $OCH_3$ | Cl | H | 4-chromanyl | — |
| 2168 | $CH_2$ | $CH_3$ | $OCH_3$ | Cl | H | 2-oxo-c-$C_5H_7$ | — |
| 2169 | $CH_2$ | $CH_3$ | $OCH_3$ | Cl | H | 5-dibenzosuberyl | — |
| 2170 | $CH_2$ | $CH_3$ | $OCH_3$ | Cl | H | 5-dibenzosuberenyl | — |
| 2171 | $CH_2$ | $CH_3$ | $OCH_3$ | F | H | c-$C_4H_7$ | — |
| 2172 | $CH_2$ | $CH_3$ | $OCH_3$ | F | H | c-$C_5H_9$ | — |
| 2173 | $CH_2$ | $CH_3$ | $OCH_3$ | F | H | c-$C_6H_{11}$ | — |
| 2174 | $CH_2$ | $CH_3$ | $OCH_3$ | F | H | c-$C_7H_{13}$ | — |
| 2175 | $CH_2$ | $CH_3$ | $OCH_3$ | F | H | c-$C_8H_{15}$ | — |
| 2176 | $CH_2$ | $CH_3$ | $OCH_3$ | F | H | 2-$CH_3$-c-$C_5H_8$ | — |
| 2177 | $CH_2$ | $CH_3$ | $OCH_3$ | F | H | 3-$CH_3$-c-$C_5H_8$ | — |
| 2178 | $CH_2$ | $CH_3$ | $OCH_3$ | F | H | 2-$OCH_3$-c-$C_5H_8$ | — |
| 2179 | $CH_2$ | $CH_3$ | $OCH_3$ | F | H | 2,5-$(CH_3)_2$-c-$C_5H_7$ | — |
| 2180 | $CH_2$ | $CH_3$ | $OCH_3$ | F | H | 2-$(CH_3)_2CH$-5-$CH_3$-c-$C_6H_9$ | — |
| 2181 | $CH_2$ | $CH_3$ | $OCH_3$ | F | H | 9-fluorenyl | — |
| 2182 | $CH_2$ | $CH_3$ | $OCH_3$ | F | H | 1-tetrahydronaphthyl | — |
| 2183 | $CH_2$ | $CH_3$ | $OCH_3$ | F | H | 1-indanyl | — |
| 2184 | $CH_2$ | $CH_3$ | $OCH_3$ | F | H | 4-chromanyl | — |
| 2185 | $CH_2$ | $CH_3$ | $OCH_3$ | F | H | 2-oxo-c-$C_5H_7$ | — |
| 2186 | $CH_2$ | $CH_3$ | $OCH_3$ | F | H | 5-dibenzosuberyl | — |
| 2187 | $CH_2$ | $CH_3$ | $OCH_3$ | F | H | 5-dibenzosuberenyl | — |
| 2188 | $CH_2$ | $CH_3$ | $CH_3$ | H | $CH_3$ | c-$C_4H_7$ | — |
| 2189 | $CH_2$ | $CH_3$ | $CH_3$ | H | $CH_3$ | c-$C_5H_9$ | — |
| 2190 | $CH_2$ | $CH_3$ | $CH_3$ | H | $CH_3$ | c-$C_6H_{11}$ | — |
| 2191 | $CH_2$ | $CH_3$ | $CH_3$ | H | $CH_3$ | c-$C_7H_{13}$ | — |

TABLE 2-continued

| | | | | | | | |
|---|---|---|---|---|---|---|---|
| 2192 | CH$_2$ | CH$_3$ | CH$_3$ | H | CH$_3$ | c-C$_8$H$_{15}$ | — |
| 2193 | CH$_2$ | CH$_3$ | CH$_3$ | H | CH$_3$ | 2-CH$_3$-c-C$_5$H$_8$ | — |
| 2194 | CH$_2$ | CH$_3$ | CH$_3$ | H | CH$_3$ | 3-CH$_3$-c-C$_5$H$_8$ | — |
| 2195 | CH$_2$ | CH$_3$ | CH$_3$ | H | CH$_3$ | 2-OCH$_3$-c-C$_5$H$_8$ | — |
| 2196 | CH$_2$ | CH$_3$ | CH$_3$ | H | CH$_3$ | 2,5-(CH$_3$)$_2$-c-C$_5$H$_7$ | — |
| 2197 | CH$_2$ | CH$_3$ | CH$_3$ | H | CH$_3$ | 2-(CH$_3$)$_2$CH-5-CH$_3$-c-C$_6$H$_9$ | — |
| 2198 | CH$_2$ | CH$_3$ | CH$_3$ | H | CH$_3$ | 9-fluorenyl | — |
| 2199 | CH$_2$ | CH$_3$ | CH$_3$ | H | CH$_3$ | 1-tetrahydronaphthyl | — |
| 2200 | CH$_2$ | CH$_3$ | CH$_3$ | H | CH$_3$ | 1-indanyl | — |
| 2201 | CH$_2$ | CH$_3$ | CH$_3$ | H | CH$_3$ | 4-chromanyl | — |
| 2202 | CH$_2$ | CH$_3$ | CH$_3$ | H | CH$_3$ | 2-oxo-c-C$_5$H$_7$ | — |
| 2203 | CH$_2$ | CH$_3$ | CH$_3$ | H | CH$_3$ | 5-dibenzosuberyl | — |
| 2204 | CH$_2$ | CH$_3$ | CH$_3$ | H | CH$_3$ | 5-dibenzosuberenyl | — |
| 2205 | CH$_2$ | Cl | Cl | H | CH$_3$ | c-C$_4$H$_7$ | — |
| 2206 | CH$_2$ | Cl | Cl | H | CH$_3$ | c-C$_5$H$_9$ | — |
| 2207 | CH$_2$ | Cl | Cl | H | CH$_3$ | c-C$_6$H$_{11}$ | — |
| 2208 | CH$_2$ | Cl | Cl | H | CH$_3$ | c-C$_7$H$_{13}$ | — |
| 2209 | CH$_2$ | Cl | Cl | H | CH$_3$ | c-C$_8$H$_{15}$ | — |
| 2210 | CH$_2$ | Cl | Cl | H | CH$_3$ | 2-CH$_3$-c-C$_5$H$_8$ | — |
| 2211 | CH$_2$ | Cl | Cl | H | CH$_3$ | 3-CH$_3$-c-C$_5$H$_8$ | — |
| 2212 | CH$_2$ | Cl | Cl | H | CH$_3$ | 2-OCH$_3$-c-C$_5$H$_8$ | — |
| 2213 | CH$_2$ | Cl | Cl | H | CH$_3$ | 2,5-(CH$_3$)$_2$-c-C$_5$H$_7$ | — |
| 2214 | CH$_2$ | Cl | Cl | H | CH$_3$ | 2-(CH$_3$)$_2$CH-5-CH$_3$-c-C$_6$H$_9$ | — |
| 2215 | CH$_2$ | Cl | Cl | H | CH$_3$ | 9-fluorenyl | — |
| 2216 | CH$_2$ | Cl | Cl | H | CH$_3$ | 1-tetrahydronaphthyl | oil |
| 2217 | CH$_2$ | Cl | Cl | H | CH$_3$ | 1-indanyl | — |
| 2218 | CH$_2$ | Cl | Cl | H | CH$_3$ | 4-chromanyl | — |
| 2219 | CH$_2$ | Cl | Cl | H | CH$_3$ | 2-oxo-c-C$_5$H$_7$ | — |
| 2220 | CH$_2$ | Cl | Cl | H | CH$_3$ | 5-dibenzosuberyl | — |
| 2221 | CH$_2$ | Cl | Cl | H | CH$_3$ | 5-dibenzosuberenyl | — |
| 2222 | CH$_2$ | CH$_3$ | OCH$_3$ | OCH$_3$ | H | c-C$_4$H$_7$ | — |
| 2223 | CH$_2$ | CH$_3$ | OCH$_3$ | OCH$_3$ | H | c-C$_5$H$_9$ | oil |
| 2224 | CH$_2$ | CH$_3$ | OCH$_3$ | OCH$_3$ | H | c-C$_6$H$_{11}$ | — |
| 2225 | CH$_2$ | CH$_3$ | OCH$_3$ | OCH$_3$ | H | c-C$_7$H$_{13}$ | — |
| 2226 | CH$_2$ | CH$_3$ | OCH$_3$ | OCH$_3$ | H | c-C$_8$H$_{15}$ | — |
| 2227 | CH$_2$ | CH$_3$ | OCH$_3$ | OCH$_3$ | H | 2-CH$_3$-c-C$_5$H$_8$ | oil |
| 2228 | CH$_2$ | CH$_3$ | OCH$_3$ | OCH$_3$ | H | 3-CH$_3$-c-C$_5$H$_8$ | — |
| 2229 | CH$_2$ | CH$_3$ | OCH$_3$ | OCH$_3$ | H | 2-OCH$_3$-c-C$_5$H$_8$ | — |
| 2230 | CH$_2$ | CH$_3$ | OCH$_3$ | OCH$_3$ | H | 2,5-(CH$_3$)$_2$-c-C$_5$H$_7$ | — |
| 2231 | CH$_2$ | CH$_3$ | OCH$_3$ | OCH$_3$ | H | 2-(CH$_3$)$_2$CH-5-CH$_3$-c-C$_6$H$_9$ | — |
| 2232 | CH$_2$ | CH$_3$ | OCH$_3$ | OCH$_3$ | H | 9-fluorenyl | — |
| 2233 | CH$_2$ | CH$_3$ | OCH$_3$ | OCH$_3$ | H | 1-tetrahydronaphthyl | — |
| 2234 | CH$_2$ | CH$_3$ | OCH$_3$ | OCH$_3$ | H | 1-indanyl | — |
| 2235 | CH$_2$ | CH$_3$ | OCH$_3$ | OCH$_3$ | H | 4-chromanyl | — |
| 2236 | CH$_2$ | CH$_3$ | OCH$_3$ | OCH$_3$ | H | 2-oxo-c-C$_5$H$_7$ | — |
| 2237 | CH$_2$ | CH$_3$ | OCH$_3$ | OCH$_3$ | H | 5-dibenzosuberyl | — |
| 2238 | CH$_2$ | CH$_3$ | OCH$_3$ | OCH$_3$ | H | 5-dibenzosuberenyl | — |
| 2239 | O | Cl | Cl | H | H | c-C$_5$H$_9$ | — |
| 2240 | O | Cl | CF$_3$ | H | H | c-C$_5$H$_9$ | — |
| 2241 | O | Cl | OCH$_3$ | H | H | c-C$_5$H$_9$ | — |
| 2242 | O | Cl | OCF$_3$ | H | H | c-C$_5$H$_9$ | — |
| 2243 | O | Cl | CH$_3$ | H | H | c-C$_5$H$_9$ | — |
| 2244 | O | CF$_3$ | Cl | H | H | c-C$_5$H$_9$ | — |
| 2245 | O | CF$_3$ | OCH$_3$ | H | H | c-C$_5$H$_9$ | — |
| 2246 | O | CH$_3$ | OCH$_3$ | CH$_3$ | H | c-C$_5$H$_9$ | — |
| 2247 | O | CH$_3$ | OCH$_3$ | Cl | H | c-C$_5$H$_9$ | — |
| 2248 | O | CH$_3$ | OCH$_3$ | F | H | c-C$_5$H$_9$ | — |
| 2249 | O | CH$_3$ | CH$_3$ | H | CH$_3$ | c-C$_5$H$_9$ | — |
| 2250 | O | Cl | Cl | H | CH$_3$ | c-C$_5$H$_9$ | — |

Key:
[a]Where the compound is listed as an "oil", spectral data is as follows:

Example 2003 spectral data: MS(NH$_3$—CI): m/e 374(M + H$^+$, 100%).

Example 2006 spectral data: TLC R$_F$ 0.20(20:80 ethyl acetate-hexane). $^1$H NMR(300 MHz, CDCl$_3$): δ 8.94(1H, s), 7.67(1H, d, J=8.1Hz), 7.57(1H, d, J=1.8Hz), 7.40(1H, dd, J=8.1, 1.8Hz), 4.83(1H, q, J=8.0Hz), 3.20–3.04(1H, m), 2.98(2H, q, J=7.3Hz), 2.50–2.38(1H, m), 2.30–2.15(2H, m), 2.03–1.93(2H, m), 1.75–1.60(1H, m), 1.42(3H, t, J=7.3Hz), 0.68(3H, d, J=6.9Hz). MS(NH$_3$—CI): m/e calc'd for C$_{19}$H$_{21}$Cl$_2$N$_4$: 375.1143, found 375.1149; 380(2), 379(12), 378(15), 377(66), 376(27), 375(100).

Example 2011 spectral data: MS(NH$_3$—CI): m/e 457(M+H$^+$, 100%).

Example 2012 spectral data: TLC R$_F$ 0.38(30:70 ethyl acetate-hexane). $^1$H NMR(300 MHz, CDCl$_3$): δ 8.94(1H, s), 7.72(1H, d, J=8.5Hz), 7.58(1H, d, J=1.8Hz), 7.47–7.40(2H, m), 7.24–7.18(1H, m), 6.56(1H, d, J=7.7Hz), 6.18–6.10(1H, m), 4.82–4.76(1H, m), 3.15–2.30(5H, m), 2.10–1.77(3H, m), 1.27(3H, t, J=7.5Hz). MS(NH$_3$—CI): m/e calc'd for C$_{23}$H$_{21}$Cl$_2$N$_4$: 423.1143, found 423.1142; 427(13), 426(18), 425(67), 424(31), 423(100).

TABLE 2-continued

Example 2013 spectral data: TLC $R_F$ 0.28(30:70 ethyl acetate-hexane). $^1$H NMR(300MHz, CDCl$_3$): δ 8.91(1H, s), 7.68(1H, d, J=8.5Hz), 7.58(1H, d, J=1.8Hz), 7.46–7.38(2H, m), 7.22–7.15(1H, m), 6.91(1H, d, J=7.7Hz), 6.42(1H, br t, J=7Hz), 5.30–5.22(1H, m), 3.43–3.33 (1H, m), 3.20–3.03(1H, m), 2.89–2.76(2H, m), 2.56–2.43(1H, m), 2.01–1.90(1H, m), 1.31(3H, t, J=7.5Hz). MS(NH$_3$—CI): m/e calc'd for $C_{22}H_{19}Cl_2N_4$: 409.0987, found 409.0987; 413(12), 412(17), 411(67), 410(29), 409(100).
Example 2014 spectral data: TLC $R_F$ 0.38(30:70 ethyl acetate-hexane). $^1$H NMR(300 MHz, CDCl$_3$): δ 8.95(1H, s), 7.71(1H, d, J=8.4Hz), 7.59(1H, d, J=2.2Hz), 7.42(1H, dd, J=8.4, 2.2Hz), 7.26–7.19(1H, m), 6.98–6.90(1H, m), 6.58(1H, d, J=7.7Hz), 6.30–6.22(1H, m), 4.60–4.53(1H, m), 4.43–4.33(1H, m), 4.20(1H, br), 2.82–2.72(1H, m), 2.69–2.58(1H, m), 2.46–2.36(1H, m), 2.18–2.08(1H, m), 1.29(3H, t, J=7.5Hz). MS(NH$_3$—CI): m/e calc'd for $C_{22}H_{19}Cl_2N_4O$: 425.0936, found 425.0926; 429(12), 428(17), 427(67), 426(30), 425(100).
Example 2020 spectral data: TLC $R_F$ 0.43(30:70 ethyl acetate-hexane). $^1$H NMR(300MHz, CDCl$_3$): δ 8.98(1H, s), 7.81(2H, d, J=8.4Hz), 7.67(1H, dd, J=8.0, 0.7Hz), 4.26(1H, m), 3.00 (2H, q, J=7.6Hz), 2.75–2.66(2H, m), 2.06–1.90(4H, m), 1.50–1.36(4H, m), 1.40(3H, t, J=7.5Hz). MS(NH$_3$—CI): m/e 412(7), 411(34), 410(25), 409(100).
Example 2053 spectral data: TLC $R_F$ 0.36(25:75 ethyl acetate-hexane). $^1$H NMR(300MHz, CDCl$_3$): δ 8.96(1H, s), 7.73(1H, d, J=8.4Hz), 7.44(1H, d, J=1.1Hz), 7.28(1H, dd, J=8.4, 1.1hz), 4.79(1H, pentet, J=8.4Hz), 3.01(2H, q, J=7.7Hz), 2.62–2.50(2H, m), 2.23–2.07(2H, m), 1.89–1.77(2H, m), 1.66–1.49(2H, m), 1.41(3H, t, J=7.7Hz). MS(NH$_3$—CI): m/e calculated for $C_{19}H_{19}ClF_3N_4O$: 411.1205, found 411.1208; 414(7), 413(34), 412(24), 411(100).
Example 2216 spectral data: TLC $R_F$ 0.13(20:80 ethyl acetate-hexane). $^1$H NMR(300MHz, CDCl$_3$): δ 8.94(1H, s), 7.48–7.02(5H, m), 6.53(1H, dd, J=7.7, 1.5Hz), 6.18–6.10(1H, m), 3.16–2.20(5H, m), 2.13(3H, d, J=4.8Hz), 2.06–1.70(3H, m), 1.23(3H, dt, J=7.4, 4.4Hz). MS(NH$^3$—CI): m/e calc'd for $C_{24}H_{23}Cl_2N_4$: 437.1300, found 437.1299; 439(67), 437(100).
Example 2223 spectral data: TLC $R_F$ 0.36(50:50 ethyl acetate-hexane). $^1$H NMR(300MHz, CDCl$_3$): δ 8.91(1H, s), 7.33(1H, s), 6.83(1H, s), 4.78(1H, pentet, J=8.5Hz), 3.94(3H, s), 3.90 (3H, s), 2.98(2H, q, J=7.6Hz), 2.58–2.48(2H, m), 2.42(3H, s), 2.19–2.07(2H, m), 1.84–1.56 (4H, m), 1.43(3H, t, J=7.5Hz). MS(NH$_3$—CI): m/e calc'd for $C_{21}H_{27}N_4O_2$: 367.2134, found 367.2120; 369(3), 368(24), 367(100).
Example 2227 spectral data: TLC $R_F$ 0.45(50:50 ethyl acetate-hexane). $^1$H NMR(300MHz, CDCl$_3$): δ 8.90(1H, s), 7.37(1H, s), 6.83(1H, s), 4.85(1H, q, J=8.4Hz), 3.94(3H, s), 3.91(3H, s), 3.19–3.11(1H, m), 2.96(2H, dq, J=7.9, 1.5Hz), 2.41(3H, s), 2.24–2.16(2H, m), 2.04–1.94 (2H, m), 1.71–1.62(2H, m), 1.44(3H, t, J=7.4Hz), 0.69(3H, d, J=6.9Hz). MS(NH$_3$—CI): m/e calc'd for $C_{22}H_{29}N_4O_2$: 381.2290, found 381.2294; 383(4), 382(25), 381(100).

The methods discussed below in the preparation of 3-benzyl-5-methyl-7-(2,4, 6-trimethylphenyl)-imidazo[4,5-b]pyridine (Example 3001, Table 3) may be used to prepare all of the examples of Structure A contained in Table 3, with minor procedural modifications where necessary and use of reagents of the appropriate structure.

The methods of Schemes 13 and 14 may be used to prepare many of the examples of Structure B and Structure C contained in Table 3, with minor procedural modifications where necessary and use of reagents of the appropriate structure.

EXAMPLE 3001

Preparation of 3-Benzyl-5-methyl-7-(2,4,6-trimethylphenyl)imidazo[4,5-b]pyridine Part A. A solution of 2,4,6-trimethylbenzeneboronic acid in benzene (0.5 M) is treated with excess n-butanol, and the solution is heated to reflux under a Dean-Stark still head to azeotropically remove water. Solvent is removed by evaporation, and the resulting dibutyl 2,4,6-trimethylbenzeneboronate is used directly in Part B.

Part B. The method of Snieckus et al. (Fu, J. M.; Zhao, B. P.; Sharp, M. J.; Snieckus, V. Can. J. Chem. 1994, 72, 227–236) may be employed here. Thus, a solution of 4-chloro-6-methyl-3-nitro-2-pyridone in dimethylformamide (0.1 M) is treated with the boronate from Part A (1.2 eq), tribasic potassium phosphate (2.4 eq), and [1,1'-bis (diphenylphosphino)-ferrocene]dichloropalladium (0.1 eq). The mixture is stirred at ambient temperature for 30 hrs., then poured into 4 volumes ethyl acetate. This is washed with 3 equal volumes of water, then brine. The extract is dried over Na$_2$SO$_4$, filtered and evaporated. Chromatographic separation affords pure 6-methyl-3-nitro-4-(2,4,6-trimethylphenyl)-2-pyridone.

Part C. The pyridone from Part B is suspended in 6 eq phosphorus oxychloride, and stirred with mild heating until the compound dissolves. The mixture is cooled, and poured over ice. After melting, the mixture is extracted twice with dichloromethane, and the extracts are combined, dried over Na$_2$SO$_4$, filtered and evaporated. The product, 2-chloro-6-methyl-3-nitro-4-(2,4,6-trimethylphenyl)pyridine, is purified by either chromatography or recrystallization.

Part D. The chloride from Part C is dissolved in ethanol, and treated with benzylamine (1.2 eq.). The mixture is heated to reflux until the starting material is consumed as determined by thin-layer chromatography. The mixture is evaporated, and the residual material is partitioned between water and ethyl acetate. The organic layer is separated, washed with brine, dried over Na$_2$SO$_4$, filtered and evaporated. The product, 2-benzylamino-6-methyl-3-nitro-4-(2,4, 6-trimethylphenyl)pyridine, is purified by either chromatography or recrystallization.

Part E. The nitro compound from Part D is dissolved in 1:1 aqueous dioxane, and treated with conc. aq. ammonium hydroxide solution. To this is added solid sodium dithionite in several portions over 2 h. The mixture is allowed to stir for an additional 4 h, then partitioned between water and ethyl acetate. The organic layer is separated, washed with brine, dried over Na$_2$SO$_4$, filtered and evaporated. The product, 3-amino-2-benzylamino-6-methyl-4-(2,4,6-trimethylphenyl)pyridine, is purified by either chromatography or recrystallization.

Part F. A suspension of the diamine from Part E above in triethyl orthopropionate is treated with conc. HCl, and heated to reflux for 1 h, then cooled and the excess orthoester removed by vacuum distillation. The pot residue contains sufficiently pure N-[2-benzylamino-4-(2,4,6-trimethylphenyl)-6-methylpyridin-3-yl]propionamide O-ethyl imidate.

Part G. A solution of the compound from Part F in phenyl ether is treated with a catalytic amount of p-toluenesulfonic acid and heated to 170° C. for 6 h, then cooled. The residual liquid is separated by column chromatography (hexane, then ethyl acetate) to afford the title product.

TABLE 3

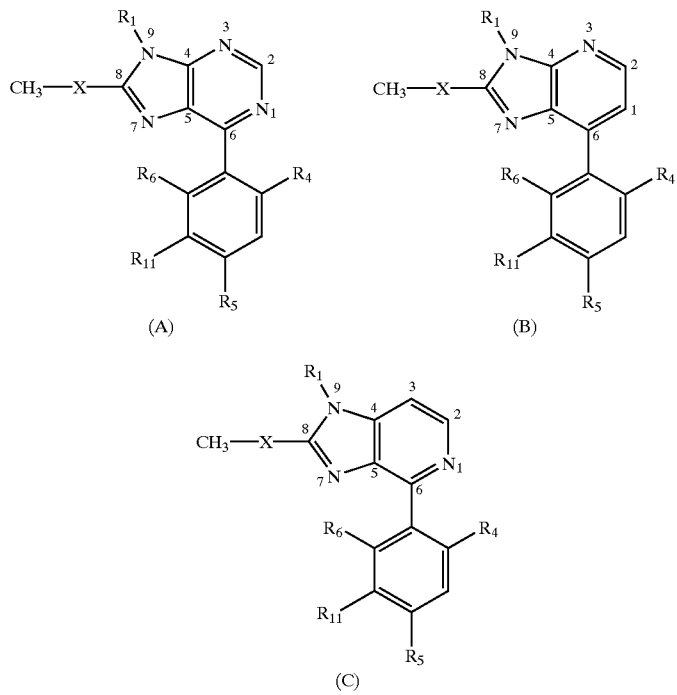

| Ex. No. | X | $R^4$ | $R^5$ | $R^{11}$ | $R^6$ | $R^1$ | mp, ° C.[a] |
|---|---|---|---|---|---|---|---|
| 3001 | $CH_2$ | Cl | Cl | H | H | $C(=O)OC_2H_5$ | — |
| 3002 | $CH_2$ | Cl | Cl | H | H | $C(=O)OC_3H_7$ | 90–91 |
| 3003 | $CH_2$ | Cl | Cl | H | H | $C(=O)OC_4H_9$ | 57–59 |
| 3004 | $CH_2$ | Cl | Cl | H | H | $C(=O)OCH(CH_3)_2$ | 80–81 |
| 3005 | $CH_2$ | Cl | Cl | H | H | $C(=O)OCH_2CH(CH_3)_2$ | 60–62 |
| 3006 | $CH_2$ | Cl | Cl | H | H | $C(=O)N(CH_3)_2$ | — |
| 3007 | $CH_2$ | Cl | Cl | H | H | $C(=O)N(C_2H_5)_2$ | 120–123 |
| 3008 | $CH_2$ | Cl | Cl | H | H | $C(=O)N[CH(CH_3)_2]_2$ | 147–149 |
| 3009 | $CH_2$ | Cl | Cl | H | H | $C(=O)(1\text{-morpholinyl})$ | 158–159 |
| 3010 | $CH_2$ | Cl | Cl | H | H | $SO_2C_6H_5$ | 132–133 |
| 3011 | $CH_2$ | Cl | Cl | H | H | $SO_2(4\text{-}CH_3\text{—}C_6H_4)$ | 154–155 |
| 3012 | $CH_2$ | Cl | Cl | H | H | $SO_2(4\text{-}OCH_3\text{—}C_6H_4)$ | 156–158 |
| 3013 | $CH_2$ | Cl | Cl | H | H | $SO_2\text{-}(2\text{-thienyl})$ | 176–178 |
| 3014 | $CH_2$ | Cl | Cl | H | H | $SO_2CH_2C_6H_5$ | 127–129 |
| 3015 | $CH_2$ | Cl | Cl | H | H | $SO_2C_3H_7$ | 100–101 |
| 3016 | $CH_2$ | Cl | Cl | H | H | $SO_2C_4H_9$ | 79–80 |
| 3017 | $CH_2$ | Cl | Cl | H | H | $C(=O)\text{-}(2\text{-}Cl\text{—}C_6H_4)$ | 110–113 |
| 3018 | $CH_2$ | Cl | $CF_3$ | H | H | $C(=O)OC_2H_5$ | — |
| 3019 | $CH_2$ | Cl | $CF_3$ | H | H | $C(=O)OC_3H_7$ | — |
| 3020 | $CH_2$ | Cl | $CF_3$ | H | H | $C(=O)OC_4H_9$ | — |
| 3021 | $CH_2$ | Cl | $CF_3$ | H | H | $C(=O)OCH(CH_3)_2$ | — |
| 3022 | $CH_2$ | Cl | $CF_3$ | H | H | $C(=O)OCH_2CH(CH_3)_2$ | — |
| 3023 | $CH_2$ | Cl | $CF_3$ | H | H | $C(=O)N(CH_3)_2$ | — |
| 3024 | $CH_2$ | Cl | $CF_3$ | H | H | $C(=O)N(C_2H_5)_2$ | — |
| 3025 | $CH_2$ | Cl | $CF_3$ | H | H | $C(=O)N[CH(CH_3)_2]_2$ | — |
| 3026 | $CH_2$ | Cl | $CF_3$ | H | H | $C(=O)(1\text{-morpholinyl})$ | — |
| 3027 | $CH_2$ | Cl | $CF_3$ | H | H | $SO_2C_6H_5$ | — |
| 3028 | $CH_2$ | Cl | $CF_3$ | H | H | $SO_2(4\text{-}CH_3\text{—}C_6H_4)$ | — |
| 3029 | $CH_2$ | Cl | $CF_3$ | H | H | $SO_2(4\text{-}OCH_3\text{—}C_6H_4)$ | — |
| 3030 | $CH_2$ | Cl | $CF_3$ | H | H | $SO_2\text{-}(2\text{-thienyl})$ | — |
| 3031 | $CH_2$ | Cl | $CF_3$ | H | H | $SO_2CH_2C_6H_5$ | — |
| 3032 | $CH_2$ | Cl | $CF_3$ | H | H | $SO_2C_3H_7$ | — |
| 3033 | $CH_2$ | Cl | $CF_3$ | H | H | $SO_2C_4H_9$ | — |
| 3034 | $CH_2$ | Cl | $CF_3$ | H | H | $C(=O)\text{-}(2\text{-}Cl\text{—}C_6H_4)$ | — |
| 3035 | $CH_2$ | Cl | $OCH_3$ | H | H | $C(=O)OC_2H_5$ | — |
| 3036 | $CH_2$ | Cl | $OCH_3$ | H | H | $C(=O)OC_3H_7$ | — |
| 3037 | $CH_2$ | Cl | $OCH_3$ | H | H | $C(=O)OC_4H_9$ | — |
| 3038 | $CH_2$ | Cl | $OCH_3$ | H | H | $C(=O)OCH(CH_3)_2$ | — |

TABLE 3-continued

| | | | | | | | |
|---|---|---|---|---|---|---|---|
| 3039 | $CH_2$ | Cl | $OCH_3$ | H | H | $C(=O)OCH_2CH(CH_3)_2$ | — |
| 3040 | $CH_2$ | Cl | $OCH_3$ | H | H | $C(=O)N(CH_3)_2$ | — |
| 3041 | $CH_2$ | Cl | $OCH_3$ | H | H | $C(=O)N(C_2H_5)_2$ | — |
| 3042 | $CH_2$ | Cl | $OCH_3$ | H | H | $C(=O)N[CH(CH_3)_2]_2$ | — |
| 3043 | $CH_2$ | Cl | $OCH_3$ | H | H | $C(=O)(1\text{-morpholinyl})$ | — |
| 3044 | $CH_2$ | Cl | $OCH_3$ | H | H | $SO_2C_6H_5$ | — |
| 3045 | $CH_2$ | Cl | $OCH_3$ | H | H | $SO_2(4\text{-}CH_3\text{—}C_6H_4)$ | — |
| 3046 | $CH_2$ | Cl | $OCH_3$ | H | H | $SO_2(4\text{-}OCH_3\text{—}C_6H_4)$ | — |
| 3047 | $CH_2$ | Cl | $OCH_3$ | H | H | $SO_2\text{-}(2\text{-thienyl})$ | — |
| 3048 | $CH_2$ | Cl | $OCH_3$ | H | H | $SO_2CH_2C_6H_5$ | — |
| 3049 | $CH_2$ | Cl | $OCH_3$ | H | H | $SO_2C_3H_7$ | — |
| 3050 | $CH_2$ | Cl | $OCH_3$ | H | H | $SO_2C_4H_9$ | — |
| 3051 | $CH_2$ | Cl | $OCH_3$ | H | H | $C(=O)\text{-}(2\text{-Cl}\text{—}C_6H_4)$ | — |
| 3052 | $CH_2$ | Cl | $OCF_3$ | H | H | $C(=O)OC_2H_5$ | — |
| 3053 | $CH_2$ | Cl | $OCF_3$ | H | H | $C(=O)OC_3H_7$ | — |
| 3054 | $CH_2$ | Cl | $OCF_3$ | H | H | $C(=O)OC_4H_9$ | — |
| 3055 | $CH_2$ | Cl | $OCF_3$ | H | H | $C(=O)OCH(CH_3)_2$ | — |
| 3056 | $CH_2$ | Cl | $OCF_3$ | H | H | $C(=O)OCH_2CH(CH_3)_2$ | — |
| 3057 | $CH_2$ | Cl | $OCF_3$ | H | H | $C(=O)N(CH_3)_2$ | — |
| 3058 | $CH_2$ | Cl | $OCF_3$ | H | H | $C(=O)N(C_2H_5)_2$ | — |
| 3059 | $CH_2$ | Cl | $OCF_3$ | H | H | $C(=O)N[CH(CH_3)_2]_2$ | — |
| 3060 | $CH_2$ | Cl | $OCF_3$ | H | H | $C(=O)(1\text{-morpholinyl})$ | — |
| 3061 | $CH_2$ | Cl | $OCF_3$ | H | H | $SO_2C_6H_5$ | — |
| 3062 | $CH_2$ | Cl | $OCF_3$ | H | H | $SO_2(4\text{-}CH_3\text{—}C_6H_4)$ | — |
| 3063 | $CH_2$ | Cl | $OCF_3$ | H | H | $SO_2(4\text{-}OCH_3\text{—}C_6H_4)$ | — |
| 3064 | $CH_2$ | Cl | $OCF_3$ | H | H | $SO_2\text{-}(2\text{-thienyl})$ | — |
| 3065 | $CH_2$ | Cl | $OCF_3$ | H | H | $SO_2CH_2C_6H_5$ | — |
| 3066 | $CH_2$ | Cl | $OCF_3$ | H | H | $SO_2C_3H_7$ | — |
| 3067 | $CH_2$ | Cl | $OCF_3$ | H | H | $SO_2C_4H_9$ | — |
| 3068 | $CH_2$ | Cl | $OCF_3$ | H | H | $C(=O)\text{-}(2\text{-Cl}\text{—}C_6H_4)$ | — |
| 3069 | $CH_2$ | Cl | $CH_3$ | H | H | $C(=O)OC_2H_5$ | — |
| 3070 | $CH_2$ | Cl | $CH_3$ | H | H | $C(=O)OC_3H_7$ | — |
| 3071 | $CH_2$ | Cl | $CH_3$ | H | H | $C(=O)OC_4H_9$ | — |
| 3072 | $CH_2$ | Cl | $CH_3$ | H | H | $C(=O)OCH(CH_3)_2$ | — |
| 3073 | $CH_2$ | Cl | $CH_3$ | H | H | $C(=O)OCH_2CH(CH_3)_2$ | — |
| 3074 | $CH_2$ | Cl | $CH_3$ | H | H | $C(=O)N(CH_3)_2$ | — |
| 3075 | $CH_2$ | Cl | $CH_3$ | H | H | $C(=O)N(C_2H_5)_2$ | — |
| 3076 | $CH_2$ | Cl | $CH_3$ | H | H | $C(=O)N[CH(CH_3)_2]_2$ | — |
| 3077 | $CH_2$ | Cl | $CH_3$ | H | H | $C(=O)(1\text{-morpholinyl})$ | — |
| 3078 | $CH_2$ | Cl | $CH_3$ | H | H | $SO_2C_6H_5$ | — |
| 3079 | $CH_2$ | Cl | $CH_3$ | H | H | $SO_2(4\text{-}CH_3\text{—}C_6H_4)$ | — |
| 3080 | $CH_2$ | Cl | $CH_3$ | H | H | $SO_2(4\text{-}OCH_3\text{—}C_6H_4)$ | — |
| 3081 | $CH_2$ | Cl | $CH_3$ | H | H | $SO_2\text{-}(2\text{-thienyl})$ | — |
| 3082 | $CH_2$ | Cl | $CH_3$ | H | H | $SO_2CH_2C_6H_5$ | — |
| 3083 | $CH_2$ | Cl | $CH_3$ | H | H | $SO_2C_3H_7$ | — |
| 3084 | $CH_2$ | Cl | $CH_3$ | H | H | $SO_2C_4H_9$ | — |
| 3085 | $CH_2$ | Cl | $CH_3$ | H | H | $C(=O)\text{-}(2\text{-Cl}\text{—}C_6H_4)$ | — |
| 3086 | $CH_2$ | $CF_3$ | Cl | H | H | $C(=O)OC_2H_5$ | — |
| 3087 | $CH_2$ | $CF_3$ | Cl | H | H | $C(=O)OC_3H_7$ | — |
| 3088 | $CH_2$ | $CF_3$ | Cl | H | H | $C(=O)OC_4H_9$ | — |
| 3089 | $CH_2$ | $CF_3$ | Cl | H | H | $C(=O)OCH(CH_3)_2$ | — |
| 3090 | $CH_2$ | $CF_3$ | Cl | H | H | $C(=O)OCH_2CH(CH_3)_2$ | — |
| 3091 | $CH_2$ | $CF_3$ | Cl | H | H | $C(=O)N(CH_3)_2$ | — |
| 3092 | $CH_2$ | $CF_3$ | Cl | H | H | $C(=O)N(C_2H_5)_2$ | — |
| 3093 | $CH_2$ | $CF_3$ | Cl | H | H | $C(=O)N[CH(CH_3)_2]_2$ | — |
| 3094 | $CH_2$ | $CF_3$ | Cl | H | H | $C(=O)(1\text{-morpholinyl})$ | — |
| 3095 | $CH_2$ | $CF_3$ | Cl | H | H | $SO_2C_6H_5$ | — |
| 3096 | $CH_2$ | $CF_3$ | Cl | H | H | $SO_2(4\text{-}CH_3\text{—}C_6H_4)$ | — |
| 3097 | $CH_2$ | $CF_3$ | Cl | H | H | $SO_2(4\text{-}OCH_3\text{—}C_6H_4)$ | — |
| 3098 | $CH_2$ | $CF_3$ | Cl | H | H | $SO_2\text{-}(2\text{-thienyl})$ | — |
| 3099 | $CH_2$ | $CF_3$ | Cl | H | H | $SO_2CH_2C_6H_5$ | — |
| 3100 | $CH_2$ | $CF_3$ | Cl | H | H | $SO_2C_3H_7$ | — |
| 3101 | $CH_2$ | $CF_3$ | Cl | H | H | $SO_2C_4H_9$ | — |
| 3102 | $CH_2$ | $CF_3$ | Cl | H | H | $C(=O)\text{-}(2\text{-Cl}\text{—}C_6H_4)$ | — |
| 3103 | $CH_2$ | $CF_3$ | $OCH_3$ | H | H | $C(=O)OC_2H_5$ | — |
| 3104 | $CH_2$ | $CF_3$ | $OCH_3$ | H | H | $C(=O)OC_3H_7$ | — |
| 3105 | $CH_2$ | $CF_3$ | $OCH_3$ | H | H | $C(=O)OC_4H_9$ | — |
| 3106 | $CH_2$ | $CF_3$ | $OCH_3$ | H | H | $C(=O)OCH(CH_3)_2$ | — |
| 3107 | $CH_2$ | $CF_3$ | $OCH_3$ | H | H | $C(=O)OCH_2CH(CH_3)_2$ | — |
| 3108 | $CH_2$ | $CF_3$ | $OCH_3$ | H | H | $C(=O)N(CH_3)_2$ | — |
| 3109 | $CH_2$ | $CF_3$ | $OCH_3$ | H | H | $C(=O)N(C_2H_5)_2$ | — |
| 3110 | $CH_2$ | $CF_3$ | $OCH_3$ | H | H | $C(=O)N[CH(CH_3)_2]_2$ | — |
| 3111 | $CH_2$ | $CF_3$ | $OCH_3$ | H | H | $C(=O)(1\text{-morpholinyl})$ | — |
| 3112 | $CH_2$ | $CF_3$ | $OCH_3$ | H | H | $SO_2C_6H_5$ | — |
| 3113 | $CH_2$ | $CF_3$ | $OCH_3$ | H | H | $SO_2(4\text{-}CH_3\text{—}C_6H_4)$ | — |
| 3114 | $CH_2$ | $CF_3$ | $OCH_3$ | H | H | $SO_2(4\text{-}OCH_3\text{—}C_6H_4)$ | — |
| 3115 | $CH_2$ | $CF_3$ | $OCH_3$ | H | H | $SO_2\text{-}(2\text{-thienyl})$ | — |
| 3116 | $CH_2$ | $CF_3$ | $OCH_3$ | H | H | $SO_2CH_2C_6H_5$ | — |
| 3117 | $CH_2$ | $CF_3$ | $OCH_3$ | H | H | $SO_2C_3H_7$ | — |

TABLE 3-continued

| | | | | | | | |
|---|---|---|---|---|---|---|---|
| 3118 | $CH_2$ | $CF_3$ | $OCH_3$ | H | H | $SO_2C_4H_9$ | — |
| 3119 | $CH_2$ | $CF_3$ | $OCH_3$ | H | H | $C(=O)$-(2-Cl—$C_6H_4$) | — |
| 3120 | $CH_2$ | $CF_3$ | F | H | H | $C(=O)OC_2H_5$ | — |
| 3121 | $CH_2$ | $CF_3$ | F | H | H | $C(=O)OC_3H_7$ | — |
| 3122 | $CH_2$ | $CF_3$ | F | H | H | $C(=O)OC_4H_9$ | — |
| 3123 | $CH_2$ | $CF_3$ | F | H | H | $C(=O)OCH(CH_3)_2$ | — |
| 3124 | $CH_2$ | $CF_3$ | F | H | H | $C(=O)OCH_2CH(CH_3)_2$ | — |
| 3125 | $CH_2$ | $CF_3$ | F | H | H | $C(=O)N(CH_3)_2$ | — |
| 3126 | $CH_2$ | $CF_3$ | F | H | H | $C(=O)N(C_2H_5)_2$ | — |
| 3127 | $CH_2$ | $CF_3$ | F | H | H | $C(=O)N[CH(CH_3)_2]_2$ | — |
| 3128 | $CH_2$ | $CF_3$ | F | H | H | $C(=O)$(1-morpholinyl) | — |
| 3129 | $CH_2$ | $CF_3$ | F | H | H | $SO_2C_6H_5$ | — |
| 3130 | $CH_2$ | $CF_3$ | F | H | H | $SO_2$(4-$CH_3$—$C_6H_4$) | — |
| 3131 | $CH_2$ | $CF_3$ | F | H | H | $SO_2$(4-$OCH_3$—$C_6H_4$) | — |
| 3132 | $CH_2$ | $CF_3$ | F | H | H | $SO_2$-(2-thienyl) | — |
| 3133 | $CH_2$ | $CF_3$ | F | H | H | $SO_2CH_2C_6H_5$ | — |
| 3134 | $CH_2$ | $CF_3$ | F | H | H | $SO_2C_3H_7$ | — |
| 3135 | $CH_2$ | $CF_3$ | F | H | H | $SO_2C_4H_9$ | — |
| 3136 | $CH_2$ | $CF_3$ | F | H | H | $C(=O)$-(2-Cl—$C_6H_4$) | — |
| 3137 | $CH_2$ | $CH_3$ | $OCH_3$ | $CH_3$ | H | $C(=O)OC_2H_5$ | — |
| 3138 | $CH_2$ | $CH_3$ | $OCH_3$ | $CH_3$ | H | $C(=O)OC_3H_7$ | — |
| 3139 | $CH_2$ | $CH_3$ | $OCH_3$ | $CH_3$ | H | $C(=O)OC_4H_9$ | — |
| 3140 | $CH_2$ | $CH_3$ | $OCH_3$ | $CH_3$ | H | $C(=O)OCH(CH_3)_2$ | — |
| 3141 | $CH_2$ | $CH_3$ | $OCH_3$ | $CH_3$ | H | $C(=O)OCH_2CH(CH_3)_2$ | — |
| 3142 | $CH_2$ | $CH_3$ | $OCH_3$ | $CH_3$ | H | $C(=O)N(CH_3)_2$ | — |
| 3143 | $CH_2$ | $CH_3$ | $OCH_3$ | $CH_3$ | H | $C(=O)N(C_2H_5)_2$ | — |
| 3144 | $CH_2$ | $CH_3$ | $OCH_3$ | $CH_3$ | H | $C(=O)N[CH(CH_3)_2]_2$ | — |
| 3145 | $CH_2$ | $CH_3$ | $OCH_3$ | $CH_3$ | H | $C(=O)$(1-morpholinyl) | — |
| 3146 | $CH_2$ | $CH_3$ | $OCH_3$ | $CH_3$ | H | $SO_2C_6H_5$ | — |
| 3147 | $CH_2$ | $CH_3$ | $OCH_3$ | $CH_3$ | H | $SO_2$(4-$CH_3$—$C_6H_4$) | — |
| 3148 | $CH_2$ | $CH_3$ | $OCH_3$ | $CH_3$ | H | $SO_2$(4-$OCH_3$—$C_6H_4$) | — |
| 3149 | $CH_2$ | $CH_3$ | $OCH_3$ | $CH_3$ | H | $SO_2$-(2-thienyl) | — |
| 3150 | $CH_2$ | $CH_3$ | $OCH_3$ | $CH_3$ | H | $SO_2CH_2C_6H_5$ | — |
| 3151 | $CH_2$ | $CH_3$ | $OCH_3$ | $CH_3$ | H | $SO_2C_3H_7$ | — |
| 3152 | $CH_2$ | $CH_3$ | $OCH_3$ | $CH_3$ | H | $SO_2C_4H_9$ | — |
| 3153 | $CH_2$ | $CH_3$ | $OCH_3$ | $CH_3$ | H | $C(=O)$-(2-Cl—$C_6H_4$) | — |
| 3154 | $CH_2$ | $CH_3$ | $OCH_3$ | Cl | H | $C(=O)OC_2H_5$ | — |
| 3155 | $CH_2$ | $CH_3$ | $OCH_3$ | Cl | H | $C(=O)OC_3H_7$ | — |
| 3156 | $CH_2$ | $CH_3$ | $OCH_3$ | Cl | H | $C(=O)OC_4H_9$ | — |
| 3157 | $CH_2$ | $CH_3$ | $OCH_3$ | Cl | H | $C(=O)OCH(CH_3)_2$ | — |
| 3158 | $CH_2$ | $CH_3$ | $OCH_3$ | Cl | H | $C(=O)OCH_2CH(CH_3)_2$ | — |
| 3159 | $CH_2$ | $CH_3$ | $OCH_3$ | Cl | H | $C(=O)N(CH_3)_2$ | — |
| 3160 | $CH_2$ | $CH_3$ | $OCH_3$ | Cl | H | $C(=O)N(C_2H_5)_2$ | — |
| 3161 | $CH_2$ | $CH_3$ | $OCH_3$ | Cl | H | $C(=O)N[CH(CH_3)_2]_2$ | — |
| 3162 | $CH_2$ | $CH_3$ | $OCH_3$ | Cl | H | $C(=O)$(1-morpholinyl) | — |
| 3163 | $CH_2$ | $CH_3$ | $OCH_3$ | Cl | H | $SO_2C_6H_5$ | — |
| 3164 | $CH_2$ | $CH_3$ | $OCH_3$ | Cl | H | $SO_2$(4-$CH_3$—$C_6H_4$) | — |
| 3165 | $CH_2$ | $CH_3$ | $OCH_3$ | Cl | H | $SO_2$(4-$OCH_3$—$C_6H_4$) | — |
| 3166 | $CH_2$ | $CH_3$ | $OCH_3$ | Cl | H | $SO_2$-(2-thienyl) | — |
| 3167 | $CH_2$ | $CH_3$ | $OCH_3$ | Cl | H | $SO_2CH_2C_6H_5$ | — |
| 3168 | $CH_2$ | $CH_3$ | $OCH_3$ | Cl | H | $SO_2C_3H_7$ | — |
| 3169 | $CH_2$ | $CH_3$ | $OCH_3$ | Cl | H | $SO_2C_4H_9$ | — |
| 3170 | $CH_2$ | $CH_3$ | $OCH_3$ | Cl | H | $C(=O)$-(2-Cl—$C_6H_4$) | — |
| 3171 | $CH_2$ | $CH_3$ | $OCH_3$ | F | H | $C(=O)OC_2H_5$ | — |
| 3172 | $CH_2$ | $CH_3$ | $OCH_3$ | F | H | $C(=O)OC_3H_7$ | — |
| 3173 | $CH_2$ | $CH_3$ | $OCH_3$ | F | H | $C(=O)OC_4H_9$ | — |
| 3174 | $CH_2$ | $CH_3$ | $OCH_3$ | F | H | $C(=O)OCH(CH_3)_2$ | — |
| 3175 | $CH_2$ | $CH_3$ | $OCH_3$ | F | H | $C(=O)OCH_2CH(CH_3)_2$ | — |
| 3176 | $CH_2$ | $CH_3$ | $OCH_3$ | F | H | $C(=O)N(CH_3)_2$ | — |
| 3177 | $CH_2$ | $CH_3$ | $OCH_3$ | F | H | $C(=O)N(C_2H_5)_2$ | — |
| 3178 | $CH_2$ | $CH_3$ | $OCH_3$ | F | H | $C(=O)N[CH(CH_3)_2]_2$ | — |
| 3179 | $CH_2$ | $CH_3$ | $OCH_3$ | F | H | $C(=O)$(1-morpholinyl) | — |
| 3180 | $CH_2$ | $CH_3$ | $OCH_3$ | F | H | $SO_2C_6H_5$ | — |
| 3181 | $CH_2$ | $CH_3$ | $OCH_3$ | F | H | $SO_2$(4-$CH_3$—$C_6H_4$) | — |
| 3182 | $CH_2$ | $CH_3$ | $OCH_3$ | F | H | $SO_2$(4-$OCH_3$—$C_6H_4$) | — |
| 3183 | $CH_2$ | $CH_3$ | $OCH_3$ | F | H | $SO_2$-(2-thienyl) | — |
| 3184 | $CH_2$ | $CH_3$ | $OCH_3$ | F | H | $SO_2CH_2C_6H_5$ | — |
| 3185 | $CH_2$ | $CH_3$ | $OCH_3$ | F | H | $SO_2C_3H_7$ | — |
| 3186 | $CH_2$ | $CH_3$ | $OCH_3$ | F | H | $SO_2C_4H_9$ | — |
| 3187 | $CH_2$ | $CH_3$ | $OCH_3$ | F | H | $C(=O)$-(2-Cl—$C_6H_4$) | — |
| 3188 | $CH_2$ | $CH_3$ | $CH_3$ | H | $CH_3$ | $C(=O)OC_2H_5$ | — |
| 3189 | $CH_2$ | $CH_3$ | $CH_3$ | H | $CH_3$ | $C(=O)OC_3H_7$ | — |
| 3190 | $CH_2$ | $CH_3$ | $CH_3$ | H | $CH_3$ | $C(=O)OC_4H_9$ | — |
| 3191 | $CH_2$ | $CH_3$ | $CH_3$ | H | $CH_3$ | $C(=O)OCH(CH_3)_2$ | — |
| 3192 | $CH_2$ | $CH_3$ | $CH_3$ | H | $CH_3$ | $C(=O)OCH_2CH(CH_3)_2$ | — |
| 3193 | $CH_2$ | $CH_3$ | $CH_3$ | H | $CH_3$ | $C(=O)N(CH_3)_2$ | — |
| 3194 | $CH_2$ | $CH_3$ | $CH_3$ | H | $CH_3$ | $C(=O)N(C_2H_5)_2$ | — |
| 3195 | $CH_2$ | $CH_3$ | $CH_3$ | H | $CH_3$ | $C(=O)N[CH(CH_3)_2]_2$ | — |
| 3196 | $CH_2$ | $CH_3$ | $CH_3$ | H | $CH_3$ | $C(=O)$(1-morpholinyl) | — |

TABLE 3-continued

| | | | | | | | |
|---|---|---|---|---|---|---|---|
| 3197 | $CH_2$ | $CH_3$ | $CH_3$ | H | $CH_3$ | $SO_2C_6H_5$ | — |
| 3198 | $CH_2$ | $CH_3$ | $CH_3$ | H | $CH_3$ | $SO_2(4\text{-}CH_3\text{---}C_6H_4)$ | — |
| 3199 | $CH_2$ | $CH_3$ | $CH_3$ | H | $CH_3$ | $SO_2(4\text{-}OCH_3\text{---}C_6H_4)$ | — |
| 3200 | $CH_2$ | $CH_3$ | $CH_3$ | H | $CH_3$ | $SO_2\text{-}(2\text{-thienyl})$ | — |
| 3201 | $CH_2$ | $CH_3$ | $CH_3$ | H | $CH_3$ | $SO_2CH_2C_6H_5$ | — |
| 3202 | $CH_2$ | $CH_3$ | $CH_3$ | H | $CH_3$ | $SO_2C_3H_7$ | — |
| 3203 | $CH_2$ | $CH_3$ | $CH_3$ | H | $CH_3$ | $SO_2C_4H_9$ | — |
| 3204 | $CH_2$ | $CH_3$ | $CH_3$ | H | $CH_3$ | $C(=O)\text{-}(2\text{-}Cl\text{---}C_6H_4)$ | — |
| 3205 | $CH_2$ | Cl | Cl | H | $CH_3$ | $C(=O)OC_2H_5$ | — |
| 3206 | $CH_2$ | Cl | Cl | H | $CH_3$ | $C(=O)OC_3H_7$ | — |
| 3207 | $CH_2$ | Cl | Cl | H | $CH_3$ | $C(=O)OC_4H_9$ | — |
| 3208 | $CH_2$ | Cl | Cl | H | $CH_3$ | $C(=O)OCH(CH_3)_2$ | — |
| 3209 | $CH_2$ | Cl | Cl | H | $CH_3$ | $C(=O)OCH_2CH(CH_3)_2$ | — |
| 3210 | $CH_2$ | Cl | Cl | H | $CH_3$ | $C(=O)N(CH_3)_2$ | — |
| 3211 | $CH_2$ | Cl | Cl | H | $CH_3$ | $C(=O)N(C_2H_5)_2$ | — |
| 3212 | $CH_2$ | Cl | Cl | H | $CH_3$ | $C(=O)N[CH(CH_3)_2]_2$ | — |
| 3213 | $CH_2$ | Cl | Cl | H | $CH_3$ | $C(=O)(1\text{-morpholinyl})$ | — |
| 3214 | $CH_2$ | Cl | Cl | H | $CH_3$ | $SO_2C_6H_5$ | — |
| 3215 | $CH_2$ | Cl | Cl | H | $CH_3$ | $SO_2(4\text{-}CH_3\text{---}C_6H_4)$ | — |
| 3216 | $CH_2$ | Cl | Cl | H | $CH_3$ | $SO_2(4\text{-}OCH_3\text{---}C_6H_4)$ | — |
| 3217 | $CH_2$ | Cl | Cl | H | $CH_3$ | $SO_2\text{-}Cl\text{-thienyl})$ | — |
| 3218 | $CH_2$ | Cl | Cl | H | $CH_3$ | $SO_2CH_2C_6H_5$ | — |
| 3219 | $CH_2$ | Cl | Cl | H | $CH_3$ | $SO_2C_3H_7$ | — |
| 3220 | $CH_2$ | Cl | Cl | H | $CH_3$ | $SO_2C_4H_9$ | — |
| 3221 | $CH_2$ | Cl | Cl | H | $CH_3$ | $C(=O)\text{-}(2\text{-}Cl\text{---}C_6H_4)$ | — |
| 3222 | $CH_2$ | $CH_3$ | $OCH_3$ | $OCH_3$ | H | $C(=O)OC_2H_5$ | — |
| 3223 | $CH_2$ | $CH_3$ | $OCH_3$ | $OCH_3$ | H | $C(=O)OC_3H_7$ | — |
| 3224 | $CH_2$ | $CH_3$ | $OCH_3$ | $OCH_3$ | H | $C(=O)OC_4H_9$ | — |
| 3225 | $CH_2$ | $CH_3$ | $OCH_3$ | $OCH_3$ | H | $C(=O)OCH(CH_3)_2$ | — |
| 3226 | $CH_2$ | $CH_3$ | $OCH_3$ | $OCH_3$ | H | $C(=O)OCH_2CH(CH_3)_2$ | — |
| 3227 | $CH_2$ | $CH_3$ | $OCH_3$ | $OCH_3$ | H | $C(=O)N(CH_3)_2$ | — |
| 3228 | $CH_2$ | $CH_3$ | $OCH_3$ | $OCH_3$ | H | $C(=O)N(C_2H_5)_2$ | — |
| 3229 | $CH_2$ | $CH_3$ | $OCH_3$ | $OCH_3$ | H | $C(=O)N[CH(CH_3)_2]_2$ | — |
| 3230 | $CH_2$ | $CH_3$ | $OCH_3$ | $OCH_3$ | H | $C(=O)(1\text{-morpholinyl})$ | — |
| 3231 | $CH_2$ | $CH_3$ | $OCH_3$ | $OCH_3$ | H | $SO_2C_6H_5$ | - |
| 3232 | $CH_2$ | $CH_3$ | $OCH_3$ | $OCH_3$ | H | $SO_2(4\text{-}CH_3\text{---}C_6H_4)$ | — |
| 3233 | $CH_2$ | $CH_3$ | $OCH_3$ | $OCH_3$ | H | $SO_2(4\text{-}OCH_3\text{---}C_6H_4)$ | — |
| 3234 | $CH_2$ | $CH_3$ | $OCH_3$ | $OCH_3$ | H | $SO_2\text{-}(2\text{-thienyl})$ | — |
| 3235 | $CH_2$ | $CH_3$ | $OCH_3$ | $OCH_3$ | H | $SO_2CH_2C_6H_5$ | — |
| 3236 | $CH_2$ | $CH_3$ | $OCH_3$ | $OCH_3$ | H | $SO_2C_3H_7$ | — |
| 3237 | $CH_2$ | $CH_3$ | $OCH_3$ | $OCH_3$ | H | $SO_2C_4H_9$ | — |
| 3238 | $CH_2$ | $CH_3$ | $OCH_3$ | $OCH_3$ | H | $C(=O)\text{-}(2\text{-}Cl\text{---}C_6H_4)$ | — |
| 3239 | O | Cl | Cl | H | H | $SO_2C_3H_7$ | — |
| 3240 | O | Cl | $CF_3$ | H | H | $SO_2C_3H_7$ | — |
| 3241 | O | Cl | $OCH_3$ | H | H | $SO_2C_3H_7$ | — |
| 3242 | O | Cl | $OCF_3$ | H | H | $SO_2C_3H_7$ | — |
| 3243 | O | Cl | $CH_3$ | H | H | $SO_2C_3H_7$ | — |
| 3244 | O | $CF_3$ | Cl | H | H | $SO_2C_3H_7$ | — |
| 3245 | O | $CF_3$ | $OCH_3$ | H | H | $SO_2C_3H_7$ | — |
| 3246 | O | $CH_3$ | $OCH_3$ | $CH_3$ | H | $SO_2C_3H_7$ | — |
| 3247 | O | $CH_3$ | $OCH_3$ | Cl | H | $SO_2C_3H_7$ | — |
| 3248 | O | $CH_3$ | $OCH_3$ | F | H | $SO_2C_3H_7$ | — |
| 3249 | O | $CH_3$ | $CH_3$ | H | $CH_3$ | $SO_2C_3H_7$ | — |
| 3250 | O | Cl | Cl | H | $CH_3$ | $SO_2C_3H_7$ | — |
| 3251 | $CH_2$ | Cl | Cl | H | H | $C(=O)\text{-}(3\text{-}Cl\text{---}C_6H_4)$ | 115–118 |

The methods used in the preparation of the compounds of Structure A of Table 1 may be used for the compounds of Structure A of Table 4. For example, replacing variously-substituted pyridine- and pyrimidineboronic acids for benzeneboronic acids in the palladium-catalyzed aryl cross-coupling method (see Examples 35 or 831) will afford the desired 6-pyridyl- or 6-pyrimidylpurine compounds.

The methods of Schemes 13 and 14 may be used to prepare many of the examples of Structure B and Structure C contained in Table 4, with minor procedural modifications where necessary and use of reagents of the appropriate structure.

TABLE 4

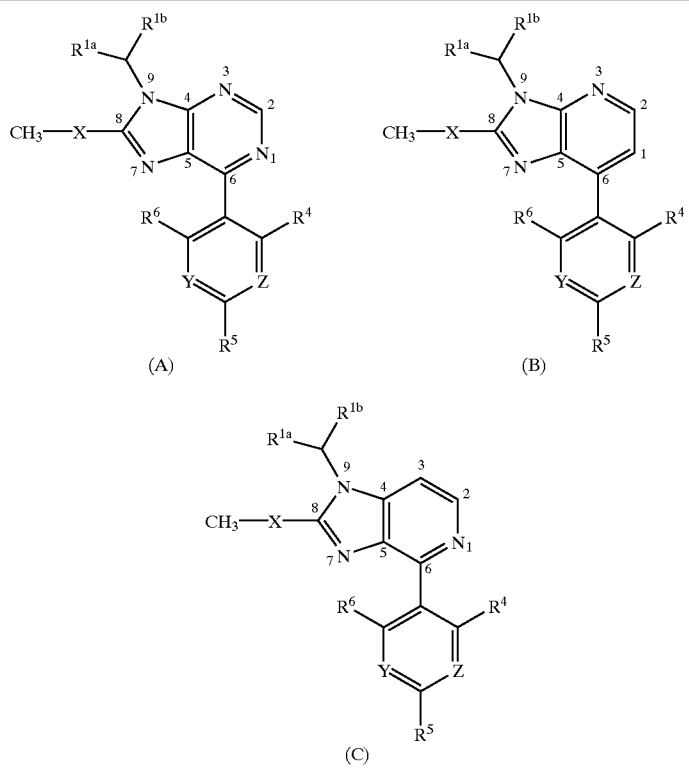

| Ex. No. | X | R⁴ | Z | R⁵ | Y | R⁶ | R¹ᵃ | R¹ᵇ | m.p., °C.ᵃ |
|---|---|---|---|---|---|---|---|---|---|
| 4001 | CH₂ | CH₃ | CH | N(CH₃)₂ | N | H | c-C₃H₅ | c-C₃H₅ | — |
| 4002 | CH₂ | CH₃ | CH | N(CH₃)₂ | N | H | CH₃ | c-C₃H₅ | — |
| 4003 | CH₂ | CH₃ | CH | N(CH₃)₂ | N | H | C₂H₅ | c-C₃H₅ | — |
| 4004 | CH₂ | CH₃ | CH | N(CH₃)₂ | N | H | C₃H₇ | c-C₃H₅ | — |
| 4005 | CH₂ | CH₃ | CH | N(CH₃)₂ | N | H | C₄H₉ | c-C₃H₅ | — |
| 4006 | CH₂ | CH₃ | CH | N(CH₃)₂ | N | H | CH₃ | C₃H₇ | — |
| 4007 | CH₂ | CH₃ | CH | N(CH₃)₂ | N | H | C₂H₅ | C₃H₇ | — |
| 4008 | CH₂ | CH₃ | CH | N(CH₃)₂ | N | H | C₃H₇ | C₃H₇ | — |
| 4009 | CH₂ | CH₃ | CH | N(CH₃)₂ | N | H | C₂H₅ | C₄H₉ | — |
| 4010 | CH₂ | CH₃ | CH | N(CH₃)₂ | N | H | H | 4-CH₃O—C₆H₄ | — |
| 4011 | O | CH₃ | CH | N(CH₃)₂ | N | H | c-C₃H₅ | c-C₃H₅ | — |
| 4012 | O | CH₃ | CH | N(CH₃)₂ | N | H | CH₃ | c-C₃H₅ | — |
| 4013 | O | CH₃ | CH | N(CH₃)₂ | N | H | C₂H₅ | c-C₃H₅ | — |
| 4014 | O | CH₃ | CH | N(CH₃)₂ | N | H | C₃H₇ | c-C₃H₅ | — |
| 4015 | O | CH₃ | CH | N(CH₃)₂ | N | H | C₄H₉ | c-C₃H₅ | — |
| 4016 | O | CH₃ | CH | N(CH₃)₂ | N | H | CH₃ | C₃H₇ | — |
| 4017 | O | CH₃ | CH | N(CH₃)₂ | N | H | C₂H₅ | C₃H₇ | — |
| 4018 | O | CH₃ | CH | N(CH₃)₂ | N | H | C₃H₇ | C₃H₇ | — |
| 4019 | O | CH₃ | CH | N(CH₃)₂ | N | H | C₂H₅ | C₄H₉ | — |
| 4020 | O | CH₃ | CH | N(CH₃)₂ | N | H | H | 4-CH₃O—C₆H₄ | — |
| 4021 | CH₂ | CH₃ | CH | CH₃ | N | CH₃ | c-C₃H₅ | c-C₃H₅ | — |
| 4022 | CH₂ | CH₃ | CH | CH₃ | N | CH₃ | CH₃ | c-C₃H₅ | — |
| 4023 | CH₂ | CH₃ | CH | CH₃ | N | CH₃ | C₂H₅ | c-C₃H₅ | — |
| 4024 | CH₂ | CH₃ | CH | CH₃ | N | CH₃ | C₃H₇ | c-C₃H₅ | — |
| 4025 | CH₂ | CH₃ | CH | CH₃ | N | CH₃ | C₄H₉ | c-C₃H₅ | — |
| 4026 | CH₂ | CH₃ | CH | CH₃ | N | CH₃ | CH₃ | C₃H₇ | — |
| 4027 | CH₂ | CH₃ | CH | CH₃ | N | CH₃ | C₂H₅ | C₃H₇ | — |
| 4028 | CH₂ | CH₃ | CH | CH₃ | N | CH₃ | C₃H₇ | C₃H₇ | — |
| 4029 | CH₂ | CH₃ | CH | CH₃ | N | CH₃ | C₂H₅ | C₄H₉ | — |
| 4030 | CH₂ | CH₃ | CH | CH₃ | N | CH₃ | H | 4-CH₃O—C₆H₄ | — |
| 4031 | O | CH₃ | CH | CH₃ | N | CH₃ | c-C₃H₅ | c-C₃H₅ | — |
| 4032 | O | CH₃ | CH | CH₃ | N | CH₃ | CH₃ | c-C₃H₅ | — |
| 4033 | O | CH₃ | CH | CH₃ | N | CH₃ | C₂H₅ | c-C₃H₅ | — |
| 4034 | O | CH₂ | CH | CH₃ | N | CH₃ | C₃H₇ | c-C₃H₅ | — |
| 4035 | O | CH₃ | CH | CH₃ | N | CH₃ | C₄H₉ | c-C₃H₅ | — |
| 4036 | O | CH₃ | CH | CH₃ | N | CH₃ | CH₃ | C₃H₇ | — |
| 4037 | O | CH₃ | CH | CH₃ | N | CH₃ | C₂H₅ | C₃H₇ | — |
| 4038 | O | CH₃ | CH | CH₃ | N | CH₃ | C₃H₇ | C₃H₇ | — |
| 4039 | O | CH₃ | CH | CH₃ | N | CH₃ | C₂H₅ | C₄H₉ | — |

TABLE 4-continued

| | | | | | | | | |
|---|---|---|---|---|---|---|---|---|
| 4040 | O | $CH_3$ | CH | $CH_3$ | N | $CH_3$ | H | 4-$CH_3O$—$C_6H_4$ | — |
| 4041 | $CH_2$ | $CH_3$ | CH | $SCH_3$ | N | H | c-$C_3H_5$ | c-$C_3H_5$ | — |
| 4042 | $CH_2$ | $CH_3$ | CH | $SCH_3$ | N | H | $CH_3$ | c-$C_3H_5$ | — |
| 4043 | $CH_2$ | $CH_3$ | CH | $SCH_3$ | N | H | $C_2H_5$ | c-$C_3H_5$ | — |
| 4044 | $CH_2$ | $CH_3$ | CH | $SCH_3$ | N | H | $C_3H_7$ | c-$C_3H_5$ | — |
| 4045 | $CH_2$ | $CH_3$ | CH | $SCH_3$ | N | H | $C_4H_9$ | c-$C_3H_5$ | — |
| 4046 | $CH_2$ | $CH_3$ | CH | $SCH_3$ | N | H | $CH_3$ | $C_3H_7$ | — |
| 4047 | $CH_2$ | $CH_3$ | CH | $SCH_3$ | N | H | $C_2H_5$ | $C_3H_7$ | — |
| 4048 | $CH_2$ | $CH_3$ | CH | $SCH_3$ | N | H | $C_3H_7$ | $C_3H_7$ | — |
| 4049 | $CH_2$ | $CH_3$ | CH | $SCH_3$ | N | H | $C_2H_5$ | $C_4H_9$ | — |
| 4050 | $CH_2$ | $CH_3$ | CH | $SCH_3$ | N | H | H | 4-$CH_3O$—$C_6H_4$ | — |
| 4051 | O | $CH_3$ | CH | $SCH_3$ | N | H | c-$C_3H_5$ | c-$C_3H_5$ | — |
| 4052 | O | $CH_3$ | CH | $SCH_3$ | N | H | $CH_3$ | c-$C_3H_5$ | — |
| 4053 | O | $CH_3$ | CH | $SCH_3$ | N | H | $C_2H_5$ | c-$C_3H_5$ | — |
| 4054 | O | $CH_3$ | CH | $SCH_3$ | N | H | $C_3H_7$ | c-$C_3H_5$ | — |
| 4055 | O | $CH_3$ | CH | $SCH_3$ | N | H | $C_4H_9$ | c-$C_3H_5$ | — |
| 4056 | O | $CH_3$ | CH | $SCH_3$ | N | H | $CH_3$ | $C_3H_7$ | — |
| 4057 | O | $CH_3$ | CH | $SCH_3$ | N | H | $C_2H_5$ | $C_3H_7$ | — |
| 4058 | O | $CH_3$ | CH | $SCH_3$ | N | H | $C_3H_7$ | $C_3H_7$ | — |
| 4059 | O | $CH_3$ | CH | $SCH_3$ | N | H | $C_2H_5$ | $C_4H_9$ | — |
| 4060 | O | $CH_3$ | CH | $SCH_3$ | N | H | H | 4-$CH_3O$—$C_6H_4$ | — |
| 4061 | $CH_2$ | $SCH_3$ | N | $CH_3$ | N | $SCH_3$ | c-$C_3H_5$ | c-$C_3H_5$ | — |
| 4062 | $CH_2$ | $SCH_3$ | N | $CH_3$ | N | $SCH_3$ | $CH_3$ | c-$C_3H_5$ | — |
| 4063 | $CH_2$ | $SCH_3$ | N | $CH_3$ | N | $SCH_3$ | $C_2H_5$ | c-$C_3H_5$ | — |
| 4064 | $CH_2$ | $SCH_3$ | N | $CH_3$ | N | $SCH_3$ | $C_3H_7$ | c-$C_3H_5$ | — |
| 4065 | $CH_2$ | $SCH_3$ | N | $CH_3$ | N | $SCH_3$ | $C_4H_9$ | c-$C_3H_5$ | — |
| 4066 | $CH_2$ | $SCH_3$ | N | $CH_3$ | N | $SCH_3$ | $CH_3$ | $C_3H_7$ | — |
| 4067 | $CH_2$ | $SCH_3$ | N | $CH_3$ | N | $SCH_3$ | $C_2H_5$ | $C_3H_7$ | — |
| 4068 | $CH_2$ | $SCH_3$ | N | $CH_3$ | N | $SCH_3$ | $C_3H_7$ | $C_3H_7$ | — |
| 4069 | $CH_2$ | $SCH_3$ | N | $CH_3$ | N | $SCH_3$ | $C_2H_5$ | $C_4H_9$ | — |
| 4070 | $CH_2$ | $SCH_3$ | N | $CH_3$ | N | $SCH_3$ | H | 4-$CH_3O$—$C_6H_4$ | — |
| 4071 | O | $SCH_3$ | N | $CH_3$ | N | $SCH_3$ | c-$C_3H_5$ | c-$C_3H_5$ | — |
| 4072 | O | $SCH_3$ | N | $CH_3$ | N | $SCH_3$ | $CH_3$ | c-$C_3H_5$ | — |
| 4073 | O | $SCH_3$ | N | $CH_3$ | N | $SCH_3$ | $C_2H_5$ | c-$C_3H_5$ | — |
| 4074 | O | $SCH_3$ | N | $CH_3$ | N | $SCH_3$ | $C_3H_7$ | c-$C_3H_5$ | — |
| 4075 | O | $SCH_3$ | N | $CH_3$ | N | $SCH_3$ | $C_4H_9$ | c-$C_3H_5$ | — |
| 4076 | O | $SCH_3$ | N | $CH_3$ | N | $SCH_3$ | $CH_3$ | $C_3H_7$ | — |
| 4077 | O | $SCH_3$ | N | $CH_3$ | N | $SCH_3$ | $C_2H_5$ | $C_3H_7$ | — |
| 4078 | O | $SCH_3$ | N | $CH_3$ | N | $SCH_3$ | $C_3H_7$ | $C_3H_7$ | — |
| 4079 | O | $SCH_3$ | N | $CH_3$ | N | $SCH_3$ | $C_2H_5$ | $C_4H_9$ | — |
| 4080 | O | $SCH_3$ | N | $CH_3$ | N | $SCH_3$ | H | 4-$CH_3O$—$C_6H_4$ | — |
| 4081 | $CH_2$ | $CH_3$ | N | $CH_3$ | N | $CH_3$ | c-$C_3H_5$ | c-$C_3H_5$ | — |
| 4082 | $CH_2$ | $CH_3$ | N | $CH_3$ | N | $CH_3$ | $CH_3$ | c-$C_3H_5$ | — |
| 4083 | $CH_2$ | $CH_3$ | N | $CH_3$ | N | $CH_3$ | $C_2H_5$ | c-$C_3H_5$ | — |
| 4084 | $CH_2$ | $CH_3$ | N | $CH_3$ | N | $CH_3$ | $C_3H_7$ | c-$C_3H_5$ | — |
| 4085 | $CH_2$ | $CH_3$ | N | $CH_3$ | N | $CH_3$ | $C_4H_9$ | c-$C_3H_5$ | — |
| 4086 | $CH_2$ | $CH_3$ | N | $CH_3$ | N | $CH_3$ | $CH_3$ | $C_3H_7$ | — |
| 4087 | $CH_2$ | $CH_3$ | N | $CH_3$ | N | $CH_3$ | $C_2H_5$ | $C_3H_7$ | — |
| 4088 | $CH_2$ | $CH_3$ | N | $CH_3$ | N | $CH_3$ | $C_3H_7$ | $C_3H_7$ | — |
| 4089 | $CH_2$ | $CH_3$ | N | $CH_3$ | N | $CH_3$ | $C_2H_5$ | $C_4H_9$ | — |
| 4090 | $CH_2$ | $CH_3$ | N | $CH_3$ | N | $CH_3$ | H | 4-$CH_3O$—$C_6H_4$ | — |
| 4091 | O | $CH_3$ | N | $CH_3$ | N | $CH_3$ | c-$C_3H_5$ | c-$C_3H_5$ | — |
| 4092 | O | $CH_3$ | N | $CH_3$ | N | $CH_3$ | $CH_3$ | c-$C_3H_5$ | — |
| 4093 | O | $CH_3$ | N | $CH_3$ | N | $CH_3$ | $C_2H_5$ | c-$C_3H_5$ | — |
| 4094 | O | $CH_3$ | N | $CH_3$ | N | $CH_3$ | $C_3H_7$ | c-$C_3H_5$ | — |
| 4095 | O | $CH_3$ | N | $CH_3$ | N | $CH_3$ | $C_4H_9$ | c-$C_3H_5$ | — |
| 4096 | O | $CH_3$ | N | $CH_3$ | N | $CH_3$ | $CH_3$ | $C_3H_7$ | — |
| 4097 | O | $CH_3$ | N | $CH_3$ | N | $CH_3$ | $C_2H_5$ | $C_3H_7$ | — |
| 4098 | O | $CH_3$ | N | $CH_3$ | N | $CH_3$ | $C_3H_7$ | $C_3H_7$ | — |
| 4099 | O | $CH_3$ | N | $CH_3$ | N | $CH_3$ | $C_2H_5$ | $C_4H_9$ | — |
| 4100 | O | $CH_3$ | N | $CH_3$ | N | $CH_3$ | H | 4-$CH_3O$—$C_6H_4$ | — |
| 4101 | $CH_2$ | $CH_3$ | CH | $CH_3$ | N | H | c-$C_3H_5$ | c-$C_3H_5$ | — |
| 4102 | $CH_2$ | $CH_3$ | CH | $CH_3$ | N | H | $CH_3$ | c-$C_3H_5$ | — |
| 4103 | $CH_2$ | $CH_3$ | CH | $CH_3$ | N | H | $C_2H_5$ | c-$C_3H_5$ | — |
| 4104 | $CH_2$ | $CH_3$ | CH | $CH_3$ | N | H | $C_3H_7$ | c-$C_3H_5$ | — |
| 4105 | $CH_2$ | $CH_3$ | CH | $CH_3$ | N | H | $C_4H_9$ | c-$C_3H_5$ | — |
| 4106 | $CH_2$ | $CH_3$ | CH | $CH_3$ | N | H | $CH_3$ | $C_3H_7$ | — |
| 4107 | $CH_2$ | $CH_3$ | CH | $CH_3$ | N | H | $C_2H_5$ | $C_3H_7$ | — |
| 4108 | $CH_2$ | $CH_3$ | CH | $CH_3$ | N | H | $C_3H_7$ | $C_3H_7$ | — |
| 4109 | $CH_2$ | $CH_3$ | CH | $CH_3$ | N | H | $C_2H_5$ | $C_4H_9$ | — |
| 4110 | $CH_2$ | $CH_3$ | CH | $CH_3$ | N | H | H | 4-$CH_3O$—$C_6H_4$ | — |
| 4111 | O | $CH_3$ | CH | $CH_3$ | N | H | c-$C_3H_5$ | c-$C_3H_5$ | — |
| 4112 | O | $CH_3$ | CH | $CH_3$ | N | H | $CH_3$ | c-$C_3H_5$ | — |
| 4113 | O | $CH_3$ | CH | $CH_3$ | N | H | $C_2H_5$ | c-$C_3H_5$ | — |
| 4114 | O | $CH_3$ | CH | $CH_3$ | N | H | $C_3H_7$ | c-$C_3H_5$ | — |
| 4115 | O | $CH_3$ | CH | $CH_3$ | N | H | $C_4H_9$ | c-$C_3H_5$ | — |
| 4116 | O | $CH_3$ | CH | $CH_3$ | N | H | $CH_3$ | $C_3H_7$ | — |
| 4117 | O | $CH_3$ | CH | $CH_3$ | N | H | $C_2H_5$ | $C_3H_7$ | — |
| 4118 | O | $CH_3$ | CH | $CH_3$ | N | H | $C_3H_7$ | $C_3H_7$ | — |

TABLE 4-continued

| | | | | | | | | |
|---|---|---|---|---|---|---|---|---|
| 4119 | O | CH₃ | CH | CH₃ | N | H | C₂H₅ | C₄H₉ | — |
| 4120 | O | CH₃ | CH | CH₃ | N | H | H | 4-CH₃O—C₆H₄ | — |
| 4121 | CH₂ | CH₃ | N | N(CH₃)₂ | CH | H | c-C₃H₅ | c-C₃H₅ | — |
| 4122 | CH₂ | CH₃ | N | N(CH₃)₂ | CH | H | CH₃ | c-C₃H₅ | — |
| 4123 | CH₂ | CH₃ | N | N(CH₃)₂ | CH | H | C₂H₅ | c-C₃H₅ | — |
| 4124 | CH₂ | CH₃ | N | N(CH₃)₂ | CH | H | C₃H₇ | c-C₃H₅ | — |
| 4125 | CH₂ | CH₃ | N | N(CH₃)₂ | CH | H | C₄H₉ | c-C₃H₅ | — |
| 4126 | CH₂ | CH₃ | N | N(CH₃)₂ | CH | H | CH₃ | C₃H₇ | — |
| 4127 | CH₂ | CH₃ | N | N(CH₃)₂ | CH | H | C₂H₅ | C₃H₇ | — |
| 4128 | CH₂ | CH₃ | N | N(CH₃)₂ | CH | H | C₃H₇ | C₃H₇ | — |
| 4129 | CH₂ | CH₃ | N | N(CH₃)₂ | CH | H | C₂H₅ | C₄H₉ | — |
| 4130 | CH₂ | CH₃ | N | N(CH₃)₂ | CH | H | H | 4-CH₃O—C₆H₄ | — |
| 4131 | O | CH₃ | N | N(CH₃)₂ | CH | H | c-C₃H₅ | c-C₃H₅ | — |
| 4132 | O | CH₃ | N | N(CH₃)₂ | CH | H | CH₃ | c-C₃H₅ | — |
| 4133 | O | CH₃ | N | N(CH₃)₂ | CH | H | C₂H₅ | c-C₃H₅ | — |
| 4134 | O | CH₃ | N | N(CH₃)₂ | CH | H | C₃H₇ | c-C₃H₅ | — |
| 4135 | O | CH₃ | N | N(CH₃)₂ | CH | H | C₄H₉ | c-C₃H₅ | — |
| 4136 | O | CH₃ | N | N(CH₃)₂ | CH | H | CH₃ | C₃H₇ | — |
| 4137 | O | CH₃ | N | N(CH₃)₂ | CH | H | C₂H₅ | C₃H₇ | — |
| 4138 | O | CH₃ | N | N(CH₃)₂ | CH | H | C₃H₇ | C₃H₇ | — |
| 4139 | O | CH₃ | N | N(CH₃)₂ | CH | H | C₂H₅ | C₄H₉ | — |
| 4140 | O | CH₃ | N | N(CH₃)₂ | CH | H | H | 4-CH₃O—C₆H₄ | — |
| 4141 | CH₂ | CH₃ | N | CH₃ | CH | H | c-C₃H₅ | c-C₃H₅ | — |
| 4142 | CH₂ | CH₃ | N | CH₃ | CH | H | CH₃ | c-C₃H₅ | — |
| 4143 | CH₂ | CH₃ | N | CH₃ | CH | H | C₂H₅ | c-C₃H₅ | — |
| 4144 | CH₂ | CH₃ | N | CH₃ | CH | H | C₃H₇ | c-C₃H₅ | — |
| 4145 | CH₂ | CH₃ | N | CH₃ | CH | H | C₄H₉ | c-C₃H₅ | — |
| 4146 | CH₂ | CH₃ | N | CH₃ | CH | H | CH₃ | C₃H₇ | — |
| 4147 | CH₂ | CH₃ | N | CH₃ | CH | H | C₂H₅ | C₃H₇ | — |
| 4148 | CH₂ | CH₃ | N | CH₃ | CH | H | C₃H₇ | C₃H₇ | — |
| 4149 | CH₂ | CH₃ | N | CH₃ | CH | H | C₂H₅ | C₄H₉ | — |
| 4150 | CH₂ | CH₃ | N | CH₃ | CH | H | H | 4-CH₃O—C₆H₄ | — |
| 4151 | O | CH₃ | N | CH₃ | CH | H | c-C₃H₅ | c-C₃H₅ | — |
| 4152 | O | CH₃ | N | CH₃ | CH | H | CH₃ | c-C₃H₅ | — |
| 4153 | O | CH₃ | N | CH₃ | CH | H | C₂H₅ | c-C₃H₅ | — |
| 4154 | O | CH₃ | N | CH₃ | CH | H | C₃H₇ | c-C₃H₅ | — |
| 4155 | O | CH₃ | N | CH₃ | CH | H | C₄H₉ | c-C₃H₅ | — |
| 4156 | O | CH₃ | N | CH₃ | CH | H | CH₃ | C₃H₇ | — |
| 4157 | O | CH₃ | N | CH₃ | CH | H | C₂H₅ | C₃H₇ | — |
| 4158 | O | CH₃ | N | CH₃ | CH | H | C₃H₇ | C₃H₇ | — |
| 4159 | O | CH₃ | N | CH₃ | CH | H | C₂H₅ | C₄H₉ | — |
| 4160 | O | CH₃ | N | CH₃ | CH | H | H | 4-CH₃O—C₆H₄ | — |
| 4161 | CH₂ | OCH₃ | N | OCH₃ | CH | H | c-C₃H₅ | c-C₃H₅ | 120–121 |
| 4162 | CH₂ | OCH₃ | N | OCH₃ | CH | H | CH₃ | c-C₃H₅ | — |
| 4163 | CH₂ | OCH₃ | N | OCH₃ | CH | H | C₂H₅ | c-C₃H₅ | — |
| 4164 | CH₂ | OCH₃ | N | OCH₃ | CH | H | C₃H₇ | c-C₃H₅ | — |
| 4165 | CH₂ | OCH₃ | N | OCH₃ | CH | H | C₄H₉ | c-C₃H₅ | — |
| 4166 | CH₂ | OCH₃ | N | OCH₃ | CH | H | CH₃ | C₃H₇ | oil |
| 4167 | CH₂ | OCH₃ | N | OCH₃ | CH | H | C₂H₅ | C₃H₇ | — |
| 4168 | CH₂ | OCH₃ | N | OCH₃ | CH | H | C₃H₇ | C₃H₇ | — |
| 4169 | CH₂ | OCH₃ | N | OCH₃ | CH | H | C₂H₅ | C₄H₉ | — |
| 4170 | CH₂ | OCH₃ | N | OCH₃ | CH | H | H | 4-CH₃O—C₆H₄ | — |
| 4171 | O | OCH₃ | N | OCH₃ | CH | H | c-C₃H₅ | c-C₃H₅ | oil |
| 4172 | O | OCH₃ | N | OCH₃ | CH | H | CH₃ | c-C₃H₅ | — |
| 4173 | O | OCH₃ | N | OCH₃ | CH | H | C₂H₅ | c-C₃H₅ | — |
| 4174 | O | OCH₃ | N | OCH₃ | CH | H | C₃H₇ | c-C₃H₅ | — |
| 4175 | O | OCH₃ | N | OCH₃ | CH | H | C₄H₉ | c-C₃H₅ | — |
| 4176 | O | OCH₃ | N | OCH₃ | CH | H | CH₃ | C₃H₇ | — |
| 4177 | O | OCH₃ | N | OCH₃ | CH | H | C₂H₅ | C₃H₇ | — |
| 4178 | O | OCH₃ | N | OCH₃ | CH | H | C₃H₇ | C₃H₇ | — |
| 4179 | O | OCH₃ | N | OCH₃ | CH | H | C₂H₅ | C₄H₉ | — |
| 4180 | O | OCH₃ | N | OCH₃ | CH | H | H | 4-CH₃O—C₆H₄ | — |
| 4181 | CH₂ | OCH₃ | N | N(CH₃)₂ | CH | H | c-C₃H₅ | c-C₃H₅ | — |
| 4182 | CH₂ | OCH₃ | N | N(CH₃)₂ | CH | H | CH₃ | c-C₃H₅ | — |
| 4183 | CH₂ | OCH₃ | N | N(CH₃)₂ | CH | H | C₂H₅ | c-C₃H₅ | — |
| 4184 | CH₂ | OCH₃ | N | N(CH₃)₂ | CH | H | C₃H₇ | c-C₃H₅ | — |
| 4185 | CH₂ | OCH₃ | N | N(CH₃)₂ | CH | H | C₄H₉ | c-C₃H₅ | — |
| 4186 | CH₂ | OCH₃ | N | N(CH₃)₂ | CH | H | CH₃ | C₃H₇ | — |
| 4187 | CH₂ | OCH₃ | N | N(CH₃)₂ | CH | H | C₂H₅ | C₃H₇ | — |
| 4188 | CH₂ | OCH₃ | N | N(CH₃)₂ | CH | H | C₃H₇ | C₃H₇ | — |
| 4189 | CH₂ | OCH₃ | N | N(CH₃)₂ | CH | H | C₂H₅ | C₄H₉ | — |
| 4190 | CH₂ | OCH₃ | N | N(CH₃)₂ | CH | H | H | 4-CH₃O—C₆H₄ | — |
| 4191 | O | OCH₃ | N | N(CH₃)₂ | CH | H | c-C₃H₅ | c-C₃H₅ | — |
| 4192 | O | OCH₃ | N | N(CH₃)₂ | CH | H | CH₃ | c-C₃H₅ | — |
| 4193 | O | OCH₃ | N | N(CH₃)₂ | CH | H | C₂H₅ | c-C₃H₅ | — |
| 4194 | O | OCH₃ | N | N(CH₃)₂ | CH | H | C₃H₇ | c-C₃H₅ | — |
| 4195 | O | OCH₃ | N | N(CH₃)₂ | CH | H | C₄H₉ | c-C₃H₅ | — |
| 4196 | O | OCH₃ | N | N(CH₃)₂ | CH | H | CH₃ | C₃H₇ | — |
| 4197 | O | OCH₃ | N | N(CH₃)₂ | CH | H | C₂H₅ | C₃H₇ | — |

TABLE 4-continued

| | | | | | | | | |
|---|---|---|---|---|---|---|---|---|
| 4198 | O | OCH$_3$ | N | N(CH$_3$)$_2$ | CH | H | C$_3$H$_7$ | C$_3$H$_7$ | — |
| 4199 | O | OCH$_3$ | N | N(CH$_3$)$_2$ | CH | H | C$_2$H$_5$ | C$_4$H$_9$ | — |
| 4200 | O | OCH$_3$ | N | N(CH$_3$)$_2$ | CH | H | H | 4-CH$_3$O—C$_6$H$_4$ | — |
| 4201 | CH$_2$ | N(CH$_3$)$_2$ | N | OCH$_3$ | CH | H | c-C$_3$H$_5$ | c-C$_3$H$_5$ | — |
| 4202 | CH$_2$ | N(CH$_3$)$_2$ | N | OCH$_3$ | CH | H | CH$_3$ | c-C$_3$H$_5$ | — |
| 4203 | CH$_2$ | N(CH$_3$)$_2$ | N | OCH$_3$ | CH | H | C$_2$H$_5$ | c-C$_3$H$_5$ | — |
| 4204 | CH$_2$ | N(CH$_3$)$_2$ | N | OCH$_3$ | CH | H | C$_3$H$_7$ | c-C$_3$H$_5$ | — |
| 4205 | CH$_2$ | N(CH$_3$)$_2$ | N | OCH$_3$ | CH | H | C$_4$H$_9$ | c-C$_3$H$_5$ | — |
| 4206 | CH$_2$ | N(CH$_3$)$_2$ | N | OCH$_3$ | CH | H | CH$_3$ | C$_3$H$_7$ | — |
| 4207 | CH$_2$ | N(CH$_3$)$_2$ | N | OCH$_3$ | CH | H | C$_2$H$_5$ | C$_3$H$_7$ | — |
| 4208 | CH$_2$ | N(CH$_3$)$_2$ | N | OCH$_3$ | CH | H | C$_3$H$_7$ | C$_3$H$_7$ | — |
| 4209 | CH$_2$ | N(CH$_3$)$_2$ | N | OCH$_3$ | CH | H | C$_2$H$_5$ | C$_4$H$_9$ | — |
| 4210 | CH$_2$ | N(CH$_3$)$_2$ | N | OCH$_3$ | CH | H | H | 4-CH$_3$O—C$_6$H$_4$ | — |
| 4211 | O | N(CH$_3$)$_2$ | N | OCH$_3$ | CH | H | c-C$_3$H$_5$ | c-C$_3$H$_5$ | — |
| 4212 | O | N(CH$_3$)$_2$ | N | OCH$_3$ | CH | H | CH$_3$ | c-C$_3$H$_5$ | — |
| 4213 | O | N(CH$_3$)$_2$ | N | OCH$_3$ | CH | H | C$_2$H$_5$ | c-C$_3$H$_5$ | — |
| 4214 | O | N(CH$_3$)$_2$ | N | OCH$_3$ | CH | H | C$_3$H$_7$ | c-C$_3$H$_5$ | — |
| 4215 | O | N(CH$_3$)$_2$ | N | OCH$_3$ | CH | H | C$_4$H$_9$ | c-C$_3$H$_5$ | — |
| 4216 | O | N(CH$_3$)$_2$ | N | OCH$_3$ | CH | H | CH$_3$ | C$_3$H$_7$ | — |
| 4217 | O | N(CH$_3$)$_2$ | N | OCH$_3$ | CH | H | C$_2$H$_5$ | C$_3$H$_7$ | — |
| 4218 | O | N(CH$_3$)$_2$ | N | OCH$_3$ | CH | H | C$_3$H$_7$ | C$_3$H$_7$ | — |
| 4219 | O | N(CH$_3$)$_2$ | N | OCH$_3$ | CH | H | C$_2$H$_5$ | C$_4$H$_9$ | — |
| 4220 | O | N(CH$_3$)$_2$ | N | OCH$_3$ | CH | H | H | 4-CH$_3$O—C$_6$H$_4$ | — |
| 4221 | CH$_2$ | OCH$_3$ | N | OCH$_3$ | CH | H | C$_2$H$_5$ | 2-furanyl | — |
| 4222 | CH$_2$ | OCH$_3$ | N | OCH$_3$ | CH | H | C$_3$H$_7$ | 2-furanyl | — |
| 4223 | CH$_2$ | OCH$_3$ | N | OCH$_3$ | CH | H | C$_2$H$_5$ | b | — |
| 4224 | CH$_2$ | OCH$_3$ | N | OCH$_3$ | CH | H | C$_3$H$_7$ | b | — |
| 4225 | CH$_2$ | OCH$_3$ | N | OCH$_3$ | CH | H | C$_2$H$_5$ | b | — |
| 4226 | CH$_2$ | OCH$_3$ | N | OCH$_3$ | CH | H | c-C$_3$H$_5$ | b | — |
| 4227 | CH$_2$ | OCH$_3$ | N | OCH$_3$ | CH | H | CH$_3$ | CH=CHCH$_3$ | — |
| 4228 | CH$_2$ | OCH$_3$ | N | OCH$_3$ | CH | H | C$_3$H$_7$ | CH=CH$_2$ | — |
| 4229 | CH$_2$ | OCH$_3$ | N | OCH$_3$ | CH | H | CH$_3$ | C$_6$H$_5$ | — |
| 4230 | CH$_2$ | OCH$_3$ | N | OCH$_3$ | CH | H | CH$_3$ | c-C$_4$H$_7$ | — |

Key:
[a]Where the compound is indicated as an "oil", spectral data is provided below:
Example 4166 elemental analysis: calc. for C$_{19}$H$_{25}$N$_5$O$_2$ C 64.20, H 7.10, N 19.70; observed C 64.13, H 6.67, N 19.30.
Example 4171 elemental analysis: calc. for C$_{20}$H$_{23}$N$_5$O$_3$ C 62.98, H 6.09, N 18.36; observed C 62.80, H 6.10, N 18.19.
[b]C≡C—CH$_3$ The methods used in the preparation of the compounds of Table 1 may be employed in the synthesis of those compounds of Structure A in Table 5 and Table 5A. The methods employed to make the analogues bearing a benzofuran group are illustrated in the following examples.

The methods of Schemes 13 and 14 may be used to prepare many of the examples of Structure B and Structure C contained in Table 5 and Table 5A, with minor procedural modifications where necessary and use of reagents of the appropriate structure.

EXAMPLE 5001

Preparation of 9-Dicyclopropylmethyl-8-ethyl-6-(6-methyl-2,3-dihydrobenzofuran-5-yl)purine Part A. Sodium hydride dispersion in mineral oil (5.05 g, 50% w/w, 105 mmol) was washed with hexane and dried under vacuum. DMF (100 mL) was added, the slurry was cooled to 0° C., and treated with a solution of m-cresol (10 mL, 95.6 mmol) in DMF (20 mL). The resulting mixture was allowed to stir for 1 h, then was treated with chloromethyl methyl ether (8.00 mL, 105 mmol) by syringe. The mixture was stirred overnight, then poured into ethyl acetate (200 mL). This was washed with water (3×200 mL) and brine (100 mL), and the aqueous phases were back-extracted in sequence with ethyl acetate. The extracts were combined, dried over magnesium sulfate, filtered and evaporated. The oily product was purified by elution through a plug of silica gel with 10:90 ethyl acetate-hexane. Evaporation then afforded the pure product, 3-(methoxymethoxy)toluene, as an oil (13.93 g, 91.5 mmol, 96%). TLC R$_F$ 0.46 (10:90 ethyl acetate-hexane). $^1$H NMR (300 MHz, CDCl$_3$): d 7.17 (1H, t, J=7.7 Hz), 6.86–6.81 (3H, m), 5.17 (2H, s), 3.48 (3H, s), 2.33 (3H, s). MS (H$_2$O-GC/MS): m/e 153 (60), 121 (100).

Part B. A solution of 3-(methoxymethoxy)toluene (5.00 g, 32.9 mmol) and TMEDA (5.30 mL, 35.1 mmol) in THF (50 mL) was cooled to 0° C., and treated with a hexane solution of n-butyllithium (22.0 mL, 1.6 M, 35.2mmol). After 4 hours, the solution was cooled to −78° C., and treated dropwise with ethylene oxide (2.00 mL, 40 mmol, condensed from a lecture bottle through a cold-finger into a graduated dropping funnel). The mixture was allowed to stir and warm to ambient temperature overnight, then was poured into satd. aq. ammonium chloride solution (120 mL). This was extracted with ethyl acetate (2×120 mL), and the extracts were washed in sequence with brine, combined, dried over magnesium sulfate, filtered and evaporated. The residual oil was separated by column chromatography (10:90 ethyl acetate-hexane) to afford the desired product, 2-[2-(methoxymethoxy)-4-methylphenyl]ethanol, as a viscous liquid (2.25 g, 11.5 mmol, 35%), along with 2.50 g recovered starting material. The $^1$H NMR spectrum showed regioselectivity in excess of 10:1. TLC R$_F$ 0.09 (10:90 ethyl acetate-hexane). $^1$H NMR (300 MHz, CDCl$_3$): d 7.06 (1H, d, J=7.7 Hz), 6.92 (1H, br s), 6.78 (1H, br d, J=7.7 Hz), 5.20 (2H, s), 3.83 (2H, q, J=6.4 Hz), 3.49 (3H, s), 2.89 (2H, t, J=6.6 Hz), 2.32 (3H, s), 1.61 (1H, t, J=5.9 Hz). MS (NH$_3$-DCI): m/e 214 (76), 212 (100), 197 (9), 182 (30), 165 (38).

Part C. A solution of the MOM compound from Part B (1.84 g, 9.38 mmol) was dissolved in 1:1 THF-isopropanol (20 mL), and treated with HCl in dioxane (2.5 mL, 4 N, 10.0 mmol). The reaction was stirred at ambient temperature overnight. Aqueous workup gave sufficiently pure product, 2-(2-hydroxy-4-methylphenyl)ethanol.

Part D. A solution of the diol from Part C (ca. 9 mmol) and triphenylphosphine (2.83 g, 10.8 mmol) in THF (20 mL) was cooled to 0° C., and treated with diethyl azodicarboxylate (1.70 mL, 10.8 mmol) by syringe. The solution was stirred overnight, then evaporated, and the residue separated by a flash column to afford the product, 6-methyl-2,3-dihydrobenzofuran (780 mg, 5.81 mmol, 65%). TLC $R_F$ 0.29 (2:98 ethyl acetate-hexane). $^1$H NMR (300 MHz, CDCl$_3$): d 7.07 (1H, d, J=7.4 Hz), 6.66 (1H, d, J=7.4 Hz), 6.62 (1H, s), 4.54 (2H, t, J=8.6 Hz), 3.16 (2H, t, J=8.6 Hz), 2.30 (3H, s). MS (D$_2$O-GC/MS): m/e 135 (100).

Part E. A solution of the above compound (780 mg) and N-bromosuccinimide (1.24 g, 6.97 mmol) in dichloroethane (10 mL) was heated to reflux overnight, then cooled, filtered and evaporated. Column chromatography (hexane, then 2:98 ethyl acetate-hexane) gave first 5-bromo-6-methylbenzofuran (270 mg, 1.27 mmol, 22%), then 5-bromo-6-methyl-2,3-dihydrobenzofuran (923 mg, 4.33 mol, 75%), both as solids. For the dihydro product: TLC $R_F$ 0.35 (2:98 ethyl acetate-hexane). $^1$H NMR (300 MHz, CDCl$_3$): d 7.31 (1H, s), 6.68 (1H, s), 4.56 (2H, t, J=8.8 Hz), 3.17 (2H, t, J=8.8 Hz), 2.33 (3H, s). MS (H$_2$O-GC/MS): m/e 215 (76), 213 (100).

Part F. A solution of the bromide from Part E (923 mg, 4.33 mmol) in tetrahydrofuran (20 mL) was cooled to −78° C., and treated with a hexane solution of n-butyllithium (3.0 mL, 1.6 M, 4.8 mmol). After 1 hour, the reaction mixture was treated with triisopropylborate (1.00 mL, 4.33 mmol) and allowed to come to ambient temperature over 6 hrs. Then, 1 mL of 6 N aq. HCl and 3 mL water were added, and the resulting mixture was allowed to stir for 1 hr. It was poured into water (100 mL), and extracted with ethyl acetate (2×100 mL). The extracts were washed with brine (60 mL), combined, dried over sodium sulfate, filtered and evaporated to afford a solid, which was purified by trituration with hexane to give 6-methyl-2,3-dihydrobenzofuran-5-boronic acid (718 mg, 4.03 mmol, 93%).

Part G. A mixture of the boronic acid from Part F (298 mg, 1.67 mmol), 6-chloro-9-dicyclopropylmethyl-8-ethylpurine (309 mg, 1.12 mmol), 2 N aqueous sodium carbonate solution (1.7 mL, 3.4 mmol) and triphenylphosphine (61 mg, 0.233 mmol) in DME (20 mL) was degassed by repeated cycles of brief vacuum pumping followed by nitrogen purging. To this was added palladium(II) acetate (13 mg, 0.058 mmol), and the mixture was degassed again and then heated to reflux for 14 hours. It was cooled, and poured into water (100 mL). This mixture was extracted with ethyl acetate (2×100 mL), and the extracts were washed in sequence with brine (60 mL), combined, dried over sodium sulfate, filtered and evaporated. The residual material was separated by column chromatography (silica gel, 20:80 ethyl acetate-hexane) to afford the title product as a solid. This was recrystallized to purity from ether (253 mg, 0.77 mmol, 69%). m.p. 147–148° C. TLC $R_F$ 0.18 (30:70 ethyl acetate-hexane). $^1$H NMR (300 MHz, CDCl$_3$): d 8.88 (1H, s), 7.60 (1H, s), 6.77 (1H, s), 4.61 (2H, t, J=8.6 Hz), 3.44 (1H, v br), 3.24 (2H, t, J=8.6 Hz), 2.94 (2H, br), 2.44 (3H, s), 2.03 (2H, v br), 1.45 (3H, br t, J=6 Hz), 0.89–0.79 (2H, m), 0.58 (2H, br), 0.50–0.40 (2H, m), 0.27–0.17 (2H, m). MS (NH$_3$-Cl): m/e 377 (4), 376 (27), 375 (100). Analysis calc'd for C$_{23}$H$_{26}$N$_4$O: C, 73.77; H, 7.01; N, 14.96; found: C, 73.69; H, 7.08; N, 14.40.

EXAMPLES 5201, 5231 AND 5232

Preparation of 9-Dicyclopropylmethyl-8-ethyl-6-(6-methylbenzofuran-5-yl)purine, 6-(2-Bromo-6-methylbenzofuran-5-yl)-9-dicyclopropylmethyl-8-ethylpurine and 6-(7-Bromo-6-methyl-2,3-dihydrobenzofuran-5-yl)-9-dicyclopropylmethyl-8-ethylpurine A solution of the compound of Example 5001 (250 mg, 0.668 mmol) and N-bromosuccinimide (119 mg, 0.669 mmol) in 1,2-dichloroethane (10 mL) was heated to reflux for 12 hours, then cooled and evaporated. The resulting mixture was taken up in ether, filtered and evaporated, and the residual material was separated by flash chromatography (silica gel, 20:80 ethyl acetate-hexane) to afford, in order, the following three products: 6-(2-Bromo-6-methylbenzofuran-5-yl)-9-dicyclopropylmethyl-8-ethylpurine: m.p. 177–178° C. TLC $R_F$ 0.23 (20:80 ethyl acetate-hexane). $^1$H NMR (300 MHz, CDCl$_3$): d 8.92 (1H, s), 7.85 (1H, s), 7.42 (1H, s), 6.74 (1H, s), 4.15 (1H, v br), 2.97 (2H, v br), 2.54 (3H, s), 2.00 (2H, v br), 1.44 (3H, br t, J=7 Hz), 0.90–0.80 (2H, m), 0.63–0.53 (2H, m), 0.50–0.40 (2H, m), 0.26–0.16 (2H, m). MS (NH$_3$—CI): m/e calc'd for C$_{23}$H$_{24}$BrN$_4$O: 451.1133, found 451.1132; 455 (3), 454 (25), 453 (99), 452 (31), 451 (100).

9-Dicyclopropylmethyl-8-ethyl-6-(6-methylbenzofuran-5-yl)purine: m.p. 139–141° C. TLC $R_F$ 0.16 (20:80 ethyl acetate-hexane). $^1$H NMR (300 MHz, CDCl$_3$): d 8.92 (1H, s), 7.95 (1H, s), 7.60 (1H, d, J=2.2 Hz), 7.48 (1H, d, J=0.7 Hz), 6.78 (1H, dd, J=2.2, 0.7 Hz), 4.40 (1H, v br), 2.97 (2H, v br), 2.56 (3H, s), 2.04 (2H, v br), 1.44 (3H, br t, J=7 Hz), 0.90–0.80 (2H, m), 0.62–0.52 (2H, m), 0.51–0.41 (2H, m), 0.29–0.18 (2H, m). MS (NH$_3$—CI): m/e calc'd for C$_{23}$H$_{25}$N$_4$O: 373.2028, found 373.2033; 375 (3), 374 (26), 373 (100).

6-(7-Bromo-6-methyl-2,3-dihydrobenzofuran-5-yl)-9-dicyclopropylmethyl-8-ethylpurine: m.p. 179–180° C. TLC $R_F$ 0.04 (20:80 ethyl acetate-hexane). $^1$H NMR (300 MHz, CDCl$_3$): d 8.89 (1H, s), 7.47 (1H, s), 4.73 (2H, t, J=8.6 Hz), 3.80 (1H, v br), 3.37 (2H, t, J=8.6 Hz), 2.95 (2H, v br), 2.44 (3H, s), 1.44 (3H, br t, J=7 Hz), 0.89–0.79 (2H, m), 0.61–0.52 (2H, m), 0.51–0.41 (2H, m), 0.28–0.18 (2H, m). MS (NH$_3$—CI): m/e calc'd for C$_{23}$H$_{26}$BrN$_4$O: 453.1290, found 453.1285; 455 (98), 453 (100).

TABLE 5

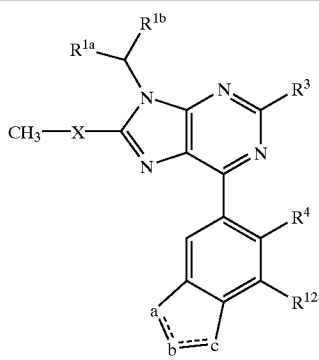

(A)

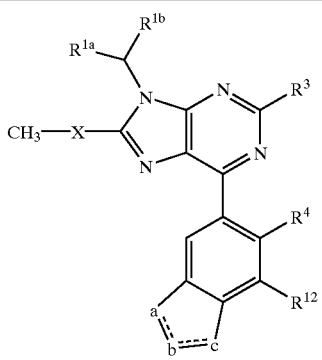

(B)

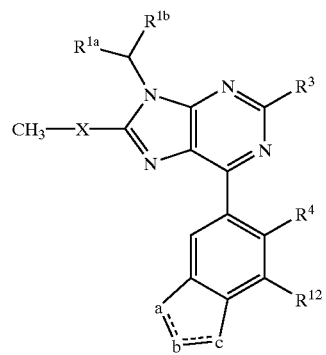

(C)

| Ex. No. | X | R³ | R⁴ | a | b | c | R¹ᵃ | R¹ᵇ | m.p., °C. |
|---|---|---|---|---|---|---|---|---|---|
| 5001 | $CH_2$ | H | $CH_3$ | $CH_2$ | $CH_2$ | O | c-$C_3H_5$ | c-$C_3H_5$ | 147–148 |
| 5002 | $CH_2$ | H | $CH_3$ | $CH_2$ | $CH_2$ | O | H | 4-($CH_3O$)—$C_6H_4$ | — |
| 5003 | $CH_2$ | H | $CH_3$ | $CH_2$ | $CH_2$ | O | $CH_3$ | c-$C_3H_5$ | — |
| 5004 | $CH_2$ | H | $CH_3$ | $CH_2$ | $CH_2$ | O | $C_2H_5$ | c-$C_3H_5$ | — |
| 5005 | $CH_2$ | H | $CH_3$ | $CH_2$ | $CH_2$ | O | $C_3H_7$ | c-$C_3H_5$ | — |
| 5006 | $CH_2$ | H | $CH_3$ | $CH_2$ | $CH_2$ | O | $C_4H_9$ | c-$C_3H_5$ | — |
| 5007 | $CH_2$ | H | $CH_3$ | $CH_2$ | $CH_2$ | O | $C_2H_5$ | $C_3H_7$ | — |
| 5008 | $CH_2$ | H | $CH_3$ | $CH_2$ | $CH_2$ | O | $C_2H_5$ | $C_4H_9$ | — |
| 5009 | $CH_2$ | H | $CH_3$ | $CH_2$ | $CH_2$ | O | $C_3H_7$ | $C_3H_7$ | — |
| 5010 | $CH_2$ | H | $CH_3$ | $CH_2$ | $CH_2$ | O | $CH_3$ | $C_3H_7$ | — |
| 5011 | $CH_2$ | H | $CH_3$ | O | $CH_2$ | O | c-$C_3H_5$ | c-$C_3H_5$ | 168–169 |
| 5012 | $CH_2$ | H | $CH_3$ | O | $CH_2$ | O | H | 4-($CH_3O$)—$C_6H_4$ | — |
| 5013 | $CH_2$ | H | $CH_3$ | O | $CH_2$ | O | $CH_3$ | c-$C_3H_5$ | — |
| 5014 | $CH_2$ | H | $CH_3$ | O | $CH_2$ | O | $C_2H_5$ | c-$C_3H_5$ | — |
| 5015 | $CH_2$ | H | $CH_3$ | O | $CH_2$ | O | $C_3H_7$ | c-$C_3H_5$ | — |
| 5016 | $CH_2$ | H | $CH_3$ | O | $CH_2$ | O | $C_4H_9$ | c-$C_3H_5$ | — |
| 5017 | $CH_2$ | H | $CH_3$ | O | $CH_2$ | O | $C_2H_5$ | $C_3H_7$ | — |
| 5018 | $CH_2$ | H | $CH_3$ | O | $CH_2$ | O | $C_2H_5$ | $C_4H_9$ | — |
| 5019 | $CH_2$ | H | $CH_3$ | O | $CH_2$ | O | $C_3H_7$ | $C_3H_7$ | — |
| 5020 | $CH_2$ | H | $CH_3$ | O | $CH_2$ | O | $CH_3$ | $C_3H_7$ | — |
| 5021 | $CH_2$ | H | $CH_3$ | O | $CH_2$ | $CH_2$ | c-$C_3H_5$ | c-$C_3H_5$ | — |
| 5022 | $CH_2$ | H | $CH_3$ | O | $CH_2$ | $CH_2$ | H | 4-($CH_3O$)—$C_6H_4$ | — |
| 5023 | $CH_2$ | H | $CH_3$ | O | $CH_2$ | $CH_2$ | $CH_3$ | c-$C_3H_5$ | — |
| 5024 | $CH_2$ | H | $CH_3$ | O | $CH_2$ | $CH_2$ | $C_2H_5$ | c-$C_3H_5$ | — |
| 5025 | $CH_2$ | H | $CH_3$ | O | $CH_2$ | $CH_2$ | $C_3H_7$ | c-$C_3H_5$ | — |
| 5026 | $CH_2$ | H | $CH_3$ | O | $CH_2$ | $CH_2$ | $C_4H_9$ | c-$C_3H_5$ | — |
| 5027 | $CH_2$ | H | $CH_3$ | O | $CH_2$ | $CH_2$ | $C_2H_5$ | $C_3H_7$ | — |
| 5028 | $CH_2$ | H | $CH_3$ | O | $CH_2$ | $CH_2$ | $C_2H_5$ | $C_4H_9$ | — |
| 5029 | $CH_2$ | H | $CH_3$ | O | $CH_2$ | $CH_2$ | $C_3H_7$ | $C_3H_7$ | — |
| 5030 | $CH_2$ | H | $CH_3$ | O | $CH_2$ | $CH_2$ | $CH_3$ | $C_3H_7$ | — |
| 5031 | $CH_2$ | H | $CH_3$ | $CH_2$ | O | $CH_2$ | c-$C_3H_5$ | c-$C_3H_5$ | — |
| 5032 | $CH_2$ | H | $CH_3$ | $CH_2$ | O | $CH_2$ | H | 4-($CH_3O$)—$C_6H_4$ | — |
| 5033 | $CH_2$ | H | $CH_3$ | $CH_2$ | O | $CH_2$ | $CH_3$ | c-$C_3H_5$ | — |
| 5034 | $CH_2$ | H | $CH_3$ | $CH_2$ | O | $CH_2$ | $C_2H_5$ | c-$C_3H_5$ | — |
| 5035 | $CH_2$ | H | $CH_3$ | $CH_2$ | O | $CH_2$ | $C_3H_7$ | c-$C_3H_5$ | — |
| 5036 | $CH_2$ | H | $CH_3$ | $CH_2$ | O | $CH_2$ | $C_4H_9$ | c-$C_3H_5$ | — |
| 5037 | $CH_2$ | H | $CH_3$ | $CH_2$ | O | $CH_2$ | $C_2H_5$ | $C_3H_7$ | — |
| 5038 | $CH_2$ | H | $CH_3$ | $CH_2$ | O | $CH_2$ | $C_2H_5$ | $C_4H_9$ | — |

TABLE 5-continued

| | | | | | | | | | |
|---|---|---|---|---|---|---|---|---|---|
| 5039 | CH$_2$ | H | CH$_3$ | CH$_2$ | O | CH$_2$ | C$_3$H$_7$ | C$_3$H$_7$ | — |
| 5040 | CH$_2$ | H | CH$_3$ | CH$_2$ | O | CH$_2$ | CH$_3$ | C$_3$H$_7$ | — |
| 5041 | CH$_2$ | H | Cl | CH$_2$ | CH$_2$ | O | c-C$_3$H$_5$ | c-C$_3$H$_5$ | — |
| 5042 | CH$_2$ | H | Cl | CH$_2$ | CH$_2$ | O | H | 4-(CH$_3$O)—C$_6$H$_4$ | — |
| 5043 | CH$_2$ | H | Cl | CH$_2$ | CH$_2$ | O | CH$_3$ | c-C$_3$H$_5$ | — |
| 5044 | CH$_2$ | H | Cl | CH$_2$ | CH$_2$ | O | C$_2$H$_5$ | c-C$_3$H$_5$ | — |
| 5045 | CH$_2$ | H | Cl | CH$_2$ | CH$_2$ | O | C$_3$H$_7$ | c-C$_3$H$_5$ | — |
| 5046 | CH$_2$ | H | Cl | CH$_2$ | CH$_2$ | O | C$_4$H$_9$ | c-C$_3$H$_5$ | — |
| 5047 | CH$_2$ | H | Cl | CH$_2$ | CH$_2$ | O | C$_2$H$_5$ | C$_3$H$_7$ | — |
| 5048 | CH$_2$ | H | Cl | CH$_2$ | CH$_2$ | O | C$_2$H$_5$ | C$_4$H$_9$ | — |
| 5049 | CH$_2$ | H | Cl | CH$_2$ | CH$_2$ | O | C$_3$H$_7$ | C$_3$H$_7$ | — |
| 5050 | CH$_2$ | H | Cl | CH$_2$ | CH$_2$ | O | CH$_3$ | C$_3$H$_7$ | — |
| 5051 | CH$_2$ | H | Cl | O | CH$_2$ | O | c-C$_3$H$_5$ | c-C$_3$H$_5$ | — |
| 5052 | CH$_2$ | H | Cl | O | CH$_2$ | O | H | 4-(CH$_3$O)—C$_6$H$_4$ | — |
| 5053 | CH$_2$ | H | Cl | O | CH$_2$ | O | CH$_3$ | c-C$_3$H$_5$ | — |
| 5054 | CH$_2$ | H | Cl | O | CH$_2$ | O | C$_2$H$_5$ | c-C$_3$H$_5$ | — |
| 5055 | CH$_2$ | H | Cl | O | CH$_2$ | O | C$_3$H$_7$ | c-C$_3$H$_5$ | — |
| 5056 | CH$_2$ | H | Cl | O | CH$_2$ | O | C$_4$H$_9$ | c-C$_3$H$_5$ | — |
| 5057 | CH$_2$ | H | Cl | O | CH$_2$ | O | C$_2$H$_5$ | C$_3$H$_7$ | — |
| 5058 | CH$_2$ | H | Cl | O | CH$_2$ | O | C$_2$H$_5$ | C$_4$H$_9$ | — |
| 5059 | CH$_2$ | H | Cl | O | CH$_2$ | O | C$_3$H$_7$ | C$_3$H$_7$ | — |
| 5060 | CH$_2$ | H | Cl | O | CH$_2$ | O | CH$_3$ | C$_3$H$_7$ | — |
| 5061 | O | H | CH$_3$ | CH$_2$ | CH$_2$ | O | c-C$_3$H$_5$ | c-C$_2$H$_5$ | — |
| 5062 | O | H | CH$_3$ | CH$_2$ | CH$_2$ | O | H | 4-(CH$_3$O)—C$_6$H$_4$ | — |
| 5063 | O | H | CH$_3$ | CH$_2$ | CH$_2$ | O | CH$_3$ | c-C$_3$H$_5$ | — |
| 5064 | O | H | CH$_3$ | CH$_2$ | CH$_2$ | O | C$_2$H$_5$ | c-C$_3$H$_5$ | — |
| 5065 | O | H | CH$_3$ | CH$_2$ | CH$_2$ | O | C$_3$H$_7$ | c-C$_3$H$_5$ | — |
| 5066 | O | H | CH$_3$ | CH$_2$ | CH$_2$ | O | C$_4$H$_9$ | c-C$_3$H$_5$ | — |
| 5067 | O | H | CH$_3$ | CH$_2$ | CH$_2$ | O | C$_2$H$_5$ | C$_3$H$_7$ | — |
| 5068 | O | H | CH$_3$ | CH$_2$ | CH$_2$ | O | C$_2$H$_5$ | C$_4$H$_9$ | — |
| 5069 | O | H | CH$_3$ | CH$_2$ | CH$_2$ | O | C$_3$H$_7$ | C$_3$H$_7$ | — |
| 5070 | O | H | CH$_3$ | CH$_2$ | CH$_2$ | O | CH$_3$ | C$_3$H$_7$ | — |
| 5071 | O | H | CH$_3$ | O | CH$_2$ | O | c-C$_3$H$_5$ | c-C$_3$H$_5$ | — |
| 5072 | O | H | CH$_3$ | O | CH$_2$ | O | H | 4-(CH$_3$O)—C$_6$H$_4$ | — |
| 5073 | O | H | CH$_3$ | O | CH$_2$ | O | CH$_3$ | c-C$_3$H$_5$ | — |
| 5074 | O | H | CH$_3$ | O | CH$_2$ | O | C$_2$H$_5$ | c-C$_3$H$_5$ | — |
| 5075 | O | H | CH$_3$ | O | CH$_2$ | O | C$_3$H$_7$ | c-C$_3$H$_5$ | — |
| 5076 | O | H | CH$_3$ | O | CH$_2$ | O | C$_4$H$_9$ | c-C$_3$H$_5$ | — |
| 5077 | O | H | CH$_3$ | O | CH$_2$ | O | C$_2$H$_5$ | C$_3$H$_7$ | — |
| 5078 | O | H | CH$_3$ | O | CH$_2$ | O | C$_2$H$_5$ | C$_4$H$_9$ | — |
| 5079 | O | H | CH$_3$ | O | CH$_2$ | O | C$_3$H$_7$ | C$_3$H$_7$ | — |
| 5080 | O | H | CH$_3$ | O | CH$_2$ | O | CH$_3$ | C$_3$H$_7$ | — |
| 5081 | O | H | Cl | CH$_2$ | CH$_2$ | O | c-C$_3$H$_5$ | c-C$_3$H$_5$ | — |
| 5082 | O | H | Cl | CH$_2$ | CH$_2$ | O | H | 4-(CH$_3$O)—C$_6$H$_4$ | — |
| 5083 | O | H | Cl | CH$_2$ | CH$_2$ | O | CH$_3$ | c-C$_3$H$_5$ | — |
| 5084 | O | H | Cl | CH$_2$ | CH$_2$ | O | C$_2$H$_5$ | c-C$_3$H$_5$ | — |
| 5085 | O | H | Cl | CH$_2$ | CH$_2$ | O | C$_3$H$_7$ | c-C$_3$H$_5$ | — |
| 5086 | O | H | Cl | CH$_2$ | CH$_2$ | O | C$_4$H$_9$ | c-C$_3$H$_5$ | — |
| 5087 | O | H | Cl | CH$_2$ | CH$_2$ | O | C$_2$H$_5$ | C$_3$H$_7$ | — |
| 5088 | O | H | Cl | CH$_2$ | CH$_2$ | O | C$_2$H$_5$ | C$_4$H$_9$ | — |
| 5089 | O | H | Cl | CH$_2$ | CH$_2$ | O | C$_3$H$_7$ | C$_3$H$_7$ | — |
| 5090 | O | H | Cl | CH$_2$ | CH$_2$ | O | CH$_3$ | C$_3$H$_7$ | — |
| 5091 | O | H | Cl | O | CH$_2$ | O | c-C$_3$H$_5$ | c-C$_3$H$_5$ | — |
| 5092 | O | H | Cl | O | CH$_2$ | O | H | 4-(CH$_3$O)—C$_6$H$_4$ | — |
| 5093 | O | H | Cl | O | CH$_2$ | O | CH$_3$ | c-C$_3$H$_5$ | — |
| 5094 | O | H | Cl | O | CH$_2$ | O | C$_2$H$_5$ | c-C$_3$H$_5$ | — |
| 5095 | O | H | Cl | O | CH$_2$ | O | C$_3$H$_7$ | c-C$_3$H$_5$ | — |
| 5096 | O | H | Cl | O | CH$_2$ | O | C$_4$H$_9$ | c-C$_3$H$_5$ | — |
| 5097 | O | H | Cl | O | CH$_2$ | O | C$_2$H$_5$ | C$_3$H$_7$ | — |
| 5098 | O | H | Cl | O | CH$_2$ | O | C$_2$H$_5$ | C$_4$H$_9$ | — |
| 5099 | O | H | Cl | O | CH$_2$ | O | C$_3$H$_7$ | C$_3$H$_7$ | — |
| 5100 | O | H | Cl | O | CH$_2$ | O | CH$_3$ | C$_3$H$_7$ | — |
| 5101 | CH$_2$ | CH$_3$ | CH$_3$ | CH$_2$ | CH$_2$ | O | c-C$_3$H$_5$ | c-C$_3$H$_5$ | — |
| 5102 | CH$_2$ | CH$_3$ | CH$_3$ | CH$_2$ | CH$_2$ | O | H | 4-(CH$_3$O)—C$_6$H$_4$ | — |
| 5103 | CH$_2$ | CH$_3$ | CH$_3$ | CH$_2$ | CH$_2$ | O | CH$_3$ | c-C$_3$H$_5$ | — |
| 5104 | CH$_2$ | CH$_3$ | CH$_3$ | CH$_2$ | CH$_2$ | O | C$_2$H$_5$ | c-C$_3$H$_5$ | — |
| 5105 | CH$_2$ | CH$_3$ | CH$_3$ | CH$_2$ | CH$_2$ | O | C$_3$H$_7$ | c-C$_3$H$_5$ | — |
| 5106 | CH$_2$ | CH$_3$ | CH$_3$ | CH$_2$ | CH$_2$ | O | C$_4$H$_9$ | c-C$_3$H$_5$ | — |
| 5107 | CH$_2$ | CH$_3$ | CH$_3$ | CH$_2$ | CH$_2$ | O | C$_2$H$_5$ | C$_3$H$_7$ | — |
| 5108 | CH$_2$ | CH$_3$ | CH$_3$ | CH$_2$ | CH$_2$ | O | C$_2$H$_5$ | C$_4$H$_9$ | — |
| 5109 | CH$_2$ | CH$_3$ | CH$_3$ | CH$_2$ | CH$_2$ | O | C$_3$H$_7$ | C$_3$H$_7$ | — |
| 5110 | CH$_2$ | CH$_3$ | CH$_3$ | CH$_2$ | CH$_2$ | O | CH$_3$ | C$_3$H$_7$ | — |
| 5111 | CH$_2$ | H | Cl | O | C=O | NH | c-C$_3$H$_5$ | c-C$_3$H$_5$ | — |
| 5112 | CH$_2$ | H | Cl | O | C=O | NH | H | 4-(CH$_3$O)—C$_6$H$_4$ | — |
| 5113 | CH$_2$ | H | Cl | O | C=O | NH | CH$_3$ | c-C$_3$H$_5$ | — |
| 5114 | CH$_2$ | H | Cl | O | C=O | NH | C$_2$H$_5$ | c-C$_3$H$_5$ | — |
| 5115 | CH$_2$ | H | Cl | O | C=O | NH | C$_3$H$_7$ | c-C$_3$H$_5$ | — |
| 5116 | CH$_2$ | H | Cl | O | C=O | NH | C$_4$H$_9$ | c-C$_3$H$_5$ | — |
| 5117 | CH$_2$ | H | Cl | O | C=O | NH | C$_2$H$_5$ | C$_3$H$_7$ | — |

TABLE 5-continued

| 5118 | CH$_2$ | H | Cl | O | C=O | NH | C$_2$H$_5$ | C$_4$H$_9$ | — |
| --- | --- | --- | --- | --- | --- | --- | --- | --- | --- |
| 5119 | CH$_2$ | H | Cl | C | C=O | NH | C$_3$H$_7$ | C$_3$H$_7$ | — |
| 5120 | CH$_2$ | H | Cl | O | C=O | NH | CH$_3$ | C$_3$H$_7$ | — |
| 5121 | CH$_2$ | H | Cl | O | C=O | NCH$_3$ | c-C$_3$H$_5$ | c-C$_3$H$_5$ | — |
| 5122 | CH$_2$ | H | Cl | O | C=O | NCH$_3$ | H | 4-(CH$_3$O)—C$_6$H$_4$ | — |
| 5123 | CH$_2$ | H | Cl | O | C=O | NCH$_3$ | CH$_3$ | c-C$_3$H$_5$ | — |
| 5124 | CH$_2$ | H | Cl | O | C=O | NCH$_3$ | C$_2$H$_5$ | c-C$_3$H$_5$ | — |
| 5125 | CH$_2$ | H | Cl | O | C=O | NCH$_3$ | C$_3$H$_7$ | c-C$_3$H$_5$ | — |
| 5126 | CH$_2$ | H | Cl | O | C=O | NCH$_3$ | C$_4$H$_9$ | c-C$_3$H$_5$ | — |
| 5127 | CH$_2$ | H | Cl | O | C=O | NCH$_3$ | C$_2$H$_5$ | C$_3$H$_7$ | — |
| 5128 | CH$_2$ | H | Cl | O | C=O | NCH$_3$ | C$_2$H$_5$ | C$_4$H$_9$ | — |
| 5129 | CH$_2$ | H | Cl | O | C=O | NCH$_3$ | C$_3$H$_7$ | C$_3$H$_7$ | — |
| 5130 | CH$_2$ | H | Cl | O | C=O | NCH$_3$ | CH$_3$ | C$_3$H$_7$ | — |
| 5131 | CH$_2$ | H | Cl | O | CCH$_3$ | N | c-C$_3$H$_5$ | c-C$_3$H$_5$ | — |
| 5132 | CH$_2$ | H | Cl | O | CCH$_3$ | N | H | 4-(CH$_3$O)-C$_6$H$_4$ | — |
| 5133 | CH$_2$ | H | Cl | O | CCH$_3$ | N | CH$_3$ | c-C$_3$H$_5$ | — |
| 5134 | CH$_2$ | H | Cl | O | CCH$_3$ | N | C$_2$H$_5$ | c-C$_3$H$_5$ | — |
| 5135 | CH$_2$ | H | Cl | O | CCH$_3$ | N | C$_3$H$_7$ | c-C$_3$H$_5$ | — |
| 5136 | CH$_2$ | H | Cl | O | CCH$_3$ | N | C$_4$H$_9$ | c-C$_3$H$_5$ | — |
| 5137 | CH$_2$ | H | Cl | O | CCH$_3$ | N | C$_2$H$_5$ | C$_3$H$_7$ | — |
| 5138 | CH$_2$ | H | Cl | O | CCH$_3$ | N | C$_2$H$_5$ | C$_4$H$_9$ | — |
| 5139 | CH$_2$ | H | Cl | O | CCH$_3$ | N | C$_3$H$_7$ | C$_3$H$_7$ | — |
| 5140 | CH$_2$ | H | Cl | O | CCH$_3$ | N | CH$_3$ | C$_3$H$_7$ | — |
| 5141 | CH$_2$ | H | Cl | O | C=O | NC$_2$H$_5$ | c-C$_3$H$_5$ | c-C$_3$H$_5$ | — |
| 5142 | CH$_2$ | H | Cl | O | C=O | NC$_2$H$_5$ | H | 4-(CH$_3$O)—C$_6$H$_4$ | — |
| 5143 | CH$_2$ | H | Cl | O | C=O | NC$_2$H$_5$ | CH$_3$ | c-C$_3$H$_5$ | — |
| 5144 | CH$_2$ | H | Cl | O | C=O | NC$_2$H$_5$ | C$_2$H$_5$ | c-C$_3$H$_5$ | — |
| 5145 | CH$_2$ | H | Cl | O | C=O | NC$_2$H$_5$ | C$_3$H$_7$ | c-C$_3$H$_5$ | — |
| 5146 | CH$_2$ | H | Cl | O | C=O | NC$_2$H$_5$ | C$_4$H$_9$ | c-C$_3$H$_5$ | — |
| 5147 | CH$_2$ | H | Cl | O | C=O | NC$_2$H$_5$ | C$_2$H$_5$ | C$_3$H$_7$ | — |
| 5148 | CH$_2$ | H | Cl | O | C=O | NC$_2$H$_5$ | C$_2$H$_5$ | C$_4$H$_9$ | — |
| 5149 | CH$_2$ | H | Cl | O | C=O | NC$_2$H$_5$ | C$_3$H$_7$ | C$_3$H$_7$ | — |
| 5150 | CH$_2$ | H | Cl | O | C=O | NC$_2$H$_5$ | CH$_3$ | C$_3$H$_7$ | — |
| 5151 | CH$_2$ | H | Cl | O | C=O | O | c-C$_3$H$_5$ | c-C$_3$H$_5$ | — |
| 5152 | CH$_2$ | H | Cl | O | C=O | O | H | 4-(CH$_3$O)—C$_6$H$_4$ | — |
| 5153 | CH$_2$ | H | Cl | O | C=O | O | CH$_3$ | c-C$_3$H$_5$ | — |
| 5154 | CH$_2$ | H | Cl | O | C=O | O | C$_2$H$_5$ | c-C$_3$H$_5$ | — |
| 5155 | CH$_2$ | H | Cl | O | C=O | O | C$_3$H$_7$ | c-C$_3$H$_5$ | — |
| 5156 | CH$_2$ | H | Cl | O | C=O | O | C$_4$H$_9$ | c-C$_3$H$_5$ | — |
| 5157 | CH$_2$ | H | Cl | O | C=O | C | C$_2$H$_5$ | C$_3$H$_7$ | — |
| 5158 | CH$_2$ | H | Cl | O | C=O | O | C$_2$H$_5$ | C$_4$H$_9$ | — |
| 5159 | CH$_2$ | H | Cl | O | C=O | O | C$_3$H$_7$ | C$_3$H$_7$ | — |
| 5160 | CH$_2$ | H | Cl | O | C=O | O | CH$_3$ | C$_3$H$_7$ | — |
| 5161 | CH$_2$ | H | Cl | O | CH$_2$CH$_2$ | O | c-C$_3$H$_5$ | c-C$_3$H$_5$ | — |
| 5162 | CH$_2$ | H | Cl | O | CH$_2$CH$_2$ | O | H | 4-(CH$_3$O)—C$_6$H$_4$ | — |
| 5163 | CH$_2$ | H | Cl | O | CH$_2$CH$_2$ | O | CH$_3$ | c-C$_3$H$_5$ | — |
| 5164 | CH$_2$ | H | Cl | O | CH$_2$CH$_2$ | O | C$_2$H$_5$ | c-C$_3$H$_5$ | — |
| 5165 | CH$_2$ | H | Cl | O | CH$_2$CH$_2$ | O | C$_3$H$_7$ | c-C$_3$H$_5$ | — |
| 5166 | CH$_2$ | H | Cl | O | CH$_2$CH$_2$ | O | C$_4$H$_9$ | c-C$_3$H$_5$ | — |
| 5167 | CH$_2$ | H | Cl | O | CH$_2$CH$_2$ | O | C$_2$H$_5$ | C$_3$H$_7$ | — |
| 5168 | CH$_2$ | H | Cl | O | CH$_2$CH$_2$ | O | C$_2$H$_5$ | C$_4$H$_9$ | — |
| 5169 | CH$_2$ | H | Cl | O | CH$_2$CH$_2$ | O | C$_3$H$_7$ | C$_3$H$_7$ | — |
| 5170 | CH$_2$ | H | Cl | O | CH$_2$CH$_2$ | O | CH$_3$ | C$_3$H$_7$ | — |
| 5171 | CH$_2$ | H | CH$_3$ | O | C=O | O | c-C$_3$H$_5$ | c-C$_3$H$_5$ | — |
| 5172 | CH$_2$ | H | CH$_3$ | O | C=O | O | H | 4-(CH$_3$O)—C$_6$H$_4$ | — |
| 5173 | CH$_2$ | H | CH$_3$ | O | C=O | O | CH$_3$ | c-C$_3$H$_5$ | — |
| 5174 | CH$_2$ | H | CH$_3$ | O | C=O | O | C$_2$H$_5$ | c-C$_3$H$_5$ | — |
| 5175 | CH$_2$ | H | CH$_3$ | O | C=O | O | C$_3$H$_7$ | c-C$_3$H$_5$ | — |
| 5176 | CH$_2$ | H | CH$_3$ | O | C=O | O | C$_4$H$_9$ | c-C$_3$H$_5$ | — |
| 5177 | CH$_2$ | H | CH$_3$ | O | C=O | O | C$_2$H$_5$ | C$_3$H$_7$ | — |
| 5178 | CH$_2$ | H | CH$_3$ | O | C=O | O | C$_2$H$_5$ | C$_4$H$_9$ | — |
| 5179 | CH$_2$ | H | CH$_3$ | O | C=O | O | C$_3$H$_7$ | C$_3$H$_7$ | — |
| 5180 | CH$_2$ | H | CH$_3$ | O | C=O | O | CH$_3$ | C$_3$H$_7$ | — |
| 5181 | CH$_2$ | H | CH$_3$ | O | CH$_2$CH$_2$ | O | c-C$_3$H$_5$ | c-C$_3$H$_5$ | — |
| 5182 | CH$_2$ | H | CH$_3$ | O | CH$_2$CH$_2$ | O | H | 4-(CH$_3$O)—C$_6$H$_4$ | — |
| 5183 | CH$_2$ | H | CH$_3$ | O | CH$_2$CH$_2$ | O | CH$_3$ | c-C$_3$H$_5$ | — |
| 5184 | CH$_2$ | H | CH$_3$ | O | CH$_2$CH$_2$ | O | C$_2$H$_5$ | c-C$_3$H$_5$ | — |
| 5185 | CH$_2$ | H | CH$_3$ | O | CH$_2$CH$_2$ | O | C$_3$H$_7$ | c-C$_3$H$_5$ | — |
| 5186 | CH$_2$ | H | CH$_3$ | O | CH$_2$CH$_2$ | O | C$_4$H$_9$ | c-C$_3$H$_5$ | — |
| 5187 | CH$_2$ | H | CH$_3$ | O | CH$_2$CH$_2$ | O | C$_2$H$_5$ | C$_3$H$_7$ | — |
| 5188 | CH$_2$ | H | CH$_3$ | O | CH$_2$CH$_2$ | O | C$_2$H$_5$ | C$_4$H$_9$ | — |
| 5189 | CH$_2$ | H | CH$_3$ | O | CH$_2$CH$_2$ | O | C$_3$H$_7$ | C$_3$H$_7$ | — |
| 5190 | CH$_2$ | H | CH$_3$ | O | CH$_2$CH$_2$ | O | CH$_3$ | C$_3$H$_7$ | — |
| 5191 | CH$_2$ | H | Cl | O | CH$_2$CH$_2$ | NCH$_3$ | c-C$_3$H$_5$ | c-C$_3$H$_5$ | — |
| 5192 | CH$_2$ | H | Cl | O | CH$_2$CH$_2$ | NCH$_3$ | H | 4-(CH$_3$O)—C$_6$H$_4$ | — |
| 5193 | CH$_2$ | H | Cl | O | CH$_2$CH$_2$ | NCH$_3$ | CH$_3$ | c-C$_3$H$_5$ | — |
| 5194 | CH$_2$ | H | Cl | O | CH$_2$CH$_2$ | NCH$_3$ | C$_2$H$_5$ | c-C$_3$H$_5$ | — |
| 5195 | CH$_2$ | H | Cl | O | CH$_2$CH$_2$ | NCH$_3$ | C$_3$H$_7$ | c-C$_3$H$_5$ | — |
| 5196 | CH$_2$ | H | Cl | O | CH$_2$CH$_2$ | NCH$_3$ | C$_4$H$_9$ | c-C$_3$H$_5$ | — |

TABLE 5-continued

| 5197 | CH$_2$ | H | Cl | O | CH$_2$CH$_2$ | NCH$_3$ | C$_2$H$_5$ | C$_3$H$_7$ | — |
| 5198 | CH$_2$ | H | Cl | O | CH$_2$CH$_2$ | NCH$_3$ | C$_2$H$_5$ | C$_4$H$_9$ | — |
| 5199 | CH$_2$ | H | Cl | O | CH$_2$CH$_2$ | NCH$_3$ | C$_3$H$_7$ | C$_3$H$_7$ | — |
| 5200 | CH$_2$ | H | Cl | O | CH$_2$CH$_2$ | NCH$_3$ | CH$_3$ | C$_3$H$_7$ | — |
| 5201 | CH$_2$ | H | CH$_3$ | CH | CH | O | c-C$_3$H$_5$ | c-C$_3$H$_5$ | 139–141 |
| 5202 | CH$_2$ | H | CH$_3$ | CH | CH | O | H | 4-(CH$_3$O)—C$_6$H$_4$ | — |
| 5203 | CH$_2$ | H | CH$_3$ | CH | CH | O | CH$_3$ | c-C$_3$H$_5$ | — |
| 5204 | CH$_2$ | H | CH$_3$ | CH | CH | O | C$_2$H$_5$ | c-C$_3$H$_5$ | — |
| 5205 | CH$_2$ | H | CH$_3$ | CH | CH | O | C$_3$H$_7$ | c-C$_3$H$_5$ | — |
| 5206 | CH$_2$ | H | CH$_3$ | CH | CH | O | C$_4$H$_9$ | c-C$_3$H$_5$ | — |
| 5207 | CH$_2$ | H | CH$_3$ | CH | CH | O | C$_2$H$_5$ | C$_3$H$_7$ | — |
| 5208 | CH$_2$ | H | CH$_3$ | CH | CH | O | C$_2$H$_5$ | C$_4$H$_9$ | — |
| 5209 | CH$_2$ | H | CH$_3$ | CH | CH | O | C$_3$H$_7$ | C$_3$H$_7$ | — |
| 5210 | CH$_2$ | H | CH$_3$ | CH | CH | O | CH$_3$ | C$_3$H$_7$ | — |
| 5211 | CH$_2$ | H | Cl | CH | CH | O | c-C$_3$H$_5$ | c-C$_3$H$_5$ | — |
| 5212 | CH$_2$ | H | Cl | CH | CH | O | H | 4-(CH$_3$O)—C$_6$H$_4$ | — |
| 5213 | CH$_2$ | H | Cl | CH | CH | O | CH$_3$ | c-C$_3$H$_5$ | — |
| 5214 | CH$_2$ | H | Cl | CH | CH | O | C$_2$H$_5$ | c-C$_3$H$_5$ | — |
| 5215 | CH$_2$ | H | Cl | CH | CH | O | C$_3$H$_7$ | c-C$_3$H$_5$ | — |
| 5216 | CH$_2$ | H | Cl | CH | CH | O | C$_4$H$_9$ | c-C$_3$H$_5$ | — |
| 5217 | CH$_2$ | H | Cl | CH | CH | O | C$_2$H$_5$ | C$_3$H$_7$ | — |
| 5218 | CH$_2$ | H | Cl | CH | CH | O | C$_2$H$_5$ | C$_4$H$_9$ | — |
| 5219 | CH$_2$ | H | Cl | CH | CH | O | C$_3$H$_7$ | C$_3$H$_7$ | — |
| 5220 | CH$_2$ | H | Cl | CH | CH | O | CH$_3$ | C$_3$H$_7$ | — |
| 5221 | CH$_2$ | H | CH$_3$ | CH | CHCH | CH | c-C$_3$H$_5$ | c-C$_3$H$_5$ | — |
| 5222 | CH$_2$ | H | CH$_3$ | CH | CHCH | CH | H | 4-(CH$_3$O)—C$_6$H$_4$ | — |
| 5223 | CH$_2$ | H | CH$_3$ | CH | CHCH | CH | CH$_3$ | c-C$_3$H$_5$ | — |
| 5224 | CH$_2$ | H | CH$_3$ | CH | CHCH | CH | C$_2$H$_5$ | c-C$_3$H$_5$ | — |
| 5225 | CH$_2$ | H | CH$_3$ | CH | CHCH | CH | C$_3$H$_7$ | c-C$_3$H$_5$ | — |
| 5226 | CH$_2$ | H | CH$_3$ | CH | CHCH | CH | C$_4$H$_9$ | c-C$_3$H$_5$ | — |
| 5227 | CH$_2$ | H | CH$_3$ | CH | CHCH | CH | C$_2$H$_5$ | C$_3$H$_7$ | — |
| 5228 | CH$_2$ | H | CH$_3$ | CH | CHCH | CH | C$_2$H$_5$ | C$_4$H$_9$ | — |
| 5229 | CH$_2$ | H | CH$_3$ | CH | CHCH | CH | C$_3$H$_7$ | C$_3$H$_7$ | — |
| 5230 | CH$_2$ | H | CH$_3$ | CH | CHCH | CH | CH$_3$ | C$_3$H$_7$ | — |
| 5231 | CH$_2$ | H | CH$_3$ | CH | CBr | O | c-C$_3$H$_5$ | c-C$_3$H$_5$ | 177–178 |
| 5232 | CH$_2$ | H | CH$_3$ | CH$_2$ | CH$_2$ | O | c-C$_3$H$_5$ | c-C$_3$H$_5$ | 179–180 |
| 5233 | CH$_2$ | H | CH$_3$ | CH | CCH$_3$ | O | c-C$_3$H$_5$ | c-C$_3$H$_5$ | — |
| 5234 | CH$_2$ | H | CH$_3$ | CH$_2$ | CH$_2$ | O | c-C$_3$H$_5$ | c-C$_3$H$_5$ | — |
| 5235 | CH$_2$ | H | CH$_3$ | CH | CSCH$_3$ | O | c-C$_3$H$_5$ | c-C$_3$H$_5$ | — |
| 5236 | CH$_2$ | H | CH$_3$ | CH$_2$ | CH$_2$ | O | c-C$_3$H$_5$ | c-C$_3$H$_5$ | — |

TABLE 5A

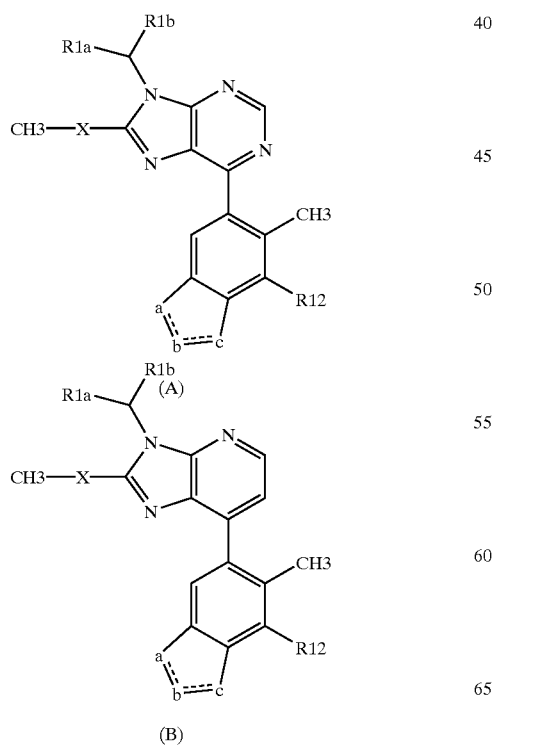

TABLE 5A-continued

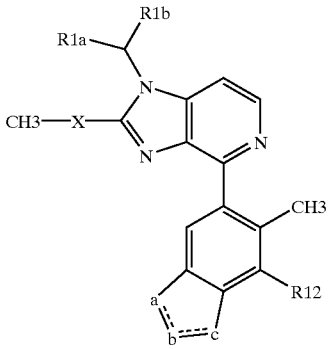

(C)

| Ex. No. | X | R[12] | a | b | c | R[1a] | R[1b] | m.p., °C. |
|---|---|---|---|---|---|---|---|---|
| 5232 | $CH_2$ | Br | $CH_2$ | $CH_2$ | O | c-$C_3H_5$ | c-$C_3H_5$ | 179–180 |
| 5234 | $CH_2$ | CN | $CH_2$ | $CH_2$ | O | c-$C_3H_5$ | c-$C_3H_5$ | — |
| 5236 | $CH_2$ | $SCH_3$ | $CH_2$ | $CH_2$ | O | c-$C_3H_5$ | c-$C_3H_5$ | — |

The methods used in the preparation of the compounds of Table 1 may be used for the compounds of Structure A of Table 6. For example, replacing variously-substituted penta atomic heteroaryl boronic acids for benzeneboronic acids in the palladium-catalyzed aryl cross-coupling method (see Examples 35 or 831) will afford the desired 6-heteroarylpurine compounds.

The methods of Schemes 13 and 14 may be used to prepare many of the examples of Structure B and Structure C contained in Table 6, with minor procedural modifications where necessary and use of reagents of the appropriate structure.

TABLE 6

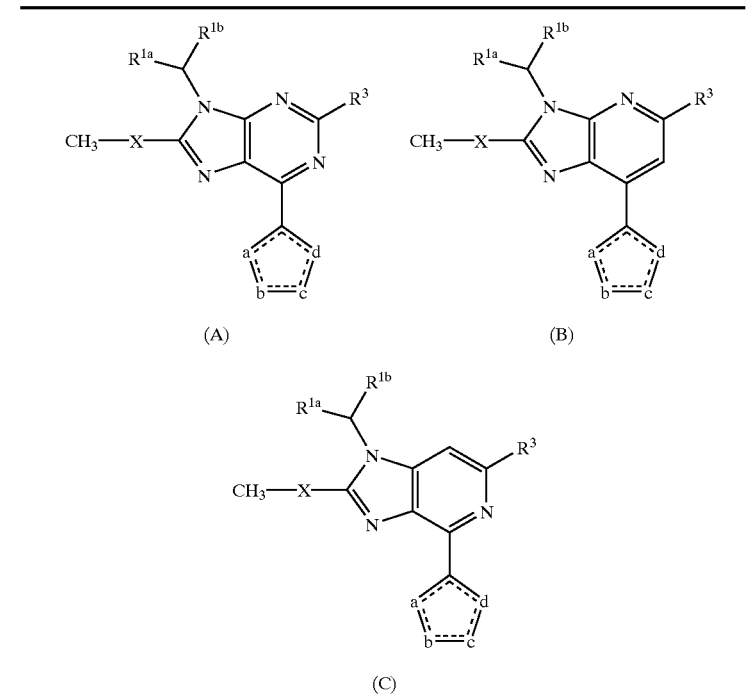

| Ex. No. | X | R[3] | a | b | c | d | R[1a] | R[1b] | m.p. °C.[a] |
|---|---|---|---|---|---|---|---|---|---|
| 6001 | $CH_2$ | H | $CCH_3$ | N | O | $CCH_3$ | c-$C_3H_5$ | c-$C_3H_5$ | oil |
| 6002 | $CH_2$ | H | $CCH_3$ | N | O | $CCH_3$ | $CH_3$ | c-$C_3H_5$ | — |
| 6003 | $CH_2$ | H | $CCH_3$ | N | O | $CCH_3$ | $C_2H_5$ | c-$C_3H_5$ | — |
| 6004 | $CH_2$ | H | $CCH_3$ | N | O | $CCH_3$ | $C_3H_7$ | c-$C_3H_5$ | — |
| 6005 | $CH_2$ | H | $CCH_3$ | N | O | $CCH_3$ | $C_4H_9$ | c-$C_3H_5$ | — |
| 6006 | $CH_2$ | H | $CCH_3$ | N | O | $CCH_3$ | $CH_3$ | $C_3H_7$ | — |
| 6007 | $CH_2$ | H | $CCH_3$ | N | O | $CCH_3$ | $C_2H_5$ | $C_3H_7$ | — |
| 6008 | $CH_2$ | H | $CCH_3$ | N | O | $CCH_3$ | $C_3H_7$ | $C_3H_7$ | — |
| 6009 | $CH_2$ | H | $CCH_3$ | N | O | $CCH_3$ | $C_2H_5$ | $C_4H_9$ | — |
| 6010 | $CH_2$ | H | $CCH_3$ | N | O | $CCH_3$ | H | 4-$CH_3O$—$C_6H_4$ | — |
| 6011 | O | H | $CCH_3$ | N | O | $CCH_3$ | c-$C_3H_5$ | c-$C_3H_5$ | — |
| 6012 | O | H | $CCH_3$ | N | O | $CCH_3$ | $CH_3$ | c-$C_3H_5$ | — |
| 6013 | O | H | $CCH_3$ | N | O | $CCH_3$ | $C_2H_5$ | c-$C_3H_5$ | — |
| 6014 | O | H | $CCH_3$ | N | O | $CCH_3$ | $C_3H_7$ | c-$C_3H_5$ | — |
| 6015 | O | H | $CCH_3$ | N | O | $CCH_3$ | $C_4H_9$ | c-$C_3H_5$ | — |
| 6016 | O | H | $CCH_3$ | N | O | $CCH_3$ | $CH_3$ | $C_3H_7$ | — |

TABLE 6-continued

| 6017 | O | H | CCH$_3$ | N | O | CCH$_3$ | C$_2$H$_5$ | C$_3$H$_7$ | — |
|---|---|---|---|---|---|---|---|---|---|
| 6018 | O | H | CCH$_3$ | N | O | CCH$_3$ | C$_3$H$_7$ | C$_3$H$_7$ | — |
| 6019 | O | H | CCH$_3$ | N | O | CCH$_3$ | C$_2$H$_5$ | C$_4$H$_9$ | — |
| 6020 | O | H | CCH$_3$ | N | O | CCH$_3$ | H | 4-CH$_3$O—C$_6$H$_4$ | — |
| 6021 | CH$_2$ | CH$_3$ | CCH$_3$ | N | O | CCH$_3$ | c-C$_3$H$_5$ | c-C$_3$H$_5$ | — |
| 6022 | CH$_2$ | CH$_3$ | CCH$_3$ | N | O | CCH$_3$ | CH$_3$ | c-C$_3$H$_5$ | — |
| 6023 | CH$_2$ | CH$_3$ | CCH$_3$ | N | O | CCH$_3$ | C$_2$H$_5$ | c-C$_3$H$_5$ | — |
| 6024 | CH$_2$ | CH$_3$ | CCH$_3$ | N | O | CCH$_3$ | C$_3$H$_7$ | c-C$_3$H$_5$ | — |
| 6025 | CH$_2$ | CH$_3$ | CCH$_3$ | N | O | CCH$_3$ | C$_4$H$_9$ | c-C$_3$H$_5$ | — |
| 6026 | CH$_2$ | CH$_3$ | CCH$_3$ | N | O | CCH$_3$ | CH$_3$ | C$_3$H$_7$ | — |
| 6027 | CH$_2$ | CH$_3$ | CCH$_3$ | N | O | CCH$_3$ | C$_2$H$_5$ | C$_3$H$_7$ | — |
| 6028 | CH$_2$ | CH$_3$ | CCH$_3$ | N | O | CCH$_3$ | C$_3$H$_7$ | C$_3$H$_7$ | — |
| 6029 | CH$_2$ | CH$_3$ | CCH$_3$ | N | O | CCH$_3$ | C$_2$H$_5$ | C$_4$H$_9$ | — |
| 6030 | CH$_2$ | CH$_3$ | CCH$_3$ | N | O | CCH$_3$ | H | 4-CH$_3$O—C$_6$H$_4$ | — |
| 6031 | CH$_2$ | H | CCH$_3$ | N | NCH$_3$ | CCH$_3$ | c-C$_3$H$_5$ | c-C$_3$H$_5$ | — |
| 6032 | CH$_2$ | H | CCH$_3$ | N | NCH$_3$ | CCH$_3$ | CH$_3$ | c-C$_3$H$_5$ | — |
| 6033 | CH$_2$ | H | CCH$_3$ | N | NCH$_3$ | CCH$_3$ | C$_2$H$_5$ | c-C$_3$H$_5$ | — |
| 6034 | CH$_2$ | H | CCH$_3$ | N | NCH$_3$ | CCH$_3$ | C$_3$H$_7$ | c-C$_3$H$_5$ | — |
| 6035 | CH$_2$ | H | CCH$_3$ | N | NCH$_3$ | CCH$_3$ | C$_4$H$_9$ | c-C$_3$H$_5$ | — |
| 6036 | CH$_2$ | H | CCH$_3$ | N | NCH$_3$ | CCH$_3$ | CH$_3$ | C$_3$H$_7$ | — |
| 6037 | CH$_2$ | H | CCH$_3$ | N | NCH$_3$ | CCH$_3$ | C$_2$H$_5$ | C$_3$H$_7$ | — |
| 6038 | CH$_2$ | H | CCH$_3$ | N | NCH$_3$ | CCH$_3$ | C$_3$H$_7$ | C$_3$H$_7$ | — |
| 6039 | CH$_2$ | H | CCH$_3$ | N | NCH$_3$ | CCH$_3$ | C$_2$H$_5$ | C$_4$H$_9$ | — |
| 6040 | CH$_2$ | H | CCH$_3$ | N | NCH$_3$ | CCH$_3$ | H | 4-CH$_3$O—C$_6$H$_4$ | — |
| 6041 | O | H | CCH$_3$ | N | NCH$_3$ | CCH$_3$ | c-C$_3$H$_5$ | c-C$_3$H$_5$ | — |
| 6042 | O | H | CCH$_3$ | N | NCH$_3$ | CCH$_3$ | CH$_3$ | c-C$_3$H$_5$ | — |
| 6043 | O | H | CCH$_3$ | N | NCH$_3$ | CCH$_3$ | C$_2$H$_5$ | c-C$_3$H$_5$ | — |
| 6044 | O | H | CCH$_3$ | N | NCH$_3$ | CCH$_3$ | C$_3$H$_7$ | c-C$_3$H$_5$ | — |
| 6045 | O | H | CCH$_3$ | N | NCH$_3$ | CCH$_3$ | C$_4$H$_9$ | c-C$_3$H$_5$ | — |
| 6046 | O | H | CCH$_3$ | N | NCH$_2$ | CCH$_3$ | CH$_3$ | C$_3$H$_7$ | — |
| 6047 | O | H | CCH$_3$ | N | NCH$_3$ | CCH$_3$ | C$_2$H$_5$ | C$_3$H$_7$ | — |
| 6048 | O | H | CCH$_3$ | N | NCH$_3$ | CCH$_3$ | C$_3$H$_7$ | C$_3$H$_7$ | — |
| 6049 | O | H | CCH$_3$ | N | NCH$_3$ | CCH$_3$ | C$_2$H$_5$ | C$_4$H$_9$ | — |
| 6050 | O | H | CCH$_3$ | N | NCH$_3$ | CCH$_3$ | H | 4-CH$_3$O—C$_6$H$_4$ | — |
| 6051 | CH$_2$ | CH$_3$ | CCH$_3$ | N | NCH$_3$ | CCH$_3$ | c-C$_3$H$_5$ | c-C$_3$H$_5$ | — |
| 6052 | CH$_2$ | CH$_3$ | CCH$_3$ | N | NCH$_3$ | CCH$_3$ | CH$_3$ | c-C$_3$H$_5$ | — |
| 6053 | CH$_2$ | CH$_3$ | CCH$_3$ | N | NCH$_3$ | CCH$_3$ | C$_2$H$_5$ | c-C$_3$H$_5$ | — |
| 6054 | CH$_2$ | CH$_3$ | CCH$_3$ | N | NCH$_3$ | CCH$_3$ | C$_3$H$_7$ | c-C$_3$H$_5$ | — |
| 6055 | CH$_2$ | CH$_3$ | CCH$_3$ | N | NCH$_3$ | CCH$_3$ | C$_4$H$_9$ | c-C$_3$H$_5$ | — |
| 6056 | CH$_2$ | CH$_3$ | CCH$_3$ | N | NCH$_3$ | CCH$_3$ | CH$_3$ | C$_3$H$_7$ | — |
| 6057 | CH$_2$ | CH$_3$ | CCH$_3$ | N | NCH$_3$ | CCH$_3$ | C$_2$H$_5$ | C$_3$H$_7$ | — |
| 6058 | CH$_2$ | CH$_3$ | CCH$_3$ | N | NCH$_3$ | CCH$_3$ | C$_3$H$_7$ | C$_3$H$_7$ | — |
| 6059 | CH$_2$ | CH$_3$ | CCH$_3$ | N | NCH$_3$ | CCH$_3$ | C$_2$H$_5$ | C$_4$H$_9$ | — |
| 6060 | CH$_2$ | CH$_3$ | CCH$_3$ | N | NCH$_3$ | CCH$_3$ | H | 4-CH$_3$O—C$_6$H$_4$ | — |
| 6061 | CH$_2$ | H | CCH$_3$ | N | NC$_2$H$_5$ | CCH$_3$ | c-C$_3$H$_5$ | c-C$_3$H$_5$ | — |
| 6062 | CH$_2$ | H | CCH$_3$ | N | NC$_2$H$_5$ | CCH$_3$ | CH$_3$ | c-C$_3$H$_5$ | — |
| 6063 | CH$_2$ | H | CCH$_3$ | N | NC$_2$H$_5$ | CCH$_3$ | C$_2$H$_5$ | c-C$_3$H$_5$ | — |
| 6064 | CH$_2$ | H | CCH$_3$ | N | NC$_2$H$_5$ | CCH$_3$ | C$_3$H$_7$ | c-C$_3$H$_5$ | — |
| 6065 | CH$_2$ | H | CCH$_3$ | N | NC$_2$H$_5$ | CCH$_3$ | C$_4$H$_9$ | c-C$_3$H$_5$ | — |
| 6066 | CH$_2$ | H | CCH$_3$ | N | NC$_2$H$_5$ | CCH$_3$ | CH$_3$ | C$_3$H$_7$ | — |
| 6067 | CH$_2$ | H | CCH$_3$ | N | NC$_2$H$_5$ | CCH$_3$ | C$_2$H$_5$ | C$_3$H$_7$ | — |
| 6068 | CH$_2$ | H | CCH$_3$ | N | NC$_2$H$_5$ | CCH$_3$ | C$_3$H$_7$ | C$_3$H$_7$ | — |
| 6069 | CH$_2$ | H | CCH$_3$ | N | NC$_2$H$_5$ | CCH$_3$ | C$_2$H$_5$ | C$_4$H$_9$ | — |
| 6070 | CH$_2$ | H | CCH$_3$ | N | NC$_2$H$_5$ | CCH$_3$ | H | 4-CH$_3$O—C$_6$H$_4$ | — |
| 6071 | O | H | CCH$_3$ | N | NC$_2$H$_5$ | CCH$_3$ | c-C$_3$H$_5$ | c-C$_3$H$_5$ | — |
| 6072 | O | H | CCH$_3$ | N | NC$_2$H$_5$ | CCH$_3$ | CH$_3$ | c-C$_3$H$_5$ | — |
| 6073 | O | H | CCH$_3$ | N | NC$_2$H$_5$ | CCH$_3$ | C$_2$H$_5$ | c-C$_3$H$_5$ | — |
| 6074 | O | H | CCH$_3$ | N | NC$_2$H$_5$ | CCH$_3$ | C$_3$H$_7$ | c-C$_3$H$_5$ | — |
| 6075 | O | H | CCH$_3$ | N | NC$_2$H$_5$ | CCH$_3$ | C$_4$H$_9$ | c-C$_3$H$_5$ | — |
| 6076 | O | H | CCH$_3$ | N | NC$_2$H$_5$ | CCH$_3$ | CH$_3$ | C$_3$H$_7$ | — |
| 6077 | O | H | CCH$_3$ | N | NC$_2$H$_5$ | CCH$_3$ | C$_2$H$_5$ | C$_3$H$_7$ | — |
| 6078 | O | H | CCH$_3$ | N | NC$_2$H$_5$ | CCH$_3$ | C$_3$H$_7$ | C$_3$H$_7$ | — |
| 6079 | O | H | CCH$_3$ | N | NC$_2$H$_5$ | CCH$_3$ | C$_2$H$_5$ | C$_4$H$_9$ | — |
| 6080 | O | H | CCH$_3$ | N | NC$_2$H$_5$ | CCH$_3$ | H | 4-CH$_3$O—C$_6$H$_4$ | — |
| 6081 | CH$_2$ | CH$_3$ | CCH$_3$ | N | NC$_2$H$_5$ | CCH$_3$ | c-C$_3$H$_5$ | c-C$_3$H$_5$ | — |
| 6082 | CH$_2$ | CH$_3$ | CCH$_3$ | N | NC$_2$H$_5$ | CCH$_3$ | CH$_3$ | c-C$_3$H$_5$ | — |
| 6083 | CH$_2$ | CH$_3$ | CCH$_3$ | N | NC$_2$H$_5$ | CCH$_3$ | C$_2$H$_5$ | c-C$_3$H$_5$ | — |
| 6084 | CH$_2$ | CH$_3$ | CCH$_3$ | N | NC$_2$H$_5$ | CCH$_3$ | C$_3$H$_7$ | c-C$_3$H$_5$ | — |
| 6085 | CH$_2$ | CH$_3$ | CCH$_3$ | N | NC$_2$H$_5$ | CCH$_3$ | C$_4$H$_9$ | c-C$_3$H$_5$ | — |
| 6086 | CH$_2$ | CH$_3$ | CCH$_3$ | N | NC$_2$H$_5$ | CCH$_3$ | CH$_3$ | C$_3$H$_7$ | — |
| 6087 | CH$_2$ | CH$_3$ | CCH$_3$ | N | NC$_2$H$_5$ | CCH$_3$ | C$_2$H$_5$ | C$_3$H$_7$ | — |
| 6088 | CH$_2$ | CH$_3$ | CCH$_3$ | N | NC$_2$H$_5$ | CCH$_3$ | C$_3$H$_7$ | C$_3$H$_7$ | — |
| 6089 | CH$_2$ | CH$_3$ | CCH$_3$ | N | NC$_2$H$_5$ | CCH$_3$ | C$_2$H$_5$ | C$_4$H$_9$ | — |
| 6090 | CH$_2$ | CH$_3$ | CCH$_3$ | N | NC$_2$H$_5$ | CCH$_3$ | H | 4-CH$_3$O—C$_6$H$_4$ | — |
| 6091 | CH$_2$ | H | CCH$_3$ | N | CCH$_3$ | NCH$_3$ | c-C$_3$H$_5$ | c-C$_3$H$_5$ | — |
| 6092 | CH$_2$ | H | CCH$_3$ | N | CCH$_3$ | NCH$_3$ | CH$_3$ | c-C$_3$H$_5$ | — |
| 6093 | CH$_2$ | H | CCH$_3$ | N | CCH$_3$ | NCH$_3$ | C$_2$H$_5$ | c-C$_3$H$_5$ | — |
| 6094 | CH$_2$ | H | CCH$_3$ | N | CCH$_3$ | NCH$_3$ | C$_3$H$_7$ | c-C$_3$H$_5$ | — |
| 6095 | CH$_2$ | H | CCH$_3$ | N | CCH$_3$ | NCH$_3$ | C$_4$H$_9$ | c-C$_3$H$_5$ | — |

TABLE 6-continued

| | | | | | | | | |
|---|---|---|---|---|---|---|---|---|
| 6096 | $CH_2$ | H | $CCH_3$ | N | $CCH_3$ | $NCH_3$ | $CH_3$ | $C_3H_7$ | — |
| 6097 | $CH_2$ | H | $CCH_3$ | N | $CCH_3$ | $NCH_3$ | $C_2H_5$ | $C_3H_7$ | — |
| 6098 | $CH_3$ | H | $CCH_3$ | N | $CCH_3$ | $NCH_3$ | $C_3H_7$ | $C_3H_7$ | — |
| 6099 | $CH_2$ | H | $CCH_3$ | N | $CCH_3$ | $NCH_3$ | $C_2H_5$ | $C_4H_9$ | — |
| 6100 | $CH_2$ | H | $CCH_3$ | N | $CCH_3$ | $NCH_3$ | H | 4-$CH_3O$—$C_6H_4$ | — |
| 6101 | $CH_2$ | H | $CCH_3$ | N | $NC_6H_5$ | $CCH_3$ | c-$C_3H_5$ | c-$C_3H_5$ | — |
| 6102 | $CH_2$ | H | $CCH_3$ | N | $NC_6H_5$ | $CCH_3$ | $CH_3$ | c-$C_3H_5$ | — |
| 6103 | $CH_2$ | H | $CCH_3$ | N | $NC_6H_5$ | $CCH_3$ | $C_2H_5$ | c-$C_3H_5$ | — |
| 6104 | $CH_2$ | H | $CCH_3$ | N | $NC_6H_5$ | $CCH_3$ | $C_3H_7$ | c-$C_3H_5$ | — |
| 6105 | $CH_2$ | H | $CCH_3$ | N | $NC_6H_5$ | $CCH_3$ | $C_4H_9$ | c-$C_3H_5$ | — |
| 6106 | $CH_2$ | H | $CCH_3$ | N | $NC_6H_5$ | $CCH_3$ | $CH_3$ | $C_3H_7$ | — |
| 6107 | $CH_2$ | H | $CCH_3$ | N | $NC_6H_5$ | $CCH_3$ | $C_2H_5$ | $C_3H_7$ | — |
| 6108 | $CH_2$ | H | $CCH_3$ | N | $NC_6H_5$ | $CCH_3$ | $C_3H_7$ | $C_3H_7$ | — |
| 6109 | $CH_2$ | H | $CCH_3$ | N | $NC_6H_5$ | $CCH_3$ | $C_2H_5$ | $C_4H_9$ | — |
| 6110 | $CH_2$ | H | $CCH_3$ | N | $NC_6H_5$ | $CCH_3$ | H | 4-$CH_3O$—$C_6H_4$ | — |
| 6111 | O | H | $CCH_3$ | N | $NC_6H_5$ | $CCH_3$ | c-$C_3H_5$ | c-$C_3H_5$ | — |
| 6112 | O | H | $CCH_3$ | N | $NC_6H_5$ | $CCH_3$ | $CH_3$ | c-$C_3H_5$ | — |
| 6113 | O | H | $CCH_3$ | N | $NC_6H_5$ | $CCH_3$ | $C_2H_5$ | c-$C_3H_5$ | — |
| 6114 | O | H | $CCH_3$ | N | $NC_6H_5$ | $CCH_3$ | $C_3H_7$ | c-$C_3H_5$ | — |
| 6115 | O | H | $CCH_3$ | N | $NC_6H_5$ | $CCH_3$ | $C_4H_9$ | c-$C_3H_5$ | — |
| 6116 | O | H | $CCH_3$ | N | $NC_6H_5$ | $CCH_3$ | $CH_3$ | $C_3H_7$ | — |
| 6117 | O | H | $CCH_3$ | N | $NC_6H_5$ | $CCH_3$ | $C_2H_5$ | $C_3H_7$ | — |
| 6118 | O | H | $CCH_3$ | N | $NC_6H_5$ | $CCH_3$ | $C_3H_7$ | $C_3H_7$ | — |
| 6119 | O | H | $CCH_3$ | N | $NC_6H_5$ | $CCH_3$ | $C_2H_5$ | $C_4H_9$ | — |
| 6120 | O | H | $CCH_3$ | N | $NC_6H_5$ | $CCH_3$ | H | 4-$CH_3O$—$C_6H_4$ | — |
| 6121 | $CH_2$ | $CH_3$ | $CCH_3$ | N | $NC_6H_5$ | $CCH_3$ | c-$C_3H_5$ | c-$C_3H_5$ | — |
| 6122 | $CH_2$ | $CH_3$ | $CCH_3$ | N | $NC_6H_5$ | $CCH_3$ | $CH_3$ | c-$C_3H_5$ | — |
| 6123 | $CH_2$ | $CH_3$ | $CCH_3$ | N | $NC_6H_5$ | $CCH_3$ | $C_2H_5$ | c-$C_3H_5$ | — |
| 6124 | $CH_2$ | $CH_3$ | $CCH_3$ | N | $NC_6H_5$ | $CCH_3$ | $C_3H_7$ | c-$C_3H_5$ | — |
| 6125 | $CH_2$ | $CH_3$ | $CCH_3$ | N | $NC_6H_5$ | $CCH_3$ | $C_4H_9$ | c-$C_3H_5$ | — |
| 6126 | $CH_2$ | $CH_3$ | $CCH_3$ | N | $NC_6H_5$ | $CCH_3$ | $CH_3$ | $C_3H_7$ | — |
| 6127 | $CH_2$ | $CH_3$ | $CCH_3$ | N | $NC_6H_5$ | $CCH_3$ | $C_2H_5$ | $C_3H_7$ | — |
| 6128 | $CH_2$ | $CH_3$ | $CCH_3$ | N | $NC_6H_5$ | $CCH_3$ | $C_3H_7$ | $C_3H_7$ | — |
| 6129 | $CH_2$ | $CH_3$ | $CCH_3$ | N | $NC_6H_5$ | $CCH_3$ | $C_2H_5$ | $C_4H_9$ | — |
| 6130 | $CH_2$ | $CH_3$ | $CCH_3$ | N | $NC_6H_5$ | $CCH_3$ | H | 4-$CH_3O$—$C_6H_4$ | — |

Key:
a) Where the compound is indicated as an "oil", spectral data is provided as follows: Example 6001 spectral data: MS ($NH_3$—CI): m/e 338 (M+H$^+$, 100%).

The methods used in the preparation of the compounds of Table 1 may be used for preparation of many of the compounds of Structure A of Table 7. The preparation of those compounds derived from cyclo addition of compounds with alkynyl-bearing $R^1$ groups is illustrated by the following examples.

The methods of Schemes 13 and 14 may be used to prepare many of the examples of Structure B and Structure C contained in Table 7, with minor procedural modifications where necessary and use of reagents of the appropriate structure.

EXAMPLE 7409

Preparation of 9-[1-Cyclopropyl-1-(3-methyl-isoxazol-5-yl)methyl]-6-(2,4-dichlorophenyl)-8-ethyl-9H-purine To a stirring solution of the compound of Example 7241 (90 mg, 0.24 mmol; prepared in a manner similar to that of Example 2 using 6-(2,4-dichlorophenyl)-8-ethyl-9H-purine and 3-cyclopropyl-1-propyn-3-ol) in methylene chloride (2 mL) were added chloroacetaldoxime (25 mg, 0.27 mmol) and triethylamine (0.038 mL, 0.27 mmol). (The chloroacetaldoxime used was previously prepared by reacting equimolar amounts of acetaldoxime and N-chlorosuccinimide in DMF, then extracting the product into diethyl ether and washing with water.) The cyclo addition reaction was monitored by TLC and additional amounts of chloroacetaldoxime and triethylamine were added until all the starting material was consumed. The reaction mixture was purified by adding directly to a column packed with silica gel and eluting using a gradient of 100% hexane to 25% ethyl acetate in hexane. 72 mg of a white foam was collected. MS ($NH_3$—CI) 428 (M+H$^+$) HRMS: m/e=428.1037 (M+H$^+$, $C_{21}H_{20}Cl_2N_5O$). Purity by reverse phase HPLC >97%.

EXAMPLES 7396 AND 7398

Preparation of 6-(2,4-Dichlorophenyl)-9-[1-(3-ethoxycarbonyl-isoxazol-5-yl)butyl]-8-ethyl-9H-purine and 9-[1-(4-Cyano-3-ethoxycarbonyl-isoxazol-5-yl)butyl]-6-(2,4-dichlorophenyl)-8-ethyl-9H-purine A solution of the compound of Example 7259 (120 mg, 0.321 mmol; prepared in a manner similar to that of Example 2 using 6-(2,4-dichlorophenyl)-8-ethyl-9H-purine and 1-hexyn-3-ol), ethyl chlorooximidoacetate (146 mg, 0.963 mmol) and diisopropylethylamine (170 μL, 0.976 mmol) in toluene (2 mL) was heated to reflux for 20 hours, then cooled and diluted with 20 mL ethyl acetate. This was washed with water (2×20 mL) and satd. aq. brine (20 mL), and the aqueous phases were back-extracted in sequence with ethyl acetate (20 mL). The organic extracts were combined, dried over anhydrous sodium sulfate, filtered and evaporated. The residual material was separated by column chromatography (silica gel, 1:4 ethyl acetate-hexane) to afford, in order, unreacted starting material (about 50 mg), then the compound of Example 7396 (58.7 mg, 0.120 mmol, 37%), and finally the compound of Example 7398 (23.8 mg, 0.046 mmol, 14%), the latter two compounds being amorphous solids. Example 7396 spectral data: TLC $R_F$ 0.27 (20:80 ethyl acetate-hexane). $^1$H NMR (300 MHz, $CDCl_3$): δ 8.96 (1H, s), 7.67 (1H, d, J=8.1 Hz), 7.58 (1H, d, J=1.8

Hz), 7.41 (1H, dd, J=8.1, 1.8 Hz), 6.86 (1H, s), 5.83 (1H, dd, J=9.9, 6.2 Hz), 4.43 (2H, q, J=7.3 Hz), 2.98 (2H, q, J=7.7 Hz), 2.91–2.78 (1H, m), 2.63–2.49 (1H, m), 1.42 (3H, t, J=7.7 Hz), 1.40 (3H, t, J=7.3 Hz), 1.39–1.19 (2H, m), 1.00 (3H, t, J=7.3 Hz). MS ($NH_3$—CI): m/e calc'd for $C_{23}H_{24}Cl_2N_5O_3$: 488.1256, found 488.1252; 493 (3), 492 (13), 491 (18), 490 (68), 489 (28), 488 (100). Example 7398 spectral data: TLC $R_F$ 0.11 (20:80 ethyl acetate-hexane). $^1$H NMR (300 MHz, $CDCl_3$): δ 8.99 (1H, S), 7.72 (1H, d, J=8.1 Hz), 7.59 (1H, J=1.8 Hz), 7.42 (1H, dd, J=8.1, 1.8 Hz), 5.40 (1H, dd, J=10.4, 5.0 Hz), 4.42 (2H, q, J=7.4 Hz), 3.00–2.90 (2H, m), 2.66–2.52 (1H, m), 2.51–2.38 (1H, m), 1.46 (3H, t, J=7.4 Hz), 1.41 (3H, t, J=7.3 Hz), 1.40–1.10 (2H, m), 0.98 (3H, t, J=7.2 Hz). MS ($NH_3$—CI): m/e calc'd for $C_{24}H_{25}Cl_2N_6O_4$: 531.1315, found 531.1315; 531 (100).

TABLE 7

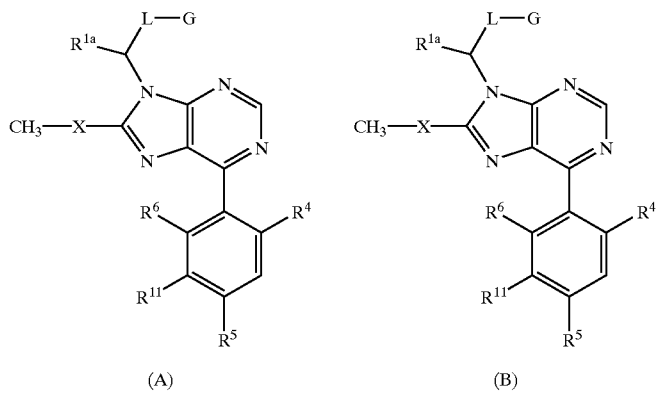

(A)    (B)

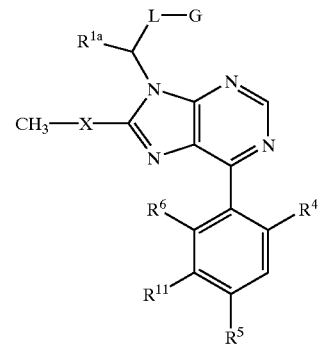

(C)

| Ex. No. | X | $R^4$ | $R^5$ | $R^{11}$ | $R^6$ | $R^{1a}$ | L | $G^a$ | m.p., °C.$^b$ |
|---|---|---|---|---|---|---|---|---|---|
| 7001 | $CH_2$ | $CH_3$ | $CH_3$ | H | $CH_3$ | $CH_3$ | bond | G1 | — |
| 7002 | $CH_2$ | $CH_3$ | $CH_3$ | H | $CH_3$ | $C_2H_5$ | bond | G1 | — |
| 7003 | $CH_2$ | $CH_3$ | $CH_3$ | H | $CH_3$ | $C_3H_7$ | bond | G1 | — |
| 7004 | $CH_2$ | $CH_3$ | $CH_3$ | H | $CH_3$ | c-$C_3H_5$ | bond | G1 | — |
| 7005 | $CH_2$ | $CH_3$ | $CH_3$ | H | $CH_3$ | $CH_3$ | bond | G2 | — |
| 7006 | $CH_2$ | $CH_3$ | $CH_3$ | H | $CH_3$ | $C_2H_5$ | bond | G2 | — |
| 7007 | $CH_2$ | $CH_3$ | $CH_3$ | H | $CH_3$ | $C_3H_7$ | bond | G2 | — |
| 7008 | $CH_2$ | $CH_3$ | $CH_3$ | H | $CH_3$ | c-$C_3H_5$ | bond | G2 | — |
| 7009 | $CH_2$ | $CH_3$ | $CH_3$ | H | $CH_3$ | $CH_3$ | bond | G3 | — |
| 7010 | $CH_2$ | $CH_3$ | $CH_3$ | H | $CH_3$ | $C_2H_5$ | bond | G3 | — |
| 7011 | $CH_2$ | $CH_3$ | $CH_3$ | H | $CH_3$ | $C_3H_7$ | bond | G3 | — |
| 7012 | $CH_2$ | $CH_3$ | $CH_3$ | H | $CH_3$ | c-$C_3H_5$ | bond | G3 | — |
| 7013 | $CH_2$ | $CH_3$ | $CH_3$ | H | $CH_3$ | $CH_3$ | $CH_2$ | G4 | — |
| 7014 | $CH_2$ | $CH_3$ | $CH_3$ | H | $CH_3$ | $C_2H_5$ | $CH_2$ | G4 | — |
| 7015 | $CH_2$ | $CH_3$ | $CH_3$ | H | $CH_3$ | $C_3H_7$ | $CH_2$ | G4 | — |
| 7016 | $CH_2$ | $CH_3$ | $CH_3$ | H | $CH_3$ | c-$C_3H_5$ | $CH_2$ | G4 | — |
| 7017 | $CH_2$ | $CH_3$ | $CH_3$ | H | $CH_3$ | $CH_3$ | $CH_2$ | G5 | — |
| 7018 | $CH_2$ | $CH_3$ | $CH_3$ | H | $CH_3$ | $C_2H_5$ | $CH_2$ | G5 | — |
| 7019 | $CH_2$ | $CH_3$ | $CH_3$ | H | $CH_3$ | $C_3H_7$ | $CH_2$ | G5 | — |
| 7020 | $CH_2$ | $CH_3$ | $CH_3$ | H | $CH_3$ | c-$C_3H_5$ | $CH_2$ | G5 | — |
| 7021 | $CH_2$ | $CH_3$ | $CH_3$ | H | $CH_3$ | $CH_3$ | bond | G6 | — |
| 7022 | $CH_2$ | $CH_3$ | $CH_3$ | H | $CH_3$ | $C_2H_5$ | bond | G6 | — |
| 7023 | $CH_2$ | $CH_3$ | $CH_3$ | H | $CH_3$ | $C_3H_7$ | bond | G6 | — |
| 7024 | $CH_2$ | $CH_3$ | $CH_3$ | H | $CH_3$ | c-$C_3H_5$ | bond | G6 | — |
| 7025 | $CH_2$ | $CH_3$ | $CH_3$ | H | $CH_3$ | $CH_2$=CH | bond | G7 | — |
| 7026 | $CH_2$ | $CH_3$ | $CH_3$ | H | $CH_3$ | $CH_3$ | bond | G8 | — |
| 7027 | $CH_2$ | $CH_3$ | $CH_3$ | H | $CH_3$ | $C_2H_5$ | $CH_2$ | G1 | — |
| 7028 | $CH_2$ | $CH_3$ | $CH_3$ | H | $CH_3$ | $C_3H_7$ | $CH_2$ | G1 | — |

TABLE 7-continued

| | | | | | | | | | |
|---|---|---|---|---|---|---|---|---|---|
| 7029 | $CH_2$ | $CH_3$ | $CH_3$ | H | $CH_3$ | $C_2H_5$ | $CH_2$ | G2 | — |
| 7030 | $CH_2$ | $CH_3$ | $CH_3$ | H | $CH_3$ | $C_3H_7$ | $CH_2$ | G2 | — |
| 7031 | $CH_2$ | Cl | Cl | H | H | $CH_3$ | bond | G1 | — |
| 7032 | $CH_2$ | Cl | Cl | H | H | $C_2H_5$ | bond | G1 | — |
| 7033 | $CH_2$ | Cl | Cl | H | H | $C_3H_7$ | bond | G1 | — |
| 7034 | $CH_2$ | Cl | Cl | H | H | $c-C_3H_5$ | bond | G1 | — |
| 7035 | $CH_2$ | Cl | Cl | H | H | $CH_3$ | bond | G2 | — |
| 7036 | $CH_2$ | Cl | Cl | H | H | $C_2H_5$ | bond | G2 | — |
| 7037 | $CH_2$ | Cl | Cl | H | H | $C_3H_7$ | bond | G2 | — |
| 7038 | $CH_2$ | Cl | Cl | H | H | $c-C_3H_5$ | bond | G2 | — |
| 7039 | $CH_2$ | Cl | Cl | H | H | $CH_3$ | bond | G3 | — |
| 7040 | $CH_2$ | Cl | Cl | H | H | $C_2H_5$ | bond | G3 | — |
| 7041 | $CH_2$ | Cl | Cl | H | H | $C_3H_7$ | bond | G3 | — |
| 7042 | $CH_2$ | Cl | Cl | H | H | $c-C_3H_5$ | bond | G3 | — |
| 7043 | $CH_2$ | Cl | Cl | H | H | $CH_3$ | $CH_2$ | G4 | — |
| 7044 | $CH_2$ | Cl | Cl | H | H | $C_2H_5$ | $CH_2$ | G4 | — |
| 7045 | $CH_2$ | Cl | Cl | H | H | $C_3H_7$ | $CH_2$ | G4 | — |
| 7046 | $CH_2$ | Cl | Cl | H | H | $c-C_3H_5$ | $CH_2$ | G4 | — |
| 7047 | $CH_2$ | Cl | Cl | H | H | $CH_3$ | $CH_2$ | G5 | — |
| 7048 | $CH_2$ | Cl | Cl | H | H | $C_2H_5$ | $CH_2$ | G5 | — |
| 7049 | $CH_2$ | Cl | Cl | H | H | $C_3H_7$ | $CH_2$ | G5 | — |
| 7050 | $CH_2$ | Cl | Cl | H | H | $c-C_3H_5$ | $CH_2$ | G5 | — |
| 7051 | $CH_2$ | Cl | Cl | H | H | $CH_3$ | bond | G6 | — |
| 7052 | $CH_2$ | Cl | Cl | H | H | $C_2H_5$ | bond | G6 | — |
| 7053 | $CH_2$ | Cl | Cl | H | H | $C_3H_7$ | bond | G6 | — |
| 7054 | $CH_2$ | Cl | Cl | H | H | $c-C_3H_5$ | bond | G6 | — |
| 7055 | $CH_2$ | Cl | Cl | H | H | $CH_2=CH$ | bond | G7 | — |
| 7056 | $CH_2$ | Cl | Cl | H | H | $CH_3$ | bond | G8 | — |
| 7057 | $CH_2$ | Cl | Cl | H | H | $C_2H_5$ | $CH_2$ | G1 | — |
| 7058 | $CH_2$ | Cl | Cl | H | H | $C_3H_7$ | $CH_2$ | G1 | — |
| 7059 | $CH_2$ | Cl | Cl | H | H | $C_2H_5$ | $CH_2$ | G2 | — |
| 7060 | $CH_2$ | Cl | Cl | H | H | $C_3H_7$ | $CH_2$ | G2 | — |
| 7061 | $CH_2$ | $CH_3$ | $OCH_3$ | H | H | $CH_3$ | bond | G1 | — |
| 7062 | $CH_2$ | $CH_3$ | $OCH_3$ | H | H | $C_2H_5$ | bond | G1 | — |
| 7063 | $CH_2$ | $CH_3$ | $OCH_3$ | H | H | $C_3H_7$ | bond | G1 | — |
| 7064 | $CH_2$ | $CH_3$ | $OCH_3$ | H | H | $c-C_3H_5$ | bond | G1 | — |
| 7065 | $CH_2$ | $CH_3$ | $OCH_3$ | H | H | $CH_3$ | bond | G2 | — |
| 7066 | $CH_2$ | $CH_3$ | $OCH_3$ | H | H | $C_2H_5$ | bond | G2 | — |
| 7067 | $CH_2$ | $CH_3$ | $OCH_3$ | H | H | $C_3H_7$ | bond | G2 | — |
| 7068 | $CH_2$ | $CH_3$ | $OCH_3$ | H | H | $c-C_3H_5$ | bond | G2 | — |
| 7069 | $CH_2$ | $CH_3$ | $OCH_3$ | H | H | $CH_3$ | bond | G3 | — |
| 7070 | $CH_2$ | $CH_3$ | $OCH_3$ | H | H | $C_2H_5$ | bond | G3 | — |
| 7071 | $CH_2$ | $CH_3$ | $OCH_3$ | H | H | $C_3H_7$ | bond | G3 | — |
| 7072 | $CH_2$ | $CH_3$ | $OCH_3$ | H | H | $c-C_3H_5$ | bond | G3 | — |
| 7073 | $CH_2$ | $CH_3$ | $OCH_3$ | H | H | $CH_3$ | $CH_2$ | G4 | — |
| 7074 | $CH_2$ | $CH_3$ | $OCH_3$ | H | H | $C_2H_5$ | $CH_2$ | G4 | — |
| 7075 | $CH_2$ | $CH_3$ | $OCH_3$ | H | H | $C_3H_7$ | $CH_2$ | G4 | — |
| 7076 | $CH_2$ | $CH_3$ | $OCH_3$ | H | H | $c-C_3H_5$ | $CH_2$ | G4 | — |
| 7077 | $CH_2$ | $CH_3$ | $OCH_3$ | H | H | $CH_3$ | $CH_2$ | G5 | — |
| 7078 | $CH_2$ | $CH_3$ | $OCH_3$ | H | H | $C_2H_5$ | $CH_2$ | G5 | — |
| 7079 | $CH_2$ | $CH_3$ | $OCH_3$ | H | H | $C_3H_7$ | $CH_2$ | G5 | — |
| 7080 | $CH_2$ | $CH_3$ | $OCH_3$ | H | H | $c-C_3H_5$ | $CH_2$ | G5 | — |
| 7081 | $CH_2$ | $CH_3$ | $OCH_3$ | H | H | $CH_3$ | bond | G6 | — |
| 7082 | $CH_2$ | $CH_3$ | $OCH_3$ | H | H | $C_2H_5$ | bond | G6 | — |
| 7083 | $CH_2$ | $CH_3$ | $OCH_3$ | H | H | $C_3H_7$ | bond | G6 | — |
| 7084 | $CH_2$ | $CH_3$ | $OCH_3$ | H | H | $c-C_3H_5$ | bond | G6 | — |
| 7085 | $CH_2$ | $CH_3$ | $OCH_3$ | H | H | $CH_2=CH$ | bond | G7 | — |
| 7086 | $CH_2$ | $CH_3$ | $OCH_3$ | H | H | $CH_3$ | bond | G8 | oil |
| 7087 | $CH_2$ | $CH_3$ | $OCH_3$ | H | H | $C_2H_5$ | $CH_2$ | G1 | — |
| 7088 | $CH_2$ | $CH_3$ | $OCH_3$ | H | H | $C_3H_7$ | $CH_2$ | G1 | — |
| 7089 | $CH_2$ | $CH_3$ | $OCH_3$ | H | H | $C_2H_5$ | $CH_2$ | G2 | — |
| 7090 | $CH_2$ | $CH_3$ | $OCH_3$ | H | H | $C_3H_7$ | $CH_2$ | G2 | — |
| 7091 | $CH_2$ | Cl | $OCH_3$ | H | H | $CH_3$ | bond | G1 | — |
| 7092 | $CH_2$ | Cl | $OCH_3$ | H | H | $C_2H_5$ | bond | G1 | — |
| 7093 | $CH_2$ | Cl | $OCH_3$ | H | H | $C_3H_7$ | bond | G1 | — |
| 7094 | $CH_2$ | Cl | $OCH_3$ | H | H | $c-C_3H_5$ | bond | G1 | — |
| 7095 | $CH_2$ | Cl | $OCH_3$ | H | H | $CH_3$ | bond | G2 | — |
| 7096 | $CH_2$ | Cl | $OCH_3$ | H | H | $C_2H_5$ | bond | G2 | — |
| 7097 | $CH_2$ | Cl | $OCH_3$ | H | H | $C_3H_7$ | bond | G2 | — |
| 7098 | $CH_2$ | Cl | $OCH_3$ | H | H | $c-C_3H_5$ | bond | G2 | — |
| 7099 | $CH_2$ | Cl | $OCH_3$ | H | H | $CH_3$ | bond | G3 | — |
| 7100 | $CH_2$ | Cl | $OCH_3$ | H | H | $C_2H_5$ | bond | G3 | — |
| 7101 | $CH_2$ | Cl | $OCH_3$ | H | H | $C_3H_7$ | bond | G3 | — |
| 7102 | $CH_2$ | Cl | $OCH_3$ | H | H | $c-C_3H_5$ | bond | G3 | — |
| 7103 | $CH_2$ | Cl | $OCH_3$ | H | H | $CH_3$ | $CH_2$ | G4 | — |
| 7104 | $CH_2$ | Cl | $OCH_3$ | H | H | $C_2H_5$ | $CH_2$ | G4 | — |
| 7105 | $CH_2$ | Cl | $OCH_3$ | H | H | $C_3H_7$ | $CH_2$ | G4 | — |
| 7106 | $CH_2$ | Cl | $OCH_3$ | H | H | $c-C_3H_5$ | $CH_2$ | G4 | — |
| 7107 | $CH_2$ | Cl | $OCH_3$ | H | H | $CH_3$ | $CH_2$ | G5 | — |

TABLE 7-continued

| | | | | | | | | |
|---|---|---|---|---|---|---|---|---|
| 7108 | CH$_2$ | Cl | OCH$_3$ | H | H | C$_2$H$_5$ | CH$_2$ | G5 | — |
| 7109 | CH$_2$ | Cl | OCH$_3$ | H | H | C$_3$H$_7$ | CH$_2$ | G5 | — |
| 7110 | CH$_2$ | Cl | OCH$_3$ | H | H | c-C$_3$H$_5$ | CH$_2$ | G5 | — |
| 7111 | CH$_2$ | Cl | OCH$_3$ | H | H | CH$_3$ | bond | G6 | — |
| 7112 | CH$_2$ | Cl | OCH$_3$ | H | H | C$_2$H$_5$ | bond | G6 | — |
| 7113 | CH$_2$ | Cl | OCH$_3$ | H | H | C$_3$H$_7$ | bond | G6 | — |
| 7114 | CH$_2$ | Cl | OCH$_3$ | H | H | c-C$_3$H$_5$ | bond | G6 | — |
| 7115 | CH$_2$ | Cl | OCH$_3$ | H | H | CH$_2$=CH | bond | G7 | — |
| 7116 | CH$_2$ | Cl | OCH$_3$ | H | H | CH$_3$ | bond | G8 | oil |
| 7117 | CH$_2$ | Cl | OCH$_3$ | H | H | C$_2$H$_5$ | CH$_2$ | G1 | — |
| 7118 | CH$_2$ | Cl | OCH$_3$ | H | H | C$_3$H$_7$ | CH$_2$ | G1 | — |
| 7119 | CH$_2$ | Cl | OCH$_3$ | H | H | C$_2$H$_5$ | CH$_2$ | G2 | — |
| 7120 | CH$_2$ | Cl | OCH$_3$ | H | H | C$_3$H$_7$ | CH$_2$ | G2 | — |
| 7121 | CH$_2$ | Cl | CF$_3$ | H | H | CH$_3$ | bond | G1 | — |
| 7122 | CH$_2$ | Cl | CF$_3$ | H | H | C$_2$H$_5$ | bond | G1 | — |
| 7123 | CH$_2$ | Cl | CF$_3$ | H | H | C$_3$H$_7$ | bond | G1 | — |
| 7124 | CH$_2$ | Cl | CF$_3$ | H | H | c-C$_3$H$_5$ | bond | G1 | — |
| 7125 | CH$_2$ | Cl | CF$_3$ | H | H | CH$_3$ | bond | G2 | — |
| 7126 | CH$_2$ | Cl | CF$_3$ | H | H | C$_2$H$_5$ | bond | G2 | — |
| 7127 | CH$_2$ | Cl | CF$_3$ | H | H | C$_3$H$_7$ | bond | G2 | — |
| 7128 | CH$_2$ | Cl | CF$_3$ | H | H | c-C$_3$H$_5$ | bond | G2 | — |
| 7129 | CH$_2$ | Cl | CF$_3$ | H | H | CH$_3$ | bond | G3 | — |
| 7130 | CH$_2$ | Cl | CF$_3$ | H | H | C$_2$H$_5$ | bond | G3 | — |
| 7131 | CH$_2$ | Cl | CF$_3$ | H | H | C$_3$H$_7$ | bond | G3 | — |
| 7132 | CH$_2$ | Cl | CF$_3$ | H | H | c-C$_3$H$_5$ | bond | G3 | — |
| 7133 | CH$_2$ | Cl | CF$_3$ | H | H | CH$_3$ | CH$_2$ | G4 | — |
| 7134 | CH$_2$ | Cl | CF$_3$ | H | H | C$_2$H$_5$ | CH$_2$ | G4 | — |
| 7135 | CH$_2$ | Cl | CF$_3$ | H | H | C$_3$H$_7$ | CH$_2$ | G4 | — |
| 7136 | CH$_2$ | Cl | CF$_3$ | H | H | c-C$_3$H$_5$ | CH$_2$ | G4 | — |
| 7137 | CH$_2$ | Cl | CF$_3$ | H | H | CH$_3$ | CH$_2$ | G5 | — |
| 7138 | CH$_2$ | Cl | CF$_3$ | H | H | C$_2$H$_5$ | CH$_2$ | G5 | — |
| 7139 | CH$_2$ | Cl | CF$_3$ | H | H | C$_3$H$_7$ | CH$_2$ | G5 | — |
| 7140 | CH$_2$ | Cl | CF$_3$ | H | H | c-C$_3$H$_5$ | CH$_2$ | G5 | — |
| 7141 | CH$_2$ | Cl | CF$_3$ | H | H | CH$_3$ | bond | G6 | — |
| 7142 | CH$_2$ | Cl | CF$_3$ | H | H | C$_2$H$_5$ | bond | G6 | — |
| 7143 | CH$_2$ | Cl | CF$_3$ | H | H | C$_3$H$_7$ | bond | G6 | — |
| 7144 | CH$_2$ | Cl | CF$_3$ | H | H | c-C$_3$H$_5$ | bond | G6 | — |
| 7145 | CH$_2$ | Cl | CF$_3$ | H | H | CH$_2$=CH | bond | G7 | — |
| 7146 | CH$_2$ | Cl | CF$_3$ | H | H | CH$_3$ | bond | G8 | oil |
| 7147 | CH$_2$ | Cl | CF$_3$ | H | H | C$_2$H$_5$ | CH$_2$ | G1 | — |
| 7148 | CH$_2$ | Cl | CF$_3$ | H | H | C$_3$H$_7$ | CH$_2$ | G1 | — |
| 7149 | CH$_2$ | Cl | CF$_3$ | H | H | C$_2$H$_5$ | CH$_2$ | G2 | — |
| 7150 | CH$_2$ | Cl | CF$_3$ | H | H | C$_3$H$_7$ | CH$_2$ | G2 | — |
| 7151 | CH$_2$ | CF$_3$ | Cl | H | H | CH$_3$ | bond | G1 | — |
| 7152 | CH$_2$ | CF$_3$ | Cl | H | H | C$_2$H$_5$ | bond | G1 | — |
| 7153 | CH$_2$ | CF$_3$ | Cl | H | H | C$_3$H$_7$ | bond | G1 | — |
| 7154 | CH$_2$ | CF$_3$ | Cl | H | H | c-C$_3$H$_5$ | bond | G1 | — |
| 7155 | CH$_2$ | CF$_3$ | Cl | H | H | CH$_3$ | bond | G2 | — |
| 7156 | CH$_2$ | CF$_3$ | Cl | H | H | C$_2$H$_5$ | bond | G2 | — |
| 7157 | CH$_2$ | CF$_3$ | Cl | H | H | C$_3$H$_7$ | bond | G2 | — |
| 7158 | CH$_2$ | CF$_3$ | Cl | H | H | c-C$_3$H$_5$ | bond | G2 | — |
| 7159 | CH$_2$ | CF$_3$ | Cl | H | H | CH$_3$ | bond | G3 | — |
| 7160 | CH$_2$ | CF$_3$ | Cl | H | H | C$_2$H$_5$ | bond | G3 | — |
| 7161 | CH$_2$ | CF$_3$ | Cl | H | H | C$_3$H$_7$ | bond | G3 | — |
| 7162 | CH$_2$ | CF$_3$ | Cl | H | H | c-C$_3$H$_5$ | bond | G3 | — |
| 7163 | CH$_2$ | CF$_3$ | Cl | H | H | CH$_3$ | CH$_2$ | G4 | — |
| 7164 | CH$_2$ | CF$_3$ | Cl | H | H | C$_2$H$_5$ | CH$_2$ | G4 | — |
| 7165 | CH$_2$ | CF$_3$ | Cl | H | H | C$_3$H$_7$ | CH$_2$ | G4 | — |
| 7166 | CH$_2$ | CF$_3$ | Cl | H | H | c-C$_3$H$_5$ | CH$_2$ | G4 | — |
| 7167 | CH$_2$ | CF$_3$ | Cl | H | H | CH$_3$ | CH$_2$ | G5 | — |
| 7168 | CH$_2$ | CF$_3$ | Cl | H | H | C$_2$H$_5$ | CH$_2$ | G5 | — |
| 7169 | CH$_2$ | CF$_3$ | Cl | H | H | C$_3$H$_7$ | CH$_2$ | G5 | — |
| 7170 | CH$_2$ | CF$_3$ | Cl | H | H | c-C$_3$H$_5$ | CH$_2$ | G5 | — |
| 7171 | CH$_2$ | CF$_3$ | Cl | H | H | CH$_3$ | bond | G6 | — |
| 7172 | CH$_2$ | CF$_3$ | Cl | H | H | C$_2$H$_5$ | bond | G6 | — |
| 7173 | CH$_2$ | CF$_3$ | Cl | H | H | C$_3$H$_7$ | bond | G6 | — |
| 7174 | CH$_2$ | CF$_3$ | Cl | H | H | c-C$_3$H$_5$ | bond | G6 | — |
| 7175 | CH$_2$ | CF$_3$ | Cl | H | H | CH$_2$=CH | bond | G7 | — |
| 7176 | CH$_2$ | CF$_3$ | Cl | H | H | CH$_3$ | bond | G8 | — |
| 7177 | CH$_2$ | CF$_3$ | Cl | H | H | C$_2$H$_5$ | CH$_2$ | G1 | — |
| 7178 | CH$_2$ | CF$_3$ | Cl | H | H | C$_3$H$_7$ | CH$_2$ | G1 | — |
| 7179 | CH$_2$ | CF$_3$ | Cl | H | H | C$_2$H$_5$ | CH$_2$ | G2 | — |
| 7180 | CH$_2$ | CF$_3$ | Cl | H | H | C$_3$H$_7$ | CH$_2$ | G2 | — |
| 7181 | CH$_2$ | CH$_3$ | OCH$_3$ | CH$_3$ | H | CH$_3$ | bond | G1 | — |
| 7182 | CH$_2$ | CH$_3$ | OCH$_3$ | CH$_3$ | H | C$_2$H$_5$ | bond | G1 | — |
| 7183 | CH$_2$ | CH$_3$ | OCH$_3$ | CH$_3$ | H | C$_3$H$_7$ | bond | G1 | — |
| 7184 | CH$_2$ | CH$_3$ | OCH$_3$ | CH$_3$ | H | c-C$_3$H$_5$ | bond | G1 | — |
| 7185 | CH$_2$ | CH$_3$ | OCH$_3$ | CH$_3$ | H | CH$_3$ | bond | G2 | — |
| 7186 | CH$_2$ | CH$_3$ | OCH$_3$ | CH$_3$ | H | C$_2$H$_5$ | bond | G2 | — |

TABLE 7-continued

| | | | | | | | | | |
|---|---|---|---|---|---|---|---|---|---|
| 7187 | CH$_2$ | CH$_3$ | OCH$_3$ | CH$_3$ | H | C$_3$H$_7$ | bond | G2 | — |
| 7188 | CH$_2$ | CH$_3$ | OCH$_3$ | CH$_3$ | H | c-C$_3$H$_5$ | bond | G2 | — |
| 7189 | CH$_2$ | CH$_3$ | OCH$_3$ | CH$_3$ | H | CH$_3$ | bond | G3 | — |
| 7190 | CH$_2$ | CH$_3$ | OCH$_3$ | CH$_3$ | H | C$_2$H$_5$ | bond | G3 | — |
| 7191 | CH$_2$ | CH$_3$ | OCH$_3$ | CH$_3$ | H | C$_3$H$_7$ | bond | G3 | — |
| 7192 | CH$_2$ | CH$_3$ | OCH$_3$ | CH$_3$ | H | c-C$_3$H$_5$ | bond | G3 | — |
| 7193 | CH$_2$ | CH$_3$ | OCH$_3$ | CH$_3$ | H | CH$_3$ | CH$_2$ | G4 | — |
| 7194 | CH$_2$ | CH$_3$ | OCH$_3$ | CH$_3$ | H | C$_2$H$_5$ | CH$_2$ | G4 | — |
| 7195 | CH$_2$ | CH$_3$ | OCH$_3$ | CH$_3$ | H | C$_3$H$_7$ | CH$_2$ | G4 | — |
| 7196 | CH$_2$ | CH$_3$ | OCH$_3$ | CH$_3$ | H | c-C$_3$H$_5$ | CH$_2$ | G4 | — |
| 7197 | CH$_2$ | CH$_3$ | OCH$_3$ | CH$_3$ | H | CH$_3$ | CH$_2$ | G5 | — |
| 7198 | CH$_2$ | CH$_3$ | OCH$_3$ | CH$_3$ | H | C$_2$H$_5$ | CH$_2$ | G5 | — |
| 7199 | CH$_2$ | CH$_3$ | OCH$_3$ | CH$_3$ | H | C$_3$H$_7$ | CH$_2$ | G5 | — |
| 7200 | CH$_2$ | CH$_3$ | OCH$_3$ | CH$_3$ | H | c-C$_3$H$_5$ | CH$_2$ | G5 | — |
| 7201 | CH$_2$ | CH$_3$ | OCH$_3$ | CH$_3$ | H | CH$_3$ | bond | G6 | — |
| 7202 | CH$_2$ | CH$_3$ | OCH$_3$ | CH$_3$ | H | C$_2$H$_5$ | bond | G6 | — |
| 7203 | CH$_2$ | CH$_3$ | OCH$_3$ | CH$_3$ | H | C$_3$H$_7$ | bond | G6 | — |
| 7204 | CH$_2$ | CH$_3$ | OCH$_3$ | CH$_3$ | H | c-C$_3$H$_5$ | bond | G6 | — |
| 7205 | CH$_2$ | CH$_3$ | OCH$_3$ | CH$_3$ | H | CH$_2$=CH | bond | G7 | — |
| 7206 | CH$_2$ | CH$_3$ | OCH$_3$ | CH$_3$ | H | CH$_3$ | bond | G8 | — |
| 7207 | CH$_2$ | CH$_3$ | OCH$_3$ | CH$_3$ | H | C$_2$H$_5$ | CH$_2$ | G1 | — |
| 7208 | CH$_2$ | CH$_3$ | OCH$_3$ | CH$_3$ | H | C$_3$H$_7$ | CH$_2$ | G1 | — |
| 7209 | CH$_2$ | CH$_3$ | OCH$_3$ | CH$_3$ | H | C$_2$H$_5$ | CH$_2$ | G2 | — |
| 7210 | CH$_2$ | CH$_3$ | OCH$_3$ | CH$_3$ | H | C$_3$H$_7$ | CH$_2$ | G2 | — |
| 7211 | O | Cl | CF$_3$ | H | H | C$_2$H$_5$ | CH$_2$ | G1 | — |
| 7212 | O | Cl | CF$_3$ | H | H | C$_3$H$_7$ | CH$_2$ | G1 | — |
| 7213 | O | Cl | CF$_3$ | H | H | C$_2$H$_5$ | bond | G2 | — |
| 7214 | O | Cl | CF$_3$ | H | H | C$_3$H$_7$ | bond | G2 | — |
| 7215 | O | Cl | CF$_3$ | H | H | C$_2$H$_5$ | CH$_2$ | G4 | — |
| 7216 | CH$_2$ | Cl | CF$_3$ | H | H | C$_2$H$_5$ | CH$_2$ | G1 | — |
| 7217 | CH$_2$ | Cl | CF$_3$ | H | H | C$_3$H$_7$ | CH$_2$ | G1 | — |
| 7218 | CH$_2$ | Cl | CF$_3$ | H | H | C$_2$H$_5$ | bond | G2 | — |
| 7219 | CH$_2$ | Cl | CF$_3$ | H | H | C$_3$H$_7$ | bond | G2 | — |
| 7220 | CH$_2$ | Cl | CF$_3$ | H | H | C$_2$H$_5$ | CH$_2$ | G4 | — |
| 7221 | O | CF$_3$ | Cl | H | H | C$_2$H$_5$ | CH$_2$ | G1 | — |
| 7222 | O | CF$_3$ | Cl | H | H | C$_3$H$_7$ | CH$_2$ | G1 | — |
| 7223 | O | CF$_3$ | Cl | H | H | C$_2$H$_5$ | bond | G2 | — |
| 7224 | O | CF$_3$ | Cl | H | H | C$_3$H$_7$ | bond | G2 | — |
| 7225 | O | CF$_3$ | Cl | H | H | C$_2$H$_5$ | CH$_2$ | G4 | — |
| 7226 | CH$_2$ | CF$_3$ | Cl | H | H | C$_2$H$_5$ | CH$_2$ | G1 | — |
| 7227 | CH$_2$ | CF$_3$ | Cl | H | H | C$_3$H$_7$ | CH$_2$ | G1 | — |
| 7228 | CH$_2$ | CF$_3$ | Cl | H | H | C$_2$H$_5$ | bond | G2 | — |
| 7229 | CH$_2$ | CF$_3$ | Cl | H | H | C$_3$H$_7$ | bond | G2 | — |
| 7230 | CH$_2$ | CF$_3$ | Cl | H | H | C$_2$H$_5$ | CH$_2$ | G4 | — |
| 7231 | CH$_2$ | CH$_3$ | CH$_3$ | H | CH$_3$ | C$_2$H$_5$ | CH$_2$O | G3 | oil |
| 7232 | CH$_2$ | Cl | Cl | H | H | c-C$_3$H$_5$ | bond | G9 | — |
| 7233 | O | Cl | Cl | H | H | c-C$_3$H$_5$ | bond | G9 | — |
| 7234 | CH$_2$ | Cl | CF$_3$ | H | H | c-C$_3$H$_5$ | bond | G9 | oil |
| 7235 | O | Cl | CF$_3$ | H | H | c-C$_3$H$_5$ | bond | G9 | — |
| 7236 | CH$_2$ | Cl | OCH$_3$ | H | H | c-C$_3$H$_5$ | bond | G9 | — |
| 7237 | CH$_2$ | Cl | OCF$_3$ | H | H | c-C$_3$H$_5$ | bond | G9 | — |
| 7238 | CH$_2$ | CH$_3$ | OCH$_3$ | Cl | H | c-C$_3$H$_5$ | bond | G9 | — |
| 7239 | CH$_2$ | Cl | Cl | H | CH$_3$ | c-C$_3$H$_5$ | bond | G9 | — |
| 7240 | CH$_2$ | CF$_3$ | OCH$_3$ | H | H | c-C$_3$H$_5$ | bond | G9 | — |
| 7241 | CH$_2$ | Cl | Cl | H | H | c-C$_3$H$_5$ | bond | G10 | oil |
| 7242 | O | Cl | Cl | H | H | c-C$_3$H$_5$ | bond | G10 | — |
| 7243 | CH$_2$ | Cl | CF$_3$ | H | H | c-C$_3$H$_5$ | bond | G10 | oil |
| 7244 | O | Cl | CF$_3$ | H | H | c-C$_3$H$_5$ | bond | G10 | — |
| 7245 | CH$_2$ | Cl | OCH$_3$ | H | H | c-C$_3$H$_5$ | bond | G10 | — |
| 7246 | CH$_2$ | Cl | OCF$_3$ | H | H | c-C$_3$H$_5$ | bond | G10 | — |
| 7247 | CH$_2$ | CH$_3$ | OCH$_3$ | Cl | H | c-C$_3$H$_5$ | bond | G10 | — |
| 7248 | CH$_2$ | Cl | Cl | H | CH$_3$ | c-C$_3$H$_5$ | bond | G10 | — |
| 7249 | CH$_2$ | CF$_3$ | OCH$_3$ | H | H | c-C$_3$H$_5$ | bond | G10 | oil |
| 7250 | CH$_2$ | Cl | Cl | H | H | C$_2$H$_5$ | bond | G10 | oil |
| 7251 | O | Cl | Cl | H | H | C$_2$H$_5$ | bond | G10 | — |
| 7252 | CH$_2$ | Cl | CF$_3$ | H | H | C$_2$H$_5$ | bond | G10 | 98–99 |
| 7253 | O | Cl | CF$_3$ | H | H | C$_2$H$_5$ | bond | G10 | — |
| 7254 | CH$_2$ | Cl | OCH$_3$ | H | H | C$_2$H$_5$ | bond | G10 | — |
| 7255 | CH$_2$ | Cl | OCF$_3$ | H | H | C$_2$H$_5$ | bond | G10 | — |
| 7256 | CH$_2$ | CH$_3$ | OCH$_3$ | Cl | H | C$_2$H$_5$ | bond | G10 | — |
| 7257 | CH$_2$ | Cl | Cl | H | CH$_3$ | C$_2$H$_5$ | bond | G10 | — |
| 7258 | CH$_2$ | CF$_3$ | OCH$_3$ | H | H | C$_2$H$_5$ | bond | G10 | — |
| 7259 | CH$_2$ | Cl | Cl | H | H | C$_3$H$_7$ | bond | G10 | oil |
| 7260 | O | Cl | Cl | H | H | C$_3$H$_7$ | bond | G10 | — |
| 7261 | CH$_2$ | Cl | CF$_3$ | H | H | C$_3$H$_7$ | bond | G10 | oil |
| 7262 | O | Cl | CF$_3$ | H | H | C$_3$H$_7$ | bond | G10 | — |
| 7263 | CH$_2$ | Cl | OCH$_3$ | H | H | C$_3$H$_7$ | bond | G10 | — |
| 7264 | CH$_2$ | Cl | OCF$_3$ | H | H | C$_3$H$_7$ | bond | G10 | — |
| 7265 | CH$_2$ | CH$_3$ | OCH$_3$ | Cl | H | C$_3$H$_7$ | bond | G10 | — |

TABLE 7-continued

| | | | | | | | | | |
|---|---|---|---|---|---|---|---|---|---|
| 7266 | CH$_2$ | Cl | Cl | H | CH$_3$ | C$_3$H$_7$ | bond | G10 | oil |
| 7267 | CH$_2$ | CF$_3$ | OCH$_3$ | H | H | C$_3$H$_7$ | bond | G10 | — |
| 7268 | CH$_2$ | Cl | Cl | H | H | C$_5$H$_{11}$ | bond | G10 | oil |
| 7269 | O | Cl | Cl | H | H | C$_5$H$_{11}$ | bond | G10 | — |
| 7270 | CH$_2$ | Cl | CF$_3$ | H | H | C$_5$H$_{11}$ | bond | G10 | oil |
| 7271 | O | Cl | CF$_3$ | H | H | C$_5$H$_{11}$ | bond | G10 | — |
| 7272 | CH$_2$ | Cl | OCH$_3$ | H | H | C$_5$H$_{11}$ | bond | G10 | — |
| 7273 | CH$_2$ | Cl | OCF$_3$ | H | H | C$_5$H$_{11}$ | bond | G10 | — |
| 7274 | CH$_2$ | CH$_3$ | OCH$_3$ | Cl | H | C$_5$H$_{11}$ | bond | G10 | — |
| 7275 | CH$_2$ | Cl | Cl | H | CH$_3$ | C$_5$H$_{11}$ | bond | G10 | — |
| 7276 | CH$_2$ | CF$_3$ | OCH$_3$ | H | H | C$_5$H$_{11}$ | bond | G10 | — |
| 7277 | CH$_2$ | Cl | Cl | H | H | CH$_3$ | CH$_2$ | G10 | — |
| 7278 | O | Cl | Cl | H | H | CH$_3$ | CH$_2$ | G10 | — |
| 7279 | CH$_2$ | Cl | CF$_3$ | H | H | CH$_3$ | CH$_2$ | G10 | oil |
| 7280 | O | Cl | CF$_3$ | H | H | CH$_3$ | CH$_2$ | G10 | — |
| 7281 | CH$_2$ | Cl | OCH$_3$ | H | H | CH$_3$ | CH$_2$ | G10 | — |
| 7282 | CH$_2$ | Cl | OCF$_3$ | H | H | CH$_3$ | CH$_2$ | G10 | — |
| 7283 | CH$_2$ | CH$_3$ | OCH$_3$ | Cl | H | CH$_3$ | CH$_2$ | G10 | — |
| 7284 | CH$_2$ | Cl | Cl | H | CH$_3$ | CH$_3$ | CH$_2$ | G10 | — |
| 7285 | CH$_2$ | CF$_3$ | OCH$_3$ | H | H | CH$_3$ | CH$_2$ | G10 | — |
| 7286 | CH$_2$ | Cl | Cl | H | H | c-C$_3$H$_5$ | bond | G11 | oil |
| 7287 | O | Cl | Cl | H | H | c-C$_3$H$_5$ | bond | G11 | — |
| 7288 | CH$_2$ | Cl | CF$_3$ | H | H | c-C$_3$H$_5$ | bond | G11 | oil |
| 7289 | O | Cl | CF$_3$ | H | H | c-C$_3$H$_5$ | bond | G11 | — |
| 7290 | CH$_2$ | Cl | OCH$_3$ | H | H | c-C$_3$H$_5$ | bond | G11 | — |
| 7291 | CH$_2$ | Cl | OCF$_3$ | H | H | c-C$_3$H$_5$ | bond | G11 | — |
| 7292 | CH$_2$ | CH$_3$ | OCH$_3$ | Cl | H | c-C$_3$H$_5$ | bond | G11 | — |
| 7293 | CH$_2$ | Cl | Cl | H | CH$_3$ | c-C$_3$H$_5$ | bond | G11 | — |
| 7294 | CH$_2$ | CF$_3$ | OCH$_3$ | H | H | c-C$_3$H$_5$ | bond | G11 | — |
| 7295 | CH$_2$ | Cl | Cl | H | H | C$_2$H$_5$ | bond | G11 | oil |
| 7296 | O | Cl | Cl | H | H | C$_2$H$_5$ | bond | G11 | — |
| 7297 | CH$_2$ | Cl | CF$_3$ | H | H | C$_2$H$_5$ | bond | G11 | oil |
| 7298 | O | Cl | CF$_3$ | H | H | C$_2$H$_5$ | bond | G11 | — |
| 7299 | CH$_2$ | Cl | OCH$_3$ | H | H | C$_2$H$_5$ | bond | G11 | — |
| 7300 | CH$_2$ | Cl | OCF$_3$ | H | H | C$_2$H$_5$ | bond | G11 | — |
| 7301 | CH$_2$ | CH$_3$ | OCH$_3$ | Cl | H | C$_2$H$_5$ | bond | G11 | — |
| 7302 | CH$_2$ | Cl | Cl | H | CH$_3$ | C$_2$H$_5$ | bond | G11 | — |
| 7303 | CH$_2$ | CF$_3$ | OCH$_3$ | H | H | C$_2$H$_5$ | bond | G11 | — |
| 7304 | CH$_2$ | Cl | Cl | H | H | C$_3$H$_7$ | bond | G11 | 88–89 |
| 7305 | O | Cl | Cl | H | H | C$_3$H$_7$ | bond | G11 | — |
| 7306 | CH$_2$ | Cl | CF$_3$ | H | H | C$_3$H$_7$ | bond | G11 | oil |
| 7307 | O | Cl | CF$_3$ | H | H | C$_3$H$_7$ | bond | G11 | — |
| 7308 | CH$_2$ | Cl | OCH$_3$ | H | H | C$_3$H$_7$ | bond | G11 | — |
| 7309 | CH$_2$ | Cl | OCF$_3$ | H | H | C$_3$H$_7$ | bond | G11 | — |
| 7310 | CH$_2$ | CH$_3$ | OCH$_3$ | Cl | H | C$_3$H$_7$ | bond | G11 | — |
| 7311 | CH$_2$ | Cl | Cl | H | CH$_3$ | C$_3$H$_7$ | bond | G11 | — |
| 7312 | CH$_2$ | CF$_3$ | OCH$_3$ | H | H | C$_3$H$_7$ | bond | G11 | — |
| 7313 | CH$_2$ | Cl | Cl | H | H | C$_6$H$_5$ | bond | G11 | 156–157 |
| 7314 | O | Cl | Cl | H | H | C$_6$H$_5$ | bond | G11 | — |
| 7315 | CH$_2$ | Cl | CF$_3$ | H | H | C$_6$H$_5$ | bond | G11 | 150–151 |
| 7316 | O | Cl | CF$_3$ | H | H | C$_6$H$_5$ | bond | G11 | — |
| 7317 | CH$_2$ | Cl | OCH$_3$ | H | H | C$_6$H$_5$ | bond | G11 | — |
| 7318 | CH$_2$ | Cl | OCF$_3$ | H | H | C$_6$H$_5$ | bond | G11 | — |
| 7319 | CH$_2$ | CH$_3$ | OCH$_3$ | Cl | H | C$_6$H$_5$ | bond | G11 | — |
| 7320 | CH$_2$ | Cl | Cl | H | CH$_3$ | C$_6$H$_5$ | bond | G11 | — |
| 7321 | CH$_2$ | CF$_3$ | OCH$_3$ | H | H | C$_6$H$_5$ | bond | G11 | — |
| 7322 | CH$_2$ | Cl | Cl | H | H | C$_2$H$_5$ | bond | G12 | — |
| 7323 | O | Cl | Cl | H | H | C$_2$H$_5$ | bond | G12 | — |
| 7324 | CH$_2$ | Cl | CF$_3$ | H | H | C$_2$H$_5$ | bond | G12 | oil |
| 7325 | O | Cl | CF$_3$ | H | H | C$_2$H$_5$ | bond | G12 | — |
| 7326 | CH$_2$ | Cl | OCH$_3$ | H | H | C$_2$H$_5$ | bond | G12 | — |
| 7327 | CH$_2$ | Cl | OCF$_3$ | H | H | C$_2$H$_5$ | bond | G12 | — |
| 7328 | CH$_2$ | CH$_3$ | OCH$_3$ | Cl | H | C$_2$H$_5$ | bond | G12 | — |
| 7329 | CH$_2$ | Cl | Cl | H | CH$_3$ | C$_2$H$_5$ | bond | G12 | — |
| 7330 | CH$_2$ | CF$_3$ | OCH$_3$ | H | H | C$_2$H$_5$ | bond | G12 | — |
| 7331 | CH$_2$ | Cl | Cl | H | H | C$_3$H$_7$ | bond | G12 | — |
| 7332 | O | Cl | Cl | H | H | C$_3$H$_7$ | bond | G12 | — |
| 7333 | CH$_2$ | Cl | CF$_3$ | H | H | C$_3$H$_7$ | bond | G12 | — |
| 7334 | O | Cl | CF$_3$ | H | H | C$_3$H$_7$ | bond | G12 | — |
| 7335 | CH$_2$ | Cl | OCH$_3$ | H | H | C$_3$H$_7$ | bond | G12 | — |
| 7336 | CH$_2$ | Cl | OCF$_3$ | H | H | C$_3$H$_7$ | bond | G12 | — |
| 7337 | CH$_2$ | CH$_3$ | OCH$_3$ | Cl | H | C$_3$H$_7$ | bond | G12 | — |
| 7338 | CH$_2$ | Cl | Cl | H | CH$_3$ | C$_3$H$_7$ | bond | G12 | — |
| 7339 | CH$_2$ | CF$_3$ | OCH$_3$ | H | H | C$_3$H$_7$ | bond | G12 | — |
| 7340 | CH$_2$ | Cl | Cl | H | H | c-C$_3$H$_5$ | bond | G12 | — |
| 7341 | O | Cl | Cl | H | H | c-C$_3$H$_5$ | bond | G12 | — |
| 7342 | CH$_2$ | Cl | CF$_3$ | H | H | c-C$_3$H$_5$ | bond | G12 | 128–130 |
| 7343 | O | Cl | CF$_3$ | H | H | c-C$_3$H$_5$ | bond | G12 | — |
| 7344 | CH$_2$ | Cl | OCH$_3$ | H | H | c-C$_3$H$_5$ | bond | G12 | — |

TABLE 7-continued

| | | | | | | | | | |
|---|---|---|---|---|---|---|---|---|---|
| 7345 | CH₂ | Cl | OCF₃ | H | H | c-C₃H₅ | bond | G12 | — |
| 7346 | CH₂ | CH₃ | OCH₃ | Cl | H | c-C₃H₅ | bond | G12 | — |
| 7347 | CH₂ | Cl | Cl | H | CH₃ | c-C₃H₅ | bond | G12 | — |
| 7348 | CH₂ | CF₃ | OCH₃ | H | H | c-C₃H₅ | bond | G12 | — |
| 7349 | CH₂ | Cl | CF₃ | H | H | c-C₃H₅ | bond | G13 | oil |
| 7350 | CH₂ | Cl | Cl | H | H | c-C₃H₅ | bond | G13 | — |
| 7351 | CH₂ | Cl | CF₃ | H | H | c-C₃H₅ | bond | G7 | oil |
| 7352 | CH₂ | Cl | Cl | H | H | c-C₃H₅ | bond | G7 | oil |
| 7353 | CH₂ | Cl | CF₃ | H | H | CH₃ | bond | G7 | — |
| 7354 | CH₂ | Cl | Cl | H | H | CH₃ | bond | G7 | — |
| 7355 | CH₂ | CH₃ | OCH₃ | CH₃ | H | CH₃ | bond | G7 | oil |
| 7356 | CH₂ | CH₃ | OCH₃ | CH₃ | H | C₃H₇ | bond | G7 | oil |
| 7357 | CH₂ | CF₃ | OCH₃ | H | H | C₃H₇ | bond | G7 | oil |
| 7358 | CH₂ | CH₃ | OCH₃ | CH₃ | H | C₄H₉ | bond | G7 | oil |
| 7359 | CH₂ | Cl | Cl | H | CH₃ | c-C₃H₅ | bond | G7 | 156–158 |
| 7360 | CH₂ | CF₃ | OCH₃ | H | H | CH₃ | bond | G8 | — |
| 7361 | CH₂ | CH₃ | OCH₃ | OCH₃ | H | C₂H₅ | bond | G10 | oil |
| 7362 | O | Cl | Cl | H | H | CH₃ | bond | G1 | — |
| 7363 | O | Cl | CF₃ | H | H | CH₃ | bond | G1 | — |
| 7364 | CH₂ | Cl | OCF₃ | H | H | CH₃ | bond | G1 | — |
| 7365 | CH₂ | CH₃ | OCH₃ | Cl | H | CH₃ | bond | G1 | — |
| 7366 | CH₂ | Cl | Cl | H | CH₃ | CH₃ | bond | G1 | — |
| 7367 | CH₂ | CF₃ | OCH₃ | H | H | CH₃ | bond | G1 | — |
| 7368 | CH₂ | CH₃ | OCH₃ | F | H | CH₃ | bond | G1 | — |
| 7369 | O | Cl | Cl | H | H | C₂H₅ | bond | G1 | — |
| 7370 | O | Cl | CF₃ | H | H | C₂H₅ | bond | G1 | — |
| 7371 | CH₂ | Cl | OCF₃ | H | H | C₂H₅ | bond | G1 | — |
| 7372 | CH₂ | CH₃ | OCH₃ | Cl | H | C₂H₅ | bond | G1 | — |
| 7373 | CH₂ | Cl | Cl | H | CH₃ | C₂H₅ | bond | G1 | — |
| 7374 | CH₂ | CF₃ | OCH₃ | H | H | C₂H₅ | bond | G1 | — |
| 7375 | CH₂ | CH₃ | OCH₃ | F | H | C₂H₅ | bond | G1 | — |
| 7376 | O | Cl | Cl | H | H | C₃H₇ | bond | G1 | — |
| 7377 | O | Cl | CF₃ | H | H | C₃H₇ | bond | G1 | — |
| 7378 | CH₂ | Cl | OCF₃ | H | H | C₃H₇ | bond | G1 | — |
| 7379 | CH₂ | CH₃ | OCH₃ | Cl | H | C₃H₇ | bond | G1 | — |
| 7380 | CH₂ | Cl | Cl | H | CH₃ | C₃H₇ | bond | G1 | — |
| 7381 | CH₂ | CF₃ | OCH₃ | H | H | C₃H₇ | bond | G1 | — |
| 7382 | CH₂ | CH₃ | OCH₃ | F | H | C₃H₇ | bond | G1 | — |
| 7383 | O | Cl | Cl | H | H | c-C₃H₅ | bond | G1 | — |
| 7384 | O | Cl | CF₃ | H | H | c-C₃H₅ | bond | G1 | — |
| 7385 | CH₂ | Cl | OCF₃ | H | H | c-C₃H₅ | bond | G1 | — |
| 7386 | CH₂ | CH₃ | OCH₃ | Cl | H | c-C₃H₅ | bond | G1 | — |
| 7387 | CH₂ | Cl | Cl | H | CH₃ | c-C₃H₅ | bond | G1 | — |
| 7388 | CH₂ | CF₃ | OCH₃ | H | H | c-C₃H₅ | bond | G1 | — |
| 7389 | CH₂ | CH₃ | OCH₃ | F | H | c-C₃H₅ | bond | G1 | — |
| 7390 | CH₂ | Cl | CF₃ | H | H | c-C₃H₅ | bond | G14 | oil |
| 7391 | CH₂ | Cl | Cl | H | H | c-C₃H₅ | bond | G14 | — |
| 7391 | CH₂ | Cl | CF₃ | H | H | c-C₃H₅ | bond | G15 | oil |
| 7392 | CH₂ | Cl | Cl | H | H | c-C₃H₅ | bond | G15 | — |
| 7393 | CH₂ | Cl | CF₃ | H | H | c-C₃H₅ | bond | G16 | 139–140 |
| 7394 | CH₂ | Cl | Cl | H | H | c-C₃H₅ | bond | G16 | — |
| 7395 | CH₂ | Cl | CF₃ | H | H | c-C₃H₅ | bond | G17 | — |
| 7396 | CH₂ | Cl | Cl | H | H | c-C₃H₅ | bond | G17 | oil |
| 7397 | CH₂ | Cl | CF₃ | H | H | c-C₃H₅ | bond | G18 | — |
| 7398 | CH₂ | Cl | Cl | H | H | c-C₃H₅ | bond | G18 | oil |
| 7399 | CH₂ | Cl | Cl | H | CH₃ | CH₃ | bond | G8 | oil |
| 7400 | CH₂ | Cl | CF₃ | H | H | c-C₃H₅ | bond | G19 | — |
| 7401 | CH₂ | Cl | Cl | H | H | c-C₃H₅ | bond | G19 | oil |
| 7402 | CH₂ | Cl | Cl | H | H | c-C₃H₅ | bond | G20 | oil |
| 7403 | CH₂ | Cl | CF₃ | H | H | c-C₃H₅ | bond | G20 | — |
| 7404 | CH₂ | Cl | Cl | H | H | C₄H₉ | bond | G1 | oil |
| 7405 | CH₂ | Cl | Cl | H | H | C₆H₅ | C═O | C₆H₅ | oil |
| 7406 | CH₂ | Cl | Cl | H | H | C₆H₅ | C═O | G21 | oil |
| 7407 | CH₂ | Cl | Cl | H | H | C₆H₅ | C═O | G22 | oil |
| 7408 | CH₂ | Cl | Cl | H | H | 4-F—C₆H₄CH₂ | C═O | CH₃ | oil |
| 7409 | CH₂ | Cl | Cl | H | H | c-C₃H₅ | bond | G23 | oil |

Key:
(a) G groups:

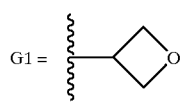
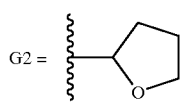

TABLE 7-continued

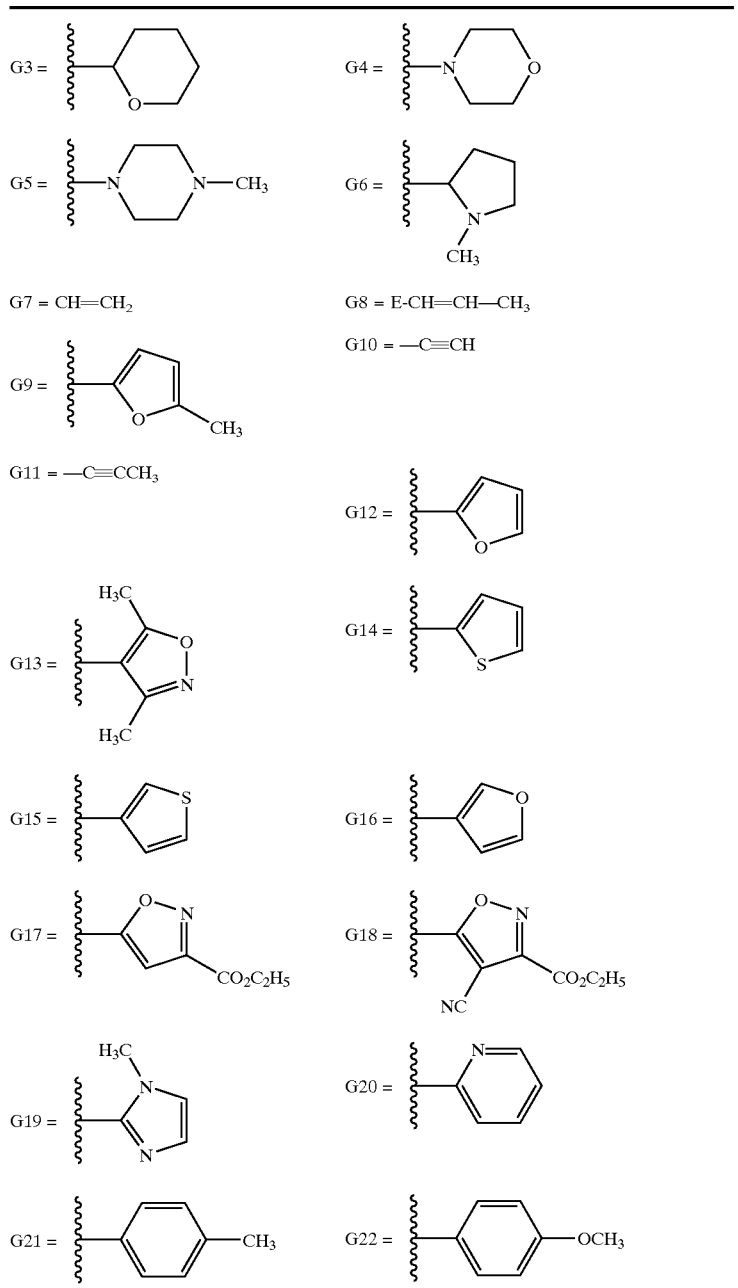

G7 = CH=CH₂

G8 = E-CH=CH—CH₃

G10 = —C≡CH

G11 = —C≡CCH₃

(b) Where a compound is indicated as an "oil", spectral data is provided
as follows:
Example 7056 spectral data: MS (ESI): m/e 363 (M+2), 361 (M⁺, 100%).
Example 7086 spectral data: TLC $R_F$ 0.25 (30:70 ethyl acetate-hexane). ¹H
NMR (300 MHz, CDCl₃): δ 8.91 (1H, s), 7.72 (1H, d, J = 9.2 Hz), 6.90–6.84
(2H, m), 6.08 (1H, ddq, J = 15.4 Hz, 6.6H, 1.4 Hz), 5.67 (1H, dqd, J =
15.4 Hz, 6.5H, 1.5 Hz), 5.24 (1H, br pentet, J = 7.0 Hz), 3.85 (3H, s),
2.96 (2H, dq, J = 7.5, 1.1 Hz), 2.47 (3H, s), 1.81 (3H, d, J = 7.0 Hz),
1.73 (3H, dt, J = 6.2, 1.3 Hz), 1.41 (3H, t, J = 7.5 Hz). MS (NH₃—CI):
m/e 339 (3), 338 (23), 337 (100).
Example 7116 spectral data: TLC $R_F$ 0.15 (30:70 ethyl acetate-hexane). ¹H
NMR (300 MHz, CDCl₃): δ 8.96 (1H, s), 7.68 (1H, d, J = 8.4 Hz), 7.09 (1H,
d, J = 2.6 Hz), 6.96 (1H, dd, J = 8.4, 2.6 Hz), 6.09 (1H, ddq, J = 15.4
Hz, 6.6H, 1.8 Hz), 5.67 (1H, dqd, J = 15.4 Hz, 6.5H, 1.4 Hz), 5.23 (1H,
br pentet, J = 6.8 Hz), 3.87 (3H, s), 2.98 (2H, q, J = 7.5 Hz), 1.82
(3H, d, J = 7.0 Hz), 1.73 (3H, dt, J = 6.6, 1.3 Hz), 1.40 (3H, t, J =
7.5 Hz). MS (NH₃—CI): m/e 360 (7), 359 (33), 358 (23), 357 (100).
Example 7145 spectral data: m.p. 78–79° C. TLC $R_F$ 0.52 (30:70 ethyl TABLE 7-continued acetate-hexane). $^1$H NMR (300 MHz, CDCl$_3$): δ 9.01 (1H, s), 7.86–7.81 (2H, m), 7.68 (1H, d, J = 8.0 Hz), 6.38 (2H, ddd, J = 17.2 Hz, 10.6H, 5.8 Hz), 5.90–5.83 (1H, m), 5.40 (2H, dd, J = 10.6, 1.3 Hz), 5.29 (2H, dt, J = 17.2, 0.9 Hz), 2.97 (2H, q, J = 7.6 Hz), 1.41 (3H, t, J = 7.6 Hz). MS (NH$_3$—CI): m/e 396 (8), 395 (36), 394 (25), 393 (100). Analysis calculated for C$_{19}$H$_{16}$ClF$_3$N$_4$: C, 58.10; H, 4.12; N, 14.26; found: C, 58.14; H, 4.28; N, 13.74.
Example 7146 spectral data: TLC R$_F$ 0.43 (30:70 ethyl acetate-hexane). $^1$H NMR (300 MHz, CDCl$_3$): δ 8.99 (1H, s), 7.84–7.79 (2H, m), 7.67 (1H, dd, J = 8.5, 1.1 Hz), 6.10 (1H, ddq, J = 15.4 Hz, 6.8H, 1.8 Hz), 5.70 (1H, dqd, J = 15.4 Hz, 6.5H, 1.1 Hz), 5.24 (1H, pentet, J = 7.0 Hz), 2.99 (2H, q, J = 7.5 Hz), 1.83 (3H, d, J = 7.0 Hz), 1.74 (3H, dt, J = 6.6, 1.3 Hz), 1.40 (3H, t, J = 7.5 Hz). MS (NH$_3$—CI): m/e 398 (7), 397 (36), 396 (25), 395 (100).
Example 7231 spectral data: m.p. 78–88° C. TLC R$_F$ 0.55 (50:50 ethyl acetate-hexane). $^1$H NMR (300 MHz, CDCl$_3$): Major isomer: δ 8.90 (1H, s), 6.95 (2H, s), 4.68–3.05 (6H, m), 3.02–2.92 (2H, m), 2.70–2.55 (2H, m), 2.32 (3H, s), 2.20–2.00 (2H, m), 2.05 (3H, s), 1.96 (3H, s), 1.70–1.45 (4H, m), 1.39 (3H, t, J = 7.7 Hz), 0.93 (3H, t, J = 7.3 Hz); Minor isomer: δ 8.89 (1H, s), 6.95 (2H, s), 4.68–3.05 (6H, m), 3.02–2.92 (2H, m), 2.70–2.55 (2H, m), 2.32 (3H, s), 2.20–2.00 (2H, m), 2.06 (3H, s), 2.01 (3H, s), 1.70–1.45 (4H, m), 1.38 (3H, t, J = 7.7 Hz), 0.90 (3H, t, J = 7.3 Hz). MS (NH$_3$—CI): m/e calc'd for C$_{25}$H$_{35}$N$_4$O$_2$: 423.2760, found 423.2748; 425 (5), 424 (29), 423 (100). Analysis calc'd for C$_{25}$H$_{34}$N$_4$O$_2$.H$_2$O: C, 68.15; H, 8.24; N, 12.72; found: C, 67.80; H, 7.89; N, 12.24.
Example 7234 spectral data: TLC R$_F$ 0.46 (30:70 ethyl acetate-hexane). $^1$H NMR (300 MHz, CDCl$_3$): δ 8.99 (1H, s), 7.87 (1H, d, J = 8.0 Hz), 7.83 (1H, s), 7.68 (1H, d, J = 8.0 Hz), 6.50 (1H, d, J = 3.0 Hz), 5.99 (1H, d, J = 3.0 Hz), 5.10 (1H, d, J = 10.6 Hz), 2.99–2.79 (2H, m), 2.20 (3H, s), 2.10–2.00 (1H, m), 1.30 (3H, t, J = 7.5 Hz), 1.00–0.90 (1H, m), 0.71–0.59 (2H, m), 0.56–0.46 (1H, m). MS (NH$_3$—CI): m/e 463 (35), 461 (100).
Example 7241 spectral data: MS (NH$_3$—CI): m/e 371 (M+H$^+$, 100%).
Example 7243 spectral data: TLC R$_F$ 0.43 (30:70 ethyl acetate-hexane). $^1$H NMR (300 MHz, CDCl$_3$): δ 9.01 (1H, s), 7.85 (1H, d, J = 8.0 Hz), 7.83 (1H, s), 7.69 (1H, d, J = 8.0 Hz), 5.24 (1H, dd, J = 8.4, 2.5 Hz), 3.28 (1H, dq, J = 15.5, 7.5 Hz), 3.14 (1H, dq, J = 15.5, 7.5 Hz), 2.56 (1H, d, J = 2.5 Hz), 1.78–1.67 (1H, m), 1.48 (3H, t, J = 7.5 Hz), 0.92–0.81 (2H, m), 0.66–0.49 (2H, m). MS (NH$_3$—CI): m/e calculated for C$_{20}$H$_{17}$ClF$_3$N$_4$: 405.1094, found 405.1098; 408 (8), 407 (34), 406 (25), 405 (100).
Example 7249 spectral data: TLC R$_F$ 0.19 (30:70 ethyl acetate-hexane). $^1$H NMR (300 MHz, CDCl$_3$): δ 8.93 (1H, s), 7.72 (1H, d, J = 8.5 Hz), 7.37 (1H, d, J = 2.5 Hz), 7.18 (1H, dd, J = 8.5, 2.5 Hz), 5.23 (1H, dd, J = 8.1, 2.6 Hz), 3.92 (3H, s), 3.31–3.04 (2H, m), 2.54 (1H, d, J = 2.6 Hz), 1.76–1.64 (1H, m), 1.47 (3H, t, J = 7.5 Hz), 0.90–0.80 (2H, m), 0.64–0.52 (2H, m). MS (NH$_3$—CI): m/e calc'd for C$_{21}$H$_{20}$F$_3$N$_4$O: 401.1603, found 401.1602; 403 (6), 402 (24), 401 (100).
Example 7250 spectral data: TLC R$_F$ 0.17 (20:80 ethyl acetate-hexane). $^1$H NMR (300 MHz, CDCl$_3$): δ 9.01 (1H, s), 7.67 (1H, d, J = 8.5 Hz), 7.58 (1H, d, J = 1.8 Hz), 7.41 (1H, dd, J = 8.5, 1.8 Hz), 5.53 (1H, dt, J = 8.0, 2.6 Hz), 3.20 (1H, dq, J = 15.8, 7.5 Hz), 3.05 (1H, dq, J = 15.8, 7.5 Hz), 2.55 (1H, d, J = 2.6 Hz), 2.42–2.29 (1H, m), 2.28–2.15 (1H, m), 1.46 (3H, t, J = 7.5 Hz), 1.04 (3H, t, J = 7.5 Hz). MS (NH$_3$—CI): m/e calc'd for C$_{18}$H$_{17}$Cl$_2$N$_4$: 359.0830, found 359.0835; 364 (2), 363 (12), 362 (14), 361 (67), 360 (24), 359 (100).
Example 7259 spectral data: TLC R$_F$ 0.22 (20:80 ethyl acetate-hexane). $^1$H NMR (300 MHz, CDCl$_3$): δ 9.01 (1H, s), 7.67 (1H, d, J = 8.1 Hz), 7.58 (1H, d, J = 1.8 Hz), 7.40 (1H, dd, J = 8.1, 1.8 Hz), 5.63 (1H, dt, J = 7.9, 2.5 Hz), 3.20 (1H, dq, J = 15.7, 7.7 Hz), 3.05 (1H, dq, J = 15.7, 7.7 Hz), 2.54 (1H, d, J = 2.5 Hz), 2.37–2.24 (1H, m), 2.19–2.06 (1H, m), 1.60–1.45 (1H, m), 1.46 (3H, t, J = 7.7 Hz), 1.39–1.25 (1H, m), 0.99 (3H, t, J = 7.3 Hz). MS (NH$_3$—CI): m/e calc'd for C$_{19}$H$_{19}$Cl$_2$N$_4$: 373.0987, found 373.0984; 378 (3), 377 (12), 376 (15), 375 (66), 374 (26), 373 (100).
Example 7261 spectral data: TLC R$_F$ 0.52 (30:70 ethyl acetate-hexane). $^1$H NMR (300 MHz, CDCl$_3$): δ 9.03 (1H, s), 7.84 (2H, m), 7.68 (1H, dd, J = 7.3, 0.7 Hz), 5.65 (1H, dt, J = 8.1, 2.6 Hz), 3.24–3.02 (2H, m), 2.55 (1H, d, J = 2.6 Hz), 2.33–2.25 (1H, m), 2.20–2.12 (1H, m), 1.46 (3H, t, J = 7.5 Hz), 1.00 (3H, t, J = 7.3 Hz). MS (NH$_3$—CI): m/e calc'd for C$_{20}$H$_{19}$ClF$_3$N$_4$: 407.1250, found 407.1243, 410 (8), 409 (36), 408 (25), 407 (100).
Example 7266 spectral data: TLC R$_F$ 0.19 (20:80 ethyl acetate-hexane). $^1$H NMR (300 MHz, CDCl$_3$): δ 9.01 (1H, d, J = 1.5 Hz), 7.38 (1H, d, J = 1.8 Hz), 7.24 (1H, d, J = 1.8 Hz), 5.70–5.58 (1H, m), 3.24–3.00 (2H, m), 2.55 (1H, d, J = 2.5 Hz), 2.40–2.25 (1H, m), 2.20–2.05 (1H, m), 2.10 (3H, d, J = 1.8 Hz), 1.62–1.47 (1H, m), 1.43 (3H, t, J = 7.5 Hz), 1.42–1.27 (1H, m), 1.00 (3H, t, J = 7.3 Hz). MS (NH$_3$—CI): m/e calc'd for C$_{20}$H$_{21}$Cl$_2$N$_4$: 387.1143, found 387.1144; 392 (3), 391 (12), 390 (16), 389 (66), 388 (27), 387 (100).
Example 7268 spectral data: TLC R$_F$ 0.29 (20:80 ethyl acetate-hexane). $^1$H

TABLE 7-continued

NMR (300 MHz, CDCl$_3$): δ 9.01 (1H, s), 7.67 (1H, d, J = 8.5 Hz), 7.58 (1H, d, J = 2.2 Hz), 7.41 (1H, dd, J = 8.5, 2.2 Hz), 5.60 (1H, dt, J = 7.9, 2.6 Hz), 3.19 (1H, dq, J = 15.3, 7.3 Hz), 3.05 (1H, dq, J = 15.3, 7.3 Hz), 2.54 (1H, d, J = 2.6 Hz), 2.38–2.23 (1H, m), 2.20–2.05 (1H, m), 1.58–1.44 (1H, m), 1.46 (3H, t, J = 7.3 Hz), 1.40–1.23 (5H, m), 0.87 (3H, t, J = 7.0 Hz). MS (NH$_3$—CI): m/e calc'd for C$_{21}$H$_{23}$Cl$_2$N$_4$: 401.1300, found 401.1300; 406 (3), 405 (13), 404 (17), 403 (69), 402 (28), 401 (100).

Example 7270 spectral data: TLC R$_F$ 0.60 (30:70 ethyl acetate-hexane). $^1$H NMR (300 MHz, CDCl$_3$): δ 9.03 (1H, s), 7.84 (2H, m), 7.68 (1H, dd, J = 9.1, 0.7 Hz), 5.62 (1H, dt, J = 8.1, 2.6 Hz), 3.24–3.02 (2H, m), 2.55 (1H, d, J = 2.6 Hz), 2.34–2.27 (1H, m), 2.19–2.13 (1H, m), 1.46 (3H, t, J = 7.3 Hz), 1.40–1.25 (6H, m), 0.88 (3H, t, J = 7.0 Hz). MS (NH$_3$—CI): m/e calc'd for C$_{22}$H$_{23}$ClF$_3$N$_4$: 435.1563, found 435.1566; 438 (9), 437 (36), 436 (27), 435 (100).

Example 7279 spectral data: TLC R$_F$ 0.31 (30:70 ethyl acetate-hexane). $^1$H NMR (300 MHz, CDCl$_3$): δ 8.97 (1H, s), 7.84 (2H, m), 7.68 (1H, d, J = 7.7 Hz), 4.74–4.67 (1H, m), 3.45–3.36 (1H, m), 3.03 (2H, q, J = 7.7 Hz), 3.00–2.93 (1H, m), 1.93 (1H, t, J = 2.7 Hz), 1.86 (3H, d, J = 7.0 Hz), 1.43 (3H, t, J = 7.5 Hz). MS (NH$_3$—CI): m/e 396 (7), 395 (34), 394 (24), 393 (100).

Example 7286 spectral data: TLC R$_F$ 0.29 (20:80 ethyl acetate-hexane). $^1$H NMR (300 MHz, CDCl$_3$): δ 8.97 (1H, s), 7.68 (1H, d, J = 8.4 Hz), 7.58 (1H, d, J = 1.8 Hz), 7.41 (1H, dd, J = 8.4, 1.8 Hz), 5.19 (1H, dq, J = 8.4, 2.6 Hz), 3.26 (1H, dq, J = 15.7, 7.3 Hz), 3.14 (1H, dq, J = 15.7, 7.3 Hz), 1.88 (3H, d, J = 2.6 Hz), 1.70–1.60 (1H, m), 1.47 (3H, t, J = 7.3 Hz), 0.89–0.78 (2H, m), 0.60–0.43 (2H, m). MS (NH$_3$—CI): m/e calc'd for C$_{20}$H$_{19}$Cl$_2$N$_4$: 385.0986, found 385.0992; 390 (3), 389 (12), 388 (15), 387 (66), 386 (26), 385 (100).

Example 7288 spectral data: MS (NH$_3$—CI): m/e 419 (M+H$^+$, 100%).

Example 7295 spectral data: TLC R$_F$ 0.19 (20:80 ethyl acetate-hexane). $^1$H NMR (300 MHz, CDCl$_3$): δ 8.99 (1H, s), 7.67 (1H, d, J = 8.4 Hz), 7.57 (1H, d, J = 2.2 Hz), 7.40 (1H, dd, J = 8.4, 2.2 Hz), 5.49 (1H, tq, J = 7.7, 2.2 Hz), 3.19 (1H, dq, J = 15.3, 7.7 Hz), 3.05 (1H, dq, J = 15.3, 7.7 Hz), 2.26 (1H, dq, J = 21.3, 7.7 Hz), 2.13 (1H, dq, J = 21.3, 7.7 Hz), 1.87 (3H, d, J = 2.2 Hz), 1.45 (3H, t, J = 7.7 Hz), 1.01 (3H, t, J = 7.7 Hz). MS (NH$_3$—CI): m/e calc'd for C$_{19}$H$_{19}$Cl$_2$N$_4$: 373.0987, found 373.0987; 378 (3), 377 (13), 376 (15), 375 (68), 374 (25), 373 (100).

Example 7297 spectral data: TLC R$_F$ 0.48 (30:70 ethyl acetate-hexane). $^1$H NMR (300 MHz, CDCl$_3$): δ 9.01 (1H, s), 7.83 (2H, m), 7.67 (1H, dd, J = 7.4, 0.8 Hz), 5.51 (1H, dt, J = 8.1, 2.2 Hz), 3.25–3.03 (2H, m), 2.35–2.13 (2H, m), 1.88 (3H, d, J = 2.2 Hz), 1.45 (3H, t, J = 7.5 Hz), 1.01 (3H, t, J = 7.3 Hz). MS (NH$_3$—CI): m/e calc'd for C$_{20}$H$_{19}$ClF$_3$N$_4$: 407.1250, found 407.1267; 410 (8), 409 (35), 408 (25), 407 (100).

Example 7306 spectral data: MS (NH$_3$—CI): m/e 421 (M+H$^+$, 100%).

Example 7324 spectral data: TLC R$_F$ 0.38 (30:70 ethyl acetate-hexane). $^1$H NMR (300 MHz, CDCl$_3$): δ 8.99 (1H, s), 7.84 (1H, d, J = 8.4 Hz), 7.83 (1H, d, J = 1.8 Hz), 7.68 (1H, dd, J = 8.4, 1.8 Hz), 7.36 (1H, d, J = 3 Hz), 6.51 (1H, d, J = 5 Hz), 6.39 (1H, dd, J = 5, 3 Hz), 5.78 (1H, dd, J = 9, 7 Hz), 3.00–2.85 (2H, m), 2.75–2.52 (2H, m), 1.37 (3H, t, J = 7.5 Hz), 0.98 (3H, t, J = 7.5 Hz). MS (NH$_3$—CI): m/e 439 (1), 438 (8), 437 (34), 436 (26), 435 (100).

Example 7349 spectral data: TLC R$_F$ 0.20 (30:70 ethyl acetate-hexane). $^1$H NMR (300 MHz, CDCl$_3$): δ 9.00 (1H, s), 7.87 (1H, d, J = 8.0 Hz), 7.83 (1H, s), 7.69 (1H, d, J = 8.0 Hz), 5.01 (1H, d, J = 10.6 Hz), 2.93 (1H, dq, J = 15.9, 7.5 Hz), 2.75 (1H, dq, J = 15.9, 7.5 Hz), 2.58 (3H, s), 2.04–1.94 (1H, m), 1.93 (3H, s), 1.33 (3H, t, J = 7.5 Hz), 1.32–1.22 (1H, m), 1.00–0.87 (1H, m), 0.74–0.60 (3H, m). MS (NH$_3$—CI): m/e calculated for C$_{23}$H$_{22}$ClF$_3$N$_5$O: 476.1465, found 476.1469; 478 (35), 476 (100).

Example 7351 spectral data: TLC R$_F$ 0.44 (30:70 ethyl acetate-hexane). $^1$H NMR (300 MHz, CDCl$_3$): δ 8.99 (1H, s), 7.88–7.82 (2H, m), 7.68 (1H, d, J = 8.0 Hz), 6.35 (1H, ddd, J = 17.2 Hz, 10.6H, 5.1 Hz), 5.33 (1H, br d, J = 10.6 Hz), 5.26 (1H, br d, J = 17.2 Hz), 4.43–4.37 (1H, m), 3.02–2.90 (2H, m), 1.99–1.89 (1H, m), 1.41 (3H, t, J = 7.5 Hz), 0.94–0.84 (1H, m), 0.62–0.52 (2H, m), 0.40–0.30 (1H, m). MS (NH$_3$—CI): m/e 411 (1), 410 (7), 409 (34), 408 (25), 407 (100).

Example 7352 spectral data: TLC R$_F$ 0.13 (20:80 ethyl acetate-hexane). $^1$H NMR (300 MHz, CDCl$_3$): δ 8.96 (1H, s), 7.69 (1H, d, J = 8.4 Hz), 7.58 (1H, d, J = 2.2 Hz), 7.41 (1H, dd, J = 8.8, 2.2 Hz), 6.33 (1H, ddd, J = 17.2, 10.6, 5.2 Hz), 5.35–5.20 (2H, m), 4.42–4.35 (1H, m), 3.03–2.88 (2H, m), 2.00–1.89 (1H, m), 1.40 (3H, t, J = 7.6 Hz), 0.92–0.82 (1H, m), 0.62–0.52 (2H, m), 0.40–0.30 (1H, m). MS (NH$_3$—CI): m/e calc'd for C$_{19}$H$_{19}$Cl$_2$N$_4$: 373.1000, found 373.0995; 378 (3), 377 (12), 376 (15), 375 (66), 374 (26), 373 (100).

TABLE 7-continued

Example 7355 spectral data: MS (NH$_3$—CI): m/e 337 (M+H$^+$, 100%).
Example 7356 spectral data: MS (NH$_3$—CI): m/e 365 (M+H$^+$, 100%).
Example 7357 spectral data: TLC R$_F$ 0.19 (30:70 ethyl acetate-hexane). $^1$H NMR (300 MHz, CDCl$_3$): δ 8.91 (1H, s), 7.70 (1H, d, J = 8.4 Hz), 7.35 (1H, d, J = 2.6 Hz), 7.19 (1H, dd, J = 8.4, 2.6 Hz), 6.42 (1H, ddd, J = 16.9, 10.3, 6.6 Hz), 5.27 (1H, d, J = 10.2 Hz), 5.14 (1H, d, J = 17.3 Hz), 5.08–4.99 (1H, m), 3.91 (3H, s), 2.99–2.90 (2H, m), 2.42–2.29 (1H, m), 2.27–2.15 (1H, m), 1.39 (3H, t, J = 7.5 Hz), 1.38–1.10 (2H, m), 0.95 (3H, t, J = 7.1 Hz). MS (NH$_3$—CI): m/e calc'd for C$_{21}$H$_{24}$F$_3$N$_4$O: 405.1915, found 405.1923; 407 (5), 406 (24), 405 (100). Analysis calc'd for C$_{21}$H$_{23}$F$_3$N$_4$O: C, 62.37; H, 5.73; N, 13.85; found: C, 62.42; H, 5.73; N, 13.48.
Example 7358 spectral data: MS (NH$_3$—CI): m/e 379 (M+H$^+$, 100%).
Example 7360 spectral data: TLC R$_F$ 0.13 (30:70 ethyl acetate-hexane). $^1$H NMR (300 MHz, CDCl$_3$): δ 8.91 (1H, s), 7.68 (1H, d, J = 8.8 Hz), 7.35 (1H, d, J = 2.6 Hz), 7.16 (1H, dd, J = 8.8, 2.6 Hz), 6.15–6.05 (1H, m), 5.73–5.63 (1H, m), 5.28–5.18 (1H, m), 3.91 (3H, s), 2.96 (2H, q, J = 7.4 Hz), 1.82 (3H, d, J = 7.3 Hz), 1.74 (3H, dt, J = 6.6, 1.3 Hz), 1.39 (3H, t, J = 7.4 Hz). MS (NH$_3$—CI): m/e calc'd for C$_{20}$H$_{22}$F$_3$N$_4$O: 391.1733, found 391.1736; 393 (3), 392 (23), 391 (100).
Example 7361 spectral data: TLC R$_F$ 0.43 (50:50 ethyl acetate-hexane). $^1$H NMR (300 MHz, CDCl$_3$): δ 8.96 (1H, s), 7.42 (1H, s), 6.84 (1H, s), 5.55 (1H, dt, J = 5.5, 2.2 Hz), 3.94 (3H, s), 3.92 (3H, s), 3.49–2.98 (2H, m), 2.54 (1H, d, J = 2.6 Hz), 2.45 (3H, s), 2.35–2.16 (2H, m), 1.48 (3H, t, J = 7.5 Hz), 1.03 (3H, t, J = 7.5 Hz), MS (NH$_3$—CI): m/e calc'd for C$_{21}$H$_{25}$N$_4$O$_2$: 365.1978, found 365.1966; 367 (6), 366 (24), 365 (100).
Example 7390 spectral data: TLC R$_F$ 0.45 (30:70 ethyl acetate-hexane). $^1$H NMR (300 MHz, CDCl$_3$): δ 8.99 (1H, s), 7.88 (1H, d, J = 8.0 Hz), 7.83 (1H, s), 7.69 (1H, d, J = 8.0 Hz), 7.30–7.22 (1H, m), 7.07–7.01 (1H, m), 6.99–6.92 (1H, m), 5.25 (1H, d, J = 10.2 Hz), 2.97–2.78 (2H, m), 2.23 (1H, br), 1.32 (3H, t, J = 7.3 Hz), 1.10–1.00 (1H, m), 0.81–0.71 (1H, m), 0.64–0.54 (1H, m), 0.50–0.40 (1H, m). MS (NH$_3$—CI): m/e calc'd for C$_{22}$H$_{19}$ClF$_3$N$_4$S: 463.0971, found 463.0960; 467 (3), 466 (10), 465 (99), 464 (28), 463 (100).
Example 7392 spectral data: TLC R$_F$ 0.44 (30:70 ethyl acetate-hexane). $^1$H NMR (300 MHz, CDCl$_3$): δ 8.99 (1h, s), 7.88 (1H, d, J = 8.0 Hz), 7.83 (1H, s), 7.68 (1H, d, J = 8.0 Hz), 7.30 (1H, br d, J = 4.8 Hz), 7.18 (1H, br d, J = 4.8 Hz), 6.92 (1H, m), 5.12 (1H, d, J = 9.9 Hz), 2.92–2.67 (2H, m), 2.13 (1H, br), 1.28 (3H, t, J = 7.5 Hz), 1.08–0.99 (1H, m), 0.79–0.69 (1H, m), 0.55–0.45 (2H, m). MS (NH$_3$—CI): m/e calculated for C$_{22}$H$_{19}$ClF$_3$N$_4$S: 463.0971, found 463.0953; 467 (3), 466 (10), 465 (39), 464 (29), 463 (100).
Example 7396 spectral data: TLC R$_F$ 0.27 (20:80 ethyl acetate-hexane). $^1$H NMR (300 MHz, CDCl$_3$): δ 8.96 (1H, s), 7.67 (1H, d, J = 8.1 Hz), 7.58 (1H, d, J = 1.8 Hz), 7.41 (1H, dd, J = 8.1, 1.8 Hz), 6.86 (1H, s), 5.83 (1H, dd, J = 9.9, 6.2 Hz), 4.43 (2H, q, J = 7.3 Hz), 2.98 (2H, q, J = 7.7 Hz), 2.91–2.78 (1H, m), 2.63–2.49 (1H, m), 1.42 (3H, t, J = 7.7 Hz), 1.40 (3H, t, J = 7.3 Hz), 1.39–1.19 (2H, m), 1.00 (3H, t, J = 7.3 Hz). MS (NH$_3$—CI): m/e calc'd for C$_{23}$H$_{24}$Cl$_2$N$_5$O$_3$: 488.1256, found 488.1252; 493 (3), 492 (13), 491 (18), 490 (68), 489 (28), 488 (100).
Example 7398 spectral data: TLC R$_F$ 0.11 (20:80 ethyl acetate-hexane). $^1$H NMR (300 MHz, CDCl$_3$): δ 8.99 (1H, s), 7.72 (1H, d, J = 8.1 Hz), 7.59 (1H, d, J = 1.8 Hz), 7.42 (1H, dd, J = 8.1, 1.8 Hz), 5.40 (1H, dd, J = 10.4, 5.0 Hz), 4.42 (2H, q, J = 7.4 Hz), 3.00–2.90 (2H, m), 2.66–2.52 (1H, m), 2.51–2.38 (1H, m), 1.46 (3H, t, J = 7.4 Hz), 1.41 (3H, t, J = 7.3 Hz), 1.40–1.10 (2H, m), 0.98 (3H, t, J = 7.2 Hz). MS (NH$_3$—CI): m/e calc'd for C$_{24}$H$_{25}$Cl$_2$N$_6$O$_4$: 531.1315, found 531.1315; 531 (100).
Example 7399 spectral data: TLC R$_F$ 0.13 (20:80 ethyl acetate-hexane). $^1$H NMR (300 MHz, CDCl$_3$): δ 8.98 (1H, s), 7.38 (1H, d, J = 1.8 Hz), 7.23 (1H, d, J = 1.8 Hz), 6.15–6.06 (1H, m), 5.76–5.63 (1H, m), 5.26–5.20 (1H, m), 2.96 (2H, q, J = 7.4 Hz), 2.10 (3H, s), 1.83 (3H, d, J = 7.0 Hz), 1.74 (3H, d, J = 6.6 Hz), 1.37 (3H, t, J = 7.4 Hz). MS (NH$_3$—CI): m/e calc'd for C$_{19}$H$_{21}$Cl$_2$N$_4$: 375.1117, found 375.1123; 380 (2), 379 (12), 378 (15), 377 (66), 376 (26), 375 (100).
Example 7401 spectral data: TLC R$_F$ 0.20 (ethyl acetate). $^1$H NMR (300 MHz, CDCl$_3$): δ 8.99 (1H, s), 7.71 (1H, d, J = 8.4 Hz), 7.58 (1H, d, J = 1.8 Hz), 7.41 (1H, dd, J = 8.4, 1.8 Hz), 7.11 (1H, d, J = 1.1 Hz), 6.87 (1H, d, J = 1.1 Hz), 5.41 (1H, d, J = 10.3 Hz), 3.34 (3H, s), 3.08 (1H, dq, J = 15.8, 7.7 Hz), 2.89 (1H, dq, J = 15.8, 7.7 Hz), 2.39–2.25 (2H, m), 1.14 (3H, t, J = 7.7 Hz), 1.07–0.97 (1H, m), 0.70–0.58 (2H, m), 0.52–0.42 (1H, m). MS (NH$_3$—CI): m/e calc'd for C$_{21}$H$_{21}$Cl$_2$N$_6$: 427.1205, found 427.1196; 429 (66), 427 (100).
Example 7402 spectral data: MS (NH$_3$—CI): m/e 424 (M+H$^+$, 100%).
Example 7404 spectral data: MS (NH$_3$—CI): m/e 419 (M+H$^+$, 100%).
Example 7405 spectral data: MS (NH$_3$—CI): m/e 487 (M+H$^+$, 100%).
Example 7406 spectral data: MS (NH$_3$—CI): m/e 501 (M+H$^+$, 100%).
Example 7407 spectral data: MS (NH$_3$—CI): m/e 517 (M+H$^+$, 100%).
Example 7408 spectral data: MS (NH$_3$—CI): m/e 457 (M+H$^+$, 100%).
Example 7409 spectral data: MS (NH$_3$—CI): m/e 429 (M+H$^+$, 100%).

Utility

CRF-1 Receptor Binding Assay for the Evaluation of Biological Activity

The following is a description of the isolation of cell membranes containing cloned human CRF-1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of PGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 mM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 mL of ice cold tissue buffer (50 mM HEPES buffer pH 7.0, containing 10 mM $MgCl_2$, 2 mM EGTA, 1 mg/L aprotinin, 1 mg/mL leupeptin and 1 mg/mL pepstatin). The homogenate is centrifuged at 40,000×g for 12 min and the resulting pellet rehomogenized in 10 mL of tissue buffer. After another centrifugation at 40,000×g for 12 min, the pellet is resuspended to a protein concentration of 360 mg/mL to be used in the assay.

Binding assays are performed in 96 well plates; each well having a 300 mL capacity. To each well is added 50 mL of test drug dilutions (final concentration of drugs range from $10^{-10}$ to $10^{-5}$ M), 100 mL of $^{125}$I-ovine-CRF ($^{125}$I-o-CRF) (final concentration 150 pM) and 150 mL of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides $K_i$ values for inhibition which are then used to assess biological activity.

Alternatively, tissues and cells which naturally express CRF receptors can be employed in binding assays analogous to those described above.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 37° C. for 10 min in 200 mL of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/mL phosphocreatine kinase, 5 mM creatine phosphate, 100 mM guanosine 5'-triphosphate, 100 nM oCRF, antagonist peptides (concentration range $10^{-9}$ to $10^{-6}$ M) and 0.8 mg original wet weight tissue (approximately 40–60 mg protein). Reactions are initiated by the addition of 1 mM ATP/$^{32}$P]ATP (approximately 2–4 mCi/tube) and terminated by the addition of 100 mL of 50 mM Tris-HCL, 45 mM ATP and 2% sodium dodecyl sulfate. In order to monitor the recovery of cAMP, 1 mL of [$^3$H]cAMP (approximately 40,000 dpm) is added to each tube prior to separation. The separation of [$^{32}$p] cAMP from [$^{32}$P]ATP is performed by sequential elution over Dowex and alumina columns.

In Vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about. 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A method of treating a disorder selected from affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, and hypoglycemia in mammals, comprising: administering to the mammal a therapeutically effective amount of a compound of formula (I):

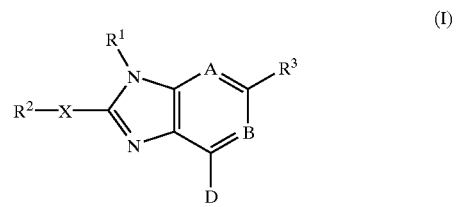

or a stereoisomer or pharmaceutically acceptable salt form thereof, wherein:

A is N and B is C—$R^8$ or A is C—$R^7$ and B is N;

D is an aryl or heteroaryl group attached through an unsaturated carbon atom;

X is selected from the group CH—$R^9$, N—$R^{10}$, O, S(O)$_n$ and a bond;

n is 0, 1 or 2;

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$—$C_{1-10}$ alkyl, —$SO_2$—$R^{1a}$, and —$SO_2$—$R^{1b}$;

$R^1$ is substituted with 0–1 substituents selected from the group —CN, —S(O)$_n R^{14b}$, —$COR^{13a}$, —$CO_2 R^{13a}$, —$NR^{15a}COR^{13a}$, —N($COR^{13a}$)$_2$, —$NR^{15a}CONR^{13a}R^{16a}$, —$NR^{15a}CO_2R^{14b}$, —$CONR^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —S(O)$_n$—, —$NR^{13a}$—, —$NCO_2R^{14b}$—, —$NCOR^{14b}$— and —$NSO_2R^{14b}$—, and wherein $N_4$ in 1-piperazinyl is substituted with 0–1 substituents selected from the group $R^{13a}$, $CO_2R^{14b}$, $COR^{14b}$ and $SO_2R^{14b}$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —$OR^{13a}$, —$NR^{13a}R^{16a}$, $C_{1-4}$ alkoxy-$C_{1-4}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than:
(a) a 3-cyclopropyl-3-methoxypropyl group;
(b) an unsubstituted-(alkoxy)methyl group; and,
(c) a 1-hydroxyalkyl group;

also provided that when $R^1$ is alkyl substituted with OH, then the carbon in the $R^1$ adjacent to the ring N is other than $CH_2$;

$R^{1a}$ is aryl and is selected from the group phenyl, naphthyl, indanyl and indenyl, each $R^{1a}$ being substituted with 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_nR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_nR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_nR^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^3$, $R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $(C_{1-4}$ alkyl$)_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and $(C_{1-4}$ alkyl$)_2$amino;

provided that when $R^1$ is unsubstituted $C_{1-10}$ alkyl, then $R^3$ is other than substituted or unsubstituted phenyl;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)— and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl; and, heteroaryl is independently selected at each occurrence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

2. A method according to claim 1, wherein the compound is of formula Ia:

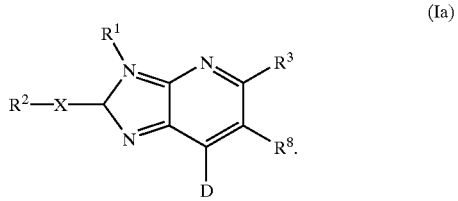

(Ia)

3. A method according to claim 1, wherein the compound is of formula Ib:

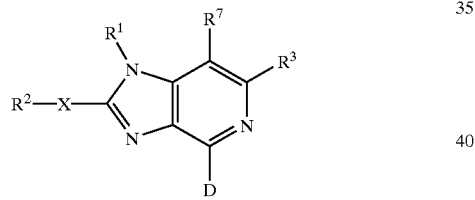

(Ib)

4. The method of claim 1, wherein said disorder is anxiety, depression, anorexia nervosa, irritable bowel syndrome, drug or alcohol withdrawal symptoms, inflammation, or stroke.

5. A method of treating a disorder induced or facilitated by CRF in a mammal, comprising administering to said mammal a therapeutically effective amount of a compound of formula (I):

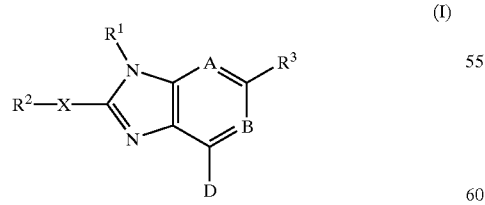

(I)

or a stereoisomer or pharmaceutically acceptable salt form thereof, wherein:

A is N and B is C—$R^8$ or A is C—$R^7$ and B is N;

D is an aryl or heteroaryl group attached through an unsaturated carbon atom;

X is selected from the group CH—$R^9$, N—$R^{10}$, O, $S(O)_n$ and a bond;

n is 0, 1 or 2;

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$—$C_{1-10}$ alkyl, —$SO_2$—$R^{1a}$, and —$SO_2$—$R^{1b}$;

$R^1$ is substituted with 0–1 substituents selected from the group —CN, —$S(O)_nR^{14b}$, —$COR^{13a}$, —$CO_2R^{13a}$, —$NR^{15a}COR^{13a}$, —$N(COR^{13a})_2$, —$NR^{15a}CONR^{13a}R^{16a}$, —$NR^{15a}CO_2R^{14b}$, —$CONR^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —$S(O)_n$—, —$NR^{13a}$—, —$NCO_2R^{14b}$—, —$NCOR^{14b}$— and —$NSO_2R^{14b}$—, and wherein $N_4$ in 1-piperazinyl is substituted with 0–1 substituents selected from the group $R^{13a}$, $CO_2R^{14b}$, $COR^{14b}$ and $SO_2R^{14b}$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —$OR^{13a}$, —$NR^{13a}R^{16a}$, $C_{1-4}$ alkoxy-$C_{1-4}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than:
 (a) a 3-cyclopropyl-3-methoxypropyl group;
 (b) an unsubstituted-(alkoxy)methyl group; and,
 (c) a 1-hydroxyalkyl group;

also provided that when $R^1$ is alkyl substituted with OH, then the carbon in the $R^1$ adjacent to the ring N is other than $CH_2$;

$R^{1a}$ is aryl and is selected from the group phenyl, naphthyl, indanyl and indenyl, each $R^{1a}$ being substituted with 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_nR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_nR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_nR^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^3$, $R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $(C_{1-4}$ alkyl$)_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and $(C_{1-4}$ alkyl$)_2$amino;

provided that when $R^1$ is unsubstituted $C_{1-10}$ alkyl, then $R^3$ is other than substituted or unsubstituted phenyl;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)— and benzyl, each benzyl being substituted on the aryl moiety with 0–1 substituents selected from the group $C_{1-4}$ alkyl, Br, Cl, F, r, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^8$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl; and, heteroaryl is independently selected at each occurrence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

* * * * *